(12) United States Patent
Prakash et al.

(10) Patent No.: US 9,714,421 B2
(45) Date of Patent: Jul. 25, 2017

(54) COMPOSITIONS AND METHODS

(71) Applicant: Ionis Pharmaceuticals, Inc., Carlsbad, CA (US)

(72) Inventors: Thazha P. Prakash, Carlsbad, CA (US); Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/888,318

(22) PCT Filed: May 1, 2014

(86) PCT No.: PCT/US2014/036466
§ 371 (c)(1),
(2) Date: Oct. 30, 2015

(87) PCT Pub. No.: WO2014/179629
PCT Pub. Date: Nov. 6, 2014

(65) Prior Publication Data
US 2016/0076032 A1 Mar. 17, 2016

Related U.S. Application Data

(60) Provisional application No. 61/818,442, filed on May 1, 2013, provisional application No. 61/823,826, filed on May 15, 2013, provisional application No. 61/843,887, filed on Jul. 8, 2013, provisional application No. 61/871,673, filed on Aug. 29, 2013, provisional application No. 61/880,790, filed on Sep. 20, 2013, provisional application No. 61/976,991, filed on Apr. 8, 2014, provisional application No. 61/986,867, filed on Apr. 30, 2014.

(51) Int. Cl.
*C12N 15/11* (2006.01)
*C12N 15/113* (2010.01)
*C07H 21/04* (2006.01)
*A61K 31/7088* (2006.01)
*A61K 31/713* (2006.01)

(52) U.S. Cl.
CPC ........ *C12N 15/113* (2013.01); *A61K 31/7088* (2013.01); *A61K 31/713* (2013.01); *C07H 21/04* (2013.01); *C12N 15/111* (2013.01); *C12N 2310/11* (2013.01); *C12N 2310/113* (2013.01); *C12N 2310/17* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2310/351* (2013.01); *C12N 2310/353* (2013.01); *C12N 2310/3511* (2013.01); *C12N 2310/3513* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,751,219 A | 6/1988 | Kempen et al. |
| 4,845,205 A | 7/1989 | Huynh Dinh et al. |
| 4,981,957 A | 1/1991 | Lableu et al. |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,319,080 A | 6/1994 | Leumann |
| 5,359,044 A | 10/1994 | Cook et al. |
| 5,366,878 A | 11/1994 | Pederson et al. |
| 5,367,066 A | 11/1994 | Urdea et al. |
| 5,432,272 A | 7/1995 | Benner |
| 5,446,137 A | 8/1995 | Maag et al. |
| 5,457,187 A | 10/1995 | Gmelner et al. |
| 5,459,255 A | 10/1995 | Cook et al. |
| 5,466,786 A | 11/1995 | Buhr et al. |
| 5,484,908 A | 1/1996 | Froehler et al. |
| 5,502,177 A | 3/1996 | Matteucci et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,552,540 A | 9/1996 | Haralambidis |
| 5,567,811 A | 10/1996 | Mistura et al. |

(Continued)

FOREIGN PATENT DOCUMENTS

| | | |
|---|---|---|
| WO | WO 97/20563 | 6/1997 |
| WO | WO 97/46098 | 12/1997 |

(Continued)

OTHER PUBLICATIONS

Adcock et al., "A Laboratory Approach to the Evaluation of Hereditary Hypercoagulability" American Journal of Clinical Pathology. (1997) 108:434-49.

(Continued)

*Primary Examiner* — Kate Poliakova-Georgantas
(74) *Attorney, Agent, or Firm* — Ionis Pharmaceuticals, Inc. Patent Dept.

(57) ABSTRACT

Provided herein are oligomeric compounds with conjugate groups. In certain embodiments, the oligomeric compounds are conjugated to N-Acetylgalactosamine.

17 Claims, No Drawings

(56) References Cited

U.S. PATENT DOCUMENTS

| | | |
|---|---|---|
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,610,300 A | 3/1997 | Altmann et al. |
| 5,614,617 A | 3/1997 | Cook et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,670,633 A | 9/1997 | Cook et al. |
| 5,681,941 A | 10/1997 | Cook et al. |
| 5,698,685 A | 12/1997 | Summerton et al. |
| 5,700,920 A | 12/1997 | Altmann et al. |
| 5,750,692 A | 5/1998 | Cook et al. |
| 5,763,588 A | 6/1998 | Matteucci et al. |
| 5,792,847 A | 8/1998 | Buhr et al. |
| 5,830,653 A | 11/1998 | Froehler et al. |
| 5,994,517 A | 11/1999 | Ts'o et al. |
| 6,005,096 A | 12/1999 | Matteucci et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,525,031 B2 | 2/2003 | Manoharan |
| 6,525,191 B1 | 2/2003 | Ramasamy |
| 6,600,032 B1 | 7/2003 | Manoharan et al. |
| 6,620,916 B1 | 9/2003 | Takahara et al. |
| 6,660,720 B2 | 12/2003 | Manoharan et al. |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 7,034,133 B2 | 4/2006 | Wengel et al. |
| 7,053,207 B2 | 5/2006 | Wengel |
| 7,262,177 B2 | 8/2007 | Ts'o et al. |
| 7,399,845 B2 | 7/2008 | Seth et al. |
| 7,399,853 B2 | 7/2008 | Freier et al. |
| 7,427,672 B2 | 9/2008 | Imanishi et al. |
| 7,491,805 B2 | 2/2009 | Vargeese et al. |
| 7,563,884 B2 | 7/2009 | Cowsert et al. |
| 7,569,686 B1 | 8/2009 | Bhat et al. |
| 7,582,744 B2 | 9/2009 | Manoharan et al. |
| 7,723,509 B2 | 5/2010 | Manoharan et al. |
| 7,741,457 B2 | 6/2010 | Swayze et al. |
| 7,750,142 B2 | 7/2010 | Freier |
| 7,851,615 B2 | 12/2010 | Manoharan et al. |
| 8,106,022 B2 | 1/2012 | Manoharan et al. |
| 8,137,695 B2 | 3/2012 | Rozema et al. |
| 8,158,601 B2 | 4/2012 | Chen et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,541,548 B2 | 9/2013 | Rozema |
| 8,546,556 B2 | 10/2013 | Seth et al. |
| 8,552,163 B2 | 10/2013 | Lee et al. |
| 2003/0077829 A1 | 4/2003 | MacLachlan |
| 2003/0119724 A1 | 6/2003 | Ts'o et al. |
| 2004/0171570 A1 | 9/2004 | Allerson et al. |
| 2005/0130923 A1 | 6/2005 | Bhat et al. |
| 2005/0164235 A1 | 7/2005 | Manoharan et al. |
| 2006/0148740 A1 | 7/2006 | Platenburg |
| 2006/0183886 A1 | 8/2006 | Tso et al. |
| 2007/0287831 A1 | 12/2007 | Seth et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0240730 A1 | 9/2010 | Beigelman et al. |
| 2010/0292140 A1 | 11/2010 | Bhanot et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0230938 A1 | 9/2012 | Rozema et al. |
| 2013/0004427 A1 | 1/2013 | El-Sayed et al. |
| 2013/0053431 A1 | 2/2013 | Tachas et al. |
| 2013/0109817 A1 | 5/2013 | Yurkovetskiy et al. |
| 2013/0121954 A1 | 5/2013 | Wakefield et al. |
| 2013/0178512 A1 | 7/2013 | Manoharan et al. |
| 2013/0236968 A1 | 9/2013 | Manoharan et al. |

FOREIGN PATENT DOCUMENTS

| | | |
|---|---|---|
| WO | WO 98/13381 | 4/1998 |
| WO | WO 99/14226 | 3/1999 |
| WO | WO 00/63364 | 10/2000 |
| WO | WO 01/49687 | 7/2001 |
| WO | WO 01/53528 | 7/2001 |
| WO | WO 02/10378 | 2/2002 |
| WO | WO 02/43771 | 6/2002 |
| WO | WO 02/092772 | 11/2002 |
| WO | WO 2004/035765 | 10/2003 |
| WO | WO 2004/011624 | 2/2004 |
| WO | WO 2004/024757 | 3/2004 |
| WO | WO 2004/063208 | 7/2004 |
| WO | WO 2004/071407 | 8/2004 |
| WO | WO 2004/078922 | 9/2004 |
| WO | WO 2004/096016 | 11/2004 |
| WO | WO 2004/096996 | 11/2004 |
| WO | WO 2004/101619 | 11/2004 |
| WO | WO 2004/106356 | 12/2004 |
| WO | WO 2005/021570 | 3/2005 |
| WO | WO 2005/065686 | 7/2005 |
| WO | WO 2005/071080 | 8/2005 |
| WO | WO 2005/121371 | 12/2005 |
| WO | WO 2006/044531 | 4/2006 |
| WO | WO 2006/047842 | 5/2006 |
| WO | WO 2007/035759 | 3/2007 |
| WO | WO 2007/035771 | 3/2007 |
| WO | WO 2007/090071 | 8/2007 |
| WO | WO 2007/131237 | 11/2007 |
| WO | WO 2007/134014 | 11/2007 |
| WO | WO 2007/134181 | 11/2007 |
| WO | WO 2007/136988 | 11/2007 |
| WO | WO 2008/098788 | 8/2008 |
| WO | WO 2008/101157 | 8/2008 |
| WO | WO 2008/150729 | 12/2008 |
| WO | WO 2008/154401 | 12/2008 |
| WO | WO 2009/003009 | 12/2008 |
| WO | WO 2009/006478 | 1/2009 |
| WO | WO 2009/046141 | 4/2009 |
| WO | WO 2009/061851 | 5/2009 |
| WO | WO 2009/073809 | 6/2009 |
| WO | WO 2009/082607 | 7/2009 |
| WO | WO 2009/100320 | 8/2009 |
| WO | WO 2009/126933 | 10/2009 |
| WO | WO 2009/134487 | 11/2009 |
| WO | WO 2009/143369 | 11/2009 |
| WO | WO 2010/036698 | 4/2010 |
| WO | WO 2010/045509 | 4/2010 |
| WO | WO 2010/054406 | 5/2010 |
| WO | WO 2010/077578 | 7/2010 |
| WO | WO 2010/088537 | 8/2010 |

(56) References Cited

FOREIGN PATENT DOCUMENTS

| | | |
|---|---|---|
| WO | WO 2010/121074 | 10/2010 |
| WO | WO 2010/129709 | 11/2010 |
| WO | WO 2010/144740 | 12/2010 |
| WO | WO 2010/148013 | 12/2010 |
| WO | WO 2011/008995 | 1/2011 |
| WO | WO 2011/038356 | 3/2011 |
| WO | WO 2011/100131 | 8/2011 |
| WO | WO 2011/115818 | 9/2011 |
| WO | WO 2011/120053 | 9/2011 |
| WO | WO 2011/163121 | 12/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/142458 | 10/2012 |
| WO | WO 2012/174476 | 12/2012 |
| WO | WO 2012/177947 | 12/2012 |
| WO | WO 2013/033230 | 3/2013 |
| WO | WO 2013/043817 | 3/2013 |
| WO | WO 2013/063313 | 5/2013 |
| WO | WO 2013/075035 | 5/2013 |
| WO | WO 2013/119979 | 8/2013 |
| WO | WO 2013/165816 | 11/2013 |
| WO | WO 2013/166121 | 11/2013 |
| WO | WO 2014/076195 | 5/2014 |
| WO | WO 2014/076196 | 5/2014 |
| WO | WO 2014/118272 | 8/2014 |
| WO | WO 2014/179620 | 11/2014 |
| WO | WO 2014/179625 | 11/2014 |
| WO | WO 2014/179626 | 11/2014 |
| WO | WO 2014/179627 | 11/2014 |
| WO | WO 2014/205451 | 12/2014 |
| WO | WO 2014/207232 | 12/2014 |
| WO | WO 2015/002971 | 1/2015 |
| WO | WO 2015/042447 | 3/2015 |
| WO | WO 2015/071388 | 5/2015 |
| WO | WO 2015/168514 | 11/2015 |
| WO | WO 2015/168532 | 11/2015 |
| WO | WO 2015/168589 | 11/2015 |
| WO | WO 2015/168618 | 11/2015 |
| WO | WO 2015/168635 | 11/2015 |
| WO | WO 2015/179693 | 11/2015 |
| WO | WO 2015/188194 | 12/2015 |

OTHER PUBLICATIONS

Allshire, "RNAi and Heterochromatin—a Hushed-Up Affair" Science (2002) 297: 1818-1819.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.
Altmann et al., "Second Generation of Antisense Oligonucleotides: From Nuclease Resistance to Biological Efficacy in Animals " Chimia. (1996) 50(4):168-176.
Altmann et al., "Second-generation antisense oligonucleotides: structure-activity relationships and the design of improved signal-transduction inhibitors" Biochem. Soc. Trans. (1996) 24:630-637.
Armstrong et al., "Localization of the Fibroblast Growth Factor Receptor-4 Gene to Chromasome Region 5q33-qter" Genes Chromosomes Cancer (1992) 4: 94-98.
Atsma et al., "Partial characterization of low density lipoprotein preparations isolated from fresh and frozen plasma after radiolabeling by seven different methods." J Lipid Res. Jan. 1991; 32(1): 173-181.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.
Bange et al., "Cancer progression and tumor cell motility are associated with the FGFR4 Arg(388) allele." Cancer Res. (2002) 62(3):840-847.
Baron et al., "Role of Hyperglucagonemia in Maintenance of Increased Rates of Hepatic Glucose Output in Type II Diabetics" Diabetes (1987) 36: 274-283.
Bennett, "Pharmacological Properties of 2'-O-Methoxyethyl Modified Oligonucleotides" in Antisense a Drug Technology, Chapter 10, Crooke, S.T., ed., 2008, pp. 273-303.
Bertina et al., "Mutation in blood coagulation factor V associated with resistance to activated protein C" Nature (1994) 369(6475):64-67.
Biessen et al., "Synthesis of Cluster Galactosides with High Affinity for the Hepatic Asialoglycoprotein Receptor" J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.
Bjork et al., "Mechanism of the anticoagulant action of heparin" Mol. Cell. Biocehm. (1982) 48(3):161-182.
Braasch et al., "Locked nucleic acid (LNA): fine-tuning the recognition of DNA and RNA" Chem. Biol. (2001) 8:1-7.
Braasch et al., "Novel Antisense and Peptide Nucleic Acid Strategies for Controlling Gene Expression" Biochemistry (2002) 41(14): 4503-4510.
Brands J Lab Clin Med. Sep. 1996;128(3):329-38. "Amplification of antibody production by phosphorothioate oligodeoxynucleotides".
Brown-Shimer et al., "Effect of protein tyrosine phosphatase 1B expression on transformation by the human neu oncogene" Cancer Res. (1992) 52:478-482.
Brubaker et al., "Structure-Function of the Glucagon Receptor Family of G Protein-Coupled Receptors: The Glucagon, GIP, GLP-1, and GLP-2 Receptors" Recept. Channels. (2002) 8: 179-88.
Connolly et al., "Binding and Endocytosis of Cluster Glycosides by Rabbit Hepatocytes" J Biol Chem (1982) 257: 939-945.
Drake et al., "Selective cellular expression of tissue factor in human tissues. Implications for disorders of hemostasis and thrombosis" Am. J. Pathol. (1989) 134(5):1087-1097.
Duff et al., "Intrabody Tissue-Specific Delivery of Antisense Conjugates in Animals: Ligand-Linker-Antisense Oligomer Conjugates" Methods in Enzymology (1999) 313: 297-321.
Dupouy et al., "Watson-Crick Base-Pairing Properties of Nucleic Acid Analogues with Stereocontrolled a and b Torsion Angles (a,b-D-CNAs)" Angew. Chem. Int. Ed. (2006) 45: 3623-3627.
Elayadi et al., "Application of PNA and LNA oligomers to chemotherapy" Curr. Opinion Invens. Drugs (2001) 2:558-561.
Elchebly et al., "Increased Insulin Sensitivity and Obesity Resistance in Mice Lacking the Protein Tyrosine Phosphatase-1B Gene" Science (1999) 283: 1544-1548.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
Geary et al., "Effect of Dose and Plasma Concentration on Liver Uptake and Pharmacologic Activity of a 2'-Methoxyethyl Modified

(56) References Cited

OTHER PUBLICATIONS

Chimeric Antisense Oligonucleotide Targeting PTEN." Biochem. Pharmacol. (2009) 78(3): 284-291.

Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.

GenBank entry NM_000163.3 (2011): http://www.ncbi.nlm.nih/gov/nuccore/334883125.

Goldstein et al., "Tyrosine dephosphorylation and deactivation of insulin receptor substrate-1 by protein-tyrosine phosphatase 1B. Possible facilitation by the formation of a ternary complex with the Grb2 adaptor protein." J. Biol. Chem. (2000) 275(6): 4283-4289.

Gu et al., "Base pairing properties of D- and L-cyclohexene nucleic acids (CeNA)" Oligonucleotides (2003) 13(6):479-489.

Gu et al., "Enzymatic resolution and base pairing properties of D- and L-cyclohexenyl nucleic acids (CeNA)" Nucleosides Nucleotides Nucleic Acids (2005) 24(5-7):993-998.

Gu et al., "Synthesis of enantiomeric-pure cyclohexenyl nucleoside building blocks for oligonucleotide synthesis" Tetrahedron (2004) 60(9):2111-2123.

Guzaev et al., "A conformationally preorganized universal solid support for efficient oligonucleotide synthesis" J. Am. Chem. Soc. (2003) 125(9):2380-2381.

Hall et al., "Establishment and maintenance of a heterochromatin domain" Science (2002) 297(5590):2232-2237.

Hanessian et al., "Synthesis of chemically and functionally diverse scaffolds from pentaerythritol" Canadian Journal of Chemistry (1996) 74(9):1731-1737.

Hansen et al., "glucagon Receptor mRNA Distribution in Rat Tissues" Peptides (1995) 16: 1163-1166.

Henkel et al., "Impact of glucagon response on postprandial hyperglycemia in men with impaired glucose tolerance and type 2 diabetes mellitus." Metabolism (2005) 54: 1168-1173.

Horn et al., "Chemical synthesis and characterization of branched oligodeoxyribonucleotides (bDNA) for use as signal amplifiers in nucleic acid quantification assays." Nucleic Acids Research (1997) 25: 4842-4849.

Holtrich et al., "Two additional protein-tyrosine kinases expressed in human lung: fourth member of the fibroblast growth factor receptor family and an intracellular protein-tyrosine kinase." PNAS (1991) 88(23): 10411-10415.

Horvath et al., "Stereoselective synthesis of (−)-ara-cyclohexenyl-adenine" Tetrahedron Letters (2007) 48:3621-3623.

Huang et al., "FGFR4 prevents hyperlipidemia and insulin resistance but underlies high-fat diet induced fatty liver." Diabetes (2007) 56(10): 2501-2510.

Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.

Jenuwein, "Molecular biology. An RNA-guided pathway for the epigenome" Science (2002) 297(5590):2215-2218.

Jiang et al., "Glucagon and regulation of glucose metabolism" Am. J. Physiol. Endocrinol. Metab. (2003) 284: E671-E678.

Jiang et al., "The Design and Synthesis of Highly Branched and Spherically Symmetric Fluorinated Oils and Amphiles." Tetrahedron (2007) 63(19): 3982-3988.

Jin et al., "Use of α-N,N-bis[Carboxymethyl]lysine-Modified Peroxidase in Immunoassays" Analytical Biochemistry (1995) 229(1): 54-60.

Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.

Khorev et al., "Trivalent, Gal/GalNAc-containing ligands designed for the asialoglycoprotein receptor" Bioorganic & Medicinal Chemistry (2008) 16: 5216-5231.

Kim et al., "Oligomeric Glycopeptidomimetics Bearing the Cancer Related TN-Antigen" Tetrahedron Letters (1997) 38(20): 3487-3490.

Kim et al., "Synthesis of Novel Phosphoramidite Building Blocks from Pentaerythritol" Synlett (2003) 12: 1838-1840.

Klaman et al., "Increased Energy Expenditure, Decreased Adiposity, and Tissue-Specific Insulin Sensitivity in Protein-Tyrosine Phosphatase 1B-Deficient Mice" Mol. Cell. Biol. (2000) 20(15): 5479-5489.

Koller et al., "Mechanisms of single-stranded phosphorothioate modified antisense oligonucleotide accumulation in hepatocytes." Nucleic Acids Res. (2011) 39(11): 4795-4807.

Kornilova et al., "Development of a fluorescence polarization binding assay for asialoglycoprotein receptor" Analytical Biochemistry (2012) 425: 43-46.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, The Concise Encyclopedia of Polymer Science and Engineering, J.I., Ed., John Wiley & Sons, 1990, 858-859.

Kumar et al., "The first analogues of LNA (locked nucleic acids): phosphorothioate-LNA and 2'-thio-LNA" Bioorg Med Chem Lett. (1998) 8:2219-2222.

Lamontagne et al., "Protein tyrosine phosphatase PTP1B suppresses p210 bcr-abl-induced transformation of rat-1 fibroblasts and promotes differentiation of K562 cells" Proc. Natl. Acad. Sci. USA (1998) 95:14094-14099.

Lee et al., "New and more efficient multivalent glyco-ligands for asialoglycoprotein receptor of mammalian hepatocytes" Bioorganic & Medicinal Chemistry (2011) 19:2494-2500.

Lee et al., "New synthetic cluster ligands for galactose/N-acetylgalactosamine-specific lectin of mammalian liver" Biochem (1984) 23: 4255-4261.

Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.

Lee et al., "Protein microarrays to study carbohydrate-recognition events" Bioorg Med Chem Lett (2006) 16(19): 5132-5135.

Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.

Lee et al., "Synthesis of multivalent neoglyconjugates of MUC1 by the conjugation of carbohydrate-centered, triazole-linked glycoclusters to MUC1 peptides using click chemistry." J Org Chem (2012) 77: 7564-7571.

Lee et al., "Reversible inactivation of protein-tyrosine phosphatase 1B in A431 cells stimulated with epidermal growth factor" J. Biol. Chem. (1998) 273:15366-15372.

Lee et al., "Synthesis of Peptide-Based Trivalent Scaffold for Preparation of Cluster Glycosides" Methods in Enzymology (2003) 362: 38-43.

Lee et al., "Synthesis of some cluster glycosides suitable for attachment to proteins or solid matrices" Carbohydrate Research (1978) 67: 509-514.

Leumann et al., "DNA Analogues: From Supramolecular Principles to Biological Properties" Bioorganic & Medicinal Chemistry (2002) 10:841-854.

Liu et al., "Protein tyrosine phosphatase 1B interacts with and is tyrosine phosphorylated by the epidermal growth factor receptor" Biochem. J. (1997) 327:139-145.

Liu et al., "Transformation suppression by protein tyrosine phosphatase 1B requires a functional SH3 ligand" Mol. Cell. Biol. (1998) 18:250-259.

Maher et al., "Comparative bybrid arrest by tandem antisense oligodeoxyribonucleotides or oligodeoxyribonucleoside methylphosphonates in a cell-free system" Nuc. Acid. Res. (1988) 16(8):3341-3358.

Maier et al., "Synthesis of Antisense Oligonucleotides Conjugated to a Multivalent Carbohydrate Cluster for Cellular Targeting" Bioconjugate Chem. (2003) 14: 18-29.

(56) References Cited

OTHER PUBLICATIONS

Maierhofer et al., "Probing multivalent carbohydrate-lectin interactions by an enzyme-linked lectin assay employing covalently immobilized carbohydrates" Bioorganic & Medicinal Chemistry (2007) 15: 7661-7676.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Martin, "New acces to 2'-O-alkylated ribonucleosides and properties of 2'-O-alkylated oligoribonucleotides" Helv. Chim. Acta. (1995) 78:486-504.
Merwin et al., "Targeted delivery of DNA using YEE(GalNAcAH)3, a synthetic glycopeptide ligand for the asialoglycoprotein receptor." Bioconjug Chem (1994) 5(6): 612-620.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.
Nawano et al., "Hyperglycemia contributes insulin resistance in hepatic and adipose tissue but not skeletal muscle of ZDF rats." Am. J. Physiol. Endocrinol. Metab. (2000) 278(3):E535-543.
Neel et al., "Protein tyrosine phosphatases in signal transduction." Curr. Opin. Cell Biol. (1997) 9(2): 193-204.
Opherk et al., "Inactivation of the Glucocorticoid Receptor in Hepatocytes Leads to Fasting Hypoglycemia and Ameliorates Hyperglycemia in Streptozotocin-Induced Diabetes Mellitus" Mol. Endocrinol. (2004) 18:1346-1353.
Orum et al., "Locked nucleic acids: A promising molecular family for gene-function analysis and antisense drug development" Curr. Opinion Mol. Ther. (2001) 3:239-243.
Pal-Bhadra et al., "Heterochromatic silencing and HP1 localization in *Drosophila* are dependent on the RNAi machinery" Science (2004) 303(5658):669-672.
Park et al., "The asialoglycoprotein receptor clears glycoconjugates terminating with sialic acid a2,6GalNAc" PNAS (2005) 102(47): 17125-17129.
Patel et al., "Essential role of fibroblast growth factor signaling in preadipoctye differentiation." J Clin Endocrinol Metab. (2005) 90(2):1226-1232.
Pavia et al., "Synthetic TN glycopeptide related to human glycophorin AM. High-field proton and carbon-13 nuclear magnetic resonance study." Int J Pep Protein Res (1983) 22: 539-548.
Petrova et al., "Carrier-free cellular uptake and the gene-silencing of the lipophilic siRNAs is strongly affected by the length of the linker between siRNA and lipophilic group" Nucleic Acids Research (2012) 40(5): 2330-2344; abstract p. 2333.
Pujol et al., "A Sulfur Tripod Glycoconjugate that Releases a High-Affinity Copper Chelator in Hepatocytes" Angew. Chem. Int. Ed. (2012) 51: 7445-7448.
Quesada et al., "Physiology of the pancreatic a-cell and glucagon secretion: role in glucose homeostasis and diabetes" J. Endocrinol. (2008) 199: 5-19.
Rajur et al., "Covalent Protein-Oligonucleotide Conjugates for Efficient Delivery of Antisense Molecules" Bioconjugate Chem. (1997) 8: 935-940.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vasc Biol (2006) 26: 169-175.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Rouchaud et al., "A New and Efficient Synthesis od Derivatives of Octahydro-4H-pyrrolo-[1,2-c]pyrido[1',2'-a]imidazole" Eur. J. Org. Chem. (2011) 12: 2346-2353.
Sanghvi Carbohydrate Modifications in Antisense Research; Y.S. Sanghvi and P.D. Cook, Eds., ACS Symposium Series 580; Chapters 3 and 4, 40-65.
Sanghvi et al., "Heterocyclic Base Modifications in Nucleic Acids and Their Applications in Antisense Oligonucleotides" Antisense Research and Applications, Chapter 15 (1993) pp. 273-288.
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Schwartz et al., "Tissue factor pathway inhibitor endocytosis" Trends Cardiovasc. Med. (1997) 7(7):234-239.
Seth et al., "Synthesis and biophysical characterization of R-6'-Me-α-L-LNA modified oligonucleotides." Bioorg. Med. Chem. (2011) 21(4): 1122-1125.
Seth et al., "Synthesis and Biophysical Evaluation of 2',4'-Constrained 2'O-Methoxyethyl and 2',4'-Constrained 2'O-Ethyl Nucleic Acid Analogues" J Org Chem. (2010) 75(5): 1569-1581.
Seth et al., "Design, Synthesis and Evaluation of Constrained Methoxyethyl (cMOE) and Constrained Ethyl (cEt) Nucleoside Analogs" Nucleic Acids Symposium Series (2008) 52(1): 553-554.
Shah et al., "Impact of lack of suppression of glucagon on glucose tolerance in humans" Am. J. Phsiol. Endocrinol. Metab. (1999) 277:E283-E290.
Shah et al., "Lack of suppression of glucagon contributes to postprandial hyperglycemia in subjects with type 2 diabetes mellitus." J. Clin. Endocinol. Meab. (2000) 85(11):4053-4059.
Shchepinov et al., "Oligonucleotide dendrimers: synthesis and use as polylabelled DNA probes." Nucleic Acids Research (1997) 25(22): 4447-4454.
Shchepinov et al., "Oligonucleotide dendrimers: stable nano-structures" Nucleic Acids Research (1999) 27(15): 3035-3041.
Sindelka et al., "Association of obesity, diabetes, serum lipids and blood pressure regulates insulin action" Physiol. Res. (2002) 51(1):85-91.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Tober et al., "Self-Metathesis of Polyol Allyl Ethers towards Carbohydrate-Based Oligohydroxy Derivatives" Eur. J. Org. Chem. (2013) 3: 566-577.
Tomiya et al., "Liver-targeting of primaquine-(poly-c-glutamic acid) and its degradation in rat hepatocytes" Bioorganic & Medicinal Chemistry (2013) 21: 5275-5281.
Crooke et al., "Toxicologic Properties of 2-O-Methoxyethyl Chimeric Antisense Inhibitors in Animals and Man" in Antisense a Drug Technology, Chapter 12, pp. 342-351, Crooke, S.T., ed., 2008.
Toyokuni et al., "Synthetic vaccines: I. Synthesis of multivalent Tn antigen cluster-lysyllysine conjugates" Tetrahedron Lett (1990) 31(19): 2673-2676.

(56) References Cited

OTHER PUBLICATIONS

Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Verbeure et al., "RNase H mediated cleavage of RNA by cyclohexene nucleic acid (CeNA)" Nucleic Acids Res. (2001) 29(24):4941-4947.
Verdel et al., "RNAi-mediated targeting of heterochromatin by the RITS complex" Science (2004) 303(5668):672-676.
Volpe et al., "Regulation of heterochromatic silencing and histone H3 lysine-9 methylation by RNAi" Science (2002) 297(5588):1833:1837.
Wahlestedt et al., "Potent and nontoxic antisense oligonucleotide containing locked nucleic acids" Proc. Natl. Acad. Sci. USA (2000) 97: 5633-5638.
Wang et al., "Cyclohexene nucleic acids (CeNA) form stable duplexes with RNA and induce RNase H activity" Nucleosides Nucleotides Nucleic Acids (2001) 20(4-7):785-788.
Wang et al., "A straightforward stereoselective synthesis of D- and L-5-hydroxy-4-hydroxymethyl-2-cyclohexenylguanine" J. Org. Chem. (2001) 66(25):8478-8482.
Wang et al., "Stereocontrolled synthesis of ara-type cyclohexenyl nucleosides" J. Org. Chem. (2003) 68(11):4499-4505.
Wang et al., "Cyclohexene Nucleic Acids (CeNA): Serum Stable Oligonucleotides that Activate RNase H and Increase Duplex Stability with Complementay RNA" J. Am. Chem. Soc. (2000) 122(36):8595-8602.
Weber et al., "Design and synthesis of P2-P1'-linked macrocyclic human renin inhibitors" J. Med. Chem. (1991) 34(9): 2692-2701.
Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.
Wiener et al., "Overexpression of the tyrosine phosphatase PTP1B is associated with human ovarian carcinomas" *Am. J. Obstet. Gynecol.* (1994) 170:1177-1183.
Woolf et al. "Specificity of antisense oligonucleotides in vivo" PNAS (1992) 89:7305-7309.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US15/28887 dated Oct. 28, 2015.
International Search Report for application PCT/US14/36466 dated Dec. 1, 2014.
Akinc et al., "Targeted delivery of RNAi Therapeutics with endogenous and exogenous ligand-based mechanisms," Molecular Therapy, (2010) 18: 1357-1364.
European Search report for application 14791863.5 dated Dec. 2, 2016.

SEQUENCE LISTING

<160> NUMBER OF SEQ ID NOS: 101

<210> SEQ ID NO 1
<211> LENGTH: 3318
<212> TYPE: DNA
<213> ORGANISM: Homo sapiens

<400> SEQUENCE: 1

```
gtgatgcgta gttccggctg ccggtttgaca tgaagaagca gcagcggcta gggcggcggt        60
agctgcaggg gtcgggggatt gcagcgggcc tcggggctaa gagcgcgacg cggcctagag       120
cggcagacgg cgcagtgggc cgagaaggag gcgcagcagc cgccctggcc cgtcatggag       180
atggaaaagg agttcgagca gatcgacaag tccgggagct gggcggccat ttaccaggat       240
atccgacatg aagccagtga cttcccatgt agagtggcca agcttcctaa gaacaaaaac       300
cgaaataggt acagagacgt cagtcccttt gaccatagtc ggattaaaact acatcaagaa       360 gataatgact atatcaacgc tagtttgata aaaatggaag aagcccaaag gagttacatt       420
```

```
cttacccagg gcccttttgcc taacacatgc ggtcactttt gggagatggt gtgggagcag    480
aaaagcaggg gtgtcgtcat gctcaacaga gtgatggaga aaggttcgtt aaaatgcgca    540
caatactggc cacaaaaaga agaaaaagag atgatctttg aagacacaaa tttgaaatta    600
acattgatct ctgaagatat caagtcatat tatacagtgc gacagctaga attggaaaac    660
cttacaaccc aagaaactcg agagatctta catttccact ataccacatg gcctgacttt    720
ggagtccctg aatcaccagc ctcattcttg aactttcttt tcaaagtccg agagtcaggg    780
tcactcagcc cggagcacgg gcccgttgtg gtgcactgca gtgcaggcat cggcaggtct    840
ggaaccttct gtctggctga tacctgcctc ttgctgatgg acaagaggaa agacccttct    900
tccgttgata tcaagaaagt gctgttagaa atgaggaagt ttcggatggg gctgatccag    960
acagccgacc agctgcgctt ctcctacctg gctgtgatcg aaggtgccaa attcatcatg   1020
ggggactctt ccgtgcagga tcagtggaag gagctttccc acgaggacct ggagccccca   1080
cccgagcata tccccccacc tccccggcca cccaaacgaa tcctggagcc acacaatggg   1140
aaatgcaggg agttcttccc aaatcaccag tgggtgaagg aagagaccca ggaggataaa   1200
gactgcccca tcaaggaaga aaaaggaagc cccttaaatg ccgcaccta cggcatcgaa    1260 agcatgagtc aagacactga agttagaagt cgggtcgtgg ggggaagtct tcgaggtgcc   1320
caggctgcct ccccagccaa aggggagccg tcactgcccg agaaggacga ggaccatgca   1380
ctgagttact ggaagccctt cctggtcaac atgtgcgtgg ctacggtcct cacggccggc   1440
gcttacctct gctacaggtt cctgttcaac agcaacacat agcctgaccc tcctccactc   1500
cacctccacc cactgtccgc ctctgcccgc agagcccacg cccgactagc aggcatgccg   1560
cggtaggtaa gggccgccgg accgcgtaga gagccgggcc ccggacggac gttggttctg   1620
cactaaaacc catcttcccc ggatgtgtgt ctcacccctc atccttttac ttttttgcccc   1680 ttccactttg agtaccaaat ccacaagcca tttttttgagg agagtgaaag agagtaccat   1740
gctggcggcg cagagggaag gggcctacac ccgtcttggg gctcgcccca cccagggctc   1800
cctcctggag catcccaggc gggcggcacg ccaacagccc cccccttgaa tctgcaggga   1860
gcaactctcc actccatatt tatttaaaca attttttccc caaaggcatc catagtgcac   1920
tagcattttc ttgaaccaat aatgtattaa aattttttga tgtcagcctt gcatcaaggg   1980
ctttatcaaa aagtacaata ataaatcctc aggtagtact gggaatggaa ggctttgcca   2040
tgggcctgct gcgtcagacc agtactggga aggaggacgg ttgtaagcag ttgttattta   2100
gtgatattgt gggtaacgtg agaagataga acaatgctat aatatataat gaacacgtgg   2160
gtatttaata agaaacatga tgtgagatta ctttgtcccg cttattctcc tccctgttat   2220
ctgctagatc tagttctcaa tcactgctcc cccgtgtgta ttagaatgca tgtaaggtct   2280
tcttgtgtcc tgatgaaaaa tatgtgcttg aaatgagaaa ctttgatctc tgcttactaa   2340
tgtgccccat gtccaagtcc aacctgcctg tgcatgacct gatcattaca tggctgtggt   2400
tcctaagcct gttgctgaag tcattgtcgc tcagcaatag ggtgcagttt tccaggaata   2460
ggcatttgcc taattcctgg catgacactc tagtgacttc ctggtgaggc ccagcctgtc   2520
ctggtacagc agggtcttgc tgtaaactcag acattccaag ggtatgggaa gccatattca   2580
cacctcacgc tctggacatg atttagggaa gcagggacac ccccgcccc ccacctttgg    2640 gatcagcctc cgccattcca agtcaacact cttcttgagc agaccgtgat ttggaagaga   2700
ggcacctgct ggaaaccaca cttcttgaaa cagcctgggt gacggtcctt taggcagcct   2760
```

| | |
|---|---|
| gccgccgtct ctgtcccggt tcaccttgcc gagagaggcg cgtctgcccc accctcaaac | 2820 |
| cctgtgggc ctgatggtgc tcacgactct tcctgcaaag ggaactgaag acctccacat | 2880 |
| taagtggctt tttaacatga aaaacacggc agctgtagct cccgagctac tctcttgcca | 2940 |
| gcattttcac attttgcctt tctcgtggta gaagccagta cagagaaatt ctgtggtggg | 3000 |
| aacattcgag gtgtcaccct gcagagctat ggtgaggtgt ggataaggct taggtgccag | 3060 |
| gctgtaagca ttctgagctg ggcttgttgt ttttaagtcc tgtatatgta tgtagtagtt | 3120 |
| tgggtgtgta tatatagtag catttcaaaa tggacgtact ggtttaacct cctatccttg | 3180 |
| gagagcagct ggctctccac cttgttacac attatgttag agaggtagcg agctgctctg | 3240 |
| ctatatgcct taagccaata tttactcatc aggtcattat ttttacaat ggccatggaa | 3300 |
| taaaccattt ttacaaaa | 3318 |

<210> SEQ ID NO 2
<211> LENGTH: 78001
<212> TYPE: DNA
<213> ORGANISM: Homo sapiens

<400> SEQUENCE: 2

| | |
|---|---|
| cagattccgg gtctcatccc tagaccaaag atatctgaat catttggcga tgggtccagg | 60 |
| aacctgcatt attcaacaca cttcccaggt gaccgtaaat gtcaaaagac aaaattacaa | 120 |
| caaacttaaa catcttaatt ggcttcattc atgattctag aatcgggcaa gacttcattc | 180 |
| ctcaaaatag cacaagtgtc ccaatgagct gagcagagga ggttggtttt atagacagaa | 240 |
| aagggctgaa aaagcagaa acaagaacaa aaagcagat tggtcatttc aaagttactt | 300 |
| tccttgtaag gcaggaacag ggaaacagaa caagagagaa ataactgatt ggtcgcatcg | 360 |
| ggttacttca ggttactttt tgttgtaagg attaaagcaa agggaacttc attatgttga | 420 |
| ttaaaacggt ctgcttggga aatcaggtg tgtatctctc ttctgatttt gtgaaaggtt | 480 |
| atcagtctga tgatgtagaa ctttagcatg agtgactcca ttttgatttt tagtctagtc | 540 |
| tgttgagacc ctaatgccag aactttttttt gtttgtttgt ttcgctcttg ttgcccaggc | 600 |
| tggagtgcag tggagctatc ttggctcact gcaacctctg cctccagggt tcaagcgatt | 660 |
| ctcctgcctc agcctcccaa gtagctggga ttacaggcat gcgccaccac gcccggctaa | 720 |
| tttttttttt tttttttttt tttagcagaa accgagtttc accatgttgg tcaggctggt | 780 |
| ctcggactct tgacctcagg tgatccacct gcgtcggtct cccaaagtgc tgggattaca | 840 |
| ggtgtgagcc accacaccca gcccttttt ttcaagacag ggtctctctc tgccacccaa | 900 |
| ggtggagtgc agtggcgcca aaacagctca ctgcagcttc cacctcctgg gctcaggtga | 960 |
| tcttcctgcc tcagcctccc cagcagctgg gccccaccac accggctaat ttttaactt | 1020 |
| ttagtagtga cgaggtctga ttctgttacc caggctggtc tggaactcct ggcctcaaga | 1080 |
| catccgcctg cctctgcctc ccaaagtgct gggattacag atgtaagcca ccgcgcctgg | 1140 |
| gctcctatga ttttatta acataatgca ccatggaatt tgtgctctgc ttagttcagt | 1200 |
| ctgagcagga gttccttgat acttcgggaa acactgaaaa tcattccatc cccatccatt | 1260 |
| cattcctgca gcacccaagt ggaaattctg cgtttcagac agggacacta cccttagaga | 1320 |
| gcagtgggct tccccagcag cgtagtgaaa catgatactc ctgagtttca tgaaaaaagg | 1380 |
| gcagacatct ggccagagct gggaggcagg aaatagagca cggtgccctc ctcccatact | 1440 |
| ccagcttgga ttactgaggc tggggcccag gccctgcagg aaaggaggtg catgactact | 1500 |
| ttaaggccac tcactctgtg actcaacggg ccgggtcggg gctggaactc aatgcccctcc | 1560 |

```
cgggcctgga gagcccacgc gccgtgggcg gggctcccgg ggtcgcctag gcaacaggcg    1620
cgcgccgcgc ccgagcccag agccccaaag cggaggaggg aacgcgcgct attagatatc    1680
tcgcggtgct ggggccactt cccctagcac cgcccccggc tcctcccgc ggaagtgctt     1740
gtcgaaattc tcgatcgctg attggtcctt ctgcttcagg ggcggagccc ctggcaggcg    1800
tgatgcgtag ttccggctgc cggttgacat gaagaagcag cagcggctag ggcggcggta    1860
gctgcagggg tcggggattg cagcgggcct cggggctaag agcgcgacgc ggcctagagc    1920
ggcagacggc gcagtgggcc gagaaggagg cgcagcagcc gccctggccc gtcatggaga    1980
tggaaaagga gttcgagcag atcgacaagt ccgggagctg ggcggccatt taccaggtgc    2040
gggagcgccc cggagcgtgg cgggcccttc gcttaggccg cttgaacatc ccctcagacc    2100
tccaggcccc agactccctc tgggtcttgc cctctgcctc gctcctactg cttgaggatt    2160
cgatgggaca gcgacgcact gcgtccccc acccttgtc cccggggcgg gcgtgtttct      2220
cgccgcagcg tcggagcccc cttcgatccc ccacctccct tctgttctcc agctcgggtg    2280
atctctcaag ccgggggacc gccggtctgt gctctcaacg cgaatccctc gcaccccgac    2340
cccgccccct gcctgtccac tctttgtccc ctggggtgat ttagcacccc cactatttcc    2400
ttttctggag tggaccacct cagactctct tcctttgtct ccctggggga aaaggttact    2460
cccccgtcc ctccttcaca tttcctttcc cctagtctca gtgtgcgtcg agtcccagag     2520
atgacagtcc cctttcccct ttctgttcat tcatttattg gataggagtt ggcaagctta    2580
ttctgtgcta ggcaccgctt aggcattgga ggtggtgttt gctaatcagg acaggcaaga    2640
tcctagcctt agtggggcct agagtcgaat agggcaatca aacacaaaag caaataattt    2700
cagatagtga caggtgctgt gaagagaacg acttcctaac ggggtacagg gtgactgcat    2760
agaaggccgg ctgtcttaga aagggggatc agggaaggcc tgtcaaagga ggagacattt    2820
gctttgtgag ctgaaccaag aggagcagaa agccgtgaga atatgggct aaagaacctt     2880
ctagccagga ggcctgcggt acccactcca ttggggccat gatattattc tttcaggcag    2940
ggactcagga aggttaacgt tttaaccctc tctaaaatag catctttcct caatgagcag    3000
cttagtcttt ggtcgtggca gagatgacct tgtcttagga gtcatctcct tgtgtgttaa    3060
aaagttagga aaggagggtt tctcatatat ctataaaaca agtagttaaa aacacaaaga    3120
gctcttcctt tcacaagcag ctgaataaga tacatactcc caattaaatg tcattgcggg    3180
ggttgttaag attaactaaa accacacttg cacagtatct taaataagcg atatacagaa    3240
tagagagatt ttgttacttg tgtaaaggga gacagcagat gattctgttt tcagcttata    3300
ggctcaaaag gcaaattgtg agatccatca gctgtagtat taaaatctat tttgagctcc    3360
gcttagaaag gaaaaaggt ttaagcagtt cttgggtatg cttgactaac aaaagccttt     3420
tttttttggca gccttgattt tcatgtggat ttacatcaag cttatttgac aggattcttt   3480
ttatttggac tgtagtgtgt atattagttt ctgctagact aatatttcta accactgtaa    3540
tctatatact aataagtatg attgatcagt atataaaatt tgtatgccat atctggtctc    3600
tgaattagct gaatgaattc cataagggac tttgagactg tgtagacaaa ttttctgcat    3660
cagtttaatg cagtagagtc taaaatgtct ttaaatgaaa attgttggtc tgaagtgttg    3720
gagttgatta tgatacaccc catcacagtg gaagcattgt ggagagaagt cttttccact    3780
gaaattgact gagttgacaa caagaaatac gtattgtaac ttagttctta gttgaatttt    3840
atttcttaca attttaagcc agagtggggtt gacctgtcac ccaagcatgg ttaaaattgt    3900
```

```
attcagcatg caactagcat ggagtgtgtc agtcttcaat tcatttcctt cattgttctt    3960 aagttttct gccacaatta aaccccacaa gttagtcaag gtgttgagat tttcactgct     4020
tcttaatgga ttgccacatt ccctgaggta gtttcttttg gtcttagaga attgtcaggg    4080
ccagcttttc tcacctccac tgtatggata ttttcttt   ctaagatctt gaaatcagaa    4140
gcttttctcc taagtgtaaa agtagctctt tgtcatacaa ctgtagcgtt ttctgaaaca    4200
gagttcagat gaccttgagt ctaaagtggc taacttcca  aggtgtgtat cgctttacca    4260
aaaccattat ttttcaagga ttcaaagaat gtgtttacaa ttgatagaaa atggaagttt    4320
aaaaaaatta atactttata gcatgttgaa atgagggcag ccttatacaa agtcatactt    4380
tgagcttgcc tagcctattg tgatcagaga ataatgtaat ttttgcttac aacttggtaa    4440
gcaggtcagt tattctaact tattttctga ttagaacaaa aagatgtaaa aacttgaaaa    4500
ctattgggaa aagaacaaag agtgaagagg acttttgagt gctgaggaat gtggcagctt    4560
ggaaaacaaa cttttaggc agagattctt tgctaggtca gtttgataaa gtgagcataa    4620 ccgtatttt  aatctttaat gctaatgaat agcatagatg ctaataagca tctaggtcta    4680 taaaagtca gctttgatag tgtatataga tggctttaaa cattgttttc tagcatttaa     4740
acactttcaa atcatccggt tgcttgattg ggcctagctg tctaagagga gagaatgagc    4800
ccagatgagg aaaagagatt gattttactg agctagaatg agaggagaga gggttgagtg    4860
aatgaaaaga atagctcatg tgctcccctc catctgtagt ttaagagggg ttgggtccgg    4920
tgttttgctt gttttctcgt ctgtaaattc tttgattctc tgacaccact cactatattt    4980
cattgtgaat gatttgattg tttcagataa aggggactgc aataataacct tgtgacatga   5040 aggcaagatt tattcatgtt agaggcaggc tttgtaaaat gggccactct tccaattgac    5100
atttgttttt atagctgttt tcattatgaa atacaatcta atgcctgact aggttaaaac    5160
catgttgtaa caatagttca ctaaaattcc ttactgatat acagcttatg ttgttatatt    5220
ccaaaaagat gaatattaaa atttgccaat aatgtttatt taaatactat tttcttcaga    5280
ggaaaaaaaa ctattttatg caaggagaa agatctatac actatgactc acttcactta    5340
aaaaaaaaaa gactaacgga aatgacatgg agagactggg aagttctagt catcttgagt    5400
gacccattag atctaaatgt tcttgtttag ccctggtttg agtgaactaa atttaggtgt    5460
ctgatcagta ctttggaaat ggtgtaaatg cctttgtaat tgtctggact gatattagat    5520
taactgggag cacaagtaga aatagtgaag gaaagaactt tttgctattg ttatttgaca    5580
tcactggcat atttatagga atactttggt gtttttggaa gtaagtaaac caaccagtgg    5640
ttctaaaaag tcagctgggg gataatggta atgccgctgt tcttagctg  caagttatct    5700 gccgttactt ctcctccatt ttgcatttta tcttgaatag ctcctcaaaa cctattaaaa    5760
tacctggtat tgaataatgt aattgaatgt gtactgaatt tcacagtgga aatgaataag    5820
aaatttcctg tggaggtttt ttgacttagc tactgaaata acggccttt  gttgtgtgat    5880 tctttccctt ttctctttgt taaagaaaac tgtcttgtga tcttgtagat tacagaatcc    5940 tttggcaat ttctgttcct agcactgctt tttctttctt tcttctttt  aaatagaaat     6000 ggggttttgc tgtgttgccc aggttggtct tgaactcctg gcttcaagcg atcctcccac    6060
cttggcctcc tgaagttggg attgcaggcg tgagcaggta cttttctga ggcctgcctg     6120 agcctatata tattttgcac aatttggcat tcctccctac agtgtttatg ctgatttgtt    6180
tctggtaaca actaatactg gcaaatcggc tgggcatgtt actttatgct gcccatattc    6240
aggaaaattg gaattctagc tgggtcattg ttcccagatg atgtagtttg gcaccagcca    6300
```

```
ttccatgttc acattttgag tatccaggag ggctggggac tttggagtag ttggtgattc    6360
cctctgccac atttcactgg ttggtcacta tggcatcctt tccaccacac tagtagtcta    6420
ggttctcaga tgttgcttat gagcctgcaa tggtttctag tttcacactg cagaaatgag    6480
tgaagccggt tacccgttaa tatggtccca tcatcactag agtaattcat tgttctaaaa    6540
ccagatctga gtctctcact cctctgcaac tacttctgat tctttcataa cacttgtaaa    6600
gtccaaactc ctctttagca tggcagccag cttccagtcc ttccctccta tgtggcttcc    6660
attctagcca gacaagaaag ggcagcgttc tccaaactca tcctcgccct tcattcctct    6720
ataccattgc tgagcacttt gttgaggatg cctctcccgt tcaatctagc ttgcatcttc    6780
cagctcgaat gtgtgcttcc ttgcaccaga gttttgttcc gtcacctgtg tgttttcata    6840
caagctggca catatctctt ctaaagccct gctgtcattg tagctgcgtc tttacaaaca    6900
tttttttttt aaattttttat aaagtcaagg tctcactata ttgcccaggc tggtctcaaa    6960
ctcctgggct caagtgatcc tcctgccttg gcctcccaga gtgctgggat tataggtatg    7020
agacactgtg cccagctgta gctgctactt tatatcccag gtctatctcc aatggagccc    7080
aagcttcctg aggccacctg ttgtatcttt ctcattcatc ttgaagtcct ctgctcctgg    7140
cacagagtag gtacctaaca agagttggga ttgaattgat ggtcagtact ttgctagcct    7200
gatggtataa agatgtacaa aacatgttcc tggctcccac tctagggggg caatgatgga    7260
aacaaataga ttagcccaca ttagtaccaa tagtagaggt cactctggga gaaggccccc    7320
accacatttt gagtcatggc ctaatgaggt aatttagtat tgcctgctgc agtggctttg    7380
gaagaaaggc tggcattctt agccagtaga agctgatacc actgatttgt ttcacagaag    7440 cttttaaatat aacaataaat ttgtgcttgg cctacggtga actttacagg caacttggag    7500
gtaatatgtt tgtctctcta agaattgttg aattcctctt ccctcatccc tcctgactgg    7560
ttctcacaag cctagcgggc cttttgcatgt ggttggttca taaaatactt tttgattttg    7620
ggatataaaa tatagttctc cataaaataa cgactgttac caagtctttg atttttttt    7680 tcaaactata aatggtaatg acattctttg gcctttgatc agaccaccct taggggcaag    7740
agagtagttt catgttttgc tttttctagt gtccctgtg tctgggtata gttgcagtct    7800
cagctgtcat actaacagtg ctgagtgagt cccttacttt cttgggttt tggtttctcc    7860 cttgtaaaaa tgatcctgga ctaactgatc attaagttca ggtcaagtaa taaaaatcct    7920
taatgtactc acaaatacaa tttaatgttc ctgaataatc cttgtaaaaa ctgcagcagt    7980
tactcagttt tgtaaggtgt ggttgggtac tattaggctc aaaagtttat aggagctttg    8040
tgagtatagt taacaactca aaagaatggg gtgttttttc ccgaggggca tgaaatgttt    8100
ttgataaata gagttcattt gacttggtaa tgtggaaaat gagtagccct gacacgtacg    8160
ctatgctttt gcagttttc tctcaagtag caattgggtg gcttttcctg taaaagatag    8220
aggaactgat tcttgagaat ttacgaaagc ttcaaccta actaggtatg caagaaatag    8280 ttgccccttta tgttgtaatt ttaggaagaa acctacatct ggtctaagtt tcatttgaat    8340
aatatgatag tttacacatc tgccatattt gagaagaaag tacctaagtc tccagcattt    8400
tagaaataat gctttacttt gtgtagaaat ggtcttttaga gtttaatagc tgctgccctc    8460
tcctttttca aagcagcttg acataatcat gagtatcttg ctgacagctt gtaaattttg    8520
attgtatgaa aactgaaaat aagaccattt cacatggaag attccctcct gccctgaaac    8580
agccaaagaa aactgtagcc atcaaatcta ttgatctctg ggctttggta caagtcacac    8640
```

```
tactacaaat aaaataatac caagtactta taaatgattt tcagtccttt taaagtttat    8700
ttttttaata ttttttttga gatggggtct tgctgtgtcg tccaggctgg agtgcagtgg    8760
cacaatcttg gctcactgca acctccacct cctgggctca agtgatcctc ccacctcagg    8820
ctcccaagta gctgagacta caggcatgtg ccatcacgcc cagctaattt ttgtattttt    8880
ttggagtaga gatgggattt tgctgtgttg cccaggctgg tcttgaactc ctgggcttaa    8940
gccatctgtc tgcctcaggc tcccaaagtg ttgggattac aggtgtgagc cactgtgccc    9000
ggcccagccc tttttttaag agaaaaacgt atgacatcgt tcgatttact gagtgcttat    9060
ggttttacta aggcagtaag gttttatgga taccctatgg taattagata gaattagtgc    9120
tctgaagtca gctctgtaat atggactcag agtaaacatg gcaaagggac acttaaggtc    9180
tgcattttct ctgggaaata aacgtattct ttactactct gaatctagtg ctgggaaatt    9240
ctaaatcctt cttgaggatt aaccacttga agtaaagttt gggtcccaa gtaggcttgt    9300
gtccctgtct ccttctcttt acttttcaga tgtttcttcc tagagactga ggtatatttt    9360
acttttacag atgaagaagg aagcctcggc tgtgtttgtg gcttttgtgg gtgagcaaca    9420
tcacttgcaa agataagatg agcatagcaa aactaggctt tcaaaataat ttttaaaaat    9480
ttcttagtga ttagaaaagg aaaactcttc ccttgtctct gttaagaaac gttttccgac    9540
tttttccctt tcttaatgga tcttttattg gcacttctct tccttttgca gaatcttact    9600
taaaagtcac tacgttacat tacagcaaac agcttagcta atttttatcc agatgggccc    9660
cggttacagg attgtacact attgcgaatt tcttacagga agtgaacat caagtaatta    9720
ttccaaatag agttctctta agaacgtgag ttacttaaaa atgtctaagg atgaagtcac    9780
ttctgaatat aacttcactc aagagaacaa ataagcaaac tgcatttagc ataacatggt    9840
aaattagctt taactctcct tgatgtttga acatttgtcg ctgttaacta ctgtttcact    9900
tttcaaatag tcagggctta gtttgcttct gtaaggataa agggaaaata cgccttcact    9960
gagtcataaa tattttgtg gctaactttt gcacagagaa aagaggcctc taagaaggta   10020
cccagtgaat ttttttttcg gggcagggag agaatatgtc atttttggt ttgttgttgt   10080
tgttgtcatt gttttgcttt gttgttttta ctctgaactg aactgtatct tgacagcact   10140
tttgaattaa gagcattact cttattgttc tctactacct ggacgccacc tccctgttgc   10200
catagtgtta aggatcatgc tccgaggtgg ggtgaggcag aatggggcca agatcagaaa   10260
gttacattaa gctacatcag gtttatacaa gcataaaacc aaattttgg agcagtcccc   10320
agaatacaac ctggtttagc cacacctaaa ggttgctctt gaatattcct tgagaatcca   10380
catccctaga atgctgggtt tcaatgggcc ctttatgtac ctatcatggt gtcatttctg   10440
agcatttcta atattccttt catgtcttac tgacagtttt tcttgaataa atcttaggaa   10500
tattagtgcc attatcagta ttttgtttgg tctgttcaca ccacaaataa ctacccaggt   10560
ctgctacttg cccctatttc tctacctgct aatgaaaatg cttttgaaag tttgagtaac   10620
agtattggag tgtgcacagt ggtattggta ggttctgtac tcatccttaa ccacttgttt   10680
tcatcctttg tgagcttgaa gtttctccaa aaaatttatc acaaaactta tcagacatag   10740
ttaatacact cagagagaga atcactgaaa agtagatgt agtttaacaa acccagtgcc   10800
tttttttttac ccatgaatac atatttgtca actaaacctc attttgcaac ttgttccact   10860
actcgaatgg taacaaactt ttggtttccc aatagatttg gaagatgttg cttttgaaag   10920
taggaaaatag atggctttag aagatggaag aatattttgt ttgaagtggg agcgtggtat   10980
gtccttagct gtctgtgaaa tgcagctgaa gatgggtgtg ggccttcatc tgcatttccc   11040
```

```
atcttcagtt tgaggaggta gttacccttc taaccactta agaactgcat ggtacatgct    11100
gttttattta cagggcaaaa ctgtgctccc gtagtttccc tggtgcttgc cttcacgtta    11160
acacagtgtc atcgtttggc agtgtttatg tgccagggtc catgttagaa ggaggaaagg    11220
tatagcgaag ttaaagggtg cagttggcct cccacccttta gttttgtaag tgcctttaaa   11280
gtttgatttt tgtaggttga tcataaggaa gtgataagta tgttaggtta tttgtggttt    11340
gagctaattt tagtctcttt ttacagcttg ctttgtatcc tttgccatta aaacatgctt    11400
tctagaaaga caacttttga atgtaggaca cagtctatat tctatacttg gctacatttc    11460
aaaaaatatt ttctcagtac tttgaagtt ggacagttgg aagcatagtg acagtattta     11520
aaaatctttg attccggccg ggcatggtgg ctcacgcctg taatcccagc actttgggag    11580
gccgaggtgg gtggatcact tgaggtccgg agttcaggac cagcctgacc aacatggtga    11640
aaccctgtct ctactaaaaa tacaaaatta gccgagcgtg gtggtacatg cctgtaatcc    11700
cagctactca ggaggctgag gcaggagaat cgcttgaatc tgggaggcgg aggttgcatt    11760
gagccgagat cataccattg cactacagcc tgggggacaa gagtgaaact ctgtctcaaa    11820
aaaaaaaaaa aaattaagtg atttctttgc tttgtgacac ttctactttt ccagcaagta    11880
aattatattc tttcatacag gtatgaaatt cttgttccaa gctagtggtt aaaaaggcac    11940
agttgatatt agaggatttg taaaagatta tgaccacgcc tgcaatgtac tgaagcaagg    12000
ctttgctggg ctgtgtatag gaaaccttcc ccagcctgtg cccttgcttg atagaacatt    12060
ttgctcctaa gggtaggtgc ctgtatctgt ctccagtact ggttagtttc acacagaaca    12120
gttgtgtttc agagctttag tctcaagctg ccctgctccc ctgaagcagc caccctgagc    12180
atgtgcactc acaggagggg acatgtgagg tcatggaaga agacgactca ggaagaagaa    12240
gacttgggtt tgggttctga ctctgccttt gactgttgtg ggattttgag gagttgcata    12300
caggatctgt aaaatgtagt cattagacta gactagacag ccatatagca ttacctagat    12360
gtaactttct acaaagacat ggtcacagga gaagaccaga gggtggggtg atctttctgg    12420
aaaaattggg gcttcatgcc ttactcatgc tagatatggt agcattatat ggctgtgcct    12480
gatccccta atctaaaagt gggacagaac tttaaaattt catattaact caaattaaaa     12540
cttgaaaaaa acccattatt tccttaaaaa taataaaatg ccctgtgggg gcataagtca    12600
cattatattt taaaattcct gaatgccaca tggatgaatg tagttccttt tgaaattctt    12660
cttttgtcta agaggaatg ttggattttg taattggact aaaaaatctt ccatttgaga     12720
gagaaacagt ctgctgcatg ttctacccct gttcaggata aaacccacta atagctaaca    12780
tttattgaat tctgtgttgt gcctcaggca ctgtgcaaag tcctttacat gcaatgctgt    12840
ttattatata ctgtcaattg gtctataaca gcaggaaatg tttcaggagg acaatgaggt    12900
cccagaccct cagtcttctc ctgtgtcctg gattcagctt cacaatagca ctatggcagt    12960
gtggccactg cttcagcttc cacatacatg gctgtgaaga gagacagggg attgtgctaa    13020
gcctccccga tttattagga cataggagga gagagtttgt agttttgac ctttgcctag     13080
ttttctaacc tctttcctag atgtcacaaa ttggccaccc acagtcatat tttgcttgct    13140
tcacgcaatg ctttttaaaa aagagaagag tttaatttgt gccattgttt ataaatgaat    13200
caggagaaat gacatgcaac tctggattct ggcctctctt gaaaaatctg aaaatcacac    13260
cgtctgagct tacactggca gtggtctgct ggactgaggg acacaactcc ttttggatgt    13320
acatgtgtgc gttgcagagt ttaccacagt cccacagtgg gtcacactgt ccttgtcggt    13380
```

```
gtacactacc tagcacttga gtttgcaacc cctaccccaa gctgagtttt ctcgtcaagc   13440
ttgatgttaa tgttatgtga tgcttggcct tgtaggtatt tggtatatta tcgttagata   13500
aaattgaagc aaagggctaa agggttggtg gcctgaggga gtgcccttga cagtaaagtc   13560
taggataaaa tcattggcca ggtactcctt cccttcccgc ccttcctctt ttctctttat   13620
cctcagcctc cttctgctat tttgaggaag ttagaagcca ccaccatttt ttcccacctc   13680
aggcaactga gtgtggctgt atttctgtcc catgttcagt tatttccagg aactattttt   13740
gatgaccaac ttgaagttac attgggtggg cctaatgggg gctgataaaa gaatgaggtg   13800
accaaatatg cttgcactga gacggctacg aagtaaggtt tttaatgact tgctttgtga   13860
cttggtcagg agtgatacca tttgtcatgt gtccaacttc atgactaaat ggttgctcta   13920
ccttatcctc atagctataa taaaataaaa taaatacata cattgcaggg aggaatgtat   13980
cttgttaaag gtctctccct tttagcaaca aaagtacata ttatgttgta aacatgcttt   14040 tttcttttgat ccttcttgaa cacctattac tctatagagg tatgttgtgt atggcaaatt   14100
agaacaagca atagataagg atgattcttt accattataa cccagtcaag gtctttgtcc   14160
taagttttgt acctttctcc agagggaaag gtatttgtat ttatttattt attttttgagg   14220 cagagttttg ctcttgttgc ccaggctggg gtgcaatggc acgatctcag ctcactgtaa   14280
catccgcctc ccgagttcaa gtgattctcc tgcctcagcc tcccgagtag ctgggattac   14340
aggtgcctgc cacgatgccc ggctaatttt ttttttttt tttgtatttt tagtagagat   14400
ggggtttcat catgttggcc aggctggtct tgaactcctg acctcaggtg atccatccac   14460
ctcggcctcc caaagtgttg ggattacagg catcagccac tgcctccggc caggtatttg   14520
tatttttagt ctctatgcct taccgtctca gatcaggagg atttggtgat ttatcgaatg   14580
tgggggaagg ggaagaagag gaaacgggag gaatgttcca gattagggaa atagctagat   14640
ggaagatgca gcccctcatc aaggtgggga cacaggaaaa ggaacgtgtg caaagaagat   14700
ggtgatctgg ttgtgaccat gttgttagag gacgtccagg gaagcatctg gtaggtggtg   14760
gggtgtttaa atatagaaca ttcggagaat gctccgaagc ttcagagaac ccttcccaaa   14820
aggacaaaac cagctcagtg ttttagcact ccgggatcat atggcatgac agcatggctg   14880
ctttatactt ttttgtgtat gtgaaattaa aaccaaccac tcaggaccaa tttctctgaa   14940 gcttttgtc aatcttttcat ttgcttttct cgtctagatt gtaagctcct tgcagccagt   15000
gtctgttgat tcagtcattc aaaaaataat acatgaacag ctactaggta ccaggctctg   15060
tgctgggcag ttgggatatg tggtgaggaa gacaaacttg gtccctgccc ttaggaagtt   15120
cagtagtcca gcagacaaag tggctgaata aagataatct cagttcacag tgataagagc   15180
tcttacaggc ctaggctcca ggtgctgtgg ggatgctcag gaaaaggtat ctaattggga   15240 tgggagcag gcaaaacaaa taaggatag tgtataaagg taatatctag ttgaagttct   15300
gaagggcaag gaggagtgag cctgtatatt tctctgagtct ctccctaatc tgggattgac   15360
ttcttgtccg tctctgttca tattaagtgt cacctaggct tgaaagggtg agatcatatt   15420
tcacttcctt cctctttggt cttaaccttt ctctgctacc ccctcacaca atgcatatgc   15480
attattctct tattgtatat attttttcctc tcttcctttt catgtttcct ctgccattac   15540
ttttaacctc gactgccata tggcctctaa acgcttccag aagggtagcc tagtggaggt   15600
tattccatca tggccttgag ctcatgcgac cagatagtga aggcatctgt gtaggtgtct   15660
tctccaggag ggtgatattt gtttcattgt aaatttgta gccctagaac accaacaaca   15720
gtgcacagta attagtaggc aggcagtaca ggattcattg aagtgaagtg ataacttta   15780
```

```
tccaagtatg tatgcagata atctttgatt tgtacaaaaa aaattatatt ttaatatgta    15840
aagattttt aaaagaatct tcaagtttta gccttcccac taggaatata ttgaaaacat    15900
gtgcctagtt cactgacttg cagctgccac tatgagaata aggtctcat ttagttgttg    15960
tgaattttaa gggatatttt caatgatgtt ggctggttta tcccattatg tggtctttt    16020
tttttttttt tttttttttt gaggtggagt ctcgctctgt cacccaggct ggagtgcagt    16080
ggcgcaatct cgactcactg caacctccgc ctcccgggtt caagcgattc tgctgtctca    16140
gcctcctaag tagctgggat tacaggcgcc tgccactacg cccagctaat ttttggtatt    16200
tttggtagag aagggtttca ccatgttggt caggctggtc tcgaactcct gacctcatga    16260
tccactcact tcagcctccc aaagtgctgg gattacaggc gtgagccacc atgcccagcc    16320
tatgtgctct tattagcaat tctcagtaca cagatagctt tgagtgattc tttcaagtca    16380
agtaccttat taaaaaactc aagtgtactg ataattatct tactttaaa tggctaagtg    16440
ataagactga atttttaggt actgtaacac ttcagattac agattctgat attttatgg    16500
ttatttatat ttatttattt ttgagatgga gttttgctct tgctgcctag gctggagtgc    16560
aatggcacga tctcggctca ctgcaacctc cgcctcccag gttcaagcga ttctcctgcc    16620
tcagcctcct gagtagctgg gattacagtc acccgccact acagccggct aatttttgtt    16680
attttttaata gagacaatgt ttcaccatgt tggccagggt ggtctcgcac ttctgacctc    16740
tggcgatccg cccgcctcgg cctcccaaag tgctgggatt acaggcgtga gccaccgcac    16800
ctggcctggt tacttaaatt taaatacaaa aattatgttg attaattctg aatgatttcc    16860
tgattgctcc ccgtttacca ttcacacatt tattaaattc ttcgcttgcc atatagaagc    16920
agtctctctg ccatatatgc catatagata acagaactag ctgtctgcaa accactgaaa    16980
ttgtgaaaac atctcccctt ttttcctgtt tctaattcta gctatgagga ttatatacag    17040
aagtagtcct ggatttgatt tttttttttt tttgatgatt gttttttgat agttgttgac    17100
tacaaatcat ttaaacgtct gaaaggggaa aggttttcct taaaaatgga tgacaaagga    17160
gaataaaaag gtattttgac tatttttttg aatgatgagt tttttttttc tctttcttgt    17220
tttcttttgg agtcatttat gtgtcactga gtggatacca tggaacatgt ggcagaagta    17280
gatatatggg gtaaaagaac catagttcat aagctccttg acagaatcac tgaagtgtag    17340
ccgttatatg gccactgtcg cagggggagg cagcagtttt gaagaagggg atgagtaata    17400
atgagtgata aaaaggcatc ctggatagaa gaccaaactc tgcagaagac cccagtttga    17460
ttatgctttt gttttctgat ttgcggagga gagtgaaaat gcctgagggg tgcggggag    17520
cacatagggt gtatgtgtgt gtgtgtgcgc gtgcagattc tctctttcac tgtatgtatt    17580
tgtatgcatg tatgtatctt aggacttaag ctttctagtc aataaattgc catagtgggg    17640
aattgcttaa ttgcttgcct tctgttgttg tatttaattt aattttattt ttaatgattt    17700
ttttggtggg gtacagggtc ttaactatgt tgtccaggct ggtcttgaac tcctaaactc    17760
aagtgatcct cccgcctcgg gctcccaaaa tgctgggatt acaggtgtga gccaccatgc    17820
ccagcttagt tgtattttaa atgggcctgt ttgcagcatt ccctactccc cttagtttac    17880
ctggctcaca acctgtcttt ccatatcaag gcttctgtca cccctggccc atgtcagtgc    17940
atttgggcag cccacccagc atcatcacct catgtcccag gaacttcct gttcctctct    18000
tccagctatt tccttccctg gcagttgaga tagtctctac ctttgaccta ctgttaagct    18060
cagaccttct gctctctagt tacagcctct gtgctgccag attccctcgc tcagttgctt    18120
```

```
tctctagttt gggttttctc ctttattcag atttccagct gtttctctcc tcccccacc   18180
gcagcctcct cacttccctc cttatgcatc tgagactgtg gtcagtcact ttagatgctg  18240
cctctccact gtacttgtgt ccatcttctt acctaccacc tctagccctg gagcaggctc  18300
ttcccctgtc tttgtcttcc tgggcccagg ctcctaagcg ctgctggaaa aaaaatcccc  18360
cagtattgag cccctagaaa tccagtcttt aatcccaaat ctgtctcccc cagcatctgg  18420
ccatcagatc taaagcttac ctgccatcct ttccacctca tttctctcac aggggaaaag  18480
gagcctttgc tcctagagtc tgcgctcctg acccttccc atctcacctg ttcaaggcat   18540
cttgcaataa ggggttggtg actctcgagg aatggatccc aggccctccc tattatcatc  18600
ttatgtatgc cagttcaacg ttctcagctt cctccagccg agacggcccc tccagccact  18660
gctttatact ctccttctct ggttgaaatt tttgaagtaa ataggtcact ctgcccatcg  18720
ttcatcttcc agtcactctg tgtgtttatc ttccagggaa gtgaggctct atgctaccaa  18780
gccactgaaa taattttttt tttttttccag actgagtctt gctctgtcac ccaggctgga  18840
gtgcagtgcc gcagtcttgg ctcactgcaa cctctgcctc ccggcttcag gcgattctcc  18900
tgccccagcc tcctgagtag ctgggattac aggtgcctgt catcacgcct ggctaatttt  18960
ttgtattttt ggtagagatg gggcttcacc atgttggcca ggcttgttgg catgttgacc  19020
atgttggcca ggctagcctc aagtgatcca cccgtcagcc tcccaaagtg ctgagattac  19080
aggtgtgagc caccgcacct ggcctgaaat aattcttgac aagatctgct tccttgttac  19140
taatacagtg gatattttgc atcctaattt taatgcagtt cagtgtggta gacctgtatt  19200
tgcatattga atattccctt ccctgtttta ataactctat ttttttcctt tcttttatat   19260
ctcctgcttc tctagctagt cctagacctt actcatcggt gtcttctctg tttgttcctc  19320
aacttgagga gttcctacag ggtttaccca atctgctgct ttcatttagc ccttttgttc  19380
tttttgagcc atctcattca ctcacccagg atgtagcatc ggcccttgaa ttcagtgtgc  19440
acacatacac tgtgcactat gggacagcct tcagaggcac tttgttcctg aaattgtggt  19500
ggtctttgcc tctcatggag ccttgcatat gctgtttcct ctgcctggaa tatcctacct  19560
tttacttaac tgattctcgt tcttctttcc agtcacatttt tgtacatttc ttctgggaag  19620
cttttctctga tttcccctttt ccacaggtcc aagttaactg ccttgtctag gtcctcccat  19680
ggccctctga aggcctcctt tcatagcacc atgtctgagt atactgtaat aacacgcatt  19740
gctctgtaat agcctgttta cttacctatt gccaagtaat ctatcaagtc ttataaaggg  19800
cggggctgct tttgttctag tcatttgtat ctcttagtac ccaatatagt gtttggcata  19860
tagaaaatac ccaacaaggc cagtcgcagt ggctcatacc tgtaatccga gcactttggt  19920
aggctgaggt gggcggatca cttgaggtca ggagtttgag accagcctgg ccaacatggt  19980
gaaaccctgt ctctactaaa aatacaaaaa ttagccaggc gtggtggcgg gtgcctgtag  20040
tcccagctac ttgggaggct gaggcaggag aatcacttga actggggagg tggaggttgc  20100
agtgagctga gatcactcca ctgcactcca gcctgggtga cagagtgaga ctccatctta  20160
aaaaaaaaaa agactccatc ttaaaaaaaa aaaaaagaa aaagaaaga aatacccaa    20220
taagtagttc ctgaatgaat agatgagaat gctgtttaga aggttcatga attggaaacc  20280
gtgattgcta gggaggcttt gagttgatgg tattgtgttg aaccatgtgt tacccaggat  20340
caatttagat tttacacttt gttttctctg ttccttttta tagtaatttt ctgtatgtgg  20400
tgttttcccc ccatgagatt gtataccatt tctcagcgag aactgtgtgt aatgcttggt  20460
ggctccctca tggtgccttg catggaattg gacttcgttt cagtggatct gatcccagtt  20520
```

```
atgttaatgc tcgatggagc taagtcttat ctcgaagcag tccatgtctt catcagctgg   20580
ccctgcctcc atgccctgca cagaccatgc cactctggag aggtagtttc cctgtggctt   20640
attagtctta tgttccagtg tgctggccaa gtatgagaga catcagtggt atgagagagt   20700
ctctctcatt caaacttcgt aggttttgta gctgggactg accagtgctg acaggaaata   20760
gaggcattta ttaaaagcca gagattttc aagttgcagg aagcaaagct cttgttagct   20820
atgattttgt ggtgggtttg gtagtccaat ataaaagtaa aaactggatg acaatgggag   20880
gagcatgctt gggtctccaa agttagatca ttttcctaa gtaatttgtc tttaaacttt   20940
tactggtttg gaatttcctg agattttgat cttgccagaa agtttatagc aaaagttctg   21000
agcagatgac acttttgcgt ctgaaaccaa atcattgttt ttgttttaa cttttttctt   21060 aatatattat ccttagttca gccctgaaga ttattctgtt atttgtggat ctcaactttc   21120 ccccatctc ctggatcttt gtgaaatgaa tggtattaat tgaatagaga aggaagatat   21180
aaacataaac ttagtcaaaa acttgttctt gactaggcaa gttgggcttt atagctttga   21240
gctgatgaca tgtctattct tgtgaaaaag ggattttag tgttggtttg gcttcttgtt   21300
atatttgatt tattattatt atcattatca ttattttga acagagtct tgctctgtcg   21360 cccaggctgg agtgcagtgg ctcaatctcg gctcagtgca acctccgcct cccaggttca   21420
agcgattctc gtgcctcagc ctctggagta gctgggatta caggcgggtg ccactacacc   21480
tggctaatat ttgtattttt agtagagaca ggtttcacca tgttggctag gctggtcttg   21540
aactcctgac ctcaggtgat ccacctgcct tggcctccca aagtgctggg attacaggcc   21600
ttagccactg tgcctggctg attttttttt tttttttttt ttaggtttg ttttaactgg   21660 aactttacgt gaatgtaatt gaatttagaa taaaagcact taatttcaca gtgtgcagtg   21720
aactttctgt tacttatttt aacagtaaaa cccttgcag taaatgactt ggagcaaaga   21780 ttgcttttt aaaaaatgtt ttaatttgtt tttcttttct tgagatggag tcttgctctg   21840
tcaccaggct ggagtatggt ggcgcgatct tggctcactg cagcctcccc gcctcctagg   21900
ttcaagcgaa tctcctgcct cagcctcctg agtagctggg actacaggca catgccacca   21960
tgcccagcta attttgtat ttttagtaga cagggtttt caccatgttg gtcaggatgg   22020
tcttgatctc ttgacccgt gatccaccct cctcggcctc ccaaagtgct gggattacaa   22080
ctgctgggat tacaagtgct gggattacaa gcgtgagcca ccacgcctgg ccaattttt   22140 tttttttttt cttttgaga cagagtttca ctctgtcacc caggctggag tgcagtgtca   22200
cagtcaaaac tcactggcag ccttaacctc ctgggctcga atgatcctcc tgcctcagcc   22260
tcccaagtaa ctgagactac aggcatgtac cactgtgccc agctaattgt ttttttattt   22320 ttatttttt gtagggacag ggtctcgcta ttttgcccag gctagtctac aactcttggg   22380
ctcaagcagt cctcctgcct tgacctccca aaatgttggg attacaggga caagccactg   22440
cacctggcca aggattgttt ttaagtgaa ctgagaccca gccttattag tggtcccaga   22500
gcagacctgg gacctgaagg gaaccctttt cttctggtcc agcgtctttc ctctgatggg   22560
ctactttcct ggagccttg attgcctgtc atcagagtaa ctgagtttga acagagtagg   22620
tagttcctct ccagaccacc acactcacca gctttcattc tgcttctctc gtttagactg   22680
tggttctgaa tcctcagttc tatttactga gtgttttaa acataaaaat gccttttaat   22740
gagattgaag gccagaggtg ggacagttga ggacaaagta gaaataaaac cttcaaggcg   22800
gggttgttgg tgggagtctt ttttgtttg tttgttttt gagactgagt ctcgctctgt   22860
```

```
cacccaggct ggagtgcagt ggcacaatct cagctcactg caacctccgc ctcccgagtt    22920
caagctattc tcctgcctca gcctccttag tagctgggat ttcaggctcc cgccaccatg    22980
cccagctaat ttttgtattt ttggtagaaa cggggtttca ccatgttggc caggctggtc    23040
tcaaactcct gacctcaggt gatctgtctg cctcagcctc ccaaagtgct gggattacag    23100
gcgtgagcca ctgtgcctgg cagggagtct tatagaagct gtcgtggaca atgtgggaag    23160
tagtgagcct ttgtattcca gtatgctggg ctccactgtg cttgctctgg ccccggtcg     23220
ctctctgtgt gttattgagt ccccatccac ggccatactc ttcgtcctgc ttctctcctt    23280
accatcctct ccccgctagt ggtaccacgg ctaccactag caattactga catgtgggat    23340
cttagggcta cttccctata aggctgcagg gcatgtggtg ttggctacgc gcatggtaac    23400
catggtagcc ctgtggttct ccacatgtgc gccttgtgac ctgggattgg ctgcagacta    23460
gtaataaact gcgtcttctg gtatggaatc tgtctgtagt tgtactttct acctctgtat    23520
ttaaggggag atctgtaacc taccaatgcc agttgaagag gatggatgat agagatgtta    23580
acaaacagct gaaaaactaa ctacaatggc ctgcaaaata gaacagcagg tttttgtggc    23640
aaaactttgt gtccatgagt ttgttttttta aatatcctca tataatctgt tttaaatcga    23700
gaggctttgg gtaaaagcca tggctagtct tacatgtcat ggagtaccta gcttgtgagg    23760
ttcacagttt attatttaca gagtgtcccc ttaaatcttc tttgggtcgg ttcagcgaat    23820
gttgctcaga tggactttt tggctgacat agagtcaaaa tggtaatcaa gcatgaaagt     23880
acagacagtc cttaacgcac aaatgtgtca tgcttgaaaa gttggaaagt tggttctctg    23940
gagctctgat tgtattgtcc tgtagaatcc gtgttgtgaa tggtggttaa atcccaaatg    24000
agtccgtaga acctatataa tctgcaatat acctgcagta ttccaattaa tatgtaattc    24060
ccccatagaa ctatgttaat gatttgtatg tatggtattt aatattatac ataataatga    24120
ttgtatgaat aaaaaacatt ctgggctcca tgtggatgat ggggtgtgtg tgtgtgtctg    24180
tctatgtgtg ggtgggtgtg tgttcataga tcccttttcc tgcaatcctg gcactggaat    24240
tggtttatc atttccaatt aagtttcatt cccatgaatt ttggagtaca gactgggtcc     24300
aggtatgcag gcatagatt agagcccctga gaaataggat aggctggaa ttgctgggtt     24360
ggagatcagt agcttccagg aacactttttt gggcctggct gtcttcatta tccccttttg   24420
ttttctcctg gggtctgcag gtattgccct gttttgttcc tctaatatca cttttttttt    24480
ttttctgctt ttgaccaggg ttttttgcctc tggtctacaa ctgaatatcc tatcagactc    24540
tcctgatttt gaaataaata tatagttttt ttgaggtgtt ctagcgaatt tctaaatcta    24600
aatgttgtgg cagagttatt acatactaat tttgctatga gaggttgtag aatcccagat    24660
gactaatctt gtaaaccata cacgcatttc catctaattc tccattgtat atcatgttgc    24720
agaaaataac agcctctaga gtttacattg cctcctttga ctatatttct tatttaagat    24780
tagttttcag ataagacctt ttcatggcag tacataactg tacagagggc ttccaacttg    24840
tcttgggagc tctcatctct gggagacatc acattaccca ctgcccccctg cccccccgccc  24900
ccagcctgga tgcactcagc ctgtaccccca tttctgtcct cagccaaaca ctgctgaaat   24960
gcaagagctt tcaattgcta gccagtgaag atgcagacta agggatttcc atgtagaagc    25020
ccgctctttt cagctggctc gtcgagagct ggaggcccct tgcttgttca catgaggctt    25080
tttgtccctg acttggtggc tgctgtttca cttctcagca gaaagggaca cccttgcccc    25140
cccccagaaa ggaagatttg atgtaccact tccgaaaggt tcagtcgggc atcactgtaa    25200
ccaagaagat aggtcaggtg aggctggagg tggaacaggg ctgctcgcta gaactccaga    25260
```

```
ttgttccaca agtgccttct ggcagagaat gatggaagct tccgtgattt ttttttctcc    25320
ttaatagtta tgagcacaga agaggagcag attgtctggc tatagaagct gtcttatttt    25380
ttattttttgt ttttgagatg gagtctttct ctcttgccca ggctaaagtg caatggcgcg    25440
atctcggctc actgcaacct ccgcctcccg agttcaagcg attctcctgc ctcagcctcc    25500
tgagtagctg ggaattacag gcatgcgcca ccatgccaga ctgattttttg tattagagac    25560
agggtttcac catgttggtc agtctggttt cgaactcctg acctcaagat ctgcccacct    25620
cagcctccca agtgttggg attacaggtg ttagccactg cacccggccg aagctgtcat    25680
attaaatagc actttctgct tttagcaaat ttaatccaaa tgagacttta gattttcttg    25740
ctctgactta ccagcagttc cttgaaacac atttaattat ttttgccaga aaatcactca    25800
agcacttacg ccattttttt accgtgaaaa tatgctgcat tattttaaaa tatattagaa    25860
gtcagtaacc ataagatttt atatgttttc taatgtattc tgtaagcttt ctgctgcttt    25920
tgtttggaag gtgtattttg taacgtagag gactgctttta tctgcttgta agcttgattt    25980
ttgtttttac tgtaattttt ttttcttttg ctgtattgag aaatacattg agtaattata    26040
aagtcagtgg catgtttata agttaatatt tgtatctatt ccttagttac tctaactcaa    26100
aacctaaagt aatcttcaac tctaatttac tctgacatcc agttgactgc caagtcctcc    26160
aacttaatcc ttatcctttt tttttttaaag agatgcagtc ttgctttgtc acccaggctg    26220
gagtgcagtg gtgcaatcat agcttactgt aacctcaaat tcctgggctc aaatgatcct    26280
cccacgtcag cctctggagt agctggggct acaggtcttt gctaccatgc ccagctaact    26340
ttttattttt attttttata gagacagagt ctcactgttg ctcaggctgg ccttgaactc    26400
ctgccttcag gcggaactcc tgccttcagg cggtcctcct gcattggcct cccaaaagtgc    26460
tggaattaca ggcccaattt tattcttggg atgtatgtct gaaactcttt ccttcacttc    26520
cttcccaagc cttagttcag gcccttctca tctgtggtct tcaaagtcgc cttcagctgg    26580
ttcaggtcct tccttttctgc tgtatctttc atgggaggac atgttatgta tcactgtcct    26640
acttgaaaac ttccattccc cattgatgag ggtgttacct ccagattcct aacacaggtg    26700
ctgaaggcat gcctggataa aggcactccc ttgatctcct ggccaggtcc ccgtacacct    26760
gcagcgcatg ctccacattc tgtctttact gatgctgtgt cttctgcctg cggagccacc    26820
caccattcta ttcacagccc ctgcctcagc ggagcacgtg cctccctctt cctacactga    26880
gctgtccttt ctattgaatc ccctcttttt tgtagtatgg gaaatatttt attatgaata    26940
ctcttttctc tgttgcctcc gtgaccacgt taactttgcc ctaattcgcc ttaggactcc    27000
atctgcttag gggaaagtta ggatttggtt acagaaagca agctgctaga aagaacagtg    27060
tttagcttct gacaggcaaa ataggatttt gcaacatgct tttccttttt aatgcttaga    27120
cattttatat gaattaatat ttttatttgg ttgcttatac attactttct ttttagctag    27180
aatgtgaacc ctataggaac atggggattg cctttcacat cttttgtatcc tcagtaccta    27240
atgttcagtc accctgtggt cttgtgtcgt atatacattt agccttcctt aattaaacca    27300
tatgtactgg tccccgtccc ccaccccccaa atagagagaa agaaattcct tgaatactac    27360
attgccagta tcaaaccaca ccttgatatc ctctggggaa agggaggtat cagttgaaaa    27420
gagaaaagag gttaaaatct aggcattaaa atgtgtaagg cttagatgct ggcaatttaa    27480
ggtatgtttt cctgaggtta attttgattg tgtgcaaatt ttacctcata tctaactgta    27540
ggatttagtc accacataag atgggatacc tccataaatc cttcagaaat gtttgtgaaa    27600
```

```
ttaaataaag ccttattgaa gactcagctc ttgagagtca tctacctacc taacagttat    27660
tcttgaacag aagagtctta cttttcccta taaggcagtg tgatagccat ctgtatattc    27720
atataattta tgttggcgct tacttcattt aaaaatgtat tccgtgaatg cagttgccag    27780
gcggtgtgct gatcagaaac gtgtaccaat ggcctctttt ataattataa gaggaagacc    27840
aacctgaaac agtcacacaa atgattaatt ttaattgtgg aggagtgctg ggaaagaaaa    27900
ataaaagatg caatgcaagt gtttacaaag gagctttgag cttgtttgaa gtggtccttg    27960
ggcacttaag caaggcttaa agaatgatgt gattagaagt ggcttagcaa ttctaaagaa    28020
cacagggaag gcgtgtggcc agaacattgg tccctagagc acatcgcctc ctgacatacc    28080
atttccttaa gttaatgttt taccactata cataggcgct ccccttttgtt tacccagatt    28140 ttttttaattt taaggatgtt tttaataact tagaatcctg taatttgttg aacagtcctg    28200 tattccctttt acttatattc cttgagattt tataaaatat tttttacatg tcccaagtct    28260
tgattatatc ttttaacctc ttgttaagaa atacttactt ttctattttt atgctatatt    28320
tcatgtttac tgtagaaaac aaaaaagta aaatttttct ttattcctat cactgcagct    28380
tataagcact ctaaacattt tgatctatat tttgccaatc atatatttta gttaaaattg    28440
ttgttgacat aattgtagat tcctgtgcag ttgaaagaaa taatacagag ctgagcgcgg    28500
tggctcacgc ctgtaatccc agcactttgg gaggccgagg caggcagatc atgaggtcag    28560
gagtttgaga ccagactggc caacatggcg aaaccctgtc tctactaaaa atacaaaaat    28620
tagctgggtg tggtggcggg cacctgtaat cccagctagt tgggaggctg aggcaggaga    28680
atcgtttgaa ctccggaggc agaggttgca gtgagccgag atggtaccat tccactccag    28740
cctgggcaac aagagcaaga ctgcatctca aaaataataa taataataat aaataaactt    28800
taaaaataaa acagagagat cccatgtgcg ctttgcctag ttcccccatc cactgcccat    28860
aacattttgc agaactgcag tacagtatca caaccacaat actgacattg atacagtctg    28920
ctcatcttat tcatatttcc ccagtgttac tcgtatccac gtgtgtatgc attgtgtttt    28980
caatactctt ttattataaa gctgttttta atgtgattca attctaggtt gttttgttct    29040
gccctcaaaa agcattccct ctcctaatca tatctccgtc ataccttgt atgttttctt    29100 taaacctgtt ttaagaaagc agctacctgt aagagaaatg agattgaaaa cagaattgcc    29160
aatctgcttg tactttataa gcctgttgat tgtttagata cggtttagcc agtttatagt    29220
taccctgggt gctgaaaggt atgctggatg atacctaacc aacagagaac cattgaatgc    29280
cgttcaaaat ggactgaagc atcagcaatg tctgaaaaag gcctgacagt aatgtacatg    29340
tcaaatggcc cgtaatttaa gcagagtaga gtaagtagaa gaataaacat ggggaaagtt    29400
ccagcaacag aggaggcttt gagcttttgc tcttcatctt gagtggatgt tgttctcagg    29460
tggtaatagg ccatcgagct ttctccactg gctgcctctc tggggaacaa ataaccgaaa    29520
agatactcag caccctggtt ggtacatagg tggtcagttg atttatactt cctggttttc    29580
agtgttgctt gaattttcta aatggaaaca cagtaccttt ataatcagaa acaatcccg    29640 agttttgatt tgagggtgtt gtaaaaagtt aaaaaaaaa aaacagaaat gtgaaaagga    29700
agttgtgtta gagtatttgg agttgagaaa gcatgaaaag gacagaagag aagctggttg    29760
tcaggttgca tggggtagct acaagcacac tgaccagaaa gtcagctgga aaaaaatgt    29820 agaaacagga gataaaacgg ccaagggggct atacaagcaa acagcaagga cctgagaaga    29880
aaactagtgg aggtgtgact gtcagagtga tgtgtacagt gtgatccttt ctgtgtaaaa    29940
acaagcagta agaattcgct gtttacgttt gcgtgtgttt ggagaagagt ggggaagagt    30000
```

```
aggcactgcc agactgtgaa cactggttag gttattgtta tatctttgta ttatatacac    30060
tggacatgtt atttgtataa tatgagaaga aattttataa atcattaaat cttttggcat    30120
ttaggaacat ttgtgttttc taatagttgc ttctatacta ttatctttat tatatgccct    30180
tcatcttctc agtgtttggc tgttgttgtg attcccnttt gtgagcagtg ttgaagttag    30240
ctaatattca tttcttctcc cttctttcac cctcctccag agtctgattt gaagtattcc    30300
tagctgctac ctataaaagc aataagcaag attgttttac ttttcacaaa ctcgtcctgt    30360
tctgtgcctc tgcctcggac atagctgtag tatagagtgt tgtctcccctt acatccttct    30420
atcttagacc tactagtaaa tattaatgct cactctaagt tcttctcaat tcttttttt    30480
tttttttttt ttttttttga gaaagagttt cgctcttgtt gcccaggctg gagtgcaacg    30540
gcacgattc ggctcaccgc aacctccacc ttctgggttt aagcgactct cctgcctcag    30600
cctcctgagt agctgggatt acagtcacgt gccaccaccc ctggcaaatt ttgtatttt    30660
agtagagaca aggtttcttc catgttggcc aggctggtct caaactcccg acctcaggtg    30720
atccacctgc ctcagccttc caaagtgctg ggattccagg cgtgagccac cgcgcccagc    30780
ctcttctctc aattcttcct gaagctcttt ctgcactaga ttcctcagga agggcttgtg    30840
ggaacaatct tctgtgaatc aacagtacat attcataata gtttgtcagc agcctattat    30900
tttaaggcca tttggtctgt atataaaaat gtttggatca cattttcttt ctttaaggta    30960
aatatgttat tctgttgtct tctggtataa agcattgctg taaatgtttg acagtctaat    31020
tatcttttgc ttataagtga cttagggttt tttgtctatg tgcccaaagg atttttttccc    31080
tctttctctc tttttttttt tttttttttt ttttaaaca gacaggatct caccctgttg    31140
cccaggcttt agtgcagtga ggcagtcaga gcttactgaa gttttgaact cctgggcttg    31200
aggaacaaag gatttttta acctttaat tcaaagtctc atcatttatg caaccatgtc    31260
ttggtgttgg ctgttttggg ttgttctccc tcaaaaatcc atgtgctctt tcaatatgta    31320
gttttaaatc ttttttttt aatttcagga aaatcttgaa ttagagtttt ccgttttcg    31380
tctggtacat tgcttgggtt tccttcttca ggaactcagc ctgttatgtg tatgtttgat    31440
cttctttgcc tgtcgtctgt ttctttcact tcctctcact ttttttaaact tcatttatta    31500
aaaaaaaatt ttttttcga gacagagttt cgctcttgtt gcccaggctg gagtgcaatg    31560
gcgtgatctc ggctcactgc aacctccgcc tcccaggttc aagtgattct cctgcctcag    31620
tctcccaagt agctgggatt acaggcatgc gccaccacgc ccagctaatt ttttgtattt    31680
ttagtagaga cagggtttct ccatgttggt caggctggtc ttgaactcct gacctcgtga    31740
tctgcccgcc tcagcctccc aaagtgctgg gattacaggc gtgagccact gtgcccagcc    31800
ttattaaaaa ttttaaaaac atacatttaa acttaacaga aaaattatga gagagaaggg    31860
ggtggtgcca ggcttttta aacaaccagc tcttacatga actcatagag tgataactca    31920
ttaccatgag gacggcatca agccgttcat gaaggatctg gccccgtgac ccagacacct    31980
cctactaggt ccattttaa cattggggat cacatttcaa cgtgagattt ggaggggca    32040
aaactacaaa ccatgtcact cagggattgg aggagcaagt accacctata ctttggactc    32100
aggtagaaag gcaaaatatc caggaaataa gctgctaccg tccagggttc agcagaggtg    32160
cccatcagcc tgccaagtac tcaagagtcc agcctctagg gagctaatca tcatggtgag    32220
ctcttcgagg cacagggagc tgggaagaca gtgcttgcca cccctgcctg aatagtgttt    32280
gcacagagag ttctgttgtg tcttgattgg gtcctcctgc cactgggaat gctgtggatt    32340
```

```
atactaggtc tctatctggc ttgtttcagg gctccatgtg aaaaccttct tgatatccta   32400
gccatccacc tgctcagtcc ctagtttgca aggaggctgt ggggagccta gattctgtgt   32460
cagatagaat gtactacatt ccgtctcagg aatgtaccac atcagaaaac agtgcgacct   32520
gcaggagaag tagaggtgaa gaggcacatt cttccgagaa atgtttctct caacacccag   32580
cattccctgg atatcagcag gaaattactc actgctagaa aatgccccat gagccttctg   32640
ttaaggaggt caagggagag aacagagaaa gttctcaaag ttgacttggt cactggtact   32700
ttcttatgcg gttcttattt tgtttgccat cgtcatcatc atgctatgtc tattttctca   32760
atccaaatcc actgctttca ccttggttct ttctgaccgg tttggcacac tcattcagta   32820
aatccttatg gagagcccaa tgtctgcata attgtgctgt gctgatgacc aagctagacc   32880
tacgagtgtc ggctcctttg agatgtacgg gacagctctt ctgtcatctc ttctgggaag   32940
cctctccagg cttggtgaac agtggcaaga tgtttaacag ttgtacatgt gtcccatgtt   33000
cctttctaag agcctgggca aaccagaccc ggtcgcaggt catcgtagta tggcgtgagc   33060
ttcctctctc ctttctgacc ttttgtgtga tggcaagaac ctgcagagtg acacaagcag   33120
caggcttctg aggttgctct agcctcagaa tggccgtccc ttctccaccc tggccctcat   33180
tgctgaggtt tcctttgaag caacagtgcc ggaacagact aggggaagca gcttggacat   33240
agctgtatga tttattacca cccattgagg ccaaccaaag tcggcaagga gaggtagcag   33300
gtcagtggtg cctggaagct tcctctttcc tttgcaccag atgtgactgc tctgcaatta   33360
ctcctaaatt tgctactctc gttttttacta gccaaccttg atgttttttcc cttcttcctg   33420
tagaatagac ttcccctctg atcagtactt tctactcaac actatttgtg ccacagtgg   33480
gaactcattg aggacaggga ccatgacatt actacctgac ccatcaacac ttggcataac   33540
ttgaaatgca aggacaaaaa ttggctgcaa gtacaatgtg gtcttcactc tgaaggtgat   33600
ccttaaaact tggctttggc atcatattgc cttaatatac ctaggggatt gggtaaaacc   33660
agttacttta aaagagttttt acaattctgg ccttctagct atcttgtctt cttaaacaag   33720
agcacaagat gaatgtatct tagtgaaatt ttatatggtt tgctttgagt aatcttgcga   33780
agattgattt ttagcacagt aggaaagaca cattctaata gtgattttttt tccccgagtt   33840
tatgtactgc tgttgcatga aaatctgact agatttaatg ttcctaaagt tctttgttca   33900
tcctgatttt tgcaggtcct agggaaagct ttgttttcct cttaacctaa cttagatgtt   33960
gtcatttcat gagctttgga ggaagagtgt atagccaatt gtgtaatgtc tttaaaggat   34020
attatctctg caatagttgt ttataaggcc taagttattc atgtaataat agtggccccg   34080
gatctgtttc tagcaatagg tatatggatt ttggttccta tatagttgta gttgtggctt   34140
tgagatattg agcaagccct tttaagaaag gatttggcat ccctcagcct tcaaaagctt   34200
ctcaaaattg atcatatgtt attagcaaag gtttactgcc tgcttccatt gtatagacaa   34260
tttattttttt atgtattccg ttctaagaag gcagatgacc aaaagatctt gcatctgttg   34320
cccaaggctt gtgactagag aggaaagaga taagaatact ttttttaaaat cccatttttac   34380
taaatatgtt gaggaagtgg taagatatat taatttgttg agattttttct gttatgccta   34440
ttatatgaaa taggtactct gaacatggct tcttaattaa atatatttga taaaatacaa   34500
cttgcttccc ctggagttta aagtcagat aactgccatg gagagctatg ctttctttgt   34560
tttaaagatc tgcttatgaa catgataaac aggaacaatt taatgttttc aatatttttct   34620
tgtatttttac tgcaagtttta tacacaacat aaatatgggg gaaggggggaa atgttttatac   34680
cagagccatc ctgcccattc tttccttaca gaaggacaaa ggagcagtat ttattttaac   34740
```

```
tacaaaaata ctattgtagg tttaaaaat tccgtatatt ttgatatctt gtgttcctct   34800
tgacctttaa tttgctaaat agttgcaaag aatgaaggta acctgcatca tcttcttaaa   34860
aaccaactct atctaattat aatagtttgt ctatctctga aaaatagtga tgtgttcatt   34920
ctgaaatcag aactaccgga tgcagctgca ttttgttact atttgaattt cgggagaggg   34980
aggaggatgc agcctttcga gctgctgaaa tacacaaaca caaagaagac accaagcata   35040
gtagaactgt gttaagctga ccaagccaga agaagcacct attctcagca tagtatgaga   35100
cgtaaaggca atataatggg catagttgaa gatggtagaa ggaaaataga ctctgatggt   35160
ttaatgttaa atgctttttt taaaaaagtg gtattccaat atcgaagaag aagactttct   35220
acttttagaa gcaataaagg aaattgcaga ggaaagggtc aataggttgg aatacataaa   35280
aattaaaaac tttaaactt tttttttttg agacagagtc tcactctgtc acccaggctg   35340
gagtgcaatg gtgcaatctc ggctcgctac aacctccgct tcctgagttc aagcaattct   35400
cctgcctcag cctcccgagt agctgggatt acaggcatgg ccaccactc ctggctaata   35460 tttgtatttt tagtagagac agggtttcac catgttgtcc aggctgatct caaactcctg   35520
acctcgtgat ccgcctgcct cggcctccca aagtgctggg attacaggca tgagccaccg   35580
cgcctggact aaattgtttc agtattaatt tttttaaaa caagatctta ctgttgccca   35640
ggctgaagta cagtggccca atcatggcta actgcagcct tgacttctgg gcctcaaggg   35700
atcctcccac ctcagcgtcc cgagtagctg ggaccacaga catgtaccac cacacccagc   35760 tacttgttt attttatt ttgtagagat gaggtttcac catgttgccc aggctggtct   35820
cgaactcctg ggcccaagca atcctcctcc cttggcctcc caaagtgctg gtattacagg   35880
tgtaagccat gcgccctgc ctgattttt aaatgtgcaa acagataagt tggaaaagtg   35940
atttccaata aagataaaga gttgatggtt ttaaaatacg taaagagctt atatgaatga   36000
gaaaaacact aacattccaa aagattagaa ggcaaaggac agaaagaaac aaatcactat   36060
gtctgggaag ggacatgaag gagcaggttc ccactgggcc agcggggctc aaacccactg   36120
gggacgtccg agagactgca agggccatgc cttcacattg ccgtacctga gaagcaagga   36180
gctggggtat ttatctcttt cacactttgg gaggctgagg tgggcggatc acctgaggtc   36240
aggagttcga gactagcctg gccaacacag tgaaaccccg tctctactaa aactagaaat   36300
aattagctgg gtgtggtggc acacacctgt aatcccagct acttgaagg ctgaggcatg   36360 agaattgctt gagcccagga ggtagaggct gcagtgagca taaattgcac cactgcactc   36420
cagcctgggt gaaactctgt ctcaaaaagt aataataatc atgataaata aaataacatt   36480
agattgttag cagaagtagc cacaggtttc tcccacctct ctgcaagttg ctgagtgtga   36540
ttcccatcaa gaggtacaat gtctttttat tttattta ttatttat ttatattgcc   36600 tatgttgtct aggctggttc caaactcctg agctcaagtg atccttctac gtcagccccc   36660
caaagtgttg ggattacagg catcagccac tgcacctggc ccagatactt tttcttgagt   36720
aggaatttcg agtcaccctg aacattgcat gccttcgtag tggggaagac aataggaaac   36780
cacaggctgt aggctaaaat gggttgtgtt tcttgtaacg tcatgacaag cataaccca   36840 tcttggcata gtaaatagta agcactcact gaactgatga ttttaaatct ttgctgttta   36900
ttcagcaata tcctaaatta gcgctatgtt agtggagttg catctcctc atggattagt   36960 ctgaaaaaga tgagaaatct gtatgtgac caagttatcc ttaaactgct cataatgtat   37020
gatgcacgtg gttttacgtg tacagcctgg taccattgtt cttaggcaca tttcagtgcc   37080
```

```
agaactctta atacccagga agaagcaaaa agaaagatgg aggtgcagct agaggttgtg    37140
gcctttgaac gattcattct gccttaataa gagtggtctg gctgagctcg gtggctcaca    37200
cctgtaatcc cagcactttg ggaggccaag gcaggcagat cgcttgagcc caggagttca    37260
agaccagccc aggcagcata gcgagacccc ccctccccccc gtctctacaa aaaatagaa     37320
acaatgagcc aggcatggtg gaacgtagtg cgtggtgcct gtagtctcag ctacccagtt    37380
ggctgaggtg ggaggatcac ctgagcccta gaagtcgagg cttcagtgag cccttattgt    37440
gccactgcac tccactctag gtgacagagc gagacaggtc ctgtctcgaa agaaagaag     37500
aagaattaaa aaaagtgatt agatcccttg tgtttgggac acttgttggc agcagggatg    37560
gtagcgttta tgagggttgc atgtaacatc gcctagctca gacatctgtt tgactgtctt    37620
cccccctgaa gcgcaggctc tgtgagggca ggtcttttgt cttcttgtt aatcttcata      37680
tgcttagtgc ttgccacata gttgatgctc agtcgatatt tggatgaatt gaagggatta    37740
atgcattgaa tctgaacctt gctttcttaa tgcatatggg gagttctttg gaaagccaca    37800
cagaggagct tggttgcctg cttcctctct tccccagatt gtcttttat tgttgtggct       37860
tcactgaagc actctcactt caaataattt tgggcattgg tcgtattta ttctttgttc       37920
cttcttcatc cttacccctc agatggtatg tagaaaagta cactacatct agaaagtact    37980
ttataaactc atttggttga taataataca tatgccttt ccttggtcct ggtagcagaa       38040
tcttgtgcca ctcttggaat acaaacgaaa ttcttaacca aagccagttt cattttgatg    38100
ttctattttc ctcccattca cactccaaat tgtgcaccaa agtatcatcc tagttttgtg    38160
aggatggttc tccatacttc agggtaggag tatcatgtgg attcctatga taccttctc      38220
cctgggacca tggagggcag cagctggtga ttgatagtct gattcccggt gaggaaagct    38280
gtgagccttc cacttgcaga tgtctgccaa ctacatgtgt ccttagtcaa ctgtaccact    38340
gtcctccggc aaacagcaga agcccagggc ctgaagttct taagctgtca ttatggaaag    38400
cagaaggtaa acaaaacaga agtgaaagta gatttaattt tttagactgt tctcttacag    38460
gaatggtttt gtggttctca gcatttaaaa aaaatagtg gttccaatat gttttattga      38520
catcaattac tgtaagtctg attcatttc tgcctattga tttctaccca aggtgaaatt       38580
catgacattt aacagaaagc ataagtgatt ttttaaaagc agacactatt agggacggta    38640
aaaataagat ttaaagtcgg gacacttgaa aaagcaattt ttataccttt ggtaacgatt    38700
ctattctgat tctttgtata aataatataa acaaaggctc tagaagctta ctataatgaa    38760
gttggtgtgc tgtttctaaa ttctggttta aggcccaaat tcattttatc tgcattaact    38820
tttttttttt tgagagtctc gctctgtcac ccaggctaga gtgcaatggt atgatctcgg    38880
ctcactgcaa cctctgcctc ccgggttcaa gcgattctcc tgcctcagcc tcccgagtag    38940
ctgggattat aggtgtgcgc caccacgccc ggctaatttt tgtattttta gtagagacgg    39000
ggtttcacta tgctggtcag gctggtctca aactcctgac cttgtgatcc gcctgcctcg    39060
gcctcccaaa gtgctgggat tacaggcgtg agccactgca cccggccgtg ttaaaattt     39120
tcagtggtag accactatgt caatatgttg ctttcactga caacagtatt ttcttaaaga    39180
taggataccc catttctaga tgaatctcat tctagctgga aaataatttt tcagttctga    39240
aactacatca ggcctcaggg aatcaaaact agctattagc cacacacata taaagtggct    39300
ttgctttata aacgatttag ggtcaccatc aatgacaatg gtccctttt attgtattt         39360
taagagtttc ttatcttaaa tggctgcata actgtagagt tttaaaaaaa ttaagtaaat    39420
gaccatgtta atgctctatt aagcttccaa acaatattgt aatttacttt gaagattttt    39480
```

```
ttttattctc aacatcctgc agcttgaccg tttgcctccg tgtctcagtg ctgcttattt    39540
tgaggtgtgg actggagtcc atctgtcccc cttgcctctg aactgctccg ttttgtgttt    39600
cgtaattctt catgctgcat cctgggcgca tttctctgta gtagcttttca atttgctcat   39660
gctttgactg ggcttagtct agcgtttatc ctatctctta aggtttttta aaaaattttc    39720
atgattattc atttatttcc aggatttctc atttcttcag tcacatctcc ttgttctggt    39780
tttacttctt cctgttttta ttcataacat cttttttata cacgattcct tcatgtattt    39840
ctaatcttaa gtatatttaa ttgcttattt gattcttttt tttttttatt gagacagggt    39900
cttactctgc caccaggccg gagtgcagtg acatagtcat agctcactgc agcctcaact    39960
acttggactc aagcgacctt cccacctcag cctcccaggt agctaggaat acaggtgtga    40020
gagccgccac acccagctga tttgtcttac tatgttgccc aggctggtct tgaattcctg    40080
ggctcatgtg atctgccctt cttggcctcc tgaagtgctg agattatagg tgtgaaccac    40140
tgcacctggc caagtatgtt tatttattta ttctaatttg agagggagtc tcgctctgtc    40200
gtgcccaggc tgtagtgcag tggcacaatc ccagctcact gcaacctctg cctcctgggt    40260
tcatgcgatt ctcttgcctc agcctcctga gtacctgggg ttacagttgc gtgccaccac    40320
acctagctaa ttttttgtgtt tttagtacag gcggggtttt accctgttgg ccaggctggt   40380
cttgaacttg tgacctgaag tgatccgccc gccttggcct cccaaagtgc tgggattaca    40440
ggcatgagcc accacgcttg gcccaagtat gtttatttt aaagtcccca acaagctata     40500
caataaattg catatggaat ggattttgt tctagttgat ttgttggtta tcatttgtag     40560
aactaactag ttgtcttctg tgtttgatac cttgcttcta ggtcattttg agttgggagc    40620
cttttgttt gttttattc tcatgctgtt tttgagccta gctgtgcctt tatggttttc      40680
tctaaattta attgaccatt gttttatatt tggagcagtg ggtgtacatc agagtgtgaa    40740
agcagcccca ccctctccac cagaaggtct ccatgccagt ttcacgaagc atttttcatg    40800
ccctcattcc tgcccttatc ccttgatttg tggggagttt gtaaagcagt tgattgtttt    40860
ttttccacgt agttttccaa gtgcacataa ttgttctgtt agtgacttgt agctccatta    40920
tctattaacc ttgccccaga ccactgtaca agcggaccca acgcttcctc cagctgtggc    40980
agggacagtt acttggtatc ctgctgcctt ttcaatgctg accagttttg ccccttcctc    41040
ccctcaaccc ctgtctttca ttcaactatc accaaaccaa aagattctgg tttgcttttt    41100
agtatgtgtt cttattcagt acatagtcat tttaaaattt aaaccaaaac agacttggta    41160
ctgattagct taattttaag cttttctctt attattaaac agtgtagttt atcttagcat    41220
ttcatattaa gtatatgatt tatttcatat tgcttatatg aatgtacaca taaatataat    41280
aaaaatattt tcctaaggtt tttgtagtaa attatatcgt ttcattaact ttcatatata    41340
gcattgcttt tgacctggaa gacattgaac ctctgatgat ttgtatattc ctcggagtat    41400
actttgttac atagaaattt tctcatttat aatgagattt gtgattaaca aaatttgttc    41460
aacatgcatt actttgaaga tctggtttct aaaattttat gctagttacc ccacccccc     41520
ttctatatat atctccctat tcagcgacta ctgcaagagt tccaggaaat gtacactgtg    41580
tgttcactta ctgcattta aatcattgcc tttactatat ttctgcattt cccttcaatc    41640
tagctctgtc tgtacatttc tgaaagccag tagcttccct gaagaaccag gtaacaaccc    41700
gaacaatcaa attagataac catttgtaga atggaggttc cggagatct tagaagatgt    41760
gatgggtgct aagggacttt gtagttccct gaagttccag tgagtaaaag gtacccttgg    41820
```

```
aattttttat tccttcagac ttttaaaaca gagatcactt tcaaaaatta ctctttctgc    41880
tttgaatcca tgttttagta actattttga cactgtttgg tcagaaggct gtgtgggtca    41940
actgcaaata aataaaataa atgtgatttc agtaatttcc attttgtaac aagtaattga    42000
gaaaatagga ttggatcaga tatttgctta tacacattcc ctttcaggag cacttctgtt    42060
ctataaagaa tgttggtata ttgttaagga cacttcaagc tttgggaacc tttgaagtat    42120
ccattgattc agttaacaaa attatgttga gtgcctaccc tgggcctggg cctgtgttag    42180
gaggggacac taagatgaga gtccaaagca cttcttctca gactcctggc tgctaatggg    42240
ttgctgcctc tacttcttca cttagcagat agcttttaaaa tgagtaatgc attttaccat    42300
ggagcccgta agagacattc acccagttgt ggaccgagga aagggtgtt aaacccagat      42360 tgtgatgttt cacttgatga agtgcttaat ataaacatgg aaatatttcc gcaaggataa    42420
actggctttt atgcctgtgt gttttcagga gaaatagaaa tctctaatca aatattgcca    42480
gcttttcacc caagtttgac tttttgccta attgagtttg ggaggtgtct gaataatgga    42540
taatgagctt tcctgaataa atataaaaat taattaactc caggctctaa ttcattctgt    42600
taccagagtt ttgtaagcat gttacccctt tgtgttcatt gggagatcat ctgttacctt    42660
cttaaatgag tggggaagga tgggaaatga ggaagagcta taaaaactat tcaggtgaag    42720
aaggtttctg cccctccttg ccccttttaa aatctccagc tcagcagatg ctttgtttaa    42780
acttgatcaa gtgcttgtga atcttcctag cctagctaaa tcataacttt ggaaggactt    42840 gctttttttct ctcatgacaa tggtttacca cagaaatgat tcagatcact ttgtgtgcct    42900
gatgcctatg taaaatgata cagtgaaatg gaaaccattt acctgtaagc tttgggcaca    42960
cccaagcctg cttcaggagc acatgatcag gcgtgcactc tgggagagcc gtacacattt    43020
gacatctatg atgtgtggcg ttttattcta tcacatttct gaaatctaca ctaagagaaa    43080
ggaggctctt aaaaaaccac tgaggtgtgg actgggggaa ggagagatcc gtaaagaacc    43140
tgtttgttac ctgttgatac tatttcccat tggtaaaatt tctaatttag tgtgatccag    43200
ccctgaaatg ctgaggcaca cactgaatga ctcctgacat ctttagtgtt tttgttcagg    43260
ggactcttct gggaatctgt ttcatggcaa gtttattatt cccttttggt ttggctcatc    43320
agtttaccca gcagtcatct taatcggttt taaaggcttt tattttattt tgttttctct    43380
gtggaaattt tacacattca gtagattaga agtagttatt taatctttgg ttagcataat    43440
aaaagatctt ctagggacat tttttgcttg cagtggaagg ctagttaaat gtgttcatta    43500
gtcatgaatc tgcttttttct atagctgttg gaaacgtagc tcccctgtga tacagttgta    43560
gaatacagaa atctcgtttt gctgttacgg tacggtagtc tacttacttt cttccaaacc    43620
attaatgtta tagttacctt taattgcgta ggtcctatca cccctcaatt ttaagactct    43680
aagcctggca ttttatctta caaatgaaa tataaagact tgtactcaga gtatgtgtgt      43740
gttttccata taccattcta aagtagagaa agatgaggga ttcgccagaa actgatttct    43800
aataaattat ccagaaactg accccttctc acctcttctg ttactgtcac tgtggtttca    43860
gccacagcat cctttgctgc attgttacct tagtttcctg actgtatcct tccttacacc    43920
attgatccct gcaatcccat ctgcgcgtag cagccagaag ggatccactt actgctgtga    43980
tcagaaatcc tcagccaggt gcagtggctc atgcctgtaa tctcagcact atgggaggct    44040
gagactggag aattatttga gcccaggagt ttgagaccag cctcaaactg ggtaatataa    44100
tgagacctca tctctacaaa caggaaaaaa aaatttttt tttttttttt aactagccag    44160
gtatagtgct aatataccctg ttctgggatc cagcatgctc tccctgacct gcagcttcat    44220
```

```
ctccaccact tgccccctca ctcccaccac aatggctttc ttctcttcct cagacatgcc    44280
gtgcgtcctc ctacctggaa tattccctc caaacattcc catggctcac tccctcacct    44340
tcatcagatc tctgttccag tgtcactttt actggaaggt cttttgtgac catcctactt    44400
attataaaaa aataatctgc ccaaccttct ccttttattt cctctacttg attttcaat    44460 ttagtactta tcagctgaca tatattttgt ctctctgtct ctctctgtct ctcatagaag    44520
gtaaattcta taaaggaagg aattttatg tttggttctt tgctgtagct ccaatattca    44580
aaacagtgcc tgacacacag taggcccttt atatttgttg aataaatgtt gacactctga    44640
tatctaattt ttgtctggtg actaatacga aaactataga gtgataataa aagcattacc    44700
ttagtagact ggaaagggat gagcgctagg atgaactttc tgcctggcga tcttgctgaa    44760
tttaggaggc agattgggt tcaaggagg ctgaaatggc taggatttgc agagcaggt     44820 actaaggatg agcaggctat gacagaaaga actccagaaa tctgcaaagg gatcaccttg    44880
agtctggctg gatacagtgt acactttgta gggtgtctct tcatgagctt ggataaagaa    44940
caactgttgg ggagtggata attcccagca ctcattcaag cttgcatcgg ccagaacgga    45000
gagagacaga cctctgtaat acgtaggata tttggtagaa acattcaacc gaaaccatc     45060 agatatgcaa aaagtaataa taataagtaa acaatgtgat gcatagctag aagaaaaatc    45120
agacattaga agcaagccca gaaatgacag atgataaatt agcagataag gacattaaaa    45180
cagctattat aaataactta gcagatttaa agaaaaacaa cataatgagg ataatggaag    45240
aaaaacaacc gaataccatt tctaaagaag aaaaatacaa tatctgaaat gagaatttag    45300
ctggatagga ttaatagttt aggcactgca gaagaaaaaa acagcatcta tatgagaata    45360
tacccaaggg aagtacagag aggaaaaaaa tgtggattgg ggggtgcctc agtgacatat    45420
ggaacaatat taaacaagtc tgcccccaaa atacttgaag gaataaggtt caagtttttt    45480
ccaggtttaa tgaaaactat aagcctacag attcaagcat ttcaacaaac cttcagcaaa    45540
ataaacaaaa ccacagtagg cctggcacac tgtctcatgc ctgcaatccc agcactttgg    45600
gagcctgagt caggaggatt gcttgagatc tgcttgggca acatagccag accctgtctc    45660
tacaaaaaat aaaatgaaat aaattagctg gatgtggagg tccacacctg taactctagc    45720
tagcctggag gctaagaagg gaggattgcc tgagcccagt agttcaaggc tggagtgagc    45780
taggactgca tcactgcact ccagcctagg caacagcaag accacatctc tctctctctc    45840
tctctctctc tctcaaaagg cagtgaaata acgacttatt tggggaaaaa ataaaggcag    45900
agaatttgtt gccagcagac tagcataaaa aaaaggaagt ccttgaaaca gaagagaaat    45960
gataaaagat ggaaatttgg atatatacta aagaatgagg attgctaaaa gtgacataca    46020 tagataaaata tgaaatatat ttttatttta aaatttattt aaagcaaaaa taaaaataca    46080
tcatatttat aacatagaaa taaaaaatgt atgataatag cataaaggat aagtggacaa    46140
atgctgttgt cgtattttg gtaaaatgca ctattattg aaagtagacc atcgtgaatt     46200
cgatgcatat tgtaaaccaa atagaacact aaaaaatgaa aataaagaga tatggctaat    46260
gtgccaatgg tggagataag atagatgcaa aaaagaaaa acattcaaaa gaaggcagag    46320
acagaggaaa aaaggaccaa agatcaaatg agtcaaatag aaagcagcta aactagcaat    46380
atggcagatt taaatctagc catgtcaata gttatattaa atgtaaatgt tctaaatacc    46440
tgaattaaag gatgaagatt gtcagattag attgaaaaag catgacccaa ctacatgctg    46500
tctgtaagaa attagaaaaa gaacaaatta aatccaaagt aagaagaaag gaaatagagt    46560
```

```
agaagttagt gaagtataaa acaaagagca aagaaaatca attaaatgaa aagctggttc    46620
tttgtaaaga tcagtaaaat tgataaattt ctagctaaac tggccaagaa aaagaaaag     46680
acatacaaat taacagtatc aggaagaaaa acagagaatt caaaggagtg taatgcaaac    46740
tttatgctag taaatgcaat aagttagatg gtatggaaaa aaatgtgaac aatacaaagc    46800
agactgtggt tgcctttggt ggcagtagcg gggtgggagt ggaaggttga attgactgga    46860
accagaagca caagtgaact ttttggggtg atggaaatgt tttgtatctt ggttgcattg    46920
atagttaaat ggttgtagac attgcttaaa actcactgaa cacttaagtg ggtatgtttt    46980
attatttgta aaatatacct caaaagcagt tttaaaaatg tattcaagta catacttaag    47040
atctttgcat tttactctga gtataccttaa attttaaaat ctgttttta aaaagtatta    47100
tgtagatacc ttttattttc ccaatgtctt tattaaatga catctccacg ttttgcttct    47160
tacctctatt ttttttttt tatttctctg tctctcaggc atgcacacac acacaccaaa    47220
aaaagtacat atgcataatc cttttggctg aataaaatca gttgcaactg ttatttcggc    47280
ccttatttgc tccgggtaaa tattcgttag ctgagtggtt tatctgtatc agatatttct    47340
tacatcttca tccagtcaca ccagctggac tgaccagatt gttttcact tcaagggcag    47400
aatttgtact cactgctgaa tgcttccaaa tgatacgtag aataacaaat ttaagactta    47460
gattttact ttttcaggtc tttttttttt tttctgtgct gtatagcatt tccctgaaag    47520
cttaatctca tctgtaagtg atgcagtgga tgtgttacta ttggattaat ttatttactc    47580
ttaggtaggt ttgtaatctg tcatcatgct gttgtttttt tgtgtgggtt tgttttggt    47640
tttgagacag ggtctcactc tgctgcccag gctggagagg ctagagtgca gtgatgtgtt    47700
tatgggtcac tgcagattca atctcctggg ctcaagtgat cttcctgcct caaccccttg    47760
tgtagatgga agcacaggtg cacgccacca cacccggcta tttttttaaa tgtattgtag    47820
agacgaggca tcattttttt gcccaaggct gatcttgaac tcctgggctc aaacaatcct    47880
cccacctcgg ctcccaaagt gctgggatta cagatgtgaa ccaccactcg agctccatca    47940
ttctgttatt agttgttctc tagtatgagt caaaaactct tacctgccct tttacagttt    48000
tataaataag taagcagaat agcagaatgt ggacatttttt taaatccaaa ttgaatatgc    48060
acatgactca aggagtcaaa tagtaccgta atcggtttat gataaaatcc agtggtttgg    48120
ctgggtgtcg tggctcacac ttgtaatccc agcaccttgg gaggctgagg caggtggatc    48180
acctgaagtc aggagtttga ccagtctgg acctacatgg tgaaactact aaaatacaaa    48240
attagctggg catggtggtg catgcctgta atcccagcta cttgggaggc tgaggcagga    48300
gaattgcttc aacccgggag gcagaggttg tggtgagccg atatcgcatt atttcagaac    48360
aattttccac aagatcagtg agtgctgtcc aatagacata taatacaacc cacatacatg    48420
actttacatt ttcttgtagc catagtagaa aaggtcaaaa gaagcagatg aaattaatag    48480
cctgggcaac aagagcaaaa ccccatcttt taaaaaataa aataaaatat ggtggtttgc    48540
tgtccccacc tcagaccatt tctctggtct ttctcattga ccaccactcc caatctttgt    48600
tctgctgatt gattacagct tgtatatatc tccatatttc taagcaaaat gtttatcttt    48660
tttaaattta taaattcttt ttattattttt tcagagacag ggtcttaact ctgtcgccca    48720
ggctggagta cagtggcacc atcgtagctc actgtagcct cgaactcctg ggctcaagca    48780
gtcttcctgc ctccgcctct caggtagctg agactacgct acaggcacat accaccatgc    48840
ccagctcaaa atgtttatct tttgatacat tattcgagac cattattaag gtggatgatt    48900
tagttttctt aaacagccat cccctttctt ttcctcccct ctgcttcacc gcccccattt    48960
```

```
tcccaatgtt ttacctttg gttaaatcag tactcattgt ttacattatt tgcctctgca   49020
catagtcaca gatagtattg tactgtactg tactgtgttt cttttttaaa cattatttct   49080
gttgttaata attgactttt taattttttt cctattttgt tttttaaaga gatggggtct   49140
tactatattg cccaggctag agttcagtgg ctcttcgcgg gcatgatccc actgctgatc   49200
agtacaggaa tttccacctg ctccatttcc aacctggacc agttcacccc ttcttaggca   49260
acctggtggt cccccattcc cgggaggtca gcatattgat gccaaactta gtgcggacac   49320
ccgatcggca taacgcatgc agcccaggac tcctgggctc aagcagtcct cccgggctca   49380
agcagtcctc ccacctaagc ctcccgcgta gctgagacta cagacacttg ccaccacacc   49440
aggttaattt ttgtgttttt tgtagaggtg gggttttgcc atgttgtcca gactcatctc   49500
aaacttctca gctcaagtga gcctcctgcc tcagcttccc aagtagctgg gattatagac   49560
gcatgccacc acaccccatg ataattgcct ttttttttaa tttgcataat tttctttgta   49620
gcttttgcta atgttcccat atcttcttat agccttacag aatgattttc cacaagatca   49680
gtgagtgctg tccagtagac atataataca acccacatac atgattttac cttttttgt   49740
agccatagta aaaaggtca aaagaagcag atgaaattaa tagtatcttt tacttaaccc   49800
agttcattca aaatgttatt tcaataaatg gtcaatattt aaaatacttg agatattttg   49860
ctttattta tttcttttgt tactaagtct tcaaaatcca atgtgtattt tacacttaca   49920
gaacatctct ttttagactg gccacatgta gctcagggtt actgtattgg acagagtggt   49980
ttcagtttca agttttttcct tggagacatc ctacttgaaa tttccattct ccatgtatct   50040
gggtggttgg tctatagact tgccactcac agctgtcatc ttgagacttt ctttgctttt   50100
cttctctatt ggatattcag tttcctggat ttcaggtctt ctcatttcc tctagtagtt   50160
ttgttaggtc atggttggta tggcatggtt gggatagcgt gttcacacag ctatctcgtg   50220
agtcatactc ctccaatcca gcctgctcgc ttcccgtgtc tgtcatgtag ttgtcaccct   50280
gctatctctc cctccagttt ttgcagaaat ttcctttgtc ttcactcttg gtcttcctct   50340
cccatccccc atgtatccta tatctttctc tttcttggtt tatttcatca ctcaggtgga   50400
aaagatgctc cagtggatta ctgggaaaag ggggagcatg gatgataaag gtattgagac   50460
cttacacgtc agggaatttt ttttttttt tttttttgag acggagtttt gctcttgtcc   50520
aggttggagt gcagtggcgc caactcggct cactgcaacc tccacctcct gggttcaagt   50580
gattctcctg cctcagcctc ctgagtagct gggattacag gtgcccgcca ccacgcccag   50640
ctaatttttt gtatttttaa tagagacgag gtttcactgt gttggccagg ctggtcttga   50700
actcctactt caggcaatcc acccacctcg gaatgttttt attgtcccctt ctcatttcat   50760
gactgctggg ctaggtatag aattccagaa tcattgttct tagaatctcg aaggcattgc   50820
ttcattgctg gccagctttc agtgttcttg caaagtctga agctgtgcta atcacctcat   50880
cctttgaaag tgaactgttt tttcttccca gaaacttaca gaacattctc tttgtccgca   50940
gaattctggg attgcaatta ctgtgcctta gaatgggtct gttttatca ttatgaagag   51000
tactggatgg gtcgggaggt tttcttgaat tacttcttga tgttttcttt ccttgtattt   51060
ttttgtttgc taattttcta ttttttttc ttggttact ttcttgggca gggggatttc   51120
ttctacttat atttgattct tcagttgagc ttgtcatttt tgctatcttg tttttaagtt   51180
tcgagagaca tctttgtttt atataacatt ctgttcttaa tacatagatg caagatcttt   51240
tctttctgag tatattaata tgtatttgaa atctttctat tctctgcagt ttgtttcccc   51300
```

-continued

```
caagggtttt ttttttttttc tggttttttgt tttttgtttt tatgttagag actttcctgt    51360
tatatctggt catcagtggt acctgcatgt ggtggagagt aggggcttat tggagtatga    51420
gaaccttgag caggtgtaag gagcctgtca acactgcgct ggcctcaggg cctctaggga    51480
ggctgccagt tgtgcattct gaggatacct ttttggttgtg cctttttgtct ggtcagatta   51540
tctagagatg ctctgcctcc tacctggagg agaagggtct agctgccagc ggtgtgagtg    51600
tctcttgggg aaaaggactc gagttcctgg tgtttggctt gtgtatggcc gcttacccca    51660
tttttggtgg agcgctcaca tcttccactg tgccaacagt cttgctgcag ttcatagacc    51720
ttctggttta catttttcca gaaagtatgt ctttagattt ctgcagaagt ctgaggagca    51780
tggaaggagc ttggggaatg agatggcaat ccaggtcttc ccagatggct ctacctttat    51840
cccctgcagg gaatcccact cctccttcct gactgggagc acagccagag ccttgggagg    51900
aatctggagt ggaaatctcg ggcggtctgg ctttcttact gttcacttgt aattttgctt    51960
tctcacaact gccaaccact aatcagcctg atttccagct tccagaattc tattgctgtt    52020
gtctgctctc ctattcccac cgtaggggat ggggctgtct tttttttttt ttttaatttt    52080
ggtaaaacat acaaaacata aagtgttcca ttttagccat ttttaggtac acagttcagt    52140
ggcagtaagt acattcacgt tgtgtgtatt tgtttttta gtaataaaca atataaaatt    52200
ttttaagtaa taaacacaa ataaaagatt gtttaatgtg attatcgtgg aattttaggt    52260
gtgatcagga gccatggtgt agtcttctgt tgaaacaggg tgataggatt tgtttaccac    52320
ctcctaggaa agcagttgga tagtttgttg gcataaaagt acattttatc tatttttaat    52380
aatcgtagct ttatagaaat tgcagttgga actcccaggc ctggcattca aggctctctg    52440
agatctgggc tacccaccca tgtcctccag ccgtctgtcg cacctcctac tgcccactca    52500
ctgttcctgg catgagatgt gatctccagc ccccatgcct ttgctgtgca gggtgttcca    52560
gagtgaattg tccctcctgt ctgtctctct gccctcttcc tcgtcttttcc atcttcctgc    52620
cccacatcac tgcctcctac ccaaggcctg tgctcattcc tcctcggttt tcccccatgg    52680
cctggtacat acctctgaat tatcaccttg catttcccat attgcccggc tctctttgat    52740
gtctgttttct ttgctgggtc ttcctcagtg tctgacggtc agttaaatgt ctttattctt   52800
ttttgtagga tatccgacat gaagccagtg acttcccatg tagagtggcc aagcttccta    52860
agaacaaaaa ccgaaatagg tacagagacg tcagtccctg taagtatcca cgtgccggt     52920
accagtcttg ctcttccttt gctgcaggcc ttttagtca agactccttt cgcctcaggg    52980
tttagtataa taataaatca atgtagcaga ggtttatgac gcgattgttt cctatagtaa    53040
aggcattaga gacttatagt aatagctcat ttttccacca ttatagaagg gctcaggttt   53100
cagtttctgg aaaattcagt gaagttcaaa gcacttttct taagctttga ctgttttgt    53160
gatgaatcat tttcctacca gctgaagcag agtatagcag gcataataaa acctttctg    53220
gatgactcag cagcagcgtc attagggcat gagcactgtg ttccgctgta atgaagcccc    53280
gcacaggcat tcgggtgggg cactgtcgtc ccctgcgctg aatatgcaag gcagctctgt    53340
ctggagtccc caccgcctcc accccccgcca acctcatcat ttttctccct ctttcctgct   53400
gttagttctt cctaggattg tcagtgtgcc tgctggcctg tggcagccct gtccgccttc    53460
tgagtgattg gctgtcagtc tgccggtagc tgaaaagtaa ataacttaac atgttagaat    53520
ttgcataaag taaggaaaac tggagctgag tacaggactt gaactgcgcc atctcctcta    53580
ggccacagag gcctttttga ccccctttcca ggtcttttaga cattgtcagg cagtgagggg   53640
tcgtagctgc cagtgtctcc atggtagcgt gctctgccag ggatgcagaa gattctccag    53700
```

```
tcattcctcc agtgggcact tcctgcaggt cctgtgccca tggctgggag tggtggctgt   53760
cattgttctc tgccagaagg gttagcagtg catcctgacc tgacttatgt ggcgcccaga   53820
ttcctggaag gggtctaaaa atggacctag acttggtgta gaacgtgtgc ctcttggcct   53880
gccaccatgg ttccctgcct ggttttgtgt gtcagctctg ccgcttaaga actgagtggc   53940
ttcgggcaag ttgttctctc tcataggagt gtgtgaagat gaagcaacat aagctgctta   54000
gcccagcgcc cagtacctca cgcagacata agtgctcagt aaatgttgtc tgtggtgggg   54060
atggttgtca ccaacatctg aagtgcactt ctaggtcatc aggtgacatg attggcgcca   54120
acacatggta ctcttgattt agcacatctc agctgaggca cctcattgat atttgtttaa   54180
aaacaaaaac aaaaaacctt ggtgattctg ctgtgaagtc ctggccagaa acctccagac   54240
cgctgatcaa cacgcaacag aaccatcacc gttcacctct ttgacatggt gccaggatac   54300
cctggatctc tagcttttgc tatagttgct ctaattaggg aataatcttg tctttaatat   54360
tcctttgcta cattttttaa catttcttat ctaaatggtt ttatgaatca gttttacaga   54420
gaaaaaaaac cagtatttaa aatattcttc caggggctgg tccaagtaca gtagtgttta   54480
caactatgtg atcacaacca gttacagatt tctttgttcc ttctccatcc ccactgcttt   54540
acttgactag ccaaaaaaaa aaaaaaaaaa agttattcca gggaaacaat tctccaactt   54600
tttcactccc aatctcactc ctcttatctt cctcccgtac tcctatcctc ctcccgtact   54660
cctatcctcc tccctactc ctatcctcca gtagaaacag tcatttgctg tgaaggttat   54720
gggggagaat gagtcaaggt agaaggtcac ctgctgccca gctcacagtg ctgctggtga   54780
tgacagcagt ccacagttac aggcacttgc tgaacgaggg gctctgtata cacctcagct   54840
cattgactct tcccacaacc ctcttgtcac ctaccattta gcaaatgaaa aaccaaggc   54900 tctgaggtga gttgtttgcc cagagtcacc cagtgctgtt tgaacccact cacataacca   54960
accaatacca ttatgtaatt tttgaggtct tttatctctg tgatccactt aaaaattatc   55020
caagtatctt tatttgtact aagcctccat aatgagaaac agtgttccag atggtggcta   55080
gttttcaaag acatctctct ttggaattct tctttagaac aaaaagcccc agaccactta   55140
tccccattca tatccccttt ggacctaggg agaaggtact atttataggt gatcacctga   55200
gtttattgtc ccttgtgctg tgccagaaat aaaggtcccc acctgctctt attagctcta   55260
ctaacaggat aaggaaagtg gccctcagag agctactgct tttgtgacaa acaaatgata   55320
caagaaaaaa aaagtggctt tttaatttta gtgacctggg gcaggacttc caaatgaaag   55380
tttatttcta aaaactaaaa ggtaaattta atatactttc agtgtttggg cttaaattct   55440
ctttcaagtg tctttgtgat atgctctgaa ttttaaaaat ttagaatcat tgaagttcat   55500
tatacttgaa ctttaaaaaa aaaaaacaaa acctcgtat aaaggtcaag gtatgacttc   55560
atgctgctgt gtacttaggt catttaatct tcaaaccact ggatagaggt taggttgaag   55620
ttcgatctta aatcctacct actgtagctc attgtaccag caacagctgt agggactagg   55680
tggaattcat ggtgggtttt gttccctttt aaagattgaa gccaccatat tttctgccct   55740
ctaaaagttt atgtcagcca ggcatgggtg gctcacactt gtaatcccag cactttgggg   55800
aggctgaggt gggtggatca cttgaggcca ggagttcgag accagcctgg ccaacatggt   55860
gaaaccccat ctctactaaa aatagaaaaa ttaggtgagc atggtggcct cgcctgtaa   55920 tcccagctac tcgggaggct gaggcaggag aaacatttga atccgggaga tggaggctgc   55980
agtgagctga gaacatgcca ctgcactcca gcctgggtga cagagtgaga ctcttgactc   56040
```

-continued

```
aaaaaaaaaa gttatgcatc agagaacaga tcctttgatg ccctcctctg ccctgaaagg    56100
tttttggggg agagtaataa gtatcacaac aagatatgac ctgagaacag atttcccaga    56160
taggacatga tccatgtttt aatatggctt actgctgttg cttcatagtg tgaagcttca    56220
gacacttctg aaaacccttt cagaaaatcc cagtcgcccc atactgatga ctaatctcaa    56280
ctaaaacagg gcttcagcca gtgtgaatgc cactaatgcc accaactcac ctttgctttt    56340
ctgtagggtg tgcacctgta tgtacacatt cagcttttcc gggattaacc tctgagttct    56400
ggtttgtctt tcagttgacc atagtcggat taaactacat caagaagata atgactatat    56460
caacgctagt ttgataaaaa tggaagaagc ccaaaggagt tacattctta cccaggtaag    56520
cagattgtct gaattttcta tttaatgtca atttaagagt ttgagagtgc tgttatccac    56580
acctcaaata aaatctgcca catcctttag aaggtcagga tttcagcata ccaaaaagca    56640
gcaaggaagg gggaaaaatc atccttcaaa ggttcagttt ggttataagg aacgctaatc    56700
ttttctggga agcataagat gacattgctg gaaatgagag cttatagaaa acaacattaa    56760
aatgccagag ttgcctgtgt ggtctgttgg cagagacagc agagccatgg ctggaggagg    56820
gtctgtacct gtgttgcttc cagaagtatt tgtcgtagag cacttgtgat ggcaaatcta    56880
agaacgttag cagtagacca ggaatctctg tccagagcca ttcagagtag ctcagcatgg    56940
ttctcattct ttggccagaa gaaaggcatc attggatcat gtgaacaagc atgaaaaatg    57000
acttaaaatt tctgttggct tttggcatct ttatggaaac aaaatcctga agtggttta    57060
ataattgagc ctcttgtaaa acactcagtg gcatgtgacc aaaagggtat ctgggaaaga    57120
ggataaaaag agtttctttt taattaatct tctcaagtct taacttgtta cctgtaagtt    57180
ggtctaaaaa gactgggttt cttatttttgt ttttcatcat aatttttgtt tctcattcca    57240
tgtcagcttt cagtcttata tggctttagg ccacagggcg attttgaaca tttgtaattt    57300
tgcttaataa ttaggaaatt aaaattctgg ggaagacaga atgctctatg aagaaaggct    57360
gctttgagca aggagctagg tcagggcgcg ttcaactgag gcctttcttc actgcctttt    57420
tgtcttgtcc cagttcctcc ccatttatga ctaaaatcag cccagatgct tctcgtcatc    57480
tgggatgcag agcatcagcc cagctgtgtt cagtcctatg gggccattga gtaagttctt    57540
ggtgcatgga tacagggcag gccttttacca ggccctgagc ccctggtcct cccagcacct    57600
ctggggtatt taggggaggc tgatggggga ggggttgat aaggcgggag atgtctgggg    57660
atgaggttga ggcaaaagtg acttcttgag gactttgctt tttggagaag tcaaatttcc    57720
tacttcttga tttcagccct tcaactctgg tatggagtca ggaagccctt taaatacctg    57780
ttgtcgggtg tatcatgtca agtgttgcat tagcaaatga ccatgtatcc ttgtgctact    57840
gtcctgccta ccccgcatcc tagcgcttcc ttgggacatg agaagctctg tctggtttgt    57900
gaggtggcac tggggatgtt gagaaactgt ttacacagtt tcccttttgcc ctggggattt    57960
actaaaggag tcgaggcagc ctgaccccaa agcatcaccc ctggacacta tgaccgaaac    58020
atttccccag tgcccaaacc aagaacaccc ttcccatttt tttttcagtg gtgttcatta    58080
tgtaataata caagtctctc ttctcatttt ttaaaagtca gaagtacaga agagcagaga    58140
ataatgtcca aggggccctc cttcacctcc ccgtgcagt gtcagctaag tgtggtgcgt    58200
gtccttgcag atcttagggg attgtgatcc ttcagaccat tctaaactgg ggtggtgctg    58260
ggagttaggg aaggcatgaa gggagtagtg gagagctgca gtgactgggg tcttcatgcc    58320
agggtggaga atgcaaggcc caggtggcca gccatgtgcc acgggatttc tggctgccaa    58380
gagctgttta tctgttcact ggggagggaa gagttaaatg tggtctgctt ttctccgagt    58440
```

```
cccttcagca cagggagtgc tgacttgtct tgttcaggta gtaagttcaa gatgagctca   58500
ggaaagaaag tgagaggaca ctgagggcta gtggttgagc caagtgtgat gggacttaaa   58560
gggagaagat ttaaagaata aggagcttat gggccgggga cggtggctta cgcctgtaat   58620
cccagcactt tgggaggctg aagcaggtgg atcacttggg tcaggagttc gaggccagcc   58680
tggccaacat ggtgaaaccc cgtctctact aaaaatacag aaattagctg ggtgtggtag   58740
tgtgcacctg taatcccagc tacttgggag gctgagacag gagaatcgct tgagcccagg   58800
aggcagaggt tgcagtgagc caggattgcg ccctgtact ccagcctggg tgatggagcg   58860
agactctgcc tcaaaaaaaa ttaaaaaaaa ataaagaggt taggtgaaaa tagatgagaa   58920
tggaaaccat gagaagaagt gatgctggcc aaggacatga caggttctga tgtggaggtg   58980
ataggcaatg tctcttccag ccactgctaa taattgagac aaactcaagg cattcatacc   59040
ctgtgtccag taaacatctg tgcccattgc caggtgagct ggattgaaat gggccagctg   59100
ctcagcagac accctcatgc cccagtgact ctgttcccct tgggccacct cattgaccat   59160
ttatgtttct acatctccta agtttgttgg gccaaggatg gaggctgtct gccgtcaggg   59220
tcctcattgc tgatggtagg aatagttgct gatgtttcat tggatgttgc tgtattctag   59280
ggactgtgct aagtacttta tagaaatgaa catacttcat tttcacagtt ttatgaatag   59340
ggactattat tagtcaagta agcgatgggg aaactgggggc agggagcgat gaagtgactt   59400
gcgcaaggtc acaagatgat gtgattggaa ccaagagaag tgttgtggtt ggccacgccc   59460
ccacactgcc tctcatctgc accaaggagt tttgtcccat agcccaaggg ccttggggac   59520
gaatctcagt ggaggccctt agcgggcctg cctgagccag aaagcagaat cggcattttt   59580
ctgtccttgg ttggcccagc cctgaactga gatgcgaaaa tcgccttcg ctgcctggta   59640 gaaaatggag ctgcagttac tgaccaccag gcagagagag gtgggtccct gtcccagcct   59700
cagccaccac tctgcctaag ctgtggggac tgagggcgct gtcgttagct gactgcagaa   59760
ggtgagcaca cgctgtagca tgttatgttt cagatgtcac atgttgtgtt attgtgtctt   59820
tgcagggccc tttgcctaac acatgcggtc acttttggga gatggtgtgg gagcagaaaa   59880
gcaggggtgt cgtcatgctc aacagagtga tggagaaagg ttcggtaagt ctcggcttca   59940
tttgctgtgt atgtgatcat gcataccact ccatatagtt accattttcg tccagatttt   60000
taaattattt ttcttgcctt tgtatttcct ttacgtagta ttttttattta aaaaaattaa   60060 aacagcagca tataaatgca tgttggttgt caaccagtta atgaagtgaa taaaagggag   60120
gaggcggaag aactgcacgg acctcttcgc ccccgccttc tcctgtgtgg tgcgtgtggc   60180
gctccgccca cctgtgctgc ctgtgcggct ctcatcacag tgtggagttg tgtgtggagt   60240
tatggagacc tgcttttatc ttgaaaagca agttcttagt gcatcttcat ggtgtctgat   60300
tttttggctg gtgagagtgt ggctacctct gcggagctgt gggagcggct gactagatga   60360
gatttgcctc cattcagtac ctagactctt gccctgccac acctcttcgg agtgagcatt   60420
gacttcagga tgtgtgtcat tctaagttcc tgcaacttt caaacacccc tcgggctagc   60480
gtgtggctgc acggtgtcca tttgtgcagg ccaccactcc tcttgcatct gggtctagcc   60540
acctctcctt cttgacttac catagttcat tttgtaccat gctttcagaa tgagctttct   60600
caaatccaag tctcaccacg gttcttccca gctgaaaacc cttgtgcggt tccctttgcc   60660
tcacaggata atacatggtg tggcttacgg aaccctgcag gtctggccct aggcccctgg   60720
acacagacct ctcaccactc ttggaacttt agccaggaca aagttttctg tttttagttt   60780
```

```
cttaccatgt tctctgggcc gaggagtccc agtgcccacg ttcatcccac ttgcaggcac    60840
ccctggacgg ctgccccag ctccccaact gcctgcattc tccctgccc tcctcactct    60900 gttggaatag ctgagaatag ccgatttctg ggcagccggc ctcctgtgta gactgtcctg    60960
tgtagactgt cctgtgtaga ttgtctgtgt agactgtcct gtgtagattg tctgtgtaga    61020
ctgtcctgtg tagactgtcc atgtaaactg tcctgtgtag attgtctgtg tagactgtcc    61080
tgtgtagact gtcctgtgta gattgtctgt gtagactgtc tctgtagacc gtcgtgtata    61140
gactgtcctg tgtagactgt ctctgtagac cgtcgtgtat agactgtcct gtgtagactg    61200
tctctgtaga ccgtcctgtg tagattgtct gtgtagacca tcctgtgtag accatcccat    61260
ttagaccatc tgcctgtgca ggcgcaggcc agtgttcagc agggccacag gctcctcggc    61320
ctccctgccc tcgctgctcc ccaacactgc caaccctgct gcgggtccca ggaggagatg    61380
ggctgaggat cgtggagacc agcaggagcg tgtggcccag gagcagggaa ctgggtgtcc    61440
ttgggccttg ccaggtccag gctcagctag gacacggctc tcacagctgt cctggttgcc    61500 tccgccaca gaagaaggtg agggctccag agaggccacc tttccaaaaa agcacagtc    61560 atggccctag aatgtaaaaa atccaagtgt taagaaggaa cacatcaaag gaaacttcag    61620
cagtgaaaac ttgaagcatt aaccacgaag cctctgcctc caccacacac aaagaaacgg    61680
ctttagttac tcgcagaaag tcttcctctt aggacagcgc gtgtttaaaa tcatagggggt    61740 ttggtttgtt ttgttttggg gttggggttt tttggggggtt ttttaccctt gcctactttt    61800
taaaaaatga aagtgtttat ttgcccaaca ataacagaca gggagcttgc ctaagtgttc    61860
tgttgatgat ataatgtatc ttgtcttaga aaaaaacttt ttcagtgaaa ggtggttttt    61920
aaattttttc ttccctcctt agtagcttga ttagtaaaat gtgaagttac aaatgtgaag    61980
caaaccccca cccttcacca ctagtcagca attttgagta aagaaacaaa gcatcaggtg    62040
ctcacagcac acactgtctt agagggaagg ggaagcctgg tggcctgtgg aagccttcag    62100
catagctcca tctgcaggct tctgaccctc agcactactg acacttgggc tggatcattg    62160
tctgctaggg atccgggcag ggagtggctg tgctgggcgc tgtaggaagt ttagcagcat    62220
ctctggcctc tatccaccag atgccagtag cacccctcc ccagatgtgg cagtcagatg    62280
tgtttctgtc tagactccag actttgtcca acgtcccctg gtaggccaaa ttgccccgg    62340 ttgagaacca ccgctctaga tggtattgag ggttgggaat tttaaatcaa gacatttatt    62400
cagaaattac cagatatagt agcatttgct tcttatttat ttctttgttg ctaagtgttt    62460
ggcaaaacct ctttgctgtg agcacaaggt ttgctttagc aattgttgtc acattacagc    62520
aaggagtggt gtccagcgct gtagttatgt atttgagcag tgtccagtgc tgtagttatg    62580
tgttccagcc tcaccaggcc ctgtgcttca ttgtctccca ctcaagactg accacaaatg    62640
gcccacagat ccactgtgac aacctttccc tttgggttac tgtggtggca tcgagaacat    62700
ggctggttgg ctttgctgta gtttactgtg ataactgtgc cagcagtccc tgctttcctt    62760
tgttaagtat cccattccac tggaggatta cttgggcgtg cagattggca tgaaaagcaa    62820
tgtatggttt gagattgtta agtttctttt gggatcaaca ttttcaattc tgtatcagca    62880
ttatccctcc cagagggctg gctgggagaa atcatgagaa gttacagtat cttatttgct    62940
cagctaatct aattataaat gatccacaca gcttgtggta aaaccagctt tgggggagtt    63000
ttcatttaat gcatacttgt cttctgattt ccttccttca ccaaatagtg taggatgctc    63060
cctcttattt ttggcaaaca tgcctgttat cttttgggac cctgggcttc ctggaaacca    63120
gttatgcaga agatgattgt gtgtgttaga ctggggtcat ccagatggct agagttctca    63180
```

```
ctggttctgt ttaaggattg actttagaca cctcagtgta ggctgcacca tggcgtaagg   63240
gttgggattg ttgtttagaa gggggaagta agcaaggtga gtttaattgg ccattgcaga   63300
atctcacccg tatctccctc ctgaaatcct cactaaagct gccgtttgct ttcaggtgct   63360
ttcatgcaca agacactgca ttttgtatca cagggtccat ataattcatt tttctctcgt   63420
acttagttct ctgtgttaag aattacttac ttagttctct gtgttaataa ttttggcga    63480
aaccaaatta cccgtcacag ggttactgta gatgtctttc ataggttttc caaacaccac   63540
ttgcccactt gtttgggaag gccccaagga ctgtttaaca tctgccttca tggtggaaac   63600
agcaactatg agagatgcta gcatgttggc actgccatgt tcctctggta ccagcccaag   63660
ataggactca atttgaggcc tggtgaagta ctgtgttcta ataaaaatcc atctactttt   63720
catggccgta tatatcaatg taataggta actggaaatg tgatcttgtg ccttttaaaa    63780
attttgtgtg tttaaaacaa aaatttctat tggaaatgac agagcatagc ttgttgctgt   63840
agacacctga gagtccttaa aaataaatat tgggttattg acacttagtt gcatgacaga   63900
attcctcact tgtacagttc caaagtctta gtctttaccc agattacaga gggttattaa   63960
gcattaggtt tggttttgaa agtgagtgct tgctgtctgg aggtgagctt taagactcgt   64020
ctgccctgct tatgagatga ggaagggtgg cctcttcctc ctgcatttct gttcttcgct   64080
tccttctctg tctgctcact ctgtggaatg cccaccccag cacgggtggg gtggaacctg   64140
tcagatcagt ctcttgtttc tggggtcttg aggcattata agatctagtt gttagaagtg   64200
tgggattaat tcatcttttc acattcttct aagttcctgc ttttagctgc cacacccact   64260
ttggctaagt gggggtcttg ccatgtaatt agcgcctcca tgccaagtgg cagaattgct   64320
tcaatggtga cagattgtcc ccattcaaga gttcactttt ggcaactcat cattgatcca   64380
ggaaggtgac atggatgaaa ctggctaaga cttcagacag gcttgtgtcc agactcttga   64440
gaaagctctg ttggcttctg gtctggcact gtgaagtttg ctgtgatgct ggcaccacaa   64500
cctggtgttt cctaatttgt ttctcccaca ttttgctttg gttttgtctt tgggcagct    64560
tccagctcca gtagagcagg accaataggc atttgtggtt ctatattcac cctcctcacg   64620
tgcttcctgg ctcctcattg cccccagatg atgccacagg tccctgggcc tgctgccagt   64680
cgtctgtgat ctgggcctct gctggcccct tctccagctg ctcttttcag cctcttattt   64740
gcagtcactg cctaggaaat cctagtcatc cttcaaaacc tgcctcttgc acagagcttt   64800
ctctgatctc tcttttctgt aaccttggct gacctgaaac atttccctct tctgaattcc   64860
tgctgcatgt ccgtagcatt tcccctcag ccctccccca tagtccacct tgtcactgct    64920
gggcacagca gtgtcttctg acagacagct ggccctgaag tggttcccct cacccacacc   64980
atcctttgcc ccagaggagg tattgagtgg gtcagtgcac gtgaactgcc agtgtcattt   65040
gccaaagagc tgttgacaca cgctgacatt tcttttgctg aaaatcataa gggctttgag   65100
cttccctctg tccaggcaca tggtcaggct gaccggtag ctctgcccct gctgacctgc     65160
cattttgtc cacaacagtt atccatgagc agaaacattt gtgtaactga ggcagaaact     65220
tagttcaagt aaaatgtcac taaattcgag tcagtttttg tcttagaccc taaatgaaac   65280
caaattttca taaattttct tgttttaaag aaaaatttaa tgagctacat ttaaactgag   65340
aacatcagat agtgtctgag attatcaaaa tagaacatca aaagtatttt tctgaatgaa   65400
ctgaaccaaa ccagaatgaa agggcaagcc ctggggagcc tgtctccaag ccttctctga   65460
aagggagtct gtatttggtg ataactgctc agcctctcca aagggcctca cctgctgtct   65520
```

```
ctcccagttt tatttttaat tgcctgtgag ttttctgtgc agggtaaggc acctacattc   65580
tatgccagca gcctgatcag gtcctgggta atgtttgaaa tggctacaca gaggagtttc   65640
aaagcctttt gttcaatctg gcttcacctc gtagacggtg agaaagcgtc agagccctgc   65700
aggatcccgt tgccacgttt gaccggggag ccgatgggtt tggaagtctg agccctgtct   65760
gcacaacctg ccccggtcag cagcttcgtg cccccacccc catctcccca tgaggcaggc   65820
atctgtgctg accatggctt ccatgttcag aaaccccag gcctttgagt tatcatgaag    65880
cttgtgggat gtgctccaag cctcctgcca tagaaaaact gccatattgc tcacaataat   65940
tcactattat ttgtttcccc agttaaaatg cgcacaatac tggccacaaa agaagaaaa    66000 agagatgatc tttgaagaca caaatttgaa attaacattg atctctgaag atatcaagtc   66060
atattataca gtgcgacagc tagaattgga aaaccttaca gtgagtatag cacacacttc   66120
agcacttcag gcggctactg gttcacatgc ctcttccttt atcccttggg tgatattacc   66180
taatgtcagt gttcctggct tttgtatacc ccgagcaaga tgtggtttgg gcactgtggt   66240
gagcggagct tacttgtgta cctaccaagt gcccagggag ggtggaggcc acagtgctct   66300
ctctgacctt taacaacagt taacaccagt tcttagggaa aggagagttt cttacccaaa   66360
agactggttc ctgcttgtgc agctgcagag ggactgagc ggcagcctgc aagtcccagt    66420
gaagcatgct gccttctttg tggtcctcag tcttcgagtc tgaagagagg gaagaagggg   66480 tatagggggct cactccagtt tcatagctag tgaaagtttt ctgggccagg tcttgggttt   66540
ttttgttgtg ggaagagttt ataacaccag ctacttgctt ggtaaaagtt ggtcttggaa   66600
catggcaagg cattgtggca agcagcactg ccgctgaacg cgctgctcct ggggctttgg   66660
aataattccc ctggatccgt aacttggggg tgttcatgtc attctgggga acagtggagg   66720
gagtgcgcgg cagcacctgg gggcaccagt gaagagtggc cagccaccaa cctctagaac   66780
ctaactgggg tcgaatcctg gccccacctt actagctcat cacagtgtct ccgtttcctc   66840
ttctgtcaaa ctcaggtttt gcgagggttc tgggaggtcc tatacgggaa gggttagcag   66900
ttaccatggg tgtgtagcac gggctttatc tgaagggaag gtggagccgt agggagacca   66960
tgtggagtgg ggctccaggg ctgtgtgggt gggagggat ctgcttctgg gttaccccat    67020
gcctcccctt ctcaagtact actttttaat catcatggct cctgccattc atttcatagt   67080
tgatgtaagc caggtgcggt ggctcacgtc tttaatccca gcacttgggg aggctgaggc   67140
caggaggatc actcgaggcc aggagttcaa gaccagcttg ggcaacatag tgagaccccc   67200
gtctctacaa aaaacaaaa acagttagtc agacatcgtg gtgctcccct atagtccagc    67260
tactcaggag gctgaggcag gaggattgct tgtgcccggg agttcaaggc tgcagtgagc   67320
tatgcttgca ccactgcact ctagcctggg tgacagagca agaccctgtc tcaaaaataa   67380
ataaataaaa aaaatagtag aagtaagatc tagaatgtag cacaggttac caggacgtag   67440 gcaagggggtt cgggctgcct ggctcttgag gatggtagca gtgcagctga tgtgagtgct   67500
ttctgccctc tggtggtgac cgcgccggag tcaccagccc tgccatagcc ctgatggggc   67560
agagggttct gagtacggtg gatggaggtg cttttctggaa gattctcagg agtaacatgg   67620
gcagtgtgtt ggaatgtgct agaggattta tgcagtagcc ttttaaaaga atgcttttta   67680
gcatttgcaa gcctgacatt aagagtgact tctgggaaac tatttgcttg ttgagggaaa   67740
ctgaatttca acagagcaga agagctgtgc gcttttttgct tggcagagtg aatacagcca   67800
gctcagaggt tttgatgtta ggatctgttt gctccaacag actttgtttt taaaaggctt   67860
ttctcagcca tagctgtctg ttctagcaca aggctggaat gagttccttg tgaaagaggt   67920
```

```
gagcaggtgt gagggagggt gtcagtgggc ggtaacccac accttcaagg attaaaggaa    67980
aacttgcatt tggcatgctt gcttcttatt caatttttaaa atacatttta acggccgggc    68040
acggtggcta acacctgtaa tcccagcact ttgaggggct gaggtgggtg gttcacgagg    68100
ccaggggttc aagaccagcc tggccaagat ggtgaaaccc catctctact aaaaatacaa    68160
aaaaaaaaaa aattagccgg gcgtggtggc gggcacctgt aatcccagct actcgggagg    68220
ctgaggcaga gaattgcttg aacccaggag gcggaggttg cattgagccg agatcatgcc    68280
actgcattcc agcctgggcg gcagagcaag actctgtctc aaaataataa taataatttt    68340
ttaaaaatac attttaagtc cttttcttcc ccacctgcct ccacccacca aatagaagag    68400
gtatttcttc ttctttaatg tcattaaggt tatatggata ccattttcta gagaggaaag    68460
aatgatggaa ttgcctagtg tgagtctagc aattatccta acatacacaa atttctcctt    68520
gttctgtgcc aagatactgt atttaatatt taatgaacat taaatattat ttactagtgt    68580
atttaatggc tgaggcaggg ttaaatatgt attatttttca tcccagcaga gttggggggag    68640 gtcctagtaa ctatgccatg agctctgtga gggtgaggtg gtgtctttgc cccgcctcc    68700 ctggcacagt gactggcaca tgattggcat agtgtggaca ttcgtcaagt gaaggaaggc    68760
atcatgagca gatctctggc ctgaatcctt ctgccatcag ctgctcgcca ggtggccctg    68820
gcactgggcc acagggaaac tctccaggct ggtatggttc ctgtctgtgg ctgtcttccc    68880
gggcccatgt taggagactt tcacttccag agcccttttcc ctctcagggc cttgcttacc    68940
aagtgactgg ttcccattta ctaggagctc ttaggtcatt gaagatgttg cgtactcccc    69000
ccagtgaggg ctgccttttg atcacagccg ccagaagcct caaggaagga gcagagctgg    69060
aaacagacgc caggccattg cttctgttcc tctggggcag acccagccac ggaagagaca    69120
ttctgggaca agggctgggg tccaccttttc aaacgtgtct gcagcaggct ctcagcatgg    69180
actctctgcc tccaaacatc cacctcctca tcggaaaatg gatgggagtg cctgcctgga    69240
gcagctggtg ggagagcgca gcgccagcac gtaggacaca ctcggttcat gggctgatgc    69300
cgttcgcatt gactgcctct tcagctgggt gttgagccac accttggagt caccagtctt    69360
tggagaccaa gtctgctact ttttttctcta aagtgacaat cctctgaaac ctccagatca    69420
tcttgaagcc cccgtctgaa agttgcccag agccagtgcc tcacctgctg ttccttgttc    69480 acttttttcac gggaggcctt gcagggcttt atgacaagat tttatgggtg gctgcccagc    69540
atcattgtga ctcgtgagac agagagaaac cagttgtaac catgtagaca gtggaagtga    69600
tagggagaaa agaggtgagg ggactcttca atccgaaggg aaatgaagtc taagcaggcg    69660
caccctgcag gttcagtgtc aagcccaggg cctggcccca gggtgtggta tttgttgact    69720
gggtgtgtgg accctgggag aaagtctgag aatgaatgtt cctcttagag gtagagagtg    69780
gaaggtgact ctgtgtgtac ttggaattag tgatttctgt acagatgatt cttttagaat    69840
catcatgagt attttttctct ttcagaccca agaaactcga gagatcttac atttccacta    69900
taccacatgg cctgactttg gagtccctga atcaccagcc tcattcttga actttctttt    69960
caaagtccga gagtcagggt cactcagccc ggagcacggg cccgttgtgg tgcactgcag    70020
tgcaggcatc ggcaggtctg gaaccttctg tctggctgat acctgcctct tgctggtaag    70080
gaggccctcg cgggtgccct ggggagctcc tctacctgct ctgctgtgat gttttttcct    70140
aagtagaaac tgaagcgctc ctcttccaaa atacagagac tcactgtgtt agtctgtttt    70200
tgcgttacta ataaaggcgt acctgagact cggtaatttg taaagaaaag aggtttaact    70260
```

```
ggctcccggt tctgcaggct gtacaagcat ggcaccagca tctgctcggc tcctggggag    70320
gcctcaggga gcttccagtc atggtggaag gtgaagggga gcaggagcaa gagatggggg    70380
aggtcccaga ctcttaacca gctctcttgt gaatgcattg cctcagggag ggcaccaagc    70440
ctttcatgag ggacctgtcc ccctgaccca gacacctccc acccagcccc acctccaaca    70500
ctagggatca catttcagca tgagattggg aggggacaga catctaacgg tgttattaac    70560
gttgcccttg agaattggac ctggctgact tatatctcct ctctggcttt cagatggaca    70620
agaggaaaga cccttcttcc gttgatatca agaaagtgct gttagaaatg aggaagtttc    70680
ggatggggct gatccagaca gccgaccagc tgcgcttctc ctacctggct gtgatcgaag    70740
gtgccaaatt catcatgggg gactcttccg tgcaggtcag cattgccttt gtttgaatcc    70800
aggtgtgacc atttcaactt ttttgtcttt gaaggaggct gtcagttgta aagttcaaa    70860 caccgtctgg tgtcagggga aatagctacc cttcatgttt aaaatagcta gaaagttgtc    70920
aaaatgttca ccatgttgca ctttgtgcct ttgaagtgct cacatagaga gcattgatag    70980
gaagacgaga ctttatttc aaaagatttc atcttccaag tacatggctg cagccctgag    71040
aggccgagag cccctcgcca agccgtcacc tctgctcatg caaagggatt tcctgacaaa    71100
ccagccgaag tgaacactaa taggacttcc tcttgctgct ctttcaagga tcagtggaag    71160
gagctttccc acgaggacct ggagccccca cccgagcata tccccccacc tcccggcca    71220 cccaaacgaa tcctggagcc acacaatggg aaatgcaggg agttcttccc aaatcaccag    71280
tgggtgaagg aagagaccca ggaggataaa gactgcccca tcaaggaaga aaaaggaagc    71340 ccccttaaatg ccgcacccta cggcatcgaa aggtaatatg attgggtccc agcttgttgg    71400
ggtgagggga aatgactttc tgttctagaa acacacgctg gtactgaaac cctgtggatg    71460
cagcctcctg ttggcaagca gcgcttccgc atccttgggg aacagggcgc gtggaccaca    71520
gccactccac tcctggctgc tggaggtccg gtattgggca cagggtggcc gcaggacatg    71580
agccacttct gtgggcttct agtgccacct tgtggtgctt gttggaatga ggggctcgga    71640
gccaccgagt aggttttttc tgccccccct gacgacagcg ccctccccca ggttccgga    71700 cagtcctgaa atgtgatgtc caggcttgag tgccctcagt ccccacagtg gtcctttggg    71760
gaatgtaacc tttttttatgt ggtcttgatt aaatcccatt ttacttcctt gcaggttaac    71820
aaccattatt gagtacctat tgatatgtgt ggtgtactga gttaactaga acatgtcccc    71880
tggtctgtgt tctagaccat cttgctggga aaaaggcaga cccaaagcat attttggtgg    71940
gggcccatgg acagtgatgt gatagaggtg tccgctgagg tggtcaggga aggctgcttg    72000
cagtaggtgg ccgtgcacgg aaagtttgca gaatgagcag gtgttagttc cagctggaga    72060
tgactgccgg ctgtgccctt ggtacctgct ttctggaggg aagttttaag acgtgtgcat    72120
acttgaccca gcagttgtat acatggagaa atttactttg cagcaactct caaaacaagc    72180
gtgtaaagat gtgtataggt agttgtgttt gttgtggcat tgtttgtagt agtgaaaaat    72240
tagagacagg ccaatgatat aaccagggac ctgatcaatt atgttctctc ccggtgttgg    72300
gatattctgt agctcttaaa gaatgagatc tgggtgtact gatgtggcca gacattgcaa    72360
ttgcagtaca tgagaaggca aatcatacag tagtgtgtac accagtgagt cctccagcca    72420
gataaatcct cacagtgacc agtcgcccag gcaccttgtg aaccctaccc tgggtgtggg    72480
tgctatctga agtacctggg ggaggggggtg acaagtggac ttcaggctga tgtgggccct    72540
ggcctggccc tccctccaag cagaggggggc tggctcgctg gaaggttaac atcatccaac    72600
tctgtctaca cgtggcttgt ttttttcctag aattcctgcc acaatagcag catccttgcc    72660
```

```
attcattttc tccaaagtga gtaacccatc tctgccctct gattcctcag catgagtcaa   72720
gacactgaag ttagaagtcg ggtcgtgggg ggaagtcttc gaggtgccca ggctgcctcc   72780
ccagccaaag gggagccgtc actgcccgag aaggacgagg accatgcact gagttactgg   72840
aagcccttcc tggtcaacat gtgcgtggct acggtcctca cggccggcgc ttacctctgc   72900
tacagggtat gtttccactg acagacgcgc tggcgagatg ctcgtgtgca gagagcactg   72960
gccgctagcc cgatggtagg attcagttct gtggtgcatc tgagccagtc tcagaagaaa   73020
cagatcaaag gttttaaag tctggaactg tggaagggct aacaagagaa ttaaggatcg   73080
atgcactggg gttttaagga gccctctggt cccaagaata taagagtcta atctcagggc   73140
cttaacctat tcaggagtaa gtagagaaaa tgccaaatac gtctgtttct ctctctcttt   73200 tttttttat tcctttgttt ttggaaaaaa atagagttac aacacattgt tgttttttaac  73260 ctttataaaa agcagctttt tgttatttct ggaacaaaaa aaaacaaagt aggcacttat   73320
gaaactttct catacccta ggtgatgtaa tcagccatat aatttatatt tgatttccca    73380
gggaaggaat cccaaacttt tacgaatgta aactcccttg gagaagaggg ttaggacgct   73440
gttgcgctca agcccccctc agctgtgtgc acactgagcc aggacagggt ctttgagctt   73500
tcccactata agaagaacag caacaaaagg ccgtctagaa aaacagaacc tgcctctgct   73560
tctgctcagg gtgtccccgc tgggtttcca ttgtcctttc tccattgctc cctcctgtga   73620
cagccatctt gctcatgtac cagccctcat caccccatcc cataaatgg gtgtcctcga    73680 ggcctctgcc tgggggtcag aggtcaccac agggtggcca ttggcatgtc aacccgctgt   73740
taattcagag aagtgggctc cacctcattg ggagaagtgc catttcagca gaaattcaca   73800
cgttagacgt gtgttgctgt taagtaaggg gaagagagag gactagcctc agagctctgg   73860
ccatggaaat gacctcctaa gacttttttcg tggtttttaaa tattttacct ctttccaggt  73920
ggcatctgag tacatcagat ggttttgcaa aatgcaaaca attttttcct tggggatgat   73980
ttttggggag aggggctac tgtaaaaaat aaaaccaaaa ccccctttgc tccctcggag    74040
gttgaagttg ccgggggggtg tggccgggggt catgcatgag cgacagctc tgcaggtgcg   74100 ggtctgggct catctgaact gttggttttc attccagttc ctgttcaaca gcaacacata   74160
gcctgaccct cctccactcc acctccaccc actgtccgcc tctgcccgca gagcccacgc   74220
ccgactagca ggcatgccgc ggtaggtaag ggccgccgga ccgcgtagag agccgggccc   74280
cggacggacg ttggttctgc actaaaaccc atcttccccg gatgtgtgtc tcacccctca   74340
tccttttact ttttgcccct tccactttga gtaccaaatc cacaagccat tttttgagga   74400
gagtgaaaga gagtaccatg ctggcggcgc agagggaagg ggcctacacc cgtcttgggg   74460
ctcgccccac ccagggctcc ctcctggagc atcccaggcg ggcggcacgc caacagcccc   74520 cccccttgaat ctgcagggag caactctcca ctccatattt atttaaacaa ttttttcccc  74580
aaaggcatcc atagtgcact agcatttttct tgaaccaata atgtattaaa atttttttgat 74640 gtcagccttg catcaagggc tttatcaaaa agtacaataa taaatcctca ggtagtactg   74700
ggaatggaag gctttgccat gggcctgctg cgtcagacca gtactgggaa ggaggacggt   74760
tgtaagcagt tgttatttag tgatattgtg ggtaacgtga aagatagaa caatgctata    74820 atatataatg aacacgtggg tatttaataa gaaacatgat gtgagattac tttgtcccgc   74880
ttattctcct ccctgttatc tgctagatct agttctcaat cactgctccc ccgtgtgtat   74940
tagaatgcat gtaaggtctt cttgtgtcct gatgaaaaat atgtgcttga aatgagaaac   75000
```

```
tttgatctct gcttactaat gtgccccatg tccaagtcca acctgcctgt gcatgacctg    75060
atcattacat ggctgtggtt cctaagcctg ttgctgaagt cattgtcgct cagcaatagg    75120
gtgcagtttt ccaggaatag gcatttgcct aattcctggc atgacactct agtgacttcc    75180
tggtgaggcc cagcctgtcc tggtacagca gggtcttgct gtaactcaga cattccaagg    75240
gtatgggaag ccatattcac acctcacgct ctggacatga tttagggaag cagggacacc    75300
ccccgccccc cacctttggg atcagcctcc gccattccaa gtcaacactc ttcttgagca    75360
gaccgtgatt tggaagagag gcacctgctg gaaaccacac ttcttgaaac agcctgggtg    75420
acggtccttt aggcagcctg ccgccgtctc tgtcccggtt caccttgccg agagaggcgc    75480
gtctgcccca ccctcaaacc ctgtggggcc tgatggtgct cacgactctt cctgcaaagg    75540
gaactgaaga cctccacatt aagtggcttt ttaacatgaa aaacacggca gctgtagctc    75600
ccgagctact ctcttgccag cattttcaca ttttgccttt ctcgtggtag aagccagtac    75660
agagaaattc tgtggtggga acattcgagg tgtcaccctg cagagctatg gtgaggtgtg    75720
gataaggctt aggtgccagg ctgtaagcat tctgagctgg gcttgttgtt tttaagtcct    75780
gtatatgtat gtagtagttt gggtgtgtat atatagtagc atttcaaaat ggacgtactg    75840
gtttaacctc ctatccttgg agagcagctg gctctccacc ttgttacaca ttatgttaga    75900
gaggtagcga gctgctctgc tatatgcctt aagccaatat ttactcatca ggtcattatt    75960
ttttacaatg gccatggaat aaaccatttt tacaaaaata aaaacaaaaa aagcaaggtg    76020
ttttggtata ataccttttc aggtgtgtgt ggatacgtgg ctgcatgacc gggtgggtgg    76080
gggggagtgt ctcagggtct tctgtgacct cacagaactg tcagactgta cagttttcca    76140
acttgccata ttcatgatgg gtttgcattt tagctgcaac aataaaattt ttttctaaag    76200
aacatgaatt tggggtgctt cccatttttt tctttgctta atagagctaa accaggatga    76260
gtaactcctg tttctttcta tccctgctga tgtgaaacag atgttgtcaa tcagctgggg    76320 ttagagttttt ccacttctaa gaattaacct cagcatccct gcattgccag cacctcagg    76380 ctggagcgct ttccttgact gtgagcttgt tgaacacctt aggcctcagc ccatttcctt    76440
cccaaattga cgctttgcct gtgtagggcc ctcagataac ttaacaaact taccagtgtt    76500
gtttgaagaa cagtgttttg agttgtaatc tcaaaccat atcccttacc caattacctg    76560
taagacacaa tggttaccac atctcagtac gtaaagtcca cttgatatag aattgactta    76620
gaaataagac agattagtat agttttttcat ttgtgtacaa aattaaacaa tgtaaattcc    76680
ccccaaagtg attttttga cttttttgaag taattttgga cttgcaaaat gttgccaaaa    76740
tagtacgaag agttccccag taccctcgaa gtttcctcga ctgtttcaaa gctggctgca    76800
ggcccaggct catgagactg ggaagaggac aggctgtggt catgtggacc cacaggggcc    76860
tggggctgca gaagtcagtg tggcttccac catttcaggt ataaaaagg gcatctaagc    76920 tttcaagaag agggaggatg ctctagggca gcggtcccca acctttttctg gcaccaggaa    76980 ccggttccat ggaagacaat ttttttcacag gcctgggggt ggtgagggat ggttttggga    77040
tagaaacttc cacctcagat catcaggcat cagattctca taaggagctt gcaacctgat    77100
ctcttgcaca cattcagttc acaatagggt tcacgctcct aagagaacct gatgctgcag    77160
ctgatctaac aggagatgga gctcaggtgg tcatgctcag tcgctcgcca ctcacctcct    77220
gccatgcagt ccagttccta acaggcctca gaccagtacc ggtctgtggc ctggggttg    77280 aggacccctg ctctaggctg gtactgctga tgcttaaaaa gagagggttt gccagaaatc    77340
agatgggaca aaagggcaaa ggccgtgcca cagagtgccc atatagggga gagcacgcct    77400
```

```
ggagccttcg agagcatgca gagaagcctg gagactgcat ttaccggagc tgctgcctga    77460
ggccaccctc caagtgtccc cacagcgcac acaagacca caggagtgac ctcctcactg    77520
gcaggtattt ggggaaacaa ctgctgtcta ctcttttggg taaaaagtga aacaccaata    77580
gtttaattga aatttcagaa aattgaacat atgaacaagg caaataaata ctaagtaagt    77640
taaaaacaca aaatatgtcc aggaagtatc gatgagaatg ttcaagttaa agttctccaa    77700
tgccattgct acagcaacct caaaccctag gttctctctg cactattaac acagacatct    77760
caggacatgg tttgcttttt tttaagactt aaataggaaa ctaattttc tttctttaaa    77820 gcaattgcgt tcttcagtga actctttctt taggccagtt gatggcttct tagcagttta    77880
ttgacgagat cctagggtag cttccgaagc tgggttgatt gattgcattt gggtgcggat    77940
ggccaaagtg agtggcccta ctgcctgtgc tgctcagggc tcctgggctg atgtggtggc    78000
t                                                                  78001

<210> SEQ ID NO 3
<211> LENGTH: 3040
<212> TYPE: DNA
<213> ORGANISM: Homo sapiens

<400> SEQUENCE: 3
ctcgctcccg gccgaggagc gctcgggctg tctgcggacc ctgccgcgtg caggggtcgc       60
ggccggctgg agctgggagt gaggcggcgg aggagccagg tgaggaggag ccaggaaggc      120
agttggtggg aagtccagct tgggtccctg agagctgtga aaggagatg cggctgctgc      180 tggccctgtt gggggtcctg ctgagtgtgc ctgggcctcc agtcttgtcc ctggaggcct      240
ctgaggaagt ggagcttgag ccctgcctgg ctcccagcct ggagcagcaa gagcaggagc      300
tgacagtagc ccttgggcag cctgtgcgtc tgtgctgtgg gcgggctgag cgtggtggcc      360
actggtacaa ggagggcagt cgcctggcac ctgctggccg tgtacggggc tggaggggcc      420
gcctagagat tgccagcttc ctacctgagg atgctggccg ctacctctgc ctggcacgag      480
gctccatgat cgtcctgcag aatctcacct tgattacagg tgactccttg acctccagca      540
acgatgatga ggaccccaag tcccataggg acccctcgaa taggcacagt taccccccagc     600 aagcacccta ctggacacac ccccagcgca tggagaagaa actgcatgca gtacctgcgg      660
ggaacaccgt caagttccgc tgtccagctg caggcaaccc cacgcccacc atccgctggc      720
ttaaggatgg acaggccttt catggggaga accgcattgg aggcattcgg ctgcgccatc      780
agcactggag tctcgtgatg gagagcgtgg tgccctcgga ccgcggcaca tacacctgcc      840
tggtagagaa cgctgtgggc agcatccgct ataactacct gctagatgtg ctggagcggt      900 cccccgcaccg gccatcctg caggccgggc tccggccaa caccacagcc gtggtgggca      960
gcgacgtgga gctgctgtgc aaggtgtaca gcgatgccca gccccacatc cagtggctga      1020
agcacatcgt catcaacggc agcagcttcg gagccgacgt tttccccctat gtgcaagtcc     1080 taaagactgc agacatcaat agctcagagg tggaggtcct gtacctgcgg aacgtgtcag     1140
ccgaggacgc aggcgagtac acctgcctcg caggcaattc catcggcctc tcctaccagt     1200
ctgcctggct cacggtgctg ccagaggagg acccccacatg gaccgcagca gcgccccgagg   1260 ccaggtatac ggacatcatc ctgtacgcgt cgggctccct ggccttggct gtgctcctgc     1320
tgctggccgg gctgtatcga gggcaggcgc tccacgcccg gcacccccgc cgcccgcca     1380 ctgtgcagaa gctctcccgc ttccctctgg cccgacagtt ctccctggag tcaggctctt    1440
```

```
ccggcaagtc aagctcatcc ctggtacgag gcgtgcgtct ctcctccagc ggccccgcct   1500
tgctcgccgg cctcgtgagt ctagatctac ctctcgaccc actatgggag ttcccccggg   1560
acaggctggt gcttgggaag cccctaggcg agggctgctt tggccaggta gtacgtgcag   1620
aggcctttgg catggaccct gcccggcctg accaagccag cactgtggcc gtcaagatgc   1680
tcaaagacaa cgcctctgac aaggacctgg ccgacctggt ctcggagatg gaggtgatga   1740
agctgatcgg ccgacacaag aacatcatca acctgcttgg tgtctgcacc caggaagggc   1800
ccctgtacgt gatcgtggag tgcgccgcca agggaaacct gcgggagttc ctgcgggccc   1860
ggcgcccccc aggccccgac ctcagcccg acggtcctcg gagcagtgag gggccgctct   1920
ccttcccagt cctggtctcc tgcgcctacc aggtggcccg aggcatgcag tatctggagt   1980
cccggaagtg tatccaccgg gacctggctg cccgcaatgt gctggtgact gaggacaatg   2040
tgatgaagat tgctgacttt gggctggccc gcggcgtcca ccacattgac tactataaga   2100
aaaccagcaa cggccgcctg cctgtgaagt ggatggcgcc cgaggccttg tttgaccggg   2160
tgtacacaca ccagagtgac gtgtggtctt ttgggatcct gctatgggag atcttcaccc   2220 tcggggctc cccgtatcct ggcatcccgg tggaggagct gttctcgctg ctgcgggagg   2280
gacatcggat ggaccgaccc ccacactgcc ccccagagct gtacgggctg atgcgtgagt   2340
gctggcacgc agcgcctcc cagaggccta ccttcaagca gctggtggag gcgctggaca   2400
aggtcctgct ggccgtctct gaggagtacc tcgacctccg cctgaccttc ggaccctatt   2460 cccctctgg tggggacgcc agcagcacct gctcctccag cgattctgtc ttcagccacg   2520 acccctgcc attgggatcc agctccttcc ccttcgggtc tggggtgcag acatgagcaa   2580
ggctcaaggc tgtgcaggca cataggctgg tggccttggg ccttggggct cagccacagc   2640
ctgacacagt gctcgacctt gatagcatgg ggccctggc ccagagttgc tgtgccgtgt   2700
ccaagggccg tgcccttgcc cttggagctg ccgtgcctgt gtcctgatgg cccaaatgtc   2760
agggttctgc tcggcttctt ggaccttggc gcttagtccc catcccgggt ttggctgagc   2820
ctggctggag agctgctatg ctaaacctcc tgcctcccaa taccagcagg aggttctggg   2880
cctctgaacc ccctttcccc acacctcccc ctgctgctgc tgcccagcg tcttgacggg   2940 agcattggcc cctgagccca gagaagctgg aagcctgccg aaaacaggag caaatggcgt   3000
tttataaatt atttttttga aataaaaaaa aaaaaaaaa                         3040

<210> SEQ ID NO 4
<211> LENGTH: 12196
<212> TYPE: DNA
<213> ORGANISM: Homo sapiens

<400> SEQUENCE: 4
tgagggagca gaaggaaggg gttctcctat ccgctgcacg gcactgcgca aagacaggg     60 gagccaggca ttccctgaag ggtgaaaagc aaggagtaga gctgggtagt agactagaat   120
ttaggagcct ggcctggggc ctgggtgggg cgaaagaggc ggagcctgaa tggggtgtgt   180
ataggggggt tgcgtgtagg ggtgtgtgta taggctgggg cggggtcccg ggagtgggct   240
gactgggtcg ggggcgggc ctccaggtg ggcgggatc ttggccaccc ctggccacac    300
ctctctccgg ctcgagctgg tctaggcggg gcggcccga gggggtgtgg caggaggtgg   360
gcgggcccga gtgggggggg gggggcgtg aaggagggg cgggcccgag caggaggggg   420
cgggcccgag gggcggggtg ggacaggagg tgggccgctc gcggccacgc cgccgtcgcg   480
ggtacattcc tcgctcccgg ccgaggagcg ctcgggctgt ctgcggaccc tgccgcgtgc   540
```

```
aggggtcgcg gccggctgga gctgggagtg aggcggcgga ggagccaggt gaggaggagc    600
caggtgagca ggaccctgtg ctgggcgcgg agtcacgcag gctcgaggtg agccggaacc    660
cttgtgggcc cgggctgcgc tcccagccgc caggggcga gaggcggcgg ggctacgggg     720
actgcccctc ccggcgcagg ggacctgggc gtccgccggg cggcagggg tggaggggc      780 ggtaaatcag taacccgcag tgcacacagg gccttttgtc ccgctccgtc caaagagcac    840
cccggccgcg gagctggtta ctcattgccc accgaggcgg gggcaggctg ccctgtgca     900 gctaccctcg ggacccattg attcgcacct ccccccaggc tggcccggca agggtgggg     960 aggacaagcg cgcttgtccc tgcggctgtc ttcgcgccgg cggcagagat gagggacctg   1020
aggccccgaa aagttcagtc acttagtgcc cgggggcctc cagcgcgagt gcgggaggct   1080
gaaggagaac ccaggactgt ctgatgccta aggcaggccc tccattccca cgtgggggt    1140 ggtcggtcag cggtcagcag ccatgggtga ctcgactaag gactctgata tcagggcagc   1200
ctggggtagg aataaactcc ccgggcctcc ccacccactc ccagcccaag ctgtgtaccc   1260
aaagagctgc cctccctgcc aagccgagct tggtaggag ttttaccaag gaggatccga    1320
ctggattcga gagttgaggt gggccagaga cagcagtatc tgagtcaggt agagaagagc   1380
aatgaggggc acagagggat gggcaagaga gcacatgtgc ccagttttga aagccaatgg   1440
cttcagcgct cctgaagggg cagacggtgt gaccaaagag ataggcagcg gcagagaggg   1500
agccctagga tgttgagctg atcctgctg ggcacaggta gccattaagg gcttgcaagc    1560 tgggggcat gacatggcag acttgcaggt ttttttgttt gtttttttat tttattttat    1620 ttttttatt tgttttttt gagacggagt ctcactctgt cgcccaggct ggagtgcagt     1680
ggcgcgatct cggctcactg caagctccgc ctcccgggtt cgcgccattc tcctgcctca   1740
gcctcccgag tagctgggac tacaggcgcc cgccaccgcg cccggctaat tttttgtatt   1800
tttagtagag acggggtttc accgtgttag ccaggatgtt ctcgatctcc tgacctcgtg   1860
atccgcccac ctcggcctcc caaagtgctg ggattacagg tgtgaaccat cgcgcccagc   1920
cgacttgtag ttttttaaaa ctctgctgga agatgaaggt tgaagagccg agggagagga   1980
tgtttccaga ggcccatgca agagatggcc atgacctgcc ttgagaaggg gcaggggaag   2040
ccagatggac tggaagtgga gtggcagtga ccaaggagga ggaggtgtga taggcttccc   2100
acgcagggta gatccagaga caccagtgcc acccataggc ccctaggact gcagtggtca   2160
ccgattcctt tgtcccagct gagactcagt tctgagtgtt ctattttggg gaacagaggc   2220
gtccttggta gcatttggaa gaggatagcc agctgggtg tgtgtacatc acagcctgac    2280
agtaacagca tccgaaccag aggtgactgg ctaagggcag acccagggca acaggttaac   2340
cgttctaggg ccgggcacag ggaggagaac attccaacac tctgcgtgcc gacgcacgtt   2400 ctctcttta tcctcaaaac agtcctatga ggatagtaag ccagagagag acagacaa     2460 ggaattacaa gttggtgaga gtcaggattt gaacttggct ctggcagatg gaaaattagg   2520
gtctgtattc tttacaaaac cgtgtgtgcc tcagatggag ttggtgcata acaagcagag   2580
gtatccaggg tcgcggtcct gcttgccacg gaaggggccg ccttgtcagt tgtgaccacc   2640
cagccctgga aatgtcagta atgctgtaag gagtggggat cggatcagat gccatccaga   2700
tgctgaagtt tgaccttgtg tcattttca cttctttttt tggctcttct gcaatcaatt    2760
catttattta gcaaaaaga aattatgtgt gccgagagca tgcagaagat atgtctccgt    2820
tctctgcttc cctccaaaaa agaatcccaa aactgctttc tgtgaacgtg tgccagggtc   2880
```

```
ccagcaggac tcagggagag caggaagccc agcccagacc ccttgcacaa cctaccgtgg    2940
ggaggcctta ggctctggct actacagagc tggttccagt ctgcactgcc acagcctggc    3000
cagggacttg acacatctg ctggccactt cctgtctcag tttccttatc tgcaaaataa     3060
gggaaaagcc cccacaaagg tgcacgtgta gcaggagctc ttttccctcc ctattttagg    3120
aaggcagttg gtgggaagtc cagcttgggt ccctgagagc tgtgagaagg agatgcggct    3180
gctgctggcc ctgttggggg tcctgctgag tgtgcctggg cctccagtct tgtccctgga    3240
ggcctctgag gaagtggagc ttggtatggc ttctgaggtg ggagagggtg gcagggtgg     3300 gaagagtggg caccaggagg gggctgctgg gctgagcaaa gctggaaagg atccttgccc    3360
aggccctgag aaggtggcgg cagggcaggg ctcaaccact gagactcagt cagtgcctgg    3420
cttccagcaa gcattcatct atcactgtgt ctgcgagaga ggactggcct tgcagggcgc    3480
agggccctaa gctgggctgc agagctggtg gtgagctcct tacctgggtg tgtgtgcgtg    3540
tgtgtgtgtg ttctgtgcac tgggtgtgtg acctaggagg tccaggcagc atgtgtggta    3600
taagcattat gagggtgata tgccccggtg cagcatgacc ctgtatgtgg caccaacagc    3660
atgtgccttg tgtgtgtgtg tgtccgtatg tgtgtgtgtg tatgcgtgtg tgtgtgtgtg    3720
tgtgtcttgg ccactgtcgt gtgcactaaa tgctgtgtgt gtgacatgcc caagagtgt     3780 ggcatttgcc ctgggtgtgg catccgcagc atgtggctgt gtgggtgtca aggagtggtg    3840
gctccttcag catgcgttgc aaagtgcttg tgccctgcat gtgcggtgtg ttctttgtac    3900
acaggaggct gcctcagatg gggctgcggg gtctgctgac ctctgccctc tgcccacaga    3960
gccctgcctg gctcccagcc tggagcagca agagcaggag ctgacagtag cccttgggca    4020
gcctgtgcgt ctgtgctgtg ggcgggctga gcgtggtggc cactggtaca aggagggcag    4080
tcgcctggca cctgctggcc gtgtacgggg ctggagggc cgcctagaga ttgccagctt     4140
cctacctgag gatgctggcc gctacctctg cctggcacga ggctccatga tcgtcctgca    4200
gaatctcacc ttgattacag gtggtaagag actctagcag ggagtgaagg gatgcctggg    4260
gagacagacc tgcccctctt ggaccttaga tgcttccctc tgtccctgat gtagactcct    4320
tgacctccag caacgatgat gaggacccca agtcccatag ggacccctcg aataggcaca    4380
gttaccccca gcaaggtcag taggtctcca aggacttgtg tccccgctgc tgctcatctg    4440
atcactgaga agaggaggcc tgtgtgggaa cacacggtca ttctagggc cttcccctgc     4500 cctccagcac cctactggac acaccccag cgcatggaga agaaactgca tgcagtacct     4560
gcggggaaca ccgtcaagtt ccgctgtcca gctgcaggca accccacgcc caccatccgc    4620
tggcttaagg atgacaggc ctttcatggg gagaaccgca ttggaggcat tcgggtgagt     4680
ctctgggttc caagaccgtc tgctcccca ttttcattcc ttcatcagtc ccctcatacc     4740
tacaagcata cctataaatc aatcgaatga gtgaagcgat tgcggggccc cggaaggagc    4800
cctggactgt ggacctgggc agctctggtt ccccttctgc tactctctgg caagtgactt    4860
aacctctcag cctcagcaac tccatttgta aagggagaag aatcactgac tggttggtct    4920
gcataagcct tagcatctca tcgtcttgat gagaccctgc agggtcggct ccatgctgtc    4980
atgaggcaac tgagtctcag agaaggcaag ggttggctca agtagcaca gctagggaga     5040 gggagagcta aaattccaaa ggctcaaacc caaggctcaa gcgccctggg gagcctactc    5100
ctttgtgcca tagtccttgg cctgggcctg atgttctcag ggcctagaga gcttgacaag    5160
agccctgtgg gcaggatgag gatctagcct cctggtcctc tggcccccttt ggtggacatg    5220 gtccggtggt cccggacact ctctctgcct gcagctgcgc catcagcact ggagtctcgt    5280
```

```
gatggagagc gtggtgccct cggaccgcgg cacatacacc tgcctggtag agaacgctgt    5340
gggcagcatc cgctataact acctgctaga tgtgctgggt gagcgcgggg ctgggaacag    5400
gggaggcctg acccattttg ggctcagttg tgccctcttg gtggggtcta gtctggcagg    5460
caggatggac tcagatgagt caggcagctt ggtgagcagg tgggtcaggg gaaagcacag    5520
gggttagtgt ggggctggag gagcagaggt ctgccaagag gaaaacaag aaggacatcc    5580 aggcagaggg cgcagcccga gcggagggcc tgagtataac aaacgccctg cacttgcagg    5640
ccagcatatt cgtagggcgt ggcgtttata tggggagcca ggtggtggag ggttttgaat    5700
gctaggctga gatgttgtcc ttgacccgaa gcaataggga gccagggaag gtttaagcag    5760
ggtaagcagg agacagacaa gaagctgcag aaaggtccct cccttgaact tgaggaaggc    5820
tggagggagg caaacagggt gcttctatgg gtgccggtgg tcagggttga ctgtctcgcc    5880
cggtccccag agcggtcccc gcaccggccc atcctgcagg ccgggctccc ggccaacacc    5940
acagccgtgg tgggcagcga cgtggagctg ctgtgcaagg tgtacagcga tgcccagccc    6000
cacatccagt ggctgaagca catcgtcatc aacggcagca gcttcggagc cgacggtttc    6060
ccctatgtgc aagtcctaaa ggtaaaaggt gcaccctgct gcagcctggg ccccattctt    6120
ctcccacctt gggttggggg gctccccagc ttccctgttg gccacagtgt ggccccaggc    6180
cctgctgtga ccccagagca tgtcccccac cccagactgc agacatcaat agctcagagg    6240
tggaggtcct gtacctgcgg aacgtgtcag ccgaggacgc aggcgagtac acctgcctcg    6300
caggcaattc catcggcctc tcctaccagt ctgcctggct cacggtgctg ccaggtgagc    6360
acctgaaggg ccaggagatg ctgcgagatg cccctctggg ccagcagtgg gggctgtggc    6420
ctgttgggtg gtcagtctct gttggcctgt ggggtctggc ctgggggggca gtgtgtggat    6480 ttgtgggttt gagctgtatg acagcccctc tgtgcctctc cacacgtggc cgtccatgtg    6540
accgtctgct gaggtgtggg tgcctggac tgggcataac tacagcttcc tccgtgtgtg    6600
tccccacata tgttgggagc tgggagggac tgagttaggg tgcacggggc ggccagtctc    6660
accactgacc agtttgtctg tctgtgtgtg tccatgtgcg agggcagagg aggaccccac    6720
atggaccgca gcagcgcccg aggccaggta tacggacatc atcctgtacg cgtcgggctc    6780
cctggccttg gctgtgctcc tgctgctggc cgggctgtat cgagggcagg cgctccacgg    6840
ccggcacccc cgcccgcccg ccactgtgca gaagctctcc cgcttccctc tggcccgaca    6900
ggtactgggc gcatccccca cctcacatgt gacagcctga ctccagcagg cagaaccaag    6960
tctcccactt tgcagttctc cctggagtca ggctcttccg gcaagtcaag ctcatccctg    7020
gtacgaggcg tgcgtctctc ctccagcggc cccgccttgc tcgccggcct cgtgagtcta    7080
gatctacctc tcgacccact atgggagttc ccccgggaca ggtgcgctga gctgtgtggg    7140
ggcagggacg cgggcgccgg gttgcagccc gccctccgca ggagtgactc ggaggtctga    7200
ggctggactt tctccatctc caggctggtg cttgggaagc ccctaggcga gggctgcttt    7260
ggccaggtag tacgtgcaga ggcctttggc atggaccctg cccggcctga ccaagccagc    7320
actgtggccg tcaagatgct caaaggtgag tgtggcccgg tgtggtggct cacacctgta    7380
acgccagcac tttaggaggc tgaggtggg aggatcgctt gaatccagga attcgaggcc    7440
agcctgggca acatggcaag acttcatctc tacaaaaaaa aaataagaaa attagttggg    7500
tgtggtggtg tgtgccttta gtctcagtta ctagggaggc tgaggcagga ggatcccttg    7560
aatccaggag ttggaggttg cagggagcca tgatcacgcc actgtattcc agcctgggca    7620
```

-continued

```
acacagtgag accctatctg aaaaaataaa taaataaata aaaataaaag gtgaacgtgg    7680
cagcctggag gaggtgctat ggcattggga ctaatagaag gggctcacgg tgccaccagg    7740
tgagccctgg agctgggaga ggctgtggga tcccacccct aaacctgcaa ttcacctctg    7800
ctcctgaccc tggcaagtga cttctgagcc tcagttttcc cttgtgtcat atggggtaga    7860
taacagtccc tactcccagc ccaaggattg tggaaagtgc ctggctcata gtcagggctc    7920
aataaatctt caccactggg gtgatgatga tgagaagaat ttggtgtgac aggcttgata    7980
tcctgtgtca gcattagtct gtgtcagctt tgacttcaca tctccttgtc agcctcacag    8040
gccctctacc tccttcctta tggttccccc cagacacacc ctcagcctcc cttggaccct    8100
ccctaggtct gcccccccacg tccactgctg taggaggaca gcccttctgc ttgcacccag    8160
gcccagcccc ggggtgctct tgctgggcac tcctgcaccc cacccatcag ggcctctcct    8220
tgcagttccc cagcccctc tgcaagaatg gcctccactg ctcttctgct cctccctcc      8280 tctctacaca gctggggcca cctggtgctc cctgggaggc agggattgag aaatgcacat    8340
tgtgtcattg gcccagggcc acaggtcagc cccaggggct cagccagaga agccaaagca    8400
gccttcttcc caagctcccc ggctgcaccc ggcctgccgc cagctccctg aattcccagg    8460
ccagttggaa gccaggccct ggtcaaacag acccccagggc gccagcctgc tttccgcacc    8520
cagaagctct gaccccatgc ggggactacc gctgacccct ccagcggcag cttccttcct    8580
tccttcctgc tccgagctct tccctctct cctgtgtcct gggcctgccc gctggaaggc     8640
ctgcctctta gatccttgat acagttgcat ccttgcaact gctgtgacag gcagggtgtg    8700
acccactgct ctgtttccca caagacgaac ctgaggttca gagacgctag gagactttt     8760 caaggccaca cagcctagca aggattcagc cctagaccta cgtagccctg gtccagtgct    8820
gcttgtcctg cacctgcctc tgcatgctcc ctcgtgcagt tggagggcag cctcttcacc    8880
ccgtctgctg cccttacaga caacgcctct gacaaggacc tggccgacct ggtctcggag    8940
atggaggtga tgaagctgat cggccgacac aagaacatca tcaacctgct tggtgtctgc    9000
acccaggaag gtggggccga ggcggggctg gctgcacggg ccgttagggt gcagagccaa    9060
agctttggca gcctctccac gctccctcca ctccctctgc agggcccctg tacgtgatcg    9120
tggagtgcgc cgccaaggga aacctgcggg agttcctgcg ggcccggcgc ccccaggcc     9180 ccgacctcag ccccgacggt cctcggagca gtgaggggcc gctctccttc ccagtcctgg    9240
tctcctgcgc ctaccaggtg gcccgaggca tgcagtatct ggagtcccgg aaggtacagg    9300
cgctagggct ctgagcccct ctcagtctct ccagctccac tctcaggcct gtggcattca    9360
atgtcccgac ttctccctct ctgctctttt tcatgacccc acctcagtgt ccccaggcat    9420
tcacgctttc ctgcattccc cactcgttcc tcacccttcc ccagaggggga gggggacgc    9480 aggagaaggc actccccgtt tctaaacctt gacctcctcc tctgtaaagt gggtggaggg    9540
cccctgcccc cgggcctgct gggggtggt gtgtgctcaa ctccaggcca ggtgtcctga    9600
ggcacccaag ccccgctcc ctgcagtgta tccaccggga cctggctgcc cgcaatgtgc     9660
tggtgactga ggacaatgtg atgaagattg ctgactttgg gctggcccgc ggcgtccacc    9720
acattgacta ctataagaaa accagcaacg tgagggagat ggggcagaac tggatggggg    9780
tggaggggca ctgggcccgg ggtggcaggc acgaggacct gtgggactct gcactgaggc    9840
cctctctccc ctccagggcc gcctgcctgt gaagtggatg gcgccgagg ccttgtttga     9900 ccgggtgtac acacaccaga gtgacgtgtg agtcctgccg gcggtcactg tcctaccca     9960 caaaaagggc aaggcactgc ccaaagtcac gtggcccag gagtcatgcg ctcgagggct    10020
```

-continued

```
ccttcagatt tggtctggga cccgagtggg cccagactcc aggaggagcc cattccccaa    10080
cagctgtggt gggtcatgtc tgtggggtcc cccgtcctag ccccggtcgt cgggagggcg    10140
ctgagccaca ctgagccctg ccctacctc caggtggtct tttgggatcc tgctatggga    10200
gatcttcacc ctcgggggct ccccgtatcc tggcatcccg gtggaggagc tgttctcgct    10260
gctgcgggag ggacatcgga tggaccgacc cccacactgc cccccagagc tgtgaggcct    10320
caccctgccc tcgaccccac tttccagtcc tcctcctcct ctgccctgac catggcctca    10380
gggtgtgtcc cggccagaag gacaacacta caacaactc ctcgtcctcc tcctcctctt     10440
cctcttcctc ctcctcctct tcctcctcct cctcttcctc ctcctcttcc tcctcctcct    10500
cttcctcctc ctccctcttcc tccttctcct cctgctcctc ttcctcctcc ttctcttcct   10560
cctcctcctc ttcctcctcc tcctcttcct cctcctcctc ttcctccttc tcctcctgct   10620
cctcttcctc ctccttctct tcctcctcct tctcttcctc ctcctcctcc tgctcctctt   10680
cctcctcctc ctcttcctcc tcctcagcct agtggagtgt cctggcctgg cttctactga   10740
tgaccctcct atccctcatc aaactcccca ccaaactcct ccccacccag agaaccccccg   10800
gtcctccct tcctcctgaa ggcctgaggc tccctgtgac cctccgcccc acctctcgca     10860
ggtacgggct gatgcgtgag tgctggcacg cagcgccctc ccagaggcct accttcaagc    10920
agctggtgga ggcgctggac aaggtcctgc tggccgtctc tgaggaggta cagcccctcc    10980
cacccaccac ctccctctgc ctgctcccct ccaggcctca tctggcctga ccgcgtggac    11040
atgcgccccg tccatcccg ggcgctgcag aggctgacca gctccgttcc ccacagtacc     11100
tcgacctccg cctgaccttc ggaccctatt ccccctctgg tggggacgcc agcagcacct    11160
gctcctccag cgattctgtc ttcagccacg accccctgcc attgggatcc agctccttcc    11220
ccttcgggtc tggggtgcag acatgagcaa ggctcaaggc tgtgcaggca cataggctgg    11280
tggccttggg ccttgggct cagccacagc ctgacacagt gctcgacctt gatagcatgg     11340
ggccctggc ccagagttgc tgtgccgtgt ccaagggccg tgcccttgcc cttggagctg     11400
ccgtgcctgt gtcctgatgg cccaaatgtc agggttctgc tcggcttctt ggaccttggc    11460
gcttagtccc catcccgggt ttggctgagc ctggctggag agctgctatg ctaaacctcc    11520
tgcctcccaa taccagcagg aggttctggg cctctgaacc cccttccc acacctcccc      11580
ctgctgctgc tgcccccagcg tcttgacggg agcattggcc cctgagccca gagaagctgg   11640
aagcctgccg aaaacaggag caaatggcgt tttataaatt atttttttga aataaagctc    11700
tgtgtgcctg ggtcttccct gagcaacatg gagtggggtg aggtggaggg atccctccag    11760
cagagttctg cctacaggac acggactgag ggcactggac caggccatgg gctccgccac    11820
ctccactgcc ccaggagcca gtgtgtgcct atctgggtcc gcctgtccca ccagccccat    11880
cttgtgtctg cgacagtgtg aatgagtatt aatgggctga gtccgcattg cactatacac    11940
ggtgggactc ctgtaccctc tgcacatgtg tgtgtgtgca tgtgtgccct gcagctgtcc    12000
ccaagggagc tggcagcccc cctcccccat ctgctcagca ttaaccaagc tgaccgttaa    12060
cacagcatga aaatctgaga gccagcctta ggccgcggcc cgctcccacg ctctgccggc    12120
tcaggctggg ggcttgtgga ggccatgccc gccccgccct ggccagtctc ccgggcagca    12180
gctggttgcc gcccgc                                                    12196
```

<210> SEQ ID NO 5
<211> LENGTH: 5192
<212> TYPE: DNA

<213> ORGANISM: Homo sapiens

<400> SEQUENCE: 5

```
ccatgacctg ccttgagaag gggcagggga agccagatgg actggaagtg gagtggcagt      60
gaccaaggag gaggaggtgt gataggcttc ccacgcaggg tagatccaga gacaccagtg     120
ccacccatag gcccctagga ctgcagtggt cacccgattc ctttgtccca gctgagactc     180
agttctgagt gttctatttt ggggaacaga ggcgtccttg gtagcatttg aagaggata      240
gccagctggg gtgtgtgtac atcacagcct gacagtaaca gcatccgaac cagaggtgac     300
tggctaaggg cagacccagg gcaacaggtt aaccgttcta gggccgggca cagggaggag     360
aacattccaa cactctgtgt gcccagtgcc gacgcacgtt ctctctttta tcctcaaaac     420
agtcctatga ggatataagc cagagagaga cagagacaag gaattacaag ttggtgagag     480
tcaggatttg aacttggctc tggcagatgg aaaattaggg tctgtattct ttacaaaacc     540
gtgtgtgcct cagatggagt tggtgcataa caagcagagg tatccagggt cgcggtcctg     600
cttgccacgg aaggggccgc cttgtcagtt gtgaccaccc agccctggaa atgtcagtaa     660
tgctgtaagg agtggggatc ggatcagatg ccatccagat gctgaagttt gaccttgtgt     720
catttttcac tttctttttt ggctcttctg caatcaattc atttatttag caaaaaagaa     780
attatgtgtg ccgagagcat gcagaagata tgtctccgtt ctctgcttcc ctccaaaaaa     840
gaatcccaaa actgctttct gtgaacgtgt gccagggtcc cagcaggact cagggagagc     900
aggaagccca gcccagaccc cttgcacaac ctaccgtggg gaggccttag gctctggcta     960
ctacagagct ggttccagtc tgcactgcca gcctggcc agggacttgg acacatctgc     1020
tggccacttc ctgtctcagt ttccttatct gcaaaataag ggaaaagccc cacaaaggt    1080
gcacgtgtag caggagctct tttccctccc tattttagga aggcagttgg tgggaagtcc    1140
agcttgggtc cctgagagct gtgagaagga gatgcggctg ctgctggccc tgttgggggt    1200
cctgctgagt gtgcctgggc ctccagtctt gtccctggag gcctctgagg aagtggagct    1260
tggtatggct tctgaggtgg gagagggtgg caggggtggg aagagtgggc accaggaggg    1320
ggctgctggg ctgagcaaag ctggaaagga tccttgccca ggccctgaga aggtggcggc    1380
agggcagggc tcaaccactg agactcagtc agtgcctggc ttccagcaag cattcatcta    1440
tcactgtgtc tgcgagagag gactggcctt gcagggcgca gggccctaag ctgggctgca    1500
gagctggtgg tgagctcctt gcctgggtgt gtgtgcgtgt gtgtgtgtgt tctgtgcact    1560
gggtgtgtga cctaggaggt ccaggcagca tgtgtggtat aagcattatg agggtgatat    1620
gccccggtgc agcatgaccc tgtatgtggc accaacagca tgtgccttgt gtgtgtgtgt    1680
gtccgtatgt gtgtgtgtgt atgcgtgtgt gtgtgtgtgt gtgtgtgtct tggccactgt    1740
catgtgcact aaatgctgtg tgtgtgacat gccccaagag tgtggcattt gccctgggtg    1800
tggcatccgc agcatgtggc tgtgtgggtg tcaaggagtg gtggctcctt cagcatgcgt    1860
tgcgaagtgc ttgtgccctg catgtgcggt gtgttctctg tacacaggag gctgcctcag    1920
atggggctgc ggggtctgct gacctctgcc ctctgcccac agagccctgc ctggctccca    1980
gcctggagca gcaagagcag gagctgacag tagcccttgg gcagcctgtg cggctgtgct    2040
gtgggcgggc tgagcgtggt ggccactggt acaaggaggg cagtcgcctg gcacctgctg    2100
gccgtgtacg gggctggagg ggccgcctag agattgccag cttcctacct gaggatgctg    2160
gccgctacct ctgcctggca cgaggctcca tgatcgtcct gcagaatctc accttgatta    2220
caggtgactc cttgacctcc agcaacgatg atgaggaccc caagtcccat agggacctct    2280
```

```
cgaataggca cagttacccc cagcaaggtc agtaggtctc caaggacttg tgtcccccgct   2340 gctgctcatc tgatcactga aagaggagg cctgtgtggg aacacacggt cattctaggg    2400
gccttcccct gccctccagc accctactgg acacaccccc agcgcatgga aagaaactg    2460 catgcagtac ctgcggggaa caccgtcaag ttccgctgtc cagctgcagg caaccccacg    2520
cccaccatcc gctggcttaa ggatggacag gcctttcatg gggagaaccg cattggaggc    2580
attcggctgc gccatcagca ctggagtctc gtgatggaga gcgtggtgcc ctcggaccgc    2640
ggcacataca cctgcctggt agagaacgct gtgggcagca tccgttataa ctacctgcta    2700
gatgtgctgg agcggtcccc gcaccggccc atcctgcagg ccgggctccc ggccaacacc    2760
acagccgtgg tgggcagcga cgtggagctg ctgtgcaagg tgtacagcga tgcccagccc    2820
cacatccagt ggctgaagca catcgtcatc aacggcagca gcttcggagc cgacggtttc    2880
ccctatgtgc aagtcctaaa gactgcagac atcaatagct cagaggtgga ggtcctgtac    2940
ctgcggaacg tgtcagccga ggacgcaggc gagtacacct gcctcgcagg caattccatc    3000
ggcctctcct accagtctgc ctggctcacg gtgctgccag gtgagcacct gaagggccag    3060
gagatgctgc gagatgcccc tctgggccag cagtgggggc tgtggcctgt tgggtggtca    3120
gtctctgttg gcctgtgggg tctggcctgg ggggcagtgt gtggatttgt gggtttgagc    3180
tgtatgacag cccctctgtg cctctccaca cgtggccgtc catgtgaccg tctgctgagg    3240
tgtgggtgcc tgggactggg cataactaca gcttcctccg tgtgtgtccc cacatatgtt    3300
gggagctggg agggactgag ttagggtgca cggggcggcc agtctcacca ctgaccagtt    3360
tgtctgtctg tgtgtgtcca tgtgcgaggg cagaggagga ccccacatgg accgcagcag    3420
cgcccgaggc caggtatacg gacatcatcc tgtacgcgtc gggctccctg gccttggctg    3480
tgctcctgct gctggccagg ctgtatcgag ggcaggcgct ccacggccgg caccccgcc     3540 cgcccgccac tgtgcagaag ctctcccgct tccctctggc ccgacagttc tccctggagt    3600
caggctcttc cggcaagtca agctcatccc tggtacgagg cgtgcgtctc tcctccagcg    3660
gccccgcctt gctcgccggc ctcgtgagtc tagatctacc tctcgaccca ctatgggagt    3720
tccccgggga caggctggtg cttgggaagc ccctaggcga gggctgcttt ggccaggtag    3780
tacgtgcaga ggcctttggc atggaccctg cccggcctga ccaagccagc actgtggccg    3840
tcaagatgct caaagacaac gcctctgaca aggacctggc cgacctggtc tcggagatgg    3900
aggtgatgaa gctgatcggc cgacacaaga acatcatcaa cctgcttggt gtctgcaccc    3960
aggaagggcc cctgtacgtg atcgtggagt gcgccgccaa gggaaacctg cgggagttcc    4020
tgcgggcccg gcgcccccca ggccccgacc tcagccccga cggtcctcgg agcagtgagg    4080
ggccgctctc cttcccagtc ctggtctcct gcgcctacca ggtggcccga ggcatgcagt    4140
atctggagtc ccggaagtgt atccaccggg acctggctgc ccgcaatgtg ctggtgactg    4200
aggacaatgt gatgaagatt gctgactttg gctggcccg cggcgtccac cacattgact    4260
actataagaa aaccagcaac ggccgcctgc ctgtgaagtg gatggcgccc gaggccttgt    4320
ttgaccgggt gtacacacac cagagtgacg tgtggtcttt tgggatcctg ctatgggaga    4380
tcttcaccct cggggctcc ccgtatcctg gcatccggt ggaggagctg ttctcgctgc      4440
tgcgggaggg acatcggatg gaccgacccc cacactgccc cccagagctg tacgggctga    4500
tgcgtgagtg ctggcacgca gcgcccctcc agaggcctac cttcaagcag ctggtggagg    4560
cgctggacaa ggtcctgctg gccgtctctg aggagtacct cgacctccgc ctgacctccg    4620
```

| | |
|---|---|
| gaccctattc cccctctggt ggggacgcca gcagcacctg ctcctccagc gattctgtct | 4680 |
| tcagccacga cccctgcca ttgggatcca gctccttccc cttcgggtct ggggtgcaga | 4740 |
| catgagcaag gctcaaggct gtgcaggcac ataggctggt ggccttgggc cttgggctc | 4800 |
| agccacagcc tgacacagtg ctcgaccttg atagcatggg gccctggcc cagagttgct | 4860 |
| gtgccgtgtc caagggccgt gcccttgccc ttggagctgc cgtgcctgtg tcctgatggc | 4920 |
| ccaaatgtca gggttctgct cggcttcttg gaccttggcg cttagtcccc atccgggtt | 4980 |
| tggctgagcc tggctggaga gctgctatgc taaacctcct gcctcccaat accagcagga | 5040 |
| ggttctgggc ctctgaaccc cctttcccca cactccccc tgctgctgct gcccagcgt | 5100 |
| cttgacggga gcattggccc ctgagcccag agaagctgga agcctgccga aaacaggagc | 5160 |
| aaatggcgtt ttataaatta tttttttgaa at | 5192 |

<210> SEQ ID NO 6
<211> LENGTH: 2807
<212> TYPE: DNA
<213> ORGANISM: Homo sapiens

<400> SEQUENCE: 6

| | |
|---|---|
| gaaggcagtt ggtgggaagt ccagcttggg tccctgagag ctgtgagaag gagatgcggc | 60 |
| tgctgctggc cctgttgggg gtcctgctga gtgtgcctgg gcctccagtc ttgtccctgg | 120 |
| aggcctctga ggaagtggag cttgagccct gcctggctcc cagcctggag cagcaagagc | 180 |
| aggagctgac agtagccctt gggcagcctg tgcgtctgtg ctgtgggcgg gctgagcgtg | 240 |
| gtggccactg gtacaaggag ggcagtcgcc tggcacctgc tggccgtgta cggggctgga | 300 |
| ggggccgcct agagattgcc agcttcctac ctgaggatgc tggccgctac ctctgcctgg | 360 |
| cacgaggctc catgatcgtc ctgcagaatc tcaccttgat tacaggtgac tccttgacct | 420 |
| ccagcaacga tgatgaggac cccaagtccc atagggaccc ctcgaatagg cacagttacc | 480 |
| cccagcaagc ccctactggg acacaccccc agcgcatgga gaagaaactg catgcagtac | 540 |
| ctgcggggaa caccgtcaag ttccgctgtc cagctgcagg caaccccacg cccaccatcc | 600 |
| gctggcttaa ggatgacag gccttttcatg gggagaaccg cattggaggc attcggctgc | 660 |
| gccatcagca ctggagtctc gtgatggaga gcgtggtgcc ctcggaccgc ggcacataca | 720 |
| cctgcctggt agaaaacgct gtgggcagca tccgctataa ctacctgcta gatgtgctgg | 780 |
| agcggtcccc gcaccggccc atcctgcagg ccgggctccc ggccaacacc acagccgtgg | 840 |
| tgggcagcga cgtggagctg ctgtgcaagg tgtacagcga tgcccagccc cacatccagt | 900 |
| ggctgaagca catcgtcatc aacggcagca gcttcggagc cgacggtttc ccctatgtgc | 960 |
| aagtcctaaa gactgcagac atcaatagct cagaggtgga ggtcctgtac ctgcggaacg | 1020 |
| tgtcagccga ggacgcaggc gagtacacct gcctcgcagg caattccatc ggcctctcct | 1080 |
| accagtctgc ctggctcacg gtgctgccag gtactgggcg catcccccac ctcacatgtg | 1140 |
| acagcctgac tccagcaggc agaaccaagt ctcccacttt gcagttctcc ctggagtcag | 1200 |
| gctcttccgg caagtcaagc tcatccctgg tacgaggcgt gcgtctctcc tccagcggcc | 1260 |
| ccgccttgct cgccggcctc gtgagtctag atctacctct cgacccacta tgggagttcc | 1320 |
| cccgggacag gctggtgctt gggaagcccc taggcgaggg ctgctttggc caggtagtac | 1380 |
| gtgcagaggc ctttggcatg gaccctgccc ggcctgacca agccagcact gtggccgtca | 1440 |
| agatgctcaa agacaacgcc tctgacaagg acctggccga cctggtctcg agatggaggg | 1500 |
| tgatgaagct gatcggccga cacaagaaca tcatcaacct gcttggtgtc tgcacccagg | 1560 |

| | |
|---|---|
| aagggcccct gtacgtgatc gtggagtgcg ccgccaaggg aaacctgcgg gagttcctgc | 1620 |
| gggcccggcg cccccaggc cccgacctca gcccgacgtg tcctcggagc agtgaggggc | 1680 |
| cgctctcctt cccagtcctg gtctcctgcg cctaccaggt ggcccgaggc atgcagtatc | 1740 |
| tggagtcccg gaagtgtatc caccgggacc tggctgcccg caatgtgctg gtgactgagg | 1800 |
| acaatgtgat gaagattgct gactttgggc tggcccgcgg cgtccaccac attgactact | 1860 |
| ataagaaaac cagcaacggc cgcctgcctg tgaagtggat ggcgcccgag gccttgtttg | 1920 |
| accgggtgta cacacaccag agtgacgtgt ggtcttttgg gatcctgcta tgggagatct | 1980 |
| tcaccctcgg gggctccccg tatcctgcca tcccggtgga ggagctgttc cgctgctgc | 2040 |
| gggagggaca tcggatggac cgaccccac actgcccccc agagctgtac gggctgatgc | 2100 |
| gtgagtgctg gcacgcagcg ccctcccaga ggcctacctt caagcagctg gtggaggcgc | 2160 |
| tggacaaggt cctgctggcc gtctctgagg agtacctcga cctccgcctg accttcggac | 2220 |
| cctattcccc ctctggtggg gacgccagca gcacctgctc ctccagcgat tctgtcttca | 2280 |
| gccacgaccc cctgccattg ggatccagct ccttcccctt cgggtctggg gtgcagacat | 2340 |
| gagcaaggct caaggctgtg caggcacata ggctggtggc cttgggcctt ggggctcagc | 2400 |
| cacagcctga cacagtgctc gaccttgata gcatggggcc cctggcccag agttgctgtg | 2460 |
| ccgtgtccaa gggccgtgcc cttgcccttg gagctgccgt gcctgtgtcc tgatggccca | 2520 |
| aatgtcaggg ttctgctcgg cttcttggac cttggcgctt agtccccatc ccggtttgg | 2580 |
| ctgagcctgg ctggagagct gctatgctaa acctcctgcc tcccaatacc agcaggaggt | 2640 |
| tctgggcctc tgaaccccct ttccccacac ctccccctgc tgctgctgcc ccagcgtctt | 2700 |
| gacgggagca ttggccctg agcccagaga agctggaagc ctgccgaaaa caggagcaaa | 2760 |
| tggcgtttta taaattattt ttttgaaata aaaaaaaaaa aaaaaa | 2807 |

<210> SEQ ID NO 7
<211> LENGTH: 162001
<212> TYPE: DNA
<213> ORGANISM: Homo sapiens

<400> SEQUENCE: 7

| | |
|---|---|
| aggctgttgc gtatgtgagt ctggagttcg gaagagacat ccaagttgct gacataaatt | 60 |
| tcggtcttca gtgtagaaat ttgatttaaa gccattgggt taaacaaacc aaccaaggta | 120 |
| agagtatttg caggtaagag aagagaccca aggacttagc cctaaggcac tccagcatta | 180 |
| tgatgtaggg gagatgagga accagcaaag gaggctgaat ggaaacagag aaggaatggc | 240 |
| gagttctgtg caagagacag gaagaaagag aatgcaaaat ggtcaaacaa taaataatta | 300 |
| agttgaatta gatggtaaag aaataaatgc aaggaaatgc aaggccatag tcactgggca | 360 |
| gacagagtaa agaacatga tgaatcaggt gagattaatc acccctcctg gaactatcag | 420 |
| aaaaagatac tcactgacag tgaggcagtc atgttagtcc ccaagttgat gactaatgga | 480 |
| aactaaggtc acagtgcaca ttaatttctt ttgaagcaaa ggataaaaac aaacaaaata | 540 |
| taaaagatta agatgtaaac gttagtgtac actaattcag agaagaatta aatgattttt | 600 |
| aaaacttcaa gaaggaggac agcattctaa atgcattgtt ctaaacgat agtaagatgg | 660 |
| gataaatagt cacactaggg tgatgatttt ggatgtgtta aatttgtcac tttgagacca | 720 |
| gatatgctcc atttcacttc atgccagctt ttaagaacat atatcataga aaagagaaa | 780 |
| agaaacagtt gaatcaaagt gaagagaaat attgtgaagc aaataaatcc agggaaaaat | 840 |

```
taataaaacc ctattcccac cctaaaaaaa agaaactaaa agaagtgcaa atataaagtt    900
caataggagt cattagagat tgtaaattgg gctctgagct tcctaccaac aaaagcacaa    960
aggaaaatat gatcactggt attaaaaaaa aacacctatg gtttccaaaa gattaaaaca   1020
aaccagcagt tttatagaag ctaacactaa aatctaaagg aactacgttc tatggagcca   1080
cttaatatgg ataaacactt tgacaatatt ctttcaacaa ctacagtaac aagtttctta   1140
gagtccattt cttttcacat ccataatgaa ttgtaaatct tttctacttc ttaagtaaaa   1200
catcaccact taattctggt aacttttcca tattaacttt ttagaacaat tgcaaacgta   1260
ccataaatga ttgttgtcac agtggtaact atttgaccct gactgttatt ttgtatatag   1320
cagcttttaa aataaaaagg caacaagttt ctaggcgtaa tttccacaga tcttttatgt   1380
aaaacaatga catcctttgc aacttctgcc atttaatcta tctcaagcaa gctctctgga   1440
aacaaatcta tttgaaagat tctattgtaa ttagaaatca gggtaactga atgcactaga   1500
tgaaaacctt ctgactgggg ccaatgaagt caataaagtc aaaactgctg tgaatgctca   1560
actgtctgca gatcagatgt cttgggatgg aatccgttct cgaggccacc atcattaata   1620
tcaatttggc catgtaatac aagcctcact tgttccactg ttacaaatgt gcttaaaact   1680
gagctcattt acaatccaaa tacatatgta ggatggtaac caaggcatca cactaattta   1740
ggtattatgt tttaggggga acaaaaggta tgttaatatt ttattcatct ccaaattaac   1800
tataaattgt gcattcttgc atagatcctc cttgggaatg agaaattagg aaaatccagt   1860
tgttaaaatg aatgcctaaa atcaaaataa aatttgtttt tctggcaccct gcttgatgac   1920
acagactaat aaccaatgac aaaattgccc ttgaacccaa gttttcattt cctcctattg   1980
tgtggtcagg ttatgtaagg gtttgctttc accccattca aaaggtacct cttcctcttc   2040
tcttgctccc tctcgccctc attcttgtgc ctatgcagac atttgagtag aggcgaatca   2100
ctttcacttc tgctggggaa attgcaacac gcttctttaa atggcagaga aaggagaaa    2160
acttagatct tctgatacca aatcactgga ccttagaagg tcagaaatct ttcaagccct   2220
gcaggaccgt aaaatgcgca tgtgtccaac ggaagcactg gggcatgagt ggggaaggaa   2280
tagaaacaga aagagggtaa gagaagaaaa aagggaaagt ggtgaaggca gggaggaaaa   2340
ttgcttagtg tgaatatgca cgcattcatt tagttttcaa atccttgttg agcatgataa   2400
aattcccagc atcagacctc acatgttggt ttccattagg atctgcctgg gggaatatct   2460
gctgaatcag tggctctgag ctgaactagg aaattcacca taattaggag agtcactgta   2520
tttctctcca aaaaaaaaaa agttataccc gagagacagg atcttctgat ctgaaatttt   2580
cttcacttct gaaattctct ggtttgtgct catcgttggt agctatttgt tcatcaagag   2640
ttgtgtagct ggcttcttct gaaaaaagga atctgcgtca tatctaagtc agatttcatt   2700
ctggtgctct cagagcagtt agcccaggaa aggggccagc ttctgtgacg actgctgcag   2760
aggcaggtgc agtttgtgtg ccacagatat taactttgat aagcacttaa tgagtgcctt   2820
ctctgtgcga gaatggggag gaacaaaatg cagctcctac cctcctcggg ctttagttgt   2880
accttaataa caggaatttt catctgcctg gctccttttcc tcaaagaaca agaagactt    2940
tgcttcatta aagtgtctga gaaggaaggt aggttatatt tttattccca ttctatagct   3000
gggtaaagtg agttctaaca aagttacttg ttaaaggtca ctcagaggtc agagcatcag   3060
aaaaaaagac aatcacaagg ctgatgttgt gtgctggata gtttaaactg aacaggaaga   3120
aaacattttt gtgggcttta tctaaaaaga aatagtttgc tctgagtttc tcagtttcat   3180
ttattcagca agtatgtgcc aagtgctatt gtaggcaatg aagatacagc agggaacaaa   3240
```

```
acaaaactga catggagctt ccaactagaa aggagaacga dacaacgcgt tttaaaatat    3300
atataatgtg ttaggtaaaa agtgctataa ggagagctaa aacacaatga gaggctagaa    3360
gagtgatagt ggcggagggg cttctctgag gagatgacat ttgatcaggg gtctgaataa    3420
agtaaagagg ccagttatgt gaatatctgg aagactcaag gggcagggcg gaaatagcca    3480
gtagaaaggc cctgaggtag gaaggtgtgt ggcaagtttg aggaaaagga aagacagtct    3540
gactggagca aagagaactg gagctgaggc catcaaggca gccaggagcc aggtgcagac    3600
tgggctttga ctctgcctgc agggaggaac tgctgaaggt tccaagcaaa ggaccgccct    3660
gacctgcctt aggtttgaac aggatccctc tggctggtgt gtgaagaatt aactgtagat    3720
gggcaagtgt ggaaggaagg agagcagtca ggaagctgcc ataaccatct acatgagaga    3780
ggtaaggcct cagatggagg ggagcagtgg aatggtggaa agtgtttatt ttgaatgtta    3840
agcctgcagg agttgctgga ggattggaca tgggggatga gaaaaagaga gaggcttaca    3900
gatcaggtaa tttagctgat cttaagcccc ttacagctta atattattcc aaggtgccaa    3960
taacagccaa ggtaaacaac cttgtcttgg acattctgcc tttatttgcc cacacaagat    4020
gaaattaaat atatatatat atatataatt taaataaata aattatatat atatataatt    4080
taaataaata aattatatat atatatattt agtgctgttt ccatcagcta ctagctgaga    4140
cacttgggca aatgagggtg atctccagtc ctcagtatcc ttgctgttaa tgagagatgg    4200
tcatttcttc tctgcctagc tcaaaagaat atgttaaata aaactctgtg aactttaggc    4260
agcacaggct tagggcttct tagtaacatc atcagcacca tcagagttaa cttcatgagt    4320
cagttgagtt gcctttgggg tatatcatta acagattcca ggaagctccc ctgcccaaaa    4380
gcctcccacc aatggcctgc cttgttgaaa gaattacaca attagcccaa ttcctttcca    4440
ttaaggcatt gtggactcca aacatcctcc tttaaaatgg aaactaaatc gagctactgt    4500
cagtcatttg tccttttagg tgacgttata tatcagatca cttttctgcc attagagcta    4560
gttgaagttt gaatagggaa aaggaacgaa tgaacgtggg gcagagaacg caatagtcgg    4620
tgggttactc agtaggctgt ggacagatgg agaggatccc ggtgggagga gcctctaaag    4680
ataaactttc tatgggaaaa tgttgacaga tttacctgag tcatggtttt tcttacacct    4740
cataaaaatg aaggcttcca agggcagctc cttgaaatag ctgtaacaag tagccacaga    4800
agttgagttg cttaaagaaa aacattgaat tcatggggaa ccgtacgctt taatagcccc    4860
tttggcttac tttgtttaaa caaactcatc ccgagcatct cacacttcac caattttgag    4920
tgtccctgct ttacctcagc ttttaaaga gtgtctttcc cctaaatatt tctgaaaatg    4980
cctaagggtg ctgacgtgca gccagaaata gttcacttct gtccccacta tggcaggaat    5040
ccatggacca aggctctgat gtttccacaa agatgcccct caggactaga aatctgtccc    5100
catccccgtt gccaccacag tcaccatcac ctggaaatcc tgcaggacca atgtttgtga    5160
atttggaata tatgctagat gccttactac cttgttatga ccttatttct ttatagcact    5220
tttaacctag cgcattacat attttaaatg tataattcag cgatccagat cactggtcca    5280
gtgtcacctc ccactcagca aagtgagatg aacacacttg gtgctacatt cagctaggct    5340
ggcactgtag atgcacccag tcccaggtat tctagtggct catgacaggg cttcctcact    5400
ggagacatgc tgagccaagc aaggcagttt ttaccaccaa ccctgatagt cgtacacata    5460
ttctgctcct ccacccccac caaggttgaa actccgctcc tgtcagcttt gcagctacca    5520
ccacccccctc agggagagtc atctctgttc ccaaacccat ataaatgtca ttcaaagcca    5580
```

```
gaggatgtaa ttgctgtagt aattgttata gtccactcat ccaggggccc cactgcaaag    5640
ctgattaaac catagtgtta ctacctttta cagagttatt attcttccaa atcaacccac    5700
tgcacctttc tccaaggcta caaaagtgcc cctagggtgg ctgtgtacag gcaagttttg    5760
atgtcagctg ggaaactacc tataaccccc actctctgct aacaccaact tttcttttc     5820 tattttattt tattttattt tactttaagt tctgggatac atgtgcagaa cgtgccggtt    5880
tgttacacag gtatgcatgt gccatggtgg cttgctgcac ctatcaaccc accacctagg    5940
ttttaagcct cgcatgcatt aggtatttgt cctgatgctc tccctcccct accccccac     6000 cccctgacag gcccgggtat gtgatgttcc cctccctgtg tccacatgtt ctcattgttc    6060
aactcccact tatgagtgag aacatgcata acaccaattt ttcttattgg aattgtagtg    6120
ccagtttagt tcttcagtgg aagcacttgt tcttctctat aatctgttct ccatctggga    6180
acaccctact ttctcagaca taggtttgca gtgcattggt gggcaggatt tcagtccttt    6240
ctctgaaagt tcctaagccc tattgaaaaa tgaatgcact ggggaagggt gtggcccatc    6300
tctctcccca gaagctcctg agccacattt cttacccagt cccggaaccc tggtatccta    6360
aaccatgtct gaacctgtac ccctgtggcc ccagaaaggg accaaacagt acatcccatg    6420
aaaccacaaa gagatcataa ccttctcctc tctcctccca catctctaca taaacaacat    6480
ttatatagat gactgaattc aagatacgtt tatttggtac tgatggtcaa ctggaagttc    6540
ctaagcagaa ttacttataa tgtgggactg tgttttagt ggttgcagtg aaggctcaac     6600 accctaaac acgtgggaa cttgctgagg aggcaggctg tgaagggcag ggtattagca      6660
tctttcctta aaataacatg tgtcttagtg tgctcaggat gctacagtaa aaataccata    6720
gatttggtgg cttaaacaac aaacatttat ttctcacagt ctggaggctg tgaagtccaa    6780
gatcaaggca ctgacagatc cagtgtctgg taaaggcctg catcctagtt catagcccgc    6840
tgtcttctca ctgtcctcaa gaggctgaaa gggtgagaga gctcttccga gactctttca    6900
taagggcact aatcccattc atagggctcc accttcatga cctaattact acaaaggcc     6960 ctacctccta ataccatcat attgggggtt aggatttcaa cgtatgaatt ttggggagac    7020
acaaacattc agtctatata acaacacgta ccgtgaaact ttcctactca taaaagtaat    7080
atatcttcac tggagaaagt aaaaaagtac agaaaaatat gtagaagaaa atctaccatc    7140
atctcacatc cagagatatc catggtaaat attttaatac aattcctgtg aagttattca    7200
gtacacatta atagagtttg aaaacataat ctaatataaa agcatgaaat tcataaagat    7260
attttaaaat aaagttaata tgtatgtgtg tatatgtatt tttatatata cacaaacata    7320
tatgcttatt atttttattg tgagcattcc cccatattat tagaaaacca tgattttttg    7380
ttctttttct ttttctttc ttttcttttt ttttttgga gatggagtct cactctctca      7440
cccaggctgg agtgcagtgg tgcaatcttg gcttactgca acctccacct cccaggctca    7500
agcaattctc ctgcctcagc ctcccgagta cagggatta caggcccctg ccaccatgcc     7560
catctaattt ttttgtattt ttagtagaga tggggtttca ccatgttggc caggctggtc    7620
ttgaactcct gacctcaggt gatctgccca cctcggcctc ccaaagtgct ggaattacag    7680
gcataagcca ccgcaccaga ccaaaaacca tgattttga tggcatcatc ttatggatgc     7740
aatataatta atttaaccat tcttctacta gttaatatta aggtcatttc caacttttat    7800
tgttgttaca ttgcctctca ttttctttat aaatatttgg ctcttttat tttggatatg     7860 ttgtagctaa aatgccatcc agatagttta ttctgattta gtgcccacca ggttctaggt    7920
gcatgactgc catagcagag atagttgcat acagttcaag tttagatttt gtttgtgagc    7980
```

```
gggagaatcc aaagaccaag ttcctaatat tcttttgcct gaaaaatggc tacataacct    8040
tgccaaatct cttaacattt tcatgccttt gtttctaata tggaaaatga agatactcac    8100
caatttgtaa ctgtaaacta ctacacaaga atgaggtatt catttaacca tatggtgaga    8160
ttttgtagtt aaaattaatt aattgtgctc agtggtcaga ctactggctt taaatcctgg    8220
atccattatt cattacttcc tattgtgtaa cctgggcaag ttacttaact tctcttctcc    8280
ttagtttcct catctataaa atgaataaca gaagcactta ccataagtga ggatgagata    8340
agatggtggt atatgtgagt ggtacacatc tgttactatt attatcattg ttatttatta    8400
ttaagcagtg aatttagact caatgtgaaa tggtttagaa gtcatcagct tcccgtttca    8460
tgttcttaaa gcactggtga taagagtatg cctgtatcat gcagttataa ctttaatcaa    8520
aatatgaaag taactttaat caaaatgcca agtcaaatta gcaaagtcag cccttttcaa    8580
aatgtgtgcc ctaaagtaat aaggtctgca gggtgtgccc cagggacctt tggtggggag    8640
tgggtggtag tcagaatggc gaaaacagtg gggattttta gggcccccac tcacattgct    8700
ttgcttttat agcaaaaatt gttggctgat gaacaaaatc atttccttttt cttggactca    8760 cagctagacc taacttccca agtcctgtac agttaaatgt taccatacaa ttacagtgga    8820
gccatatgtg tctgtctcaa ccacccaagc ctgccattgc agtgtgaaag cagccatagg    8880
caatacttaa acaagggat gtgctgtgtt ccaataaaat gttaccaaac tttcctatag    8940
tttgccagcc cctgaactag agcatggtaa ggcaagagag aattgtagaa cgtggttgga    9000
aaggcagaag gagtcaggga ggaaagacct tgtggaactc tagcacaaag tttggatttt    9060
atcctaaaag cagaagggaa gcctttgaag ggttttagaa aagggtatga cctgaattac    9120
agaagctcag tcctcagcag atcagtattt caacattcac tcaccatgtg aaccattgat    9180
cccattttgt tacttcctct gtagaatctc ctcttaagga aattgaaagc aagctcctga    9240
atgagatggc attttcaggg aaagaccagg aggcagaccc caaggggctt cacaagatgg    9300 cattttgtg gccttggtgg atttgccatg accttggctt ggcaggatca gaaacctgaa    9360
tctattcgcc tgtaagtcct cttttcttgt aagtcctata agacttacac taagttcagg    9420
tgattaacat attaagtcaa aaagcccatt ttagtaattt ttaatgaaaa acataattgc    9480
cacatgtgag aagcccattc tattttcata gacatactta tattagaata acaatgacca    9540
taatggttag catttattaa caataacatt gtgccaggca cagtgtcaag cattttccat    9600
gatgacctca caagtctatc ggtaggaatt gtggttaaaa ccctcttata gataaagtca    9660
gaggttctaa acttataaga tcacaatgct agtgagtggt agagatgaga tttgaaccca    9720
cacagtgtaa accagagtgt ggatacctag ccactacaac atagtgtctc ataggagaca    9780
tgttcagaag gttgctagtg gacattgaat ccatggggga aaagaaggca gaaaaatctg    9840
attttaatgt tatcaggtta atggggcctg atgcagccat cttgcagaag aacggtattg    9900
ctagcaggtc ctccatgttt gtttacaaca ctggctacgg ccttcccact aggatgggaa    9960
ttcccaaatc ctataatttc ctagatggtg ctggaagagg cactgctgag gtttgttttg   10020
ccaactatct ttcccctctt cttcttgcct tatttgtcat tctatccatt aaggtgactt   10080
ttcatccatt ttatatgaat ttcataatta acctctcagg gtaattcccc cagcccaccc   10140
tactatcagg gcagtcccca atatgactaa tcattcccac atactaagac cacagactgc   10200
ttcagaatct gtatttatat tttcactatt aaaaaactat gctatcgttt cctgaaatct   10260
ctatgaaaaa aaatactaa gctatatctg gagtgaaatg gtcagtaaga acacagtttg   10320
```

```
tcacacaaaa taatgaaaat gctatttctt acttatagtg cagactgggg ttcttcctct   10380
agaattagaa atattaggct tgctaagatg tgatggggag ttcattgggg ctagtgtttt   10440
agcttttgaa ctcttcaaaa ggaacagaaa tgaagaaaaa gacctgcttt aataaacaag   10500
gttaagtctg tatgatttat ggacttatga gcaaatctga catccactca catgggtggt   10560
cctcccaagg gataaacttc gtaaaagcac atttaagaaa aagggagcag atactgttgg   10620
tgccctcttc accaggagac acactgaaag gctgcagtag cacatcagag cctcacaggt   10680
cagcatcagc caaacagctg ttctgtgcat cacaagaatt cgtacatatt tcaaaatgac   10740
taatttgtac ctatgagaca ggatttgacc cactaatttt tgtaccgtaa cgttttaata   10800
aaaattgttt tttcaaagcg aagctttgct gagcagatga attatcatgt gggagtttaa   10860
aaattagtca aaggagtctt gacaactaag tcctttaagc ttggccttcc cttggcctct   10920
gcctactcct gatcataatc tgaataaact ttaacttttc gactagaatg caaaacacgt   10980 gttttttgtaa aacgaatatt aatggcataa ctcgtgcttt attattttag ctgatttgta   11040
tcaatgtatc aacattccaa agaaaatagg gagcatatgt tggttaataa ttttttgttat  11100 gactattgac atgtaattca catgacataa actttaccat tttaaaaagt acaattcagt   11160
gagtttgagt atgttcttaa ttttgtacaa ccatccccgc tatcaaattt caaagcatat   11220
ccatcacacc aacaataaac tctggttcta ttagtagtca ctcccaattc cctttttccct  11280 agccccctgg cgaccactaa ttaattattt ctctgtctct atggatttgc ctaccatgaa   11340
cattgcatat aaatggaatc acacaatatg tagtcttttg tgtctggcac cttccactca   11400
acatactgta ttaaaggttt ctccatgtta tagcatgcat cgatccacac ttcatttcct   11460
gttatggctg aataacattt tgtcctctga atctaccata tttgtttatc cactcatgag   11520
ctgatcactt aggctgttgc cacttattag ctattatgaa taatgttgtt atgaacgttc   11580
atgtacaagt ttttgggcag acatgttatt tctcctgggt aaattcctag gagttgaatt   11640
gctgggtcat atagtaactc tatgtttacc ttttttgagaa aactgccaat atgttttcca   11700
cagtgtctga accatttttat aatttcgctg gcaatgtatg agagttccac tttctccaca   11760
tcttcaccaa catttatttt cctttttttta aaaaacaatt attgctgtcc tagtgggtat   11820
gaagtgatat ctcctgtatt ttcaatttgc atttctgtaa tgaataatga tattgtgcat   11880
cttttatgtg cttattggct agttgcacat cttcttttaga gaactatcag gtcatttgcc   11940 ttttttttgaa atgttggttg tcttttttatt gttgaaatat aaaagttctt tatatattct   12000
agatctagac ctttactgga tatatgactt gcaaattcta ccatttctgt acgttgtcta   12060
caatttcaac cattctgtgg gttgtctttt tatttcttc acaacgtctt ttgaagcaga   12120
atagtttttc attgtgatga agtccagttt gactatttttt ttcttgtgct tttggtattg   12180
taactaacaa accattgact aatccgagat tctgatgtac atacatgctt tcttctaagt   12240
tttataattt tagcttttac atttaagttt ttaatccatt ttgagttaat tttttaaata   12300
ttcttttgca tgtagctatc cagttgtccc aatgctattt gttgaatagg tgattctttc   12360
ctcattgaat ggtcttggta ttcttgtaaa aaatcagttg actgtaggca tatgggtttc   12420
tggactctca attctacccg actgatctga atgcctatcc tcatgccagt actacactgt   12480
cttgattact gcagctttgt agtatgtaag tagtagtacg ttttgtgagt cctcgaactt   12540 tgccttttttt tatagattgt tttgctattt tgagttaagt atttttttaa aacatcaagt   12600
taaaaatgaa gctgccactc tctaaaggag gacaatttca gaaaggcact gagacctgtg   12660
cttggtatgt agtaggtgct tttgaaaatg tttgttgcat ggaatggatt gatttcatct   12720
```

```
ctattctaac actcaatgcc atgttcattt ccccttttgga gcctttcatc tctcccttct   12780
cttttctaag aaaatcagta actctctcat tcatacattg tacacataca tatctttatt   12840
tgtttatgtg tctatttcc actaattaga ctataatgcc atataaggct agaattacat    12900
ctaattcatt gctgggtccc aaagccatgc ttaagaccat aagtatatag ggttttttt    12960 tcttttaaaa agttttatt tttaattatt atggatacat aagagttaca gatatgtaaa    13020
gggtacatgt gacattttga tacaagcata caccatataa tgatcaaatc agggtaactg   13080
ggatatccgt cacctcaagc atttgtaatg tatttgtgtt agaagcattg caattccact   13140
cttagttatt ttgaaatata caataaattt ttgttaactg tagtcaccct gttgtctact   13200
gaacactaga tcttattcct catatctgac tgcattttcg tatccattaa acacccctct   13260
tttttatttt ttattttatt tattattatt atactataag ttttagggta catgtgcaca   13320
atgtgcaggt tagttacata tgtatacatg tgccatggtg gtgcgctgca cccattaact   13380
cgtcatctag cattaggtat atctcccaat gctatccctc cccctcccc acaccccaca    13440 acagtcccca gagtgtgatg ttccccttcc tgtgtccatg tgttctcatt gttcaattcc   13500
cacctacgag tgagaatatg cggttaaaca cccctcttt atccccctc cccactaccc    13560 ttcccagacc ctagtaacca tcattctatt ctttctctct ctgagttccc acatatgagc   13620
aagaaatgtg atatttgtct ttctgtgcct ggcttatttc tcttgcataa tgtcctccag   13680
ttccatccat gttgatgaaa gagacataat ttcattcttt tttatggctg aataacattt   13740
cattgtgtat atgtacaaca ttttctttat tcatctgttg gtggacactt aggttgattc   13800 catacctttgg ctattgtgaa tagtgctgcg gtaaacatgg gagtgcagat atctcttcga   13860
tatactgatt ttcttctt tgggtatatg tccagcagtg ggattgctgg gtaatatggt    13920
agctctattt tgttgttgtt gttgttttta ggaaccttca tactgttctc catagtggct   13980
gtactaattt acgttcccac caacagtgta tgagggttcc cctttctcca cacttttgag   14040
agcatccgta attccctgtc ttttgatag aagcaatttt cactgggatg agatgatatc    14100
tcattgtagt ttagacttat atttctctga tgattaagga tgttgagtat tttggccat    14160 tcgtatgtca tctattcaga tcttttgacc atttttaaat caaattattt tttcctattg   14220
agttgtttac acaacttata tattctgttt attaatccct tatcagatag gtagcttcca   14280
gatattttat tccattctgt gagttgtctc ttcactttgt tgatggtttc ctttgctgtg   14340
cagaagcctt ttagcttgag gtgatctcat ttgtccactt ttgcactggt tgactgtgct   14400
tttgatgtct tattcaaaaa atatttggcc agaccaatgt catctcttgc catatacaaa   14460
aatcaaatca aattggatta aaaacctaaa tcgaaggcct gcaagtatga aaccactaga   14520
ataaaacaat atatatgtgt tggagggaga aagaaagta atgaagaaag aaaggccagg    14580
tgagaaagta agagagaagg gaaaatgaac aagaaagaca aaagtcattc caggcactgt   14640 tttaagggc atctcattta ttcttacaac cttatgagat aagcactctt actttcagtt    14700
tgttcaggat gctataacag aatcccatag actgcgtggg ttataaacaa tagaaattta   14760
tttctcttag ttctagtgac tgggaagtcc atgatcaagg cactgacaga actgttatct   14820
ggtgaggacc tgcttcctgg tttacaaatg gacagccatc ttctcttctt gctttgtcct   14880
cacatggtgg gaagggtaa agaagctccc tgaggcctct tttatatggg cactaatccc    14940
attcatgagg gctctgccct catgaccaaa tcacctccca aaggttccac ctcctaatgc   15000
catcaccatg gggttaggat ttcaacagga atttggaaag gacacagaca ttcagaacat   15060
```

```
agcaccccca ttttacagat aagaacagtg agaaacagag agttaaataa ttttctcaag   15120
gtcatacaac gaacccgtag cctaggcagc ctggctcttt ggtcatgttc ttaaatacta   15180
tgccatactg tctctcaaat aaacactaaa atcaagatac ttgggatgat cgttgggagg   15240
cagagcccag atatctatac tttaaacaaa ttcccaaatg atctgatggg caactcagat   15300
gaaaatcaat gcttcaagaa atagccaaat aaaactctat ggaaggtaaa gatggggaga   15360
gcttggtgag atgtcatact tgggaggaaa agccagggaa agtaagagaa aactgggtat   15420
tagtaaagat catggagaag ggaaaacaca agatattgct aggctaaaaa agaggcagac   15480
ctgatgaagc agtgaacacc acttcagcca ctccctacct tggccccagc tggccctggc   15540
tgtgactgtg ttccatactc tgcaatgaca tgtaacttcc accacgtcca tatcatacct   15600
aaagcctact tcagtgtgtc cacaaaagca agtaagaata aaaagtaaga gaaacaactc   15660
acatttattt gctgcttatt atgtgccagg ctatgtcctt ttttttttga gatagagtct   15720
cactctgtca cccaggctgg agtgcagtgg tgtgagcttg gctcactgca acttctgcct   15780 cctgggtca agtgattctc ctgcctcagc ctcccaagtg gctgaaatta caggcacgtt   15840
tagtagagat ggggttttgc tatgttggcc aggctgatct tcaattccag acctcaagtg   15900
atgtgcccac ctcagcctca caaagtgctg ggattacagg tgtgagcctc cacacccatg   15960
tgccaggcta tgttttaagt gctctaccca tgagaactca cttagtcctc ataacaatcc   16020
tgtgaggtag gtactattgt ttcccccccat tttacaggga aggactctga agcacacaga   16080
ggttaaggag tttatcaagg tcactgtagc taacaagcag cagaaccaga ttcaaacccg   16140
gagcccacac tcttaatcac tatgttgctt ctagaagaaa gaaaataagg gatgaaggat   16200
agtaaaaaca tgcaagccct tctgagcccc ctgttgttgg ccccactttg gcaggagtgt   16260
taggaagact atgggaactc aaaggtgaca cttagcactc tcctccagag gctacaggag   16320
ccatcattgg tagctagcca tttgtatccc ccgtgatggt ggagaaaagc ccacactgtt   16380
gcaagtttcc agaattttct ctgctctgga aaagactccc aaactagggt taatcaagta   16440
tcttttttgg tgaatttcat taaaattacc acataaaaaa agaagaattt gtcctgaatt   16500
atacatatag gagaaaaatg ataaaataaa ataatttcca ttatctttgt agcaaaaaaa   16560
gttggaatga ttccaccagg ttctctgaag gactttgttt tcaaggagga tgttaaaatg   16620
tgtaaaatat ccaaaggata cacttttgca gctgaattta ggatcttaag aaacatggtt   16680
ttaccgtgtt tcccaatgat tgttgaaaag aagcagtgac tgggttacat ctagggcagg   16740
gtttctcagc ctcggcacta ttgacatttt gggccgggta attctttgtt gtgggggct   16800 gtgctatgca ttgcaggatg tttagcagga tccctggctt ctacccacta gatgccaata   16860
agattctccc tttccatctg tgacaaccaa aaatgtctcc aggaatttcc aaatatcccc   16920
tagggccaaa atcacccagt tgaaaactag tgttctaggg aaaaccatta taattaatag   16980
catgtctatg atctcccctg ttgcgggaag tcagggaccc caaacggagg gaccagctga   17040
agccatggca gaagaacgtg gattgtgaag atttcatgga catttattag ttccccaaat   17100
taatacttct ataatttcct atgcctgtct tcactgcaat ctctaaacac aaattgtgaa   17160
gatttcatgg acacttatca cttccccaat caataccctt gtgatttcct atacctgtct   17220
ttactttaat ctcttaatcc tgtcatctcc taaactgagg aggatgtatg ttgcctcagg   17280
accctgtgat aattgtgtta actgcacaaa ttgtagagca tgtgtgtttg aacaatatga   17340
aatctgggca ccttgaaaaa agaacaggat aacagcaatt gttcaggtaa taagagagat   17400
aaccttaaac tctgaccgcc ggtgagccag ggggaacaga gccatatttc tcttctttca   17460
```

```
aaagcaaatg ggagaaatat tgctgaattc tttttctcag caaggaacat ccctgagaaa   17520
gagaatatgc ccctgagggt gggtctctga aatggccccc ttgggtgtgg ctgtcttcta   17580
tggttgaaac tgtagggatg aaataaaccc cagtctccca tagcgctccc aggcttatta   17640
ggaagaggaa attcctgcct aatatatttt ggtcagacca gttgctctca aaccctgtct   17700
cctgataaga tgttatcaaa gacaatggtg cccaaaactt tgttagcaat tttaatttcg   17760
cccccgtcct gtggtcctgt gatttcgccc tgcctccatt tgccttgtga tattctatta   17820
ccttgtgaag cgcgtgatct ctgtgaccca cacctattcg tacattccct ccccttttga   17880
aagtccctaa taaaaacttg ctggttttgc ggcttgtggg gcatcacgga acctaccaac   17940
atgtgatgtc tcccccagac gcccagcttt aaaatttctc tcttttgaac tctgtccctt   18000
tatttctcaa actggctgac gcttaggaaa atagaaaag aacctatgtg actatcgggg   18060
caggttcccc gatactcccc aaagtattgc atggaatgcc acatttcttt tatcatagtg   18120
cttcaaataa gtatttcagt gtgttactga aaatatttat aaacaaaata tatttgatag   18180
cagggtatga atatgcccgt gtccttggaa gagaaagagg ggacaagaga acaggtataa   18240
cagcatgttt ttggtgaaaa taaattggta gtaatataga ttgaatatcc cttatccaaa   18300
atgcttccga caggaagggt tttggatttc agatattttc agattttgaa atatttgcag   18360
aatacataca ggtagagcat ccctaatcca aaaatccaaa atctgaaatg ttccaatgag   18420
catttccttt gagcatcatg atagcactca aaaagctttg gattttggag catttccgat   18480
ttcagaattt gggattaggg atatttgacc tatagtaatg ccaaatactg cactaaaatt   18540
agcaaatgta atctcattga attgtgacaa cagccttaag aggaaacccg atcattatgc   18600
ctacttagta gatgaggaaa cagaggtaac taggtcaagg tcacacaact tggagtgtca   18660
gagtctggat tctttctagt tctgccctcg tccaagccag ttctgttaac actattcttc   18720
ctttcagcat aatctgtgtc atcactggag cttatgtcta cctgcctgcc acccagcacc   18780
aactgtttac cctttaagtc tcattctgcc tcctccagga gccttccctg accccctgcct   18840 tcaccttctg acctgtgccc cttcacaccc tgtgccctct taactgggaa agccctgagg   18900
gcaggggcca taccttattt acctctatct ccagctcact gcacagaggc attcagcaga   18960
tgaccagtaa atatgggctg tctagtaaaa acttttgcagt tagagataat gaaagaaaca   19020
taattacttc tgtgtgggtt gagaaagaag ggaagggaaa gtccagatac ttaagcagaa   19080
aaaggcaaac agtccaaaag gggaaaagta acttgcccaa atcatgcagt tgagggcagg   19140
aagaaagggg gacaaagcca aaaccaaaac ccagtcccctt gtcccagccc agtgctttgt   19200
ctgctacgtt acacaaactg tgattgtgaa attaaagggt ttttgatggc actgatataa   19260
gtaaataaat ggcttatga gttaacacat gacaagcaat aaactcataa aagtaaata   19320 ttgacaactg aagattatat atcactatgt ttagtgtgtg gagaacccaa ctaggaatta   19380
ggaaagcttg cacattcagt ctggtttctt ggcaaatcaa tgagacttca aacaaatcat   19440
tttatttctc tgtgcttctg tttctttttgg ctgtagtatt ttgctggtta aagagcacgt   19500
gatcaatgtc tatgctttta aatgtctgtc tttatttgag catgctcagc tggatgtgga   19560
aaacctatgg ttctcttggg tttcataagg atcaaatccc acagtgatat gtaaacttgt   19620
gtggtttata gaattatagg acctcaaagc tgggagaggc ctgataaatc atatagtgaa   19680
aatttccagc cagtgcctgg atttcttttta cagaatcttt cttttattgg acaggtgctc   19740
ccttcacaat ccatgatgta aggagaaaag gggcttcgtt tgaaggaagt tagtgtattg   19800
```

-continued

```
tgtatgggcg tgtactttct gcttggggtg tgcctacagg gctatctcac tttctgaaag   19860
cgtaataata agttacttta ccatgcatta attaaatgtc agagaccatg ctaaatgctt   19920
tacagagaat atctttttta atctgtataa gaacctcctg aggcagataa tattattaac   19980
cttactttc  agataaggaa actaacattc agaaaagtta agtaacttgc taaagacatg   20040
tgtctactag gaggtagagt ctcaagtcta tttcaagctc ctaataagta aataaatgtc   20100
tattgaatcc aactaatgac atcccactcc atattcccct gccactgatg agagagagaa   20160
gtataaagtt tatgtaaata agacagaagc aatgttttat ataagcattg tggatttaat   20220
tccactaagg gattgatttt tcatcttaat ggaactttt  cttcagctat caagtttcag   20280
tttcaagatc gcaaatgcta agaagatatt aaaatatttt aatacataat tccactagat   20340
catatttata ggtactgtta atatattacc aaatctacta taaacaaaac aataaaacaa   20400
aaggctggat caatatggaa agtagagtaa taatttaggc cctaaagaaa aactacgtaa   20460
gacatttctt agaggattac caggtttctc tctctctctc ttttaaaca  cagcctaaaa   20520
tagaaaagca atttatgtat taataaaaaa aatagaaacc tgaggcagat gtaaccagaa   20580
taggtgaatt aactgaagac tgatattctt atttatgttt gtgtatttta aataaagaag   20640
gagtttgacc atctcatcta gttaatcatt aaaaggaaac tcgagccaaa cttgtgaagc   20700
aggtaaagtt tatttttaga cattcaactg gcttctcttt tgggctcccc ttttcttttg   20760
gggtcatcct ccatgtctgg taaccttaac ctccctgtct cttccagaag gagcaacacc   20820
cccatgtttt agacctttac ttctgatgtc aggaccctt  ctgatgcaag tgttagctaa   20880
ctccagctgg ctgaagagga aggaggagga agagaaggag ggggaataat gtattgaagt   20940
gtgtaatagt caagtctagg agcagccctc accttaggat ctagacattc atattatata   21000
attgggaatc tatttccaga tctctttgct tttttttttt gcaaacctca atccaatgga   21060
gtctctaagt ggtagaccac agctgctcca agcttgcatc gtatcagctt agctattcct   21120
gttgagaaac aagacaagtt tccaagtagt cccagaaagc caagaattaa ggtgtatctg   21180
tccctgtcat gtgcctatct ctgatattac cagacctggc ccatgcagag ttacagatgg   21240
gttaatacca ccataagcgc atggaccaaa gttagggaaa ggatagtttt ccaaaggaaa   21300
tgttaggtcc tagtatcata tgtggagagg ggatacttgg caagtaaaac agtacctatc   21360
taccatgtgg ccacaacagg gcagatcagg gtccctggta ggatggaggc agccatcaag   21420
cattatggta tccctgaata atcccttccc agttcatatg taaaccaatc ctcttaaatt   21480
gttaatgcat ttaacataag gatggattca gcaaaactgt atcaatagca aaacatgagg   21540
ggtctccagc tagtagcctg tcctgcatag ccatccatga ctactgctct aattgatttt   21600
ttctagaatg tctaaaggaa gatgaaagta gaaaatgagc tgtagtggac aagcattttt   21660
aaaatgagcc caataatgta gcacttttgg gtgcttgata attgttgcaa atcacatttg   21720
cctgagaaat ttcaattcta taataattgt acaatagcag aaagatctag atacaaaaat   21780
attcattgca gcatggcttg caatagtgaa aaattgaaaa caatttacat atacttcaat   21840
aaggaaaggt taaacaatg  gtatactatg ctactattac ctgaaaatat tgaaaagatg   21900
aaagatgtc  caataacatt tgatgaataa aggttgaaaa atacatgtag taaaatctca   21960
tttttgtttt taaaaaacat atatgcatgc atgcatccat gtatagacaa aaaggatttg   22020
aaaatataca ataaattata gttaatcaca tttaccttat ggtactgcag aacatcagaa   22080
ctcattcctc ttatctagct gtaattttgt aatcgttaac taatctctcc ccatcctccc   22140
cttcccctg  cccttcccag cctctgatag tcacaattct actttctatt tcacataata   22200
```

```
aaagttttta aagagggaa taatggggtg ggggatctgg aatatacata aaaactcaaa   22260
aataattaca aatttgttgc catcaaaata taaaagaaa aaaatagtta catctgcaaa   22320
atgggattgt gtgaggaagt ttttaccttt atacatttct accttctgta tgtttggatt   22380
tttacaataa gtatgtgtta ttttctagca tcttttgaag ttttttttctt aaaggcataa   22440 gtaatatcta aagttatttt tcatccttct aatgccgtct acacaaagat aacgattttt   22500
cttggatggc cccaatctct cttctgtaag atctttcccc atttgtcata tccataactc   22560
ataacctcct caccctcac tgctctccat tttctctata aagtgagccc agtcagtact   22620
tgtaggcttg ttaagcatta cttctaataa gaaagactaa cttgtaaagc aaatgtggaa   22680
atgtactaat atagcatcaa gcacaaaata gccattcaat aaccgaacta tttaattcct   22740 ttttttcac acttcatcct ttccctaatt ccagaaagaa cttgaactgg gtcataacaa   22800
agacaaattt agacagacag ataaagatat ctcataggta gaaataaaac tgagtgatta   22860
taaactaatc acaggaggct ctgttagtct gatgaacaga aacacacgtg ataaaatcac   22920
agagaggtaa aatagaaaat gaaaatcagg atcaagaaaa gggaaataaa aatatgctgg   22980
acatcattca ataactattt gctgatggta attatagga tggaaaaccc atcaggccta   23040
tggagctaaa attaatcagc aagtattcac agagtgccta ctgcttctat tactggttct   23100
ggcttcctgc ctgcccagtg cagaggcttg agacatttgc gtgacattca gcttgtcaag   23160
acagaaggag caaatagc agacagaggc tcactgcagc cgcctatacc catcatattg   23220
ttggaatcat attcaagtga gacaaactcc ttcagtggaa gacgataaaa ctagcttaaa   23280
agttgtaaac atcacttcat cacccaaaaa aggcccaatt aagtggagat actatttctg   23340
caaagcaatc atcaattcat ttgtgtaaca tttgaaattt caagtacaa acccacattc   23400 tattaaaggc aggaagtgaa accaataaaa cttgtaacaa ctatacttaa ttttcagggt   23460
tctttccatt gctgacaaac attttaagtc atgtctattc tcttaaaatg taaaatatga   23520
tgtttatgtc actgttaata ttttgataaa aagctattgt catggacatc tgggttttt   23580 tctgcatgcc cagaaatccc ttttctccta tttaaattta aaatctccaa ttatttggag   23640
aagcacctcc tcttctctct ctttcatttg tacccccattc ttaggtgtca gtggtgggca   23700
cttgagctag gctttgccca tcatagtaca cattcctgac atcccttggt catagttatt   23760
ggtccaggga taagcatttg aaccaactag accagtgaaa cccctcccag gaacaactac   23820
taaaattatg ggaaaagaac tctttccact gaagttacta acctggcagg atgtgttaaa   23880
tccaggtgcc acaggccacc aggtggagag gtggagataa tctttccaga aaacaaaaca   23940
aaacaaaaca ggaaaatgaa gctaagggat aaaatttaag ccctttggac ttcatttgag   24000 ccctgaatc cagtcatgcc tcctgaaatt aaacttcccc tggactttc agtgaatcaa   24060 aaactctgt ttttaacagt ggggtttctt ataaatgcac caaaaatga cctaatgaat   24120 gttgtctaca agcttccatt agaagtatta tcttcaagag aaaaaaaaa caaataactt   24180 gaagaaaacc cttcataatt caagtcagtc ctgctaacct ctaggaaacc ctccgtgacc   24240
accatctcca tatccacacc cattttccta accttaaaca ccagatgact tcttgaagct   24300
tatgaagtgc cctatgcatc taacacattt ctgtaagtct gcattgttct ataatgactt   24360
gtaaccgtat ctgtctccat ttcctccaga gaagagattg ttatcatttt gatatccctg   24420
cagccttata ctggggccta acatataata gttgctattt tgttgaagga attgtatttt   24480
gttgaaggaa ttctcttttg ttgaaggaat gaatggagag aatattaatt aagaaagtct   24540
```

```
cttctattaa taaacattcc ctgattgatt gaaaccatgc ctaaaatagc taatcatcag    24600
aagaccaaag taaacaacat atccaaactg aatcctcaaa gtgttagtca ttggtagctg    24660
tatagctgag aatctttcct tcttctggtc attagggttg aaagggtggg tgaatgtgga    24720
gacatgattc tttcttttgc aaaacattta ctatttttta aactccataa aatgtaataa    24780
cttctcttga aaaatgttaa aacccaaaca aaaaaacctg taatgtggaa tatagattgt    24840
aggttataat ggaggaagca gggaaagtgg ggaaaactgt ggttgccaga agttttctga    24900
taactaatag gcaagacaat agggtggctt ttggtagggt ccttctttat ggcatagcaa    24960
agaaaaatag gaatgaagaa gtgagaagca tgaaaggggga cagcaatata tgtgtaacac    25020
agggtgattc agtgtgagag ttttataatt aaaattgcca aatgtgagaa aaaaaaatct    25080
actataaatt gggataggct caaggcatgg agatgaacaa ataacccctc catgtgggca    25140
aaaatcaatg aaattactag atgagtagct tagtatgtga gttccagttg caacatgtta    25200
ctggtatttg gggcttcccc tccccctcc ccccctgcac tttgaggcaa ttcgacattt    25260
gactaacaat ccagcctaac tttctccatc tgatataaag atatttacct tgaaatccta    25320
gaactgccaa catctcctac ttcctactac aaccctccct gactccttt ctctggcaca    25380 gctttctatg cactcaccc attcaactaa gcctgcttac tcttcaccag aaggtcttct    25440
cttagcataa aaagttcctg gaagtccatc tctttcatag agctgctgga tgactgcttt    25500
gcttaccttt ggccttcaaa atacctctcc tgtccaacca tagctcccca gctccctgc    25560 cattgcaacc aatacaaact tcgtcatctt tccttgggcc aatgtgcctg tctcctcact    25620
gctctccctg ctttctccct tagccccctac aactcatact ccacatcgca agcagaacga    25680
gcttttcaaa tagtaaatta gattatgtcc attagtgtgt tagtaaatgt ttaacagctc    25740
ctgaggggaa cagagtatct atgtgtttta aattttttac atatatgtat cacataattt    25800
acaaaaagca agaaaaaata taacactctt aatagtaaat tctatatggc catgtgattt    25860
tcacagaacc atttcagtga tttttgcaga atatttgtgt ccatagccaa cctacagcta    25920
aaattcaaac acgtttggca aaatcagacc acaaataaat atctgattaa tatccaatca    25980
gcaaagaagt cattcatggt actgaagtcc caacatgaat gttggttgat atttttacat    26040
taatgagcga gataaaagtg aagcaacaaa aatggatgtt ggaactaaac tcgttcatta    26100
atgacagaag tgacttcttt tgctgataat agctttcaag tactagaaaa atatttcctc    26160 aagttttgt gttcacaaac taaggcactt ttaagttcaa tcttcattat taaaatttct    26220
tctactctgt cagtctagac aatcaacaaa acaaatcaag ctctggtttg tcatgtttcc    26280
caatttctat agtataggta ctccaccatg gttgatttca aactaccaaa ataacatttc    26340
tgaatgcagc gttaggaagg atacgctgc atcataccat cgtatggtat gttcttatac    26400
agaacagaca gaaataactt taagaacata gataatagta aaatggagta aaataattag    26460
gcagtaaagt cttcagcatt tattttttgtt gttaaaatat ttgattgtga gtttataaat    26520
aatttggttt ttaataatga ctgtgattaa caaccaactt acaaaatctc tgaaaattta    26580
acagtcagtg cttgcaagct ggtacaattg tttccggtgc actactgaat tatcactccc    26640
ctgcctaaaa ttccagactg cccattgcac tgattccctg ggaataagt gaaaagagac    26700 aatgataatt ttcattttttg ttgtggtgaa gtgatagtgc aaaaattcca taagctcctc    26760
taagttttcc aaataaagct tagtgtttaa aaacgtttga acacatgatc ccatgtaagg    26820
cctacattac ttcctgtgtg ataggtgggg tagatatcat tatccttcct ttacagattg    26880
aaaaacaagg ctgagaaaaa tcaaatgcct accccaggct cattcaagta agtaaatggc    26940
```

```
agaatagggt ctaaaaacca ggtcttgtat tgaaaattca acaagaggat agagaaaatt    27000
taattgacaa atactgatct caaaacaatt ttttttttcaa tggtgacaaa tgtcctttgt    27060
agcactttgg agtttgatat gaagtatctt cttatcttgt taagggatcc ctataccaag    27120
aatgttttca tctcaacccc actatttcta agttagctta aaaacaaaac aaaaccctgt    27180
gtgctctaat aagaagatat aagaaccaaa atggaaatgc aggttctcaa atgagctgaa    27240
agattccaca tagcagcggg gcagattgaa acactcttta ccaaaggaac atgggagaga    27300
aaaggagatt aaatcaagaa aggaagaaag ctaatgacat atgaggagcc acaaatgcca    27360
caaatgaaaa aacaaagtac gtaatacttg ttgcaattat tcagtgtgct tgctctaatg    27420
cctccaaaca ttaaaaacat tgagttcctg cttatggcaa catttatctc atttatctgc    27480
tgatagctgc ctcatccttg aatcaggtat tgcttaaact aagttctgcc agcataaaga    27540
ataaagtcaa ccaggacacc cattgggcat ttcacgcata tgagcacaaa ttgtgatatt    27600
ttaggttgct tatgatgaaa tcattgaaag catcatgaaa gacagcaaaa cagcaggaaa    27660
gctagtaata atttagcatt tcccagtcca ggcgggaatg ttaattctaa ttacaacgag    27720
gaataccaaa gtggagttca ttatgattaa gaacttgctg tactagtgtg aattgtttat    27780
aataggcatg tctggcataa aatacaaata ttgaagcaga cagagatggc tcattcaaag    27840
ctcagctggg ttcccttgaa cctcttacct tataaagtta aataggaata gaagtatttt    27900
ccaaagtcaa gatattattt taaagagaca aataatagct atgatagctg caggaataat    27960
tttttaaagt aagttctaac caccaataaa agctgtttgt gtgggcttaa catgttcaaa    28020
atacacaata cacatgtaca caatacacgt atacatggtt cccatttata tttaacatca    28080
cacatttaaa gtgagagagt acagaaaaaa agaataaatg gaaactgaag ccatgacaaa    28140
gaatcacgga ctataggaaa ataagtcaca aagaagtatg cttatgtaag aggaaatata    28200
tgtgataaac aacaggagac atgggaatga atgtggtgtc ttatgtcctt tctttaacag    28260
aatcgtgtaa cagacactac tcaatatcga tctcaactga tccagttctc cagtctccct    28320
ggaaaacaat ggattgatgc ccagggtgcg ctgaacactg gaaccatggt cacttctgca    28380
cttcacacga ttctgctccc accagttgag ctaccaacag ttcctggtgc ttttgcttcc    28440
caaacatgtt tatgccattt gttgcttatt actgtactta cttaatttga ttaaatatta    28500
agtaaaatga tgaaatgagt gtaaaaaatt gttctataaa atctaaatgg aaagatgccc    28560
tatagccttc cttgacttac agttgcgtca agtaaggtgg atgtaagaca attttaaaag    28620
actggtgtgg gggcaggagt gaggaatcat aaaaaatttag aaatctgcac gaaaattatt    28680
ctaaaagtac acattgaaca tccctaactt gaaaatctga attttgaagt gctccaaaat    28740
ccaaaacttt ttgagcattg ttatgatacc acaaatgaaa aatcctacat ggaagtactt    28800
accacaaact ttgcttcatg ccccaaatta ttttaaatat tgtataaaat tatcttcagg    28860
ctataaggtg tatatgaaac aaaaaatgaa tttcctattt agacttgggt cccatggccg    28920
agatatctca ttataatgca aatattccaa aatcagaaaa aaaaaaatcc aaaatctaaa    28980
acactttcag tattaagcat ttcaggtcat ggatactgaa tgtgtatctt taatttcttg    29040
ttctactttg tttaaaaaaa agggggaaaa tagtaattct acagatgaat aataattgct    29100
aatgatgagc aaatacttcc tatgacccag gaattcgtct aagcacttca catatatcaa    29160
actggtttaa tctttataaa tcagtactat tattatcccc attttacaga tgatggaaaa    29220
aggcacagag agttagcctg cccaaggtta cattccttttt agtggtggag actgtatttg    29280
```

```
gcctttatag tctggctttt aactgctaca ctatatcaat gcattacagg tatagtttat    29340
acacacacta aagaagacat ggaactccag tcagtgggct cataaaagct ttagaccttc    29400
atcaaaagat tagaaaataa atgttcaatc acaggtttta ggtttcaaaa gtttcaaaag    29460
tttaaagttt gcaagttatc tttcttaaaa ttatttcctt cttttaacta attttaaat    29520
taaactccag ttcaatcaca tccactagaa ggcttcactt tctacaaagg ggtaggtaaa    29580
ggtgatgatc ttaaatacca tactgggagt tgggatctgt gtagcactag aatcaagagt    29640
tattgtatat acttgagaag gagcacagcc tgatttagtt gatgttttgg aggggtaatc    29700
tggcagtaca gcttggatta ttttagtggg aatggagatg acaaaacatg aagagaatgg    29760
gagaactcac ttgggtaata tatcagtttc tgaaatcaat gtatcaagtg gtttggttat    29820
tagtcaggct taaggtttta ttggccttag gacatagtct ctaagaccat atattatctt    29880
cattcattca tttaaccaac acccactgag caccaactat gcactagtga tacagggggtg   29940
aacaaacaga cacagtccct gcctttgcag aacttatgtt ctggtgggtg atacagagaa    30000
ataacaaatg agggcacaaa taatgaacta tcattgtaat gtgctaacaa agtatgcaga    30060
atactataag aacatacaat caagaatcta atctagttta ttttaaaaaa aagtgggggg    30120
agcactcaga tgtttaaaca caaaacaata aaaatgagga tcttgagggt tatctgtaca    30180
cttttattta acccatttgg ccacaacaat aacccagtaa aagtgatttt acatctagtt    30240
aactagttga ctcaatgtta ttataaccct gtaatgtatt tgttgggtgc ctgctatgta    30300
gtgggctgtg ttccaggagt gggacataaa gctatgacaa gatagatcag gtccttgcct    30360
tgactgagtc tgaatacatc accttcattt ccacctctgc ttctaagaca atcaaatacc    30420
ttcccactca gatagggatt catcctatt t cttgtagtaa ttataagttc ccagggttac    30480
agattagtaa atgccatacc taaagactta ggatactgtg cataaaacac tttcaatagt    30540
gtctgtcaga cagcagatgc gcaataaatg ttgactttcg ttagaattgt gttattatta    30600
taatgctaaa tctcacgtcc tttctggcac actggagttc atctcttcaa ttaaattccg    30660
taagcacata ttgtaagtag tctatcagaa ttgatatact acttcatgtt aatgattgag    30720
atcagtgagg aaaaccactt taatattgtc taattcctct cttaatgcat aggagccatg    30780
tgaacttaga caagcatcaa cctctgtaag cctgttgtcc tcatattgaa aaatcgaata    30840
acaataccta tctcatttaa ttgttgtcag caaaagtggg cagcagaaga gtggggatca    30900
ataaatgtta gccacaaatc ataactattt gtattactct gaaaagagg ggttaactta     30960
tagttcatgc atgcttccaa atgaatgtga aagactaaag aatgagaatt ttttgctat    31020
caaattaaaa aattaacagg cacatttaga ttgctgaaga gagaaattag gataagtttt    31080
ttttttttt tgctcaatta aaaacgtttt caatggcata tttaaaacta cgtattcttc    31140
cccattaaga tctgcagaga aaaaaatg aagggagaat aattgggaac tcttgtgaaa     31200
tcataaatta tttaagcaga gtacctacca ctaaggattt gagcatgtat gagcgatgag    31260
gtggattctt agagcagaga ttcagcagtg agacaggcta atggcatggg gagatgtgtt    31320
ctattagaca actgtattgt ccccttaatt atatacatat atatgtatat aatatatatg    31380
tgtatacata tgtatacata catgtatata taaatagaat tcttaatcat tttaagcagt    31440
gtacaaggat aattattagc atgggctatt taactcactt ttaaaacgtg taaaacatta    31500
ttgtaggtt gggtcttgat ttgtttccca tgaaactgtt ggtagtttag gggccaaatt     31560
aacgaaagac atctcattct agtgcttgag gctcagaaat tggaaaaacg ggcaactagg    31620
tcaagcagtg ttctcatagc ctcacagatg agcatccaaa gcaagggcct ccttctagtt    31680
```

```
gacttgtgcc aagggacagg agaagcggag tctgccttct gggtccagaa gggggttttg   31740
ttaacatgga gttgctcagc gcccttcata aaaattcttc tggctgaggg ttctacgttg   31800
gcatacggtt ggttccctct tcttttccga ggtggcgagt atctcttcct ttgccaagat   31860
ggcggctcca gaatcctctg gaggcggccc ccgtagatcg tctccggaca agaggcttgc   31920
tgaaagccta cttctttcct ttcacatcag acaatgcaca gggaaccgtt tacccttgag   31980
aaccaaggaa ggacggctta ggctacccgc gatcgcgaac ctttgccaag atggtggccg   32040
cggggacggg ctggcgacac tgtaccctac caagatggcg gcgggcggct tccgggacgc   32100
gcttccccaa tcgtcttcaa gatgtcagag caggggagc cgccgtcagt ctgagcgcgg   32160
cgggaggtga gagagtggct gtggccgagc gcccgagcag gattaggtgg agctgcggca   32220
gcccccgccc gtgtcaggag ctggcaagcg atgtcacctg tgggggcgca aaagttacct   32280
ccccaaaccc taaacccaca cagcacaacc tttcccagag tcacaaaaat cataatctgt   32340
gccgcacaag gtaggaggct cggtcccggc atcgtccaag ccttcccgac gcggcgagct   32400
ggggaaggga gctggggcgg gggcttcccg cacgggcacc cctcgcccca cggccctctc   32460
ctttctcagg acggaccacg agttcccttc cccttggact gagggggaag ctcctaacag   32520
gaacatctgt agggagttga acgctggcat tttaaagctg cctgtatttt gttttatttg   32580 tagggggcagg ggtcctatga acgtgatagg gtgagcaacg cacagagtcg agggcagcaa   32640
atgtcaagat tcgggggtgg ggcctgcacc gggaacttgg acgcgggccc tggccggggt   32700
ggaagaagag gtcaggagtt tcggaagggg ggctatattt cgccagcaac ttactatttc   32760
gcctgcaact tgcttttaag cctgccgccc cctgcttttcc ttaatcataa taataaaaaa   32820
aaagtgcaaa gaaatccagc tcgctggagg ttttgcattt ggcgtgcaac ttccttcgag   32880
tgtgagcaca ttgggcggga ggggtggggg ttgaacttgg caggcggcgc ctccttctgc   32940
cgccgccgcc gcctcgcaga ctcggggaag agggtggggg acgtcgggg cgcggggag   33000 ggtgggttct gctttgcaac ttctctccca gtgcgagagc gcggcggcgg cagctgaaga   33060
cccggccgcc cagatgatgc ggtggtgggg gacctgccgg cacgcgactc ccccgggcc   33120 caaagtacgt atgcgccgac ccccgctatc ccgtcccttc cctgaagcct ccccagaggg   33180
cgtgtcaggc cgcccggccc cgagcgcggc cgagacgctg cggcaccgtt tccgtgcaac   33240
cccgtagccc ctttcgaagt gacacacttc acgcaactcg gcccggcggc ggcggcgcgg   33300
gccactcacg cagctcagcc gcgggaggcg ccccggctct tgtggcccgc ccgctgtcac   33360 ccgcagggggc actggcggcg cttgccgcca aggggcagag cgagctcccg agtgggtctg   33420
gagccgcgga gctgggcggg ggcgggaagg aggtagcgag aaaagaaact ggagaaactc   33480
ggtggccctc ttaacgccgc cccagagaga ccaggtcggc cccgccgct gccgccgcca   33540 cccttttttcc tggggagttg gggggcggggg gcgaagcgcg gcgcaccggg cggggcggcc   33600
acgccagggg acgcgggcgt gcaggcgccg tcggggccgg ggtggcgggg cccgcgcgga   33660
gggcgtgggg gcagggaccg cgggcgcccc tgcagttgcc aagcgtcacc aacaggttgc   33720
atcgttcccc gcgccgccg cgcggcccct cggcgggga gcggccgggg gtggagtggg   33780
agcgcgtgtg tgcgagtgtg tgcgcgccgt ggcgccgcct ccacccgctc cccgctcggt   33840
cccgctcgct cgcccaggcc gggctgccct ttcgcgtgtc cgcgctctct tccctccgcc   33900
gccgcctcct ccattttgcg agctcgtgtc tgtgacggga gcccgagtca ccgcctgccc   33960
gtcggggacg gattctgtgg gtggaaggag acgccgcagc cggagcggcc gaagcagctg   34020
```

-continued

```
ggaccgggac ggggcacgcg cgcccggaac ctcgacccgc ggagcccggc gcggggcgga   34080
gggctggctt gtcagctggg caatgggaga ctttcttaaa tagggctct ccccccaccc    34140 atggagaaag gggcggctgt ttacttcctt tttttagaaa aaaaaatat atttccctcc    34200 tgctccttct gcgttcacaa gctaagttgt ttatctcggc tgcggcggga actgcggacg   34260
gtggcgggcg agcggctcct ctgccagagg taagaagcga ggcgggaggg ggccggggcg   34320
cgctcgctcc cccgaggtgc cgctgggacc ggagacaact cggggccgc cgcgggagcc    34380 tacaaacttt tattagcctc ggggagtggg ggtgggggc tggcaagggc cgggcgacgg    34440
tgacgaaagg gcagcgcgcg ggtgacagcg ctggcctctt cctctccctc cgcaggcgtc   34500
ccctggccgg gccgaggggg aggaacctga cctcggacgg cgagcggagc cctgtcgaac   34560 tgccggggc ttcgagcctc tcattcctcg cgggaatcct ggcctctttt ctcccctag    34620 tgtccccttt ccctccaagg gggtcgcccg acacccgttt tcgtggtgaa cgctaagccg   34680
cgtctgaatt ttactcgccc gaatatttgc acgccacccc ggcgcgcccg agcgcgagcc   34740
cgggctccgg ggaggccccg gcggcgcctg gcttgaggag ggcgtgcggg gcgcgtgagg   34800
gtgcacacgc gggggctga cagcccgcaa cttggagact gcggccgggg ccggcgttat    34860
ctgttagaag tgggcgtgtc ggagagagaa ctcaacaggt ctggacgtac ttctcttta    34920 acctcgcact ttttctctt ctccacccc gccccgcaag ggcttgctct ttagcgtttg     34980
ttgttaattc gcgcctgagg tttctaagtg ccccttta gaaaagacc ccctgtaacc      35040 gtaatggttt tgtgctgcga tttttacaag tgctagtttg acgtttgggg ttgcagactt   35100
gataattgca accttgtaat accacttaag accctctggc atggttcatt agggccaatt   35160
aatgtggctg ggttatttgc aacttaaact gggggataat gtcgcttgag ggagcgtttt   35220
cgttttagga aatattgttt tggtttcggg tttgaaggca gctgtcaaaa aagcggcatg   35280
gaaattcatt gggctccatt cgatacctcg tgtttagaga tcgttatcgc ctcagataaa   35340
cggggcagag aggtggggag ataagcagtt taccctcaag atttgtagtg gcaagtccac   35400 accctctct ctaccttcat attcactttt cagtgagggc cagtgacatt tatgctgcct    35460
aacgtcatcg cataggaaaa gttacctttt attggacggg atttgactat agtgtcccaa   35520
atgcgcttct ccgtcttagc ccatctctta aaacaccctg attaacgata tactaacagt   35580
cttactctct tgagaatagg ctgagaattg ggataggtga aggtttggat aggtgaaggc   35640
agagaaaatt attttgaaca ttttactgga tacagttgta cctgaattta tatgaatgtg   35700
attttacggt tctgtgtttt tccatttttc agtacttcga tatttgtttg gaaaggaaag   35760
aacttagaga tgtaatagca tttcatattg aggatctcaa gcaatgtaaa caaatgtagc   35820
ttaatctaga tgttttgtg agttatgata agggtcagct atatttaagt tatgtaagct     35880
aacaacgtag tgagaaacta ctacaccttc tcttctgctc tttaaaatct aaattttagt   35940
tggcctatat aaagtgtatc tcatttcata tatccaaaat ttggaggtag gcacatccag   36000
tcagaagtat gggttaaaaa gccttttccc agcctgtcgg aagataagca gatcagcatt   36060
gtttattttt caaagaaaac gtgcatggtt caccagttgg ttgtactcaa aggtttggat   36120
gtgtgactag ctggtaggag ggaaatttgg aagtaattag ggattgagaa ttctagcata   36180
gtatttatca aatgttatat gtattggttc tcagaaaagc aaacagccgt gattgaaaag   36240
aggtaggaat tttaatgatc acacttcctt tttttgaaat taaatacttt gacatcaact   36300
tgaaccttca gaataatcag atgtaatgaa ttataatgtc tgtgattaac aaagctacac   36360
gttcagtgag cggcaggatg aatagccaag cttagttcga tacacttttg ccctcagctg   36420
```

```
tgcaaatgga ttgcattgta cttttaaatg tggcatgctg aatgggagca ggggacatgg   36480 cttttttattc tggaagatag aaactactct tctggtaaca aagaatttga ttcggagtta   36540
actaaaaggt tcatttaaca agctgcctct tactaatcgg atcaggaaga taatgtgact   36600
ttagagctta tgatgttttc ccccgtttt tgttttttgt tttgtagttg atattcactg   36660
atggactcca aagaatcatt aactcctggt agagaagaaa accccagcag tgtgcttgct   36720
caggagaggg gagatgtgat ggacttctat aaaaccctaa gaggaggagc tactgtgaag   36780
gtttctgcgt cttcaccctc actggctgtc gcttctcaat cagactccaa gcagcgaaga   36840
cttttggttg attttccaaa aggctcagta agcaatgcgc agcagccaga tctgtccaaa   36900
gcagtttcac tctcaatggg actgtatatg ggagagacag aaacaaaagt gatgggaaat   36960
gacctgggat tccacagca gggccaaatc agcctttcct cggggaaac agacttaaag   37020 cttttggaag aaagcattgc aaacctcaat aggtcgacca gtgttccaga aaccccaag   37080 agttcagcat ccactgctgt gtctgctgcc cccacagaga aggagtttcc aaaaactcac   37140
tctgatgtat cttcagaaca gcaacatttg aagggccaga ctggcaccaa cggtggcaat   37200
gtgaaattgt ataccacaga ccaaagcacc tttgacattt tgcaggattt ggagttttct   37260
tctgggtccc caggtaaaga gacgaatgag agtccttgga gatcagacct gttgatagat   37320
gaaaactgtt tgctttctcc tctggcggga gaagacgatt cattcctttt ggaaggaaac   37380
tcgaatgagg actgcaagcc tctcattta ccggacacta aacccaaaat taaggataat   37440
ggagatctgg ttttgtcaag ccccagtaat gtaacactgc cccaagtgaa aacagaaaaa   37500
gaagatttca tcgaactctg caccctggg gtaattaagc aagagaaact gggcacagtt   37560
tactgtcagg caagctttcc tggagcaaat ataattggta ataaaatgtc tgccattcct   37620
gttcatggtg tgagtacctc tggaggacag atgtaccact atgacatgaa tacagcatcc   37680 cttttctcaac agcaggatca gaagcctatt tttaatgtca ttccaccaat tcccgttggt   37740
tccgaaaatt ggaataggtg ccaaggatct ggagatgaca acttgacttc tctggggact   37800
ctgaacttcc ctggtcgaac agtttttttct aatggctatt caaggtaaga tcagtgtttt   37860
tctgtttctt aagaatggta catttaaggt agattaatag atgtaaatct tcattgattt   37920
atatgtgttc tctaaagatt catgtgcttt tttatatgaa taagtttaag tggccttttg   37980
aaagtaggaa aggtagacaa cctaagtgac atctgtacgt aaccatttca ggtttttttcc   38040 ttaaatagtg gttttcagta tcccattggc caacggtgag gattttattt aacattttta   38100
aaataatgtt gctcattaac agatatctta acgaaaaatt atataaattc aggagagtat   38160
aatgtctcat aatatcatat tgtgttgtgc atggtcattc agctgttta gaatatgttc   38220 ttatattaca ataaatgata cccttactta catagtcaaa agttgtgctg ccttatttgt   38280
aaattcgtta agtgttagct tgagattaaa gagttaaaag cagaagtact aacaaagagc   38340
cctattcttc aaactgaatc ttctgttaaa gaattttgagt tttgaagttg ctaaagcaat   38400
gcagtgaaca gtgtaccaga ccatagtatt agacacaggt cttgctcaca gggttcttgc   38460
cataaagtag acaagttatg tctgctgatc aatctcttta agagaggaat tggtgtcaac   38520
atggtgcaaa acaaaatttt acgttcaaat gttcctgcaa gttctcaagt agataactga   38580
tggccaaaat tgttaagctt caattttcag ctttcgtttg attttttctct tttttttact   38640 cagtcgttta taagcatact gatatttttg tctgacccaa aaaggtcaga aaatggaatt   38700
atcagaaaaa agttctaaat gtagatatac gtgttggtag gggtgaattt ctctaccccg   38760
```

```
taacctcatc cccaattcag ataaatgcta ggttttatat ccatttagt tgtgaaggaa      38820
aatataaaaa tgtggattgt agtgacacaa gattgattaa tcagcgggtt tttttaaaag    38880
aagacatggt agacagtgat ttatttgtat gtaactattg aagttttttc ttaaatgtta    38940
gtgatattca tcgttcccat taactagtta ttcagatttt tgaaaatcct ttttctgtga    39000
aagctatcct aacctggagg atgtctcttt tctttcctct gtacttaaga agcttttctt   39060
gttagggaaa taatttagaa ttagatttag gctatgttct gttcttctaa aaggcttagt   39120
tgtcaaaaaa aaaaaaaaaa aaaccaaaaa accttggttc ttacatgtct taatgtgaac   39180
tacctcctaa tctattgttt aaataattat cctttattta gaagaacact acttcaacct   39240
gagttgaagg tttaaaatct tttcagtaag gagatttgag atctttatta ttgcataagc   39300
tgttgtgttt taaatgctaa aagacatgct gtgttttaaa attttcaatt gcaaattttt   39360
ggcaatagaa ttcgcatact tggttttctt aaaagagtta agtacggttg atttgactaa   39420
gctatctgta ggaaactctt aaattgattt ataaaacatg taattataca aagaaaaata   39480
aaacatctta ggaaactctt ggggattatt aatggatttt gccctgataa tcatcatggc   39540
atggttttca ttttccttac tataaagaaa aggcaaggga caaaacttat tttccatttg   39600
ctatgaactt ttaaaccta taaaatctgg gatatagagt ataagtagat gaacatagtt   39660
actcttaaat cactaaaggt gatttaatg ctttaacttt tatagtactt catgacataa   39720
agtatcttta cgtattttta atttgggtcc cataacctta tggaggtagt aggcaaggca   39780
atgatgatgc ggctctttag aagttcttta atatcaaatg aaattattat ttttatgcca   39840
atctgtgatt gggaaatata atcagtagtc tgtgtcctaa caagaaggta taatacttta   39900
tacagggtat tttgttaata tttgaagatt ttatacctta tggcattaac ttagcactgg   39960
gaactatgat tacccaaaac aaagcttcat ccaaataaat tgaaacagtg tttctttaa    40020
accatcattg aattagtcta ttgtttccaa acaacagccc tgatatagct aaaattagtt   40080
gctttctctt ctctatatgt tacatgactg tagccaaaca tttgctatga ccagtgaccc   40140
tgagtgatca gcaaataatc aacacattga gaccacaact tgaatactga ccttctgact   40200
ttacgaagaa aaatattaaa tgccactaat aacttgaatt ccttttaaat taaaaaaagt   40260
tataaattgc aatttgactt tttaaaatgc cacctaaaat tgtttttatc agaatactta   40320
aaaaaaaatc ctcactttat tctctggggg tgggaagagg caattccttc cttccaccac   40380
aacattgaat tatcacataa aattgtaaaa ttatgaatat tatgattgag cttagtaaag   40440
catttttctaa gttcatttat agtaaaacaa gagaaaccttt attctcaaaa tctattcttt   40500
aagtaaaaca aactagtcat tctaacttaa tatgctttta aaaatactga agttcagtac   40560
atttagcata aacttattga cgaaggcaca tttctgcatt atttgatttt cagccttgtt   40620
tcatttaagc attaatgaca gaggtagaga acagaaatgg ttttaggtgg tattagagct   40680
tttattggga ttatgttgaa attttagtgt taaaaaattg ttcgtatcct gaagggaggg   40740
attattggag agaatgaatg atgtaggatg aacttgtaaa ttcagttttc ggcagagtct   40800
aaaattaagt gatgattggc acttaatgaa gctactaaaa tttatgtaga ttttaatgtc   40860
tcattagtaa tcgcatctgt atctggtttt ataaagtaa tgaaattgaa gacctgtaca   40920
aatacagaat gaatgaagca aattctgcta acatcatgtt gaatgttttc tcagaaaaag   40980
aggaaatacg aagagaagag atttgttttg actgtgattt accctcaccc ccatggatac   41040
tttctttact tcctaccttt tttctttttc ttttccttct aaagattctg gcaatggtg    41100
tttcagtgtt ttttaagctt aatatttctg gtactcattt atgtaaagtg atttctgaat   41160
```

-continued

```
gttaaaggag atttcttttt aaatatattt tcacttattt ttagctttat gatgagaatc   41220 ttattttta aatctgtaac ttgttatggc tacatgatta gtaaaaaaag tttttaaaac    41280
acactgtgta ttcaggtgtg tcattttagt gtgaaatgac taatgcagaa atatgtgact   41340
agcatgtggt cagattttat tgaaattact tacgatgttc ctatggctag tccccttgta   41400
tttttataat tggtaacata attcatatgt tattttggtc ttgtctattt gtgttacatg   41460
tattttagtc tgaccacttt tgctacttat ttaatgttta tacattttat gaaagactta   41520
ttctgaaata taccttgcat aaatgtaggt taaatgcaaa ttgtattaat agtgaaatgg   41580
atatgtgggt agagatcact ttaggggcct tttgagattt agtgaaggaa agattggatc   41640
aaaagggttt actttaatgt gactgcctaa tgtgaaagtc ggaacatctg cattaattgg   41700
ttagttacat aaatcttagt ctactctggc ctgcaggtga ctgaaacagc ccaggaaatc   41760
ttaatttaca ttaagcttag acaaggtctg aggcttaggc ttagttctta aagcacattc   41820 tttttttactt taatgattat tcctaatttt aatgagcagt gggttctcat tgtgtactag   41880
tacttaggtg ggcaaattaa ataagcaaaa taggtttgtg ctgaatagca tttacccttc   41940
tgaggacatc ctggtaatat tttcatcaag agtaattgtg taatgcaata tttacaggta   42000
tttgccagat taatgggcac ttgttttcat atttctgagt catggaaaat atacattgat   42060
gattcctgtt gcataaagag ttttcaagaa aattttgttg aattaagcta taactacaaa   42120
aaaaaatcca ttacatattg acctttagaa aggatttta aaagcccatg ctgtccttat    42180
ttctgcagct tcagagagcc gactgctctt attttcttct ggcatattct attaatactt   42240
gggttttgta tttttcaagt aaataaaata ttcctattga gaatttcaat tttaaaaaag   42300
aaaaggtcta ctaagtgttc ctttccctgt tgaattatgt gtgatcattt ctatgctaaa   42360
ctagattagg gtgtgacttg tgatggtgat ttttgttcat tttacatatt aagaaagaaa   42420 tagaattta ttgcagttca aaattatttg tagacagtgg ttttaacccc cagacaccta    42480
attgtgacag gttgctttcc ttagtgctca atactgttgt aaatgtctct aaatacagaa   42540
tttccagtgg agttcatgaa ttaattgggg gtggagggtg aagagggagg agcaacagag   42600
atgtgggatg ctatagataa gtttaggaat atccagatca gttctgaaaa ctaacagttt   42660
ggatcaactg tcatgaatta gaggtttaag aaaagaaaaa tttaggacta taggtacaag   42720
ggaatgcatc aatcagaatt acaatttaat ttcttttatt tcaggtagaa atctaaaact   42780
gaccatggct atataatact aattttgag ttatgttgtt tcttactatg ctttattatc     42840
aaaaaaggat aaaatgcaca ttttacttga agattatttt agctaagatt aagttcatat   42900
ttttctcatt tttatttaag ctgctgttta ataaatgaaa atctaatgac ttgaatgtag   42960
tcgacctaat gtcttaatgt tgatataatc atttcatata tcatagtgcc cttttacagc   43020
cattgtcaac tgactggaga gcaacccttt tctttggtaa tatatttcta tgggttatgt   43080 attttctgc tggaatattg agaaaattaa tttttcataa tatgcagaat aaattatggg    43140
gttctgcaag tgctagacag tcacttaaac catttatatt gcaatacatt ccttaaattc   43200
agtattttga atgaaagtgt gttatccccg aattttatca cttgtccaat ttaaatatta   43260
attacatccc aatagagctg catgcttaaa catgcttttt cagagtaacc caagtattaa   43320
tttcgagtgc ttttaaatat ttttctttt tagcaagttt caacaacatt aatcctgtct    43380
ataatgcagc aagttcagtg aaagtacctg ttgttttata attttttttt cattctcact   43440
gtagggcacc aaaaatatat ataagggaa aaaagtttta atgatatgat tagttgtaaa    43500
```

-continued

```
tgtttacgca ttatcttacc ttgaattttt attttttgtaa ctaataattt gagagttcaa    43560
taagtatgca gtgtttaaga catagtttgt tgcaaaaagt gttaacttac tatttctttt    43620
tacaataaaa ttagccttta ttctagttga tttcataact gtccataata tttagctgtg    43680
gctattatga aagtatattt gatagccaaa ttttgaaagc tattatgaaa tgatacaatt    43740
cactacatga tttattattt catgctggtt ggggcagtgc tgtgacttat gaccttatga    43800
ttgtcacatg ctgaacacta aagctctacc agtttgttat ggacactgtt ttactttatg    43860
ttatcgtttt aatgttttct tttataatta ttgaggataa gagcttcctt aattttaaga    43920
ctatttaaat tgcagatttt gcttttttat tttttttaacc atcccttcca aagaatttga    43980
tttagatatt cagtagtaga aacagaagaa aaatactcaa ctaaaagtcc aaagacctag    44040
tttctaatgc taagggagac agtccatggc ctccaactag gtactttgga gtcaaaaata    44100
cttcctttac aactgtgttt gaattgtttt caaaacacct gtgtgtgtgt ttctaaaatt    44160
ccacaatcct tttaacccgt caatttgatg agggaagtaa ttagggtagg aatggtata    44220 acaaagttgg ttcctttgaca ttttctttat agattatcga atgtaagaca aatagatgtg    44280
aatgcagatt tggtgttttt ataagataag gattttaaaat aatgtagttg gtgatatata    44340
aaaataaact attgctgctg ttagcacccg agaggtgggg ctcttgggtt ctcagagctt    44400
gttttctatg ttcgttacag ttatttttaga ttagaactta aaagaacttg agagtttccc    44460
taattctacc ccctaatttt ttcgaatgag aaattgagat ccatagaaag tgttgaggta    44520
aagatcacaa aacacttaat gagcggtgtt gccagtttga atatctcaat tcttagttat    44580
ctaagttccc tggtaggctt ctttaattat ctgggtctct tctagacatc tggaacaaat    44640
agttgattga cataatacag actagccaca tattttataa gagttacttt tgactcattt    44700 agattttttaa aatatacagt gtctgtattc ttctctattc attttgttaa ttttttttta    44760
cctaataatg attaagcacc aattatgtga cagcactatg ctaagcactt tgcatgcatt    44820
catctcattt aaatctcaac tctgtgaaag ttttttattct agttactgta ttaagtctca    44880
attctgtcaa tatccatgaa gcacagaagg cagctgttat ttaccttaat tttacagatg    44940
tgaaaactaa aggcatttaa agagaaaaag aaaaaaaaaa ccaggaaacc ttaacactta    45000
tctgaaggga aatatttaat attgggtatg ttagttcctc atgtatcttt aataattttt    45060
gtcaacagcg aatctttaaa taaaatataa aggatcaggc ctctgctctc ctgcatatat    45120
ttgtaaagtc acttactgct ttttgtcaca gtttcaattt ctgtaaaata gtgagagggt    45180
ttttacctga caggatttgt gcatgtacgt ttactttgaa aattaaaaag cattaggcca    45240
ggcgcggtgg ctcacgcctg taatcccagc actttgggag gccgaggcgg gcagatcatg    45300
aggtcaggag attgagacca tcctggctaa cacggtgaaa ccctgtctct actaaaaata    45360
cagaaaatta gccgggcatg gtggctggtg cctgtagtcc cagctactcg ggagcctgag    45420
gcaggagaat ggtgtgaacc tgggaggcgg agcttgcagt gagccgaggt tgcaccactg    45480
cactccagcc tgggcgacag agcgagtctc cgtctcaaaa aaagaaaaa aaaagaaaa    45540 gaaaattaaa aagcattata aaaatgcaag gtggaatttt taaagctctg ccaagtccac    45600
ttagcttaaa ccagcatgac tctcattggc taagtacgtt atgacatctg tgactgtggt    45660
gtaggtattg cctataatca agaatctttt agggtctgct atgtgcaatc cctgaagggt    45720
catggatcgc agtttcataa agactgctgt attttaaagc cttcaaatgc caacgtagta    45780
tcttcacaat gatttttttt ttcagtttta ttattttttg aaagcgcctt cgacaaagtt    45840
ttcagtggat tttgttgagg gatattaagt atgccatcta cataatagcc atagtgataa    45900
```

```
ctccaaccac attgttatat ttttattaat aaatgctaga gtattctctt tctggtattt    45960
cctattctga tattttttata taatcaagta tgcaaagatt ctttgtcatt ggaaaccctta   46020 atttgcctga aaatgggaat gaaattttca ggtttaaaat tttttttacat ttattacatt   46080 tattgaagct gtctgaaaaa gctcttgagt atattgaata ccaaaattta tcctaactgc    46140
ataaagttgg gaggattgtg aaacttgact gcactgactt gttttctta ttgatcaaat    46200 ggttgaaaaa aacttcagtt aaacaaattt gatctattaa accaaagtta taaaagcaga   46260
ggaaagcata gaattattaa acggcagttt aaattggtaa acataccgat gtagaaccta   46320
agtttgtagg cagctttctt agatggaaac ttaaaaaaat tttaatcaga acattatgtg   46380
aaatttgtca tctggaattc agctgggttt attaaggaca aagtgtatgg ctataaaata   46440
gattgagttt ttttttttaaa acagaaaacc caaaataaat gttctaagtt tccaccttag   46500
gaggctatgt atattgctcc tctttgaaac tgccttcaga accaccttgt aagccataaa    46560
agaaaatcgg actcattgca ctatagtaac acctaactgt tcttgctcaa agaaaatgta   46620
tttatccctt agctttatttt gtgtgactcc aaatcatatg agtattgcca gatatttaga   46680
aatttaatcc tctctcgaat gataacattt attttctttg aggttttta aaagagccca   46740 catagatatt tctacagaaa atgtttaatt ctgttttgaa tatgcctgga ataagtgaat   46800
agcttcccag ggtgactatt ctgaaatggg tgatgcttag tggttaagtt ctgatttgtg   46860
ttttcttgaa gttattaagg aactttatga taacagttta tatattccct cttcttggca   46920
tagtaatgaa gtaatagaga ctattcacct ctaagcctga tttttttaaat aagtgtttat   46980 tttatgttta agtaaggtag gtctgctttt ggcttggact tgaatttggc aatagcagat   47040
ataaagtaaa cataatgtga attcctacaa cagtctccca aacagtttaa tttctcattc   47100
atacacattt cccttagtgt atcagggaat taagtatctg attatcagta tagcaagaac   47160
aactcaagta tactgaagtt atttatactc ataaaatagt ttgagttata gctacaatat   47220
aaaattaata tattttttgac ttttattcct cacaacctga aaaaaacctc tgcgattact   47280
gatagtactt ttaaaaacta aatgaatttt gttactacta tttgctaaat ttagtcatgt   47340
ttactgttca aaaaatgcta ggttaaaatg gatcctaatc tttgaaatga tgaagacatg   47400
tgtagtggtg tcaaaaatag gatattcatt ttgtaactat tctgttagtg ccgaagttct   47460 tagaattttct ttgtgacaac agcctgctta agaactttag attttttaga attgtactaa   47520
aagcaaactg ttttcttgga tatttgttct ttctccccaa aagatgattt ataagttttc   47580
agagctaaga aatgggaagg aagagccatc ctagcatggc aggtaatgtt ttactgctaa   47640
caggttttct ctgcactgct ttatttgcct tgaacctctt actttgttct gtcagctggg   47700
aggctggtag atttttctatt aggtagcaaa tgcttctcat cactaaacac atatcatggg   47760
ctggtgttag tgcagtctgt ggatgggcac tacattttta atcaagaaat gttttttaaag   47820 gaaagacaaa ttggtgaagt aatttctaat tcagtatttt agggatgagt gacctttttaa   47880 ttgataatga tatttaacag agctgtacag tgctttgggg gtcccacaga catgtttaaa   47940
caagaaaaca gtaaataagg aagccagaag gaaaagttat aaaactatta agaaagaaaa   48000
tgaaaattct aaacttcaat tctggtgcct ggctaaattt gattttttgta tgcctcagtg    48060 tttctctatg gacactggga aatcaataag caacctagct acgttattat gttcgtaagt   48120
ggaagaacta aagaactaca aagacatgtt ctaggccaag aattctggtg gtaggtagag    48180
tgggaggtta actagatgat ctccaaggtc cttctaattg cacttggcag cagcaagcat   48240
```

```
ttatcaagct agacactggg catatggaga tgaagaagat gaatatcccc agcagcatgg    48300
agagcactct gatgatagtc atccctgcct cccctccct cagtttgctt tttgaaatgt    48360
gagcttgaaa gatctcaaac tccttcctgg gaagacataa ctgaaacttc atggaggaaa   48420
gtgcatgaat gaatgggaaa caagatttga ttcaactatt tggaataaga aaaggggcaa    48480
caaggagtct gaaacaaatg aaagaaaaga tggaagaat tagttgacta gatgaggact     48540
gagtacatag gaatgagcca acaggagact tcagcaacta atggatgaaa gtattatgtg    48600
catgcatgtt gtcatcaaat atcacatgat acaagacaag gagaaaacat gactttcacc    48660
ataacctcag tttgtgtacc ctagttgcaa gatatttttt tcttctagtc acttaagaat    48720
atccttattg tctaggagaa ataatcctct ttctgggctc cccagtgtat aagcccaaat    48780
ctgaggaaaa tttacctgaa atgttctttc cccagatacc cacatggttt actctctcat    48840
ttaaatgtca gctctgtaaa agagatctct gactgctcta tctgaaatag tagaatcttt    48900
cacagtcttt ccttcttctt gacatcatct atttgtgtct tatctgctca cctgctacaa    48960
tgtaagctcc atgagagcag tgatactgtc tgccttgctt actcctgtat gccagcgtct    49020
agaatagtgt ctagcacata gtaagacctc tacaaataca tgttgaatac ctaaataaac    49080
aaaatttaac atataaacca aaaagatata taggaatgga ttatatttct aatctttctc    49140
gagtgaggaa aatgtcagca gatagtgaat atcactgaga gagagatgat agcccaggtt    49200
atcttcccca gatagaaata agccttaaga ctgacaggtg tatatgaata cagagagtat   49260
acataaagaa gatgtatttt caattgacag tctctaaatt tgctttaaga cttcgaaatg    49320
gattgctttt cataatttct tagaataact ctggtctgtt taccattgaa aaattagagt    49380
agccaatgtt tgtaaatgaa gggttagagg gttttttcct ttggtggttt gttaaaagct    49440
tgctcaaggc agtaacatag taaattgtca atataggaac ttttgtagca gaagctttat    49500
gcttttcact tttataagaa ttgagattat ttaagcagat gagtctaatg tatatgtttg    49560
tactgactta cctagaaggt caggcaagaa atcggtttcc tcatttttca gataagtgtg    49620
tgtgtaatca ctgagtacct taagagagga ggggtgtttt attttttgcct gaattttcaa   49680
aatatctttc ttcagcttat ttatatttta gatttgactt attctgtcta tagtatataa    49740
cagtcaggag gttggtagga taagttcatc tcttctacta agagttatag gagagttcaa    49800
cctaatatgg caatgacagt cgcagaaaag agaaaatgca agttaagtag gtgttagcca    49860
tagcaagaaa atcagatgag gtcatttaag aatgaactgc tctaatgttc aggaaaaaag   49920
agggagggga caaggacagg gctctagaag gcaaccaaag agagcagcca caaaataaat   49980
gaatagctga agaattagga gacaacaatc ttaaaatgtg gcagggagag ggtagttgtc    50040
acattaacta gcatagaaga gacagaatag aataacataa atatatgagt gattattgtt    50100
cttgaaacca gtctttaaaa catgggaaca ttcccaaaaa tcaaagccag ataaattagg    50160
gaaatcttaa atggcacaat ataactagtg atttcgttta atttttttt aaaaggaga     50220
cttaaatttg aaatttagat gtaattaaag cagataataa gaaacatact tctgagacca    50280
caaagaccct gagattcagt taagagtaag gtagaaaggc tggaagccag aagggaatta    50340
agtttctgtt ccctgagaag ccaacacaac aggaaaaaac tggccacacc ctagttcaaa    50400
ctcttattac tcttatcaat agtctcctaa ttgtttctct agttttctcc tctcccttct    50460
taattcattc tgcagtctac tgccagatta atcttcctag aacaccactt tcagtattat    50520
tccctgatc aaaaaatgtc tgtggttttg ttgctcatag catagtggtt ctccttcttt     50580
gtaccacagc ccatatgcac gatgatagat ggtgggtagc cacatgaact ctccataacc    50640
```

```
tttggaggat tgggttata cacagtctgt tatccaagaa agcatatctg agtgtaagtg    50700
agcattatag ggatagtctt ataattgact ccttttaaaa tttgttcttc tttttgcaaa    50760
tgccccttca gaatttacag aaatagtgtg ttcattccat cagtaaaatt atacccaaa    50820
atgttaataa gcttatttcc atcacgtctc ctttcctatt tctttctttc ctctttcttc    50880
ctgcacatct cccttatcc tccacatttc tctgtaatta cataagcata aacagacaca    50940
tatgagattt tctgggttgc ttgccttttaa ataaagaat gggattatct tatacccctt    51000
tgtctgcagc ttgctttct cacctaacaa gtacaccctg aacatccttc caggttaaca    51060
gatgcggatc ccattctttt aaatagacaa tattctattc atgtggtttc gtgattttg    51120
ccactacaag caagtttcta ataaacaccc ttttctatgt acccttaca aatagcaact    51180
ttttttctaa atataaatgc tatggtttgg ctctgtatcc ccacccaaat ctcatcttga    51240
attataatcc tcacatatca ggggagggc ctggtgaaag gtgattgaat cctggaggca    51300
gacttctcct ctgctgttct catgatagtg agttctcatg agatctggtt gcttgaaaat    51360
gtatggcact tccctcttca ctcactgtct ctcctgctct gccatgtgaa aacatggttt    51420
ctttgccttc cactgtgagt gtaagttccc tgaggcctcc cagtaatgct tcctgttaag    51480
cctgtggaac tatgagtcag ttgaacctct tttctttgta agttacccag tctcagttag    51540
ttctttatag cactgtgaaa atggactagt acagaaactt ggtaccagga cagtgggca    51600
ttgctataaa gatacatgaa aatgcggaag caactttgta actggataat gggcagaggt    51660
tgcaacagtt tggaggactc agaagaagac aggaagatga gggaatgttt ggaacttcct    51720
agagacatgt tgaatggttt tgaccaaaat gctgatagtt atatggacaa taaagtccag    51780
gctgaggtgg tctcaggtgg agatgaggca cttattggga actggagcaa agttcacttt    51840
tgctttgctt tagcaaatag actgacagca ttttgcccct gccctagaga tctgtggatc    51900
tttgaacttg agagagatga tttagagttc gtggcagaag aaatttctaa gtagcaaagc    51960
attcaatatg tggcctggct gctcctaaca acatacagtc atatgtgttc acaaagagat    52020
ggtctgaagt tggaacttag gtttaaaaga gaagcagagc ataaaagttt ggaaaatttg    52080
cagcctgacc ttgtggtaga aaagaaaaac ctattttctg gggagcaatt caagtgagct    52140
gcagaaatat gcatagatga agagtagcct aatgttaata gccagtagaa tagggaaaat    52200
gtttccaggg catgtcagag accttcatgg cagcccttcc tatcacaggc ctggaggtct    52260
aggaggaaaa aatggtttcg tgggccaggc ccagggttgc gctgctctct gcagcctcag    52320
gacatggtgc cctgcatccc agctgctcta gctccagctg tggctaaaag gggccaggag    52380
ataatcttgg gctgttgctt cagagggggt aagcctcaaa ccttggcagc cttcatgtgg    52440
tgttgggcct atgggtgtgc agaaggcaag agttgaggct tgaaagcctc tgccttgatt    52500
tcaggatgta tggaaatgcc tggatgtcca tgcattctgc aggggcagag ccctcatgga    52560
gatcctctgc tagggcagtg cagaggagat acatgggggtt agagccccca cacagagacc    52620
ccactggggc actgcctagt ggagccgtga gaagagggat accatcctcc agactccaga    52680
gtggtagatc cactgacagc tttcaccatg tgcctggaaa agctgtaggc actcaatgct    52740
agcctgtgaa agcagctgca gggtctgtac ccagcagagc caccagggca gagctgtcca    52800
aggccttggg agctcacccc ttgtgtcagc gtggcttgga catgagacgt ggagtcaaag    52860
gagatcattt tggatttta agatttaatg actgtcctgc aggttttgg acatgcatgg    52920
ggcctgtagc ctctttgtct taaccaattt ctctagtttg gaatggggga atttacccaa    52980
```

```
tgcctgtatc ccaatttttt cttggaagta actagttttt gattttacag tctcataagc    53040
agagtggact tgccttgacc caagaagact ttgtacttgg acttttgagt taatgctgga    53100
aggagttaag acttccgggg actattgaga atgcaagatt gtgttttgaa atgtaagaac    53160
atgagattta ggaggggccg ggggcagaat aatatggctt ggctgtgtgt ccccacccaa    53220
atctcaatca cttgtaatcc ccacatgtca ggggaggggc ctagtgggag gtgactgaat    53280
cacaagggtg gacttccctc ttgttgttct catgatcgtg agttctcatg agacctggtt    53340
gtttgaaagt gtgtggcact tccccctttct ctctctgtct cctcctctgc catgtgaaca    53400
tgtgcttgct tctccttcaa cttccaccag gattctaagt ttcctgaggc ctctcagtca    53460
tgcttccttt gaagcctgtg gaactgtaag tcaattaagt ctctgttctt cataaattat    53520
ccagacacag gtagttcttt attgcagtgt gaaaacggaa taatacaata gatttcccca    53580
aagttgggtt cctgagtcag gggtatgtgt atttaaaatt ttaacagata tttccaaatt    53640
acttttttcg aggattatgg caagtcacag ttcccctgg cagtgtttat acttttcttt    53700
ataataaaaa tacataaatc attattacta acaaattcct tgccatgagt cctaaattga    53760
taacaacata ccagtgtgcc atataacata gctgaggact gttgcagtct agaattcagg    53820
ctccttctct ctgcttttaa caatatgtgt aatgttcaag accaatttag tgccacttat    53880
tttgtatgct ttcctttatg tagtccaggc catagccccc cacctcatct gatggtatcc    53940
tctggcagcc acagaccaca cagttctttc tacctaaatt agtcattagc acatagtagg    54000
tacccagtaa atgtttgttg aattaatact gtttatatat ttctaatta tctccaagta    54060 aatccagtct ccttaaggac aaggaacgtt ttcactataa cacctagcac ttaaggtact    54120
caatttaggt agggctgttt gaacaaagaa ccacagagga agcaaatagc atggccttgc    54180
ctttaataca tatattttac tttctcttag ggaaaactgg aactgtaaga atctagtaac    54240
aataataaga acagcacttt tattgagcag ttactatatg tgaggcacag ttcaaactgc    54300
agaggataca acagtggaca aagctttagt tgttttctgcc tttctgaagc ttatggttta    54360
tgggtgttac attcaagaca tttgtaggac acattctaaa atgccatcca atttcaggct    54420 cttccagca gaaactgtgg aatattttc cgttcattca gcatttactt agtgcctgct    54480
ctgccaggaa ttgaagagaa agcccaaaga caggcagacc ttacctgaga ggtagtgaac    54540
tgaccaggat gactgtgggc agtagacttg tttcccaaac tagcctcacc atttctgtat    54600
ttgcatatac gaggaaagga ttagatatag ggattcatgt cagcatacac cccagggaca    54660
tttgttttta gtgaaaggtg ccagtcttca tccctgtacc cagtacacaa accacgaaga    54720
agtatgctcc cgtcattgtc aaagaatcat agaattccaa atggagctag ttttgatatc    54780
cagatctcac ttcatatgag gaaactaggt ccagtattgt gagtaagaat taggactctt    54840
cagattccct gggtatgaat ctgactaaca actgtgtgaa cttgaccaaa ttcataaccc    54900
tgtaaactct gtttcctcac tttttaaaatg ggcacaacaa agtgatgcat gtaaactgca    54960
tagcacagtg tctggcactt aaaaagcact cctgaagtta tttttagtga tgtgttttaa    55020
gattagacaa ctccttaatg ccaaaggttt ttacttgaga actctgtctg ttgtgccata    55080
ctacacgctg ttcataagat aagccttttt cattaattga tctcaaactg gcttcattat    55140
gatcttaact ttatttcagt tttatttta aaatttattt ttaattttta tgggtatata    55200
gtaggcatat atatttatgg ggtacaggtc atgttttaat gcaagcatgc aattgtgggg    55260
gtgatatata attgactggg gtgagatatc tcattgtagt tttgatttgc atttctctga    55320
tgattaagga tgttgaacat ttcttcatac acctgttggc catttgtatg tcttttgaga    55380
```

| | | | | |
|---|---|---|---|---|
| aatgtctatt | cagatctttt | gtccatttttt | taagttggat | tgtttgattt ttttcctgttg 55440 |
| tctgaactct | ttatatattc | tagttattaa | tcccttctca | gatgggtagc ttgcaaatat 55500 |
| tttcttccat | tttgtgggtt | gcttctttgt | tgtttccgtt | gctgtgcaga agttttttag 55560 |
| cttgatgtga | tcccatttgt | ccatttttgc | attggttgcc | tgtgcatttg aggtattact 55620 |
| aaagaaatct | tgcccatac | cagtgtcctg | gagagcttcc | caaatgtttt cttttagtat 55680 |
| cctagtttca | ggtcttagat | ttagggcttt | agtccatttt | tatttgattt ttatatgtgg 55740 |
| tgagagatag | gggtctagtt | tcattctgcc | tatggatatc | cagtttttccc agcaccattt 55800 |
| attgaagaga | ctgtccttttc | cctagtgtat | gttcttggca | cctttgctga aaatgagttc 55860 |
| actgtaggtg | tatgaatttg | tttctgggtt | ctctaggtct | gtgtatctgt ttttatgcta 55920 |
| gaactatgtt | gtttgggtta | ttatagttttt | gtagcataat | ttgaagtcag ataatgtaat 55980 |
| tcctccagtt | ttattttttt | tgttcaggat | ggctttggct | attccggggc ttttgtggtt 56040 |
| ccatataaat | cctatgatttt | ttttttttcta | tttctgtgaa | gaatgtcatt gatatttatt 56100 |
| aataaagatt | gcattgaatc | tgtagattgc | tttgggtagt | atggacatttt taacaatatt 56160 |
| gattcttcca | atccatgagc | atggactatc | tttctttttt | tgtgtgtcct cttcaatatt 56220 |
| tttcctcagt | gtttttattgt | tttcattgta | gagctctttc | acttctttcg ttgagtttat 56280 |
| tcctaggtgt | tttatttttat | ctgtagctat | tgtaaatgag | attacttttct gatttctttt 56340 |
| ttagattgtc | ctctgttggc | atctagaaat | gccacagatt | tttgtatgtt gattttgtat 56400 |
| cctgtaactg | tactgaatttt | atctgttcta | atatttttttt | ggtggagtct ttaggctttt 56460 |
| ccaataagat | catacagtct | gcaaacaaga | ataatttgac | ttcttccatt ccattttgga 56520 |
| ttcccttttat | atctttctct | tgtctgatta | ctctaggtag | gtcttccagt acttccagtt 56580 |
| gaataacagt | gggcactctt | gtcttgttgt | agatcttaga | agaaaggctt tcagttttttc 56640 |
| cccattcagt | atgatactag | ctgtcagttt | gttgcagatg | gcataacttt caaactaatt 56700 |
| gattatagtt | aggaagtgga | tactttaact | tgtggtacca | ttatcagatt tatatttcgg 56760 |
| ccataagctt | gaagaggagc | tgaaaaatgc | atatgtgatg | catatgcttc ctatttggct 56820 |
| ctcttctccc | accccctgc | cctataatcc | acacaagttc | ctctctcagt cactcatcaa 56880 |
| ctacttgaac | ctctgaggaa | cttggggtta | aggtaaatta | gaataaaact gtctgaagaa 56940 |
| gagcaagcct | ttcatgtctt | gagaaattct | tggggtttta | gaaataactt cattgctttt 57000 |
| tttctccagt | tactttggct | tcttcttaaa | gagaatacta | acactttgaa cgtcataata 57060 |
| ctaaggttct | gcctcttcaa | ataaagactt | taaaaaaaaa | tggttttttgt atgattcagt 57120 |
| gtgaattaaa | tcccacagtg | taaaggactt | tactttctta | atgtagattt tcaaatacac 57180 |
| aattactgat | gtttataagt | agattattta | caccaaagca | cctagcaaat tcttgaatgg 57240 |
| atcaggtctt | atttttcagt | cttactttgc | aaatttaagt | caaataatta aggatttgtt 57300 |
| aaatatttgt | cttaatatca | agcttttgca | tatcggggcc | ctcttttata agctttataa 57360 |
| gcaatctttt | gttttctctg | cttgctcaaa | gtagctatgt | ttgttgtatc tgttagtatt 57420 |
| tgctctataa | caaacatact | gggtgccttc | ccacttagat | ttgcaattta tcactcctgt 57480 |
| aaatgagata | ttacataaga | taggaaaaag | aacagtatct | ttccaagaag aatagtatcc 57540 |
| ttccatatta | acagtttaga | gctgactgct | tttaaaatttt | agtggcttta aaataacaac 57600 |
| catttattat | tcttcatgag | tctacaaatg | aggtgggcag | ttctgctgat ctggccaagc 57660 |
| tgaacttatc | tcagctgggc | acattcagcg | tatctgctgt | cagttggctg gttggctgta 57720 |

```
gcaatgaatg gtgaaagtag gctgcccttu acttttttcac acagtagcat tagagttaca   57780
aaagaaccag cagaaccatg caaaactctt taagacctag gcttggaaca actatatttc   57840
taccacattc tattggtcaa agcaaatcac ggggctagtc tagattcaag tgggtggagg   57900
agctgcaatt acactgcaaa ggagtgtgac tgtagggaga ggtgtttttt tatttttatt   57960
tttttgcgat ttgtcacagt agttgtagga atcaggtgta tttaaaattc tgatccttct   58020
gtgatatccg aattgttcat gaaccttgcc tctggtggaa aggcagaatc attgtgacag   58080
aaggataaaa tcttggaatt tagagactaa caaaggttca gattccagct ccatcactta   58140
tttctgcaat cctgcagaag ttaatcttcc tgataggcat tcagtaatga ttgattcacc   58200
tgaacctcag attctttatg tattttaaag aaagggctag gtaaatgcaa agcacttatg   58260
taactgcttt tattattgca aacctggctc ccacactcca ttcaaggtgt aagactcagt   58320
gtcttccttg aattaaaaag gaagagaaag tgtgttaggg aaaggaagag aaatatttga   58380
ctaattgtgg ccccaataaa gtgaccactc actgggggta ttttcctgta agaaaagaat   58440
ggttgaggct cagagttaag agatacaaat ccaaaagtct ccttgggta ggattccctg   58500 tgattcatgg gttgagaggt gtaacattag acacagtccc agtctagatt ttttttttaa   58560
agaattgtag tccatcctat acacactggg tgccttaata ctatatgtgg caattatcac   58620
tcctataaat caggttttac ataagatagg aaaaagaaca gtatcattcc acattaacaa   58680
ttgaaagatg actgcttta aaaaattaaa agggccatat agaaataaaa tcacataaat   58740
ttcttgtgtt aaacatagtt gtcatattgg atgaggacta acacctaaa ttcatccaac   58800 tagtagtaat agaaaagatg aaacacacac acagtaaaac tagattaatt taatttatac   58860
aaagggccag atatctcaga attcagacag tcagagatgt tgactagagt taatgcctct   58920
tttaggagag gtaccaggta agtgttctca aagaactgga aactgagacc accacctctg   58980
gcattatcta tttgtgaaca caagcaagtc tgaatttttc cgcaccatag ctacctttca   59040
tgtaagcttc ttttcttaga agaaaagaag gtaacatttg ggtgtaattt tttattaagg   59100
gtgaaattta gtgtagagag taaaggcatt tggcatagaa gcccttagtt tttttttgttt   59160 ttaagttgaa ctgccagcct ttatggattg cagtcttcgc tgttttgatt gacatttccc   59220
aattcatttt gtattattta ttttttttaag agacagggtc tcactctgtt acccaggctg   59280
gagtgcaatg gggcaaactt ggatcactgc agccttgaac tcctgggctc aagcaatcct   59340
cccacctcag cctcccaagt agcttggact ataggtgtgc accaccatcc ttggctaatt   59400
ttttaaatct tttgtagaga cagggtagtg ctctgttgcc caggctggtc tcacattcct   59460
ggcctcagtt gatgctctgg tctcagcctt ccaaaatgct gggattacaa gtgtgagcca   59520
ctgcacctgg cccccaattt catcctttac aaagactact ttcaaccata aatcaacgga   59580
aacttcagct ccctcagaca tatttgggat ccaaggatat tttcccaaat gattaatgct   59640
aatttcatat caatacattt ttgcaaaacc tacaaaaatg gactagtaaa gaaagactct   59700
taatttggga aagacagtta cttggagaga agagaaactt aagaggcagg tcgagttcag   59760
tgttcagaaa tgagaggatc ataaagagat agccataaaa atgtttctcc ctatattgcc   59820
tgctgatagg gtgtatcagt gaaggtctta ctaaggacct tgtacctttt cagcgctgca   59880
ctgcgtgctc ataggagga aagataaatc atgtgttttt tctgacctca aggagcctg   59940 tatctggcta gagagacatg atgcagacac atgaaataat taagaaacaa ttaactgtag   60000
caggtgctga agaatatacc aggaggtcag agaatgtag agctagtgtg ggcgaaggta   60060
tagcccagag catcatcaga tgattcttcc ttatgcaaat tcacatctcc tctgggtcaa   60120
```

```
gtatcatcct ggcatgcagc agctccatag gtaatgccct aaggctagcc tgaggcaagt   60180
tgcaaaagcc atcatattga gtcatggcct tttttgtgt gggggagggg gaatggcatc   60240
cccttcctgt ctgccaaatc aaggaataca gtgccctcct aaacctgctt tgttttagtg   60300
gattgttaaa aagaagtgaa tgaatttatg cttcattagg gaaaggttac agtggaatac   60360
tgaggagtaa ggggtatttc tatttaacaa atgacataac ttgaaggaat gaaatcataa   60420
ggatggaatt tcaggcatta ataaaaagct gatgagagat actttgagac aaaagagcct   60480
tcccagtgta accgagatca cagcacctac ttcacataca caggaaacca gtcctatctg   60540
tctctcccat agagcagtag ctgccttgtt tttcctccct cctccatcat tcattctaaa   60600
tctccagtcc tccaccgcac cttatccaaa ccctgatacc cttaagtcac agatggtgaa   60660
tcagtcaaaa gtagtattaa aaactagtgg tacacagcta cacctggaat gcagtaagaa   60720
aaatacggat ttctgtacat catcttccct ccctgctctt accccatttt aagagttaca   60780
gggtcagaac ccaagagtct gagttttga aagtccctaa aaattttgga tgatcaccta   60840
catttagaac cactgcacta agaaggacaa caaatatgcc aataaattct gttgccaagg   60900
aggtgattat gcaagctgga accctgataa catgaggaga atcccacaat agccaaatag   60960
tccatgtact agttacatta aataaagcc aaaagcagca ggcctacctg actttctcct   61020
gaggtctatc atgagcttag agagaaggaa cgtggacata tagaggtagc tctagatgga   61080
gaagggcact aggtgtcatg gaaagaatca tgtgcaagaa gtaaagaggt gctctgaatg   61140
tcctagccct gcttaggtgt ctgtgtcctc acatgagaat ttatccacag ttctttcccg   61200
ctgtaacaat ctttggttcc aactgcattt gtgagacagc aaaaagctat ggtccagtct   61260
ccttccattg tatcatctca tcaatgtatt tctcccacta cccttgtgtg aaatacaaac   61320 tttttggct tattgtgatt atgcaaggtg tatgccaact ttttttttt ctccacatct   61380 ttcagctttc tgatgggtaa aaattttcct tattttgctt tagaaaaatt ctcattggca   61440
tagatctaat ttcagggagc ctcccttgaa agctaaataa cattgagaat tcatgaaaat   61500
ataatgtaga gcattatgcc tgttagcata ttagtttaaa tagaagtggt tcatgaaaat   61560
ttttgaaatg ccagaccctg tcctgtgttt tgtattctcc caaatactca tccagatact   61620
gttcagaatg taacatgatt atttgaaat aaagatttc ccctagtttt taaaaaagtt   61680 acttataca ttaacccta tgttcctctt tgatcaattt ttccagtagt gtaaacagtc   61740
ttcagggaag tagatttctt acagaaattg tcaagtggct ctctgctgtt agcatggtta   61800
ctaatctttt ggttactttt catatttttt atactttctg gaagtggaca acttacttgt   61860
aaataaaagt gcataatttg tattaaaaat ttttagtaac aatctaattt gtaaatagaa   61920
tgtgagcagc atgaatgtgt gtgatatgcg tacatacgaa ttatgtctct taaaaatgta   61980
tcacagacat ctttccgtgt ccaaacaaat ctacctcatt cttctaata gccatatggg   62040 tataccataa tatatttaac taggccccta ttaaaagaat tttgactctt ttgtagctac   62100
tatagtgttg cagtgtgtat ctgtgtatgt atctttgtgt gtgtatcttt gtacgagtgt   62160
acatatattt tcccccttggc tatttcagat tttttttag gtttaaatct taggaaaggt   62220
tttgaaattg tcttaagtat tttcagaagc attaaatcat ggttttttta catttttctt   62280
ttagaagttt tatgtcatct ctatgagtag ctttcagtaa tttgttctgc ataaaattcc   62340
cgaaaacttc catttaaaaa taggtggcat gactagactt tctcagccga aagagtgagg   62400
tcccaggaag gattttggag aagctgtgtt caaatatagc tgctgacctg atgtctgcct   62460
```

```
agagtctggc aaggtgatgt gttgaatcta gtgtctgcct gcatgccagc atcccttac  62520
tgatgagatt tgtggttttc atcacttcat ggtaatcatc ccaagttata agatggagtc  62580
tctagaaaat cagtagagta tgaaggccca agtaaaatac atgtgagtgc atgtatgtgt  62640
gcatacaaat tacttctctt aaaaacgtat cctgggcatt taaagaatga ggacctccga  62700
aggattttgt ggaagctgtg ttcaagtaca gctgctgagc gtatgtcagc ctggagcctg  62760
gcaaggtgaa gtgttgaatc tagtgtcttt ttgactcact gttttttttg actcactgtg  62820
ctttgaagcc cttgtcattt gggctcataa aatagatttc tgtatactgt ctctcctccc  62880
tgccctcgcc cccatttaaa agtatagtgg cagaacccaa gaatcagagt tactaaaaac  62940
tctctagaaa atttggatga tcacccacct gatcatgtct tttttactca ctatgttttt  63000
tttttttttg agacagagtc tcgctctgtc gcccaggctg gagtgcagtg gcatgatctt  63060
ggctcactgc aagctccgcc tccctggttc acgccattct cctgcctcag cctcccatgt  63120
agctgggact acaggcctg ccaccgcgcc cggctaattt tttgtatttt tagtagagtc  63180
ggggtttcac tgtgttagcc aggatggtcc cgatctcctg acctcgtgat ccacccgcct  63240
cggcctccca agtgctggg attacaggcg tgagccacca cacccggccc tttactcact  63300
atgtttttaa gcccttgttt tcatttgctc cactgtaaaa cattcccaa gccaatctgg  63360
agctgaggca aattttaac aatttaaaat ctggggaata taaatattgg ataatgatca  63420
tcctgaaaaa acaatgaagg tagtagcata atacttata tatcaataaa atggcaaaat  63480
aagacagttg ttgaaggaca gaaagagtaa ctgaagttag gagcttatct taacacattt  63540
tttgtgtcat accataggca tcatattttt taaattttt ttatttcata cacataggaa  63600
aatatatgtg tgtaagaaat aataaacacc tctttgtacc taccacccaa cttaaggaac  63660
agctcattgc tattccctt ggtgctcgct ggatgcccct tcccagtcac atccccctcc  63720
cttcccatct gcaggactat actagtaaat tttgtatttt ttgcattatt ttgctttgtt  63780
ttatgatttt actacctatc tacatatccc taaataatac attatttagt ttcatatgtt  63840
ttaactttat gttgtggaat cacattaaat gtagtcttt tttttatat tatactttaa  63900
gttctagggt acatgtgcac aacgtgcagg tttgttacgt aggtatacat gcgccatgtt  63960
ggtttgctgc acccatcaac tcgtcattta cactgggtat ttctcctaat gctatccctc  64020
ccctagcccc ccaccccccg ataaatgtag tctttataac ttgttttttt aactcaacat  64080
tgtttgtaag attcatccat gtaagctgaa gctttttat agagatcttt gttaagcctt  64140
ttaatgaata cagtacatac atttctctgt tcccctgtta gtggacactt ggattgtttc  64200
cagagttttg ctgttttgaa caacgctgct gtgaaaatgt ctcctgaaac acatttataa  64260
gagttttttt ttccccaagg gaattatacc tagaaattga ataactagat cacaaggcat  64320
acacatctac aacttctgct aggtaatgcc aaattgtttc caaggagcgt tagaagtgtt  64380
ctcatcaact tttactagtg ctagtctttt acatttgtgg cagtatggtg ggtgtgaaat  64440
atttatgttt agttttctt ggtgccattt aataattttt ataaaaaata tttagaagtc  64500
aaggcagttt tttgtttttg ttttattttt ttgcttgttt tgttttaatg cagacattga  64560
gattacgact tggaataaac attggttgca aagttcctaa aaggaaaact ttttttggta  64620
ttctggagct tttctggtac tgaataaaat aagtatgtta aattatgcat gtgtagttta  64680
gaagtcagag caataattgt gattgttgaa cagaatggca gtaaaagtt tctaaacgat  64740
tgtactgtac aagggacact tgttgtgggt cagtttagc ctccccaact tttatgttaa  64800
aagttgcaac aaggtttaag ggcttatgtt tgataggcca gatggtgacc agctgtgata  64860
```

```
aaacacaggg aacccttgca aaggatttca aaatttatgc agtagtccgc cttatctgca   64920
gttttgcttt ccaaggtttc agttacccgc agtcaactgt gttctgaaaa tattaagtga   64980
aaaattacag aaataaagaa tcgaagagtt ttaaatttta tgcttcccac ccatcccacc   65040
tgggatgtga atcattcctt tgttcagcat ctccatgctg taggtgctgc ctgcccctta   65100
gtcacttggt agccatccag gttatcagat tgactcttct agtattacaa cacttggctt   65160
caagtaatcc ttattttact tcatagtggc cccaaagtgc aggagtggtg atcctggcaa   65220
ttcagatatg tcaaagagaa gctgtaaatt gcttccctta agtgaaagat gaaaattcta   65280
gacttatata taaagaaaag aaatcatatg ctgagactgc taagatctat gataagaatg   65340
aatcttttat acatgaaatt gtgaagaatg aaaagaaat gcgtgctggt tttgctgtca    65400
tatctcagac tgcaaaagtt tgcagccaat gtgtatgata agtgcttagt taaaaggaaa   65460
aaggcattta aggtaagtat atatagtgtt tggtactacc tgtgatttca ggcatccatt   65520
gggggtctcc tgagtataag gggagactac tcttttagtg ttaaatgaac actaaggaac   65580
agagatgggg aagaggttgg agaagattag ttcagcagtt tgagtatagg taaacagttg   65640
tttgagaaag aagaaaaatg tgattagtat tttaccttag caatagtggc atagataatg   65700
ataaattata gtcacacaga actcttagta tttacagaac gttcacattt gtgatcccat   65760
ttaacaataa ctctgaaaga aaggtatcat ctaccactgc tttattgata aagatataaa   65820
aggtaagaga gatgaaacat attggccaat gatacccatc tggtaagaga cagggatggg   65880
gtgggacccc aaggctcttc tcgccaagcc cacggttttt ttgctttata cttttttgcc   65940
tcctgatcac catggctgca gtttctactg tggacaatgt ctgtcagcaa gcattgatcc   66000
cctgccttca gcactcttac gtcttagcaa ggactggaaa gaaaaagcca ggagtttaca   66060
gtctgctgga gcaacagaaa agaatgatat gaaatatgaa gagaccaaaa tgatttataa   66120
taaggtgcta gactatgtag taaaaatctg ctttagctgt aagtcaaaag caagagcagt   66180
cttttcagaa tggaatagaa atgttggaat taaaggaatt ttcaaagttg tgaattttt    66240 tcaagataaa catgttttat tttggtaatt atggtattac taatttgata accttcaggg   66300
agccacctaa tattatagaa gatgtacata taatgacaaa agcaaacatt ttattttaa    66360 ggaccacaat ctaatctaaa acaaaatttc ccccttttct ggtctttggt taattaagga   66420
cttatttaaa tatcaaagaa agacacatag aaaacattta gtatatttct atacttttat   66480
taatgtcctc catccttac acagatactt gacttggcta tggtctagat aatccatgaa    66540
aatttaaagg acagattta acaactttat gctaaattga tagatctcta ggatcagatt    66600
gccatcactc tcagatgcga agcttccaac cacttatagg ttcctgatat cttgctttta   66660
tacagaccta atttctcttc ctttaaactt tcttttcctc agttgctatt tgattgaaat   66720
attgagtcat taaaaatttc caagtgggaa ttttttgtgtt tcttcatcta tcatgaagct   66780
gctcaaataa gtaggtgttt gaataggagt agaaacagta ataggctgaa gccagaccaa   66840
tacagcttca gctaaatgcc gaccttgcta aagtctggga ggaccggtgt ggtattctac   66900
aatgtacaag tctgtagccg gtgcccttaa tatgttggct tcatgtctca tgactctctt   66960
ctgtaaatat gcagtttaaa aaatacaagt tattctgctg tagaagatac atttgcaaaa   67020
ttgatgtatc ccctctaagt aaagttggct aaacaataag gacatattta taattaatga   67080
atttgagaag aatgctgacg atatgcatta ttctttgaag ttaacatttt tcaggtccta   67140
aataaacaaa aagtaggtta cttctgtctg gagtgtatgc aaggggtacc atcttgtcct   67200
```

```
tggttcctgg ctgctattcc aaggtgctat aaagtcagct aaagagagca atcataatac   67260
attgatagca tccctcaatg tgtttctgag ctacttgaga atcttatttt tgaataggta   67320
gcaggaaacc atctttgcag ggcagcatgg gcaaagggat tggagggact attattataa   67380
agatccactg aactgcttca gtatcataat atcttaaact aaaggactgg aaagagccag   67440
attccaattt aatctgctct tctatgaatt cttagctggg ttcatttaaa aagaaaaaac   67500
ttgaagattg caagattttg aagacatctt aaaataggtg aactccaagg tgcactttaa   67560
acttgagact gataactgaa tactccttca ccttttgatc tgatattgtc aaaatgaatg   67620
aggacttagt gctctagtaa gtttggaaca gaatgatatt aatttatttt ctcatgattg   67680
attcttttt gcttttaat agattaaact tcaccgtaga acagtttctc aacctctgga   67740
ctattgacat ttttgattgg ataattcttt gctgtcaggg ctgttctgtg tgttgcagga   67800
tagttagcaa catccctgac aatcacaaat gttactttct gtctctatgg atttgcctat   67860
tctggacatt tcgtataaat agaatcatat atatgtggct tcttgtacct ggcttatttc   67920
acttaacatg ttttcaaggt tcatccatat tgtagcatgt aacagcactt catttctttt   67980
ttatggctga gtaatattct gttatgtgga tatactacca tattttgtct atccactcct   68040
tagctgatgg tcttttaggt tgtgtccatt cttttggctat tataaataat gctgttaaga   68100
acattcatat acaagtttct gtgtagacat atatctttat ttctcttgtg tggatatccta   68160
ggagtagaat tactggatca tatgataact ctatgtgtta ccttttgagg aactgccaaa   68220
cattttcta cagtggctgt atcattttac actcccatca gcaatgtata agaattccaa   68280
tttctctgtc cttgcctata tttattaact gtcttttctt attagccaac tgctgtggtt   68340
cgaatgtttg tcccctccaa aactcatgtt ggaacataat ccccaatgtg gcagtattga   68400
gatgtgaggc ctttaagaag tgcttgggtc atcagaggtc tgccctcatg aataggctaa   68460
tccattcatg agttaatgta ctaatgggtt atcactggat tgggactagt ggctttataa   68520
gaagaggaag agaactaatc tagtaagctc agccttctca ctatgtgatt gctgccctgt   68580
gtcaccttgg gactctgcag agagtcctcc agcagcaaga agttcttcat cagctgtggc   68640
cccttgacct tggacttccc agcctccaga aatgtaagaa atccatttct ttttttaat   68700
aaattacaca gtctcacgta ttcagttata ccaacagaac acagactaag acaccatcct   68760
attgggtatg ggtatctcat tgtgtttttt atttgtgtct cccaaatgac taacgatgtt   68820
gaacatcttt tcatctgctt tttggacatt tgtgtatttt ctttgaagaa atgtctttaa   68880
cattctttgc ccattttaaa attaggttgt cttttttattg ttgagttgtc ggtgtgtgtg   68940
tgtgtgtgtg tgtgtgtgtg tgtgtatcta gaatatatgt gtatgtatat atgcagatat   69000
attctaaaca ctagacccctt atgaaatata taatttgagg acaatttctc ccatttaaaa   69060
ggccatcttt tcacttcttg atagtgtcat ttgactcaca agttttaat ttttatgaag   69120
tccaattat ttttaattc tttgttttg gcactgtatc tttaaaaagt tgcctgatct   69180
aaggtcaaac tgatttcac ctatgttttc atctaagaat tatagttta gctcttacat   69240
ttaggccttt gatccatttt gaattaattt gtgtatatgg tgtgaagtag ggctctaact   69300
tattctttg tgtaatgata cctagttgtc ccagcaccat tgttgaaaa gattattctt   69360
tccccattga atggtcttga taccttgttg aaatcaactg accataaata tataggctta   69420
ttcctggact cacaattcta tgagtctgta tgtctaatct tatgccagta ccacactgtt   69480
ttgattatta catctttgta caaagttttg aaattgggaa atgtgagtct tccaactttg   69540
ttctttttta agattacttt gcctatattc cgtgttcgtt gcaaactcat atgaattta   69600
```

```
aatcaactct ccatttctgg aagaaaaaaa gaggcaattg aagttcagat agggattgca   69660
ttgaacctgt agatcagttt ggggaatatt gccatcataa caattagtag gtcttccaac   69720
ccatgaatac aagacttctt tccatttctg tagatattta gtttctttca ttaatatttt   69780
gtagttttca atataaaagt cttgtacttc gattaaattt attcttgaat attttgggtt   69840
ttgatgcttt tatgaatttg ttttcttaat ttcactttaa gattgttcat tgctactgat   69900
tagtaatgca actgattttt gtgtgttgat ttttgtatcc tgcaacctag ctgaaatcat   69960
tgattagcat aatagagtat ttaatagatt taggatttct atatataaga tcatgtcatc   70020
tgcaattaga gataatttta cttcttccct ttcaatctgg acatttttta cttctttttc   70080
ttgcctagtt gccctagcta gaacctccag tgcagtgttg aatagcagtg gtgagaatga   70140
gcatctttgt gttggtcttc atcttgtggg gaaacctttc agtttaagtg tgttgttgtg   70200
gggttttcat agttgtcctt tatcagattg agaatgttcc tttctgttcc tagtttgttg   70260
agtgttttct ttttgattgt tttaatcagg aaagggcatt agattttgtc aaatgctttt   70320
tctgcagcta ttgagatttt tgtgtgtttt tctggtcttt tatggtttat cacattaatt   70380
gattttcata tgtcaaacaa accctgtgtt cttgggtttc atctcacttg gttatggttt   70440
ataatccttt ttatatactt gtagattcag tttgccagta ttttgttgag gatgcttgca   70500
tttatattta aagggatat tggtctgttg tagctgacca gtaagtatag taagctgtat   70560
agtttactaa gtgttccctc tgttttgggg gagactttga aagaaggat tgttggtaat   70620 tgttctttaa acatttggta aaattcacta gtgaagccat ctggggtctt ctttggaagt   70680
tttttgatta ctaacttaat gtctttactt gtttgttata agtccattca gatttttttc   70740
tccttgagtc attttttgaca gttggttgag gaatttgttc atttcatgta gttatctaat   70800
tggttagtgt ataattattc atagtattcc tttataatct tatttttttg ctgtaaggtc   70860
agtcataatg ttcactcttt catttcggat tctggtaatt taagagtctt ctctccttt   70920 ttttcttggt cagtctagct aaagtaaagt tttgtccgtt ttcagggaa cagctttttt   70980 ttttttttg aggcagaatt tccatcttgt cacccagtct agagtgcagt ggtgcaatct   71040
cggctcattg cagcctccgc ttcccgggtt caagagattc tcctgcctca gcttgccaag   71100
tagctgggat tacaagcgcc caccaccacg cctggctaat ttttttatatt tttagtagag   71160 acggggtttc accatgttgg gcaggctggt ctcgaactcc tgacctcagg tgatctgcct   71220
gccttggcct cccaaagtgc tgggattaca ggtgtgagct accgtgccca acccagcttt   71280 ggttatttt gttgacctac tctattgttt ttctcttctc tatttcactt atttctacac   71340 tggtcttat tattttcttc cttatgcttg ctttggactt agttcttctt tttctagtct   71400
cttaaggtgg ataattaagt tcctgatttg aattcttact tctttgtaag gtggtcatgt   71460
actgctatga atttccttct cagaaatgta tatgctttca ctgcatccct taagatttgg   71520
tatgttgtat ttttgttttc atttgtctca aggtatagtc ttctgatttc cattgtgatt   71580
tcttccccct ctaacccgtt tattatttag gaacttgttg attccacat acctgtgaac   71640 tttccagatt tccttctttg ttaattctca gtgtcattcc attctggtcc gagaacatac   71700
tttgtatgat ttctatcttt taaaatttat ttggcttgtc ttatgaccta atacattgtc   71760
tatcctggag gatgtttcat gtacacttga aagaatgtg tattctgctt tgttgggta   71820 gagtgtttga caggtgtgtt ggtacatagt tctgttcaaa tctgtttcct tgcagatttc   71880
tatctagttg ttctgtctat tggaagtagg atattgaaat ctccaactaa tattgctgaa   71940
```

-continued

```
ttgtttattg ttttcttcag ttctgtcact ttttgcttta tatattttga aattctattg    72000
ttaggtacaa gtaagtttat gattattata tcttcttgat agattgattc ttttatcatt    72060
atacagtgcc ctataagaac aattttatc ttaagtctat ttgtctatat tagtatagcc     72120
acttcagctt tcttttgttt actgtttgca tggaatattt tcttcttta ctttctattt     72180 gtgttcttga gtctaaggtg aatctctgta gatagcaatt ggatctgcca atctttgctt    72240
tttatttggg gagtttaaac cattgacatt taatgtaatt attgatgagg aagattactt    72300
ctgatatttt gccatttgtt tcctttattt tgtgtctctt gttcttaaat tcttccatta    72360
ctaccttctt tcttttgtat tacatatttt ctagtgtaac gattttaatt tctttgtcat    72420
ttcttttgtt gtatgttttt agttattttc ttagtggttg ccacggagat tttattgtca    72480
ttttaacagc ctaggttggg cacagtggct catgcctgta atcccagcac tttgggagac    72540
tgaggcagga ggatagcttg agtccaggag ttcaagacca gcctgggcaa cttactgaga    72600
tactgtctct acaaaaaaat acaaaaatta gccaggcatg gtggtgtgtg cctgtagtcc    72660
cagatgcttg agaggctgag ttgggaggat agcttgagcc caggaggttg aggctgcagt    72720
gaactttgat cacaccactg cactccagcc tgggtaccag ggcaaaacta gcccaaagaa    72780
atgaaggaaa aaaaaaatct aatttagatt aatatcaact caacttcaac agtgtataaa    72840
aactttgcct ctgtatacct cttctgcttc cactctgtgc tgttattgtc atagattttc    72900
atctttctac actgtgtgtt tatcaatgta gatttaaaaa tattgcttag tagttgtctt    72960
tagaatccga tacggagaaa aggagatata aacaaaagat gcattttac tgtcttgtat     73020 gtttacttat gtaattccct ttcctgatgt tgtatttcta aaggcaaagt agggttattg    73080
tgagtgtcct tttgtttcaa cctgaaagac tccttttagc atgtgttgga gatatgctaa    73140
tgatggactc tcacagtttt tgttatctgg gaatgtgtta atttatcctt catttttgaa    73200
ggatagtgtt ggcaggatac agaattcttg gttgacatgt aattctttca gcattatgaa    73260
tatgtcatcg tactgtcttc tgacctccat ggtttctgat aaggaatcaa ctgttaatct    73320
tattgaggat cacttgtttg taatgacttg cttgtcgtgc tgctttcaag attcattctt    73380
tgcctttagc ttttggtagt ttgattgtga tgcatttagg tgtgtacttt attagtctgt    73440
tctacttgga gtttgttgag cttgtagat gtatttcatc agatgtgtca agttcttttg     73500
ccactatttt ttttttaaat aatctttttg ccccttccg ctccttctgt cactctgatt     73560
atttgtgtgt tgctttgttt ggtggtgtcc cagaagtctc tgagactctg tccagttttt    73620
tcctccccat tctttttct ttcacttcct cagactggat gatctcaatt tgacctatct     73680
tcgagttcat ggattttctc ttctccaagt gacatctgtg agatgaattt ttttctagag    73740 aattttcat ttcagttatt ctacttcaaa atttctcttt ggttcagttt tatcattgct     73800
atctttatat tattctcagt ttaatgagat actgttat actttccttt agttctttag      73860
acatagttta tgtcactgaa tatatttaaa atagctgatt ttaagtcttt ttttttttat    73920 tttttttggag atggagtctc gctctgtcac ccaggctgga gtgcagtggc acgatctcag   73980
ctcactgcaa gctccacctc ctgggttcac gcaatgattt taagtctttg tctatgaagt    74040
ctagtatctg ggcttcctca ggcatagttt ctgttttctt tctttctttt cctgtgtact    74100
tcgtttcttt gtataccttg taattgttgt tgttaactgg acattttgaa tattatagtg    74160
taacaactct ggcagtcaga ctgtctcccc tccccagtat ttgttgttgg tgagtattgt    74220
agatgtttgt ttagtgactt tcatggcta attctgtaaa tttatattc tttgaagatt      74280 gtgggcaccc tgaagtctct gtttgttagt ttagtggtca cctaataatt aacagagatt    74340
```

```
tcattaaatg cctagaagca aaatatcttc cagtctttgc ccatggcctc tgtgtatgca    74400
ttagggcagg ccttgaactc ttacccaggg agtttacaac cctgccttag cctttactac    74460
cagcttctgc agagcattaa ggtcaacagg tggtgagagt ttggagccta ctccatcttt    74520
cctgagcata tacacagccc tactcatgca tgtggccctc tagatttcca ggagtatgtt    74580 ggacccttc aaagccctta cagactcccc agcttttcct ctcaatcttt agactagtgt    74640
gttgttttct tcaacagtta tctgtcaggc agcagcaaat taagagatta gcataaatgt    74700
tttcaactcc tccacccgtc atgtgcccca gggaagcact aagccagttc taagttaggc    74760
aaaataaaga caatcctttt gaggtggtct tccatggagt caccagacag gtaaaccaaa    74820
taattaatta caagtctttg gctggataca gtggctcaca cctgtaatcc cggcactttg    74880
ggaggctgag gcaggtggat cacaaggtca ggagattgag accatcctgg ctaacacggt    74940
gaaaccctgt ctctactaaa aaatacgaaa aaataggtgg ctgtggtggc gggcgcctgt    75000
agtcccagct actcgggagg ctgaggcagg agaatggaat gaacccagga ggtggagctt    75060
gccgtgagcc gagatcacac tactgcactc cagcctgggt gacagagcaa gactccgtct    75120
caacaaaaaa aaaaaaaaac aagtcttcat gaaagaggtc cattctgctg tctttcatac    75180
caggaatgtg gaatgtggac tgttattttc atggctactg ctaagctagg aatcaaggga    75240
tagatgggga ctgggtaaaa caccacagag tttgctgttc ttaccaagaa taagctgggg    75300
aagagggttg ttttttgtttt tcagtaaaaa ttccctgggc tgcttcaagc cgttgattaa    75360
ttttcaggtt ccgaaaaagt tcagtttgac agtttttgcc ctttttattt gcttttatgg    75420
atatgtagaa cttgagttct tttttccacc agttttgctg acattgtttt aaaagcactt    75480
tttgtaaaac ccaaatgttg tctctctcaa ggctagccaa taattaaaaa tactgttact    75540
cccctttgat tttggaaatg aattcgtatt gaccaaaatt caatactaga ggtctttcaa    75600
gctgttttac catttatcta aactttagaa tctaatgatt cctgtacatt gtctagcata    75660
ctggtggtcc tcaattgtca taagttcaac tttggaacaa atgaactttt tgtgtgcaag    75720
tttccaattg tttggaaatt acattgatgc cccctccatc aaactgttat tcgtgggaca    75780
tctaggaatt tcttacagca gctgacaaat atttcaagtc agtgcctggt agtactgtcc    75840
accaggcaac agcttcagta gtagagcgat cttatctat aaggcagtgt ttgagcaatt    75900
gtttattagt gttttcctaa ctactcagaa gaactatcag gggttataga ggtagctcag    75960
agagttgggt gcaagtagag aaatccaccc ggcttgcatt acacatctta tttctagaga    76020
agctttcctt tgaagaagga gttctaaggt ttaaaaaatt accttgaatg ccacttatat    76080
tgcattttaa ttttattttta gagaaatcaa tggaaagtag aaaaattaag gcactgatac    76140
tagtgttaag aatgttggtt aaagcttctg gcaattaatt ttttatttcc ttttttaatt    76200
ttattaaaat ttaacaattt tcagtttatg ctgtaatcca gaccaaggtt tcaatctaat    76260
gaagttaatg ccagtgttgc tgctacctat tttgtctttta gtcattcagc catgcttcct    76320
acttatactg aataagctag cttaatctaa caatcaaaaa agaaagctgt tgcctaagtt    76380
aagaaaaaca gtttgaactg ttttcaaact aaatacccag tagactctct agttgttgac    76440
aggagaatgc ttaattcaga attgtcctgc agtagatcat tttatctcat tcctgttctt    76500
ctataggata gcttatttgt ttgaaattgt atttaatatg ttgtgatttt tgtgtgcttg    76560
tttctatttt tcactggata gactcaagat aaaacctggt accctgcagt gtagctatca    76620
gtttatagca gaggaaattt acattagaac ttggctgtgt atttacatgt atctaacttg    76680
```

```
gaggtcactc tgcttactgt tgatatatca gtcatattag atgagtccct aatgagatac    76740
cagaaacccc ggaaacatca ttaggtggaa cagtgtcctt aatgctttat taagtgttat    76800
aggtaagaca aagcctagta ctatttgtgg catcaaggtt aggtgtttaa agacctgtat    76860
tcttctattg tcatgttgaa attgttccct tgatgtagca atagaaaatt ttagattagg    76920
cttaagttaa tcagcaaaca aagataaaag tctgatacta tcctaaatat tttgtgtttc    76980
taaataattt aacagtgatc caattagcta ctccctgtaga aatgtaattg ataaactttt    77040
cactctcttt taaattgcca tcttgaattt tacctgtttt ttaaagctgt ctcaagtcct    77100
ctctaaaaaa aggcagtcat ttataaattt agaaaagctt gatagcacag aaagtcacag    77160
aaaaatgtaa acatagttta aaactgaatt gtatacaagc cactagaagt acttttatta    77220
agtttacaaa tattagtaga gtggaactca tgcatttaat atgtttgaaa cttttgatca    77280
aatactgtgc tatgaaaaac attttagata attattcttt aatcatgtgt gtgtaaaatg    77340 tggcttttt tgacaaccaa gtagctttc tgtgtgccaa actgtgactt taaaatttta    77400
aagtactcaa cagagtaaac aaaccacaaa taccacttaa actgtacaca tttgcacatg    77460
catttcctat aaatagtaca tgggtttcaa gtcttcactt ttgaaattca gaatgggtt    77520 ttttctcctt ccagtagaaa taaaaacttg atttatttta tttatttatt tattttattt    77580
ttgagacgga gtctcgttct gtggcccagg ctatggtgca ggaggtgat ctcagctcac    77640 tgcaacctct gcctcctggg ttcaagtgat tctcctgcct cagcctgccg agtagctggg    77700
attacaggtg cctgccacca tgcccagcta attttgtat ttttagtaga tgggggttt    77760 ctccatgttg gcaggctgg tctcgaactc ctggcctcag gtgatctgtc tgtctcagcc    77820
ttccaaagtg ctggggatta caggtgtgag ccaccgcatc cagctaaaaa cttgattttt    77880
aaaaatccaa atcgaagaca gaattgtgta ttttagtaca tttattagca gccttgacgc    77940
tataccatat ggctgtttat catttaaaca gcttgtaaaa gcaaacactt caggattcat    78000
gagtggcaga aggactgagt actttgggaa ataagagaga acttttgttg aggatggttg    78060
aggaagagtc caagacaata ataggcagaa taagcaaaaa tctagagact cattgtaggc    78120
actcaagtat gtatttgtta gaatgaatgg ctgaacttgg tatattgagg aacactgaga    78180
aagccatact gactggaaga tagttcctac aagaaactgg tgagacatat gttacagtct    78240
agattttggt gagccttgtt aaagtttggg ctttattttt atacggggag aaagtttcac    78300 agggggtttgg aaatgaggct tggagctgtt aatggggaca cagtgaggtt ttagggtagt    78360 ggcttttcaaa ctgtttaaat ccaaactttg atgataaccc tgacataact attgtttata    78420
acttccattt cagttgtatt ggttttatca aaacatcttc attgatctta ctgattgctt    78480
cctatgcaga ttaatattat aaatttgaat gtacaaagga agcttagca gtaaaatagc    78540 aacttttatc tgtcttacgt attggaggtt ctgcataaga tttaatttt ttttttttg    78600 aaatggagtt ttgctcttgt tcacggggct ggagtgcaat ggtgtgatct cggctcacca    78660
caacctctgc ctcccgggtt taagtgattc tcctggctca gcctcccaag tagctgggat    78720
tacaggcatg tgccaccatg cccggctaat tttgaatttt agtagagacg gggtttctcc    78780
atgttggtca ggctggtctc gaactcctga cctcaggtga tccgcctgcc tcagcctccc    78840
aaagtgctgg gattacaggc gtgagccacc gcgcccggcc aagatttaat ttttttaaaag    78900 aaaatatttt gctaagggtt tggaaactct tgttttagca agaatggatt aagactgatt    78960
aaaactaaag gcaagagga ggctcttatg tttggaattc tttgctaata tttacacaat    79020
ataattctct ccacaaatat ttaatggtac cagatattag atggttataa tggcaaaagt    79080
```

```
gttcaaagga tgctatcata ttcatgattc atgatcaaaa tgaacattat aaggctatcc    79140
ctcttcagaa ttaaatacgt tactcctgtg gaaaacttgc ttttaatgta gaagttgtcc    79200
cagagccttt cttcctttct catgtcctct tatgtccact gctgagctaa catgggtctc    79260
actgaatgat taagaaaaaa catcttaggt ggggagttct gtatatagta aatgtttaat    79320
ttattggggt ggtgaacggg aagtgctgct ggcaagagag gatgggaaga gaaatctacc    79380
caaatcctta cccgctttac agaacataaa cttcctattc agtagtacac aataacttaa    79440
cgatcaaggc atcttaactt ttctgttttc agatgaaaga actatcgttt ggcttgatca    79500
agtatttagt atttattcgt tcactcaagt gcttacgttt ttttgttatc tcagggtttt    79560
acgttagtta ttaaccaaaa gaactagttt tagttctgga agtctaaaat atataagaga    79620
aggtgaggag taataagaga agatgaaggg agactttcgg aatggcctat gaacttctag    79680
taactatacc accttaaaat agacaaatta caatgcagtt atgaagatat gtattttca    79740 gtgaagacaa ctaaaatgtt tgcacagaat tttcttttt attgagtgtt agaaattcta    79800
ttttggagat actaccttgc acaacataaa aagaaaagt gagtgtggaa tctaggaatc    79860
tacgtggctc taggaaattt tttaagtgtg gaaactgaag gagagcaaga gaaagggagc    79920
atggcattcc cctgtttgta gttcatgagg tgggtttaaa ttgccttttg ccaatgcagc    79980
tgcacactga ggattacaga attcttttta aatgtttgta gaattatttt tcacttatta    80040
ggtaaaacgt gtatttttg attttctcca atttcagctt tctcatgttg ctatgctcaa    80100
ttttgtatac catatatagt tttgttaaat tgacaaagtg gtgttttttg ttcttctttt    80160
tcccattggt taaaatttaa agagaaagtg gaagctagaa atttatctaa aaaatgtaac    80220 tttcctgta attattaaag tatcaatcta aatttgaatt ttctttgtgc ataatctttt    80280
ttcaagctat ttaccatgtt gacaaacttg ctttcctgtg gcaaatacac tagcaatacg    80340
ttataaatat gtaactttca acctatttac agttgatgct tttttagccc tttggattta    80400
aaatacaagc actgaagagg tgaggaagta ccactgctgc ctcagcatta tttcgaaatt    80460
ctgtttataa actatacaat ttccaaggtc atgaatccag cacctttcca ggtactaact    80520
attgggacaa agatagaatt tgattttatt tatttaccta ttgactgaag tctaacttaa    80580
atcttgcacc tagtaagatc ttagaaataa cgtgtgtact ctgacctgta aactaatcct    80640
agtattctgt gtgtatattc tttctcattt gggctcttaa aaggaaaagt aacgtacatc    80700
tgatgatcat tagcactgag cttttcagc aaaaagtata tgtttataaa gaagtatagg    80760
ataatttagt aatttaataa tgtgacaaca tttgcgtgtg ttttttttt tgagaaatac    80820 aaattgtgag aaacagaaaa gtaaagaag cagcagcaga aatatcacta taggatcaaa    80880
agattgcagg aaccaaaact ccaaaattat tgggcataat gtactaaaaa cagggcagtg    80940
gaggaaaggg acagtccaga ctagctctga gggtccaaag aaagtattaa atattgttac    81000
tggagtgatt tgctctgcta tttgggcttg ggaattaagt gaaattgttg atatactaga    81060
cagatacttc ccacccattt ttctcttgat aatcagggtt cattttttct attttctatt    81120
tctctggatg ctccatttct taatattaat attaatatta agctctcagt ctttatgcta    81180
aaaattggtt atttaaaaca atttaaatca acttcagtct aattggctta agttcaaatc    81240 catttttaaga tcgatattgt gtcctttaaa aattttattt aaaagatatt taaactgatg    81300
agaggatact acccattcca ctgataaact attactgtaa gtttgtctat tgagggctag    81360
ttatttggtt taaaaatgct gagattatgg aaagtggatt ggaatatttt ggagcaatat    81420
```

```
taaaaacagt atctgtaaca atttaataaa cttataaatt cctctttctc tgttgatcta    81480
tcttgaaaag acactctatg tctctaggca ttccttctct gtggtgtgat tggtagacag    81540
ggagtaaaca acttactgta aatgggcacc atgccagttg gcttcaggca gcatcaagct    81600
tgtgactcac agtcagggtt aggaaaatgc cttttaactt gtttgtctct gcctcttttta   81660
aacattaaag gcacaactgt actaattatt aagtatttca taggtctttt tagggcttat    81720
aagatctttt aggaatggcc tggaagttat tagtactgtt tcattgaatc tgaataccit    81780
taacatgata atgagaagtt tttaaagggt ggttttatag ttaaacggaa tttctcaaat    81840
tggcttgctc cttatgttga tttatttagg atcacatttg ggagtttctc tgccctactt    81900
tcaatgtatt taatttactg accatcacta tttgggggga aaatgttata tgatatttag    81960
aaaccaagag ttttggagtt tttcccccat tagatgtatt tatttatta tttattattt      82020
tttaaagaca gggtcttgct ctgtcaccca ggctggagca cagtggcatg atcctagctc    82080
actgtattct tgaactcctg ggctcagact gtcctccac ctcagcccaa gtggctaagt     82140
atcaagtaag aatcacctgg caaattccaa ggctgtatac cagatttcct aaattagaat    82200
tttgggggttg ggtatctgaa ttttagtaaa gccctccaaa tgtttctggt attgcttcta   82260
agaacaattg ataacataat agctgtggcc attataggg tattctgtca tatttagata    82320
taagcatacc ttgttttatt gtacttccca aatattgcgt gtttattttg ttttgtttca    82380
cttacaaatt gaaggtttgt ggcaacccta tattaagcga gtctgtcagt gccatttttc    82440
caacagcttg tgctcatttt gtgtctctgt gtcacatttt ggtaattctc tcaatatatc    82500
aaacttttttc atcattttg tatctgttac gaccagtgat cagtgatctt tgattttttc    82560
ttttttttt ttttttgag acggactttt gctctgtcac ccaggctgga gtgcagtggt      82620
tcaatcttgg ctcacagcaa cctctgcctc ccaggttcaa gcaatcctcc tgcctcagcc    82680
tccccagtag ccgggcctac aggcgtgtgc caccacgcct ggctaatttt tgtattttta    82740
gtagagatgg ggattcccca tgttggccag gctggtctcg aactcctgac ctcaggtgat    82800
ccgctcacct tggcctccca agtgctggg attaccgtgc cagcctgatg ttactatttt    82860
aattgttttc aggcaccata aacctcacct gtataaggca ccgtacttaa ttgataaata    82920
ttgcgcatga tctgactgct cttccaactg gccattccct gtctgtctcc ctcttcctgg    82980
gactctcaaa tccctgagag acaataatat taaaattaag ctaattaata accctacagt    83040
ggcctctaag tgttgaagtg aaagagttgc atgtctctca ctttaaataa aaagctagaa    83100
gtggctaaac ttagtgagga aggcacatca aaagccaaga caggccaaaa gcaaggactc    83160
ttgtactaaa cagctaaatt gtgaatgcaa aggaaaagct cttgaaggaa ataactagtg    83220
ctactccagc aaacatgtga atgatcagaa agtgaaacag ccttcttgct gatacgaaga    83280
aagttttagt ggtctggaca gaagatcaaa ccattcacaa cattcctta agccaaagct     83340
taactctctt caattctatg aaggctgtga gaggtgagaa agctgcagaa gaaaaattgg    83400
aagctagcag aggtcggttg atgaggttta gggaaagaag ccagcgctgt aacataaaag    83460
tgtaaggtga agcagcaagt gctgatacag aaactgcagc aagttatgta gaagatctag    83520
ctaagattac taaataatag attttccatg tagatgaaaa agccttttgt tggaagaaga    83580
tgccatctag gactttcata gctagaaagg agtcaatgtc tggcttcaga ggacaggctg    83640
acattcttgt tagggctaa tgtagttggt gactttaagt tgaagccagg tctcatttac     83700
cactccaaaa atccgaagac ccttaagact tatgcttaat ctactctgct tgtactctag    83760
aaatgaaaca acaaagcctg gatgacagca catctgttta tagtatgctt cactgaatat    83820
```

```
tttaaggcca ctgtaaagac ctgttcaact gctcagaaaa aaatgattac tttcaaaata   83880
ttgctgttca ttgacagtgc acctgggctc acccaagagc tctaatggaa ttgtacaaca   83940
agatggatgt tgttctcatg cctgccaaca catcatccat ttgtagccca tgaatcaggg   84000
agtgatttca agtttcaaat cagtacattt tgtaaggcta tagctgctat agacagtgat   84060
tgctctggtg gacctgggca aagtaaatca aaaaccttct gaaaaggatt ggccattcta   84120
gatgctatta agaatttgtg attcgcagga ggaggtcaaa ggatcaacat tagtagcagt   84180
ttgaaagaag ttgattccaa cagttataga tgaatttgag gggttcaaca cttcagttta   84240
ggaagtcact gcagatgtgg tagaaacagc aagagaacta gaattagaag tggagcccga   84300
aaatgtgacg gaattgctgc aatctcatga gaaaacgtga atggatgagg agttgcttct   84360
tatggacaaa tgagcaaata aatttttttc ttgagatgga atctactcct ggtgaagatt   84420
ctgtgaacct tgttgaaata caacaaagg atttagagta ttacataaac ttaattggta   84480
aagcagcagc atggtttgag tggattcatt ccagttttga aagagtttct actgtgggta   84540
aaatgctatc aaacagcatc tcgtgctaca agaaatctt ttatgaaaag aaaagtgaaa   84600
cttcattgtt gtctacttta agaaattgcc acagccaccc caccttcagc aaccacctct   84660
ctgatcagtc agcaggcatc aacactgaag caagaccctc cacaaggaaa aagattacaa   84720
ctcactgaaa gttcaaatga ttgttagcat ttttaagcaa tatttaagaa ttaaggtaaa   84780 tacatttta aagacacaat gctattgcac acttaataga ctacagtata gtataaatat   84840 aactttata tgtagtggga aaccaaaaaa ttcgtctgac ttgctttgtt gcaatattca   84900
ctttattgtg gtctagaacc gaacctgaaa tatctcagag gtatgcctgt attaatatta   84960
ttttgcaagt aaaaaaccca gcatataaaa aaacgtaga atatgttgag agttcagtaa   85020
tatggatgaa aatgttttc tctaactgaa gaacatgata aattataatt agggaaggat   85080
ataaaccaag aaaatatgtc tgagatagcc aattcttgca gttcataata tgaaaactca   85140
ttataccaat ctcagtaaga atacttttaa tagctgttat ttctttggga tatagaattt   85200
ataaagtaca cagtaatctt cttatgatca atcctaggat cactttacaa ccacttaccc   85260
catattacaa tgtagtacca agacaagcag accaaattat agaaggacaa agttttttgct   85320 aagcatattt tgtcatcagc ataccgcatt gtgtgtgcat gcatgtgtgt gtttgtgcat   85380
gtgtgtgatt gtataaaata ttagaaagcc accccagaaa agttaaatga ctaggaatgt   85440
tgtgaaggga ttaagctacc cctaaaatta tataacaaaa ctctcttcat ctattattag   85500
gtcatcttta gaacatcttc tcttaaattt gttataggtc tctctcatct gtttggatta   85560
aaattggtct gaaagcctaa aatggctttt tacctatata attatttccc aactagcttg   85620
tagtataggt gcaaagctat cacacttgct aggttagtga agtatgtaaa aactaccatc   85680
tttcaattag gaaccatcgg atagcttcta caggattgct ggggagaacc tttataaaga   85740
aagttatatc tttataaatt ttttgtcatt ttacttagct gagaatataa aataagttag   85800
ctaataatag agtagaaatg ttttctgtaa cagattaata ttgatcaaat gtgttattaa   85860
atgctaaaac accattttt ttctctgtaa gccatgtgtt tcatgccaca acacaaaagg   85920
gacaattgtc tgtgttttat gacagttctg ttctgtcaga tgctgtttgt tcattttggt   85980
gaataaatga agagagccct ggacacatct ttttttcctc aacaaagag gaaaattatt   86040 cttgtctgta tgtctataat cctgactctt tgaatggctt taattttttt aaagtcagca   86100
tttttttata agataggtg tttggaatgt gggcgatatg gctggacagt tagattggga   86160
```

```
ccaaataatg gaaggctttg aacatcatgc taagaggttt gggttttact ctgaaggcag    86220
tagagaacca ttatgttttt aagccaggat tgacttgttc taagctgtac cttagaaata    86280
ttactctggc agttgtacat aggatgagct gtatgttgct ttgttttgtt tggggagaca    86340
gttctcgaag agagactaca tacgaaggca gttatatgag tcattactaa aggtctggca    86400
agaagtagta aaagcattaa ctggagtggt agcagtaggg aaggaaataa aaggatagat    86460
gtgggagtca tttggaaagt atgaggcaat tcattgacct tacagaatca ctggttttct    86520
gcttccactc cattcacatt gacctttcca aggttatcag tgacctgctt gtccttaaat    86580
tcagtgggca ctttccagta acctactgtt ggcaccagcc ctgtgctaga caccaggatc    86640
ctgtttgtaa aggcatctgc cagtggtttc tgtgacacaa ttctgtttct agttttcctc    86700
cttctacttc tctagcctct tggcaagttc ttctttcaga gtttctcaga gctttgtgct    86760
aggccctctt ctcatttttct ccttctctaa gtgatcccat cctttctgt tgcttcagtt    86820 accatttgtc cttatgcaaa ggacagccat atctactgta tctccagctc agatgtatct    86880 cttttgcctcc tgacccatat ttccaactat ctaactgggt atcttttctt ggatgagtta    86940
taggtctctc aaacacaaca tgtccagaat aattcattga cttattctaa ggcctgcttc    87000
ctctttctcc tgtagtccct atctcaggaa atatatggtg ctatcaaccc caaagcagaa    87060
atctggacat aatccctaac tacccttttc ccctctctgt gcacataatt tcagtcatta    87120
ggcctcatag attggactaa ataaatacct cgcaaaccct tctacttata ttcttaactg    87180
ctcctacctt aagccaggct accataattt tgtagctgga tgactgcatc atcatcttga    87240
ctggctccct tgtcatcttc aatctatatt ctatactgca gctagagctt tcaaacataa    87300
acatgtgatc agattagtcc cctctttaga cacccctagg gttctcactg tcctgagtac    87360
agtctaaggg tttaccatgg cttacagggt cttttatgat ttggtgagct ttttattgta    87420
taacctttct aaactgcctt tacttccctc tttcttggct ctgtgtcttt gcataatgct    87480
gttccctata cttcacctca cgtctaacct tcatctcctt ttcacttctc ctcttcctcc    87540
aaaatccagc tgaatatcac attgtcatgc aggcccattc ttgatctccc acgtttgggt    87600
tagatatccc tcttcagtac catcaccgca ccaggtgtgt cccctatcct agcatttgcc    87660
tcattgtatt acaactactg tgtactcgtc tctacagctc ctgctagtct aaaagttttg    87720
ggagagcaaa ggttcatgtt tgtgtttttc actgtggtat acccccagtgc ctagtatatg    87780 ataagctctc aaaatatttg ttagatgtat gaagaaatga gaaagagaac aggaagaggg    87840
taagtttcaa gactaggaaa caaggctatg aaagctgcag gaaagcagca ggttaaaacc    87900
tagaagaaga gtttgtttta ggaaatactg tgttttaaac cactataact gaagcaaaaa    87960
cccaaggcct gggtgtggat agagtccact atctgataac agtggatact gatgcatggc    88020
agagttggag aggaagagag ccagattcca aaacagaagg ggtaaagtct tctaagaaga    88080
tagattatag taagaaggat taggggatag aaatatgagc ctgttccact catagatctc    88140
aaacatgaaa tgatgagtca tcatgaagag agtaggcaat tgtccagtga agaagggat    88200 gctaacccctt cttaaccttg aatctctcag gtagaagcag ttagagaagg aacagccatc    88260
atcagatagt gttgtaagga aaatgatatc cttggggaaa cctgcatttt ggtaaagcaa    88320
agcaactaag aaagaatata ctaccactgt ttaacaatcg ccacaaaaag acagtaggat    88380
catctttgac cccctccatc ctttctcagg aacttggagg actaagaaga gagaaatctg    88440
tagaagaggc ttctctctct gatcctccct ccacttcagt tttaccacat gtaatgcaac    88500
aataattaag aatttgtgta aaatttcacc aggttggcat gcatggagag aaaaattatt    88560
```

```
cagatgtttt cctttgtcaa taatacaagg agcatttgta gggaaaaata tttacaaata    88620
cagtaagacc tattctctttt ctatatttat gggaaaattt taagttgtgc ccttgtttca    88680
tgtgtgtttc tatttaaaga taccatactt aatatatatt gttgattcat taacattgaa    88740
ctcatggcta acagcactat aaatcatgtc tgatcaaaac ttatgataca tgtactttct    88800
tcgtaaggta catcatagtc ttctcgtaca tgggaactct aggtagtact tcaggactat    88860
gcatagaggc cattttaaac agcaaaattc ccaacaaaaa gcacaaaact caaaaaatgt    88920
gccactaaat ttaccatgaa aaggacactt gtttacagtt tgagagctaa aacaagaagg    88980
tggcgtgtca cttcgtttga cttcagctgg gaacatgcat atcagtcgac tcaaatttt     89040 tgctattctg tgcttatcca cgaatcgata ggaaagcaag tgtggatttg ggggttacaa    89100
ataaaatgta gcaaatgtgt aaacttgcag atgtggaatc tacaagtagt tagaatcaac    89160
tatgttagtc tgatcattaa atcagttttt taaagtacta ttgtaacacc ttataacctg    89220
ccccattcac tgagtgttgt agtttatagt ttcattgggc attttcagta gttttatctg    89280
aagtcacatt tcaaattttg taattgaagc tccaaagtat gctaccggaa acacgagctg    89340
atgctgtgag acaaaatcaa caggtaatcc accatcacaa ctgtgggcta gaatgctcaa    89400
gaaaccttgg aggcccagag agctgagatg aatactgaag aatcataggc aggtttactc    89460
tgtcaagctg cctgtatttt gagggtgtag tcctcaaacc aaaaagacac caatgaaca     89520 aactcagatg gcctcactgg ggaacagaga ttgaaagctg cactggaat gtgtacttaa     89580 aaaaatgaga gcccgttttg gaaaggcaga ctgggcacag aatgtggaga gctatatttg    89640
ctaactgaag aaatttagac tttatcctct acaaaacaaa gctattggtt tttgaaggtt    89700
gcataaaagc tgcattttag cagcatatat tttggtagag ctgttacctg cctgaaaaca    89760
tcaatgtcat ttcacacaaa tgatacttat cccttggtgt ttgatctaaa tttctacaat    89820
gagaatgtga ttttatagtc tttactgggg aaggaagtag gttttcagg ccgaaattct     89880 tgtgtagcaa aaattaacac ttaagttagc ccttggcaat ctccagttct ataatggtaa    89940
aatggatttc ccagaaagtc actctctatc cctttgaata gacattagaa ataacatgta    90000
ctttaagtgg gatttacaga ggaagggggc ctttaattct ttactagtgt gatgccctgt    90060
aaaaaaataa ctaacattag agttgaggcc tagaaatagc agcactgggt taaagtctgt    90120
tttcaagtgc aagttttct tttattcgt gtgtgtgtgt gtctgtgtgt gtttcacata      90180
gaaggaggaa atgccaattt cagttcttac aaatattaat gactgcaact tataaaaatg    90240
ttacagacta tattcttccc ttttgtaaca gatgagaaga ttttgaaatt tagtctctac    90300
tttttagttt ggtaagacaa tttgaataaa ctgcaataat tgcaaaagaa ttctgaatat    90360
ttgaacattt gacattttct atgtcaaata tacatttctt gtactatata aacattctag    90420
aaaagagaga caggcaggga ggaaagtgct cattaaaaag agcttcaccc tctctgaaaa    90480
gggatttcct ttacagtgct gtgtactaaa gcctgtgttg taaatcagaa agcactgagc    90540
acacatgttg ctgctttggt agcatcagaa gtcgattttc attagcctta taccattcac    90600
tatttctgcc aagcaatctt aaattataaa agaatcttat ttgattttgt gattctcttg    90660
ttttctgctc ataaagaaaa tatcctaaat tgaacaatgg catgctacgt ttttagtttt    90720
taagacagct aatgtgtaaa aagacattta aagtatagtt gtgttaagtt tttgaagttt    90780
acagttgttt caattttgct gctatacttt gttaacatat tttaggaata tttcatttta    90840
gtcacaacta ggatataaac attattttgg tggcgatctc cttgtaatca cgacgtcaac    90900
```

```
caaatttggg aaattttgat tgttagatt tataaatttt acagtaacac aaaagtctaa    90960
tttcctatat attttcaagg cccctatacc tttgtcaaaa taaagtatca atgaaaaatg    91020
aaaaaatcat aaactatgtt caggccaaac tgatactgac tttgttaaaa ggctagatag    91080
aaatctgttt tcctcttctg ttacatctcc tcttctggag accactctgt gtggactgaa    91140
ggtttgagat cctaggacct aggctagaac agattaggag attgtgctgt atgttaagtg    91200
gcagatacca tggaattcta agcctgttac gaaggaggag aagaagaggc acaatgaccc    91260
tgacacagcc cctgggttga ccacagcaga tatctcactt gagcaagtag atatcatctc    91320
aattgcttgc tgattatctc taacttgtca gtaacttact ttgataacct agatttagga    91380
gtctgacagc atgcagtgta tgcctcataa taatctgctg tttatgaaag tcataacatt    91440
gtatgtttag cataatggtg aagagcctgc catctggaat ggtctactta tttgggatcc    91500
acatacagta agctctcact taacatcatc agtaggttct tggaaactgt gaccttaagc    91560
aaaacaacct ctaatgaaac caattttacc acaggctaat tgatataaac aagagttaag    91620
ttcctgtggc atatttctgg tcacaaaaac atcactaaac ttctaaataa agacccaaaa    91680
cacttataat attaaccact gaaataaatg tgagctatat atatacattt aagaataata    91740
aaaacaaaaa ataattattt acccaatttt tggtgaacca gtgagtgata gtgatcatag    91800
tgatggtgga tgaaatcaag gaataaatat ttgcaaagtg aaaattgtaa gaagcacccc    91860
ctgtcaccac atagctcaga aataataatt agggcaggct tgctgagcat ttttaaactg    91920
cactgtttat tgtcatgcat ttgaatgatt atcgcagact ttatgaattt tcattttata    91980
ttaatttgta ggccaggcac agtggctcac gtctgtaatc ccgcacttt gggaggccaa    92040 ggcaggcggg tcactggagg tcaggagttc aacaccagcc tgaccaacat ggggaatccc    92100
catctctact aaaaatacaa aaattagcca ggtgtggtgg tacacacctg taatcccagc    92160
tatttgggag gctgaggcag gagaattgct tgaacctggg aggtggaggt tgcagtaagc    92220
cgagattgtg cccctgcact ccggcctggt gacagagcta gactctgtct caaaaaacaa    92280
taataataat ttgtattcat tcattttcca atgtgttcat tccagttcag ggtccagggg    92340
gcctgcagct tatactcata gctcagagca actgacccta tagacaggac gccacccccat    92400 tgtagggtgc actcaaatgc acactcacac tcaaactggg acccttcaga catgccagtt    92460
accgtatcac acacagcttc gggatgtggg aggaaagcga agtatctgga gaaaaactac    92520
acagacatgg gaagaacgag ccaactctac acagacagtg gccctggaca gagctgggca    92580
ggcatcagtt tttttttctttt tttttgtggg gggtgagggt ggggcatgga gtctcactct    92640
gtcacccagg ctggattgca gtgcagtggt gtgatctcag ctcactacaa cctccacctc    92700
ccgggttcaa gagtttctcc tgcctcagcc tcccaagtag ctgggattac aggcgcccgc    92760
caccacacct ggctaatttt tgtatttta gtagagacaa ggtttcacca tgttggccaa    92820
gctggtctgg aactcctgac ctcaggtgat ccacccgcct tggcctccca aagtgatggg    92880
attacaggcg tgagctaccg cgcccagtca gcatcatttt ttttttctca tcaacgttaa    92940
aacaatgttg aacaaaacat tattcaaaga cctgccgtat ggctattttc tagttgtgtg    93000
actttctttg ggaaagttag caacccttc tgagcttaaa tgtcctcatt cataaaatgg    93060
ggctagtaat aatgcataag gttttgtaa gaattagaat taataaagta cttagaccat    93120
aataactaat tagtattagt tgttgtcttt gctattattt tgatgtggtg gttgtttggt    93180
ttcacctgtg tactatcagg acatgctgaa ataaatttta agaattggct ttataatatt    93240
agaaaagcaa acttttgtac gatatgggta tgaaaaattg ttgggagtct acttttctc    93300
```

```
tcttacctaa tttgtcttag tcttttttaaa gcttagattt tccaaatgag ccatagcaaa    93360
atataatgtt taaaaatgtt taaattctaa gcactatgtc atagttaaat aacttaaagg    93420
tgctacatct tatacagtcc aaaaggaaca taattagtaa aattctacaa tttagaaaaa    93480
aaaatagctg acagtgactg atttataaaa gtaaaatatc ttttgttaat actaatattc    93540
tttttataaa ttaattgatg acaaaaaatt gagtgaatga gatttgcagt tcatttatct    93600
atgatgctgg tttatttaat ctctataatt tgctgtattt gaaagagcat agtgatagag    93660
gtcatgataa aatctaggcc cagtgccaca actaaatccc tgtaggaact ctcaaggttt    93720
tgatttcatc tctgaatggg aataacacct tccaagaata ttatgaagat taaaaagtta    93780
cgtatcataa atacacacag agtaacaata ctgggaatat tgcaacttgt aagaaagagg    93840
aagcatatgg catattctga tggttaggga tatggactct gtagctggga tgcctgaaag    93900
agaactctga ctccactaat ggctagttat atgaaattgt gcagataatt taacttctct    93960
gagtttgcat ttttctttgt ctatataatg gggataataa tagtacctac ctcacacata    94020
gtgttaattt ctattagtgg ttctcattaa gatagtattg ttgttcatcc ctggttgtta    94080
gccatcatgt atctgagtta gagagtcatt gatttagaa agtcccgagg agactatcag    94140
gtcaagcaac ctgcctcctg ctagacaatt agctttatcc atgagttacc aaagagggag    94200
ccgaaaccca gggaagctga aagagctgtt gattgtcacc ctgtgagttg gtgatagaaa    94260
gatatctgga atcccagtag ttgcccattt cctagttctg ggctctgcat tgcactagaa    94320
tactgtgcca ttctaaatat gaaaaggcag tatgaccatt gtgcttgtca ctttccattc    94380
cctagatgct atcttatatt tgtccttatg aaatttaacc tgtgactttc agatcactta    94440
gaaccttggt tggacagtgt tttctagtgt tatttagtat attttttttgt catcttctgt    94500 tgtctttggg ttcccctaaa agagctatac tctgggtgcc aggaaacttc acacatgact    94560
gtcttctctt cctcgacttc cctctctact tacctttcca gctcgtagca aatcagaaga    94620
cttctctgac acctctctat gtctaaaggt cctttgatat tctcacatgg cggcatgaat    94680
cacagtgtat tttaactggc cttttccttg tatgtctcct acaatgagct gttgaagctt    94740
catgaaaaca caatctgttt tactcagggc agttataatt ccaattacaa agcacatttc    94800
ctggctcctg gctaggaact cgatcatttt tcgatgcttc cttgctcagg actttctgat    94860
tccttcttaa aacattttgg ggcatctcct tctcctggtt tttggaaaca tattctcata    94920
ctgctatgaa ggttttact gacatttcca acttctctta aattgattca gcaaatgttt    94980
ttccataata aatgtcattg atatgtcatc aaatatggaga gcaacaacag aatgcattga    95040
gtaaactcct cccctggagg tctgagaatc tagattccag ttctcacaga gccaccacct    95100
tggtgacctt ggacagtaga ccttctaagc ctcagtttcc ttatccctta agtggggata    95160
ttaatagaac ccattctcag agatgttgcc aagattaaaa taaccaagat aattcctgta    95220
gatgatttgg catagtgcct gccacgtact aagcaagagt tagcctccgt cattatagta    95280
tgatcataaa aaatgaacag actaaacgaa gtaaccagaa ggaaagaaat tttaattctt    95340
aaaatgtaat agtttcttgg tttttttttt tctgtgaaac acctgcatgg caccttttttg    95400 ttattcatac tgtttttgact gtggctgtcg tagattcttg ttgaaagtct gagagactga    95460
gacttgtcat tttgaacatg gcatcagtgg aacagcttat gattcaataa ttgcatcatc    95520
ctggacaagc accagtagaa gtgagtcagg acatgtgata aaaagacatt cattttgccc    95580 ctcctcccctc tctgtatttt ctttgctata aaattattga tgttaagccc atagtactaa    95640
```

```
tatttcagtt caattcataa taaaatttga gggcatttga atatattatc tgttgtaaat    95700
tataatttta tatttgacca cagagtattt gaagtgggtc ttttctttcc ccaaaattct    95760
attttaataa ctaaaaaata ttcttaggag aagtattatt taagaacagg tttatattaa    95820
ataacatcat ttcactttca actttctggt ggtcaaaaaa tatgctaata ctaattagga    95880
tatgatacac atgttctgtt agaacagttt tggcagttag aagacttctc ttcttgtgtt    95940
tgaaagggat gttacttggg gtagttatga gccatgtatc cagatgtcct gaaaggacca    96000
gtggtagatg tatttctatt tttgtctttt cttttttctt tctggcattc tagttgctga    96060
gtgactgact tttgttttca gctcttctca caatcaccat tgttctaata actttgctta    96120
aatagaatgt ctccttttgc tataagccat ggggccattt accgttaatt ttttaaagta    96180
ctgaaatgag aacctcataa attaaagaac actcctgatt ctgagttagc agatcctact    96240
aagcctttg cagatggaaa tttcctttaa attggtttgt tttcctttaa cattccatta    96300
tcctattgtt cattctttgg agctgtgatt tgtttaatat atttcaggct tcttaataaa    96360
tcaagtcatg taagttatta tttggatcat ttcgaaacta caacagctta tcaaacctct    96420
gaaagaagaa ttttgtgttt gcccacagac tgaagaactg attcagtttt attggctgag    96480
ctaccttcat tattcatatt taattcctgg tactgagggt gggaggaggg agaggagcag    96540
aaaagataca actattgggt actgggccta atatctgggt gatgaaataa tatgtacaac    96600
aagcccccgt gacatgtgtt tacctatta acgaaccctc acatgtatcc ccaagcctaa    96660
aagtttaaaa atatatattt ggtaaatcaa ttgatgtgtt ttaaaaaata tcgcctttg    96720
gccgggtgtg gtggcccatg tctgtaaccc cagcactttg ggaggccaag ccgggcggat    96780
cacgaggtca ggagttcaag accagcctgg ccaacatggt gaaaccctgt ctctactaaa    96840
aatacaaaaa atagctgggc gtggtggcgc gcacctgtaa tcccagctac tcgggaggct    96900
gaggcagggg aatctcttca acccaggagg cggaggttgc agtgagccaa gattgtgcca    96960
ttggactcca gcctgggcga cagagcgaga ctctgtctca aaaaaaaaaa aaaaaaaaa    97020
aaatcatctt taagagata actaacccct ccccagaagg cagggccaaa gtctaaggtt    97080
cttccaggtc ctttgtattc cctataaatt ttagagtcag cctgtcaatt tctatacaca    97140
cacaaaaaaa gcctgctggg attatgattg gtattgcatt gaaattaaat caatttgggt    97200
ataagagact tcaatttggg gattgagtct atattgagtc ttccaatcca ggaacactgt    97260
atatctctcc atttagtcag atatttagtt tatttcaaca atatttcag atctttagtt    97320
cctttcagca atattttctc attttttcctg taaagctctt gcacatcttt tgtcccatat    97380
ctattgtgta tatgtgtttt gctagttatt aaattatatt aatataaatt ttatttttcca    97440
attgtttgtc gcatatatag aatgttttaa aaatattgtg tcctgtgacc atgctaaatt    97500
aactaattct agtcattatg tcttcattat ctttctcttg aattttcatt gtcttcccct    97560
tctgggactc cattcatatg taaggccatt tgatactgtc tctcaggtcc atgaagttct    97620
gttaattttt cttcattctt cttttttctct gtgttcttca actgaatgaa tgccattaat    97680
aatttggtat gtaatggctc acttaaactt ccttttgttt ttaagatatt tctactctca    97740
gctgtgtctg gaatcctta gtccggagcc ccaccaaccc tcagcctaga aggaaggag    97800
agaaggatag ggtgaaagga aggggagagc ttctagcttc aggacagaga tcagaacaaa    97860
caacagagca gtcatcttgg ataaggaaac ttccctcaaa cctattactt atatcctcag    97920
aaataagaaa aataatgcat ttatcaaatt aaaggatttt gaaaagggga acattcagag    97980
aataaaacta aactcttgaa agttaaaagg atgataacat aaatgaaaag ctcagttgaa    98040
```

```
ggattgaaag ataaaagtaa gaaaatatcc cagaaataag agcaaaaaga cagcaatgta   98100
aaataggga gaagataaga gaattagaga accagcttag gagttctaga aagagaaaat   98160
gtagacaaca aaaggtaaga aatcatcaaa gactggagta ggggaggtca tgctatctgt   98220
ttctttttct atttttatt ttgagttaca ttttttttta ctgtgaaaca agcatatgta   98280
catgagaatg aacaaaacaa atatgcagtc atgtattgct taacaacaga gataggttct   98340
gagaaatgca tcattaggcg atgtcatcat tgtgcagaca tcatagagtg aacttacaca   98400
aatctgaatg gtatgtccta cagtacacct ggaccatatg gtatagctgt tgcttccagg   98460
ccacaaactt acagcatgtt actgtactga acactgcagg cacctctaat acatcggtaa   98520
gtatttatgt atctaaacat agaaaaggta caataaaaat acaatataaa gaggaaaaa    98580
aatagtacac ctgtataggt gcttactgtg aatagggctt ccaggattgg aagttgctgt   98640
gagtcattga gtagtgagtg aatgtgaagg cctaggacat ttattatatg aagtctactg   98700
tagtgtaaac tctgtagact taggctacac taaatttata gaaaaatttt cttcaataat   98760
aaattaacct tagcctactg taactttttt actttgtaaa cttttaattt ttttaacatt   98820
ttgactcctt tttagtaaca cttagcttaa aacacacaca ttgtacagct gtaaagaaaa   98880
ttttatgtcc ttcttctgta agctttttc cattttaag atgtttttat ttttaaaact    98940
gttactaaaa actaatacac aaacacacac attaacctag gcctatacaa agtcagtgtc   99000
atcagtgttc aaccttcaca tgttatccca ctggaaggcc ttcagggca ataacaaaca    99060
cagagctgtc gttttctgtg ataacagtgc ctttttctga tatacctact gaaagacctg   99120
gctgagagtg tttgacagtt aacaaaaaaa aaaaaggaca agaagtacac tctaaaataa   99180
tgaaaaagt ataatacagt aaatacataa accaccaaca tagtcattta ttatcattat    99240
cgagtattat gtactgtaca cagttgtatt tgctgtactt ttctataact ggtagcacgg   99300
taggtttgtt tataccagca tcaccacaaa cataagcatg gtgttgtatt acaatgcaca   99360
gctgcagcta agtgatagga cttttttcagc tccattataa ttttatggga ccatcactat   99420
aaatgctgtc catcattgac tgaaatttat gtcgtgcatg accatacata caatttaatg   99480
aaaaataata ataataaagc tagcagtgtg taattaccaa ccagggcaag aaatagaata   99540
ttgccaatac cttggaggcc tccagtatga ccatataagt ttacaaatcc tattttgttc   99600
ctcctcccca gaggtaacca ctgccctgac aaatgtgatc gttgttttct tgttttttctt   99660
actacctata taaacatcct taaacaatat aactcagttt gtatattttg aattccatgt   99720
taatagaata tcatatgtat atgaattta tgtgaataga atattatata tgtcattttg    99780
catcttgctt ttttcattca acattgtagg attcattcat gttgtagtgt acagctgtcg   99840
tttattcatt gctgtataga attatatcct cagagataag atatatggat gtttataaat   99900
cattccacta ttatgaacat ttgactagtt tgtagttttt atttaaccaa aaaaatgctg   99960
ctgccaacat tcttacacat tttactgtat atgcacatta atttatttac aagtataaat  100020
ttcttttga atacatatct attgatggag ttgctacatc ataggacatt cttgtctttg   100080
actttactgg ataataccaa actgtcttcc aaaatgatta catccttaaa ctcaggacac  100140
atcttattgt caaatgttta attttgtca gtctgatggg tatgtaagtt attttattgt    100200
cgttttaatt tgcatttccc tgattactaa ttaagctgag taacttttca tatgtttatt  100260
ggccatttgg agttcctgta ttgtaaagta taagttttt tgtccatttt tctagttttc   100320
tgtccttta gttgaaatcc aaatttgcct aaatctgtta ttctctgagc acaagtaact  100380
```

```
tgggatgctt tcctttagat ttagcctaat tctttatcat tttgtcagct tgatggtgct   100440
tttaaggaga tatatatgtg tgtgtgcgca cacatgtgcg tgtgtgtata tatatatatg   100500
tatatgtatg tatgtatttt ttgagacagg gtctcactct gtcacccagg ctggagtgca   100560
gcggcacagt cttggctcac tgcagcctcc acctcctggg ttcaagcttt tccctgtctc   100620
agcaacccga gtagctagga ttacaggtat gccaccatac ccgctaattt ttgtatttaa   100680
tagaaacagg gtttcgccat gttgacaggc tggacttgaa ctcctcactt gaactcctca   100740
cgtcaagtga tctgcctgct ttagcctccc aaagtgctgg gattacaggc atgagctacc   100800
gcgcctggcc tggatatttt ttaaaaatat ttttttatcta gcactttggt ttttggcagg   100860
caggttggca ctcatagtct gacctaccat ttctataaaa agaaacctgt aaatgttctt   100920
aaacagactt tgaaccagtc ttcctgattt tgaacccct cctttacccc cagttttga    100980
gcctttcaga attttttttc ataataatta ggttgcttct tagctttccc cactggtgac   101040
ttaacagatc ttaggaagcc aacaatcctt gtccatctgc tttctgtctt gtgaactgtt   101100
gctggtattg tctcttctct ttattcttag aggtgtatgc ttttaaaaac atatactggg   101160
tttgagaggg agctgaaata aaagcatgtg ttaaatatac catctttaac cagaactaca   101220
tttgactggt cattttatt tcaagctcac atacacttca aacagagata tggctaaagg    101280
aattatcatg tgaacaacag ccagggctct gaacatcaca gattatatca tcatacttga   101340
aatatttgaa atttttgattc aaaatgagag ctttatagct atgtcctcaa tggactaagt   101400
gtttaagtac ttaacatcca aaacattctt actaatcaag agaagacaaa caccccaaca   101460
gagaaatagg caaattttat caatagccag ttcaccagat ttgttttctg ttagaagcga   101520
atatggggaa atacatgtgt ccatgttttg cctactttc ctggagcagg taaggagagg    101580
cagtttaagg atccatgtga taaaccctaa agttgtccat cggctttcca gtcccttcta   101640
ggaatttaac ttagggaaat aatcagacat ttgcaaaggt gtgtacagtg gtatttataa   101700
tagtgaaaaa ccaaagaatg accaataacg ggagaatgga agttacagcc aaatacttta   101760
caactactaa agaatcatgt aaaatatcta ttgacatagg agttttatca aatgtgaag    101820
tatacagatg aatagtacca cacataaaaa gcaaggtgca aattagccat ttatattgtt   101880
atccccaaaa taaatagatg cagttttttt aaaagatgca ggctatatat ggaagtgttt   101940
gctggttttc tgtcaaaaga atggcgactt tattttctaa ttttaaacttt ttgctgtttt   102000
ctaaattgtc taaatagtta tagtttttat aatgtaaaag tatcttccaa tttagcttca   102060
tttgacaaat tacctttca ttctatctag ctatgtaatt ctaaatgaat ttacagcagt    102120
aatcttagag cagatgaatt tacaacaata atcttagagt agactacgga ttagatgtaa   102180
aaacatgagt tgggctttat ggttacagag agttttcctc agtgtgggga tcatagctgt   102240
attgagttta ttcagttttc ctttcccaca tgaatgaaaa atggggccag cctacaactg   102300
gaagggcctc ggcatgtacc actgtactgt gtatgatgtg atttcttgat gctagtaggg   102360
agagaatcaa attgcctcct attcaaacca agacccacaa atagcgtcaa ccagtcattt   102420
cagctactcc ctgcagtgtc aagaaggtgt gaacccctca tgttctctat tgcatacct    102480
tgtctaattc agtgttcttt cttcttttca ggttttggct ttatgctaca tttcagaaat   102540
cataataacc ttttctggta ttattttatt cttttcgca ctgtgagaaa aattaaactt    102600
tcaagtggat gcttcttata aactattat accctttgc tcccttttgg gaggcaggga    102660
cagggacaga gttcctcctc aggctaacta agaaaactta ctgcttccaa tgtaatttaa   102720
aagatctccc tctttctatt gctctctgta ctcttaattc ttttttttttt tttcacagc   102780
```

```
agagacaagt gaacatttat ttttatgcct ttcttcctat gtgtatttca agtctttatc 102840
aaaacaaggc cccaggactc tccagattca attatgtcct tgggcttggt cgactgctgt 102900
aggagtctca gggagccttc tacaaatgct agagtgactc atttaccaac attaaaccct 102960
aggatacatg caacaaagca ggactccttc ctccatggaa tgtgccgatt tcagatgaca 103020
cagcacccaa tgtagaaaac gctggaattt ttccttggaa ctagactgtg atgagaggtg 103080
cttgacatga acataagcta ctgtcttttc tttttttttg agacagagtt tcgcttgttg 103140
cccaggctgg agtgcaatgg cgtgatctca gctcactgca acttccacct cccaggttca 103200
agcgattctc ctgcctcagc ctcctgagta gctgggatta caggcacgtg ccaccatgcc 103260
cggctaattt ttgtattttt agtagagatg gcatttctcc atgttggtca ggctggtctc 103320
gaactcccaa cctcaggtga tctgcctgcc tcagcctccc aaagtgttgg gattacaggc 103380
atgagccacc acgaccggcc agctactgtc ttttctttga ccctcctttt ccagttttg 103440 aagataaagc aggaaataat cttctctgaa gatacttgat aaaaattccc aaaacaacaa 103500
aacgcatgct tccacttcac tgataaaaaa tttaccgcag tttgtcacct aagagtatga 103560
caacagcaat aaaaagtaat ttcaaaaagt taagatttct tcagcaaaat agatgattca 103620
catcttcaag tccttttga aatcagttat taatattatt cttteccat ttccatctga 103680 atgactgcag caatagtttt ttgtttgttt gtttgtttgt ttgtttgttt tttgagatgg 103740
agtctcgctc tgtcgcccag ctggagtgca ctggcgcaat cttggctcac tgcagtctct 103800
gcctcctggg ttcaagcgat tttcctgcct tagcctctcg agtagctggg actacaggca 103860
cgtgccacca cacccagctc attttgtat ttttagtaga cagggtttt caccatgttg 103920 gccaggatgg tctcaatctc ctgacctcat ggtctgcccg ccttggcctc ccaaagtgct 103980
gggattacag gcgtgagcca ccgcgcccgg ccagcaatac agttttagt tactcgacat 104040 ctttaagcct ataactctta ggctatgcat agcccatgt cctaatcagg cattcactga 104100
tcccagcagg tctccatcta tttgtaccag cctcctctttt cctcccaatc tcaaggttac 104160
tcttaaatac tagtaaatgc aaaaagaact tgtaaagtgg caaggcatgg cctatcaaaa 104220
gtcagcccaa gggcagttttt cagccctgcc tcacctgggt ctagttcagc tgacggatga 104280
gctgattgat gcgttcaccc cgatagccag gtgtgcccat ctccttgagg aagcccactc 104340 tattttggt agcatgatgg gccactgaga ggtggaaagg gcgcaagaac catgagatct 104400
cctggaaatg cttccctggg aaggcaattt catgaatgag gtcttccaag caaatgaagc 104460
caaacttccc caggtgctcc tcaatcactg tgttgtctgt cagagggatg gtcttattct 104520
tgaccttggc ttgtccacgt ttcaaaatga gttctcggac agacttcaga tttggaaatc 104580
cccaggtcac ataaggttcc actatatgca gcattttag attctagggg gtaacttta 104640 caaagatacc actaaaaatt ttctttaggc gaagtcttgc agtggttctc tgcacccgta 104700
aactcacgcc atcaatcctt tcgatgcgta caacaaaggc caaggaatgt ttatctggca 104760
attccaaggc atgaggtttc acttctagtc gtctgagacg caccttgtca cgtttctgcc 104820
gccaggaatc atgtaggaat gattccagtc gcttaaacct gagccctttt cctttcttct 104880
gtcttgctac tgccatcttt ctagtggtgc agctactcaa ttctttttt aattataatt 104940 tttattttaa gttccagggt acatgtgcag gatgtgcagg ttacataggt aaacatgtgg 105000
ccatggtggt ttgctgtacc tatcaactca tcaggtatta agcccggcat gcgttagcta 105060
tttttcctaa tgctgtcccg cccccccacc caacgggccc cagttacact cttaatcctt 105120
```

```
atagctcaga tgttatgatc cacagtgtgg ttcttacaga agttatgga  ttaaaaaaaa   105180
aaaaaaacac tcaaagtgcc cgaactttct taaaataatc ctggtacagc taaactcatg   105240
cactgactgt ccacctaata tttaacagtc tgtgttgtga tatattgttt taatgttctg   105300
aatgcttgtc agctttcagt attgaagatg tgaatcattt atcagcaatg acacatttag   105360
tctaaggttg tcagctattt atgctacaaa ttaatgactt gtccttaaaa tatcaatttt   105420
gtgattcatg ttttggcagg tggttagatg ttttgtgttc taattttaaa ctatggataa   105480
aggttttgtc ataatcattg ttttattggt tccttttctc ccctgcccac tccccaaaaa   105540
accctgcaat tctttttttgt taaacttttta ttttaggttc agaggtacat gtgcaggttt   105600
gttatatagg caaattttgt gccacagggg tttgctgtac agattatttc atcacccagg   105660
aaataaacac agtacttgat ggataggttt ttagtcttca ttctcttccc accctcaagt   105720
aggccccagt gtctgtcctt cccttctttg tgtccctgtg tactcaatgt ttagttccta   105780
gttataactg agaagaacat gtggtatttg gttttctatt cctgtgttag tttgcttagg   105840
ataatggctg ccagctccat ccatgttgcc gcaaaggaca tgatttcatt ctttttatcg   105900
ctgtgtagaa ttccatggtg tatatgtacc acattttctt tatgcagtct tctgttgatg   105960
ggcttttagg ttgattctat gtctttgcta ttgtgagtag tactgcagtg aacatacaca   106020
tgcatgcgtc tttatggtag aatcatttat attcctctgg gtatataccc agtgatggga   106080
ttgctgggtc gaatggtagt tctgttttaa gttcttgag  aaatcatcaa actgctttcc   106140
acaatggctg gattaattta cacttccacc aggagtgtat aagcatttcc ctttctctgc   106200
aacctcacca ggatctatta ttttctgact ttttaataat agctgttctg actggtgtga   106260
gatggtatcc cagcaccatt tattgaatag ggagtccttt ccccattact tgttttttgtt  106320
gactttgttg aagattggat ggttttaagt gtgtggtctt atttctgggc tctattctgt   106380
tgcattggtc tatgtgtctg ttttgtacca ataccatgct gttttggtta ctttagcctt   106440
gtagtagttt gaagtcgggt aatacggtgc ctccagcttt gttcttttgg cttaggattg   106500
cttttggctat ttgtgcccctt ttttgattct atatgaattt taaaatagtt ttttttctaat  106560
tctgtgatga atgtcattgg tatttttgaga gcaaatagcac tgaacccgct aattgctttg   106620
ggcagtatgg cgattttaac aatatcgatt cttttctatcc cctgcaattc tttgttgttg   106680
tatttaacta ttttttacttg tgaagttttt tcagggatga ttttgttgaa agtgacaact   106740
ctaaaaatta tgttggtaat taaaatttta agtaatgact tttattttca gagattccac   106800
ttctcttaga ctttggagct gttaacagca gtgtccaatc tgcagtggta ctcagcagtt   106860
tctgttttcct gcatgcagaa ctgcttatat gaaaacacag ttttaaaaat gctttcttat   106920
ggctgacatt cacattctta ttccttttga ttcttttcaa gagggatttg gtttgttaaa   106980
attaatttt gcaatacttt tatgaagata caaactctga caaagctttt aaaacaagtt   107040
tgagagaata cagtattgat ttcacttgta aatctgacga ttattttaga aaaaggaaa   107100
atattattta ctattatttt gcttataaat gtttatcaat tttaaagctt ccacattgca   107160
catctcccac tacaacagta gctaccattt attctttctc aaaaaaagtg ctaagtgtgc   107220
ccttgaaatt tttacattgt gcagaatatc cctaaaattt taaaacaaaa attacatcat   107280
cacttgcttt aaatgtttct tctttatttta acatacagtt tctaaaatgt tagcaaatag   107340
cattttagaa gagacacgtt acttttctaa tgaatgttct aaaatgaacc acagtaacct   107400
atacttactt agactgtgaa aaacaaaact tatattctat tgttaaattt tcaaagtgaa   107460
aactacacga tagtttactt ggcacatcac tctgttattg tgaattgaca aatgtatatg   107520
```

```
tagacaaata tgtgaaaatc agagtacata tacattatat gcagcaccac aatacatttt    107580
ttagtatgtt ttgactgata tttaattata taatttacca agaggatctc accagaatgt    107640
agaaaagtat tgaattttag aacaattcac atatttaaaa aaaatgtagt cagccctttt    107700
atctgtatct ggagaatgca gggtaaagga ataaacatg agtattggta tttaaaaaaa    107760
ggtgttaatt tcttacctat gatacctgtt actttgggta tcatttaacc tttatttctg    107820
tgaaatagag gagttctaac atcctctaat tattataata ttgttctaat ttaatctatc    107880
ttaatctgtg atacagtttg aaaaccaagc ttttactatt ggcatgtgca aaaaaataaa    107940
gcagcagtag acttggaatc ttgaatgcaa atttagattt tgcctcttaa taaatgtata    108000
atatagtgtt ctgggaccaa ttctctaaca tttctgagtc ctagtttctg catctgtcaa    108060
atgggattag agatacctac tttcaggatg tgatatggtt tggctctgtg tccccaccca    108120
aatcttatct tgaattgtaa tccccatata ttgagggagg gacctggtgt gaggtgtttg    108180
gatcatggaa gtgatttcct ccatgctgtt ctcgtgatag tgtgggagat cgcaaaacat    108240
ctgatggttt aaatatggca gtttcccctg tgctttctct ctctcctgcc accatgtaag    108300
actttccttg cttcctcttt gccttctgcc atgattgtat gtttcttgag gcctccccag    108360
ctatgcagaa ctatgagtaa attaaacctc ccttataaat tacccagtct cagatattct    108420
ttatagtagt gtaaaaactg actaatacag agaattggta ctgcagggt tgggtactgc    108480 tataaagata atctgaaaat gcggaagtga ctttggaact gggtaacagg cagtggttag    108540
aacagtttgg agggctcaga agaaaactgg aagatatagg aaagtttgga acgtcctaga    108600
gacttgtttt gaatactttt gaccaaaatg ctgatagtga cgtggacaat gaagtccagg    108660
ctgaaatggt cccagagatg aggaacttat tgggaactgg agcaaaggtt atttttgcta    108720
tgctttagca aaaagactgg cagcatttta cccctgccct agagaactga tgaactttga    108780
gatgatttag ggtatttggc agaagaaaat ttctaagcag caaagcatcc tagtggtgac    108840
ttggctgatt ctgaaagcgt tcagtcatgt gcattcacga agatatggtc tgaaattgga    108900
acttaggttt agaagtgaag cagaacataa aggtttggaa aatttgcagc ctgaccatgt    108960
agtagaaaag aaaaccccat tttctgggga ggaattcaag ccagctgcag aaatctgaat    109020
aagtaacaag gagtaataag taataataag taaaaagtaa taagtaataa gtaacaagga    109080
gccaaatgtt aataaccaag acaatggaga aaatgtctcc agggcatggc agagatcttc    109140
ggggcagccc ctcccatcac aggcctgaga actaggaggg aaaaatggtt tcctgctcag    109200
ggccttgctg ctctgtacag cctcacgaca tggtgccctg catccctgat gctccagctc    109260
cagctgtggc tgtaaggggc caagttacag ctcgcaccat tgcttcagag ggtgcaagcc    109320
ccaagctttg gcagctttca cgtggtgttg ggcctgcagg tgcgcagaag acaagagttg    109380
aggtttggga acctgtgcct atatttaaga ggatgtatag aaacgcctgg atgtccaggc    109440
agaagtctgc catggaggca gagccttcat ggagaacctc tgctagggca atgcggaagg    109500
gaaatatggg gttggatccc tcatacagag tccccactgg ggcactacct agtggagctg    109560
tgagaagagg gcctctgtcc tccaggcccc agaaaggtag attcaccgac agtttgcagt    109620
atacgtctgg aaaagccaca gaatgccagc ctgtgaaagc cacaggggta ccctgctgag    109680
ccacaggggc ggagctgccc aagggtatga agcccaccc cttacttcag tgtgccctga    109740
atgtgagaca tggagtcaaa ggagattttg gagcttttag atttaagggc tgcccagctg    109800
ggtttcagat ttcatggggc ctgtggccct tggtttgacc agtttctccc atttggaaca    109860
```

```
ggaacattta cccaatgcct gttccctcat tgtatcttgg aagtaactaa cttgcttttg   109920
attttatagg ctcatacgtg gaagggactt gccatgtctc agatgagact ttggtcttgg   109980
acttttgagt taatgctgta ataagacttt gggggactgt tgtgaaggca taattggttt   110040
taaaatgtaa aaagacatgg gatttgagag ggagcaagtg caaaataata tggtttggct   110100
ctgtgtcccc acccaaatct aatcttgaat tgtaacccgc atgttttggg ggagggacct   110160
ggtgggaggc agttggatca tggggggggtt ttttccatgc tgttcttgtg atagggagtt   110220
ctcaggagag ttgatggttt aaatgtggca gtttcccttg tgctctttct ctctcctgct   110280
gccaggtgag acgtgtcttg cttcccctgc cccttccacc atgatcataa gtttcctgag   110340
gcctccccag ccatgcagaa ctgtgagtca attaaacctc ctttccgtat aaattaccca   110400
gtctcagata gtatctttat agcagtgtca gaatggacta atacaggata gtaatgaaga   110460
ttacagaata tgtagatgaa gaagtgctaa gtaaatagca gctattatta tgtagtcaaa   110520
ttgaatgtat acattgtggt acttcagtgt cctttaaatt gaataactag aaatttgttg   110580
gctttctcaa tctgctcaca tcagatgaca tgttaattta tgcctatact tttttctagt   110640
taatagatat aaatctattc actcaacttc tattgacaga actggtagtg tggcaagaca   110700
tctcatttct agttaaggct gtataatatt aagttcattt tacttaaatt aactatggtt   110760
tgggaaatgc ttttcatgtc atcatgtatg cccaatttga tactttagtg ggacagtata   110820
tttcagaaaa aaacaaatgc ttccccaaaa attccagggt tgaatacatt agtcagacat   110880
ataacaatgt acttcagagt tcctctaagg gcaaaaatcg tggtatgaat atacaaaaca   110940
ctcctattta tacttttgta tttttgaaat gtagtcttca tgttaattta gcatttcaat   111000
gaccagcatg acattatctt aataatttgg aatgccaata tgttcattta agacttaata   111060
tagtaagtat ctaaagaaaa aaatggaagt gactgaatgc ttttgtatct cttaattata   111120
atttgtgctc cattgtgata tgaaggatag aaggggcagg atagatagaa aacagaaatt   111180
aactttgatg tttaacctta ccttaagact gtctgttaag tgacccacat aatcttaaaa   111240
aactctgtca agcttaatgg atgctactct gcaggcccct gccaggcaac agtcacaagg   111300
ttatgaggtg catagatttt ggaattaggc agagctgaat tcagatccag gtgttgcctt   111360
ataatgcgac tttgggcaaa taaaaggccc aattttgta ttcttatctg taaaatggac   111420
tcagtaaaaa ttatttgaga taattttattt gtgtactgta cctaggcatg cagcttgaca   111480
cacagaatta caagtcagta gtttccagta tgattattat tgtgaaagag atattttgtt   111540
tcacctactg aaaacttttt tcagtcttaa atttttatc taactggctg tattgcagat   111600
gtctgctata taacttttat ataatttttaa aaactatttc tttcctcctt gatcttctag   111660
gggtaaggtt accaatgttt tcattattta ctaaatatag cagcccccac cccttattca   111720
tggaggatag gttccaaaac ccctagtgta tgcttgaaac cacagaccac agataatccc   111780
aaatcctata tgtatattgt ttttcctata catacatacc tatggttaat gtttaaccta   111840
ctaattagga agagtaaaag agtaaatagta actaataata aaataaaaca attgtaacaa   111900
tattccagca tcactattct tgtgctttag ggccaccatt aagtaaaata agggttactt   111960
gaacacaagc actgtgatac tgtggcagtc caactggtaa cagagatagt gatgcggttt   112020
ggctgtgtcc tcaccagaat ctcaacgtga attgtatctc ccagaattcc tatgtgttgt   112080
gggagggacc caggggggagc taattgaatc acagggtctg gtctttccct tgctattctc   112140
gtgatagtta ataagtctca catgatctga tgggtttatc aggggtttcc ccttttgcct   112200
cttcctcatt tttcttttgc caccaccatg taagaagtac cttttgcctc ccgccatgat   112260
```

```
tctgaggcct ccccagccct gtggaactct aagtccaatt aaacctcttt tgttcccag    112320
ttttgggtgt gtctttatca caagcatgaa atggactaa  tacagtaaat tggtaccagt   112380
agagtgggtg ttgctgaaaa gatacccaaa aatgtggaag cgactttgga actttggagg   112440
actcagaaga gacgggaaa  atgtgggaaa gttaggaacc tcctagagac atgttgaatg   112500
gctttgacca acatgctgat agtgatatga acaataagat ccaggctgag gtggtctcag   112560
atggatatta ggaactttt  gggaactgga gcaaaggtta ctatgttatg ttttagcaaa   112620
aagactggca gcattttgcc tctgccctag agatttgtgg aactttgaac ttgagagaga   112680
tgatttaggg tatctggtgg aagaaatttc taagcagcaa agcactcaaa aggtgacttc   112740
ggtgctgtta aaagcattct gttttaaaag ggaaacagca taaaacttca gaaaatttgc   112800
agcctgacaa tgcagttgaa aagagaaacc cattttttga gaagaaatta aagctggctg   112860
cagatatttg cataagtagc aaggagccta atgttaatcc ccaagaccat ggggaaaatg   112920
tctccatggc catgtcagag accttcacag cagcccttcc catcacaggc ccagagaccc   112980
aggaggaaaa agtggtttcg tgggccaggc ccacggtcct catgctatgt gtaggctagg   113040
gactttgtgc cctgtgtccc agctgctcca gctgtggctg aaaggagcca atatagagct   113100
caggctgtga cttcagaggg tggaggcccc aagccttggc agcttccaca tggtgctgag   113160
cctgtgggta cacagaagtc aagaattgag gtttgggaac ctctgcctag attttagaag   113220
acgtatggaa acacctagat gcccaggcag aagtattact gcagggcagg gctgtcatgg   113280
agaacctttg ctagggcagt gcagaaggga aatgtgggat tggagccctc acacagaatc   113340
cctactgggg cactgcccag tggagctgtg ggaagagagc cgtcatcctc cagaccccag   113400
aatggtagat ccaccaacaa cttgcaccat gtacctggaa aagccacaga cactcaatgc   113460
cagcctgtga aagcagccgg gaggtaggct gcaaagtcac aggggcggag ctgcccaaga   113520
ccatgggaat ccatcttttg catcagcatg acctggatat gagacctgga gtcaaaggag   113580
atcattttgg ggctttaaaa tttgactaac tcactggatt tcagacttgc atgggccccg   113640
taaccccttt gttttggcca atttctccca tttggaacag ctgtatttaa cctgtgcacac  113700
cccctaccc cctgccccc  atccctccgg cccttgtatc tggaagtaac tagcttgctt   113760
ttgatttat aggctcatag gcagaagaga cttactagcc ttgtctcaga tgagactttg   113820
gactgtgac ttctgggtta atactgaaat aagctaagac tttgggggac tattgggaag   113880
gcatgattgg ttttgaaatg tgaggacatg agatttggag gggccagggg tggaatgata   113940
tggtttggct gtgtccccac cctaatctca acttgaattg tatgtcccag aattcccatg   114000
tgttgtggga gggacccggg ggtgggggtg cagtaattga atcatggggg ctggtctttc   114060
ctgtgctatt tcatgatag  tgaataagac tgacgagatc tcatgggttt atcagggggtt  114120
tccaaaactt ttgcctcttc ctcattttc  tcttgccacc accatgtaag aagtacccttt  114180
cacctcctgc catgattctg aggcttcccc agccatgtgg aactgtaagt ccaattaaac   114240
ctcttttctct tcccagtttt aggtatatct ttatcagcag tgtgaaaaca actaatacag   114300
atggctagta aggactaac  cggcaggag  cgtctccagt gtggatatgc tggacaaagg   114360
gatgattcac gttccagggc ataagatttc attactcaga attgcacaga atttaaaact   114420
tattaattat ttctggaatt ttccacttaa tgttttcaaa ctgtggttga ctgcaggtac   114480
ctgaaactgt caaaagtgaa accacagata agtgggagt  cctgtaccta agattattcc   114540
tttaaattgt ttcagtggat atgtaggggac ctgagtgtga agtgagagca gcagcatcaa  114600
```

```
aacctgaggg aaatccagat agcaaaagaa acttgtctag tatactggca tgacagagaa 114660
accaaaaagt tctcaagtta atgtgagaat ctaagaatta aagaattaag cctttgcctt 114720
tgagggaagg aaagggtaa tgtggcttta aatcaggttg agattggttc tgagggttcc 114780
ttttccttcc tttatattga tatgaatata gacacaactg ttctgcattt ccatttgttt 114840
ttataaatgt ctttttagga tttaggaact gctaattatg caatatgaga tatctgttag 114900
tttgaggaac atttgaaaat ttggtcaaat gacacagatc gtcacacagt tttaagacaa 114960
atgttttac ctatttgacc tagtctggca atccctattt gggcaaaaat cttcatttgc 115020
aggtcatgat tggaggcagg cacagaaaaa aaattgccac cttttttgca ttatgtcatc 115080
aagacatcaa acttcagcct acaaagtaga aagtgttatt tctcaagttg aaggcctgga 115140
tatacctcag cttctcagtt ctgacacttt atcatagtgg aaaatgaaga agattgctta 115200
agaacactga tgttggtgtc agaaagacct gggtttgaac cctgacttta ctagttactt 115260
agatcacttt aggcaactca acttttctaa atcttgtttc ttcatctgta aatgctgaaa 115320
atagtaccca cctcttaggt ctgtggagag gattaaatga gataatctat acaaagaaag 115380
agcttgcata atagtgccaa gtaatggtga ggttatacct gtattctgat tataatctca 115440
taaatattta ccatgttagc tgtctcagag ttcttttgca aaacagataa agatagaaag 115500
tataaataag aaaaataagt gaacatatac tgaactttgt acaagatgct ggcgatatgg 115560
agagacccaa gacatgggcc ctacctaaaa gagattattg ataaaacag gatacatata 115620
catcaaaagg taacatagga tcatctgtgc aaagtgctat atggcagtgt tttaggaagt 115680
ctagaagctg tcatggatca ggaataccat ggtggacact tcaggcaggg aaaacagatc 115740
ttagcaaaag ctactcctat cataggtact tgataaatat ttgtagaatc caggatccct 115800
gtagtgataa agaaactaca tggattatgt aggggagtga taagacatat gactggaaaa 115860
ataaaaagac caaattatgg accatactga gcttgtacta taaacagtgg aggagccctt 115920
cagatttta atcatgttga gaaaagagtt ttagcagtgt gtgggggata gaatggaaag 115980
agaagccagt gccagaagga ctacttagta tcaaccattg cagtggttaa agcaagaggt 116040
gagagaaggc atgcattaga atggcagcgg tcagagtgga tgggaaggaa taggtcctga 116100
catagtgtta cagggagtaa taaataggat gtggaagatg ggttagaatt ggcaaaatct 116160
ctgcatgtaa gtctgggtta ctaaatatag tgagagaaat tcaaatctct ctttaagaat 116220
cgaataaaat atttagaaat aagttactgt tgtatttgag gtgaacacaa atggcatttc 116280
aaagatgctc gagataccctt gttggaaaaa gtcaataact gcactattgt ctccaacatg 116340
ttcttgcctt ctctgaagac atcatgttcc taattctgaa ttatgaacca tctattatcc 116400
ttgtatgctc ttatgtgtga ggaaccataa ggtgggaaca aaatccggtc ttcattctag 116460
aaataactat gcgatcaaaa agttttagt ctttcttctt accatactgg ttcttggtat 116520
tctgtttacc attcaatgta ctattattgc ttctgcttaa aactcgcatc ccctaatgca 116580
agcctgagca aacagaactg ataacacaca gcctgagaag ggagtgcttg gggtctcaag 116640
acttattctg ttttttctcca tctttgacac ttggtttgaa gagcaaagaa ggatacagct 116700
gttaggaagt aagttaccca aacacagtga ccaaactgga ttaattcttc caatgagaaa 116760
gaaatacatt atttctgtga gacagattag actttaagta gcatagataa catgattata 116820
ttctctctac aaataaatac acaggaccta agaaaccctt tacagatcca agtgttttcc 116880
tctccacttt tccatcccca aacccatctt gcaagatatg gccagcttat ttggagtaa 116940
ttaaatcaag accttcgttt tacagacagg gaaaccaagc ccagagacac tgagtagtag 117000
```

```
gccactggtg tcttagaggt ctgaaaaatc ctttactgaa cattctcttg atctattaat   117060
gtataggttt tgttgctgta accctctccc caagaggagt gaatataaat gatgcagagt   117120
ttggatgaac tatcttaata agaacctaaa gttgaaacca atgcaaacct ctctcaataa   117180
atgcaaagca aagagaataa tcagtctttc tttggcttgt taaataagat aaaatgtgtt   117240
ctgctaaaac catttaacag aaatattgtg aaaggtttcc cctaaagcat ttttctattt   117300
gatttgaaaa ctattccata gcttattatc aaacaaatca gtaattcttt agctaatgca   117360
gagataaatg ggcagtcaga aaatataatc acctggtgtg tgcagctgag tatttacatt   117420
tttcctaatg aacaaagata agaaaagtgc aggtgacttt aatgtgtaaa aactacctttt  117480 tagtgctagc gctagaggga aaagaaatt actggctcaa gccaatcctg tacttgataa    117540
ctaagccgta tagtccatgg cttggcttca gttctgtttt gaatctcttt ttggacttgt   117600
cttgaatgga ctgtttaggg ctgcttcagt agtgcagttg ttgcattttt aagcatagtt   117660
taggttttaa aatgtttctg gtccctttt tttttctttt tccactttat gttgcttaaa    117720
gctttatggc caggttttct catcctcagc attattgaca tttgaagctg gatacttctt   117780
tgtggtgggg gctgtcctgt gccttgtagg ctggttagca gcatccctcg cctcttctca   117840
cttagatgcc aatagcattt ccccaaccgt gataaccaaa agtgttttca gacactgcca   117900
aatgtctcct agagagcaaa attgctctct gttgagaact actgtgttac ggtgtttgga   117960
caaaaactga caagccaatg ggaatattct attggtagtt gtaaaaaatt aatccagtta   118020
tagcagctgt atttctggaa ttttttttcca tattaacact tgcttttctga ggtgataata  118080 tctttgtttt ttttctccca aatagatttc ttgcattaca ctgaaaaatt gctgattaat   118140
tcacttaaat tgaagactaa gccaatcatg tcatttgggt aatagtttac caactctgcc   118200
cctttctctg tcagggaagc ctctaattta gtaagcgata ctgtatcctt ttgtcaggta   118260
cattaccatt cctattagca ataggggcaat tgagattgag aaagattaaa aggtcaccaa   118320
gctattacat tgtagaatta ggttatgaat tgtagcctat ctggtttaga atctttacct   118380
tactagtctc cataacaaca attcttccag tgtggtccat ggggccctgg gagtctcccc   118440
ttaaagggca gactattttc acagtaacac gtacttttatt tgccatttca ttatgtcagc  118500
atttgcaata atggtacaaa agcaaagatg agtaaaactg ttggcatctt agtatacagt   118560
agttactgta ttcactgtca tgcacttaaa atctttgaag aagcaaaaaa attattaatt   118620
acattaaatt tcaacccctta aatacatgtg gtctttctca tgtcagtgtg acaaaatgag  118680
aaggtgcata atccacttat atcgcatata gcatttgata gttgtctcaa agaaaagtgt   118740
ataagattaa actgtgagtt aacctacttt tttttcatgga gtaccatgag agataaactc  118800
tggttttcag ccttgggtat ttggcgatgt tttcccaaaa atgactgaag taaacttagc   118860
actttaagga aaacaactta aagtatttgt tgccaattga taaaatatag gtttcaagca   118920
aaaatcagaa ttttttgaaga cttgtatctg ccactgtgag cttgacaaat gtgactcttt  118980
tatattacat aatgaactat gtcaacattt gaaagatctg cataactcag tgaaccagta   119040
ttttccagat gactaatgca tgataataca aaatcatgca tgggtaaaag atacattcaa   119100
agtgcaagat agactgacat atttcaatgt aacaatcaaa agttcattga taacagtttt   119160
ggattccaca ttgcaatact aaaaccttta aaaaacgaaa ttgtccaatt ttggtgtagt    119220
aatcagaaaa ggcaatctat aattacctga acttaagttt ctggaggacc attaaccttc   119280
tacaggctca tggggaagac tgtagcactt ctctttccct aagatcctcc agaaaggaag   119340
```

```
aaggtaatcc ttgggggtag ggtagagacc tattgtgtga tgatcaccaa gtatgtaaca    119400
atgctttata taactctaat atatataatc cacacaaacc ccctaaaatg cactaataa    119460 gggaatggac tcaaagaagt taagtcagct agccactgtc acagctatta gagcactgga    119520
actaggattt gaacccagat ttgtctgtat gtaaagctga ttctcttcgt aatagtactg    119580
agacacaaga ggcggctaca aaatattctg gtactccatc ctagaccaga gtttcaaggt    119640
tcgttatcat ttgtagcatg atactggatc ctcacagtgc ttgcctttca ttcaggtgcc    119700
aggaaacgtc tgcctgaatg aatgggtgta atttacctgc acattttaca tgcttctcta    119760
ggtgtgtgat taactcataa tccatccatg acttctccc ataatcctcc ttgtagcaat    119820
tgctttgctt gcaacaaaac taagtagaca tatctagctt tatgcatggt tttctctctc    119880
tgaactctaa cataaactca gcctcaggaa ttattcggtt tctactacat ttgccattct    119940
gattgggaac caccagcatt caggtattca cctggaacaa ggcattttgt tccaagggtt    120000
cctcacttaa aagcaagcac cctagcaata gttcataatg gaacttctta acattctcag    120060
aatgtttggc acagctgtga gtgaacacac attgagcaat caataactat tacagataat    120120 gatgcccta agaccaggat attttagctt tcccattcaa aggggtgaa atatgcactc    120180 ttactatggt atacttttgg ttccttctgc catgtatcct taataaaaga tgtcaattcc    120240
atatggtttt ctcttgagtt ctaaccattt tgttgtaccc tagcccttt aacaatatca    120300 aacttgcaac tgaataccat ttagcattca tccattttt ccaatggtgt tcattatagg    120360
ctatcttact cctcctattt gtatgacaaa aattggcttt tttcaccgat gtctatggta    120420
catctggcag cttccatgt actcagttct tatctgatgt agcccagaac gactgcctga    120480
agggatgcca aaagcctgat tgaggttcca aattttcagc tactgtacta tcaatccatt    120540
tgttcatttt tactttccct tgtcatctgt agcttacagt tgagtggcct gaacatgttt    120600
tgcatacatt gtaatatcta agaatttggg aatacggtcc taggatttag acttaatact    120660
accttccatt tatataatac ttactcataa aatcttcagt gttcctgaaa aagaaaaagg    120720
aacatgtatt gagtgcctgc tagaagcagg aacttgtagt agattttcta tgtgttacct    120780
tattttcaca acacacacac aggtgatatc cttcccagtt tactgatgag gaaactcagg    120840
ggtcaaagta gtagatacct acccaaggta acagaagctg tgaagtggta cagctgggat    120900
ctaaaatatg tcagcttcac cgtagatagg ctccctgatg aaccacctgc cacggcccgt    120960
atgaccgcat ccagggtga tgatgtcatt ttcacagggt tattgagagc taaaactacg    121020
aagtactaca aactattatt taaaatataa atacatacta tatatgcata tgtgtgtata    121080
tataattaat ggggtaaaca ttacagaata ctgtcctaac ctttaaacaa tgcactcgtt    121140
ttctgtaaac taatatacaa acaactgttt ggtccctaaa aatagatgtc aggtgacaga    121200
gactggctga gcaagaatag gagtatcttc agaatagaag ccagaggagt ttttgcttcc    121260
ccaacacatt gtcgcaccat tcactgttcc aggaccttcc tacttctctg gaaaactctg    121320
gcccaaagca gctcctctac attagtcaca gtttccatt aatcagggt ggcctgtgcc    121380 ggacctacag cagagtcatt tcaggttatt ctgttacagg ctttcgacgt gtagtcagtc    121440
cactcgccca atctagcag ggaatgaatg ccttgtaata cggaagcatc tacaaattct    121500
tcttaacagt gttcagagaa caatgtgaaa ccctggggcc ttttcccaga attagggtgg    121560
tgggaatgct gtcctattga ctaagcctgt taggtaagca ggcagttggc aagattcagg    121620
aagcttcatt tgaagataga atttagggcg atcgttgga tttactggct taattactta    121680
aggtaacatt tataaaagaa attgtcattc cattattatt accttttaac ttttattcct    121740
```

```
aaacggaaca ttagcaacaa actacattac ttgataaatg taatttctaa ccagattgat 121800
aactagaaaa aaattttaag ttactttgct ctgtgaatta gtttaaacat atttgtaatt 121860
gagacttact actgttattg gctgaaataa ataaaagcaa gagataataa agaataacag 121920
agacaacgaa cacccaattt aagtttattt ctaagttcca tctttttag agaaaaggca 121980 aattaagaaa agtttagaga gaggtactag tatatttatg aacttgtata gatgataagc 122040
aaaacggact ttaatatgta gaattccaga atcaacaggt tgccagcatc catgtttttg 122100
aagatttgct taagaacaca accaaaaatg gaatgggcag tctctaatta caagcagaag 122160
gctacaaaat catttagct gcataataca gttttggttc taaagtcagc acgtaagagg 122220
aaaattcctt aggaaaatac aacattgaaa accattgtgt catgtaatat gaaatgcaat 122280
aattaatttt tcctccagta atagaaagat cactgtttca ttggtttata aaatatatc 122340 tttatcatta aatgtggcaa aatgttaaga cttggtgaat attggtgaaa agtatatatc 122400
cattgtacaa ttcttttccaa tttttttga gattgaaaat ttttaaaaca acaaattatc 122460
ttttaaacag ctaataatca ctagacctgc actctttgtg gtgagactat gaaaaatgtt 122520
agagacctag taagagaagc agattcacat ttctgtcttc ttcttcaagc caaacagtca 122580
tagagtggag tgggcagaat ggaactcact tttgaaagcc tagtgctttg tccaatctta 122640
ctgcaagcca gacaggaagg ttatagaaaa tgtttctgga tcagtcttct ctgagtcata 122700
tgaaattgtg gtttcagcca agatgacatt aggaattaga gacatgggac aaaaacttta 122760
agattgtaaa aaaattttga ctctagtagg aaacatgggt agaattgtaa tgacacttga 122820 ttgaattta aaagatgcct gtataagatc ttaaaattag gaaaaaaatt atggcctaag 122880
caattaaagg cataggaggc atctttttgg gatgatggaa atatcctctc tcctgattgt 122940
gatagtagtt acatgaatat tcatttaaca aaaaccataa attatagact tagaaaacag 123000
taaatgttac tgtatgtgac accttaataa acgtgattat aaaaataaat cctaagcatc 123060
taaaaaaaaa aaaaaaaga agaagaagtg aaccagaacc acaccattct attttggaga 123120
cacttcaaaa gaaatgacct cattcttaat tttgtttaaa gaagaatata acatgatttg 123180 aatatatttta gctaggatat tttagtgcct gctagcactt gaagccagag ttcactgtga 123240
gcattctgac tatgaagtga gaagctaaga gaactgtatt ttgatattcc tttgacagtt 123300
aaatcataac actgttcttc cccttcttta gccccagcat gagaccagat gtaagctctc 123360
ctccatccag ctcctcaaca gcaacaacag gaccacctcc caaactctgc ctggtgtgct 123420
ctgatgaagc ttcaggatgt cattatggag tcttaacttg tggaagctgt aaagtttct 123480 tcaaagagc agtggaaggt agtgtgtgtt ttgaagagtt tattttcct ctacttggtt 123540 ttcatttctc agggtggatt ttgaaatttc cattatatgc aaagcccatg aaaggctaaa 123600
tatcagttaa gaggggagag gagggtggct cctaggtcct ctaatgggca ggaaagtatt 123660
taaaacaaca atacaaaaag atctagaata aaatagaaaa gtacaagttg atgtctggga 123720
gtttggtcag ggagcataag gtaacactat aagaaagtgc tatcatatga aatgatggtg 123780
ttaagtttgg gcataacata atgttcattg tattagaaac atgggcttta acttccataa 123840
gctaataggt ttcaaagtca ccaactttac tggcctggca aaaatgagtc acagtgagaa 123900
ctgtgacagg aaaaaaaaaa gatattcatt tcatttctta ttcatttttt ttttctatta 123960
agccagggca ctgtgctaag tggtataaat accaataaga cctgatcctt accctctggg 124020
aagtcacact ccactgaagt gaaagatgag ttaacaatga caaggtacag agattataat 124080
```

```
atagatgagg gagagagaaa ctcggcctga ggaggtcagg aaaggtattt tagagaaact  124140
gatttcacta tataaatgtt gtattaacac aaatcttact ttgttatgga ttcagactgc  124200
tgacagggca acagcattat ctccctaaag aatgagaaat tcattccata gcaaatttat  124260
tagaagagag tctaaaatgt cctaatacta ccagtgactc ctctaggaaa aaaattgtca  124320
tataatttag ttatttctaa agcagtttga aagtagcttg gcctaaagct ctgattatat  124380
taatttttta aagaaacaat tattcattca ctgtatgagg attattatta tttgtctcat  124440
gttgtgtttg catatccatg agagttagat gagtcatttt cttttgtttt acttttaat  124500 acattagcaa attataaaat tactcatatt acaccacaaa gattacaagg atggcagctt  124560
tggccagtgt agtagtccca cctattgatt agagtcaaaa gtaaagccca gccctgcttt  124620
gtgcattgct cctaataaag tggatgttac ttaacacata cgcagaagac agaagcgtct  124680
tcgtgtcctc actttactcc tcactttctt aactgcttaa gtatttccac gatataaatg  124740
cagtgataat aataatacgg acagtccctg acttaacgat ttttcaactt ttatgatggt  124800
gggaaagtga tacgcattca gtatggctcc tcgacttaca atggggttgc ctccagataa  124860
acccattgtg aattgaaaat atcttacact tagcactcca ttcttaatac ctgctagaat  124920
tatagattat ccctcaaaat tggcatagta taatatgggt atcagcaagt tgttgcactt  124980
tattcagagc tttacactag gcagggtgg gctttacttt tgactctaat caataggtgg  125040
gactactaca ctagccaaag ctggcatcct tgtggtctct gtggagtaac gtgagtagca  125100
ttataattta catcccccat aacaaatgat ccaagagagt atgtgatcaa tgcagcagaa  125160
ctattgtctt ttattatctg atttcacatg taacatgcca tcacttctgc catattttat  125220
tggccacaca gaccaatctt ggtaaaggac ggaaagggac tgcacaagac catgcattca  125280
aggaggcaga gatcactggg ggccatcttg ggaggctggc taccacaccc accataaata  125340
gaaaaccaga attatttgcc aaaaatagac tttaaccaca aaaatgaata ccatataaac  125400
aaaacaaagt cacaaaattt cagctgactt gaagactcat cttctatta gttagaaagg  125460 gaatttacca agtagtagaa gacacaggaa ctccaaaata agatatctca ttgtcttatc  125520
agaagggttg acaggaaaat gggctgggca ctgtggctca aggaaaatgg gctgtgcact  125580
gtggctcaca cctattatcc cagcaatttg ggaggccaag atgggaggat tgcttgaggc  125640
ctggagtttg agaccagcct gagcaacata acgagacccc gtctctacag gaaaaaaaaa  125700 aaaaaaaaa acgttatcca ggcatcgcac ctgtagtctc agctactcag gaagctaaag  125760
caggagattc aggctgcaaa gagctatgac acaccactgt actccagcct aggcaacgta  125820
gcaagaactt gtctaaaaat aaataaataa atgagtcaag gaatgaatga atggattgac  125880
aggaaatgac tattagttgt acgtggccat gtgttatgaa atagtgaata ctagttaaaa  125940
ctcctcattt tatagataag gaacagatag atagacttgt ccaacttcat gctaataacc  126000 acaagggct atttttaact tatgaaggta cattgcctct gatcctatag ctcagagtct  126060
tagctgtgca caagacatac ctgggataaa gaaatcaaga ttggcgtaat gtgcacatcc  126120
tgacatttca gttggatata aacaaaactt tggaatttt catttttagc agtgggtgat  126180 ttttttttctt tttttcttcc agtaactgta ggacagtgat ttagagattc cttatagggt  126240
ataacttttt tgtattataa ccacttcatc aatagatgta tctgttgatc gtacttttga  126300
tttatagggg atagaattgg gttagtgctt ccatttctg tccaagtaaa gaagctagga  126360
tatttataga gtacaaaaag aaattgaaac agctggtaca gatatttggc attggagagc  126420
agctctgaac aaaggtgaat tatagtctag tggtcaattt tgtggcctat tctttacaaa  126480
```

```
gaattgaacc tgatacagtt aaccatctac cccaaactat tatttgttta aaacacaatc    126540
tattggctgg gcgtggtggc tcatgcctgt aatcccagca catcgggagg ccgaggcggg    126600
tggatcacga ggtcctgaga tcgagacaat cctagccaac atggtgaaac cctgtctcta    126660
ctaaaaatat aaaaattagc caggcgtggt ggcgtgcacc tgtaatccca gctactcggg    126720
agtctgagcc aggagaattg cttgaacctg ggaggcagag gttgcagtga ggtcatgcca    126780
ctacactact acactcccag cctgggcgac agagcgagac tccatctcaa aaaataaaa    126840 ataaaaaaac ataatctatc aaactgtgta aaacacagtt tatcaaaaaa gtagttaccc    126900
ttggtgggta ctggctggaa ttgggcagaa aggggggcctg ttggggtact gttctgtttc   126960
ttgatctgag agctgattac ataaaggttc ttggtttgta aaaatttatt aaatggttca    127020
ctgatttgtg tactttttttt atatgtgaat actgcaataa ggttttttat tgcactgttt    127080
tcagtttgtt gaacagaaaa agggagactc ttttttgttgt ttttgacctc tcgacctcat    127140
aatggcaatg taggcaagaa cattccctca aggcaatacc tgtgggtgtc ttggttatat    127200
tccaccggaa acaaagacag aggctgtcct tataaaatat gtttgaagac ctgtgaaact    127260
ttaatagtgc cttttattcc atataggaca gcacaattac ctatgtgctg aaggaatga    127320 ttgcatcatc gataaaattc gaagaaaaaa ctgcccagca tgccgctatc gaaaatgtct    127380
tcaggctgga atgaacctgg aaggtaatat aaatatctga aagcaattgt ttgtctctgt    127440
agcttataaa aatttatcat tttacttttg aagatacacg taagcagatg taattaatgt    127500
agtcagttca gtatatatat gcttgactag cataatgtta ctgcccaata aaaatgggaa    127560
atttttttca tgaatatgtc atattgtttg tttatccacc agttcttctt acacacactg    127620
aattcagtac agccagacta tatacaaaga aaggaaatta tgtaataatg aaacttacac    127680
aacatgcagc aactttatta ttcttactcc ttttttcagc ctcaaaacta ttccctaggg    127740
ttggaaatgt ttctgtatca gacatattta catgtccatt tttctgtttg cctttaaaa    127800 gcatacccttt tacttggaga tctgtgtttt attacagatc ttcaagcggg gggtggtggg    127860
aaaaaaaaaa cctcaaggaa gaactggatg ggttttgttt tggttttcaa gtaaagaaga    127920
aacctgggcc gggtgcagtg gctcacgcct gtaatcccg aagtttgtga gaatccttct    127980
gtctagtttt tatgtgaaga tattaccttt tccaccgtag gcctcaaagc gctccaaata    128040
tccacttgca gattctataa aatgagtgtt tgaaaaactg ctcaatcaaa agaaacgttc    128100
aactccatga cctgaatgca cacaacagtg agaagtttct gagaaagttt cttggtctcc    128160
ccgcactttg ggagaccaag gcaggcggat cacgaggtca agagatcaag atcatcctgg    128220
ctaacatggt gaaaccctgt ctctgctaaa aacacaaaaa ttagcggagc gtggtggtgt    128280
cacctgtagt cccagctact caggaggctg aggcaggaga tcacttgaa cccgggaggc    128340 agaggttgca gtgagccgag atcacaccac tgtactccag cttggcgaca gagcaagact    128400
ccgtcttgga aaaaaaaaa aaaaagaaa cctgaaacta gttataagtt agagtttcat    128460
atccctgttt atataacaag ttgtataatt aacactgatc tcagcattaa aaaatttcc    128520 tctgaaaaaa gtttggaatt ctgctgtggt tgaaattgca agttctgtga aggtagtggt    128580
gatctcataa cacatatgct tagtatttat tgtgaaatta gcacttttat tcaacaaata    128640
tgcaccaaca aggcagtcac taggtataaa atgaataaaa tagtgcctgt attcaagtag    128700
tttatctgct agttaggttg cagagtcagt cacaaaatag catggcacac catagagggc    128760 ataggccac aggaacaaga ggaaggtcac ctaattctgt cttggaagtc aaggaagaag    128820
```

```
taacattgaa ttttaaatct ataagctgag taggaattag atagatgaaa ataagggca 128880 gagacatgat cagatttgta ttttacaaag actaatctta catggagaga ccaattaagt 128940
gaatatggca gtcctccaga taagagatgg cagtactgag agagaatgga aaccatgtgg 129000
ttccttttat gattatgatg attattatta ttttagagac agagtctaac tcttgtcacc 129060
caggctggag tgcagtgaca tgaacatggc tcactgcagc cttgaactcc tagactcaag 129120
ccatcttccc acccagtagg gctacggatg tacactacca tgcccagctg attttttttt 129180 aattttttgtt ttaattttt gtagagacaa agggtcttg ctatgttccc aggctggtgt 129240
ctaactcctg gccttaagtg atcctcccaa cgtggcctcc caaagtgctg gtattacagg 129300
tgtgagccac tgcaactgac ctatgtggtt cttttgatag gagagactaa ttgttggtgc 129360
tatctagcac acactgtgtg tagacatctt gttaaataga aaatagattt atgggtatga 129420
ctatgaagag tctaattccc caaaccacac acacaactct atctacgttt gaccaggcta 129480
tttaaactta actgcagagt gtcagcatgt taaacattga tttacataaa atgatagctg 129540
cccactttct tgtaaatgtt ataaaaactg tagagattaa ctaaaaaatg cacacagaag 129600
tttgctttca gttccacaag ggtagtttat ttttgttata aaaacagtat tccccacttt 129660
cttagatacc agatctctgc ccagatttta cccagtttca tcttgctgct ctctaatctc 129720
ctatgtatgt aatatacttt gaccatttaa atatgtatta agacacttga gtttttagtg 129780 cccttttggtt tatttttctcc ggtcccaatt atctctaatc ttcattttt catttttacct 129840 attttatatt tcgaaatagg ttttgaatga agctcaaagg acaaacccaa ataaaattct 129900
gtcgtatctc taatatattg tggttgctta cccagtaaca tttttaggtg cttttctgaa 129960
tacatataaa gtttaagatc tttggagttt taagtatata atgttttct gggcaatttc 130020 tccctatcca aactgaggg gccttctttc atcaaaagaa aaaagatata tcaactacaa 130080
agtaatgatt ttgatggact aggctacgaa atctgtccat ttttttcctcc ttcttacagt 130140 ttaatagcaa ttgcagtgcc cttttgcccctt actgtactag aagacgaccc caggcagtga 130200
ctgacatctg attttttctat taattatacc atcactgcca tttccagttg aatctttttgt 130260 tggacatcag aaattttttct tacatgaata aaatttaagc atacggttgg gcgcggtggc 130320
tcatgcctgt aatcccagca ctttgggagg cctaggcagg tggatcacga ggtcaggaga 130380
tcgagactat cctggctaac acggtgaaac cccgtctcta ctaaaaatac aaaaaaattag 130440 ccaggcgtgg tggcgggcgc ctgtagtccc agctactcgg gaggctgagg caggagaatg 130500
gcatcagccc aggagttgga gcttgcagtg agccaagatc gcgccactgc actccagcct 130560
gggcgacaga gcgagactcc gtctcaaaaa aaaaaaaaa aaaaaaaaaa aaaaaaaaa 130620 aaaaatttaa gcatacaatt taggctgcag tttctcaaaa tattgtatta aaataacca 130680 attatatgct tttatagtca gtataacgta tccagttagt gtagaaattg gcatttgttg 130740
aaaactacta catgttagtc tttgatatac attcttctac ttttttggacc ctgattatta 130800 aaaacacctt tgaatagggc catgatttac tttatatcca ttttttatact acatagtgga 130860 agaaaattct gatttgttat ttcctactat gatatgtacc gtgtggcaca tatcatataa 130920
atgatccaat tctacttgta gatgaattga aagaaaggct taaaaagtt cttagggttt 130980 gtgtgtgtgg tttcactgta aaactatcat ttttgtattg aactaacctc agtatacata 131040
aaatctttat ttggcctggt atgtacgtat gccaggaatc tttggcagac cctaacactt 131100
acaatacaga tgagccatgt gtttcacact ttttttttaa caaccttcag aaatattctc 131160
ttgttcatca gagtgcttcc cctaagccaa gcagtttcga tgatagcccc agaataactt 131220
```

```
tgcccaagtc tctccataaa tgtaacttag gactccaagt ggtgtatttt tatactcttg    131280
ccccatacca agtaaatctc aagatttatt ttaagggagt ggccttcact gcttaaaggg    131340
cctagcattt aagaacagat aagattttta atggtgatcc taaatgtttt tttttaaaaa    131400
acttgcttgt ttttctcttg aaactaaatg ttttttattca cttcatttta agatatattg    131460
taatcaatcc aaagtatggc tttattttta gtataaacag tcaaatgaag cttagtcttg    131520
tggcattgtc agatttataa ccaaatatta ctgaaactaa ttttttttaag ttcaaaaacc    131580 caatctagta gtttctctct tattttcaac ttttatttta gattctaggg gtacatgtac    131640
aggtttgtta ctaagataca ttgtgtgatg ccggtgtttg gagtatgatt gaacctttca    131700
tctaggaagt aagcacagta cctaacaggt gcttttaac ctgtgcctcc cttcctctat    131760
cccccctctt gtatttccca gtgtctgttc ccatctttat gtctatgtgt actcaatgtt    131820
tagctcccat ttataaatga gaacatggta tttgtttttc tgcattagtt catgtaggat    131880 actgccgcc tgctacatcc atgttgctgc aaaggacgtg atttcattct ttttgtggcc    131940
acatagtatt ccatggcata taaataccac attttcttta tccagtccac tgttgatggg    132000 cacctggggtt ggttccatgt cttttgctatt gcaaaccatg ctgcagtgaa catatgggta    132060
catgtgtctt tttgatagaa tgatttattt ttctttgggt atattcccag caataggatt    132120
gctaggttga atggtagtta aactcttaat tctttgaaga atctccaaac ttctttccac    132180
agtggtgtca ttgtggtttt gacttgcatt tctctgatga ttaacaatca gcatttttcc    132240
atatgtttgt tggccacacg tatgtctttt tttgagaagt gtctgttcat gtcctttgcc    132300 cattttttaat ggggttgttt ttgcttgtta atttaagttc catataaact ctggatatta    132360
gggctttgtc agatgcatag tttgcaaata ttttctccca ttctgtagat tgtgatagtt    132420
tctcttgatt tgcagaaact ctttagttag gtcccattgt caattttttgt ttttgttgca    132480 gtttctttttg gggattagtc ataaattctt tcccaaggcc aatgtcgaga aggttatttc    132540
ctaggttttc ttctaggatt ttcatagttt gaggtcttac atttacatct ttaatccacc    132600
ttactaattt ttatatggca gtaggtaggg gtccagtttc attcttctgc acatggatag    132660
ccagttatcc cagcaccatt aatggaatag ggagtctttt ccctatggct tattttttatc    132720 aactttgtgt agattacatg gctgtaggtg tgtgtctttta tttctggact ctattctgta    132780
ccattgtgtg tggttttttt ttaccagtac catgctgttc cggttactat agcctgtagt    132840
atagtttgat ttggggtaat gtgatgttgc caactttgtt ttttttgctt aggattgctt    132900
tggctatttg gggcattttt tggttccata ggaattttag aatgcttttt gctaattctg    132960
tgaaaaatga cattgtagtt tgataggaat agtgttgaat ctataaattg ctttgggtag    133020
tatgaccatt ttaactatac tgattctacc agtccatgag catggaatgt tattccattt    133080
gtttgtgtca tctttgattt cttcagcag tgttttgtag ttctccttgt aaaaattta    133140 aactaactta gatgcattcc taggtattt actcttttttg tgactgttac aaatgggatt    133200
gcattcttga tttggctctc agcttgaaca ttactggtgt atagaaatgc tactgatttt    133260
tgtacattga ttttaaatcc tgaacctta ccaaagttgt ttatcagctc caggagcctt    133320
ttgacagagt cttcagggtt ttctaggtat agaatcataa gtgaaaagag atcgtttgat    133380 tattatttttt cctatttgga agccttttat ctctttctct tacctgattg ttctgactag    133440
gatttccagt actatgttaa attggaatgg tgacattggg catccttgtc ttattgcatt    133500
aaggggaatg cttccagctt ttgcccattt ggtatgatgt tggctgttgg tttgtcatac    133560
```

```
agggctcttt attactttga ggtatgttcc ttcaatacct agtttggtga aggtttttat    133620
catgaagaga tgctggattt tatcgcaact ttttctgcat ctattgagat gatcattatt    133680
ttttttgtta tgtggtgaat cacatttatt gatttgcata tgttgaacga gccttgcatc    133740
ccagaaataa agcctacttg attgtggtga attaactttt tgatgtgcag ctggattcag    133800
tttgctagtg ttttgttgaa gattttttgta tctgtgttca tcaggdatat tggcctgtag    133860
ttttgttgtt gttgttgttt ctctaccagg ttttggtatt agaatgatgt ttcccttgta    133920
gaataagtta gggatgaggc cctctttcta gattgctttt ttagaatagt tttagtagga    133980
ttagtaccag ctcttctttg tacatctggt agaatttggc tgtgaatcca tctggtcaag    134040 ggctttttt aattggtagg ttttttatta ttgattcaat ttcagaactc gttattggtc    134100
tgttcagaat ttcagtttct tcctggttca atctaggcag gttgtgtgtt tccatttcca    134160
catacatact tactccaaat aatggcttta tatatacggg ggtcagctga aaacaaaaat    134220
gatactttca tagtaaactc cacccgcccc cccacccaca tacacacaca cataaaccct    134280 agattttta aagcctttgt tccaatttat ccatttcctc tagattgtct actttgtgtg    134340
catagaggtg cttgtaatag tgtgaagatc ttttttcactt ctgtggaatc tcttgtaatg    134400
tcatctttta cattttttat tgtgcttatt tgggtcttca ctctttttttt ctttgttaat    134460 cttgctagtg gtctatcaat cttgtttatc ctttcaagta accacttttt ataaactagg    134520
ttttaagcta attaagattt ctctactttc attaagaagg aagtagtgtt accacagact    134580
catgaacact tctgtggagc tcctgtattg actgctaatc aactatatgc tccaatgggt    134640
caggaattta tataaagttg tattaactaa gttgctttaa aatagtgatt gcttaactaa    134700
atgattcagt tcagttaact ccttcctgaa gatatttttga aaattaatt agtattattt    134760 cttgctctag tcagtacagc acagttgggt tcaattgtac tttctgagct gtattgaaaa    134820
acatcagttt tctcatttag aactatatat aagtagtgag aaattaatta caaactgagt    134880
catagaaaat gttttttttt aatcctccag cttgttactc tttcttcctt gttctaatgt    134940
ggagtaaaga aatatgcatt ccaaaccatt taaagttatg actaattgag gctgtcaaag    135000
tactgtttca gtgtattgat ttggcacatg tgtgttctct tttacattgt caacaaaagt    135060 acatttatg attttggatc aagatttcac tgagatactt ctggttgttt aaagagtttc    135120
tttatgtatt ggtgtctttc ctttttaaaa ttttatcact cctctattaa gttgtgatat    135180
ccaaatttaa aatattctaa aaacatgttc tcctgcaagt tgaggtaatg atagttgtta    135240
tgtggtactt actataatat atgccaggaa ctgttctaag cattttacat atttaattct    135300
cacaacaacc ctatgaggta gggactaata ttgtcctcat tttacagaag gggaaatgaa    135360
gagtcaggga gtaacttgca cagatatcca gctacaacat ggcagaacca ggacttaaat    135420
ccaaatatgc tgatttcagg tttctgccct ttagtcctat atcatactgt gcctccaaga    135480
gagcatggta aactaattag catggttcta tcatgattct gtttctattt tgaactatta    135540
ataaaaattt ttgcaattct cagttacccc atttagtata gaacacaata agaatggaac    135600
cattctattc taacattgta cattgagata tcgttcccac caccatatct gtcctccata    135660
gactatatgg tgtgtcattt taaggacaga ggatctaaaa atgattttta aaggtgattt    135720
acatttactc ttcccttttgc aaaatggttt gcatccctaa taatttagac aagtacattt    135780
cttcgtgata taaattacat ttcttgcctt tccctggaat tctgagtact ttccctctga    135840
gagaacaatg taattcttat ttatttagtc actaaaataa cttcaggagt atgaataagt    135900
ctactaaaaa gtctacagga tccatgttgt agtttgagta gatggttcca taccaagtca    135960
```

```
aggtaaaaga taatttatat ataatatgaa aatggctgct ttaggtttat agagtaatca   136020
atataaatct tccttataaa agggaaattt cccacttata atttatgtaa tgtaaagttt   136080
ttcatttcat cttcccaaat gttttttagtc ccacgcagta tttatgttag tacctatgta  136140
aaggtgaaaa gtgaattttt tctactggta gaactaatac tatttttagc atgtaatctg   136200
ctgtcatctt cctatcttta taagtggctt tgaacaagtg taaatagtgt aattctcttc   136260
attatatata ctaccatgat ttagattaat cttaaaccac agtttgtaat ccgttactcc   136320
aagcttagat ttttttttca gtttatagta agagtaattt gccttatata accaatgaaa   136380
ttgttgcatt tagagtgaaa gtgagataaa aaaataattt atagaagaat ttacaaaagt   136440
tatttactca gattgtttta acataccgtt ataatacttt gtataaggaa taactctaat   136500
gaagtttctg gcctatttgt aggcaaaatt aattgggaat aggttcctct ggatcttttg   136560 cttttcagaaa aaaaaaagtt ttttctcctt ttccatgtca ctttatcata attgctaaat  136620
aaaatatttc tcccatctta atagttttag aaagtaaaaa tacttcttga ataaactgtg   136680
tagcgcagac cttcccatta cagttcattt ctatgtattt gtttaaatac ccacagctcg   136740
aaaaacaaag aaaaaaataa aaggaattca gcaggccact acaggagtct cacaagaaac   136800
ctctgaaaat cctggtaaca aaacaatagt tcctgcaacg ttaccacaac tcaccctac    136860 cctggtgtca ctgttggagg ttattgaacc tgaagtgtta tatgcaggat atgatagctc   136920
tgttccagac tcaacttgga ggatcatgac tacgctcaac atgttaggag ggcggcaagt   136980
gattgcagca gtgaaatggg caaaggcaat accaggtaag atgcaaaaca taaaagagca   137040
actatataaa cctttgtgtt ttcttcagca aaaacacttt ggcttttata tcatcgtgag   137100
cccatggctt atcttgtttc tcttagttct ggggactatg aagggagag tcaggtgaat    137160 acaggtgata gggagtttat aataaaacat ttacattact ccctgctttt caaatcatta   137220
tgcacaggat ggtaatttca cataggatga tgtaatatca gaattcaagt tacaagactc   137280
actcaaaact ccttttacac tgaagtttgg ggaaagaaaa tgttttttagt taattccatt  137340 tgttttcctt cattgtgcca cttttaaaaa tcaggttgtt tgtaagattg gtaaacatca   137400
agtatgttga ttgtcaaaat ttgtactaaa gtagaatgat tttaaccctt cactaaatga   137460
aatgctacac attgaatgta attttaaaga taattttaaa taaaagttac cctattggaa   137520
tttggtgtgg aatggcagag gtcaatgtta gtgtcagctc tgactttaaa gacagggaat   137580
tgacaagcct gtgttcacgc aaatagttag ggagagagca agaaagtaac ctgacctcct   137640
gtcatccttg ttttattaag ggggaaagag gtgtgaatag cagggcaaat gttttgctta   137700
actcattgat taatacctca agccaagatt cttttctgtt ttttaaaatc aatacataat   137760
agttgtacat atttactgta catatttata tttaggggt acatgtaata atttaataaa    137820
agcatacaac gtgtaaggat caaatcagag taactgggat atccatcacc tcaaacattt   137880
gtttggggaa cattccaaat cttctctttt agctattttg aaatataaag taaattattg   137940
ttaactatag tcatcctgtt gtgctactga acactaaaac ttatttcttc taactgtatt   138000
tttgcacccg tcaaccattc ccgcttcatc cccatcacca ctatctttcc cggtcactgg   138060
taaccgccaa gccaagaatt ttggctattt tactatttag ttcatgttta cttaagcaga   138120
cagaggtgac aaaactggct tttttttttt tttttttacat taaaagctat taaaaagcac   138180 ctaggggct gggtgcgatg gctcacgcct gtaatcccag cactttggga agcccaggtg    138240
ggtggatcag ttgaggtcag gagttcgaga ccagcctggc cagcatagca aaaccccatc   138300
```

```
tctactaaaa ttacaaaaat tagccgggca tggtggtatg aatctgtatt cctagctact    138360
tgggaggctg gcactgagaa tcacttgaac ccgggaggcg gaggttgcag tgagccgaga    138420
tggcaccatt gcactccagc ctgggtgaca gagcaagact ttgtctcaat taaaaaaaaa    138480
aaaaaaaaaa aaaacacaag agggtttgtg agtcttaaag tgtcagatga cagaagaaaa    138540
ctgtgtctac ctagtattta atttccattt tctgttaggg gtgcccttgt tttgacaggg    138600
ctaattgatc tcattgctcc ttggcaattc ccacagagat gatcttctga agagtgttgc    138660
ctcatacctt tatttctctt aattcaggtt tcaggaactt acacctggat gaccaaatga    138720
ccctactgca gtactcctgg atgtttctta tggcatttgc tctggggtgg agatcatata    138780
gacaatcaag tgcaaacctg ctgtgttttg ctcctgatct gattattaat gagtaagttg    138840
tatgtgtgtc attttccctg tattcatagg gtatctttaa ccagctgatg ttttcctgat    138900
tgactgctat tgtgataatt caggactgaa acaatcctac taggtatcta ggatctaggc    138960
aaactggaaa tagagttatg agtgcttggg gcaggacaag tgtaatgtaa agcaaatgta    139020
catgtggcat tattactgtc ccaggacatg tttgaggata tttaacagca tatctgaggt    139080
tagtaaagtc tgtcgcaagc aacaaggaat cttactgtga tatcatttac ataaccctat    139140
tccagaaaga aaaaggagca tggtaaaact catgtggatt cagtggggac aattgtagat    139200
gaggatatct aggctgatgg ggtgggacat atggacccag acacaagagg tatctctttg    139260
catggcaagg ctcacccagt gtctgtggtt taagaatatg ggaacaaatt tgttttgttt    139320
aactgagaga agaccaagcc tttaagattt tataaatcag ctattctctt atcctctaag    139380
cttattcctg tgtctgcgaa atacttcagg tgtccatttc cccttacctc attgcagttg    139440
tttcctcact cgttttctcc ctccagtgta acgttcatca tgttggctaa tgtttgcttc    139500
ctcaagcaca gtctgactgc atcacatatc tccccagtac acagattgtc ttcagtatct    139560
tcccactgac cctccagtac atattctgca tgatttcaga cttccagaa tctgacctca    139620 cttcctctcc cattgttttc cttcacacac tcttcattcc catccatcct ttccagcata    139680
ctcttagact cttggtgttc acatcaccag atacacagca gagaagtcac atcctagtta    139740
ctctcacttt ctaccttgta ttactacttt tcgtacccct agcttattgc tattagtaca    139800
atgtaaacag ggagttcaca cacacatacc cctggtctaa gaagaataaa aaatgaagga    139860
gatttctgtt tgtatagaaa acagaagtca ccttgacttt tattgccaaa agaggactg    139920 ttcaaactac tgcatcacaa tgtaacaaga ttaggtagtt ggatccaatt ttaaattaac    139980
tggtaaatat atttagtttc tggggaaact gaagacatta ttactcatca taatcctacc    140040
atgctgttta aaaaatacca tgttggcagt atttgttttt tagtcacttt ctaatatgta    140100
atttgaaggc atttaagtgg aattaaaagc ataaacagat ttgtatgaaa caccaactta    140160
tcctggttta taaaactaac ctaatttagg gttttttatta ttagggcatt cagatttagc    140220
tttaagcagt cacagcaaaa tctaatcatg ccacatacat tccttacata aagtgggatt    140280 tataatttt tttcctcaac agatttacat tagtttcatt ttcattaagg gatatgtact    140340
tcctattctt gtgttctcat gctgctgcct aaaagatggg cagtcctcca cctttttctt    140400 ttctttttttt tttttttttt ttttgagacg agtcttactc tgtcacccag gctcaagtgc    140460
agtggtgtga tcttggctca tggcaacctc tgcctccagg gttcaagtga ttctctgcct    140520
cagcctcccg aatagctggg attacaggcg cactccacca cacttggcta attttttgta    140580
tttttagtag agacggggtt ttgccatatt ggccaggctg tcttgaact cctgacctca    140640 agtgatccac ccactttggc ctcccaaagt gctgggatta caggtgtgag ccaccgcacc    140700
```

```
cagccctcca ccctttttc ttagcccact atgtttccat actgctctgg tgtctgtgac  140760
aggcagatat tgcatatcag aaagtatgca ttcaagttct gaccctctat agagctgtca  140820
aacagtctct catggttgcc cttaggtcag aacgttgtgg gggaaaaaaa aattgttgtt  140880
gttttacag ccaacaagaa tgagttttta cttattctac tacactataa ctttgttgaa  140940
atttcagtt atatgagtat aaccatgtac aagaaactaa aggaaaaaaa ggtgcctccc  141000
agaaaaggag tgctttacct actattaagg actagggagg tgcctcttcg gtaagagcag  141060
atttaaatt tgaagagcct ctgatcactt tggcagcata taagtcatgt ctaatttatt  141120
ttatataaag gaataaacca catattcagt agagaaaaat aataaccttt ctgttgttaa  141180
gtccaagacg actttctgtc agaaacttaa aaaaaaaaaa aaatcttgaa gcattttaaa  141240
agctgtgaac tgggcccagt ttcaggctct tagtgtcatt tcacaagtca ggaaacttta  141300
gagacctatt tgaaaatcat aggtatgtaa tgacttcaga atcataagca agaattggtt  141360
tagtaccttt agtttaaaga atattaaggc atatgcctgt cagaggcaga ttttgagcat  141420
cagaagtcta gaatcaagtt ctaggtctcg ccctctgcat aactgtgaac agtgtcacac  141480
atttttgtct ttaggatgga ctgctgtgaa aaaatttacc tttaaaaatc aagtgtgtag  141540
gacctaaaac tgtcgtctaa ttgaccgtat tcaaatgata aaccttgatt taaatgagca  141600
actagtaata agttctataa gaattctaac actttaatta aataataaaa taatacatgg  141660
catgcatgat agaaaataat atctccactg ttacattaga ttattcatta gtctatttaa  141720
acagccaaga tgcaggaagt ttaaggaaag ttctccaaaa ttctgattt ataggggaatt  141780
agcaataata ttattgcagt agttgttttt ctttatgagt tcatagtttt gcaaaacaaa  141840
acaaaaatgt gctttttggg gggaagtagc agtatttcta actaataccc tgctatttat  141900
ctttcacagg cagagaatga ctctaccctg catgtacgac caatgtaaac acatgctgta  141960
tgtttcctct gagttacaca ggcttcaggt atcttatgaa gagtatctct gtatgaaaac  142020
cttactgctt ctctcttcag gttggtagaa caccttttca ccttatgtca aaagcatgaa  142080
atatgaaggc ctagaaacaa aggttaattt atatacatag tactaataat tataccaagt  142140
ctactattat ttcctactag tcagatgatt tttatgaatg taaaatatta gaaaggcaca  142200
gtaagtgaca ccaagattaa taagacaaat aggtatggca gaaacagaga ggtatatgag  142260
ctgcataggg atctctgttg ataagaatct gtgtagactt ttttctcctt ccttccttg   142320
atctttgatc atgggaagac atggaaaaag aaagctaact acagtgattt tgtccactac  142380
actgttattt ggtaaaaaat tttagttcc taatgagtat tagcatgtat gagaaattat   142440
gggagaaaaa ggcgcatcct agaaaaggtg tgcttaatta ctattgggga ttggttaaca  142500
tagcatggga gctggattgt cagagattca ttatctagaa aatggcaaca agagtttata  142560
aaacgaactt ctgtgagatt acttttttagc tagcaaagac aaagatgtcc ttcagtaggt  142620
gaagtgataa actatgatac atccagatga tggaatacta ttgaggacta aaagaaaata  142680
agctgtcaag ccatgaaaac acatggaggg acgttaaatg catattacta agtgaaaaaa  142740
gctaatctga aagggctaca tactgtgtga ttctaactat ataacattcc ataaaaggca  142800
aaactgtgaa gacagcaaaa aaaaatcagc ggttgccagg gtttagaagg aagggaggga  142860
taaatgtgca gagcacagag gattttagg gcagtgaaaa tacttcgtat gatactacaa   142920
tggtggaaac atgtcattat acatttatcc aaacccaaag aatgtccacc accaagagtg  142980
aaccctcaac tatggacttt gggtgatgat gtgtgggaca ggaggtatat gaaaaatctc  143040
```

```
tgtaccttcc tcccaattttt gctgtgaact taaaactgct ctaaaaaaag tcttttttaa  143100
aaaaagctct atgaactagt tggtattata aaccttaggc catttcaagt aaaaattaca  143160
tatcaatgtt tattaaatac tgagttaata gctgaatacc tctttcatat acaaataagt  143220
acatttgcaa ttttttaaaa agtcttaatt ccattagtaa ctgtggtttc atagttgcca  143280
aataactgta agctatggat gttgcacaag actgtgattt tatttaatca tttcatatct  143340
atttaaacat ttccaaagcg cacattcatc ttaatgtttt cacactattt ttgctcaaca  143400
aaaagttatt ttatgttaat ggatataaga agtattaata atatttcagt caaggcaaga  143460
gaacccgata aagatcattg ctagagacgt ttaatgttac ctgtagcggt acacttgtta  143520
aagaagtgat taagcagtta cataaaattc tgatcatagc tttgattgat accatgaagg  143580
tataattcag tgcctggata ctaacaactt tacttgttta aaaaaaaaaa aaaagaatg  143640 gtttcaattg tatacatccc agactaattg agctatatga ttttttttcat tgtaaataat  143700 atcacgagtt cttcttgtta aaaataata gaatcataag gatggaaata tataccttaa  143760
gatatagact tctactatga tagactactg gaataggtat ataacctccc accaaaaatg  143820
ctagactaaa aaaattaaga actaagtgaa ggcaggaacc tacagagata agtggaactc  143880
aagccaactt gctctttgac ggcatttgta gaacctggta aattagtaag tttagtaagt  143940 tgggttttt ttaagtttat aatctttttt aaaatgattt caataggttt ttggggaaca  144000
ggtagtggta ggttacatga ataagttctt tagtggtgat ttctgggatt ttggtgcacc  144060
catcacccga gcagtgtaca ctgtacccaa tgtgtagtct ttcatccctc atcccctccc  144120
caaccctagt ccacaaagtc cataatatca ttctcatgcc tttgcatctt catagtttag  144180
ctcccactta gaagtgagaa catgcaatat ttggtttccc attcctgggt tacttcactt  144240
acaataatgg tttccagttc catccaggtt gctgcaaatg ccattatttt gttccttttt  144300
gtggctgagt agtattccat ggtatatata taccacattt tctttatcca ctcgttgatt  144360
gatgggcatt tggactggtt ctgtatattt agtaagttta aaaacaaggg atggaaatat  144420
aaatgcagtt gaaaaggcag tggatggatc taaaagcaga agaatacaat tgtttttaat  144480
gattgtgtat atgtttgtgt atataaacca caagggaaat ctgtaggtac tgaaaatcac  144540
aacaggaaaa tggcaacaaa gctatagaaa ctggaaaagc aatgactttt cttagatccc  144600
tcagagaatg gaggtcatag gacaaaccac cacttcaaaa tctagaagaa tagacaaata  144660
cagagaaaca gccaagatca gcttactggg aaaagatgcc actgaagcca ggaagactat  144720
ggcaatttgg gaaagatgc cactgaagcc aggaagacta tggcaatttt gatgaattgc  144780
tggaggctga gtgaggacta gcttcagagt taaaaactcc cagggaccca gtcttagtgg  144840
gggtttcctg caatttcttg ggtttacccc acaaaatttc taacttccag aaactccaca  144900
aggttcttat ggtgaagatg caagaaaaat tccctccttt ttctggtagg agtagaggga  144960
aggtaaaatt tggaaatacg tagcagagtg ttcacaacaa aaggcctgcc ctgtaaggaa  145020
aactaattca acaggccctt atgtgacctg ggggaaaggc aaatagagga ttctagccct  145080
tccttagcct tcttgtctca tttctgaaag tcacagccca gggattcaga cccactaaaa  145140
aaaactgaga tttaatcata aagattaaaa aacaattccc ctcccctcc ccaacaccctt  145200 accaccatat aaacagggct ccaggataaa ataacagtgg attacaactg agagagctgc  145260
aagacacaag ctgtttaagg agctcttagg aaacccaaaa acaacagaag aaaagtaaa  145320 taaaaacaag gaaactagag gaaactgaag cctccagtac ctacaattat ggcaaacatt  145380
aaatacagcc cagctcctag ccagattagc atgaaacctc acactaaaag tctaattact  145440
```

```
tcagttttga tatatcaatc atgtccagct ttcagcaaaa aaactacaag gcatgctaaa  145500
aggcaagaaa aacccacggt ctgaagagac aaaacaagca tcagaagcag tcctcagata  145560
tgacacaaat atttcaatta tcagatgggg aatttacaat acctatgatt agtaggttaa  145620
aggctccaat ggaaaaaagt agacaacatg caagaagtga tgtacgcaga gagatggaaa  145680
ctctaaaaat aaatgctaag gaatgctgta aggaaatgca gaatgatgtt gatgggctca  145740
tcagtagact gagcacagcc aagcaaagag tcagtgagct tgaagataga taggtcaaag  145800
gaaattcccc caaactcaaa tgcaatataa acatagtaga cattaatcca gctgtatcag  145860
taattacttt aaatttgaat gctctaagta caccaatcag ctatttttttt aactaggagg  145920 tgaaaataaa gtttgccacc agatgctcac taaaaaatta ttagaggata tatcccagcc  145980
aggcgtggtg gctcacaccg gtaatcccaa cactttggga ggctgaggca ggcagatcac  146040
agagtcaaga gatcaagacc atcctggctt acgtggtaaa accccatctc tactagaaat  146100
acaaaactta gctggggggtg gtggtgcgcg cctgtagtcc cagctactca ggaggctgag  146160
gcaggagaat cacttgaacc tgggacgtag aggttgcaga gagccaagat agcaccactg  146220
cactccagcc tagtgacaga gggagactcc atcttagaaa aaaataata aaagtaatcc  146280 catctttaag aaggactgaa gaataacaaa agtggtaaat aatatagata catttaaact  146340
gacatttact atgtatataa aataacaaca gtaacaattt ccttgagggc taaaaagtag  146400
aactaaagta agtttcaagg atgacaacta gaaatagggt atgcagggta tgcaaagtac  146460
caaaccattg ggggaagaga ataccctaaga aaaacaatcc aaaagaatga aagacatgag  146520
aggagggaga aaaaaatgca taaacaaggg catgataaca ggaagtaaca gataaggtac  146580
attagtacag ctaaattcaa acacatcagt agtttagttt cattaaatat agagatgggg  146640
ccaggtgtag tggctcacac ctataatccc agcactttgg gaggctgtgg gcagatcact  146700
tgaggtcagg agttcgagac cagcctgacc aacatggcga aaccccgact ctactaaaac  146760
tataaaaagc cgggtgtggt ggtgcatgcc tgttatccta gctactcggg aggctgaggc  146820
acaagaatca tttgaacctg ggagatggag gttgcagtga gccaagatcg tgccactctt  146880
ctccaaactg ggtgacagag ggacactgtc tcaaaaataa aataaatgta gagatggact  146940
gaatgctcca agctaatctg acaggatttt agaataatc caaatttatg ctatttaaaa  147000
aaagctatat ctgaataaag atattgaaag gctgaagtaa aaggatctac tttgcatagt  147060
ataacccaag acatggccaa ctttttctgt aaagggccag atggtaaatg ttgttagctt  147120
tgcacagtct ctgtcacagc tactaaactc tgcccttgtg gcaggaacat agtcattgac  147180
ggtactcaaa tagaacaggc atggctgtgt tccaataaaa ctttatttac aaatacaggc  147240
tgcaagtagg atttggccca taggccaaag tttgctggcc cctatattga ccaaaacaaa  147300
accgaaggag ctacattatt accaagcaaa atagatgtta aggcaaaata ctccttaaag  147360
catttgttca ggaaaaataa ttgtaaatat atagtttcaa attacataat acaaaaattc  147420
atagaacaag aatacttaga taaatctagt aaaaataatg agattttact atacctttct  147480
tacaaattaa gcagacaaaa aaataaggat atggatgtac atttcatctc tcttgggtca  147540
atactgaggt gtgagatcac tgggacatag gttgagtgtg tgtttaaatt tatttttaaa  147600
attgccaaac ttttccgcaa ttgttaacat ttaccagaaa tgtatgagac ttcttaagat  147660
ccattctata tcctcctcag tacttggtac tgtcagcctc tttcatcgta ggtatactga  147720
tgattaaaaa tattaagcat cttttcatgg gcttattggc cacctatatt tcttatttgg  147780
```

```
tattgtgcct cttttaatct tttgcccatt ttttaactgg gttttaagaa ttgttcaaat 147840
attctcaatg tggcccttttg ttaaatatat gttttgcatg ttttctttaa gtggattaca 147900
tttacagttt tcttaaaaaa atgtagagat gagcaaaagt gtataatttt gaagaaagct 147960
tcgtgtcttt gttactaag aaagttttgc ttaatccagg gttaaaaga ttttctacta 148020 tttgttttct tatagaaatt ctgtagtttc agctcacatg cttaagtata tgatgcaagg 148080
taagggacaa ggttcatttt cttccccaaa atccatatct ggttgctcca gaacttgact 148140
ctcttttccc tattgagtta cttggcaatt ttgtagaaaa tcagttgttt gtatatgtgt 148200
gggtctactt tcagactctt tttcttaccc aacgatctgt atttcttacc caatgatctg 148260
tatgcctata ttcatattga taacaccctg tcttgattac tgttgcatta cagtaaatct 148320
tgaaatttgg taatatgaat ctccaaatc tgttgttctt ttccaaactg ttgttttgga 148380
tattctagtt tccttgcatt tccacttcct tttttttttt tttttttgag atggagtctc 148440
actattgttg cccaggctgg agtgcagtgg catgatcttg gctcatcgca gcctcagcct 148500
ccccagcagt gggattgcag gcaccccacca tcatgcttgg ctaattttttg tattttagt 148560 agagacgggg tttcgccatg ttggccaggc tggtctcaaa ccctgacctc aggtgatcca 148620
cccacctcgg cctcccaaag tgctgggatt acaggcatga gccactgtgc ctggtcttcc 148680
acgtattttt taattagctt gacaatctct accaaaaagt cttttggggc tgggtgtggt 148740
agttcatgcc tgtaattcca ccactttgag aggccaaggc aggcagatcg cttaagccca 148800
ggagtttgag accagcctgg gcaaaatgtc gaaaccctgt cactacacaa aatagaaaaa 148860
attagccagg catggtagct tgtgcctgta gtcccagcta cccaggaggc tgaggaggga 148920
ggtcaaggct gcagtgagcc atgatcatgc cagtgcactc tagcctgggc aacagagtga 148980
gactctgtct caaaaacaca gtctgataga atttttatta ggatagcctt gaatctatag 149040
atccatttga aaataattaa catcttaaat ttccaatttc tggccgggcg ctatggctca 149100
cgcctgtaat tccagcacgt tgggaggccg aggtgggcag atcatcaagt caggagttcg 149160
agaccagcct gaccaacatg gtgaaaccct gtctctacta aaaatacaaa aaattagcc 149220 aggcgtggtg gcacatgcct gtagtcccag ctactcagga ggctgaggca ggagaatcgc 149280
ttgaatctgg gaggcagagg ttgcagtaag ccgagattgt gccactgtac tccagcctgg 149340
gcaacagagt gaggctccgt ctccaaaaaa aaaaaaaaa attccagttg ttgagaaaga 149400
ataggaattc cagctttgga ggagtgggga gaccatcaaa tcctctttcc aaaaatacta 149460
ctaaaatact actgagcaga gtatagttcc acaaatagtc ttctgtaaag agactcacag 149520
tacatatttg tctttgtagg ccatatagtc cctgttgcaa tttctcaatt ctacagctat 149580
aacaggaaag cagctatata cagtatgtga atgcttgtgt tctaatacaa atttatttgc 149640
aaaatcagga aaatggcttg aaatggttta agatctagtt ttctgactag atcatggtat 149700
ataatctttt ccatatatat tttgaatttg gtttgctaat attttgctga tcattttat 149760 atctctcttt atgaaggatg ctgatctaca actttctttt cttgtgatat cttttctgg 149820 ctttgctacc agggtagtac tagcctctta aaatgagttg agaagtattt tctgttttct 149880
taaagagttt atagagtatt gatcttattt attcttaaa tatttgatac atgttaccag 149940
tgaagccatc tgggtctgtg ttttctttca gggaagattt ttaattattt gcttatttgt 150000
tatatagatc tattcagaat ttatattttt ccttgacata gttttgtaat tgtgtgtttt 150060
ctatgaaatg agccattttg tctgagttgt ctaacttggg cataaagttg tttgtaatcc 150120
tttaagtttt gtaggatcca tagaggtgtc ccctccatta tagattttca taatttgtgc 150180
```

-continued

```
ctgatcatct tttttcatg gtcagtctag ttaaaatttt atcaattttg ttggtcttta    150240
caaagaacca atttttagtt tcattgaaat ttttagtttc attgattttc tctttttgtt    150300
tcctatgtca ttgattatta tttcttcttt tctgcttgct tttcatttaa tttgttcctc    150360
tttttctagt ttaaggtaga agcttccatt gttagttgaa gaccttatttt tcttatatag   150420 atgtttaaag ctatacattt tttgtatatt ttcattcatt tcattttcta atgtccttca    150480
tgattttttt cattgaccca tgtgtattgc ttaattttta tatatttggg gattttccat    150540
atctcttcct attcatttct aatttaattc cactgaggta ggaggtacat tgaaggactc    150600
taatattgaa tgactccaat aagtcttctg agacttttt aggcacttgc atatggtcta     150660
tcctgagtgt tccatgagtg cttgaaaaaa aacttactgt gctcttgtta agtagagttt    150720
tatgaacgtc agttaggtca agttgattga tagactaatt caagttttct gtatctttgc   150780
tgattttctg tctagttgtt ctagatccta caactttgtc tacatccttg ccagagcttg    150840
gtatggtttt tttattatcg ctatcctaga gagtatgtag ttgaccccttg tgacttgcca   150900 tgcatttaat gactgcccat gttcatagca gcattattca taatagcaaa aaaaactttt    150960
atcatatgct tttgtgcctc aagatcatat attttttcgtt tttagtcact aatatggtat   151020
aatggtataa tatactgttt aatttctgag taattgacta gcctttcatt ccggggataa    151080
atcctatttg gttatgatat agtatccttt ttacatatag ctgaattcat tgtactaaaa    151140
ttttggtatt tttgcatcta aatccatgag ggatatattc tatagctttg gtgttatgat    151200
aatatggtat tatttctttc ttaaacgttt ggtaaaactc agcagtgaag ctgtcttggt    151260
ttgtttggag cctttttgt agaaaggttt tcaagtacaa gttcatcaaa tgtttactga     151320
taatatgttt attcttgagt gagctttgtt ggtttacatc tttgaaggaa tttaactgtt    151380
tccttcaaat gttgaattta ttggtataaa gttaagttat tcataatatt cccataatat    151440
ccttctaatg gctccagtat ctctagtgtt attcccttc attcccgaca ttggtattta     151500
atatattctt gctttttttt ttttttttta atcagtctgg ctaaaagttt ttcagttta    151560 ccaatgtttt catagaacca gcttggtctt gattttgttg ttgttatgc atgttcttag     151620 ttattcgttt ctactcttta tccttccat tttcttgtg tttagggtag aagcatatat      151680
aattaattga gaccttctcc ttctaatcaa agcttttaat gctgtaaatt ttctaagcac    151740
tgtcttcatt gcatcccaca catttgata tgctgtgttt tcagtactag agattttaa      151800 ttttatgata ccttatttaa tcatgatgcc ttatttaatc tatagcttat taaatgtcaa    151860
attctaaaca tttgggtttt tctccagata tgtttgttac tgacttctat tttaatctca    151920
tttttgtcag acagcattca ttgtatgact taatcctcct aaatgtattc agacttgttt    151980
tatgttctag attaatgttc tgtgtatact tgaaaagaat gcaagttctt gggtagactg    152040
tttcagaaat gtcagtcaaa tttaagtctt gtttattctt attgattctg agacaaaggt    152100
gtttataatg ttagatttgt ctgctatatc tctgacattg ccaaatatcc ccttggaggc    152160
aaaatctccc cctccctttt gagaaccact gatctatgta gccttttttc tgggactaat    152220
ttagccttgc ttctgagatg tggccccctag gtctctactg aatgcccggc atatttaatt   152280 agatcttct ttcctctatg gcctcaaggg atttcacccct aagtatgcac aaattttttat   152340 tcagccgaag actgtacaga tttctggagg ccttttctttg tgtacctcct tcgtttccag   152400
tagtctgacc cataaattgt acagatttct ggaggccttt ctttgtgtac ctccttcgtt    152460
tccagtagtc tgacccataa attgtacaga tttctggagg cctttctttg tgtacctcct    152520
```

```
tcgtttccag tagtctgacc cataaattaa agctgcttta gcctccccaa acttcaatct   152580
ctttctcctc aacccagcaa gattgctaga ccctgggttc cctttccctt cactgcagta   152640
tgataattac tttcaagcac aaaggtttag aattaagatt tcttactcct gggctaggta   152700
tggcttaccg tatttgtttc tcttttccta gggatcataa tcatgtattg cttgttgtcc   152760
agttttccag taggagggga attccaggct gtacttactt cctgcagcca aaagaggaag   152820
taatgttagt gatttcaata ttaaaacatt aaaaaaaaat ttaagatgga tgaaattctt   152880
ttatatgcat attgaattgg gcttcaccat agttatttt agaattagga ctaaccggca    152940
gggaaaaaaa ctatacggca gggaaaaaaa ctataagcca tcgctgtttt acaatttgc    153000 aataattaga ttttctgtag tatagtaatg tgtaaaatta acccattgtt aatatagaat   153060
gccgttatca ctcctgatta agcggtcttc attttcatgt taatactgat gtcttgtaat   153120
gctttatgga atcaaacatt ttcatacata ttcattagtc taattctaat cataatccaa   153180
tgaaaaagag caggaaagat gctcaaggag gttatattca agtccacatg gcaagtaaga   153240
aataagacta ctcggctggg catggtgact tactgcctga atcccagca ctttgggagg     153300 ccaaggtgag cggaattgct tgaacctggg aggcggaagt ggcagtgagc tgagatcatg   153360
ccaatgcact ccagcctagg caacacagca agactctgtc tcgggaaaaa aataataata   153420
ataagacttc tagaagctcc taaatccata gcttttcctc tataccagca tcttctaaaa   153480
atgtcagcag cagtgaagtt tcagtttggg aaataatgca tttcccctct ctggagagtg   153540
cacagttata tctccaagaa gtactgaaat tcagaagtct gcctaatatg tattaaacat   153600
ttagcttttc tcaaactttg accaccaaat cctttgtctc gctctaacta tagttaacac   153660
agaatcagtg ttcccaggag cacactgtga aaaatgtagc actctacaaa agtcctaatc   153720
tccacaggat taagtgaaac catgattaac cctctgttcc ttgtccttat tagtaccatt   153780
ttctgaagag taatgtatcc ccccaaaact tttatactag tttcactaac cagaatccat   153840
gtacataagg aaggacagat atttgctccc tactaagaca tatctattag ctacattaaa   153900
aaaagtattg catgccgatt ttaaagttat aattaactgg tgatatcaca gatattccaa   153960
gatataattg ctggaataaa cactgttgtt gaagccttct atctatctca gtactagaat   154020
taaactcaag tgcagaatgg cagacaaagt taactaaaaa tcactgtatt atttcatttg   154080
gtcctccaaa tagctttgtg agctaaggag gagaaggtgt atcatcacca cttccattt    154140 atagatgaga aatcaagtga tttactcaag gttaagtcct ccaattcttt gttatcctgc   154200 atttctctt ggctgtagtt taattaataa tcctaagaaa atgcttatat tttagagtgc     154260
agtaagagta cataaacaat gttaaatgcc catcttgcat gtataaaaag ttatagcaag   154320
aaatctggct gggaatggtg gctcacacct gtaatcctgg cactttggga ggccgaggca   154380
ggaggattgc ttgagcccag gagtttaaga ccagcctggg caacataggg agatcctgtc   154440
tctacaaaaa aatttagcca gacacagtgg cttgtgtcct agctactcag gaggctgagg   154500
tgggaggatc acttgagcca aggaggtcaa ggctccagtg agctatgatt atgccactca   154560
gacatggtgg cttgtgccta cagtcctagc tactcaggag gctgaggtgg gaggatcact   154620
tgagccaagg aggtcaaggc tccagtgagc tatgattatg ccactgcact ccagcctgga   154680
tgacacagtg agaccctatc tatctcaaaa aaaaaaaaa agaaaagaa aagaaaaga      154740 aaatccttta actgacttca tcttaacctt ttagttccta aggacggtct gaagagccaa   154800
gagctatttg atgaaattag aatgacctac atcaaagagc taggaaaagc cattgtcaag   154860
agggaaggaa actccagcca gaactggcag cggttttatc aactgacaaa actcttggat   154920
```

```
tctatgcatg aagtaagtgt caaacataaa gccaaatata agagttttct gggacaaagt 154980
atgttttgat tagtgaatat aattatatac cagcagcgcc cccaccccg cccccagttt 155040
gtggatgttg gtgatagctt gagttcaact tatgaacttc agttttgtag acattttcc 155100
taaggccaat tatgaaatat cctttcacct agtcatgtgt atataaaatc accatgttat 155160
tacagaattt agtaatactg tttttaaaaa gtatgattaa tccattaaat tagaataatg 155220
caccctttcat atattatggt actacagtga ttcatgaaat aattctatat aattctacat 155280
acaatcaaag aaatataaaa tgtgttttgt acggaagtgc ttattttca tctgggaat 155340
tccagtgaga ttggtatatt ctaggccaga taatttttc aaaatagagg acaacaaaca 155400
tgagatgttc ccactgacca atttggaagc ctgatcatta ccatatcttc tcttgcaggt 155460
ggttgaaaat ctccttaact attgcttcca aacattttg gataagacca tgagtattga 155520
attccccgag atgttagctg aaatcatcac caatcagata ccaaaatatt caaatggaaa 155580
tatcaaaaaa cttctgtttc atcaaaagtg actgccttaa taagaatggt tgccttaaag 155640
aaagtcgaat taatagcttt tattgtataa actatcagtt tgtcctgtag aggttttgtt 155700
gttttatttt ttattgtttt catctgttgt tttgttttaa atacgcacta catgtggttt 155760
atagagggcc aagacttggc aacagaagca gttgagtcgt catcactttt cagtgatggg 155820
agagtagatg tgaaattta ttagttaata tatcccagaa attagaaacc ttaatatgtg 155880
gacgtaatct ccacagtcaa agaaggatgg cacctaaacc accagtgccc aaagtctgtg 155940
tgatgaactt tctcttcata cttttttca cagttggctg gatgaaattt tctagacttt 156000
ctgttggtgt atccccccc tgtatagtta ggatagcatt tttgatttat gcatggaaac 156060
ctgaaaaaaa gtttacaagt gtatatcaga aaagggaagt tgtgccttt atagctatta 156120
ctgtctggtt ttaacaattt cctttatatt tagtgaacta cgcttgctca ttttttctta 156180
cataatttt tattcaagtt attgtacagc tgtttaagat gggcagctag ttcgtagctt 156240
tcccaaataa actctaaaca ttaatcaatc atctgtgtga aatgggttg gtgcttctaa 156300
cctgatggca cttagctatc agaagaccac aaaaattgac tcaaatctcc agtattcttg 156360
tcaaaaaaaa aaaaaaaaaa gctcatattt tgtatatatc tgcttcagtg gagaattata 156420
taggttgtgc aaattaacag tcctaactgg tatagagcac ctagtccagt gacctgctgg 156480
gtaaactgtg gatgatggtt gcaaaagact aatttaaaaa ataactacca agaggccctg 156540
tctgtaccta acgccctatt tttgcaatgg ctatatggca agaaagctgg taaactattt 156600
gtcttcagg acctttgaa gtagtttgta taacttctta aaagttgtga ttccagataa 156660
ccagctgtaa cacagctgag agactttaa tcagacaaag taattcctct cactaaactt 156720
tacccaaaaa ctaatctct aatatggcaa aaatggctag acaccatttt tcacattccc 156780
atctgtcacc aattggttaa tcttttcctga tggtacagga aagctcagct actgattttt 156840
gtgatttaga actgtatgtc agacatccat gtttgtaaaa ctacacatcc ctaatgtgtg 156900
ccatagagtt taacacaagt cctgtgaatt tcttcactgt tgaaaattat tttaaacaaa 156960
atagaagctg tagtagccct ttctgtgtgc accttaccaa ctttctgtaa actcaaaact 157020
taacatattt actaagccac aagaaatttg atttctattc aaggtggcca aattatttgt 157080
gtaatagaaa actgaaaatc taatattaaa aatatggaac ttctaatata ttttatatt 157140
tagttatagt ttcagatata tatcatattg gtattcacta atctgggaag ggaagggcta 157200
ctgcagcttt acatgcaatt tattaaaatg attgtaaaat agcttgtata gtgtaaaata 157260
```

-continued

```
agaatgattt ttagatgaga ttgttttatc atgacatgtt atatatttt tgtagggtc    157320
aaagaaatgc tgatggataa cctatatgat ttatagtttg tacatgcatt catacaggca   157380
gcgatggtct cagaaaccaa acagtttgct ctaggggaag agggagatgg agactggtcc   157440
tgtgtgcagt gaaggttgct gaggctctga cccagtgaga ttacagagga agttatcctc   157500
tgcctcccat tctgaccacc cttctcattc aacagtgag tctgtcagcg caggtttagt    157560
ttactcaatc tccccttgca ctaaagtatg taaagtatgt aaacaggaga caggaaggtg   157620
gtgcttacat ccttaaaggc accatctaat agcgggttac tttcacatac agccctcccc   157680
cagcagttga atgacaacag aagcttcaga agtttggcaa tagtttgcat agaggtacca   157740
gcaatatgta aatagtgcag aatctcatag gttgccaata atacactaat tcctttctat   157800
cctacaacaa gagtttattt ccaaataaaa tgaggacatg ttttttgttt ctttgaatgc   157860
tttttgaatg ttatttgtta ttttcagtat tttggagaaa ttatttaata aaaaaacaat  157920
catttgcttt ttgaatgctc tctaaaaggg aatgtaatat tttaagatgg tgtgtaaccc   157980
ggctggataa atttttggtg cctaagaaaa ctgcttgaat attcttatca atgacagtgt   158040
taagtttcaa aaagagcttc taaaacgtag attatcattc ctttatagaa tgttatgtgg   158100
ttaaaaccag aaagcacatc tcacacatta atctgatttt catcccaaca atcttggcgc   158160
tcaaaaaata gaactcaatg agaaaaagaa gattatgtgc acttcgttgt caataataag   158220
tcaactgatg ctcatcgaca actataggag cttttcatt aaatgggaaa agaagctgtg    158280
cccttttagg atacgtgggg gaaaagaaag tcatcttaat tatgtttaat tgtggattta   158340
agtgctatat ggtggtgctg tttgaaagca gatttatttc ctatgtatgt gttatctggc   158400
catcccaacc caaactgttg aagtttgtag taacttcagt gagagttggt tactcacaac   158460
aaatcctgaa aagtatttt agtgtttgta ggtattctgt gggatactat acaagcagaa    158520
ctgaggcact taggacataa cacttttggg gtatatatat ccaaatgcct aaaactatgg   158580
gaggaaacct tggccacccc aaaaggaaaa ctaacatgat ttgtgtctat gaagtgctgg   158640
ataattagca tgggatgagc tctgggcatg ccatgaagga aagccacgct cccttcagaa   158700
ttcagaggca gggagcaatt ccagtttcac ctaagtctca taattttagt tccccttttaa  158760
aaaccctgaa aactacatca ccatggaatg aaaaatattg ttatacaata cattgatctg   158820
tcaaacttcc agaaccatgg tagccttcag tgagatttcc atcttggctg gtcactccct   158880
gactgtagct gtaggtgaat gtgttttttgt gtgtgtgtgt ctggttttag tgtcagaagg   158940
gaaataaaag tgtaaggagg acacttaaa cccttttggt ggagtttcgt aatttcccag    159000
actattttca agcaacctgg tccacccagg attagtgacc aggttttcag gaaaggattt    159060
gcttctctct agaaaatgtc tgaaaggatt ttattttctg atgaaaggct gtatgaaaat   159120
accctcctca ataacttgc ttaactacat atagattcaa gtgtgtcaat attctatttt    159180
gtatattaaa tgctatataa tggggacaaa tctatattat actgtgtatg gcattattaa   159240
gaagcttttt cattattttt tatcacagta atttaaaat gtgtaaaaat taaaccagt     159300
gactcctgtt taaaaataaa agttgtagtt ttttattcat gctgaataat aatctgtagt   159360
taaaaaaaaa gtgtcttttt acctacgcag tgaaatgtca gactgtaaaa ccttgtgtgg   159420
aaatgtttaa cttttatttt ttcatttaaa tttgctgttc tggtattacc aaaccacaca   159480
tttgtaccga attggcagta aatgttagcc atttacagca atgccaaata tggagaaaca   159540
tcataataaa aaaatctgct ttttcattat gtgactccaa catgctttg tagaacttgt     159600
acagttccga ttgtccaatc tgattttgt ttactgaaag tagagttacc cctgcttcag    159660
```

```
gaaccttaag ataatatggt gggcatttaa atgtcagtgt ggcaatgttc gcctgctaat 159720
atggcataga ttcaaaataa gcttaaccct ggtgccaaag acctgaagat tatcccatcc 159780
atgcctcaaa tggttgtgtg ccaattactg caaagggtac taagggaagg agaaattcac 159840
tcctgaggct gcttcaaatg tatgtcttta tcacaaaaga tgacatttta tgtaagctaa 159900
tgttatctag tcaaaattct tagcttattt taaaatcaac tcttcaagaa aaggaataaa 159960
catttaatat aaatatcata gcagtattgc acatagaata gaaaggtcgg gcagggtagt 160020
ggaagtcagc tattctatac aatccattcg gtattttcca aaacatttga tgttcaggcc 160080
atatccagga actggatgac ctaacaaact tctctgagta ccttttttc cacaagagat 160140 ctccatcact aagaaaaaaa gcattgtgat ttaaaagcca aatttgcctt atccatcatc 160200
atgtgcacca agtatttgct acctgcctac tatataatat tgaagataca atgtgaataa 160260
gaaaaatact attgctaccc tcaatcagag tatgtgattg gaaaagtgta taacaaacct 160320
ttcccagtgt cttcaggtat aatgcagaga taccagatac ggcatcaatg tgtatacaca 160380
ttatggctgt accattcact ttaagtagta accttacatt tctgtagaac accttcacat 160440
acatttttaa caagcctcac tgaatgaatt aatgacatga aaataatgag gcagattatt 160500
ctcgtttcca ttttataagg aagtaaactc tgtaagaaag taaacaggct cagaatttaa 160560
gcactgattc atagcccta gctcccatgt tattgaaatt tgaatggaaa gcctctaatg 160620
aggccattca tctatcagat gtcaaagagc atgtctctgg cctatgagcc tctcagggaa 160680
ctggttatgt ttttctgttt taaattaaac taatgcttta ctgagcactt actatgtgcc 160740
acgcacaatg ataattcaat atattatttc atttaatcat agtacccctc taaagtacta 160800
ctgtaaagca gtgctattat cctcattgca tttatatcag gaaactgtgg cttaaagaat 160860
tgagtaactt gcctacagtc acaaagctag ctccagaatc catagtttta aaaaccacta 160920
ttgagaaatt actaatatga gctaactagg gcgaatgaac ccatattgat cattatgtgt 160980
ctggcctttt gacatgtcct catttaatct aatccctttt gctaccgtat caattttgac 161040
ttagaaattt aacaatgata cattagtccc cgcttatcta cggaggatat gttccaagac 161100
tcccaatgga tgcctgaaac atagatagta ctgaactgca tgttttttcc tatattcat 161160 acctatgata aagttaattt acaaattaga tgcagcaaga gattaacaat aactcaatta 161220
caacaatata ctgtaataaa agttatgtga atgtgagctc tcaaaaaatc gtactatact 161280
gagggtaact gagaccacgg aaagtgaaac cgcagataag gcgggcacta ttgtatttcc 161340
ttctcttaaa aacgtgtcct gtaccctggg gtggttgatg gtggaaaata ctagttgccc 161400
acagattaca gaatgcccct tggtttgtct aatatacaac agggagcctg tctcactaat 161460
gcccacagaa aaatcaaaca tttcttcaag tgatatggag catataggt acagtcaaac 161520 caaggaagaa agttgtttat aaatgagaac tatagtgcaa gttaaaattt gctcctagtt 161580
ttgcaggtaa agagccagac tttgggtgta gaaaaaagt tgaaaatact gaggctttta 161640
cataaggtga tttttttttt tttttttttt ttttagaatt tcaactaatc tcttttaact 161700
taagtcgttc ttaacagtat tggtaacttc atagcacttt ctttctggtg aaataacccc 161760
atcctccctc ttatttaggc ttcctgtttc ctagttaaaa tggggcagta ctttgttagg 161820
gaagtatttt tacttcactt ggttacaaac atgtaagtct cagaacaaaa gagtttgtgc 161880
agaccatatc agacactcaa aagactttct tcactctacc cacttgagta agagacaatt 161940
tatattctgt tcaccttatg taccctcacc aaaaatattc aataggtaa taatgtgtat 162000
``` a                                                                                  162001

<210> SEQ ID NO 8
<211> LENGTH: 2051
<212> TYPE: DNA
<213> ORGANISM: Homo sapiens

<400> SEQUENCE: 8

| | | | | | |
|---|---|---|---|---|---|
| agtttgcacc | gaccccgatc | tggcagcgcc | gcgaagacga | gcggtcaccg | gcgcccgacc | 60 |
| cgagcgcgcc | cagaggacgg | cggggagcca | agccgacccc | cgagcagcgc | cgcgcggacc | 120 |
| ctgaggctca | gaggggcagc | ttcaggggag | acaccccac | tggccaggac | gccccaggct | 180 |
| ctgctgctct | gccactcagc | tgccctcgga | ggagcgtaca | cacccaccag | gactgcattg | 240 |
| ccccagctgt | gcagccctg | ccagatgtgg | gaggcagcta | gctgcccaga | ggcatgcccc | 300 |
| cctgccagcc | acagcgaccc | ctgctgctgt | tgctgctgct | gctggcctgc | cagccacagg | 360 |
| tccctccgc | tcaggtgatg | gacttcctgt | ttgagaagtg | gaagctctac | ggtgaccagt | 420 |
| gtcaccacaa | cctgagcctg | ctgccccctc | ccacggagct | ggtgtgcaac | agaaccttcg | 480 |
| acaagtattc | ctgctggcg | gacacccccg | ccaataccac | ggccaacatc | tcctgcccct | 540 |
| ggtacctgcc | ttggcaccac | aaagtgcaac | accgcttcgt | gttcaagaga | tgcgggcccg | 600 |
| acggtcagtg | ggtgcgtgga | ccccgggggc | agccttggcg | tgatgcctcc | cagtgccaga | 660 |
| tggatggcga | ggagattgag | gtccagaagg | aggtggccaa | gatgtacagc | agcttccagg | 720 |
| tgatgtacac | agtgggctac | agcctgtccc | tgggggccct | gctcctcgcc | ttggccatcc | 780 |
| tggggggcct | cagcaagctg | cactgcaccc | gcaatgccat | ccacgcgaat | ctgtttgcgt | 840 |
| ccttcgtgct | gaaagccagc | tccgtgctgg | tcattgatgg | gctgctcagg | acccgctaca | 900 |
| gccagaaaat | tggcgacgac | ctcagtgtca | gcacctggct | cagtgatgga | gcggtggctg | 960 |
| gctgccgtgt | ggccgcggtg | ttcatgcaat | atggcatcgt | ggccaactac | tgctggctgc | 1020 |
| tggtggaggg | cctgtacctg | cacaaccctg | tgggcctggc | caccctcccc | gagaggagct | 1080 |
| tcttcagcct | ctacctgggc | atcggctggg | gtgcccccat | gctgttcgtc | gtcccctggg | 1140 |
| cagtggtcaa | gtgtctgttc | gagaacgtcc | agtgctggac | cagcaatgac | aacatgggct | 1200 |
| tctggtggat | cctgcggttc | cccgtcttcc | tggccatcct | gatcaacttc | ttcatcttcg | 1260 |
| tccgcatcgt | tcagctgctc | gtggccaagc | tgcgggcacg | gcagatgcac | cacacagact | 1320 |
| acaagttccg | gctggccaag | tccacgctga | ccctcatccc | tctgctgggc | gtccacgaag | 1380 |
| tggtcttcgc | cttcgtgacg | gacgagcacg | cccaggcac | cctgcgctcc | gccaagctct | 1440 |
| tcttcgacct | cttcctcagc | tccttccagg | gcctgctggt | ggctgtcctc | tactgcttcc | 1500 |
| tcaacaagga | ggtgcagtcg | gagctgcggc | ggcgttggca | ccgctggcgc | ctgggcaaag | 1560 |
| tgctatggga | ggagcggaac | accagcaacc | acagggcctc | atcttcgccc | ggccacggcc | 1620 |
| ctcccagcaa | ggagctgcag | tttgggaggg | gtggtggcag | ccaggattca | tctgcggaga | 1680 |
| ccccccttggc | tggtggcctc | cctagattgg | ctgagagccc | cttctgaacc | ctgctgggac | 1740 |
| cccagctagg | gctggactct | ggcacccaga | gggcgtcgct | ggacaaccca | gaactggacg | 1800 |
| cccagctgag | gctgggggcg | ggggagccaa | cagcagcccc | cacctacccc | ccaccccag | 1860 |
| tgtggctgtc | tgcgagattg | gcctcctct | ccctgcacct | gccttgtccc | tggtgcagag | 1920 |
| gtgagcagag | gagtccaggg | cgggagtggg | ggctgtgccg | tgaactgcgt | gccagtgtcc | 1980 |
| ccacgtatgt | cggcacgtcc | catgtgcatg | gaaatgtcct | ccaacaataa | agagctcaag | 2040 |
| tggtcaccgt | g | | | | | 2051 |

<210> SEQ ID NO 9
<211> LENGTH: 20001
<212> TYPE: DNA
<213> ORGANISM: Homo sapiens
<220> FEATURE:
<221> NAME/KEY: misc_feature
<222> LOCATION: (1)..(993)
<223> OTHER INFORMATION: n is a, c, g, or t
<220> FEATURE:
<221> NAME/KEY: misc_feature
<222> LOCATION: (2653)..(2743)
<223> OTHER INFORMATION: n is a, c, g, or t
<220> FEATURE:
<221> NAME/KEY: misc_feature
<222> LOCATION: (5539)..(5563)
<223> OTHER INFORMATION: n is a, c, g, or t

<400> SEQUENCE: 9

```
nnnnnnnnnn nnnnnnnnnn nnnnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnnnnnnnn nnnnnnnnnn nnnnnnnnnn       180
nnnnnnnnnn nnnnnnnnnn nnnnnnnnnn nnnnnnnnnn nnnnnnnnnn nnnnnnnnnn       240
nnnnnnnnnn nnnnnnnnnn nnnnnnnnnn nnnnnnnnnn nnnnnnnnnn nnnnnnnnnn       300
nnnnnnnnnn nnnnnnnnnn nnnnnnnnnn nnnnnnnnnn nnnnnnnnnn nnnnnnnnnn       360
nnnnnnnnnn nnnnnnnnnn nnnnnnnnnn nnnnnnnnnn nnnnnnnnnn nnnnnnnnnn       420
nnnnnnnnnn nnnnnnnnnn nnnnnnnnnn nnnnnnnnnn nnnnnnnnnn nnnnnnnnnn       480
nnnnnnnnnn nnnnnnnnnn nnnnnnnnnn nnnnnnnnnn nnnnnnnnnn nnnnnnnnnn       540
nnnnnnnnnn nnnnnnnnnn nnnnnnnnnn nnnnnnnnnn nnnnnnnnnn nnnnnnnnnn       600
nnnnnnnnnn nnnnnnnnnn nnnnnnnnnn nnnnnnnnnn nnnnnnnnnn nnnnnnnnnn       660
nnnnnnnnnn nnnnnnnnnn nnnnnnnnnn nnnnnnnnnn nnnnnnnnnn nnnnnnnnnn       720
nnnnnnnnnn nnnnnnnnnn nnnnnnnnnn nnnnnnnnnn nnnnnnnnnn nnnnnnnnnn       780
nnnnnnnnnn nnnnnnnnnn nnnnnnnnnn nnnnnnnnnn nnnnnnnnnn nnnnnnnnnn       840
nnnnnnnnnn nnnnnnnnnn nnnnnnnnnn nnnnnnnnnn nnnnnnnnnn nnnnnnnnnn       900
nnnnnnnnnn nnnnnnnnnn nnnnnnnnnn nnnnnnnnnn nnnnnnnnnn nnnnnnnnnn       960
nnnnnnnnnn nnnnnnnnnn nnnnnnnnnn nnntacttgg ccctcctaat tgggtgttct      1020
cagtgaaaac gaggacactg ctaatatgct ttagaaaata gccctcacat tctccctgtt      1080
cccaatcccc cacttactct aagctcccca ggtagcaata attcagaagt caaattgctc      1140
agcactccta tggttcaagt gattcttgtg tctcagcctc ccaagtagct gggactacag      1200
gagcccacca ccacgcccag ttaattttg tattttttag tagagatggg gtttcaccat      1260
gttgaccagg ctggtctcga actcctgacc tcaagtgatc cactggcctc ggcctccaaa      1320
agtgttggga ttacaggcgt gagccactgc gcccagcctc aaccttctag tgaaccctcc      1380
atgctctgtt atcttttatt cctcttggat ttttgttgtt tcttttcttt tcttcttct      1440
ttttcttttc ttttttttttt tttgagatgg agtttcattc ttgttgccca ggctggagtg      1500
caatggcaca accttggctc actgcaacct tcgcctcctg ggttcaagca atttgcctgc      1560
ctcagcctcc caagtagctg ggattacagg catgtgctac catgcctggc gaattttgta      1620
tttttagtag agacagggtt tctccgtgtt ggtcgggctg atctcaaact cccgacctca      1680
ggtgatcagc ccgccttggc ctcccaaagt gctgagatta caggcatgag ccaccacacc      1740
```

```
cagccttttt gttgtttctt ctgagagatt tcttcaactc aattttccaa cccttctatt    1800
aaatttttta aattccagat attctatttg cagccggcaa ggactcttcc tgcgctctgc    1860
ttgttttcca aagcattccg ttctagtttt tatgggagca tcatcctttc atgtctctaa    1920
ggataatcag agtggttaaa atgttcttga agttttcttc tgttccctgc agtagctctg    1980
tttcctccag tttcctcttt cccaagtgat tggtctgtct catataccta gaggtcttgc    2040
tttgcattca catctaaggg caaaaggcgc taggatgcag tgcggaggtc cattcgcttt    2100
gtcgtaaggt ttgtgccttt cttagtcctg cagtggttga gtaaaacctg accatcccac    2160
accctcaaat actaagtgcc cctgggtagt gatgtggagg ggccttctta ttaatgtgag    2220
gaaatgcttg tgttataggt tgtggtgaga acgctggtt acaaaactat atcaaagtaa     2280
aaatgtatta atgcacagta aagacacctg gaaaaaaaat gccctttaat gctcacagaa    2340
ggtctctccg aggggcagcc ccaccaccct cctgtttccc ttcctgcatt tccacgtttt    2400
tctgggccca gatgcagcct cccctcccac ccctggtccc tccgccttgg cttccggctg    2460
tcgctttcat ccctcctcct catcagcccc ttgcagaact ccagggtggg gcttctgagt    2520
ctcgctggca gtatgggctc cataagtctt gctggacacc gaaattaagt tctgcaggtg    2580
ccgtctccag aatccccagc acagatagac aaacccacat ctcaggggtg gggggtgcag    2640
acctgccccc agnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnntcccagc tgccctctgt    2760
ttatatgtct caccaatgtc aagggaaacc agaactggat agcagttgaa acacatattt    2820
tgttcgggac tattgtaata ggggaaaaaa gattttagta tagacctggg ctcaactctc    2880
aatgtggcac aggcaagtgg ggatttagat ctgaggagca gggcggggtc agtgggtgga    2940
aaattactgg cacgaaacac ctgtctggag gattctggct aaacccagga acaggaagc     3000
ttgctgaggg caggcagggt tagcagacat cgcctggggg tggcggaggc tgagaaccct    3060
acccaggtaa aatgaagctt gctgacggca gacagggtta gcagacacgg cctggaggtg    3120
gcagaggcta aggaacctac ccaggtaaaa cgaagcttgc tgacggcaga cagggttagc    3180
agacacggcc tggaggtggc agaggctaag gaacctacca aggtaaaatg aagcttgctg    3240
aaggcagcca gggtgagcag atattgcctg ggggtggcgg aaactgagga ccctacccag    3300
gtaaaaggaa gcctgctgaa ggcaggcagg gtgagcagac attgcctgtg ggtagcagag    3360
gctgaggact ctacccaggt aacaggaatc ttgcttaagg caggcaaggt gagcagacat    3420
cgcctggggg tggcggaggc tgaggactct acccagataa caggaatctt gctgcgggca    3480
gccagggtga gcagacgtcg cctgggggtg gtggaagctg aggaccctac ccaggtaaaa    3540
ggaagcttgc tgaaggcagg caaggtaagc agacatcgcc tggggtggc ggaggctgag     3600
gaccctgatc agatatgggg ggatggaggc ttcttgccaa actgacttag cagagttctt    3660
gctgaatctg gattttataa ggcagaatgc agatgagcct gtgagaaggt tctgaagccg    3720
gactacagtt tggtcaagca aacaatcttg tcatggattc agtcatataa ataagggtca    3780
cccagcccag gggaggtgcc ccaccccatc tgttccctct ccctcccac actgagtccg     3840
aaccttcag gctttgcccc cttcacacac tccaaattta ttcttctact tctcttcctg     3900
caggtaccag actccggcca cccagcgctt acctgggact gctgggcctc tgcccgtgg     3960
ggacctgtcc tccaggaaac aaggccagac acaggagggc agggaggact cttctccagg    4020
gccggtgcgc cgtctcttca gccccatggc acttgactta ggcagagcct acagcaccct    4080
caccccagtc cctgcagcca ccaggaggtg gtccccctca tcccattagc catcaccgcc    4140
```

-continued

```
attcacagag gtctcggact gaggctggca gggggagcac catgacccaa gatcagaacc     4200
ctgttgtctg tgcctctgga gaggtggggg caggagctga gggagggttt gggtggagag     4260
gggagaagat gcagtagcag gagcagatgc tggcaggtag agacaaactt ttatgacctt     4320
tgccttctga cctttgcctc tggccactgc tccaactaaa acagaatggc ccctctgggg     4380
aacagggctt cctatgggct gggaagcatg gagcccccac agtgtggcta tgcaggggag     4440
tgaggaccag gtgggggcag gcctgtgggg gtcacagagc tgggctaagc ttcagaggga     4500
agtggcccct gggagggggga atggctgggg ttaagaccct gggttcccac gcccccaaaa     4560
cagaagtaga attagggaga aaggaccccc aagaccaagg acggcaccta tcagaggagc     4620
tctccacggg caggaggtgt cccagggtga gggtggccag gacaggtcta gggaaatgca     4680
ggtggagcag gacccagaga tggattggag atgccgagg ggaggcttcc tagcgggagc     4740
ggagacaggc actgcagaca agtgtcagcg ggaggggctc tgggtgggga agaagactgg     4800
gacttggagg aagacctctc cagggagaag ggaggagggg gaaggagaag gggaggaagt     4860
gggaggagga gagtgctcat cctggaagcc acagcctcgg agagaacttt ctagaaggaa     4920
ggcatgacca tcagtgtccc aggatgctga gaggccagga aggtgaggc ctcaaggcgc     4980 catggggttg tggtgacccc aagatcactg gcacagagc agggatggct gggggtggaa     5040 ggggagggggc gcgggctgag gttctagggc cccaaagcca ggtgtgatgt ggctctaggg     5100
ggagtgagga aggggagaat gtccctctga gcgtgcctct tggggaaggc aggggttctg     5160 gctgggctt ctccactccc aggaaaggag gtggtgtgga aggagcgggt gggacggagg     5220
agagagcgcc ccgcggccgc aggaccagca ggtgggggac cagggtcagc gctgctggag     5280
gggccttagc gcgacaggac tggccagaga ccggggatgt ggcacagaaa gagttaaagg     5340
gcaccccagg gaccgccctg ccggtccacc catgtcaccc atgttggccc ctactccagc     5400
ccccgtctgc tctgcagggg aaggaaccgg gagccgcggt gggggcgact gggggtgtcg     5460
gtctttccag aaaatcaggc aggcatcagg aaagaagggg cgagaacccg gggacgcgag     5520
aggaaggggg cgagggggnn nnnnnnnnn nnnnnnnnnn nnncgcgtcc cagggcgtcc     5580
cctcccggga ctgggaccca ccgcgaccac cacctgctgg gccagggtcc gcgggctcag     5640
gggtctgcag gattagggtc tgcggaacca ggaccgtgg gacaaaggtc tgtggggcgc     5700
gggtccgcgg ggtggaattc agcgcgccga gtctgcgtat ggccggggta cgaggcgctc     5760
cctgcgcagg gtgggcagga ccgaagctcg ccgggagctg cgcggagggc gggcggggac     5820
cctccggtgc cgctcccacc ccgcggggcc gcccccgagc ccgccctccg ccgccgccct     5880
cgccctcgtc ccgccggaa agtttgcacc gaccccgatc tggcagcgcc gcgaagacga     5940
gcggtcaccg gcgcccgacc cgagcgcgcc cagaggacgg cggggagcca agccgacccc     6000
cgagcagcgc cgcgcggtga gcacctgggc cgcggacccg aggggacgtt ggggagtcga     6060
cccggtgggg acagagaccg cggggcggc gcggcgggc cggggcgcg gggagcgggg     6120 agccggccgg gcggtctccg gggtccgggc tggtgcgctc ctcagtcccg tcagacaccc     6180
ccgttcccaa ccccggctcg gacaccaccc ggtcctgcac cgtcgggcag gtccaggggt     6240
ctcagcccct ccccgttct ctggtcctgg ggggcgcggc tggggcggg ggtgtcgctg     6300 gccgcctggc gccctgcggc ggccacactg cagcggccac actccccact cagggccccg     6360
ggccccgccg ccctggggag cgcacaaagc gccgcggacg cgtccccgag gcgcggggtc     6420
tcaccagcgc tgtctcccct cggtgggctc ctgccccgag gactgccgg tggcaccggc     6480
```

```
gcggcccagg atggggtgag gggtgtctgc gccccgcctg gccgctcctc ttccgcggcc      6540
cacactggcg actttgaccc cggcaagcgg gtcactgccc tgcccggctc cggcccccc       6600 ggcgcccac cacccggccg actcggccac cgggcttatg ctccgactct gaaccgactg       6660
accccggccc cctcggcgcc cgcatcctcc aaggaccggc cagggctgct ctctgccctt      6720
ggtattgggg acatcagggt tgggggggtct gggtgcaccc acgcctgccc cgccccacg     6780 gggtgagggc gcagggatag ggctttgtca acagcctgtg gcccctgatc ccgcccggt      6840 gccctgacct tccactacct tctctggttt cacaaaaaca tcccggctcc catcccggag     6900
ctcctcaaag cgtctgagag gcccttgcg gacgccctgg gagccccgct gccttcctgg      6960
accagtggcc gctccaccca tcctggggc ccagctccag gtctgcgggt ccctcagccg      7020
cccccagtgg gaatcggtgg agcctgacgc agccaggagc gcccaagagt cacgtgttct    7080
gccagggagg acatgggaca ggacacgggg tgccagccct gcaaagcggc cggggcagtg    7140
gagctcaggt ggccctaagc cctggtggtg gctggtgtgg cccggcaggc agctgtggga    7200
gggaggaagg gggtggcatg cggtgggggt ctagagaagg cgggcagggc acctcgggag    7260 ccccccatt gggcacctcg ggaacccccc acattgggca cctcgggaac cctcccattg     7320
ggcacctcgg gaacccccca cattgggcac ctcgggaacc cccgcattgg gcacctcggg    7380
aaccctccca ttgggcacct cgggaacccc ctattgggc acctcgggaa ccccacatt     7440 gggcacctcg gaacccccc ctattgggca ccttgggaac ccctcccta attctcagct      7500 gactccaagg cctgagaagg agcttggtca cctggactgt gaaggtggag ggtggggtcc    7560
ctggtgggtc gtcccaccta ccagctgtgt cgccggaagg gtaatacgga gcactgtggc    7620
cccggggagc cccgagtggc agctccacag ctgggagttt ctgtccactc cttcagtcaa    7680
caaacattga tcctgggctg accggggccc ggggtgtca gtgtctcctc tcggggagga    7740
gggctgggtg agatcaacag aggagcctcc cttcttccct tcaggctggt gtcaccttca   7800 gtgatgggc agggtcccca cttgggaagt taaatcgtcg tccccgtccc aggaccacag   7860
cagcctcagc cctgctctcc aggccaggct ctctcatggg tgctcagctg gaaattggtc    7920 ccccccggc tccacccacc cctgttgggg tgaggagctg gagtctccct acccatatgg    7980
gacccaccac ccgcagggaa cggaggacgc tcacacttct gcacctcctg cctcactatc    8040
agagacccag tggagaattg cctcccacct cacctcttgt attcagaggc cctgaccct     8100 agggatccgg gactaggggt gccctatggg gagcccacct gtggcctgtg gatgctgagc    8160
tgtcggggga atcctccagg atccccagcc ccaccttccc aaccttctgt tgaggctgag    8220
gggacacaga gccccactcc tgggtcctga ctgtttcaaa gaaaggcctg ggggactggg    8280
cagccaaccc ctccctcggc tcgctggggt ctccagactg gctgcccggc tggaaggtgg    8340
ggccctggca cgcgaggacc tcatgtgtgg aggcactggc ttgggggtg ctcccagtgg    8400 ctctagagtc aacatgacag gcatcgaatg gctcctgttt ctctggcaga gttggggcag    8460
agccaggctt ggccacgctg ggctctaagg ggctgtcatt ttgcccaggg agctcctggc    8520
tgggtggtcc tccccccagg gtgagcacgc gtcccccca cccccacttc gaggcgccca   8580
ggcagggaac agctcattgg ccagtgtcct tcctccttgt ccccgcctg catctccacc    8640 atccaccctg ctccagctgc cccttgtccc tctccccgtc cctgcccag agcccaggt      8700 ctcccctgca cccctgagcc tgcccaccta gcagtgcccc tcgtccaggg ccctctgggg    8760
ttgggggtgc acacagtggg gagaggcggc tcctgctgct cctcacccag cccggctcag    8820
tggccggagc cgcccaggac agtggcagta gatggggctg tttgatcagg atcagggaag    8880
```

```
ataaggcccc ttgcgtgacc ccagagctgg ggacgccaaa actgcccctc ctcccccacc   8940
cgcctgccgc tgtctccgcc agggagaggc ccctactctg tgggtccttc gccccagcac   9000
caagcctgca tggctgctca cctggctcag gaactgggga tcagcgacac acgggtcctg   9060
cctcccatcg gcccctacat gagcccaggg tccaagggct gcggttggga gctctttagc   9120
agtctgtgac gcaggtgcct gtccctgtca ttcagctgtc acactgcttg gggcatctca   9180
ggccccgtta gcggggcagc cctgggtgga gctggcccca cgcgggctca cccagccgct   9240
acctggagga ggctaaaatc caggctgtcc cgtggcagcc agcagtccag gcctgcccgg   9300
aaaccctctg ctccagctgc agccttcgcc catctccttg cccctctccc cggcttcccc   9360
ctggcactgc cttccagctg gctggccctc catctgccca gccatccatc cacacctctt   9420
attccatttg agggtgcccc aaagaagagc ccgtaacagc ccgggggctc atagccagcc   9480
actcgcggga ccccgcacat gcacgtggac ccacaggaag accctccctg cttctcccac   9540
agaattcagt tggtgcagaa actgggctct gtagcaacga aaggccgatt tgtgtagctg   9600
ttgccacccc gaactcccag ctcagatgct ggctgtggca tggggaccag gggctgtgac   9660
tcccacagcc ctggcaggca ccacggggga tgtcctcccc accctgtgcc cccaccctag   9720
gccagctcct cctccaagtc gacgcccgca gtgctaacct caaaggactg tgcagccagc   9780
ctgtggcgtc ccatgggatc caggaagccc aaccgagcct tgcacggcac ccacgaggca   9840
cctaggcacc ccggtgctgg gcaggggggca cacatgtgac acagacccct gagtgtgggc   9900
cccacacact tggcctggca cagctgcaag ccagcccagc cactttgctc gctgtggcac   9960
tggggccaag tgatggaagg tccaggcacc gccaccctca cgcttggcac attggctcag  10020
gtcagcctgg caagccagct ttcccagggg ctaagaatag gtgaggagga tggtgaggaa  10080
gcagccgggg gctgtcaact gagggaggag gtcaccatct ggggaggctg gtcccccacc  10140
caagagcatt gggtcaccct gcaggaaggt ggctgccacc agcaatgaga cgaggggctc  10200
tgcgaccctc agagctgcca gccagccagc cctgggtggc aagagtgact cctcctgggg  10260
tctcctccct cctatcgccc tctttttttt tttttttttt tttgagacgg agtctcgctc  10320
tgtcacccag gctggactgc aatggcgcaa tctccgctca ctgcaagctc tgcctccgg   10380
gttcacatca ttctcctgcc tcaagctccc gagtagctgg gactacaggc gcctgccacc  10440
acgcctggct aattttttgt attttagta gacatgggt ttcactgtgt tagccaggat  10500
ggtctcaatc tccagacctc gtgatccacc ccctcggcc tcccaaagtg ctgggattac  10560
aggtgtgagc caccacgccc agcccccagc tccctcttta tccctaggac cctgaggctc  10620
agaggggcag cttcagggga ggacacccca ctggccagga cgccccaggc tctgctgctc  10680
tgccactcag ctgccctcgg aggagcgtac acacccacca ggactgcatt gccccagctg  10740
tgcagcccct gccagatgtg ggaggcagct agctgcccag aggcatgccc cctgccagc   10800
cacagcgacc cctgctgctg ttgctgctgc tgctggcctg ccaggtgagg actcacagca  10860
ccctcagcac ccaggggccc tcctgtgagg actgcacact gatggctctc tgtctgcctg  10920
cctgcctgcc tgcctgtctg cctgcctgtc tgtctgtctg cccgtctgcc tgcccatctg  10980
cctgtctgtc tgcctgtccg tctgtctgtc catctgtcca tctgcctatc catctgcctg  11040
cctgtctgcc tgtccgtctg tgtctgtgtc tgcctgtcca tctgtccatc tgcctatcca  11100
tctgcctgcc tgtctgtcgg cctgcctgcc tgcctgtctg tctgctgcct gtctgtccgt  11160
ctgcctgtct gcctgtccgt ctgcctgcct gtccgtctgc ctgtccgtct gcctgcctgc  11220
```

-continued

```
ctgtctgtct gcctgcctgt ctgcctgcct gtccgtctgc ctgtccgtct gcctgcctgt      11280
ctgcctgcct gtctgcctgt ctgcccgtct gcctgtctgt ctgcctgtcc gtctgcctgt      11340
ctgtccgtct gtccatctgc ctatccatct gcctgcctat ctgtctgtcc gtctgcctgc      11400
ctgtctgtct gcctgtctgc ctgtctgtct gcctgtctgt ccatctgcct atccatctac      11460
ctgcctgcct gtctgcctgt ctgtctgcct gtctgtctgc ctgcctgtct gtctgtctgt      11520
ctggttgctt gtgcatgtgt cccccagcca caggtcccct ccgctcaggt gatggacttc      11580
ctgtttgaga agtggaagct ctacggtgac cagtgtcacc acaacctgag cctgctgccc      11640
cctcccacgg gtgagccccc cacccagagc ctttcagcct gtgcctggcc tcagcacttc      11700
ctgagttctc ttcatgggaa ggttcctggg tgcttatgca gcctttgagg accccgccaa      11760
ggggccctgt cattcctcag gcccccacca ccgtgggcag gtgaggtaac gaggtaactg      11820
agccacagag ctggggactt gcctcaggcc gcagagccag gaaataacag aacggtggca      11880
ttgccccaga accggctgct gctgctgccc ccagcccag atgggtaata ccacctacag       11940
ccccgtggag ttttcagtgg gcagacagtg ccagggcgtg gaagctggga cccaggggcc      12000
tgggagggct cggtggaga gtgtatatca tggcctggac acttggggtg cagggagagg       12060 ataggctgg aggactcacc cgggaggcag tgcctgggtt cggatgaggg aggcagccac       12120
cactgggcag agggggcag gtgtggcagc ctccattggg cagagggagc agatgtggca       12180
gccacaggtt tggcgatgca cctgggaagg atgaaaatgg cattgggtt cagcccccag      12240 agagggaggt gctgagagaa ggtcacggag aatgggggac cccagtgtgg gtttggggca      12300
catttgagat gggggggtctc caagggaagg tgtcctgcag agctgcaatt cagggctggg      12360
ctgggcgtgc tagcggaggc tggtccaggg gaggtggatg gtcaggtgag gaaggtggag      12420
gtcagatggg ggaggtggag gtcaagtggg ggagggagca gcccaggcca tgtcctgggc      12480
gaggtgacgg ccgagctcag gcttccagag agaggagaga ggcctgctga gggagcccct      12540
tctcccaccc tgccctgccc tgctctgccc tgccctaccc tacccctgcag agctggtgtg      12600 caacagaacc ttcgacaagt attcctgctg gccggacacc cccgccaata ccacggccaa      12660
catctcctgc ccctggtacc tgccttggca ccacaaaggt acccatagag gggaggaact      12720
gtgggggggg cgggcccagg gtggggctga ccccagcctc cccccacacc cccagtgcaa      12780
caccgcttcg tgttcaagag atgcgggccc gacggtcagt gggtgcgtgg accccggggg      12840
cagccttggc gtgatgcctc ccagtgccag atggatggcg aggagattga ggtccaggtc      12900
agtgggcggc aggcaggcgc ggtggggctg gatgggaacg ggcatggggg ccctgcctg       12960 gccctcacag gccactgtaa ctcgcagaag gaggtggcca agatgtacag cagcttccag      13020
gtgatgtaca cagtgggcta cagcctgtcc ctggggggccc tgctcctcgc cttggccatc      13080 ctgggggggcc tcaggtagga ttccgccagc gcccggggcg gccgcagagg acagggagga      13140
ggacgggcgc tgactggctg tgcccacagc aagctgcact gcaccgcaa tgccatccac       13200 gcgaatctgt ttgcgtcctt cgtgctgaaa gccagctccg tgctggtcat tgatgggctg      13260
ctcaggaccc gctacagcca gaaaattggc gacgacctca gtgtcagcac ctggctcagt      13320
gatggagtga gccccctcg gcggcccag gcaggtgggt gggtgggcag ccaggcaggt       13380
ggccacgtag ccgcgctcac actgcacctg taccaggcgg tggctggctg ccgtgtggcc      13440
gcggtgttca tgcaatatgg catcgtggcc aactactgct ggctgctggt ggagggcctg      13500
tacctgcaca acctgctggg cctggccacc ctccccgaga ggagcttctt cagcctctac      13560
ctgggcatcg gctggggtga gtgggctggc atgagagggg gttaaggcag gctgaccaag      13620
```

```
cctttgggac cacagctgct gccccccaca ggtgccccca tgctgttcgt cgtccctgg    13680
gcagtggtca agtgtctgtt cgagaacgtc cagtgagtat gagcggctgg acagcctggg    13740
gagggaccgg ggggctgggg tgcggcgctc tggcctgagg cagggagggg ccggggatga    13800
gcctggtgcc tggggagggg gtcatttgtg accttctccc ttccttttct gagacccgaa    13860
ttagatcctg gcaaaatcgg gacggggtg ctgaggggcg gaggggctgg gggctgtgcc    13920
ccagtatgtg agtggcctgg cctcgcaggt gctggaccag caatgacaac atgggcttct    13980
ggtggatcct gcggttcccc gtcttcctgg ccatcctggt gaggaaatga agagccagga    14040
gcgcacccca ggcccctcct cccttggcgt cctgaggctg ccccaggaga cagcagcatc    14100
ctgtctgaga gcgctgggag ggagccggca cccagacagg acaccaggac actggccagc    14160
accctggaca ctgagccagg ctgttcctcc tggctgtgt gcccaccagc cccagggcta    14220
tgtggcccag ggcctatctt gctgccaggc ccacctgcag gagggtcagg tggggccttc    14280
caagggcaca gagctgttcc ctggggctcg ggatgcccct gactcgcacc cttctcacac    14340
agatcaactt cttcatcttc gtccgcatcg ttcagctgct cgtggccaag ctgcgggcac    14400
ggcagatgca ccacacagac tacaagttcc ggtgggtgcc gcggcagctg gcgtctcgag    14460
acctggagac cctcagggcc agagggcagc tgggggtggg gactccaagc tccacgtgga    14520
tggtgcgggc cgagggtggg ggcggtgggt gactcaggcg ctgcctctgc aggctggcca    14580
agtccacgct gaccctcatc cctctgctgg gcgtccacga agtggtcttc gccttcgtga    14640
cggacgagca cgcccagggc accctgcgct ccgccaagct cttcttcgac ctcttcctca    14700
gctccttcca ggtgcccgcc cgcccgccgg ctcccccgcc cggggcgcag tgtgccaccc    14760
ctgaccaccc tgtctctcca gggcctgctg gtggctgtcc tctactgctt cctcaacaag    14820
gaggtaggtg ggagtggggg catctgagac catcagcact ggccgtcggg gtcagggca    14880
gagagaggca cagggatgcc agccccaccc ctgcccgggg gttggaacac gtggggccca    14940
agccttctcc tcccctgct cttattgggt gcagttgcca tggcgctggg tgtcaggccc    15000
ccaggacagg ttggcctcag ccccatcgct acggtgtcca ccgtggggt ccccaggtgt    15060
ctgcagactg cttccgtgg cgatgctggg tggcatagct gtgcccagca gggagcttgt    15120
gtcgctctgc accctcaga gcggagactg ggcatctccg atgaggccca cagcaggtcc    15180
cggtggggtg gagaggacag gcaggcccta ggactggcct gccccgtccc cctccccagg    15240
tgcagtcgga gctgcggcgg cgttggcacc gctggcgcct gggcaaagtg ctatgggagg    15300
agcggaacac cagcaaccac agggcctcat cttcgcccgg ccacggccct cccagcaagg    15360
agctgcagtt tgggagggt ggtggcagcc aggattcatc tgcggagacc cccttggctg    15420
gtggcctccc tagattggct gagagcccct tctgaaccct gctgggaccc cagctagggc    15480
tggactctgg cacccagagg gcgtcgctgg acaacccaga actggacgcc cagctgaggc    15540
tgggggcggg ggagccaaca gcagccccca cctaccccc accccagtg tggctgtctg    15600
cgagattggg cctcctctcc ctgcacctgc cttgtccctg gtgcagaggt gagcagagga    15660
gtccagggcg ggagtggggg ctgtgccgtg aactgcgtgc cagtgtcccc acgtatgtcg    15720
gcacgtccca tgtgcatgga aatgtcctcc aacaataaag agctcaagtg gtcaccgtgc    15780
atgtcctgga aagcagggct ggaaatgctg gggccgaagc agtggggat ggaacagcgg    15840
tgggtggtca gcgccagtgc gggctgttga agggtccccc tgctgtccca gttcactcag    15900
agttggcact ggaaccccgg aggatcccga aggcagccag cctgtgccca tctgagcagg    15960
```

-continued

```
tcctggccac cttcccatcc tggttctggc gggcagtccc cctggacgct ttggccacca   16020
gagggtcacc attcaccagc agagacgtga ggggcacagt ggctaaggcg catgaggca    16080 tcacagtccc ctgaccgacc ccatcagcac tggattcacc cgagggcgtc ttctccctgg   16140
aggccgtgag gacactggca cctggctcat cggcccgccc ttcctctgag cctcctggcc   16200
tccgtttcat ctcagctcca gcccctcgg gcaatttaca ggccacgtag cagattgaag    16260
cgggaagaaa tgggcctgaa cattgccgcg gtccaggcg acggaggagg gcaggttgcc    16320
caacttctgc acaggacccg gggtgcgcca cacacacgcc agtcctcgtg ccacacagag   16380
aggtccggcc tacgccagtc ctcgtgccac acagagaggt ccggcctacg ccagtcctcg   16440
tgccacacag agaggtccgg cctacgccag tcctcgtgcc acacagagag gtccggccta   16500
cgccagtcct cgtgccacac agagaggtcc ggcctacgcc agtcctcgtg ccacacagag   16560
aggtccggcc tacgccagtc ctcttgccac ctcgtggtgg gtgggcgccc tgcttgccag   16620
ccagggagca ccaggaaaga gctgcctcct gcgtgctgga cacaggaggt gcttcagggt   16680
ggggtctccc attgtgtggg gcccaacctg agtctaaggg cccagggacc acacagcggg   16740
ggtggagaca aattcagggt agaagctgtg aggggcctgt ggtcagcccc ccgggggtc    16800 cctgcagcag gcactgtgag acctactgag gtgtgtgcat gggctgggga aggagccagt   16860
caggtgcccc tgctctgagg agctgctggg aagtgctgct gggccctggg ggaaggggtg   16920
ctcacagccc ctgcctgggc cacgtgggct ggagccgctc aggcagagcc ggactaattg   16980
gggcaaatga ggggacagga ggcctctgag gaaaggtaaa tagaattact cacccgccag   17040
gcactggggc cctcctgggg gggccctcac cctgccaccc accacagggc tgcatgcag    17100 cagggaggga agtgagctga ttaggcaagg ctggacccett ctggggccct ggggttgctg   17160 tgattggac ggcaaggcca ggagacggtc ccctgagctg cacctgctgg aggcctgtga    17220
tctcagacct taaggcttca ggccagctct acgcccctcc ggcctcaggt cctggctctc   17280
ctctgagccc tggatgcccg ggtgcctgtg tgggcacgag gctgctccga gtcagcacac   17340
ggaggtggac attctccttc atgccagctg agctcagggc tggtgactgc cctggggaaa   17400
ctgcccctca cctgggacct cctgacagcc ctccccattc ccgagtccct ctgcccttgt   17460
cctctttcac ctctgtcccg ccctcatccc taagggaact ggagcaggct ggtggagttg   17520
ggtggagttg gggactggca gggggtggac tcacccaggc aataaacact ggccctaacc   17580
aggcagtcct gcaggcaggt aggtggaggg actgtttttt ttcttttttg gagatagagt   17640
ctcactctgt tgcccaagtt ggagtgcagt ggcatgatct tggctcactg caaactccac   17700
ctcccaggtt catgtgattc tctgcctcag cctcccgagt agctgggatt ataggcgtgt   17760
gccacgacac ctggctaatt ttttttttt ttttttgag acggagtttc actctcgttg   17820
cccaggctgg agctcaatgg cgcgatctca gctcaccgca acctccgcct cccaggttca   17880
agcgattctc ctgccttagc ctccctagta gctgggatta caggcaggta tgtgatgccc   17940
ggcatcccaa aggggtatct gcaagagttg ggtgctgtgt gtgcatggct gggaggaaga   18000
tgactttgat accctggaat ctggtgtctg tggacacaaa aatactacta aaatgagagt   18060
ggagaccagg aaaaggaag acatgaacta catgaaggac caaatctagg agagtcagaa    18120
gtgcgtcaca ggaatagggg accttgagcc agacagaagg ctcagcagag acaccctcaa   18180
ggggatgaaa gggattgagt gcactaatat ttagaggaga gagttcagga cttgattagt   18240
gactagtaca tagaaaacta aacaaatgag gctgggtgca gtggctcatg cctgtaatcc   18300
cagcactttg gggggccaag gcgggcgaat cacctgaggt caggagttcg agaccagcct   18360
```

```
ggccaacatg gtgaaacctc gtctctactg aaaatacaaa aattagccgg gcgtggtggc    18420
gggcgcctgt agtcccagct acttgggagc ctgaggcagg agaatcgctt gaacctggga    18480
ggcggaggct gctgtgagcc aagatggtgc cattgcactc caccctgggt gacagagcaa    18540
gactccgtct caaaaaaaaa aaaaagaaa gaaaaaacca agcaaatgaa aaagaaggc     18600 aattaataat tccaaagaaa agaaaaattt gggcagaaaa gaacaaaaca agcagaattt    18660
accatgactc agttctgaat acaaacacag acatcataat gtaaacacca acactgatgc    18720
aaccagaatc atgggagaaa aagatctag ggagggtggt ggacgggaat atcacgtatg     18780
tactgggggt aggggagaga acaaaatggg aaaaatcaag aataattcac gttagaaata    18840
aaaatacaga gcaaaattta aaaatgcaaa gaatgaggtg aagagttcaa agtggtcacc    18900
tcggggccgg gcgcggtggc tcacgcctgt gatcccagca ctctgggagg ctgaggcggg    18960
cggatcacaa ggccaggagt ttgagaccat cctggctaac aaggagaaac cccatctcta    19020
ctaaaaatta gccaggcgtg gtggtgggcg cctgtagtcc cagctactcg ggaggctgag    19080
gcaggagaat ggcgtgaacc caggaggcgc agcttgcagt gagccgagat cgcgccactg    19140
cactccagct tgggcaacag agtgagactc cgcctcaaac aaaacaaaac aaaacaaaaa    19200
aacaaagtgg tcatctctag gcaaggtggg tgggagatgg ctagggctgc aggtccacta    19260
cgtgagctgg ctcagcctat ccccagacac cctgcactca ctcagcccgg ggtcctcccc    19320
ctgcactcac tcagccccgg gtcctcccct gcactcactc agccccgggt cctcccctg     19380 cactcactca gccccgggtc ctccctgcc tgctctttct ctgaccctgc cctccactgt    19440
tcctttttct tctttctctc cctgttgtgt ccaggaacca ggcaccaccc tcatttcttc    19500
ttgatcaatc tttaaaaacc agcagtgctc agctaactct tcatctatct ccccgacct    19560 ggggctctgc tgaatccacg ctttagaccc agctatcagc tcggcatgta cagctggatg    19620
tccacaccga gctgctcacc ctgtcccag cttcttcctc ccactgtcca ctgcagaagc    19680
ctcctaacag gaccctgct gctaccccgg accctgcaac ccattccac acagcagcca     19740 gatgctttga cacccgaagt ctcctatgaa tccgatgagg cctctgcacc acacctcatt    19800
ttacagaagt acagggaaa cagggtgctg ttgacaccac agagatgcag ctggccaaag    19860
gcagaatgtg gggtacacga ctgtcaaacg ccagggtcc ttacgcaat ggtggaaaaa     19920 gagggcatg ttacgatgg aggctcggga cacatgggcg ccgccttccc atgctgccag    19980
caacccacca ggaacctatt a                                             20001
```

<210> SEQ ID NO 10
<211> LENGTH: 18001
<212> TYPE: DNA
<213> ORGANISM: Homo sapiens
<400> SEQUENCE: 10

```
gaagtcatca gcaatgcaac tgttcacatg gaggatactc cctgcttgag gggtcagaca      60
ggcctgctgg gcaacccagg aggcttggat gaccgtctac cccagtgttt ttgggatgga    120
aagttccaca ttctgagaac cctcagtccc tgggcaacct ggggtggtta gtcaccacag    180
cttgtggctt gggcccatga cagcaggtag aaatgacgtg gactgccgcc agccgggcac    240
agtggctcac gcctgtaatc ccagcacttt gggaggctga ggcatgtgga tcacttgagg    300
tcaggagttc gaaccagcc tggtcaacac ggtgaaaccc catctctgct aaaaaaaaaa     360
aatatatata tataaattag ccaggcatgg tgacgtgcac ctgtggtccc agctactcag    420
```

```
gaggctgagg cacaagaatc acttgaaccc gggaggtgga ggttgcagtg agattgcacc      480
agtgcactct ccagcctggc aacagagcaa gactctgtct caaacaaaca aaacaaaaca      540
aacaaaaaga cgtaagatgt ggaccgctgg agaatggggg tgctgcctgc agtcaaaacg      600
gagtgggggt gcccagctca gggccagaat gatcctattc ccggcacttc tcagtgaggc      660
tctgtggctc acctaagaaa ccagcctccc ttgcaggcaa cggcctagct ggcctggtct      720
ggaggctctc ttcaaatatt tacatccaca cccaagatac agtcttgaga tttgactcgc      780
atgattgcta tgggacaagt tttcatctgc agtttaaatc tgtttcccaa cttacattag      840
gggtttggaa ttctagatcg tatttgaagt gttggtgcca cacacacctt aacacctgca      900
cgctggcaac aaaaccgtcc gctctgcagc acagctgggg tcacctgacc tttctcctgt      960
ccccccccact tgagctcagt ggctgggcag caggggatgc atggccactg gccggccagg     1020
tgcagctctc agctggggtg ttcagaggac gcctgtgtcc tcccctcccc catccctctg     1080
tcacccttgg aggcagagaa ctttgcccgt cagtcccatg gggaatgtca acaggcaggg     1140
gcagcactgc agagatttca tcatggtctc ccaggccctc aggctcctct gccttctgct     1200
tgggcttcag ggctgcctgg ctgcaggtgc gtccggggag gttttctcca taaacttggt     1260
ggaagggcag tgggcaaatc caggagccag cccgggcttc ccaaacccg cccttgctcc      1320
ggacaccccc atccaccagg agggttttct ggcggctcct gttcaatttc tttccttcta     1380
gaaaccagca tccaggcaca ggaggggagg cccttcttgg tggcccaggc tttggcggga     1440
ttattttttca aagaacttta ggagtgggtg gtgctttcct ggcccccatg ggcccctgcc     1500
tgtgaggtcg gacaagcgca gggagtctgg ggcctctcag agtgcaggaa gtgcgcacag     1560
ggtgctccca ggctggggag cacaggtagg ggacggtgcg tgggggatgg cgcctggggc     1620
atggggatg gggtgtggga acggcatgt ggggcgtagg ggatgggtg tggaggatcg       1680
ggggtgggga tggcgtgtgg ggtgtggggg atgggccgtg gggggtggg gcctgggaaa      1740
cagcatgtgg ggcatgggt gtgggggtga ggtgtgggaa agtgtgtggg gtgtggggga      1800
tgggcatgg aaagggcgtg tggggtgcag gggatggggc atggaggtgt gggggatggg      1860
gtgtgtgggg tgtcggggat ggggcatgtg gggtgtgggg gatggggcat ggaaagggcg     1920
tgtggggtgc agaggatggg gcatggggg gtggggatgg cgagtggggc tggggcctgg      1980
gaatggtgag tggggcatgg ggatggcgag taggggtgt ggcgtgagga tggctagtgg      2040
ggcgtgggga tggcgtgtgg ggatggcgag tggggggtgg gctgtgaggg acagtgcctg     2100
ggatgtgggg ctgcagccct agctcacagc atggccttat gacccggcc accttcctgc      2160
cccaggcggg gtcgctaagg cctcaggagg agaaacacgg gacatgccgt ggaagccggg      2220
gcctcacaga ggtgagcagg gactgccact ggttttgtcc tggggcccag tgggggccaa     2280
catcacctcc ttccctccc atggcaaaga gccagcccgc ggggtggcta ctgcagtgcc     2340
ccccaaggag ggtgttccct gctcgagagg aagtgaccgc tccagcttgg ccttccctgg      2400
gactggggtg caggcgattt tatcttcttt gctccattct gttccttcca gataatcgtg      2460
tgttcttcat caggttttcc tcagttcttg agagcttttc tgatgcaaat ctgctttcac      2520
cccaggcggg tcaccggctc tgctcacacc agcctccaag ggtgtgggtg tcccgggagt      2580
gtgggtgtcc cggggcgtg ggtgtcccag gagtgtgggt gtcccggggg cgtgggtgtc      2640
ccggagtgt gggtgtcccg gggcgtggg tgtcccggga gtgggtgt cccggaggcg        2700
agggtgtccc gggagtgtgg gtgtcccggg ggagtgggtg tcccgggagt gtgggtgtcc     2760
cggaggcgag ggtgtcccgg gagtgtgggt gtccggggg cgtgggtgtc ccggagtgt       2820
```

```
gggtgtcccg ggggagtggg tgtcccggga gtgtgggtgt cccggaggcg agggtgtccc    2880
gggagtgtgg gtgtcccggg ggagtgggtg tcccggagt gtgggtgtcc cggaggcgag    2940
ggtgtcccgg gagtgtgggt gtccgggggg cgtgggtgtc ccgggagcgt gggtgtcccg    3000
ggggcgtggg tgtcccggga gtgtgggtgt cccgggggcg tgggtgtccc gggagtgtgg    3060
gtgtcccggg ggcgtgggtg tcccgggagt gtgggtgtcc cgggagtgtg gtgtgttccgg   3120 aggcgagggt gtcccgggag tgtgcgtgtc cggggggcgt gggtgtcccg ggggcgtggg    3180
tgtcccgggg gcgtgggtgt tccggaggcg agggtatccc agaagtgtga gtgtcccagg    3240
ggcgtgggtg tcccggggt gtgggtgtcc cgggggcgtg ggtgtcccgg gagtgtgggt    3300
gttccggagg tgagggtgtc ccgggagtgt gggtgttccg gaggcgaggg tgtcccggga    3360
gtgtgggtgt cccgggggcg tgggtgtccc gggagtgtgg gtgttccgga ggtgagggtg    3420
tcccgggagt gtgggtgttc cggaggcgag ggtgtcccgg gagtgtgggt gtcccagggg    3480
cgtgggtgtc ccgggagtgt gggtgttccg gaggcgaggg tgtcccggga gtgtgggtgt    3540
tccggaggcg agggtgtccc gggagtgtgg gtgtcccggg ggcgtgggtg tcccggggt    3600 tgtgggtgtc ccgggagtgt gggtgttccg gaggcgaggg tgtcccggga gtgtgggtgt    3660
tccggaggcg agggtgtccc gggagtgtgg gtgtcccggg ggtgtgggtg tcccggggt    3720 gtgggtgtcc cggagtgtg ggtgtccgg ggagtgggt gtcccgggag tgtgggtgtt    3780
ccggaggcga gggtgtccca ggagcgtggg tgtcccggag gcgagggtgt cccgggagcg    3840
tgggtgtccc gggggcgtgg gtgtcccggg agtgtgggtg tcccgggga gtgggtgtcc    3900 cgggagtgtg ggtgtcccgg aggcgagggt gtcccaggag tgtgggtgtc ccgggggcgt    3960
gggtgtcccg ggagtgtggg tgttccagag gcgagggtat cccagaagtg tgagtgtccc    4020 ggggggtgtgg gtgtcccggg ggtcgtgggt gtcccggag tgtgggtgtt ccagaggcga    4080
gggtgtcccg ggagtgtggg tgtcccaggg gtgtgggtgt cccgggggcg tgggtgtccc    4140
gggagtgtgg gtgtcccggg ggagtgggtg tcccggagt gtgggtgttc cggaggcgag    4200
ggtgtcccgg gagtgtgggt gttccggagg cgagggtgtc ccgggagcgt gggtgtcccg    4260 gggcgtggg tgtcccggga gcgtgggtgt cccagggtt gggtgtccc ggggcgtgg    4320 gtgtcccggg agtgtgggtg tccgggggg gtggatgtcc cgggagtgtg gtgtgttccgg    4380 aggcgagggt gtcccgggag tgtggtgttt cggaggcga gggtgtcccg ggagtgtggg    4440
tgtcccgggg gcgtgggtgt ccgggagtg tgggtgtccc ggggcgtgg gtatcccaga    4500 agtgtgagtg tccagggggc gtgggtgtcc gggggcgtg gtgtcccgg gggtgtgggt    4560 gtccgggggg tcgtgggtgt cccgggagcg tgggtgtcgg ggactgcagg gacatgggcc    4620
tcccctccca ctcctgccgc ccagggcacc tcctgtgagg actcggagtc cgtgagttcc    4680
cacctccttg agcccgattc tttggtgtcc ccgcctgcat cctcagcctc cttccaaacc    4740
agaccagttc tctaggggcg tcgacgtgtg aaactgattt taaagaaaac aggcagtggc    4800 cttctctcg gccccacgtg gcccagtagc gctcaccttc cgtcccttct tccgcgctca    4860
gtaaccaatt taggccgctc ctgcagaact cgggctcctg cccaccggcc cacagcgtcc    4920
acctgaggcc tcgtcctccc agcaaaggtc gtccctccgg aacgcgcctc ctgcggcctc    4980
tccagagccc ctcccgcgcg tcctctcagc ccgctcgcc tcctcccggg gcctccctct    5040
cccgcctgcc cccaggcccg tctccctctg cgggctgagg caggttcggg cagcacggcc    5100
gccccggggc ggggtcact ctccaccacc gcgtggtgcc cacagctcac ggcgctcccg    5160
```

-continued

```
ggtgacggtc ccctcggctg tagggcgtcc tgaagagcgg cctgctcgga gctgagcgca    5220
cggggttgcc tcgccctggg cgtctctggc cctcaccagc cccgtcttcc catgggcaaa    5280
acggcggtcc tgtttgtcca caagtaaccg tcggggttac ggaggggcca ggagctgcgg    5340
cgggggggctg tgctctcagg accgccccca ggaggatccg cgcgaggtct ggagctctca    5400
ggggtcgcgg gggacagagg ggccccaagc ggaggcgggg aaggcggcag aagcccagga    5460
ccgccaagag ctggcgagga agcccgggc tcgctgtcgg gggagccggg caggggccgc    5520
gcctcggacc aggacggagg cctggggaag gcggatctgg ccgccggaga cgcggtgcgg    5580
gtggagacga gggatttgga tttccgcggg cggctgtacg gatttccacg cgcggttcac    5640
gtgggcccca gggggttgcc cggcacccgg ggccgcgccg ccttctcctc gccggcatcg    5700
acccgcagcc tcacgtttac gcggcggcgc ccgcagcccc cttcggcccg gcttccgcgc    5760
gtgccccga gcgcgccctc gggatcagcc cccggaagca gagaggccag gccgggaagg    5820
atgggcgacg ggggtggctg acccgggagc acggcaggga ggacacccag ccaggcccgc    5880
gagcagcgcc gctcccctcc tccaggacgg gcggaacct gcgatgcccc cgccgcgtgg    5940
gccgtgggc ggtctccgag gcactgggcg gggcacgcgg tgggcgcttc acggaactcg    6000
catttcccag tcttcgtaac ccaggaggaa gcccacggcg tcctgcaccg gcgccggcgc    6060
gccaacgcgt tcctggagga gctgcggccg ggctccctgg agagggagtg caaggaggag    6120
cagtgctcct tcgaggaggc ccgggagatc ttcaaggacg cggagaggac ggtgagccca    6180
gcctcggggc gccccgcgcc gcggacactg caggcggcgg tgaaccaggc cgcgtggggc    6240
cgcctgcgtc tctttggctg cggctgtggg cggcgaacac gcagcggcgc ccgcgcggcg    6300
ctttctgcgg gggtcgcttt ccgcccgggg tgactccgct ttcctgggcg atgccccca    6360
cccccaggca cgcgctctcc ccgtgcggcc gcaccgcgca tgccggtttt cacatcagaa    6420
aatacgattt gcaaagcaca cttagggtgt cccccttaac ttcccaaggg agtcccccca    6480
gtccccgaag ggtccagggc agcctgcgca tcgcagacgc gcgcggctcg cagaagggac    6540
gtggtgagaa gctggcccac agcatgccac cagcggcacc tcctcagggc acgtgtcggg    6600
gagaaacaac acttagggac ctgggacttt tccagctca cgctcacggg tcacctcaca    6660
ctccaagatc acctcaaaga ggacacctca cacagggcac acttcacact cacaggtcac    6720
ctcacactca caggacacct cacactcaca gggcacactt cacactcacg gtcacctca    6780
cactccaaga tcacctcaaa gaggacacct cacacagggc acacttcaca ctcacaggtc    6840
acctcacact cacaggacac ctcacactca cagggcacac ttcacactca cgggtcacct    6900
cacactccaa gatcacctca aagaggacac ctcacacagg gcacacttca cactcacggg    6960
tcacctcaca ctcacaggac acctcacaca agacacctca cacggggcac acttcacact    7020
cacaggtcac ctcacaccca caggacacct cacacagggc acacttcaca ctcacgggtc    7080
acctcacact cacaggacac ctcacacaag acacctcaca cggggcacac ttcacactca    7140
caggtcacct cacacccaca ggacacctca cacagggcac acttcacact cacgggtcac    7200
ctcacactca caggacacct cacactcagg gcgcacttca cactcacggg tcacctcaca    7260
cccacaggac acctcacaga ggtcacctca cacaggacac ctcacactca gggtgcactt    7320
caaacccaca ggtcatttca cctcacactc acaggacacc tcacacaaga taccacacgg    7380
ggcacacttc acactcacag gtcacctcac actcacagga cacctcacag aggtcacctc    7440
acacggggca cacttcacac tcacaggtca cctcacaccc acaggacacc tcacagaggt    7500
cacctcacac ccacaggaca cctcacacag gacacctcac agaggtcacc tcacacccac    7560
```

```
aggacacctc acactcatag gtcacctcag tcttacagga caactcacac tcacaggtca    7620
ccttactctc acaggacacc tcacactcac aggtcacctt actctcacag gacacctcac    7680
tctcacagga cacctcacac agggcacact tcactcccac aggtcaccat acctcacaca    7740
gatcacctca tactcacaga tcacttcatt ctcacaggat acctcacact cagggcacac    7800
ttcacactca caggtcacac ctcacacaga tcatctcatt ctcacaggac acctccctct    7860
cacaggtcac ctcacactca caggacacct cacagaggtc acctcacacc cacaggacac    7920
ctcacagagg tcacctcaca cggggcacac ttcacactca ggtcacctca cccacagg     7980
acacctcaca gaggtcacct cacacccaca ggacaactca cagaggtcac ctcacacagg    8040
acacctcaca aggtcacctc acacccaca ggacacctca cactcatagg tcacctcagt     8100
cttacaggac aactcacact cacaggtcac cttactctca caggacacct cacactcaca    8160
ggtcacctta ctctcacagg acacctcaca cagggcacac ttcactccca caggtcacca    8220
tacctcacac agatcacctc atactcacag atcacttcat tctcacagga tacctcacac    8280
tcagggcaca cttcacactc acaggtcaca cctcacacag atcatctcat tctcacagga    8340
cacctccctc tcacaggtca ccttacactc atctcacact cacaggtcgc cacacctcac    8400
actcacagga tgcctcacac tcacagaacc acatctcata tgcacaagac acctcacact    8460
caggacacct catgctcaaa gaagcctcac actcacagga ggtccagctg tctgaggcaa    8520
aggctaacat gacccctttcc agacaaattg aggatggtca tgcctagcat ttttatacac    8580
ctagttttga aagcatttct catctgttgt attctcacag cacccgtga gtttaagttc     8640
aggtggccaa cagtttcttc agcaatcact ttttctgtg gagtgctttt gctgtttgtg     8700
gaatatttg catctgctac tgcaccctct ccccgtatgt gtggccaccc tgtcagaggt     8760
ggagctgtgg ctcagagcct gtgtacctcg tcccaggtcc acagctcagc gacagaagag    8820
tcagggttga acctcgggtg ttctgacttg ggagcaggaa atgtgtggtc acccatagtt    8880
ccagatgtcc tggggagggg ccaagattag aagaaaccta cctcagctcc agaggaaagt    8940
ctggcttcct gagcccaccc cgccagaccc aggtccaagt cccccaaccc cagttcatgg    9000
tgtgtccagt gcttaccgtt gggtgctctg gtgaaggtgc atctcacgag gcttgctctc    9060
ttgttccttc agaagctgtt ctggatttct tacagtggtg agtggatgat caccaccagt    9120
cctgcctgca acccttctca gcttactgac accagcccac tccacagatg gggaccagtg    9180
tgcctcaagt ccatgccaga atgggggctc ctgcaaggac cagctccagt cctatatctg    9240
cttctgcctc cctgccttcg agggccggaa ctgtgagacg cgtaaggccc cactttgggt    9300
cccatatttg cagagggccc tggggagctg gtggaggtgg cctggccaac cgggctgcag    9360
ggtgcacaac ctggtggggt gtgtaggccg ggcattcagg gctcagcccc agttggaaat    9420
tggtctaggt gaccttgaaa tcccttccag tctgaggtct ttgacaggga cccaaggttc    9480
tgattatcag actcagtggc cccttgggct cccggcccctg gcaattctc agccctcgag    9540
atggcccagc tgagagtccc tgtgtccctg tcccacttcc acatcccacc acgcaggacc    9600
gcttggtaaa cttccccttc tctactttcc attacaaagg tttgagggt ttgttttttt      9660
tttaaccatc tgaatattaa attatcacaa agtttgaggc ccccaacctc ccttgggttc    9720
agtaattcac tagaaggact catagaatcc actgaagtgg atacactcac aggtaccgtt    9780
tattacagca aaggatgcag gcttaagtct gcagagggac caggcacaag cttccccttg    9840
tcctctccct gtggggtcat gtggacagtc cttaattctc ccagaatgac gtgtgacgag    9900
```

```
acgtgggaag tactgccaac ttgggaagct ctacgagccc cggtgtccag aggttttatc   9960
agggctcaat cacatagacc cagctgacca cccgcatggc tgacctcagt ctcagcccct  10020
ccagaggcta cgccgatagt gcggcccaag gccccaccat acatcacatt gtcagctaga  10080
ccatccagca tggctcaagg cccagtaaa caccaacatt ccctcaggca agaccttcca   10140
agggcttagc ggtcatttcc caggagccaa ggcaaaggct acccttctc tggcacagca    10200
gttcatcctt gaccacccaa gaccacattc ttacactgaa tgagctctcc tgtgcagcag  10260
ccattttctt ctctaagcag aagagagccc agcaagctgg aggaggctga agagagaggc  10320
ttcctgctgg tcatctgggt ccagaatgcc tggagatctc tgctcagccc tggtgcccag  10380
cagccctggt gtgcatcctg cagggcaggc cttcccgccg gagtcctgga cttgctcagg  10440
gccactcccc ttgcccatgt caaccaaagt caggctgccg gttctgcttc ttctgtctga  10500
gcccatgacc agtgctggga ctaactgtcc ccaggcgggc tcacggtggt acgaggccag  10560
cttggagaac tgtctcagct ctctggtcct ctcgtcagtt gggtctctga ttggaaagtc  10620
ccttggacac ttttaccatc cccattggac tttcactttc ccccaggctc ccatcagctg  10680
ctcggaagag tggtcaccct ggaggccact gcccaccagc caggcacccc ccaaatgcaa  10740
ccgcagccaa cactgccagc cactggcaag gctgttcaga catgtggctc ctctgatcca  10800
cgccttgtcc tttggatcag tccacggagc aggtggtgcc aagctcaggc tctgtcaccc  10860
acagctcagt gccaccttcc aggcagaaca ccactgctga cccagggcat ggccaccccg  10920
ggggctggct ctcgctgacc cccagaagcc cctctcaggg tgtcccttc ctgtccccag    10980
acaaggatga ccagctgatc tgtgtgaacg agaacggcgg ctgtgagcag tactgcagtg  11040
accacacggg caccaagcgc tcctgtcggt gccacgaggg gtactctctg ctggcagacg  11100
gggtgtcctg cacacccaca ggtgaccagg cttcatgtcc cagtcccaga tgacaccagt  11160
ccctgtccca ctacggatta tcttactgga caaaagacgg gtgggagtgg cttcacatct  11220
actgagcact aactatgcac tgaccaattg tgaggtggga tctgggcacc aagggtggca  11280
caggccagag cgacagtgac taggatgggc accctggggg caatccctga atggcctcag  11340
gccccctgcc aattctaggc agaccagggg agccaagcaa ggcactatct cacgtccaac  11400
tcccactcgc aggacctccg ccagggttca tgaatctact tcggcacagc caatgtctgt  11460
actgactgct gccactctg cattccaaaa ctcgtaaagg ctcctgggaa atgggatgt    11520
ttctccaaac cagcctggaa cgaatgggct gcacttccaa aagcagggac accccacacc  11580
cactgtgtct caaagaggcg gacgtgccca ccctggccac acagcctggg actcagcctg  11640
ccacctcctc gggcttcctt tctggcccaa gaccttgatt gaagcagatc aaaactaagc  11700
atgggatcaa acaacacag tttgattcat ctttaggtag aatttcattc accttctact   11760
aaagtcaaac aacacatctt ctccctgaaa agtgagcaga gggcggtttt aagacgtaag  11820
ccctctgttt cctccaaaac cagccctgac cattgtctcc tcagccagcc acttcttcaa  11880
gggcctctca tggccgggcc ccaccagtca ggccagccg aggccctgcc ttccaccacc   11940
cctgggccct gggagctcct gctcctgggg gcctcccata gcctcggcct caaggcctct  12000
cagaggatgt gtgtttctga atctttccta gtggcacgtt catccctcac aaatctctgc  12060
atctttctga cttttgtttt acacagttga atatccatgt ggaaaaatac ctattctaga  12120
aaaaagaaat gccagcaaac cccaaggccg aattgtgggg ggcaaggtgt gccccaaagg  12180
ggagtgtcca tggcaggtaa ggcttcccct ggcttcagga ttccaagccc tgagggtctt  12240
gaagcctttt gaatgtgaac aacagctctg gaagggaaaa tgggcaggtc agccccaagc  12300
```

```
ccaccaggct ccaagtcagc acacctagca cctccagctc gcggcacccc catgctttta   12360
gtggggcaag gaaggagaaa agaaaacgac actcactgag ggtctaccct gtgcagagaa   12420
ccctgcgaga tgccccatcc gagttgtcac gtcgtcctca cggttactct ttgaggtggg   12480
atctttgcct gatcttttgca aaatcaggag cattggatca aagctatgtg aagatcctgt   12540
gaggtgaaca gtgaaatctc acagcgacat ttgtattctt gggccgtgcc aagagcacg    12600 tctcggctag agaggggcac agcctcccag agccaggtct gagcagcttt gcctgggagg   12660
gatctgcaaa gaccccagga tttcagaaag aaattgtgca atgccagagg ttccttggca   12720
tgcccgggag ggcgagtcat cagagaaaca atgacagcaa tgtgacttcc acacctcctg   12780 tcccccgcc caggtcctgt tgttggtgaa tggagctcag ttgtgtgggg ggaccctgat    12840
caacaccatc tgggtggtct ccgcggccca ctgtttcgac aaaatcaaga actgaggaa    12900 cctgatcgcg gtgctgggtg gtaccactc tccctgtcc gaccgcggtg ctgggtgggt     12960
gccactcttc cctgtccgac cgcggtgctg gtgggtgcc actctccct gtccgaccgc     13020 ggtgctgggt gggtgccact ctccctgtc cgaccgcggt gctgggtggg tgccactctc    13080
cgctgtccga ccgcggtgct gggtgggtac cactctcccc tgtctgaccg cagctctcaa   13140
gtgtctcagg ggctgtggct ctgggcttcg tgctgtcact tccacagaca gacagacatc   13200
cccaaaaggg gagcaaccat gctgggcacg actgctgtgg ccaccgtgct ctcagccact   13260
ttcccatgcc caaataaaac gataaaagac tgggggcttc tgcccatcct gcctcacttg   13320
accaagagcc cagaagagga tgcgacaccc agggcctcat ggaccaccg gctggcaggg    13380 gttctgctca ctgggtttat gggtgagacg agcactccca ggagggccac tgggccggga   13440
agaactgtgg agaatcgggg cacgcccgt cctcccagct gccagggcac agcatccctt    13500
ccccacctca acacccagac cccagattca ccccagttca cttgtcccca cacgagccac   13560
aggctgccac ctggggcagg ctggcccac cttggggtta gatgcaggtc ccttgcccc    13620 agaaggagac tgcagcccct gcagacctag aaatggccac agcccatccc catgcaccag   13680
ggggtgaggt ggcaggtggt ggaaagggcc tgagggggc ttcttccttc caggcgagca    13740
cgacctcagc gagcacgacg gggatgagca gagccggcgg gtggcgcagg tcatcatccc   13800
cagcacgtac gtcccgggca ccaccaacca cgacatcgcg ctgctccgcc tgcaccagcc   13860
cgtggtcctc actgaccatg tggtgcccct ctgcctgccc gaacgacgt tctctgagag    13920 gacgctggcc ttcgtgcgct tctcattggt cagcggctgg ggccagctgc tggaccgtgg   13980
cgccacggcc ctggagctca tggtcctcaa cgtgccccgg ctgatgaccc aggactgcct   14040
gcagcagtca cggaaggtgg agactccccc aaatatcacg gagtacatgt tctgtgccgg   14100
ctactcggat ggcagcaagg actcctgcaa ggggacagt ggaggccac atgccaccca    14160 ctaccggggc acgtggtacc tgacgggcat cgtcagctgg ggccagggct gcgcaaccgt   14220
gggccacttt ggggtgtaca ccagggtctc ccagtacatc gagtgctgc aaaagctcat    14280 gcgctcagag ccacgcccag gagtcctcct gcgagcccca tttccctagc ccagcagccc   14340
tggcctgtgg agaaaagcc aaggctgcgt cgaactgtcc tggcaccaaa tcccatatat    14400
tcttctgcag ttaatggggt agaggagggc atggagggga gggagaggtg gggagggaga   14460
cagagacaga aacagagaga gacagagaca gagagagact gagggagaga ctctgaggac   14520
atggagagag actcaaagag actccaagat tcaaagagac taatagagac acagagatgg   14580
aatagaaaag atgagaggca gaggcagaca ggcgctggac agaggggcag gggagtgcca   14640
```

```
aggttgtcct ggaggcagac agcccagctg agcctcctta cctcccttca gccaagccca    14700
cctgcacgtg atctgctggc ctcaggctgc tgctctgcct tcattgctgg agacagtaga    14760
ggcatgaaca cacatggatg cacacacaca cacgccaatg cacacacaca gagatatgca    14820
cacacacgga tgcacacaca gatggtcaca cagagatacg caaacacacc gatgcacacg    14880
cacatagaga tatgcacaca cagatgcaca cacagatata cacatggatg cacgcacatg    14940
ccaatgcacg cacacatcag tgcacacgga tgcacagaga tatgcacaca ccgatgtgcg    15000
cacacacaga tatgcacaca catggatgag cacacacaca ccaatgcgca cacacaccga    15060
tgtacacaca cagatgcaca cacagatgca cacacaccga tgctgactcc atgtgtgctg    15120
tcctctgaag gcggttgttt agctctcact tttctggttc ttatccatta tcatcttcac    15180
ttcagacaat tcagaagcat caccatgcat ggtggcgaat gccccaaac tctcccccaa     15240 atgtatttct cccttcgctg ggtgccgggc tgcacagact attccccacc tgcttcccag    15300
cttcacaata aacggctgcg tctcctccgc acacctgtgg tgcctgccac ccactgggtt    15360
gcccatgatt cattttggga gccccggtgt ctcatcctct gagatgctct tttctttcac    15420
aattttcaac atcactgaaa tgaaccctca catggaagct atttttaaa aacaaaagct     15480 gtttgataga tgtttgaggc tgtagctccc aggatcctgt ggaattggat gttctctccc    15540
tgccacagcc cttgtcaatg atatttcaca gagaccctgg gagcacctgc tcaagagtca    15600
gggacacacg catcactaaa tgcaagttcc caggccctgg ctgcagtggg aggacctggc    15660
aagctgcact cttgctgagt ccccaggggtg gtggaagaag aatgagaaac acatgaacag    15720
agaaatgggg aggtgacaaa cagtgccccc actcagactc cggcaagcac ggctcagaga    15780
gtggactcga tgccatccct gcagggccgt cctgggcacc actggcactc acagcagcaa    15840
ggtgggcacc attggcactc acagcagcaa ggcaggcacc agcaacccac ctcgggggca    15900
ctcaggcatc atctacttca gagcagacag ggtctatgaa ctacagccgt gggctgcttc    15960
caaggcaccc tgctcttgta aataaagttt tatgggaaca cacccatatt agtgtccatg    16020
gagtggccgt ggcagagacg tccagccgga cagaccagct gacccgccaa gcccagcatg    16080
gttagtgtca ggacctctgc tgaagatgct tgctgaccct ggccagaccc cggttcctaa    16140
tgccccctaa acgggacggg agccagtggc gggccctgat ccaggtcaga gctggctctg    16200 cttttctcttt tgtccgagtg accatgcctc agtttcctca tgtgtaaaac aggagcccac    16260
cgtgatgctt atggtgggat gagatcagca tggatggaac aaggccctgg aagggcccat    16320
gccatggtca tcgacagcaa agccactctg cagacagatg cttcagtgaa ttggtagaaa    16380
attctgcaac cagaatgccc ggggctcctg agggcctaag cccagcccag ggttctggaa    16440
gccactctga cttcttggga gtggaagttg gcaggactct tcctgggaag aagcggaggg    16500
tggggatgag aggacagttc aggagcccac ccagacccac aggaggaaac tagggagtc      16560 atgcggggtc ctggtggagc gccagcctcc cttcctgcca atgggaaatg caggcgccca    16620
cctcatggtg ctgccggagg aggggccccg ggactcccca gaggcttcgc tgaagggcct    16680
gggcgccccc aaaggctaca tgtttcatat gggacgtgcc acctgccacg gctcagctcc    16740
agctttctgt gagtggcgag atagaatacg gggaggccac tggccatggg cctgggacag    16800
ggtgggatga ggcggcaggc ttgggccacc aaagccagca tcgccaccca gcattgatga    16860
caaagactgc gtgtctgcca tgagcatcct gctgttggtg cacacaccgc attggtctct    16920
ccatacaaac atgcctagag gcgatgtcag agggtggaga ccaggagagg caggagtcag    16980
acatctggtg ccaccaggaa ggcccttctc agaggaccag gctgtgcgtg gtgcccgccg    17040
```

```
tgggaggcca gcctggcgtt ggcatccagc atcatcagtt tgtgcagtcg ggtgggctc      17100 agtgagtgcc tcctgtgtgc caggcacaat gacgcacaat gtgtgcacac caggctcatg     17160
tgcaggtggc tgcgagacag ggcgacccat caaggcagat gcaccatgag gcagtggcca     17220
gtgctgtggg tgttagggc attgctcccc ggccactacg gcatagcagg cagtgatcgc      17280
cacactggcc aagctttaga ccatttattc cagagacccc agaggcaaaa agcccggctg     17340
cacctcccag tgactcccac agccattgag cagagacact caggaccttg tgatgggagg     17400
tttctgcact ggagaacgag cccagaagcc ctctcagcct cggaacagtg tggccagtgg     17460
tgggcaggtc aggaggggct tcagacacag cctgtccctc cagatggtca cgggaaggtc     17520
actccccaca gaagtacgtt ttggggccat gcgggcacag aaggtttggg ggtgggtggg     17580
gcaggtgcca gcctggcctg tgggaggcca tggtgcagat gccaagcccc ccccgtgaca     17640
tgagaccacc tgataccacc cagagagtgg ctgtgagcgg aagggcccgc ccagaaacaa     17700
gcagggcctt ggggcagaag tcctgggctc agatcccacg ctcactgcca gcggcctcgg     17760
ctcaggcttc tgcgctctct aaacttagtt ttctcttctg gaaaaatgat ggggaaaatg     17820
atatttgtat gtgaggactg agagttaaat gtaaacatct ggaaactaca aaatgagcac     17880
gaaatgatgt ttttattctt agaacagaaa gtccccacac ccgcggccct ggtgactgat     17940
gaggatgagg ttctgcgggg cctctctggc cgcccagctc tgcctgggga aggtggggcc     18000
a                                                                     18001
```

<210> SEQ ID NO 11
<211> LENGTH: 3075
<212> TYPE: DNA
<213> ORGANISM: Homo sapiens

<400> SEQUENCE: 11

```
agtcccatgg ggaatgtcaa caggcagggg cagcactgca gagatttcat catggtctcc        60
caggccctca ggctcctctg ccttctgctt gggcttcagg gctgcctggc tgcagtcttc       120
gtaacccagg aggaagccca cggcgtcctg caccggcgcc ggcgcgccaa cgcgttcctg       180
gaggagctgc ggccgggctc cctggagagg gagtgcaagg aggagcagtg ctccttcgag       240
gaggcccggg agatcttcaa ggacgcggag aggacgaagc tgttctggat ttcttacagt       300 gatgggacc agtgtgcctc aagtccatgc cagaatgggg gctcctgcaa ggaccagctc       360
cagtcctata tctgcttctg cctccctgcc ttcgagggcc ggaactgtga gacgcacaag       420
gatgaccagc tgatctgtgt gaacgagaac ggcggctgtg agcagtactg cagtgaccac       480
acgggcacca gcgctcctg tcggtgccac gaggggtact ctctgctggc agacggggtg       540
tcctgcacac ccacagttga atatccatgt ggaaaaatac ctattctaga aaaagaaat       600 gccagcaaac cccaaggccg aattgtgggg ggcaaggtgt gccccaaagg ggagtgtcca       660
tggcaggtcc tgttgttggt gaatggagct cagttgtgtg ggggaccct gatcaacacc       720 atctgggtgg tctccgcggc ccactgtttc gacaaaatca gaactggag gaacctgatc       780 gcggtgctgg gcgagcacga cctcagcgag cacgacgggg atgagcagag ccggcgggtg       840
gcgcaggtca tcatccccag cacgtacgtc ccgggcacca ccaaccacga catcgcgctc       900
ctccgcctgc accagcccgt ggtcctcact gaccatgtgg tgcccctctg cctgcccgaa       960
cggacgttct ctgagaggac gctggccttc gtgcgcttct cattggtcag cggctggggc      1020
cagctgctgg accgtggcgc cacggccctg gagctcatgg tcctcaacgt gccccggctg      1080
```

```
atgacccagg actgcctgca gcagtcacgg aaggtgggag actccccaaa tatcacggag        1140
tacatgttct gtgccggcta ctcggatggc agcaaggact cctgcaaggg ggacagtgga        1200
ggcccacatg ccacccacta ccggggcacg tggtacctga cgggcatcgt cagctggggc        1260
cagggctgcg caaccgtggg ccactttggg gtgtacacca gggtctccca gtacatcgag        1320
tggctgcaaa agctcatgcg ctcagagcca cgcccaggag tcctcctgcg agccccattt        1380
ccctagccca gcagccctgg cctgtggaga gaaagccaag gctgcgtcga actgtcctgg        1440
caccaaatcc catatattct tctgcagtta atggggtaga ggagggcatg ggaggggaggg       1500 agaggtgggg agggagacag agacagaaac agagagagac agagacagag agagactgag        1560
ggagagactc tgaggacatg gagagagact caaagagact ccaagattca aagagactaa        1620
tagagacaca gagatggaat agaaaagatg agaggcagag gcagacaggc gctggacaga        1680
ggggcagggg agtgccaagg ttgtcctgga ggcagacagc ccagctgagc ctccttacct        1740
cccttcagcc aagcccacct gcacgtgatc tgctggcctc aggctgctgc tctgccttca        1800
ttgctggaga cagtagaggc atgaacacac atggatgcac acacacacac gccaatgcac        1860
acacacagag atatgcacac acggatgcac acacagat  ggtcacacag agatacgcaa        1920
acacaccgat gcacacgcac atagagatat gcacacacag atgcacacac agatatacac        1980
atggatgcac gcacatgcca atgcacgcac acatcagtgc acggatgcac acagagatat        2040
gcacacaccg atgtgcgcac acacagatat gcacacacat ggatgagcac acacacacca        2100
atgcgcacac acaccgatgt acacacacag atgcacacac agatgcacac accgatgc          2160 tgactccatg tgtgctgtcc tctgaaggcg gttgtttagc tctcactttt ctggttctta        2220
tccattatca tcttcacttc agacaattca gaagcatcac catgcatggt ggcgaatgcc        2280
cccaaactct cccccaaatg tatttctccc ttcgctgggt gccgggctgc acagactatt        2340
ccccacctgc ttcccagctt cacaataaac ggctgcgtct cctccgcaca cctgtggtgc        2400
ctgccaccca ctgggttgcc catgattcat ttttggagcc cccggtgctc atcctctgag        2460
atgctctttt ctttcacaat tttcaacatc actgaaatga accctcacat ggaagctatt        2520
ttttaaaaac aaaagctgtt tgatagatgt ttgaggctgt agctcccagg atcctgtgga        2580
attggatgtt ctctccctgc cacagcccctt gtcaatgata tttcacagag accctgggag       2640
cacctgctca agagtcaggg acacacgcat cactaaatgc aagttcccag gccctggctg        2700
cagtgggagg acctggcaag ctgcactctt gctgagtccc cagggtggtg aagaagaat         2760 gagaaacaca tgaacagaga aatggggagg tgacaaacag tgcccccact cagactccgg        2820
caagcacggc tcagagagtg gactcgatgc catccctgca gggccgtcct gggcaccact        2880
ggcactcaca gcagcaaggt gggcaccatt ggcactcaca gcagcaaggc aggcaccagc        2940
aacccacctc ggggcactc aggcatcatc tacttcagag cagacagggt ctatgaacta        3000
cagccgtggg ctgcttccaa ggcaccctgc tcttgtaaat aaagttttat gggaacacaa        3060
aaaaaaaaaa aaaaa                                                        3075

<210> SEQ ID NO 12
<211> LENGTH: 564
<212> TYPE: DNA
<213> ORGANISM: Homo sapiens

<400> SEQUENCE: 12
atcatggtct cccaggccct caggctcctc tgccttctgc ttgggcttca gggctgcctg         60
gctgcaggag gaagcccacg gcgtcctgca ccggcgccgg cgcgccaacg cgttcctgga       120
```

```
ggagctgcgg ccgggctccc tggagaggga gtgcaaggag gagcagtgct ccttcgagga      180
ggcccgggag atcttcaagg acgcggagag gacgtggtga gtggatgatc accaccagtc      240
ctgcctgcaa cccttctcag cttactgaca ccagcccact ccacagatgg ggaccagtgt      300
gcctcaagtc catgccagaa tgggggctcc tgcaaggacc agctccagtc ctatatctgc      360
ttctgcctcc ctgccttcga gggccggaac tgtgagacgc acaaggatga ccagctgatc      420
tgtgtgaacg agaacggcgg ctgtgagcag tactgcagtg accacacggg caccaagcgc      480
tcctgtcggt gccacgaggg gtactctctg ctggcagacg gggtgtcctg cacacccaca      540
gttgaatatc catgtggaaa aata                                             564

<210> SEQ ID NO 13
<211> LENGTH: 15001
<212> TYPE: DNA
<213> ORGANISM: Macaca mulatta
<220> FEATURE:
<221> NAME/KEY: misc_feature
<222> LOCATION: (3049)..(4102)
<223> OTHER INFORMATION: n is a, c, g, or t

<400> SEQUENCE: 13
tcaaaacaga gtggggctgc ccagctcagg gccagaatga tcctattccc agcacttctc       60
agtcaggctc tgtggctcaa ctaagaaacc ggcctcccct gcagacaatg gcctagctgg      120
cctggtctcc tggaggctct cttcaaatat ttacatccac acccaagata tgctctccag      180
aattgactcg cattattgct atgggccaag ttttcatctg cagtttaaat ctgtttccca      240
acctacgttc ctatgtccta ggggtttgga attctagatc gtatttgaag tgttggtgtc      300
acacacacac cttaacacct gcacgctggc aacaaaacca tccgctttgc agcacaactg      360
gggccgcctg accttttctcc tgtcctccct gcttgagctc agcagctggg cagcagggga      420
tgcatggcca ctggccggcc aggtgcagct ctcagctggg gtgttcagag gacgcctctg      480
tccccccctc cccatccct ctgtcgccct tggaggcaga gaactttgcc cgccagtccc      540
atgcggaatg tcaacaggca gaggcagcgc tgcagagatt tcatcatggt ctctcgagcc      600
ctcgggctcc tctgccttct gcttgggctt cagggctgtc tggctgcagg tgcgtccggg      660
gagattttcc ccataaactt ggtggaaggg cagtgggcaa atccaggagc cgacccgggc      720
ttcccaaacc gtccttgctc tggacacccc cattcaccag gagggttttc tggtggctcc      780
tgttcaattg ttttccttcc agaaaccagc atccaggcac aggaggggag gcccttctta      840
gtagcccagg ctttggtggg attatttttc aaagaacttt aggagtgggt ggtgctttct      900
tggcccccat gggcccctgc ctgttaggtt ggacaagcac agggagtcgg gggcctctca      960
gagtatggga ggtgctcaca ggctgctccc aggctgggga ggacaagtgt gtggggatg      1020 gtgcctgggg catggggat ggggtgtgga ggatgggggt tggggatggc atgtgggggtg      1080 tggaggatgg gccatgaggg ggtgggtcct gggaaacggt atgtgggggta tgagggatgg      1140 ggcgtggggt gcgggagggg ggtgtgggaa agtgtgtggg gtgtggggga tgggatgtgg      1200
gaagtggcat gtggagtgca aggaatgggg catggaggtg ttgagcatgg ggtgtgtcgg      1260
gtgtgtgggg tgtggggggag gggaatgga aagggtgtgt ggtgtgtggg ggatggggtg      1320
aggggatggc gtgggaggtg gggcatgggg atggcaggtg tggcgtgggg atggcgagta      1380
gggggtgggg cgtggggatg gtgactgtgg ggtggggatg gcgagtgggg ctggggcctg      1440
ggaatggtga gtggggtggg gatggcgagt acagggtgtg gcatggggat ggcgaatggg      1500
```

```
gcatgaggat ggcgtgtggg gatggcgagc agggggggtgg gctgtgaggg acagtgcctg    1560
agatgtgggg ctgcagcccc agctcacaca tggccttatg accccagcca ccttcctgcc    1620
ccaggcgggg tcgctgaggc ctcaggagga gaaaacacag gacctgctgt ggaagccagg    1680
gcctcacaga ggtgagcagg gactgccact ggtttagtcc cggggcccag tggggggccaa   1740 catcacctcc ttggcctccc atggcaagga gccagcccgc ggggtggcta ctgcactgcc    1800
ccccaaggag ggtgttccct gctcaagagg aagtgaccgc tccagttcag ccttccctgg    1860
gactggggtg caggtgacct tatcttcttt gttaaatcct gttccttcca gacaatcctg    1920
tgttattcat caggtttgcc tcagttcttg agagcttttc tgatgcaaat ctgctttcat    1980
cccagggcgg taggggctca gctcacgcca gcctccaggg gtgtgggtgt cctagaagtg    2040
tgggtgtccc gggggcgtgg gtgtccctgg agtgtgggtg tcctgggggc atgggtgtcc    2100
cagagcgtgg gtgtccctgg agtgtgggtg tccaggggc gtgggtgtcc cggaggcatg    2160
ggtgtcccgg ggcgtgggtg tcccggggcg tgggtgtccc aggggcgtgg gtgtcccgga    2220
agtgtgggtg tcccggggcg tgggtggctt ggggcatgg gtgtcccggg ggcgtgggtg    2280 gcttggggc gtgggtgtcc cggggtgtg ggtgtcccgg gagcgggtgt cccgggagtg    2340
tgagtgtcct gggggtgtgg gtgtcccggg agtgtgagtg tccaggggc ctggatgtcg    2400 ggggactgca gggacaccct tcccactcct gctgcccggg gcacctcccc tgaggactcc    2460
gcctccaaga gctcccacct cctggattct ttggtgaccc ccgcctgcat cctcagcctc    2520
cttccaaacc agaccggttc tctagggacg tggacgtgtg aaactgattt taaaggaaac    2580
agacggtggc gtttctctgg gccccacgtg gcccagtagc gcccaccttc cgtcccttct    2640
tccgcgctca gtaaccgatt taggccgctc ctgcagaact cgggctcctg cccacctacc    2700
acctgcgtcc acctgaggcc tcgtcctccc agcaaaggtc gtccctcccg aacgcgcctc    2760
ctgcggcctc tccagagccc ctcccgcgcg tcctctcggc ctcctcccgg gcctccctct    2820
cccgcctgcc ccacggcccg gccagtctcc cctcgcgggc tgaggcgggt tcaggcagcg    2880
cggccgcccc gggggtcact cctcgtccac caccgcgtgg tgcccacagc tcacagctcc    2940
cgggagacgg tcccctcagc tgcagggcgt cctgaagaac ggcctgctca gagctgagcg    3000
cacgggcttg cctcgccctg ggcgcccttg gccctcgccg accccgttnn nnnnnnnnn    3060 nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
```

```
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnaccctacc aggcacacgc tctccctacg cggccactcc    4140
gcgcatgccg gttttcacat cagaaaatac gatttgaaaa gcacacttag ggtgtccccc    4200
ttaacttcct aagggaggcc ccccaatccc ataaggatcc ggggcagtct gcgcatcacg    4260
gatgcgcggc tcacagaagg gacgtggtga gaagctggcc tgggggagct gctcgcggcc    4320
cacaccatgc caccagcggc acctccgcag ggcacatgtc ggggagaaaa acatgtggg    4380 gacctggggc tttctccacc tcacactcac gggtcacctc acacaggaca cctcacactc    4440
agggtgcact tcaaactcac aggtcattac acctcacaca ggacgcctca cacaagacac    4500
ctcacatggt gcacttcaca ctcacaggtc acctcacatt cgacacctca cactgagcac    4560
acttcacact cgggacacct cacactcagg gtgcacttca aactcacagg tcattacacc    4620
tcacacagga cgcctcacac aagacacctc acagggca cacttcacac tcacgggtca    4680
cctcacattc gacacctaac acagatcacc tcactcagag gacacctcac actgggcaca    4740
cttcacactc aggacacctc acactcaggg tgcacttcag actcacaggt catgacacct    4800
cacacagatc acctcactct ataggacac ttcacactca cagatcacct cactctcaca    4860
ggacacttcg gacaggacac acttcacaca ggccacctca ggttatgtca aactcacagg    4920
tcccctcaca cagtcacctc acacagtgta cacttcacac tcacaggtcc cctcacacag    4980
gtcacctcac acagtcacct cacacagtgt acacttcaca ctcacaggtc ccctcacaca    5040
ggacacctca cacagtcacc tcacacagtg cacacttcac acaggtcccc tcacacagtc    5100
acctcacaca caggcacac ttcacactca caggtcccct cacacaggtc acctcacaca    5160
agatgcactt cacactcatg ggtcccatca cacacaggac acctcacact cgtcacctca    5220
cacatgttac atcaaactct caggtcccct cacacagtca cctcacacac agggcacact    5280
tcacattcgc aggtcacctc acaccaggcc cacgactctc acaggtcacc acacctcaca    5340
cacatcagct cacatagatc atctcaccct cacaggacat ccatcacact cacaggtcac    5400
gtcacactca tacctcaccc acaggtcacc tcacacaaat caccttgctc acacagatca    5460
cctcacacgc agggcacact tcacactcac aggttccctc acacaggaca cctcacactc    5520
acagatcacc tcaacaccga tcacctcaca caggggacac ttcattctca caggtcacct    5580
cacataggac atctcacaca caggtcacct cactcacaga tcacttcaca cagggcacac    5640
ttcactcaca gatcacacct cacctcccgc tcacagatca cctcactctc acagggcacc    5700
tcactctcac aggacacctc atacagggca cacttcactc ccacaggtca ccatacctca    5760
cacagatcag atcacttcat tctcacagga tacctcacac tcagggcaca cttcacactc    5820
acaggtcacc tcacacaagg cacccttcac acaggtcacc acacctcaca cagatcatct    5880
cactctcaca ggaccctca cactcagatt atctcacact caggtcacca cacctcacac    5940
tcttaggatg tctcacgcag gatgcctcac agtcacagag aaccacatct catatgcaca    6000
agacacttca cattcacagg acacctcatg ctcacaggaa gcctcacact cacaggaagt    6060
ccagctgtct gagacaaagg ctaacatgac ccttccgggg caaattgagg atggtcatgc    6120
ctagcatttt tatccaccta gttttcaaag catttctcat ctgttgtatt ctcacagcac    6180
cctgtgagtt taagtttagg tggccaacag tttcttcagc aatcactttt ttctgtggag    6240
```

-continued

```
tgcttttgct gtttgtggaa gattttgcat ctgctactgc accctctccc ggtgtcagcc    6300
ggtgtgtgtg gccaccctgt cagagatgga gctgtggctc aaagcctgtg tacctcatcc    6360
caggtccaca gctcagcgac agaagagtca gggctgaacc tcgggtgttc tgacctggga    6420
gcaggaaatg tgtggtcacc catagtttca gaagtcctgg ggaggggcca agattggaag    6480
aaatctacct cagctctgca ggaaagtctg gcttcctgag cccacccccgc caggcccagg    6540
tccaagttcc ccaaccccag ctcgtggttt gtccagtgct caccgttggg tgcactggtg    6600
aaggtgctca cgaggctttc tcttttgttc cctcagaagc tgttctggat ttcttacagt    6660
ggtgagtaga tgatcgccac caatcctgcc tgcaaccctt ctcctcagcg tactgacgcc    6720
agcccattcc acagatgggg accagtgtgc ctcaaatccg tgccagaatg ggggctcctg    6780
caaggaccag ctccagtcct atatctgctt ctgcctccct tccttcgagg gccggaactg    6840
tgagaagagt gaggccccac tttgggtccc atatttgcag agggcctggc caaccgggtt    6900
gcagggtgca caacctggtg gggtgtgtgg accgggcatt ctgagctcag ccccagttgg    6960
aatttggtct aggtgacctt gaagtcccct ctagtctgag gtctttgaca gggacccaag    7020
gttctaattc tcagactcag tggccccttg ggctcccggc cctgggcaat tctcagccct    7080
cgagatggcc cagctgagag tccctgtgtc cctgtcccac ttccacgtcc caccaggcag    7140
caccgcttgg taaacttccc cttctctact ttccattaca aaggtttgag gtgtttttg    7200
ttttgtttgt ttgttttgg ttttgtttg ttttgtttac catctgaata ttaaattatt    7260
gcaaagtttg aggcccccaa cttcccttag gttcagtaat tcactagaag gactcataga    7320
acccactgaa gtggatacac tcacagttac catttattac agcaaaggaa gctgacttaa    7380
gtctgcagag gaaccgggca caaacttccc attgtcccct ccctgtgggg tcatgtggac    7440
acttctccca gaaagacgtg tgatgagacg tgggaagtac tgccaacttg ggaagctcta    7500
tgagccccgg tgtccagagg ttttatcagg gctcaatcac acagacccag ctgaccaccc    7560
acacggctga cctcagtctc agcccctcca gaggccaagc caatagtgtg gcccgaggcc    7620
ctgccatcat cacattgtca gctagaccat ccagcatggc ccaaggtccg ggtaaacacc    7680
aacattccct cagggcttag cgatcacttc ccaggaaatg tgtggtcacc cttccaaggg    7740
cttagcgatc acttcccagg aaatgtgtgg tcacccttcc aagggcttag cgatcacttc    7800
ccaggaaatg tgtggtcacc cttccaaggg cttagtgatc acttcccagg agccaaggca    7860
aaggctaccc tttccctggg aacagcagct catccttgac cacccaaggt ggttcattct    7920
cacactgaac gagctctccg gcacagcagc cactttcttc tctaagtaga agagagccca    7980
gcaaggtggg gcaggctgaa gagagaggct tcctgctggt catctgggtc cagaatgcct    8040
ggggatctct gctcagccct ggtgcccagc agccctggtg tgcatcctgc agggcaggcc    8100
ttcccgccgg agtcctggac ttactcaggg ccactgccct tgcccacatc aatcaaagtc    8160
gggctgccgg ttctgctgct tctgtctgag cccatggcca gtgctgggac tgactgtccc    8220
taggcgggct cgcggtggca tgaggccagc ttgagaaact gtctcagcgc tctggtcctc    8280
tcgtcagttg agtctctgat tggaagtccc ttggatactt ttaccatccc tacgggactt    8340
tcactttccc ccaggctccc ctcagcttcc catcagctgc tcggaagagt ggtcaccctg    8400
gaggccactg cccaccagcc aggcaccccc ccaaatgcaa ctgcagccag cgctgccccc    8460
gactggcaag gctgttcaga cgtgactcct ctgatccagg ccttgtcctt tggatcagtc    8520
cacggagcag gcggtgccaa gctcaggctc tgtcgcccac agctcagtgc cccttccagg    8580
cagaacgccg ctgctgactt agggcatggc atccccgggg gctggctctc actgacccaa    8640
```

```
agaggcccct ctcagggtat ccccttcctg tccgcagaca aggatgacca gctgatctgc   8700
gtgaacgaga acggcggctg tgagcagtac tgcagtgacc acgcgggtgc caagcgctcc   8760
tgttggtgcc acgaggggta ctcgctgctg gcagacgggg tgtcctgcat gcccacaggt   8820
gaccaggctt catgtcccag tcccagatga caccagtccc tgtcccacta cggattctct   8880
tactggacaa agacgggtg ggggtggctt cacatctgag caccaaccat gcgctgacca   8940
accgtgaggc aggatctggg caccaagggt ggcacaggcc agagcgacag tgactaggat   9000
gggcaccctg ggggcagtcc ctgaatggcc tcaggccccc tacccatgct aggcagacca   9060
ggggagccaa gcaaggctct atctcacgtc caactcccac tcgcaggacc tccgctgggg   9120
ttcgtgaatc taccttggca caggcagtgt ctgtactgac tgctgcccgc tctgaattcc   9180
aaaacttgta aaggctcctg ggaaaatggg atgtttctcc aaaccagcct ggaacaaatg   9240
ggctgcactt ccaaaggcag ggacacccca cgcccactgt gtctcgaaga ggtggacgtg   9300
cccaccctgg ccacacagcc tgggactcag cccaccacct cctcaggttt ctttctggc    9360 ccacgacctt gattggagca gatcaaaact aagcgtggga tcaaaacaac agagttgttt   9420
gtgacgttga ttcatcttta ggtagaattt cattcacctt ttactaaagt caagcaacac   9480
attttccccc tgaaaagtga gcagagggca atattaagac gtaagccctc catctcctcc   9540
aaaaccagcc ctgaccattg tctcctcagc cagccacttc cgcaagggcc tctcatggcc   9600
cagccccacc agtcaggccc agccccacca gtcaggccca gccgaggccc tgctttccac   9660
catccctggg ccctgcagc tcctgctcct ggggcctcc catagcctcg gcctcaaggc     9720
ctctcagagg atgggtgttt ctgaatcttt cctagtggct cgttcatcct tcacaaattt   9780
ctgcatcttt ctgactttg ttttacacag ttgaatatcc atgtggaaaa atacctattc    9840
tggaaaaaag aaatgccagc aaaccccaag gccgaattgt cggggcagg gtgtgcccca    9900 aaggggagtg tccatggcag gtaaggcttc ccttggcttc aggattctaa gccctgaggg   9960
tcttggagcc ttttgaatgt gagctgaaca acagttctgg aagggaaaat gggcaggtca  10020
gccccaaggc caccaggctc caagtcagcc cacctagaac ctctagctcg ctgcaccccc  10080
atgctttcag tggggcaagg aaggagaaaa gaaggcgaca ctcgctgagg gtctacccty  10140
tgcagagaac cctgcgagat gcccctcccg agttgtcacg tcgtcctcac tgttactctt  10200
tgaggtggga tctttgcctg atctttgcaa aatcaggagc attggatcaa agctatgtga  10260
agatcccgtg aggtgaacag tgaaatctca cagcgacgtt tgtattgttg ggctgtgccc  10320
aagagcacgt ctcggctaga gaggggcgca gcctcccaga gccaggtctg agcagctttg  10380
cctgggaggg atctgcaaag accccaggat ttcagaaaca aattgtgcaa tgccagaggt  10440
cccttggcgt gccgggagg gcgagtcatc agagaaacaa tgacagtaat gtgacttcca   10500
tgcctcctgt ccccccgccc aggtcctgtt gttggtgaat ggagctcagc tgtgtggagg  10560
gaccctgata aacaccatct gggtggtctc tgcggcccac tgtttcgaca aaatcaagag  10620
ctggaggaac ttgaccgcgg tgctgggtag gtgccgctct cccctgtgtg accgcggtgc  10680
tgggtaggtg ccgctctccc ctgtgtgacc gcggtgctgg gtaggtacca ctctcctctg  10740
accgcgttgc tgggtgggta ctgctctccc atctgactgc tgtgctggtt acgcgccgtt  10800
ctcccgtctg acgatggtgc tgagtaggcg ccactctccc ctgtctgacc acggctctca  10860
agtgtctcag gggccgcagc tctgggcttc gtgctgtcac ttccacagac agacagacat  10920
ctccaaaagg ggagcaactg tgctaggcat gactgctgtg gccaccgtcc tctcagccac  10980
```

-continued

```
tttcccatgc ccaaataaaa tggtaaaaga caggggttct gcccatcctg cctcacctgg   11040
ccaagagccc ataggaggat gcaacttcca gggcttcatg ggaccactgg gtggcaggga   11100
ctgtgctcac tgggtttaca ggtgagatga acattcccag gagggcactt ggctgggaag   11160
aactgtggag aatcagggca cccctgccc ccccagctgc caggtcgcag caccccttcc   11220
ccacctcaac gcccaggccc cagattcacc ccagttcaca cgtccccatg tgagccacag   11280
gctgccacct gcggcaggct ggccaggtca ccttggggtt ggatgcaggc cccctcacc   11340
ccaaaaggag actgcagccc ctgcagacct agaaatggcc acagcccgtc cccatgcacc   11400
aggggccag gcagcaggta gtgggatggg cctgagcaag gctccctcct tccaggcgag   11460
cacgacctca gcgagcacga aggggatgag cagagccggc gggtggcgca ggtcatcatc   11520
cccagcacgt atgtcctggg cgccaccaac cacgacatcg cgctgctccg cctgcagcag   11580
cccgtggtcc tcactgacca tgtggtgccc ctctgcctgc ccgaacggac gttctccgag   11640
aggacgctgg ccttcgtgcg cttctcgttg gtcagcggct ggggtcagct gctggaccgt   11700
ggtgccacag ccctggagct catggccctc aacgtgcccc ggctgatgac ccaggactgc   11760
ctgcagcagt cacagaaggc agaagcctcc ccgaatatca cggagtacat gttctgtgcc   11820
ggctactcgg acggcagcag ggactcctgc aaggggggaca gtggaggccc acacgccacc   11880
cgctaccggg gcacgtggta cctgacaggc atcgtcagct ggggccaggg ctgcgcggcc   11940
gtgggccact tcggggtgta caccagggtc tcccagtaca tcgagtggct gcaaaagctc   12000
atgcactcag agccacgccc aggcgtcctc ctgcgagccc catttcccta gcctagcagc   12060
cctgccccct ggagagaaag ccaaggctgt gtagaactgt tctggcacaa aatcccatcg   12120
attcttctgc agttcatggg gtagaggagg gcatgggagg gagggagagg tggggaggga   12180
gacagagaca gaaacagaga gacaaagaga caggagaga ctgagggaga ggttctgagg   12240
acatggagag actcaaagag actccaagat tcaaagagcc taatagagac acagagaagg   12300
aatcgaaaag atgagatgca gaggcagaca ggcgctggac agaggggcag gggaatgctg   12360
cggttgtcct ggaggcagac agcccagctg agcctcctta tctctcttca gccaagccca   12420
cctgcccgtg atctgctggc ctcaggctgc tgttctgcct tcattgctgg agacactaga   12480
ggcatgtaca cacgtggatg catacacaca caccaatgca cacacagga gatatgcaca   12540
cacacgggatg cacacacaga gggtcacaca gagatatgca aacacactga cacacacata   12600
cagagatatg cacatacaca gatgcatata cacagatatg cgcacacacg gatgcgtgca   12660
caccacacca atgcacacac acactaatgc acccacacgg atgcagagag atatgcacac   12720
accgatgtgc acatacacag atatgcacac acatggatga gtgcacacac accaatgtac   12780
acacacagat atgcacacac ggatgcacac acaccgatgc tgactccatg tgtgctgtcc   12840
tccaaaggcg gttgtttagc tctcactttt ctcgttctta tccattatca tcttcatttc   12900
agacaattca gaagcatcac catgcatgtt ggcaaatgcc ccaaactctc ccccaaatgt   12960
gccgggctgc acaggccgtt ccccaccggc ttcccaactt cacaataaat ggctgcatct   13020
cctccgcacg cctgtggggc ctgccaccca ccgtgtagcc tgtgattcat tttcagagcc   13080
tccagtgctc atcctctgag atgctttttt ctttcacagt tttcagcatc actgaaatga   13140
accctcacat ggcagctgtt cttttttaaaa acaaaagctc tttgatagat gtttgaggct   13200
gtagctccca ggaccctgtg gaattggttg ttctctccct gccacagccc ttgtcaatga   13260
tatttcgcag agaccctggg agcacctgct tgagaatcag ggcatacca ctaaatgcag   13320
gttcccaggc cctggctgca gtgggaggac ctggcaagct gcactcttgc tgagtcccca   13380
```

```
gggtggtggg ggaagaatga gaaacacatg agcagagaaa tggggaggtg acagacactg    13440
cccgcactca gactccagca agcatggctc agagagcgga ctcaacgcca tccctgtagg    13500
gccgtcctgg gcaccagtgg cgctcacagc agcaaggcag gcaccagcaa cccacctcgg    13560
gggcactcag gcaacatcta ctttagagca gacagggtcc gtgaactaca gctgagggct    13620
gcttctaagc cacccggctc ttgtaaataa agttttatgg gaacacaccc acgttagtgt    13680
ccatggagtg gccgtgacag agatgtctag ccagacagac cagctgacct gccaagccca    13740
gcatgattag tgtcaggacc tctgccgaag atgctggctg accctggcca gccccagtt     13800 cctaatgccc ccacacaggg acgggggcca gtggcgggcc ctgatcaggt cagagctggc    13860
tctgctttct cttttgtccg agtgactggg gagtcatgcg gggtcctggt ggggtgccag    13920
cctcccttct tgccaatggg aaatgcaggc acccacctca cggtgctgct gaaggagggg    13980
gcccgggact ctccagaaac tttgctgaag ggcctgggca ccctcgaagg ctacatttct    14040
tatgggacgt gccacctgcc atggctcagc tccagctttc tgtgagtggc gagatagaat    14100
acagggaggc cactggccat gggcctgcga cagggtgggg cgaggcagca ggctcgggcc    14160
tccaaagcca gcatcaccac ccagcgttga tgaaaaagac tgcatgtctg ccatgagcat    14220
cctgctgctg gtgcacacac cacattggtc tctccataca aacgtgccta gaggcgatgt    14280
cggagtgtgg agaccacgag aggcaggagt cagacatctg gtgccaccag gaaggcccct    14340
ctcagaggac tgggctgtgc gtggtgccca ccgtgggagg ctaccctggc gttggcaccc    14400
agtgccatca gtttgtgtag tcgggtgggg cccagtgagc acctcctgtg tgccaggcac    14460
aatgacgcac aatgtgtgca caccaggccc aggtgcaggt ggctgcgaga cgggcaacac    14520
atcaaggcag acacaccgtg aggcagtggc cagcactgtg ggttttaggg gcgttgctcc    14580
ggccactacg gcatagcagg tagtgattgc cacactggcc aagttttaga ccatttattc    14640
cagggacccc agaagcaaaa atcctggctg cacctcccgg tgactcccac agccattgag    14700
tggagacgct cagggacctg gtgacaggag gtttctgtgc tggacaatga gcccagaagc    14760
cctctcagcc ttggaacagt gtggccagtg gtgggcaggt caggagggggt ttcagacaga    14820 gcctgtccct ccagatggtc aggggagggc tactccccac agaagtacat gttgggacca    14880
tgtgggcaca gaaggtttgg gggtgggtgg ggcaggtacc agcctggcct gtgggagacc    14940
gtggtgcaga tgccaagccc ccccgtgaca tcagaccacc tgacaccacc cagagaatgg    15000
c                                                                    15001
```

<210> SEQ ID NO 14
<211> LENGTH: 3278
<212> TYPE: DNA
<213> ORGANISM: Homo sapiens

<400> SEQUENCE: 14

```
aggcacacag gcaaaatcaa gttctacatc tgtccctgtg tatgtcactt gtttgaatac      60
gaaataaaat taaaaaaata aattcagtgt attgagaaag caagcaattc tctcaaggta     120
tatttctgac atactaagat tttaacgact ttcacaaata tgctgtactg agagagaatg     180
ttacataaca ttgagaacta gtacaagtaa atattaaagt gaagtgacca tttcctacac     240
aagctcattc agaggaggat gaagaccatt tggaggaag aaaagcaccc ttattaagaa      300
ttgcagcaag taagccaaca aggtctttc aggatgattt tcttatatca agtggtacat      360
ttcattttat ttacttcagt ttctggtgaa tgtgtgactc agttgttgaa ggacacctgc     420
```

```
tttgaaggag gggacattac tacggtcttc acaccaagcg ccaagtactg ccaggtagtc    480
tgcacttacc acccaagatg tttactcttc actttcacgg cggaatcacc atctgaggat    540
cccacccgat ggtttacttg tgtcctgaaa gacagtgtta cagaaacact gccaagagtg    600
aataggacag cagcgatttc tgggtattct ttcaagcaat gctcacacca aataagcgct    660
tgcaacaaag acatttatgt ggacctagac atgaagggca taaactataa cagctcagtt    720
gccaagagtg ctcaagaatg ccaagaaaga tgcacggatg acgtccactg ccacttttc     780
acgtacgcca caaggcagtt tcccagcctg gagcatcgta acatttgtct actgaagcac    840
acccaaacag ggacaccaac cagaataacg aagctcgata aagtggtgtc tggattttca    900
ctgaaatcct gtgcactttc taatctggct tgtattaggg acattttccc taatacggtg    960
tttgcagaca gcaacatcga cagtgtcatg gctcccgatg cttttgtctg tggccgaatc   1020
tgcactcatc atcccggttg cttgtttttt accttctttt cccaggaatg gcccaaagaa   1080
tctcaaagaa atctttgtct ccttaaaaca tctgagagtg gattgcccag tacacgcatt   1140
aaaaagagca aagctctttc tggtttcagt ctacaaagct gcaggcacag catcccagtg   1200
ttctgccatt cttcatttta ccatgacact gatttcttgg gagaagaact ggatattgtt   1260
gctgcaaaaa gtcacgaggc ctgccagaaa ctgtgccacca atgccgtccg ctgccagttt   1320
tttacctata ccccagccca agcatcctgc aacgaaggga agggcaagtg ttacttaaag   1380
cttcttcaa acggatctcc aactaaaata cttcacggga gaggaggcat ctctggatac    1440
acattaaggt tgtgtaaaat ggataatgag tgtaccacca aaatcaagcc caggatcgtt   1500
ggaggaactg cgtctgttcg tggtgagtgg ccgtggcagg tgaccctgca cacaacctca   1560
cccactcaga gacacctgtg tggaggctcc atcattggaa accagtggat attaacagcc   1620
gctcactgtt tctatggggt agagtcacct aagattttgc gtgtctacag tggcatttta   1680
aatcaatctg aaataaaaga ggacacatct ttctttgggg ttcaagaaat aataatccat   1740
gatcagtata aaatggcaga aagcgggtat gatattgcct tgttgaaact ggaaaccaca   1800
gtgaattaca cagattctca acgacccata tgcctgcctt ccaaaggaga tagaaatgta   1860
atatacactg attgctgggt gactggatgg gggtacagaa aactaagaga caaaatacaa   1920
aatactctcc agaaagccaa gataccctta gtgaccaacg aagagtgcca gaagagatac    1980
agaggacata aaataaccca taagatgatc tgtgccggct acaggaagg agggaaggac     2040
gcttgcaagg gagattcggg aggccctctg tcctgcaaac acaatgaggt ctggcatctg   2100
gtaggcatca cgagctgggg cgaaggctgt gctcaaaggg agcggccagg tgtttacacc   2160
aacgtggtcg agtacgtgga ctggattctg gagaaaactc aagcagtgtg aatgggttcc   2220
caggggccat tggagtccct gaaggaccca ggatttgctg ggagagggtg ttgagttcac   2280
tgtgccagca tgcttcctcc acagtaacac gctgaagggg cttggtgttt gtaagaaaat   2340
gctagaagaa aacaaactgt cacaagttgt tatgtccaaa actcccgttc tatgatcgtt   2400
gtagtttgtt tgagcattca gtctctttgt ttttgatcac gcttctatgg agtccaagaa   2460
ttaccataag gcaatatttc tgaagattac tatataggca gatatagcag aaaataacca   2520
agtagtggca gtgggatca ggcagaagaa ctggtaaaag aagccaccat aaatagattt     2580
gttcgatgaa agatgaaaac tggaagaaag agaacaaag acagtcttca ccattttgca    2640
ggaatctaca ctctgcctat gtgaacacat ttcttttgta aagaaagaaa ttgattgcat   2700
ttaatggcag atttttcagaa tagtcaggaa ttccttgtcat ttccatttta aaatatatat   2760
taaaaaaaat cagttcgagt agacacgagc taagagtgaa tgtgaagata acagaatttc   2820
```

```
tgtgtggaag aggattacaa gcagcaattt acctggaagt gatacctag gggcaatctt    2880 gaagatacac tttcctgaaa aatgatttgt gatggattgt atatttattt aaaatatctt    2940
gggaggggag gctgatggag atagggagca tgctcaaacc tccctaagac aagctgctgc    3000
tgtgactatg ggctcccaaa gagctagatc gtatatttat ttgacaaaaa tcaccataga    3060
ctgcatccat actacagaga aaaaacaatt agggcgcaaa tggatagtta cagtaaagtc    3120
ttcagcaagc agctgcctgt attctaagca ctgggatttt ctgtttcgtg caaatattta    3180
tctcattatt gttgtgatct agttcaataa cctagaattt gaattgtcac cacatagctt    3240
tcaatctgtg ccaacaacta tacaattcat caagtgtg                            3278

<210> SEQ ID NO 15
<211> LENGTH: 26001
<212> TYPE: DNA
<213> ORGANISM: Homo sapiens

<400> SEQUENCE: 15
atgccctcca taggctttca gaccttcttc aaggccaaag ggaaggcctt catggaaata      60
taattatgtg aaacacccca gattttttc acaaactttc ctgcctataa acgccaggtc     120
ctaccactgt ccagtgtccc acttcccact gtccagtggg aagactccct ccaggacaaa    180
accacccttt ccttcaggga tgtgacgtgc tgtgctttcg ttgacagtca tgcagctgct    240
agacatgtca cttcctagct ctccattcgg gtctgtgtcc caggacctaa agaaagctaa    300
aagaagccgg gcgtggtggc tcatgcctgt catcccagca ttttgggagg ctgaggctgg    360
cggatcactg gagatcagga gtttgagacc agtctgacca gcatggtgaa accctgtctc    420
tactaaaaat acaaaaaaag aaagaaaaa agaaaaaaa ataagctggg cgtggtggcg    480
cgggcctgta gtcccagcta ctccggaggc ggaggcagga caatcacttg aacctggaag    540
gcggaggttg cagtgagctg agatcgcgtc attgcactcc agcctgtgcg acgagagact    600
ctgtctcaaa agaaagaaag aaagagagaa agaaagaaag aaagaaaaga aagaaagaaa    660
gaagaaagaa agaaaagaaa gaaagtaaga agcaagcaag ctgaaatagc ttatttttct    720
gttttaaaaa atagactttt agtgttcaca agtaagaata aaaaaaaaaa aagcttggcc    780
ttaggaggaa tcctatctgc ttaggcctct gagaggcagc gtcacctgaa gggaaactga    840
ctgggcaaga gccaggctct taggagctgt ctgtactttg cttcccatcc gtccgctctc    900
ccccagcagc caaagtctcc tccctccatt atattgcaaa tcaatgaatc cattagactt    960
tccatgtttt cttttagac tttgagattc aaggtcagct agaattaatg gttaacagct    1020
gacaggtgaa agtgtggtta atgcagcttt ggctagcag gcacacaggc aaaatcaagt    1080
tctacatctg tccctgtgta tgtcacttgt ttgaatacga aataaaatta aaaaaataaa    1140
ttcagtgtat tgagaaagca agcaattctc tcaaggtata tttctgacat actaagattt    1200
taacgacttt cacaaatatg ctgtactgag agagaatgtt acataacatt gagaactagt    1260
acaagtaaat attaaagtga agtgaccatt tcctacacaa gctcattcag aggaggatga    1320
agaccatttt ggaggaagaa aagcaccctt attaagaatt gcagcaagta agccaacaag    1380
gtcttttcag gtacagtttc agaacttact atttaacatt cctctcaagc aaatacgcct    1440
tgaaatgctt tttaaatc ataggaattt aaaaacactt tacaatagag aatgattgat    1500
ttttaaaatg tgtctgattt agctttgtag agatgttccg ctaatatcca taactaatct    1560
gagaggaaat gtggaacaac agaagagtaa cagtgtctac tcagtaacaa gcgttttacg    1620
```

-continued

```
agttaaaaag acatccaaat gcagtactga aaaatcagaa gtcttgattt gtctcactga     1680
tgactccgtt tttcctagag cagtctgttt aatgcttact ggagataaat agatttatag     1740
gtgaccaaga caatcgatta atgtatcagc cacagacttt tttaaataga aaattttcta     1800
agtaggaaat cattcatagc tctttgaaag atatagggag aggcctcaag gaaagaaaga     1860
aaggaaaaaa attgggaaag gaaacaaaga tgaaaaattg gggtggggag agcggtcaga     1920
tggtggccat gagaaggatc tgaacacaga gagcggcggg gccggcgggg aaggagggag     1980
gaggggagag cgctgcttcc ctgtgggttc cggcttctgc agagctgtaa gagttgaatg     2040
ccacacacag tcacactaag gaatgctcca ggattgggaa agaaaattca acattataat     2100
gagaacactg tgaatgctat tgaattaact actcccctct ctccctattt cttgtaagtc     2160
ttagtgtcag taaactaatt ataaatttac attttatgtt ctaaaagcat gcacctttttt    2220 ctcattgtag gatgattttc ttatatcaag tggtacattt cattttattt acttcagttt     2280
ctggtggtaa gtagagtgtt atcttaacta tgggctggga gagggaaatc acactgcaat     2340
ctccacacat gtgggagaat cccacaccat ttatgccggg aaggaaataa aatgttttta     2400
ttaacttcct gcctgaggct ccagaggttt tcaaagcagg gtaggaattg aggtgaaaaa     2460 attgttttgta ctggtaggaa tctgtgtcta tatgtgtacc atatctacat ccatgcctac    2520
atacatcatt catttaaatg atatttaaaa gcaatattaa aaagaagaaa tcttgatttg     2580
cctcactaat tagttggttt ttcataaagc agtcagttca atggaacata cacacacaca    2640
taaaatagga attttgtact gaaaaatgtt atgtaactat tcatacacag tttatgcatt     2700
tcaataattt aactaccctg ttaattctcc accctatgtc acatctgcta aatttgttta    2760
taaattactt agccaatatt aagtaggata tatcagtaca ggtattgttt agttccatga     2820 ccattccttta tttaaaatga aagctgaagc attcctttag aaaaatagct tatgtctaca    2880
tgttatattt aatttctgat actattgcta gcattttaag catagtaaat tctttttgct    2940
ggcctatgtg aaaaaaggca aacctaggtg aagatattaa aagtaaattc cacttaatat    3000
attaaattac acagctcata atttcaattt tctctgtgac aagactactg ctcaggttat    3060
aatattcctt tgttataatt atctggaaat tgtattgtta tttcattgat aaatatgtca    3120
gcgctaaata atttgatata ttttgaacac tggacccaat aactacataa acaattgacc    3180
ctgaatcagg ggttccacat ccatggattt aaacaacatt gaagtgaaat ttttaaaaa     3240 aaattatatc tgcactcaac atgtgcagag ttttttcttg tcattattcc cgaaacaaca    3300
cagtataaca acaatttgca tagtatttac attgtactag gtattataag taatctagag    3360
atgatttaaa gtacacagga ggctgtgagt aggttatatg taaatactat gccatttttct   3420 atcagggact tgagcgttca tggatttttgg tatctgcagg aggtctggca gccaatccct   3480
catagatatc aaggaatgat agtgtacata tttaggtcct ttatacatgc acatggaaca    3540
tttacaaata ttgaccacac acaagcctct gaaacaaggc tcaacaaatt ttaagggggtt   3600 aaaattatac tgatcatgtt attcaatcac cgtgaatggg agctagaata ataataaaaa    3660
gggaattgaa atctgcaaaa cgtttgaaaa ttgagtattt ataatcaccg tgaatgggag    3720
ctagaataat aataaaaagg gaattgaaaa tctgcaaatg tttgaaaatt gagtatttat    3780
acctttttag attaagatga atcagagatg aaatcacaat ggtaattaga aaaggaattg    3840
tacaataatg aaagtacagt atatcaaaac tttgagatgt aaccgaatca gtgttgagat    3900
caaatgtata gatttacatg tatacattag aatacagaaa agggaaaaat taatgatata    3960
agatgacaag aagatagaga atagcaactt aagtgctaag aaattagaag gcagaaagaa    4020
```

```
gaaatcgcag aaattaatta aatggaagac acacatattt gagaggtcaa cataacccct    4080
ttctagccca tttttataagg tcagggtaat cttgacacca aaatctgata ggaaaattct    4140
gaggaaaaaa agtcacaggt cttttatctt atgaacatat gtacaaatgt cctaaacaaa    4200
atattatcca acttaaccca gtagattgtt aaaaaaatta aaggatgatt acattgtgat    4260
attgtgacaa agttgggttt attccaggaa tgaaagttg  atttaacatt caaaaatcaa    4320
tagatgtgtg acttcggggt acataccgaa aaaaagaag  ggaaagcagg aactcacaca    4380
gatatacttg tacacccatc tcatagcagc attattcaca ctaacccaaa ggtggaagca    4440
gcccatgtgt ttatcaacag gtgactggat aaagtgtggt acatacatac aaaggaatat    4500
tactcaaccc taaaaagaaa ggaaattctg acacatgcta tgacatggat gaaccttgag    4560
gacattacgc taagtgaaat aagccagtca caaaagaaca atactgtgg  gatctcactg    4620 ataggaggta cttagggtag tcaatttcat caagacggaa attagaacag aggttgccag    4680
gggccgaggg gccaggggaa gggctgaggg ttggtgttta atgggcacag agcatcagct    4740
ggcgaagttg aaaagttctg gaggtggatg gtgctgatgg ttgcacagca atgtaaatac    4800
ccttagtgcc acagaactgt acactcaaga tggctacatg gcacatggta tgctatctgt    4860
cataataaaa aataaaaata attttaaatg ttaatatgtg ccgaaaaatg cttgctaaaa    4920
ttctattaat gatcaaaact ttaaataaac tggaaatgga agagaacttt catcagctat    4980
taaacgatat tttaaacaaa agcaaacaaa aatccaaacc aaaaatcttc aagaaacata    5040
atacgtaata gcggaatatt gaaagctttc ccaagggatt gagaatagga caagaatact    5100
tcccattatt tccatttact cttgactgga ggtactcgtt ggtgcggtaa ggaagggaaa    5160
taaaaggaaa acgattagga ggaacataag ctctcgtttt tcacagatga tgtgattgag    5220
tacctagaaa aatccaaaat taaccatcac ataaattatt tgagccaatt aattaaatga    5280
gtaagaagtc tcgatacaac gtcaatatac aacagcaagc acttgctcgt tcgcaaaagc    5340
agatgaacta gtttttactg acactagaag cagcatgtgt tccatgtgtt ccacatccat    5400
gcactcaaac aaccttgacg tgaaatattt tttaaaaaat tgtatctgta ctcaacgtgt    5460
gcagagtttt tttccaaaat tgttttccaa aaatttttaa atgtttatat gtttaggggg    5520
tgtaagtgca gatttcttac atacatatat tatgcggcgg tgaagtgccg gcttttggtg    5580
tacccatcac ccaagtagtg aacacagcct ccaacaggta atttttcaac gctcaccccca   5640 ctcccatcct cccatctagt ggcatattga aaatcaattt gtcttgtaaa attaaataat    5700
ccaattagga gggggatata ttctaaggaa attagtgcat gatgcacaca cacacacaca    5760
cacagaacac gtgtgtgcgc atgtgcacat gagagagagt gagagagaaa ctgggtcttg    5820
ctctgtcgcc caggctggat tgcagtggta aaatcacagc tcactgcagc ctcaaactcc    5880
caggctcagg agatcctcct acctcagcct cccgagtagc tgggattaca ggtggaaaca    5940
accatgccca gctagtattt tttttttttt ttgtattttt tatagagaca gggtcttgcc    6000
atgttgccca ggctggtctt gaactcctca gctcaagcaa tctacctacc ttagcctccc    6060
aaagtgctgg gattacacgc atgagccact gcgcccactc cgcattatta aatatagaac    6120
atttatttga ttcatcagtt aatattcttc ttaaaagtac tattttaatg tagcaagatt    6180
gctttccacc aaaaggtggg gtttccacgg tgggtttcc  aaattattct caatggggtg    6240
aggatgtgtg ttatcacacc cccgagccat cagatgctgt cagaaagtga tcactctgaa    6300
gtctttgttt caaataagca cagggtttgg ataaagagac gcaattagga aaggaaaaag    6360
```

-continued

```
cagaaggctc gttccagacc tggatgagat cctaaaaagc agcagctttt gccagtaaag    6420
atccttgaaa tgattcaatt accctcaaag cactccttgt ctccaagaca atcactcata    6480
agcacaattc cattgaagcc aacgtaccat tttgtgattt tcgtttccac ctgaggctgt    6540
tcattcaata aactcacata aaagtgttta ttgccttgat ttccaaattc aggcgtattt    6600
cctggtaagt agagctactt gccttgcctt tatgagatta ccacctaact agatgtatgc    6660
ccagtaaaat ccaacataac gcatgccatg tactacatca cagaatgtgt gactcagttg    6720
ttgaaggaca cctgctttga aggaggggac attactacgg tcttcacacc aagcgccaag    6780
tactgccagg tagtctgcac ttaccaccca agatgtttac tcttcacttt cacggcggaa    6840
tcaccatctg aggatcccac ccgatggtaa atgcttatgt ttctacatcg aggagacaga    6900
tttttaaagg gagattgcta ttcttaacac atttccatct aacattttat aaaatttaac    6960
attaacaact ggaagataaa ttgtctttca gttgaaatat tgttacagaa agaagtgatg    7020
gtgtttacgc aatttagaaa agaataaata tgcctccaag tgtagacttt ccagcctctc    7080
ctatagtctc atattaatgg tatgtttctt ctgtttgtct caattttac acttcttaaa     7140
catttcacac tttgcttttc tatcgattat taattttgt cgtgcttctc aacaaactgg     7200
aacttctccc aactatttta ttagaaaaaa ataaatatt taaaagaaa atttgaaaaa       7260
aagtacagta cagtgatccc cctgccacca ccaaaaccgc aatgtttgct atatttgtac    7320
agcaatatac aatatacaat acctatattt gtatacatgt ttaaccgttt gaataaattt    7380
taaacatga cactttaccc ctaaatactt cagcatgcac tatcctacac aaaagacata     7440
cgaaatttaa caagaattcc tttatattat ttcagttttc cctcaaatat aatttatagt    7500
aattaaccag aatcttacca agagtcactc actgcattgg gtggtttgtc aggtttaaaa    7560
cattttaaac agtccaccaa ccatttgtat tcccatcctg agcttgaaaa tttaataata    7620
agcctttctg tagaattaag ttttcaacat ctttattatt gctacattca caggcattta    7680
tgtagcaccc agaacttata aaatttacta ttccagaacc tagagcaggg attggcaaat    7740
gtcttcttaa taacgcagag taaatatgtt aggctttgtg ggcaaaaccc acagtaaagc    7800
caaggatatt atttaagtat ttatgtcacc acttaaaatg taacaatttg aaaatataaa    7860
aatcattttg tatagctaac aggctaaaca gaaacacaca gatttttggt tgcattttac    7920
caacaggtcc tagttgacac attcctgttt gttcctatta gaaaggagta ttacatgcag    7980
tctcttaagt gtagggatat tgaagtaaaa aacaaactca gaatcttgct aagaaaatat    8040
ttgtttggc atgagataaa gtagtttgtt tccttctttt tggctttctg tgtgctgact     8100
tttaagatcc attattttaa aaacataaat tcctattcat taatatgtat ttttttaaaaa   8160
aacaggttta cttgtgtcct gaaagacagt gttacagaaa cactgccaag agtgaatagg    8220
acagcagcga tttctgggta ttcttttcaag caatgctcac accaaataag cggtaagata   8280
tgttctcaga atcaacaaat accagctgtg atgtacacat atcgccacat cggatgtggt    8340
tttaaggcta tgaaatgaaa cactgctatg tggaaataaa ccccccttaat gaagttcttt   8400
cagtgtagag tataaactag tatacataca tgcctgccct ccaacacact gtaaaaacct    8460
ctttacctca tagaaagaca tatcttacta cctcacttcc catcatttat ttatattctt    8520
tctatttccc agcctaaaat cttaaatgaa agtctttttt tttttgagac agggtctcac    8580
tctgttgtcc aggctggagt gcagtggtgc aatcacagct cactccagcc tcaacctcct    8640
gggttcaagt gatcttcctg ccttagcctc tggagtagct gggaccagag gcatgcacca    8700
acattcccag ctaatttgtt catttttcct agagacaggg tctcactgta ttgcccaggc    8760
```

```
tggtctcaaa ctcttggcct caagtgatct gcccgcctcg gccttccaga gtgccgggat    8820
tccatggtgc ccagtcgaaa ttctttatta aacgtattaa tccaaattga aaggagcaaa    8880
tataaaggtt gaagtgacac ttgtcttaat agtgaataga tacttgaatc agttaattag    8940
cgaaataatc agtgcagtta gggagaagag aggctaggtc agaaaatcaa aatgtgaatt    9000
tacaagtcta aaattgttac agtgtaagaa ggacattggc attcttttac tgcttccatt    9060
caagaataag aattttgcag attaatataa cgaaagacct ctgaggaaag gtgggtgaaa    9120
aagttgaaag gatgagtcag gagggacagt tgcttaggtc attgcccta gaatctggaa     9180
ggtactcatg tcttctgctt ttatttccag cttgcaacaa agacatttat gtggacctag    9240
acatgaaggg cataaactat aacagctcag ttgccaagag tgctcaagaa tgccaagaaa    9300
gatgcacgga tgacgtccac tgccactttt tcacgtacgc cacaaggcag tttcccagcc    9360
tggagcatcg gtgagtgagt cccaggacat tcgagtggtc gatgaaaaac agaatcgtga    9420
tttactaaaa agcttttgcc atcaacttta tgccagaatt tattttgaac ccctaaaaga    9480
catttctata atagtactcc tagttttctt catgaaaaat acacttaaag cctaatttgg    9540
atgcatttca tttatggtaa ggagtctatc ttttaataac actgtcagaa aaatatatat    9600
acttggctaa tttcaaaagc gctacacttt taaattggca cttttgaaac agctgcaatt    9660
ggtatgattg tcagtgccct tcccagtcta aaaaatgtta cagtctaaca gaataaaaat    9720
aaaaacctac tctctctctc tctaaataac agttccttac ctaagacaaa atactcatgt    9780
aaaaagtctt atcctgctcc atactggatt ttgaaatatt tcaaggataa atctatcaca    9840
taaggattta aaaattatct gatctctaat aaccaaatct gtgttctcat ctttaaaaat    9900
ttactaggga aatagattat taatttgtat attcagaaat atttgagatg atttagattt    9960
tcatagtaaa ctgcatttat ctggaatcaa cagaaaagtg aaaaacattc aaattactaa    10020
tacttgcgtt ttaacattgg atttaacat tctgctctcc acattcacaa agaggagtga    10080
acagaaagca aacaaagcat caacgagtta tttcaaaaac aacagtggtg aaaaacacac    10140
acaccaaacc cctaaattca tgatttgact tgtaaggctt atctttagct cagctcagac    10200
gacagctttt atgtctaaga cttaacagaa tgtgaactgc aagacaagaa attggaggtt    10260
tctaagcaag ataaagttaa gtcattaaaa gtaagaagga cttagccagg cgcggtggct    10320
cacacctgta atcccagcac tttgggaggc cgaggcgggc agatcacctg aggtcaggag    10380
ttcgacacca gcctgaccaa tatggtgaaa ccccgtctct actaaaaaag aatacaaaaa    10440
ttagccaggc gcggtggtgg gcgcttgtaa tcccagctac ttgggaggct gagacaagag    10500
aatcgcttga acccaggagg cggaggttgc agtgagccaa gatcgtgcca ttgcactcca    10560
acctgggcaa cagagtgaga ctccgtctca aataaaaaaa aacaaaaaat gagaagggct    10620
tgagaagtca ttcattcatg cactctcctt cttcatgtgg tcactctctc aagctgtcat    10680
tatactgaag aagaaataaa cttacacaat tcacaggtgc ttagcaacac tgctgggacc    10740
atgcccagcc attcagcctc ccagatggat gcttcgggt ctcgcaggtc ctctctccaa     10800
aggggacttt cttaatatct catgtttttt cctccttgca gttggaagaa taagacactt    10860
ttccttttc tttttattca gtaacatttg tctactgaag cacacccaaa cagggacacc     10920
aaccagaata acgaagctcg ataaagtggt gtctggattt tcactgaaat cctgtgcact    10980
ttctaatctg ggtaattatc gacttcttga tgatgtaatt caaccattaa atatgctgat    11040
gattacagta gatctcactc aggataccag cttatgctca cgatgaaacg gacccaaaga    11100
```

-continued

```
tctttacctt cttcatgtga tagatttcat catgtcctat acagttagat cctctattta  11160
aatttccagt ttaaaataat catgccattt tcttctaaat aaaaaaaaat taaaagatct  11220
tgggatacac ttaaattttt taatatggaa tttacacata ctgtgaccgg aattttcctg  11280
atagctggtg aattgagtcc ctgacatagt tcttccgtcg cgcagcttgt attagggaca  11340
ttttccctaa tacggtgttt gcagacagca acatcgacag tgtcatggct cccgatgctt  11400
ttgtctgtgg ccgaatctgc actcatcatc ccggttgctt gttttttacc ttcttttccc  11460
aggaatggcc caaagaatct caaaggtaag gagttaacaa gtaaggataa tttgttatct  11520
tctaaaaata gctgatcaaa atccatcatt aaaaattcca agtaactaaa aatttactct  11580
aaatgtcagt ataggataaa agttgcaaag aatttctagc ccctctccct ttctattccc  11640
cacctactta ccacaaaccc aacattaccg aggactcttt tttttttttt ttttttttg   11700
agatggagtc tcgctctgct gcccaggctg gagtgcggtg catgatttc agctcactgc   11760
aaccttcgcc tcccaggtcc aagcgattct cctgcctcag cctcctgagt agctgggact  11820
acaggcatgg gacaccacgc ccagtaattt ttttgtatt tttagtagag atggggtttc   11880
accatgttgg ccaggctggt ctcaaactcc tgacttcagg tgatccacct gcctcggcct  11940
cccaaagtgc tgagattaca gggttgggcc accgtgcccg gccagtaaat tttaaaataa  12000
atataaatat tacttcacct aaataaattt taggtacagg tacagttgtg ttacatggat  12060
atactgtgta gtggtgaagt ctgggctttc agtgtagcca aatagtatac attattccca  12120
ttagataatt tctcctgcct caccctcctc tatcctccca actctctgag tctccaatag  12180
ctttcattcc actgtctctg tgcctgtgta cactttattt agctcccact taaaagtgag  12240
aatctacaat atttgacttt ctgtttctga gttgtttcac ttgagataat agcctccagt  12300
tctatccatg ttgctgcaaa agatatgatt ttatgatttt tttatggcta agtaacattc  12360
tatagtatat tctatacacc acatttcttt tatccattca tttgctgata gactcttagg  12420
ttgatccata tctttgttat tgtgaatagt gctgcagtaa acatgtgagt gtaggtatct  12480
ttgtgacatg attttttttt cttctttc ctttggctat gtacccagta gtgggattgc    12540
tggaggtctc caccttggca aaggggcagt tgtctagttc taaatgaaat gaagagattc  12600
catttccatt tcatgacaac taaaagacaa ttcagtccaa tgctttgttt aaaataattg  12660
aaccaggaac agaaagagct gaaaatgtca gtgaaatgtc aaacccaaag tggagagaga  12720
gagagaggtg gaaatgaatg tctccatcaa gtgggttagg gtggtggtgg agggaggttt  12780
gagaattgag tccctgtttc cttaccaatg gaaattaaca taggacatca gaaacagcat  12840
ggaaaatttc tttgattatc aaaagtacac tagctaaggt tgctgtccct cttttattta  12900
tttatttatt tgagacaggg tcttgctctg tcactcagat ttggttgcac tgggtgtgat  12960
ctcagcccac tgcagcctcc acttcctagg ctcaagcaat ccacccgtct catcctccca  13020
agttgctggg accacaggtg tgcaccacca cccccagcta atgtttgttt ttttgtagag  13080
acagagtttc gccatgttgg ccaggctggt ctagaactcc tggcctcaag caatccacct  13140
gccttggtct cccacagtgc agggattaca agcctgagcc actatgccca gcttgctatt  13200
cctcattgac aacattcact taaacaagca aacaaatatc cgtaaaatta agtcagcttt  13260
aaaacctggc ttgtatatat tctctgaattg gaactctcag agccctcagc acttgcctga  13320
ttggcctcct gttgatgaaa agttgtcctc cagacaactc agccaaggga ggccctgtgt  13380
gccttgccta tcacatgagc ctcactttcc actgagtgag gctgtcattt cagaagcacc  13440
gggtctgtca catgaaaata tatctgttac catcacttac taaacaaatt tagtagaatt  13500
```

```
tgtttggtgc ttattatgta tcaggcattg ttctgaaggc tggggatacc atttagtgaa   13560
ctaaatcgac aaaaactttg cctattggac cagagtggag atgagagaga agtgaccaga   13620
tcgatctgtg ttatcagcag acagccaata agatttgctg ataggttgga ccacggattg   13680
tgaaggagtc agtgatagca ccaagacttt tggcccaagg aactggaaag atggaaatgt   13740
caatgacaga atgtggagga tttcgcaagc agcagagtgt aggagaagca atgcccttgg   13800
ctcatctagg gcaaagggtt gaattggcaa ctggaaatag aagtcaaatt cagaagagag   13860
gtttatgtgg acatctgtgt ttaggtgtca ccaatataca gctgatactt tttaaaaatc   13920
tagtgaaatt atcaaagggt taaatgcaga gagggaagaa agtaggtcca aagatcaagc   13980
cttgggacat tggaagttta gaaataagaa agatgtcatt gtcacttgta attttgtgct   14040
agtcactgct cttttctttt gtcttattac cttactgacc aattcctaga ataggaataa   14100
cacatttgat ctttaataca gtatgtgata ggaacatggc ttctataagc ccaaacttgg   14160
caatttaaat ttaaatttat taaaattaaa taaaactggc tgggtgcagt ggctcacgcc   14220
tgtaatccca gcactttggg aggccgaggc ggtgaatcac gaggtcagga gtacgagacc   14280
atcctggcca acatggtgaa accccgtctc tactaaaaat acaaaagtta gccaggtgtg   14340
gtggcatgtg cctgtaatcc cagctactca agaggctgag gcaggagaat cacttgaacc   14400
cgggaggcgg aggttgcagt gagccaagat cgcgacactg cactccagcc tgggtgacaa   14460
gagaaagact atgtctcaaa aaaaaaaaaa attttaaata aaactaaaaa ttcaccttcc   14520
cagctgtgtt agccacattt caagtgccca atagccacat gtagttggca gttactgtat   14580
tggatggcac aggcatagaa tatttccatc actgcagaaa gatctatgga cagtcttgct   14640
ctagactgtg attttgtcta cttaggaaaa gtcactcttt tccaggaaga tgcttccagg   14700
gtgtggagta aacgacggac ttcacccatc tccttataaa cctattgcaa ccctggatag   14760
gaggtttcta ggtagcatga agactcttga atctttaaga taggctggga gtgttgaaag   14820
gaaggaaatg aaaagggaag atactaggaa gactgacaat agagcaagct cagaaaattt   14880
ttatggaggt gatttagtta gaaaatttgt ctgcaaccta agggccatgg agtgtgactc   14940
catggtttat gggtgtaact ccgtggttta tgaagagtac tttcaaaata ggaaaatctt   15000
cacaactaag tgctagcatg agctgacttt actttctcta ggtgctgtaa aaatgttttt   15060
atgtgtttga tatgatatat ttctacttcc cttttgtttt tgttagaaat ctttgtctcc   15120
ttaaaacatc tgagagtgga ttgcccagta cacgcattaa aaagagcaaa gctctttctg   15180
gtttcagtct acaaagctgc aggcacagca tcccaggtaa actgagagtt ctgcattctg   15240
gctgagagtg accagccccg aggaggctga tacatgctga gggagggtct cactctgaca   15300
tgtggtctgc tgtctagtgt tctgccattc ttcattttac catgcactg atttcttggg   15360 agaagaactg gatattgttg ctgcaaaaag tcacgaggcc tgccagaaac tgtgcaccaa   15420
tgccgtccgc tgccagtttt ttacctatac cccagcccaa gcatcctgca acgaagggaa   15480
gtaagccata tgaagggtta tgcagacacc cttgtcccgt ctgcctgtga ggtgcattat   15540
gtttataccg ttttgtttcc aactgcaggg gcaagtgtta cttaaagctt tcttcaaacg   15600
gatctccaac taaaatactt cacgggagag gaggcatctc tggatacaca ttaaggttgt   15660
gtaaaatgga taatggtgag tataatgtca cttgaaaaaa tatagctgaa ggaattattc   15720
catgcttcat acatcacaat caagactgtc agttatagcc acagaaggga gaacattcag   15780
gaaataacaa attttgcaat tttctattat tttcactcct gtcactcaag ctgaccatgt   15840
```

```
tttaaaggta aatattgagg cttgactaaa ctgtacattg cctagtatta actaaatata   15900
tgctttaatt tgacacattt atacacctgg catttctgtt ttctttcttt cttttttttt   15960
tttttttttt tgagacacag tctcactctg ttgcccaggc tggagtgcag tgatgtggtc   16020
agtgttcact gcagcctctg gcttgaactc ctggactcga acaatcctcc caccttagct   16080
ccctgagtag ctggggctac aggcgtgcac cacaacactc ggctaatttg ttgtagagat   16140
gggatcttgc catgttgccc aggctggtct tgaactcctg gctcaagca atcctcccgc    16200
tttggcctcc caaagttctg ggattacagg cttcagccac tgcacccagc cacaactggc   16260
atttcctaat gagacccaga ctctgccaac actcctgtta tcaaggccag taatctttcc   16320
tattatcctt tgtaagggaa ttatcgatca gcactttggt tagtcaaatt actaattttc   16380
ttccaaaaat tgtgtatcta ttcaagaaat actggagcac ctcctttta gggtctttat    16440
tcagattcca tgcagggttc tggagactta gggattggca aaggttaagg taaaacttta   16500
ctagtaacaa tgagtgtggt aggatggaaa taagtgttta gattacacga gacctgtaat   16560
aacataaaag ttcaataaa aatccaacca gcagtgtttc catcccagtg ccaatttct     16620
gagcatagtc acgagagatg ctttgtaggc aaacagaatt gttctaaggg acaaaatccc   16680
caacaggaaa gaacacacca caaacactcc tgcttaaatt accatagtaa cttaggatgg   16740
ctttactata tattgattta cataaagctg catgttctta tactgtttat tgccaaatgt   16800
ccaatattac aatacactat aaggtgcaac tgagatttaa tgaataaaat ggaagtaaca   16860
atcctgcctc gtgatagttt tagaagcaca aaaacattct gtgtcagatt atctgctgta   16920
ccgagaaggc gaatcaatcc ttaatttctg agaacttgtt ttgtagaaca taagacgtt    16980
atattgcctc caacactggt atcctaacta acagactatg ccttcctaga gcttagaggc   17040
gctccgatga aaatctctgg atggctcaag acttcttaaa aagcaagtca attacgtcgt   17100
atctcataca ttctgttttc ctcacaataa atttccctaa gacaagaagg agcattcggc   17160
accattctgt tgtctttctt ctacttctaa gcgttagaag ggacacttag caaatgttgc   17220
tgttaagtaa tgttgacatg gtttaataaa atgggaatga gcacgtatac ctcaatacat   17280
tgcagactgc attttccccc ttccttcttc attatggttt tctctgttgg atttatagac   17340
tctggcctgt agaagttaca gaatatgcca ggtatagatt gatagctaca ggagaaaatg   17400
taagataaag gaaataaag tcttacgtct tttcagtgca actttggagg gagtgaatta   17460
gataactagg ttttttactgc gctgtatttg atgaaataac cccctaatgt gaaagggaat   17520
agctgcgtga gatatttatg gtgccttgtc tgtcactggt ctacaatgta acttaacttt   17580
ctgaagatag atagcagcac cattaaaata aacatttctt accacaaaat atgattctaa   17640
acacatattt tcagcatttc gtttaaactg agaaacagca taggatgaac ctcaaggcct   17700
ctcacctgga ccttgagtta tttctaaaat atcttagtta ctatttacct attaattttc    17760
ctaaaattta cctttatgac gcttcccacc ttgcagaaat tccagaatag atggccctcc   17820
aaaatgaatg ttcacccttc cggctctaaa atgagagcct ctgttcaggc ttccgaagtc   17880
acatcgtgct cgttctcacc tcagttgctg ttagctgctg tttccttccg aactccttct   17940
ctcatcctct cctcctattt gaaatctgcc ccagaattat acactcattt tcctaccaag   18000
gaaaaaagg cctagaaagg ttgttttaca cccacaaaac tagtgaatgg accttctagg    18060
acccggcttc tcatcagtga ttcttctgtt aacttagact cctcccttag ctcaggacgc   18120
ggagccttct gagcacctga gcctggttat tctaaatgtg atctgggcac agcacattga   18180
catcacctgg gagcttgtta gaaagaattt caggacccac acagatgtta ctgagtcaga   18240
```

```
atctgcattt tgaaagctac acaggcaacc cacaggcaca taaattttga gtcgcatagg    18300
tgtgtgcgtg tgtgtgcgca tgtatgtgtg cgtgtgtttg tgtgcacgtg tgtgtgtgtg    18360
tgtctagaat actgctgtct acgaacaccc tattcccatc catctgtgtt ccatggctcc    18420
aaccgggagg gtgggttctt gtgtcgggca tccagtaagt agaaatagag ggcactgtcc    18480
tgtctaggca gccccaagag aaaagaaaca gagggatgag cctgagtcaa agtccctgaa    18540
aagtaccaag gaccccagag aatcccaaac tgtcaacaag gccaaaggtc agaggaagtt    18600
catagcagat cagtcttact ttggacgtgg gtggagcagg agtgactggg atcatggtca    18660
gcagagtcac tgggacaggg caggaactgg acaatggctg cagcctgcgg gcaaggtgct    18720
tgccttttct ttctaagagc agttctcaaa cgccagcagg gctggttcaa acacagatgg    18780
ctgagcttcc aggctggagt ttctcattca ctggatctga ggttgggctg aagaatgtgc    18840
atttctaaca cgttcccagg tgacgctgtt ggtctggaga ctgcacttga caaccactgg    18900
tttaaaaaca ccattcacgt tatcatttga aggagggtaa gacagccttg tagtaccaca    18960
caaggagggc tacattctta ggggtgtgta attacaagat gacttagtca attccatttt    19020
tcatgtgcat gttttgcttt ggcagcttga ttataaagtc tctgtaactc agggtcatga    19080
taaactattg acttgaggaa aggttttctt cttgttcctg aaggagcata attactgatg    19140
gaaaggaaga tgtaggaagc tgctcatcac aatgcttctg ttgcagagtg taccaccaaa    19200
atcaagccca ggatcgttgg aggaactgcg tctgttcgtg gtgagtggcc gtggcaggtg    19260
accctgcaca caacctcacc cactcagaga cacctgtgtg gaggctccat cattggaaac    19320
cagtggatat aacagccgc tcactgtttc tatgggtcag taccacggct gttttttatta    19380 gttcatcttc ttcacacatt tataaaaaat attactagca tgttaggaaa taaatacttt    19440
aaccaattag attgtcttat ttgcaaaatt aattaattgc ttcagtggta aaaaacgcaa    19500
aaaggaagag ctcatggtct cccagcatca gaacaggtgc aggtacaagg ctgcttgact    19560
gcctgctatt ccgcttccca tttaaccgca ttcacatccc aagggccttt catgttattc    19620
cctgcaagag catacctccc tctgtgcctc gctctgtgca ctgtgcccgg aactaaactc    19680
acagaggatt taccattgtc tgaatcaaat ttctaatatg tgtgtgtgtg tgtgtgcgtg    19740
tgtgtttaaa tacagaaagt ggccaggtgt ggtggttcac gcctgtcatc tcagcacttt    19800
gggtggctga ggtgggagga ttgctcaatg ccaggagtct gaggtcagcc tgggcaacat    19860
agtgagacct cgtctctaaa aaatatttaa aaactagcct ggcatggtgt tttgtgtgcc    19920
tgtagcacca gctgctcaga agtctgaggt aggaggattg cttgagccca agagttcaag    19980
ggtgcagtga gttactacag tgccactgtg ctccagcctg agcaacagag caagaccccta   20040 tctctaagta aataaataaa atacagaacg agttcggtat gcatcctcac attggattcc    20100
ttacttaggt cactttcagc gttggccaaa caaaaaggct ccagctgggg gtatatatat    20160
tccagggaag ttaagttggc caaactttcc gtttgctact tcagtatcct ccgagttgtt    20220
tccagacaca gttttgtgtg cttttttagtt ttggttttct tttttaatca atctgcagca    20280
cactcatgtt aaactcaaga acacatgtga ggccaagagt tcccgttacc tgtcacatat    20340
gggaatggag tagcagaaag cctagttcct gtcacagcta gttactggcg agattgagac    20400
tgagtccagc ggtcttcgtg tgtgtgtgtg cgtgtgtgtc tgtgcagtgt gcgtgtgtgt    20460
gcgtgtctgt gtgtgcgtgt gcgggtgtgt gcgtgtgtgt gtgttggagc acggagggag    20520
tgctcattca tttttgtgt ataatggatt ttctttatag ggtgaatatg ttttttatcc     20580
```

```
cgaaaaatct taggataaaa tcactttttt ctacctaaat gtccatcatt ggcagaaaat   20640
attagtaata attaaacagc cacacacttc acaatgtctg ggaattattt ttagtaaagg   20700
aaatttcttt ccctctgttg tttgctcctt agggtagagt cacctaagat tttgcgtgtc   20760
tacagtggca ttttaaatca atctgaaata aagaggaca catctttctt tggggttcaa    20820
gaaataataa tccatgatca gtataaaatg gcagaaagcg ggtatgatat tgccttgttg   20880
aaactggaaa ccacagtgaa ttacacaggt acggagaatt ttatccggaa agttgtctcc   20940
aatggtgaac tggataaaat gtttaacact actagactta cggcctgacc ctgccaatct   21000
ctccatgcgt tatcatcatg aaagggagag ggcctggaat gctagtcatt cactctgcta   21060
aggctgacac actttcctgg ctattgaaac ttattttggg aatgtgggta aagagatacg   21120
ttttcctgag tcttcttcag gtgcatagaa tgacataatt tcataatact ttggaatagt   21180
aaagataatt tagtctaaag ataatttatt aaagataatt tagggatgaa ggattgaagg   21240
ttagaacaat taagcaactt gtgcaggatc aaagtgagtt ggatgaggag ttagcggtga   21300
gggtgaggct tgtctctctc tcgccctctc atcctggcac atgtgcgata tcgtgctgaa   21360
cctgagggag gaaaatacac gacaacaagg caaaaaatga atatagtaaa caaagaaaac   21420
acagataatg tacagtggaa gaagagtctc ttctggaaaa gaggatatat tttgcgtctc   21480
atatttaaac cacgattttt taaatttaga ttctcaacga cccatatgcc tgccttccaa   21540
aggagataga aatgtaatat acactgattg ctgggtgact ggatgggggt acagaaaact   21600
aagaggtaaa aatgatgttg ttatatgtgc tccatcctag aaatgaagag cggaaccttt   21660
tctgccctgt caagtcatgt agctgaagca caactcgagt cacactactc agttgcagga   21720
agcggattaa taaagatgga gaggcaaaaa tcacccaagt gaggctggtg cctcatatgt   21780
ttgattggaa attttaaatg tgactaaatc tctttaaaga ctaattatat ttaatgaagt   21840
ttaatgtgaa gcctagcact tttcagtaaa tgttctagcc tgctatccaa ttactttctt   21900
gggaagtcat tccagttaga gtcataatta atttttgaac ttaattaaca ttaacaaaat   21960
ggtacacgca atagtgggaa taatgtcttc ttcatacttg taattataaa aggtctgtga   22020
agtaaatcta acatttttc cttctagatt tttatataga catgagtttt gtgttgttgt     22080
tgttttgaga tggactctcg ctctgtcgcc caggctggag tgcagtggca cgatctcggc   22140
tcactgttac ctccaccttcc cgggttcaag tgattctcct gcctcagcct cccgagtagc   22200
tgggattata ggtacccaac caccacccca agctaatttt ttgtattttt agtagagacg   22260
gggtttcatc atgttagcca ggatggtctc aatctcctga cctcgtgatc cacctgcctc   22320
ggccttccaa agtgctggaa ttacaggcgt gagcccccac acccgtccat gatttttatt   22380
ttaaatatat gtggcccagc accactggtg gctcacgcct gtaatcccag cactttggga   22440
ggccaagatg ggtggatcac ttgaggtcag gagttcaaga ctggcctggc caacatggtg   22500
aaaccctgtc tctactaaaa atacaaaaat tagctgggca tggtggtgtg tgcctgtaat   22560
cccagctact cgggaggctg aggcaagata tcgcttgaa cttgggaggt ggaggtagca    22620
gtgagctgag attgcaccac tgcactccag cctgggcgac agaaagagac tccgtctcaa   22680
ttaaaaatat atatatatat atatttatat gtatgcatat atgtttatgt gtattgtgta   22740
tggttattct acaaacgaac caaaaaaatt tttttcagac aaaatacaaa atactctcca   22800
gaaagccaag ataccttag tgaccaacga agagtgccag aagagataca gaggacataa    22860
aataacccat aagatgatct gtgccggcta caggaaggga gggaaggacg cttgcaaggt   22920
aacagagtgt tcttagccaa tggaatatat gcaaattgga atgcttaatg cgttggggtt   22980
```

```
tttttgtttg ttttgttttt tttgtttgtt ttttttgag acagagtctc gctctgttgc   23040
ccaggctgga gtgcagtggc tcgatctcag ctcactgcaa gctctgcctc ccaggttcac   23100
gccattctcc tgcctcagcc tcccaaatag ctgggactac aggcgccagc taccaagccc   23160
agctagcgtc ttttttttt ttagttttag tagagacggg gtttcaccat gttggccagg   23220
atggtctcga tctcctgacc tcatgatctg cctgcctggg cctcccaaag tgctgggatt   23280
acaggcgtga gccaccgcgc cgggccgctt aatgcatttt aaaaagcagt cttctgccaa   23340
tgagcaggga acacagtgta tttgtttgac ttagactgaa atcaaaagca aggagattga   23400
ctggatgaac gcaagcaccc aggttctctg cagtatatta aggggccaag acaacatttt   23460
aggcaaaatc agcctgagca agatgtgctg aagatgggaa gcgtctgagt tgatctgtgc   23520 acctttctt gtctccctc gttctaggga gattcgggag gccctctgtc ctgcaaacac   23580
aatgaggtct ggcatctggt aggcatcacg agctggggcg aaggctgtgc tcaaagggag   23640
cggccaggtg tttacaccaa cgtggtcgag tacgtggact ggattctgga gaaaactcaa   23700
gcagtgtgaa tgggttccca ggggccattg gagtccctga aggacccagg atttgctggg   23760
agagggtgtt gagttcactg tgccagcatg cttcctccac agtaacacgc tgaaggggct   23820
tggtgtttgt aagaaaatgc tagaagaaaa caaactgtca caagttgtta tgtccaaaac   23880
tcccgttcta tgatcgttgt agtttgtttg agcattcagt ctctttgttt ttgatcacgc   23940
ttctatggag tccaagaatt accataaggc aatatttctg aagattacta tataggcaga   24000
tatagcagaa aataaccaag tagtggcagt ggggatcagg cagaagaact ggtaaaagaa   24060
gccaccataa atagatttgt tcgatgaaag atgaaaactg gaagaaagga gaacaaagac   24120
agtcttcacc attttgcagg aatctacact ctgcctatgt gaacacattt cttttgtaaa   24180
gaaagaaatt gattgcattt aatggcagat tttcagaata gtcaggaatt cttgtcattt   24240
ccattttaaa atatatatta aaaaaatca gttcgagtag acacgagcta agagtgaatg   24300
tgaagataac agaatttctg tgtggaagag gattacaagc agcaatttac ctggaagtga   24360
taccttaggg gcaatcttga agatacactt tcctgaaaaa tgatttgtga tggattgtat   24420
atttatttaa aatatcttgg gaggggaggc tgatggagat agggagcatg ctcaaacctc   24480
cctaagacaa gctgctgctg tgactatggg ctcccaaaga gctagatcgt atatttattt   24540
gacaaaaatc accatagact gcatccatac tacagagaaa aaacaattag ggcgcaaatg   24600
gatagttaca gtaaagtctt cagcaagcag ctgcctgtat tctaagcact gggattttct   24660
gtttcgtgca aatatttatc tcattattgt tgtgatctag ttcaataacc tagaatttga   24720
attgtcacca catagctttc aatctgtgcc aacaactata caattcatca agtgtgattt   24780
tttttttttt ttttgagat gaagtctcac cctgttgccc aagctggagt gcagtggtgt   24840
gatctcggct cactgtaaac tctacctcct ggattcaagc gattgtcctg cctcagtctc   24900
ccaagtagct gagattacag gcacatgcca ccatgcccgg ctaattttg tatttttagt   24960 agagacgggg tttcactatg ttggccaggc tggtcttgaa ctcctgacct cgtgatctgc   25020
ccacctcggc ctctcaaagt gctgggatta caggtgtgag tcactgcgtc tggccatgga   25080
aaatatttat tgagcacaat tatgtgagag catcatgctg agctttgaag atacagtggt   25140
gagcaaacat atatcctggc ttcatgaaga ttatactcta gttaacatga gcaacaaaat   25200
aaaataatca cacaaaatat ataggttcaa gctgaaatga gtggctgcac cagattctat   25260
gagataagaa aggaagaagg acattttca ccaagttcaa agactgggat acaaaggaat   25320
```

| | |
|---|---|
| ttgtcctgac aaaggcaaaa caaaaacaac aacaaacaaa aaacccaaaa gagcaaaatg | 25380 |
| acagtagaac ataacggggc cagatcaaaa atgctgacag gttcccaaaa gaataaaatg | 25440 |
| acggtaggac atgacggggc cagatccaaa atgctgacag gttcaaacaa aattggaatt | 25500 |
| gaaaatcaga gtgcgttcaa gagtatcaaa caatactatc ttgttacttg cttattacct | 25560 |
| tagtagactg gaagcaacac ttcacacaaa aaaagggttt ggatgtaatt tcggataaga | 25620 |
| agagatgttt ctgtaaagtc tttcctgaga agcatattat ttgagaaaaa cacatatttc | 25680 |
| tgtttttagt atttcacttt gtataatgtc ttaattttg aagagctggt atattcctat | 25740 |
| gattcattaa tgaaagttct ataagatata aaatatacaa tgaggagatc tcctcttctg | 25800 |
| taccagaaga gtgcacattc tacacactgc gtagcacctt tctcacttac gttctgtctg | 25860 |
| ggcacacttc tgattgacac gcagagggct ctctctgtct ggggatattt ctgatgggta | 25920 |
| ccgagagagc ttcctctatc ttgggttatt tctgatgcgt agagaagggc tgcctctgtc | 25980 |
| cattatggaa ggctggtgtt c | 26001 |

<210> SEQ ID NO 16
<211> LENGTH: 2246
<212> TYPE: DNA
<213> ORGANISM: Mus musculus

<400> SEQUENCE: 16

| | |
|---|---|
| ggataccggc tcacgtagaa aaaggacaag actataggaa agaaagcaaa cactccgccg | 60 |
| aggactacag caaagacaga aagtatctgc aggatgacct cattacatca ggtgttatat | 120 |
| tttatctttt ttgcctcagt ttctagtgaa tgcgttacta aggtcttcaa agacatcagc | 180 |
| tttcaaggag gtgacctgag tactgttttc acaccgagcg ccacatactg ccgcttggtc | 240 |
| tgcactcacc acccacggtg cttgctcttc acgttcatgg ctgagtcatc ttcggatgat | 300 |
| cctaccaaat ggtttgcctg catcctgaag gacagcgtca cagaaatatt gccaatggta | 360 |
| aacatgacag gcgcgatctc tggatattcc ttcaagcaat gccctcagca attaagtact | 420 |
| tgcagcaaag atgtgtacgt gaacctagac atgaagggca tgaactataa cagctctgtc | 480 |
| gtgaagaatg ctcgagaatg ccaggagaga tgcacagacg atgcccactg ccagtttttc | 540 |
| acatacgcaa cagggtattt tcccagtgtg gaccatcgta aaatgtgtct tttgaagtac | 600 |
| acccgaacgg ggacgccaac cacaataacg aagctcaatg gcgtggtatc tggattttca | 660 |
| ctgaagtcct gtggactttc aaacttggct tgtatcaggg acattttccc taacacggtg | 720 |
| ctggcagacc ttaacattga cagcgtggtg gccccagatg cttttgtctg tcgtcgcatc | 780 |
| tgcacgcatc accccacttg tttgttcttc acattctttt cccaagcatg gccgaaagaa | 840 |
| tctcagagac atctttgtct ccttaaaacc tctgaaagtg gattaccaag cacacgcatt | 900 |
| acaaagagcc acgcccttc gggcttcagt ctccagcact gcaggcacag tgtcccagta | 960 |
| ttctgccatc cgtccttta caacgacact gatttcttgg gagaagagct ggacatcgtc | 1020 |
| gatgtgaaag gccaagaaac ctgtcagaaa acgtgtacca ataacgcccg ctgccagttc | 1080 |
| tttacctact atccatcgca cagactgtgc aatgagagga accgcagggg cagatgttac | 1140 |
| ctaaagcttt cctccaatgg atctccaacg agaatacttc atgggagggg aggcatctct | 1200 |
| ggatactcac tgaggctgtg caaaatggat aatgtgtgca caactaaaat caaccccaga | 1260 |
| gtggtaggag gagctgcgtc tgttcacggt gagtggccat ggcaggtgac tctgcacatc | 1320 |
| agccagggac acctgtgtgg aggctccatc attggaaacc aatggatact gacagcagct | 1380 |
| cattgtttct ctgggataga gacacctaaa aagctgcgtg tctacggtgg cattgtaaat | 1440 |

```
caatcagaaa taaatgaagg gactgctttc ttcagggttc aagaaatgat aattcatgat    1500
cagtatacga cagcagaaag tgggtatgat attgccctgt taaaactgga atcagccatg    1560
aattacacag attttcagcg gccaatatgc ctgccttcca aaggagatag aaacgcagtg    1620
cacacagaat gctgggtgac tggatggggg tacacagcac taagaggtga agtacaaagt    1680
actcttcaga aagccaaggt tccattggtg tcaaatgaag aatgtcagac aagatacaga    1740
agacacaaaa taaccaataa gatgatctgt gcaggctaca aagaaggagg gaaggatacg    1800
tgcaagggag attctggagg gcccctgtcc tgcaaataca atggggtctg gcacttggtg    1860
ggcatcacaa gctggggtga aggctgtggt cagaaggaga gaccgggggt ctacacgaac    1920
gtggccaagt acgtggactg gattctggag aaaactcaaa cagtctgaaa gagttcaact    1980
ggtatcactt tgtggccctg gaagattatt ccatagaaat gagcttgacg tctctgatga    2040
agacactggg atactgactc ttccactgta accaattgaa tggccttgat gtacgtaaga    2100
acacccagaa agaaaactat tattttcaga attcctgatc tgggagaacc actggttgtt    2160
ttctgcatcc agctactact caaggaaaca aatacagcaa ggagatttta aaaataaaaa    2220
cacatcagat atataaggaa aatatc                                         2246
```

<210> SEQ ID NO 17
<211> LENGTH: 24001
<212> TYPE: DNA
<213> ORGANISM: Macaca mulatta
<220> FEATURE:
<221> NAME/KEY: misc_feature
<222> LOCATION: (1)..(1629)
<223> OTHER INFORMATION: n is a, c, g, or t
<220> FEATURE:
<221> NAME/KEY: misc_feature
<222> LOCATION: (6013)..(6032)
<223> OTHER INFORMATION: n is a, c, g, or t
<220> FEATURE:
<221> NAME/KEY: misc_feature
<222> LOCATION: (11485)..(12230)
<223> OTHER INFORMATION: n is a, c, g, or t
<220> FEATURE:
<221> NAME/KEY: misc_feature
<222> LOCATION: (21634)..(21910)
<223> OTHER INFORMATION: n is a, c, g, or t

<400> SEQUENCE: 17

```
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
```

| | |
|---|---|
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnng cactcctcgt ctccaagaca atgactcata agcacaattc cattgaagcc | 1680 |
| aatgtaccat tttgtgattt tcgtttccag ctgaggctgt tcattcagaa aactcacata | 1740 |
| agtgttcctt gccttgattt ccaaattcag gtgtatttcc tgttaagtag agctacttgc | 1800 |
| cttgcctgta tgagattatt acctaattag atatatgccc agtaaaatcc aaaataaagc | 1860 |
| atgccatgtg ttacatcaca gaatgtgtga ctcggttgtt caaggacatc cactttgaag | 1920 |
| gaggggacat tgctacggtt ttcacaccaa gcgccaagca ctgccaggtg gtctgcactc | 1980 |
| accacccacg atgtctgctc ttcactttca cgggggaatc tgcatctgag gatcctaccc | 2040 |
| agtggtaagt gcttctgttt ccacatcaag gagacggatt tttacaggga gactgctgtt | 2100 |
| cttaacacat ctccatctac cgttttacac aatttaacat tgacaactgg aagatcaatt | 2160 |
| gtctttcagt aaaaatatta ttacagaaag aagggatggt ggttaggcag ttcagaaaag | 2220 |
| aataaatatg cctccaagtg taggcttttcc agcctctctt atagtctcag tattaatggt | 2280 |
| atgtttcttc tgtttgtctc aattttatg cttcttaaac atttcacact ttgcttttct | 2340 |
| atcaattatt aattttttgtt gtgctttaaa ctggaacttc tcccaactat tttattagaa | 2400 |
| aaaaaattaa atatttaaaa agataatttg aagaaatagt acagtaccat gatcccttgc | 2460 |
| caccaccaag actgcaatgt ttgctatatt tgtatagcaa tatacaatac acaatataat | 2520 |
| atataatgca atacacaata cctatatttg tacacatgct taaccatttg aaataatttt | 2580 |
| aaaacatgac acttaccccc aaatacttca acatgcatta tcctacacaa aagacatacg | 2640 |
| aaatttaaca agaattcctt tatattactt cagttttccc tcaaatgtaa tttatagtaa | 2700 |
| ttaaccagaa tcttaccaag agttacacat tgcactgggt tgtttgtcag gttgaaaata | 2760 |
| ttttgaacag tccgccaacc atttgtgttc ccatcctgag cttgaaagtg taataataaa | 2820 |
| cctttctgta gaattaagtt ttcaacatct ttgtgtatta ttgctgcatt cacaggcatt | 2880 |
| tatataaacac cctgaactta taacatttac tactccagaa tctagaacag ggtttggaaa | 2940 |
| atgccttctt aataaagcag agtaaatata ttaggctttg tgggcaaaac ccgcagtaaa | 3000 |
| gccaaggata ttatataagt atttatgtca ccacttaaaa tgtaaccatt tgaaaatata | 3060 |
| aaatcatttt tgtagagcta acaggctaaa caaaaacaca cagattttttg gttgcatttt | 3120 |
| accaacaggc catagttcac ccactcctgt ttgttcctgt taggaaggag tattacacgt | 3180 |

```
agtctcttaa gtgtagggat gttgaagtaa aaagcaaact cagaatcttg ctaagaaaat    3240
atttgttttg gcatgagata agtagtttg tttccttctc tttggctttc tgtgtgctga    3300
cttttaagac ccattatttt aaaaacataa attcctattc agtaatacgt atttttaaa    3360 aaacaggttt acttgtgtcc tgaaggacag tgttacagaa acactgccaa gagtgaatag    3420
gacaggagcg atttctgggt attctttcaa gcaatgctca caccaaataa gcggtaagat    3480
atgttgttag aaccgacaaa taccagttgt gatgtataca tatagtcaca tcagatatgg    3540
ttttatggca atgaaataaa acactgctat gtggaaataa accccttaa cgaagttctt    3600 tcaaagtaga gtataaacta gcatacatgc atgcctaaaa attccttacc tcatagaaag    3660
acatatctta ctacctcact tctcatcatt tatttatatt gtttctactt cccagcctaa    3720
aatcttaaat gaaagtcttt ttttttttt tttttttttt cttttttttg cgacaaggtc    3780
tcactctgtt gtccaggctg gagtgcagtg gtgcaatcac agctcactgc agcctcaacc    3840
acctgggttc aagtgatcct cctgccttag cctctggagt agctgggacc agaagcatgc    3900
accaccattc ccagctaatt tgttaattgt tcctagagac agagtctcac tgtattgccc    3960
aggctggtct caaactcctg gcctcaagtg atccacccgc ctcggccttc tagagtgctg    4020
ggattccatg gtgcccagtt gaaattcatt attaaacata ttaatccaaa tcaaaggag    4080 caaatataaa agttgaagtg acacttgtct taatagtgag cagatacttg aatgagttaa    4140
ttagtgaaat aatcagtgca gttaaggaga agagaggcaa ggtcagaaaa tcaaaatgtg    4200
aatttatgag tctaaaattg ttacaataca agaaggacat tggcattctt ttactgcttt    4260
cattcaagaa taagaatttt gtagattaat gtaacaaaag acttctgagg aaaggtgggt    4320 gaaaagttc agggtgagtc aggagggaca gttgctgagg tcagcgcttc tggatctgga    4380
aggtactcac gttgtctgct tttatttcca gcttgcaaca aagacattta tgtggaccta    4440
gacatgaagg gcataaacta taacagctca cttgccaaga gtgctcaaga atgccaagaa    4500
agatgcacgg atgacatcca ctgccacttt ttcacgtatg ccacaaggca gtttcccagt    4560
ctggagcatc ggtgagtgag ccttggcatt cgagtggcca gtgacaaaca gaatggtgat    4620
ttactaaaaa gttttgtca tcaactttat gccagaatta attttgaacc cctagaaggc    4680
atttcaataa aagtactcct ggttttcttc atgaaaaaca cacttaaagc ctaatttgga    4740
tgcatttcat ttgtggtaag gagttatct tttaataaca ctgtcagaaa aatatataca    4800
cttagctaat ttcaaaagtg ctacacttt aaattggcaa ttttgaaaca gctacaattg    4860
gtctgattgt cagtgcccct cccagtctaa aaaatgttac agtctaacag aataaaaata    4920
aaaccctact cctctctctc tctctctccc tctaaataac agttccttac ctaagacaaa    4980
atactcatgt aaaagtatt atcctgctgc atactggatt ttgaaatatt tcaaggataa    5040
atctattgtg taaggattta aaaatgatct gatctctaat gaccaaatct gtgtcctcat    5100
ctttaaaaat ttccatggga aatagattat tttgtatatt cagaaatata cattatacaa    5160
tatacaatat tatgcaatat tgtatacaat atacaacatt atccaatatt gtatacaata    5220
tacaacatta tacaatatta attgtatat tcagaaatat actgagataa tttagatttt    5280
catagtaaac tgcatttatc tggaatcaac agaaaagtga aaaacattct aattactaat    5340
atttgtgggt ttcttcttt ttttttttg acaagtttc gctctttgtt gcacaggctg    5400
gagtgcaatg gcgcgatctc ggctcactgc aaccttagcc tcctgggttc aagtgaatct    5460
cctgtctcag cctcctgagt agctggaatt ataggtgccc accaccatgc ctggctaatt    5520
```

```
tttgtattttt tagtagagat ggggtgtcac catgttggcc aggctggtct cgaactactg    5580
acctcagata atcctcccgc cttggcctcc caaagtgctg ggattgcagg tgtgagccac    5640
cgcacccggc ctaatatttc tgttttaacg ttggatttta acattctgcc cgccacatta    5700
acaaagagga gtaaacggaa agcaaacaaa gcatcaatga gttatttcaa aaacaacagt    5760
gattacacac acacacacac acacacacac acacacacac acacacccca aaccccctaac    5820 ttagccatttt gacttgcaac gcttgtctgt agctcagctc agatgacagc ttttatgtct    5880
aagacttaac ggaatgtgaa ctgcaagcca agaaagtgga ggcttctaag caagataaaa    5940
aaaagtaaaa tcattaaaag taagaaggac ttggccaggt gcagtggctc actttgcgag    6000
gctgaggtgg gcnnnnnnnn nnnnnnnnnn nnaaaaaaaa aaaagtgag aagggcttga    6060 gaagtcattc actcatgcag tctccttctt catgtggcca ctctctcaag ctgtcactgt    6120
actgaagaag aaataaagtt acacggttca caggtgctta gtggcactgc taggaccacg    6180
cccagccact cagcctccca gatggatgct tcagggtctc gcaggtcctc tctccaaagg    6240
ggactttctt ctcgtctcat gttttctcct ccttgcactt ggaagaataa gacactttc    6300 cttttttcttt ttattcagta acatttgtct actgaagcac acccaaacgg ggacaccaac    6360
cggaataatg aagctcgata aagtggtgac tggattttca ctgaaatcct gtgcactttc    6420
taatctgggt aactattgac ttcttgatga cgtagtgcaa ccattaaaca tgctgatgat    6480
caggacaata gatctcactc aggataccag cttatgctca caatggaacg gacccaaaga    6540
cctttacctt cttcatgtga tagatttcat catgtcttgt acagttagat cctctatttta    6600 aatttcaagt ttaaaataat catgtcattt tcttctaaat aaaaaaaatt taaaagatct    6660
tgggatacac ttaaatttt taatatggaa tttacaaatg ctgtgactgg aattttcctg    6720
atagctggtg aactgagttc ctaacacagt tcttctgttg cgcagcttgt atcagggacg    6780
ttttccccaa cacggtgttt gcggacagca acatcgatag tgtcatggct ccagatgcct    6840
ttgtctgtcg ccggatctgc actcatcatc ccggttgctt gttttttacc ttcttttccc    6900
aggaatggcc caaagaatct caaaggtaag gagttaacaa gtaaggataa tttgttaatc    6960
ttttaaaaat agctgatcaa aatccatcat taaaaactcc aagtaactaa aaatttactc    7020
taaatgttag tataggataa aaattgcaaa gaatttctag ccgctctccc attctattcc    7080
ccacctactt agcacaaacc cgacattacc gaggactctt ttttttttttg agacggagtc    7140 tcgctgtact gcccaggctg gagtacaatg gtgtgatctc agctcactgc aacctttgcc    7200
tcccgagttc aagtgattct cctgcctccg cctcctgagt agctgggatt ataggcatgg    7260
gccaccatgc ccagctaatt ttttttttttt tttttgtatt tttagtagag acagggtttc    7320
accatgttgg ccaggctggt ctcgaactcc tgacctcagg cgatccgcct gcctcggcct    7380
cccgaagtgc tgagattaca gggttgagcc accatgcctg gtcaataaat tttaaaataa    7440
atattatttt acctaaataa attttaggta caggtacagt tttgttacat ggatatactg    7500
tgtagtgtga agtttgggct tttgttgctc caccctcccc tatccttcca actgtctgag    7560
tctccaatag cttttcattcc actctctctg tgcctgtgta catttatttt agctcccact    7620
tataagtgac aacatggaat atttgactttt ctgtttctga gttgtttcac ttgagataat    7680
agcctccagt tctatccatg ttgctgcaaa agacatgatt ttatgatttt ttatggctaa    7740
gtaacattct atagtatatt ctatacacca catttttcttt atccattcat ttgttgatag    7800
actcttaggt tgatccatat ctttgttatt atgaatagtg ctgcagtaaa catgtgagtg    7860
taggtatctt tgagaaataa tgatttttttt tcttctttt cctttggaca tgtacccagt    7920
```

```
agtgggattg ctggaggtct ccaccttggc aaagggagag ttgtctaatt ctaaatgaaa    7980
tgaagagatt ccatttccat ttcatgacca ctaaaagaca attcagtcca atgctttgtt    8040
taaaataatt gaaccaggag cagaaagagc tgaaaatgtc agtgaaatgt caaacccaaa    8100
gtggagagag agaggtggaa atgaatgtct ccatcaggtg ggttaggatg gtggtggagg    8160
gagatttgag aattgagttc ctgtttcctt accaatggaa attaacacag gacatcagaa    8220
acagcatgaa aaaattcttt gattatcaaa aggacattag ctaaggttgc tgtccctctt    8280
ttatttattt atttgagaca gggtcttgct ctgtcactca gatttgggtg cactgggtgt    8340
gatctcagcc cgctgcagcc tccacttcct aggttcaaac aatccacctg tctcatcctc    8400
ccaagttgct gggaccacag gtgtgcacca ccatgcccag ctaatgtttg tattttgta    8460 gcgacagggt ttcgccacgt tggtcaggct ggtctagaac tgctggcctc aagcaatcca    8520
tcggccgtgg cctcccacag tgcagggatt acaagcctga ccaccatgc ccagcttgct    8580 cttcttcatt gacaacattc acttaaacaa acaaacatcc ataaaattaa gtcagttta    8640 aaacctagct tgtatatatc tttgaattgg aactctcaga gccttcagca cttgcttgat    8700
tggcctcctg ttgatgaaaa tatgtcctcc agacaattca gccaagggga gccccgtgtg    8760
ccttgcccat cacacaaacc tcgctttcca ctgagtgagg ctgtaatttc agaagtgcca    8820
ggtttgtcac atgaaaatat atctgttacc atcacctact gaacaaattt agtagaattt    8880
gtttggtgcc tattatgtat caggcattgt tctgaagact ggggatacca tttagtgaac    8940
taaatagatg aaaaccttgc tgattggacc agagtggaga tgagagagaa gtgaccagat    9000
tgatacgtgt tacagcagag agccaataag atttactgat ggattggatc atggattgtg    9060
aagtagtcag tgatagcacc gagacttttg gcccaagaaa ctggaaagat ggaaatgctg    9120
atgacagaga tgtggaaagt tcacaagcg gcagagtgta ggagaagcaa tgcccatgac    9180
acatctagag gaaagggttg aaccgacagc tggaaataga agtcacattc aggagagagg    9240
tttatgtgta catctgtgtt tatgtgtcgc caatatacaa ctgatatttt tttaaaatct    9300
ggtgaaatta tcaaagaatt aaatgcagac agggaagaaa gtaggtccaa agatggagcc    9360
ttggggtgtt ataaagttca gaaataagaa agatgccatt gtcacttgta attttgtgtt    9420
cgtcactgct ctttttcttt gtcttattcc cttaccgacc aattcctaga ctaggaataa    9480
cacatttgat ctttaataca gaatgtgata ggaatatggc ttctataagc caaagcttgg    9540
caatttaaac ttaaatttat taaaattaaa taaaactggc tgggtgcagt gcctcatgcc    9600
tgtaatccca gtactttggg aggcagaggc aggtggatca cttgaggtca ggagttcgag    9660
accatcctgg ccaacatggc gaaaccccgt ctctaccaaa aatacaaaac ttagcctgat    9720
atggtggtgt gtgcctgtaa tcccagctac tcaggaggct gaggcaggag aatcacttga    9780
acccgggacg tggaggttac agtgagccga gatcgggaca ctgcactcca gcctggatta    9840
caagagaaag actctgtctt aaataaataa ataaataaat aaataaataa aactaaaaat    9900
tcaccttccc agctgtattg ccacattcc aagtgcccag cagccacatg tggttggcgg    9960
ttactgtatt ggatggcata gacatagaat atttccatca ctgcagaaag ttctagggac   10020
agccttgctc tagactgtgg ttttgtctac ttaggaaaag tcactctttt ccaggaagat   10080
gcttccaggg tgtagagtca acgatgtact tcactcatct ccttataaac ctgttgcaat   10140
cctggatagg aggtttctag gtagcatgaa gactcttgaa tctttaagac aggctgggag   10200
ttttgaaagg aagaaaatgg aaagagaaga tactgggaag actgacaata gagtaagctc   10260
```

```
agaaaattgt tatggagcca ggtgatttag ttagaaaatg tgtctgcaac ctaagggtca    10320
tggagtgtga ctctgtggtt tatgagtgtg actctgtggt tcatgggtgt gactctgtgg    10380
tttatgagtg tgactccgtg gttcatgggt gtgactctgt ggtttatggg tgtgattcta    10440
tggtttgagt gtgactccat ggtttatgag tgtgactctg tggttcatgt gattctgtgg    10500
tttatgagtg tgactctgtg gtttatgggt gtgactccac ggtttgggtg tgactctgtg    10560
gtttatgagt gtgactctgt ggtttatggg tgtgactcca tggtttgagt gtgactccgt    10620
ggtttatggg tgtgactcca tggtttatgg gtgtgactcc gtggtttatg ggtgtgactc    10680
tgtggtttat gagtgtgact ctgtggttta gggtgtgac tccatggttt atggtgtga    10740 ctctgtggtt tatgagtgtg actccatggt ttatgagtgt gactctgtgg tttatgagtg    10800
tgactccatg gtttatgagt gtgactctgt ggtttatggg tgtgactcca tggtttgggt    10860
gtgactctgt ggtttatgag tgtgactctg tggtttatgg gtgtgactct gtggtttatg    10920
agtgtgactc tgtggtttat gggtgtgact ctgtggttta tgagtgtgaa tctgtggttt    10980
atgggtgtga ctctgtggtt tgagtgtgac tttgtggttt gagtgtgact ccgtggttta    11040
tgggtgtgac tccatggttt atgagtgtga ctccatggtt tatgagtgtg actccatgat    11100
ttatgagtgt gactccatgg tttatgagtg tgactccatg gtttatgggt gtgactccat    11160
ggtttatgac ttcgtggttt gaatgtgact ccgttgttta tgggtgtgac tccgtggttt    11220
atgagtgtga ctccgtggtt tatgagtgtg actccatggt ttatgggtgt gactccatga    11280
tttatgagtg tgactccatg gtttatgagt gtgactctgt ggtttatggg tgtgactcca    11340
tggtttatga gtgtgactcc atggtttatg ggtgtgactc catggtttat gggtgtgact    11400
ccatgattta tgagtgtgac tctgtggttt atgggtgtga ctccatggtt tgagtatgac    11460
tttgtggttt gaatgtgact ccgtnnnnnn nnnnnnnnnn nnnnnnnnnn nnnnnnnnnn    11520
nnnnnnnnnn nnnnnnnnnn nnnnnnnnnn nnnnnnnnnn nnnnnnnnnn nnnnnnnnnn    11580
nnnnnnnnnn nnnnnnnnnn nnnnnnnnnn nnnnnnnnnn nnnnnnnnnn nnnnnnnnnn    11640
nnnnnnnnnn nnnnnnnnnn nnnnnnnnnn nnnnnnnnnn nnnnnnnnnn nnnnnnnnnn    11700
nnnnnnnnnn nnnnnnnnnn nnnnnnnnnn nnnnnnnnnn nnnnnnnnnn nnnnnnnnnn    11760
nnnnnnnnnn nnnnnnnnnn nnnnnnnnnn nnnnnnnnnn nnnnnnnnnn nnnnnnnnnn    11820
nnnnnnnnnn nnnnnnnnnn nnnnnnnnnn nnnnnnnnnn nnnnnnnnnn nnnnnnnnnn    11880
nnnnnnnnnn nnnnnnnnnn nnnnnnnnnn nnnnnnnnnn nnnnnnnnnn nnnnnnnnnn    11940
nnnnnnnnnn nnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnnnnnnn nnnnnnnnnn nnnnnnnnnn    12180
nnnnnnnnnn nnnnnnnnnn nnnnnnnnnn nnnnnnnnnn nnnnnnnnnn cctatgcccc    12240
agctcaagca tcttgcaacg aagggaagta agccatgtga agcgctatgc agatacccct    12300
gtctcgtctg cctgtgaggc gcattacgtt tataccattt tgtttccaac tgcaggggca    12360
aatgttactt aaagctttct tcaaatggat ctccaactaa atacttcgc gggacaggag    12420 gcatctctgg atacacatta aggctgtgta aaatggataa tggtgagtat aatgtcactt    12480
gaaaaaatac agctgaagga attattccat acggaatcca tcacaaccaa gactatcagg    12540
tccagccgca gaggggagaa cgttcatgaa ataaacacat tttgccatt tccgttgttt    12600 tcactcctat cacccaagct gaccatgttt taaacgtaaa tactggggct tgaccaaact    12660
```

```
gtacattgcc tagtattaac caaatatatg ttttaatttg acacatttat acacctggca    12720
tttctgtttt ctttctttct ttcttttttt tttttttttg agacagagtc tcactctgtt    12780
gtccaggctg gagtgcagtg atgtggtcag tgtttactgc agcctctgcc ttgaactcct    12840
ggactccaac aatcctccca ccttagctcc ctgagtagct ggggctacag gcgtgcacca    12900
caacacccgg ctaattttt gtagagatgg ggtcttgcca tgttgcccag gatgctcttg     12960
aactcctggg ctcaagcgat cctcccgctt tggcttccca aagttctggg attataggtt    13020
tgaaccactg tacccagcca caactggcat tcataatga cccagact ctgccaacac       13080
tcctgtgatc aaggccagta atctttccta ttatcctttg taagggaaat atcgatcaat    13140
actttggtta gtcaaattac tcattttctt ctaaaaaatg tgtatctgtt caagaaatac    13200
tggcacacct cctttttaga ggtctttatt cagattccat gcagggttcc agagacttag    13260
gaattggcat aggttaaggt aaaactttac taacaacaat gagtgtggta gggtggaaat    13320
aagagtgttt agattataca agacctatgg taacataaaa gttgcaagaa aaatccgacc    13380
agcagtgttt ccatcccagt ggccagtttc tgagtatact cgcaagagat ggtttgtagg    13440
caaatagaat tgtcccaagg gacaaaatcc ccaacaggaa agaatgcacc acaagcactc    13500
ctgcctaaat tactgtcata acttaggatg gctttactat atactgattt acagaagctg    13560
tatgttctta actgtttact gttaaatgtc caatattcca atacactgta agatgcaact    13620
gagatttaat gaatgaaatg caagtgataa tcatgctttg tcatagtttt agaagcacaa    13680
aaacctttcg tgtcagatta tctgctgtac tgagaaggcg agtcaatcct tcatttctga    13740
gaacttgttt tgtagaacat aaagatgtca tattggccgg gcgcggtggc tcacgcctgt    13800
aatcccagca ctttgggagg ccgagacggg tggatcatga ggtcaggaga tcgagaccat    13860
cctggctaac ccggtgaaac cccgtctcta ctaaaaaact agccaggctg gtggcggcg    13920
cctgtggtcc cagctacttg ggaggctgag gcaggagaat ggcgtaaacc cgggaggagg    13980
agcttgcagt gagctgagat ccggccaccg cgctccagcc tgggccacag agcgagactc    14040
cgtctcaaaa aaaaaaaaaa aaaaaggaaa aaagatgtca tattgcctcc aacactgata    14100
tcctaactag taaactgcgc cctcctagag ctcagaggcg ctccgatgag aatctttgga    14160
tggctcaagc ctccttaaaa agcaagtcga ttaagtcgta tcccatacat tgttttcctc    14220
accataaatt tccctaagac aagaaggagc attcagcacc attctgctgt ctttcttcta    14280
cttctgagca ttagaaggga cgcttagcgg atgttgttgt taagtaatgt tgacatgatt    14340
taaaaaatgg gaacgagcac gtataccttta atacattgca gactgcgttt ccccttcct    14400
tcttcattat ggttttctca ttggatttac agactctggc ctgtagaagt tacagaatat    14460
accagataaa gattgatagc tgcaggagaa aatgtaagat aaaggaaaat aaacttatgt    14520
cttttcagtg caccttttgga gggagtgaat tagataacta ggttttgct gcactgtatt    14580
tgatgaaata actccctaat gtgaaaggga atagctacgt gagatgttga tggtgtcttg    14640
tctgccattg gtctacaatg taacttaact ttctgaagat agatagcagc accattaaaa    14700
caaacatttc ttaacacaaa atatgattct aaacacgtat tttcagcctt tcgtttaaac    14760
tgagaatcaa aataggatga acatcaaggc ctctcacctg tacttaatag ggtcttgatt    14820
gagttatttc taacatacac tagttactgc ttacctatta atttccctaa aatttacctt    14880
tatgacactt cccaccttgc gaactataaa ggcttcgag aaattccaga atagagggcc     14940
ctccaaaaca aattttcacc ctaccagctc taaaatgaga gcctctgttc aggcttccaa    15000
```

```
agacacagcc tgctcgttct cacctcagtt gctgttagct gctgtttcct tccaaactcc    15060
ttctctcttc ctctccttct atttgaaatc cacgccagaa ttatacgctc attttcctac    15120
catggaaaaa aaggcctaga aaggttgttt tatacccaca aaactagtga gtggatcttc    15180
taggatccgg cttctcatca gtgattcttc tgttaactta gactcctccc ttagcttggg    15240
acacagagcc tctctgagca cctgagcctg gttattctaa gtgtgatctg ggcacggcac    15300
attggcatcg cccaggaggt tattagaatt tcaggaccca cacagacgtt acggagtcag    15360
gatctgcaat ttaaaggcta tgcaggcgac ccataggcac ataaaagtat gagtcgcata    15420
ggtgtgtgcg tgtgtgtgca tgtgtctaga atactgctgt ctacgaaccc cgactcccat    15480
gccatctgtg ttccatgtgt gcgtgtgtgt gcgtgcgtgt gtgtgcatgt gtgtgttcgt    15540
gtgtgtgtct agaatactgc tgtctacgaa ccccgactcc catgccatct gtgttccatg    15600
tgtgcgtgtg tgtgcgtgcg tgtgtgtgca tgtgtgtgtt cgtgtgtgtg tctagaatac    15660
tgctgtctac gaaccccac tcccatgcca tctgtgttcc atgtgtgcgt gtgtgtgcat    15720
gtgtgtgtgt gcatgtgtgt atgtgtatgt gcatgtgtgt gtctagaata ctgctgtcta    15780
caaacaccca aatcccatgc catctgtgtt ctgtgtgtgt gtgtgtacgt gtgtgtgtgc    15840
atgtgtgcat gtgtgtgtgc atgtgcatgt gtaagtctag aatactgctg tctacgaaca    15900
ccccactccc atgccatctc ttttccttgt gtgtgtgggt acgtgcatgt gtgtgcacgt    15960
gtgtgtgtgc atgtgtgtgc acgtgtgcgt gtgtgtgtgt ctagaatact gctgtctaca    16020
aacaccccat tcccatgcca tctctgttcc ttgtgtgtgc gtgtgtgtgt gtgcatgtgt    16080
gtgcatttgc gtgtgtgtac acacgtgggt gtgcatgtgt atgtgtgtgt acatgtatgt    16140
gtgtgtctgc atgtgtctag aatactcttt actaacaccc cactcccatg ccatctgtgt    16200
tccatgtgtg cgtgtgtgtg catgtgtcta gaatactctt taacaccccca ctcccatgcc    16260 atctgtgttc cgtgtgtgtg tgtgagtgtg tgtgcatgtg tgtgcacatg agtgtgcatg    16320
tgtgcgactg tgtgcatgca cgtgtgtgcg attgtgtgca tgtgtgtgcg tgtgtgtgtg    16380
cgtgtgtgtg tctagaatac tgctgtctat gaacacccca ctcccatgcc atctgtgttc    16440
cgtgtgtgtg tgtgtgtgtg tgtctagagt atgaacaccc cactcccatg ccatctgggt    16500
tccatggcag gctgggtcaa ggttccagcc tggaggatgg gttcttgtgt tgggcatcca    16560
gtaagtagaa agagaaggaa ctgttgtttc taggcagccc caagagtaaa gaaacacagg    16620
atgaacctaa gtcaaagtcc ctgaaaagta ccaaggaccc cagagaatcc caaactgtca    16680
acaaggccaa aggtcagagg aagttcgcag atcagtctta ctttggacgt ggatggagca    16740
ggagtgactg ggagtcatgg tcagcagagt cacgggaaca gggcaggaac tagataatgg    16800
ctgcagcctg agggcaaggt gctcgccttt tctttctaag agtagttctc aaacgccagc    16860
agggctggtt taaacacaga gggctgagct tccaggctgg agtttctcat tcactggatc    16920
tgaggtgggg ctgaagaatg tgcatttctg acaagttccc aggtgacact gttggtctgg    16980
agactgcact cgacaaccac tggtttaaaa gaaccattcg cgttatcatt tgaagaagga    17040
taagacagcc tcgtagtacc acacaagagg gccacatcct ttggggtgtg taattacaag    17100
atgaattagt tacttccatt tttcatgtgc atgttttgct ttggcaactt gattataaag    17160
tctctggaac tcagggtcat gataaactgt tgacttgagg gaaggttttc ttcttcttgt    17220
tactgaaaga gcacaattac tggtggaaag gaagatgtag gaagctgctc atcgcaatgc    17280
ttctgttgca gagtgtacca ccaaaatcaa gcccaggatc gttggaggaa ctgcatctgt    17340
tcgtggtgag tggccatggc aggtgactct gcacaccacc tcacccactc agagacacct    17400
```

-continued

```
gtgtggaggc tccatcattg gaaaccagtg gatattaacg gccgctcact gtttctatgg    17460
gtcagtacca cggctgcttt tattagttca tcttcttcac gcatttataa aaatattac    17520 tagcatatca ggaaatactt taatcaatta aattgtctta tttgcaaaat taattaattc    17580
cttcagtggt aaaaaaggca gaaaggaaga gtccctcatg gtctcccagc atcagaacag    17640
gtgcaggtac acggccgctt gactgcctgc aattctgctt cccgtttaac cacatccaca    17700
tccccagggg ccttcatgtt attccctgca agagcatacc tcctccctgt gtgcctcgct    17760
ctgtgcgctg cgcccagaac taaactcaca gaggatttac cactctcgga atcaaatttc    17820
taatatgtgt gtgtgcgtgt gtgcgtgtgt gtgtgtgttt aaacacagaa agaggccagg    17880
tgtggtggtt catgcctgta atcccagcac tttgggtggc tgaggaggga ggatcacttg    17940
atgccaggag tctgaggtca gcctgggcaa catagtgaga ccctgtctct aaaaattatt    18000
taaaaacgag tcaggcctgg tggtttgtgc acctgtagca ccagctgctc agaaggctga    18060
ggtaggagga ttgcttgagc ccaagagttc aagggttcag tgagttacta cagtgccact    18120
gcgctccagc gtgagcaaca gagcgagacc ctatctctaa gtaaataaat aaaatacagg    18180
aagagttcag taggcatcct caaactgggt tccttactta ggtcactttc tgcactggcc    18240
aaacataaag gctccagctg ggggtatata tattccaggg aagttaagtc agccaaactt    18300
tctgtttgct actttagtat cctcctagtt gtttccagac acagttttgt gtgcttttta    18360
gttttagttt tcttttttaa tcagtctgca gcacactcat attaaactca agaacacatg    18420
tgaaatcaag agtccccgtt acctgtcaca tatgggaatg gagtagcaga gaggccgcct    18480
gagtttctca gtgtcacagc tagtcactgg cgagggtgag actaagtcca gtgatcttcg    18540
tgtgtgtgtg tgcttgtgtg tgtgtgtgtg tgtgcctctg tgtgcctgtg tgtgtgtgtg    18600
ttggagcatg gaggggggtgc tcattcattt tttgtgtata atggattttc tttatagggt    18660
gaatatgttt tttatcctga aaaatcttag gaaaaaaatc actttttttcc acctaaatgt    18720 ccgtcattgg cagaaaatat tagtaatagt taaatagtca cacacttcac aatgtctggg    18780
aattattttc agtaaaggaa atttcttttc ctctgctgtt tgctccttag ggtagagtca    18840
cctaagattt tgcgtgtcta cattggcatt ttaaatcaat ctgaaataaa agaggataca    18900
tcttcttttg gggttcaaga ataataatc catgatcaat ataaaatggc agaaagtggg    18960
tatgatattg ccttgttgaa actggaaacc acagtgaatt acacaggtat ggagaatttt    19020
atctggaaag ttatctccaa tggtgaactg gataaaatgt ttaacgctgc tagatttacg    19080
acctgagcct gccagtctct ctgtgtgtta tcatcatgga agcgagaggg cctggaacac    19140
gagcttcatt ctgttaaggc tgacacacgt tcctggcgat tgaaacttat ttggggaatg    19200
tgggtgaaga gatacgtttt cctgaggctt cttcaggtgc atagaatgac acaatttcat    19260
aatacattgg aatagtaaag ataatttagt ctaaagataa tttagtaaag gtaatttagg    19320
gatgaaggat tgaaggttag gacaattaag caacttgtgc aggatcacaa actgagttgg    19380
atgaggagtt agtggccagg gtggggcttg tctctctctc gccccctcat cctggcgctt    19440
gtgcaatatt atgctgaacc tgagggagga aaatatacga aaacaaggca aaaaagaat    19500 atagtaaaca aagaaaacac agataatgta cagtggaaga agagtctctt ctggaaaaga    19560 ggatctatttt tgcatctcat atttaaacca tgattttta catttagatt ctcaacgacc    19620
catatgcctg ccttcaaaag gagatagaaa tgtgatatac actgactgct gggtgactgg    19680
atgggggtac agaaaattaa gaggtaaaaa tgatgttgtt atatgtgctc cagcctagaa    19740
```

```
atgaagaacg gaaacctttc tgccctgtca agtcatgtag ctgaagcaca agtcgagtca    19800
cactactcag ctgcaggaag cggattaata ccgatggaga ggcaaaagtc acccaagtga    19860
ggctggtgcc tcatctgttt gattggaaat tttaaatgtg actacatctc tttaaagact    19920
aattatattt aatgaagttt aatgtgaagc ctagcacttt tcagtaaatg ttctagcctg    19980
ctatccaatt actttctctg ggaagtcatt ccagttagag tcataattaa ttttggaact    20040
taattaacat taacaaaatg gtacatgcaa tagtgggaat aatgttttct tcatacttgc    20100
aattataaaa ggtccgtgaa gtaaatctaa cattttttcc ttctagattt ttatataggc    20160
atgattgttg ttgttgttgt tgttgttgtt gttgttgttt ttgaggtgga gtctcgctct    20220
gtcgcccagg ctggagtgca gtggcgcaat ctcggctcac tgcaagctct gcctcccggg    20280
ttcaagcaat tctcctgcct cagcctccca agtagctggg attacaggtg cccaccacca    20340
ccccaagcta gttttggta ttttagtag agacagggtt tcaccgtgtt agccaggatg    20400
atctccatct cctgaccctg tgatctgcct gcctcggcct cccaaagcgc tgggattaca    20460
ggtgtaagtc actgcgcccg gctgtgattt ttattttaaa tatatgcggc cgggcgcggg    20520
ggctcacgcc tgtaatccca gtgctttgag aatccaagat gggtggatca cttgaggtca    20580
ggagttcaag accggcctgc ccaacacggt gaaactccat ctcaactaaa atacagaca    20640
ttacccgggc ataatggcaa gtgcctgtac atgccatgta ctcgggaggc tgaggcagga    20700
gaattgcttg aacctgggag gcggaggttg cagtgagccg agatcgcgcc actgcactcc    20760
agcgtgggca acaaaagag actccgtctc aattaaaaaa aaagtgtgtg tgtgtatgtg    20820
tgtgtgtgta tatatgtata tacgtttatg tgtattgtat atggttattc cacaaacaaa    20880
ccaaaaaatt ttttcagac aaaatacaga atactctcca gaaagccaag ataccccttag    20940
tgaccaatga cgagtgccag aagagataca gaggacataa aataacccat aagatgatct    21000
gtgccggcta cagggaagga gggaaggatg cttgcaaggt aacgcagtgt tcttagccaa    21060
tggaatatac acaaattgga atgcttaatg tatttttttt ttgaaatgga gtcttgctct    21120
gtcacccagg ctagagtgca gtggtgtgat ctctgctcac tgcaacctcc acctccaggt    21180
tcaagcgatt ctccagcctc agcctcctga gtagctggga ttataggcgt gcaccaccac    21240
acctggctaa tttatttgt attttagta gagacgaggt ttcaccatgt tggccaggat    21300
ggtctcgatc tcttgacctc gtgatccacc cgccttggcc tcccaaagtg ctgggattgc    21360
aggtgtgagc caccgtgccc ggccgcttaa tgcattttga aaagcagtct tctgccaatg    21420
agcagggaac acagtgtatt tgcttgactt ggcaaaaatg aggagactga ctggaagaac    21480
gcaagcaccc gggttctctg cagtatatta agagtccaag acagcattta cacaaaatca    21540
gcctgagcaa gatgtgctga agacgggaag cgtttgagtt gatctgtgca ccttttcttg    21600
tctccccttg ttctagggag attcgggagg cccnnnnnnn nnnnnnnnnn nnnnnnnnn    21660
nnnnnnnnnn nnnnnnnnnn nnnnnnnnnn nnnnnnnnnn nnnnnnnnnn nnnnnnnnnn    21720
nnnnnnnnnn nnnnnnnnnn nnnnnnnnnn nnnnnnnnnn nnnnnnnnnn nnnnnnnnnn    21780
nnnnnnnnnn nnnnnnnnnn nnnnnnnnnn nnnnnnnnnn nnnnnnnnnn nnnnnnnnnn    21840
nnnnnnnnnn nnnnnnnnnn nnnnnnnnnn nnnnnnnnnn nnnnnnnnnn nnnnnnnnnn    21900
nnnnnnnnnn ggcttggtgc tggtaggaaa atgccagaag aaaacaaact gtcacaagct    21960
gttatgtcca aagctcccgt tctatgatca ttgtagtttg tttcagcatc cagtgtcttt    22020
gtttctgatc acgcttctaa ggagtccaag aattaccata aggcaatatt tctgatgatt    22080
actatatagg cagatatatc agaaaataac caagtagtgg cagcagggat caggtagaag    22140
```

-continued

```
aactgataaa agaaaccacc ataaatagat ttgttcaatg aaaaatgaaa actggaagaa   22200
aggataacaa agacagtctt caccattttg caggaatcta cactctgcct gtgtgaacac   22260
atttctttgt aaagaaagaa tttgattgca tttactggca gattttcaga atagtcagga   22320
attcatgtta tttccatttt aaaacatgtt taaaaaaatc agtttgagta gacacaagct   22380
aagagtgaat gtgaaggtac cagaatttct gtatggaaga gggtgacaag cagcaatgta   22440
cctggaagtg gtaccttagg accaatctta aagatacact ttcctgaaaa atgatttgtg   22500
atggatcgta tatttattta aaatatcttg ggagggagag gctgatggcg atagggaggc   22560
aagctgaagc ctccataaga caagctgcta ctgcgactgt ggcccccaaa gagctacacc   22620
gcatatttat ttgacaaaag tcaccattga ctacatccgt actacagaga aaaacaatt   22680
tgggcacaaa tggatggtta cagtaaagtc ttcagcaagc agctccctgt attctaagta   22740
ctgggctttt ctgtttggtg caaatattta tctcattatt gctgtgatct agtccagtaa   22800
cctagaattt gatttgtcac cacatagctt caacctgtg ccaacaatta tacaattcat   22860
caagtgtgaa tttttttttt tttttttttt tttgagacga agtctcactc tgttgcccag   22920
gctggagtgc agtggtgtaa cttcgactca ctgtaaccta cacctcctgg gttcaagcga   22980
ttgtcctgcc tcagtctccc aagtagctga gactacaggc acgccacc atgcccagct   23040
aattttata tttttagtag acgtggtt tcactatgtt ggccaggctg gtcttgaact   23100
tctgaccttg tgatccaccc acctcagcct ctcaaagtgc tgggattaca ggcgtgagtc   23160
actgcacctg gccttggaaa atatttattg agcacaatta cttgagagca tcatgctgag   23220
cttttgaggat acagtggtga gcaaacagat atgtcctggc ttcatgaagc ttatactcta   23280
gctaacatga acaacaaaat aaaataatca cacaaaatat agaagttcaa gctgaaatga   23340
gcggctgcac cggattctat cagatgagaa aggacagttt tcacaaagtt caaagactgg   23400
ggatacaaag gaatttgtcc tgagaaagac aaaacaaaaa caacaaacaa aaacccaaa   23460
agagtaaaat gacggtaggg tataacgggg ccagatccaa aatgcggaca ggttcaaaca   23520
aaattggaac tgaaaatcag agtgccttca agagtagcaa acgatattat cttgttacct   23580
gctaattacc ttagtagact ggaagcaaca cttcacacac aagagggttg ggatgtaatt   23640
tctgataaga agaggtgttt ctgtgaagtc tttcctgaga acatattatt tgagaaaaac   23700
acatattgtt gttttttagca tttcactttg tataagtctt aattttttgaa gagcgggtat   23760
atgcccatga tttgttaatg aaaatactat aagatataaa atatacaatg agaagatctc   23820
ctcttctgtg ccaggagagt gcacattcta cacactgcgt agcacctttc tgacttccgt   23880
tctgtctggg cacagttctg attgccatgc agagggctcc ctctgtctgg ggatatttct   23940
cacgggtacc gagagagcct cctctatctt ggggtatttc cgatgcgtac agaagggctg   24000
c                                                                   24001
```

<210> SEQ ID NO 18

<400> SEQUENCE: 18

000

<210> SEQ ID NO 19

<400> SEQUENCE: 19

000

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agcttcttgt ccagctttat                                          20

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
agcttcttgt ccagctttat a                                        21

<210> SEQ ID NO 22
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 22
tcagtcatga cttc                                                14

<210> SEQ ID NO 23
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 23
tcagtcatga cttca                                               15

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gctgattaga gagaggtccc                                          20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tcccatttca ggagacctgg                                          20

<210> SEQ ID NO 26
<211> LENGTH: 15
<212> TYPE: DNA
<213> ORGANISM: Artificial sequence
<220> FEATURE:
<223> OTHER INFORMATION: Synthetic oligonucleotide

```
<400> SEQUENCE: 26
atcagtcatg acttc                                                        15

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
cggtgcaagg cttaggaatt                                                   20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gcttcagtca tgacttcctt                                                   20

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 29
gcttcagtca tgacttcctt a                                                 21

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 30
agcttcagtc atgacttcct t                                                 21

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tggtaatcca ctttcagagg                                                   20

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 32
tggtaatcca ctttcagagg a                                                 21

<210> SEQ ID NO 33
```

```
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 33
tgcttcagtc atgacttcct t                                              21

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
cactgatttt tgcccaggat                                                20

<210> SEQ ID NO 35
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 35
cactgatttt tgcccaggat a                                              21

<210> SEQ ID NO 36
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 36
aagcttcttg tccagcttta t                                              21

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
acccaattca gaaggaagga                                                20

<210> SEQ ID NO 38
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 38
acccaattca gaaggaagga a                                              21

<210> SEQ ID NO 39
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 39
```
aacccaattc agaaggaagg a                                             21

<210> SEQ ID NO 40
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 40
atggtaatcc actttcagag g                                             21

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tcttggttac atgaaatccc                                               20

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 42
tcttggttac atgaaatccc a                                             21

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
attcactttc ataatgctgg                                               20

<210> SEQ ID NO 44
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 44
attcactttc ataatgctgg a                                             21

<210> SEQ ID NO 45
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 45
atcttggtta catgaaatcc c                                             21

<210> SEQ ID NO 46
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 46
atgcatggtg atgcttctga                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cagctttatt agggacagca                                              20

<210> SEQ ID NO 48
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 48
cagctttatt agggacagca a                                            21

<210> SEQ ID NO 49
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 49
acagctttat tagggacagc a                                            21

<210> SEQ ID NO 50
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 50
ttcagtcatg acttcc                                                  16

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: bases at these positions are RNA
<220> FEATURE:
<221> NAME/KEY: misc_feature
<222> LOCATION: (15)..(18)
<223> OTHER INFORMATION: bases at these positions are RNA

<400> SEQUENCE: 51
gcuucagtca tgactucc                                                18

<210> SEQ ID NO 52
<211> LENGTH: 21
```

```
<212> TYPE: DNA
<213> ORGANISM: Artificial sequence
<220> FEATURE:
<223> OTHER INFORMATION: Synthetic oligonucleotide

<400> SEQUENCE: 52
tgctccgttg gtgcttgttc a                                           21

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tgctccgttg gtgcttgttc                                             20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
aaatggttta ttccatggcc                                             20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
aatggtttat tccatggcca                                             20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ggtttattcc atggccattg                                             20

<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 57
aatggtttat tccatggc                                               18

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
```
ggcacactca gcaggacccc                                        20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
gcacactcag caggaccccc                                        20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
aggcacactc agcaggaccc                                        20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
gccaggcgac tgccctcctt                                        20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tgccaggcga ctgccctcct                                        20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
cgctctccat cacgagactc                                        20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
cacgctctcc atcacgagac                                        20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
cttccagctt ctctgggctc                                          20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggtagaaata tagttgttcc                                          20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ttcatgtgtc tgcatcatgt                                          20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gcagccatgg tgatcaggag                                          20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gcatccagcg agcaccaaag                                          20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
gtctggatta cagcataaac                                          20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
ccttggtctg gattacagca                                          20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
agccatggtg atcaggaggc                                               20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ggtctggatt acagcataaa                                               20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
agccatggtg atcaggaggc                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
cagccatggt gatcaggagg                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gtgcttgtcc aggatgatgc                                               20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
ccttggtctg gattacagca                                               20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
gcactttgtg gtgccaaggc                                              20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
tccacaggcc acaggtgggc                                              20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
gcaaggctcg gttgggcttc                                              20

<210> SEQ ID NO 81
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 81
ggttcccgag gtgccca                                                 17

<210> SEQ ID NO 82
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 82
gggcaatgca gtcctgg                                                 17

<210> SEQ ID NO 83
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 83
gggttcccga ggtgcccaat g                                            21

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
atgcatggtg atgcttctga                                              20

<210> SEQ ID NO 85

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
gctaaacaac cgcctt                                                        16

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ccctcctgtg cctggatgct                                                    20

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
catggtgatg cttctg                                                        16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
agagctaaac aaccgc                                                        16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
actcccggga caccca                                                        16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ggacacccac gccccc                                                        16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
```
acaccctcgc ctccgg 16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
gcctccggaa caccca 16

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
tgcacagttt ctggcaggcc 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
acggcattgg tgcacagttt 20

<210> SEQ ID NO 95
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 95
gcacagtttc tggcaggc 18

<210> SEQ ID NO 96
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 96
ggcattggtg cacagttt 18

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
cacagtttct ggcagg 16

<210> SEQ ID NO 98
<211> LENGTH: 14
<212> TYPE: DNA

```
<213> ORGANISM: Artificial sequence
<220> FEATURE:
<223> OTHER INFORMATION: Synthetic oligonucleotide

<400> SEQUENCE: 98
acagtttctg gcag                                                    14

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 99
gcacagtttc tggcaggc                                                18

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
cacagtttct ggcagg                                                  16

<210> SEQ ID NO 101
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 101
acagtttctg gcag                                                    14
```

COMPOSITIONS AND METHODS

SEQUENCE LISTING

The present application is being filed along with a Sequence Listing in electronic format. The Sequence Listing is provided as a file entitled BIOL0255USASEQ_ST25.txt created Oct. 30, 2015, which is 504 Kb in size. The information in the electronic format of the sequence listing is incorporated herein by reference in its entirety.

BACKGROUND OF THE INVENTION

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced siliencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compounds efficacy.

SUMMARY OF THE INVENTION

In certain embodiments, the present disclosure provides conjugated antisense compounds. In certain embodiments, the present disclosure provides conjugated antisense compounds comprising an antisense oligonucleotide complementary to a nucleic acid transcript. In certain embodiments, the present disclosure provides methods comprising contacting a cell with a conjugated antisense compound comprising an antisense oligonucleotide complementary to a nucleic acid transcript. In certain embodiments, the present disclosure provides methods comprising contacting a cell with a conjugated antisense compound comprising an antisense oligonucleotide and reducing the amount or activity of a nucleic acid transcript in a cell.

The asialoglycoprotein receptor (ASGP-R) has been described previously. See e.g., Park et al., PNAS vol. 102, No. 47, pp 17125-17129 (2005). Such receptors are expressed on liver cells, particularly hepatocytes. Further, it has been shown that compounds comprising clusters of three N-acetylgalactosamine (GalNAc) ligands are capable of binding to the ASGP-R, resulting in uptake of the compound into the cell. See e.g., Khorev et al., Bioorganic and Medicinal Chemistry, 16, 9, pp 5216-5231 (May 2008). Accordingly, conjugates comprising such GalNAc clusters have been used to facilitate uptake of certain compounds into liver cells, specifically hepatocytes. For example it has been shown that certain GalNAc-containing conjugates increase activity of duplex siRNA compounds in liver cells in vivo. In such instances, the GalNAc-containing conjugate is typically attached to the sense strand of the siRNA duplex. Since the sense strand is discarded before the antisense strand ultimately hybridizes with the target nucleic acid, there is little concern that the conjugate will interfere with activity. Typically, the conjugate is attached to the 3' end of the sense strand of the siRNA. See e.g., U.S. Pat. No. 8,106,022. Certain conjugate groups described herein are more active and/or easier to synthesize than conjugate groups previously described.

In certain embodiments of the present invention, conjugates are attached to single-stranded antisense compounds, including, but not limited to RNase H based antisense compounds and antisense compounds that alter splicing of a pre-mRNA target nucleic acid. In such embodiments, the conjugate should remain attached to the antisense compound long enough to provide benefit (improved uptake into cells) but then should either be cleaved, or otherwise not interfere with the subsequent steps necessary for activity, such as hybridization to a target nucleic acid and interaction with RNase H or enzymes associated with splicing or splice modulation. This balance of properties is more important in the setting of single-stranded antisense compounds than in siRNA compounds, where the conjugate may simply be attached to the sense strand. Disclosed herein are conjugated single-stranded antisense compounds having improved potency in liver cells in vivo compared with the same antisense compound lacking the conjugate. Given the required balance of properties for these compounds such improved potency is surprising.

In certain embodiments, conjugate groups herein comprise a cleavable moiety. As noted, without wishing to be bound by mechanism, it is logical that the conjugate should remain on the compound long enough to provide enhancement in uptake, but after that, it is desirable for some portion or, ideally, all of the conjugate to be cleaved, releasing the parent compound (e.g., antisense compound) in its most active form. In certain embodiments, the cleavable moiety is a cleavable nucleoside. Such embodiments take advantage of endogenous nucleases in the cell by attaching the rest of the conjugate (the cluster) to the antisense oligonucleotide through a nucleoside via one or more cleavable bonds, such as those of a phosphodiester linkage. In certain embodiments, the cluster is bound to the cleavable nucleoside through a phosphodiester linkage. In certain embodiments, the cleavable nucleoside is attached to the antisense oligonucleotide (antisense compound) by a phosphodiester linkage. In certain embodiments, the conjugate group may comprise two or three cleavable nucleosides. In such embodiments, such cleavable nucleosides are linked to one another, to the antisense compound and/or to the cluster via cleavable bonds (such as those of a phosphodiester linkage). Certain conjugates herein do not comprise a cleavable nucleoside and instead comprise a cleavable bond. It is shown that that sufficient cleavage of the conjugate from the oligonucleotide is provided by at least one bond that is vulnerable to cleavage in the cell (a cleavable bond).

In certain embodiments, conjugated antisense compounds are prodrugs. Such prodrugs are administered to an animal and are ultimately metabolized to a more active form. For example, conjugated antisense compounds are cleaved to remove all or part of the conjugate resulting in the active (or more active) form of the antisense compound lacking all or some of the conjugate.

In certain embodiments, conjugates are attached at the 5' end of an oligonucleotide. Certain such 5'-conjugates are cleaved more efficiently than counterparts having a similar conjugate group attached at the 3' end. In certain embodiments, improved activity may correlate with improved cleavage. In certain embodiments, oligonucleotides comprising a conjugate at the 5' end have greater efficacy than oligonucleotides comprising a conjugate at the 3' end (see, for example, Examples 56, 81, 83, and 84). Further, 5'-attachment allows simpler oligonucleotide synthesis. Typically, oligonucleotides are synthesized on a solid support in the 3' to 5' direction. To make a 3'-conjugated oligonucleotide, typically one attaches a pre-conjugated 3' nucleoside to the solid support and then builds the oligonucleotide as usual. However, attaching that conjugated nucleoside to the solid support adds complication to the synthesis. Further, using that approach, the conjugate is then present throughout the synthesis of the oligonucleotide and can become degraded during subsequent steps or may limit the sorts of reactions and reagents that can be used. Using the structures and techniques described herein for 5'-conjugated oligonucleotides, one can synthesize the oligonucleotide using standard automated techniques and introduce the conjugate with the final (5'-most) nucleoside or after the oligonucleotide has been cleaved from the solid support.

In view of the art and the present disclosure, one of ordinary skill can easily make any of the conjugates and conjugated oligonucleotides herein. Moreover, synthesis of certain such conjugates and conjugated oligonucleotides disclosed herein is easier and/or requires few steps, and is therefore less expensive than that of conjugates previously disclosed, providing advantages in manufacturing. For example, the synthesis of certain conjugate groups consists of fewer synthetic steps, resulting in increased yield, relative to conjugate groups previously described. Conjugate groups such as GalNAc3-10 in Example 46 and GalNAc3-7 in Example 48 are much simpler than previously described conjugates such as those described in U.S. Pat. Nos. 8,106,022 or 7,262,177 that require assembly of more chemical intermediates. Accordingly, these and other conjugates described herein have advantages over previously described compounds for use with any oligonucleotide, including single-stranded oligonucleotides and either strand of double-stranded oligonucleotides (e.g., siRNA).

Similarly, disclosed herein are conjugate groups having only one or two GalNAc ligands. As shown, such conjugates groups improve activity of antisense compounds. Such compounds are much easier to prepare than conjugates comprising three GalNAc ligands. Conjugate groups comprising one or two GalNAc ligands may be attached to any antisense compounds, including single-stranded oligonucleotides and either strand of double-stranded oligonucleotides (e.g., siRNA).

In certain embodiments, the conjugates herein do not substantially alter certain measures of tolerability. For example, it is shown herein that conjugated antisense compounds are not more immunogenic than unconjugated parent compounds. Since potency is improved, embodiments in which tolerability remains the same (or indeed even if tolerability worsens only slightly compared to the gains in potency) have improved properties for therapy.

In certain embodiments, conjugation allows one to alter antisense compounds in ways that have less attractive consequences in the absence of conjugation. For example, in certain embodiments, replacing one or more phosphorothioate linkages of a fully phosphorothioate antisense compound with phosphodiester linkages results in improvement in some measures of tolerability. For example, in certain instances, such antisense compounds having one or more phosphodiester are less immunogenic than the same compound in which each linkage is a phosphorothioate. However, in certain instances, as shown in Example 26, that same replacement of one or more phosphorothioate linkages with phosphodiester linkages also results in reduced cellular uptake and/or loss in potency. In certain embodiments, conjugated antisense compounds described herein tolerate such change in linkages with little or no loss in uptake and potency when compared to the conjugated full-phosphorothioate counterpart. In fact, in certain embodiments, for example, in Examples 44, 57, 59, and 86, oligonucleotides comprising a conjugate and at least one phosphodiester internucleoside linkage actually exhibit increased potency in vivo even relative to a full phosphorothioate counterpart also comprising the same conjugate. Moreover, since conjugation results in substantial increases in uptake/potency a small loss in that substantial gain may be acceptable to achieve improved tolerability. Accordingly, in certain embodiments, conjugated antisense compounds comprise at least one phosphodiester linkage.

In certain embodiments, conjugation of antisense compounds herein results in increased delivery, uptake and activity in hepatocytes. Thus, more compound is delivered to liver tissue. However, in certain embodiments, that increased delivery alone does not explain the entire increase in activity. In certain such embodiments, more compound enters hepatocytes. In certain embodiments, even that increased hepatocyte uptake does not explain the entire increase in activity. In such embodiments, productive uptake of the conjugated compound is increased. For example, as shown in Example 102, certain embodiments of GalNAc-containing conjugates increase enrichment of antisense oligonucleotides in hepatocytes versus non-parenchymal cells. This enrichment is beneficial for oligonucleotides that target genes that are expressed in hepatocytes.

In certain embodiments, conjugated antisense compounds herein result in reduced kidney exposure. For example, as shown in Example 20, the concentrations of antisense oligonucleotides comprising certain embodiments of GalNAc-containing conjugates are lower in the kidney than that of antisense oligonucleotides lacking a GalNAc-containing conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly for non-kidney targets, kidney accumulation is undesired.

In certain embodiments, the present disclosure provides conjugated antisense compounds represented by the formula:

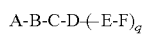

wherein

A is the antisense oligonucleotide;

B is the cleavable moiety

C is the conjugate linker
D is the branching group
each E is a tether;
each F is a ligand; and
q is an integer between 1 and 5.

In the above diagram and in similar diagrams herein, the branching group "D" branches as many times as is necessary to accommodate the number of (E-F) groups as indicated by "q". Thus, where q=1, the formula is:

A-B-C-D-E-F where q=2, the formula is:

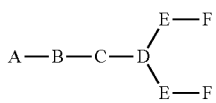

where q=3, the formula is:

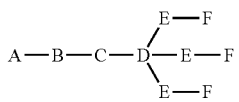

where q=4, the formula is:

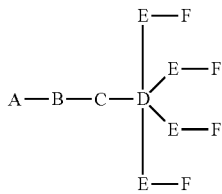

where q=5, the formula is:

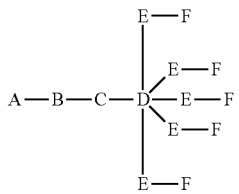

In certain embodiments, conjugated antisense compounds are provided having the structure:

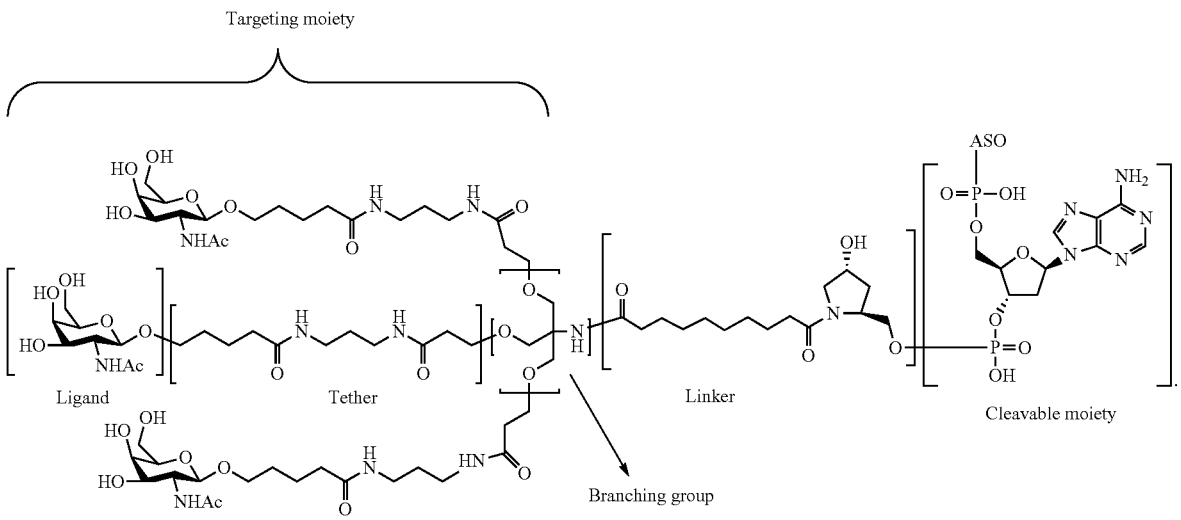

In certain embodiments, conjugated antisense compounds are provided having the structure:
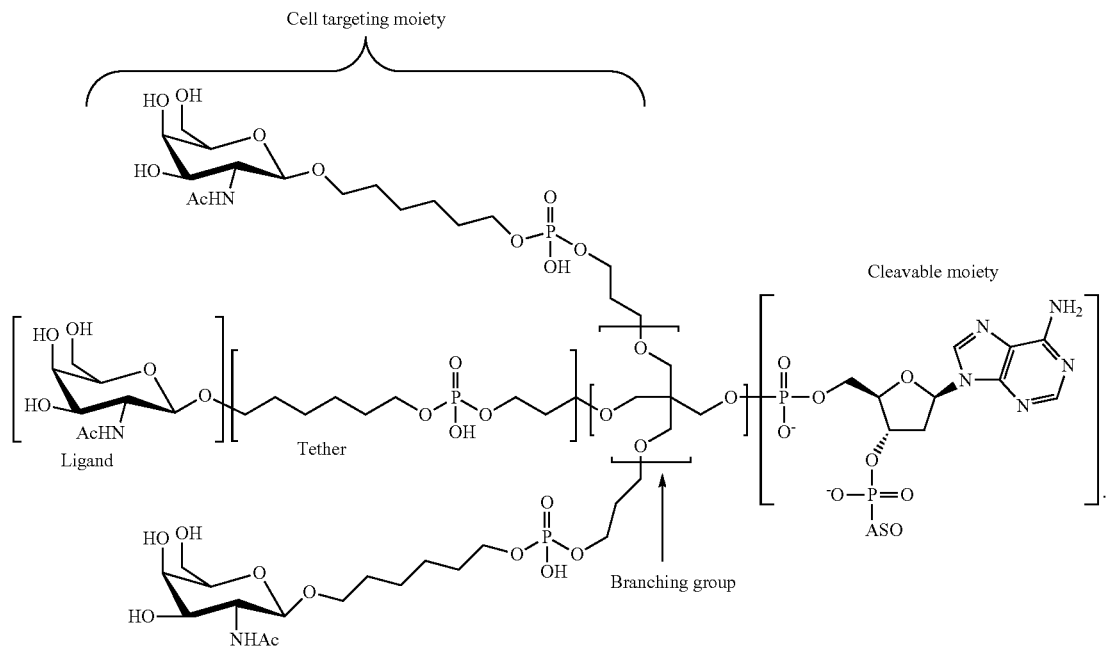
In certain embodiments, conjugated antisense compounds are provided having the structure:
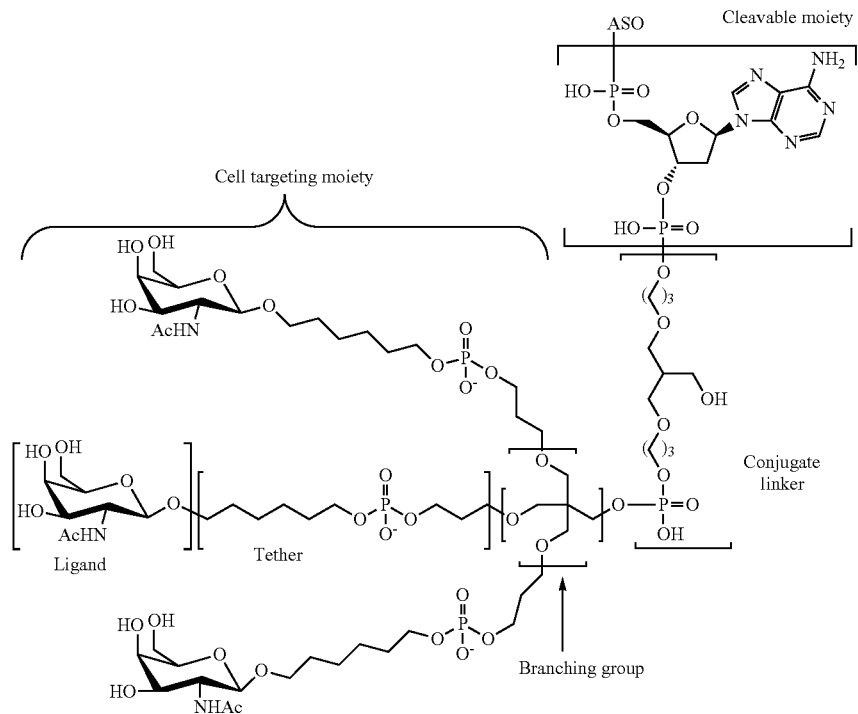

In certain embodiments, conjugated antisense compounds are provided having the structure:

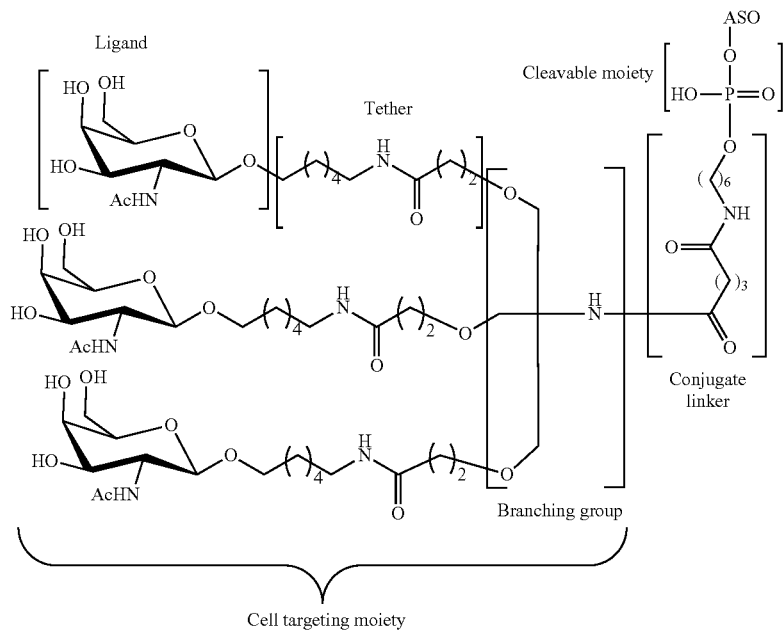

The present disclosure provides the following non-limiting numbered embodiments:

Embodiment 1. The conjugated antisense compound of any of embodiments 1179 to 1182, wherein the tether has a structure selected from among:

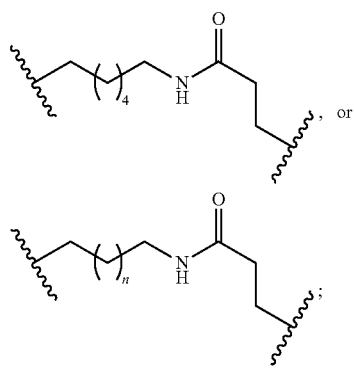

wherein each n is independently, 0, 1, 2, 3, 4, 5, 6, or 7.

Embodiment 2. The conjugated antisense compound of any of embodiments 1179 to 1182, wherein the tether has the structure:

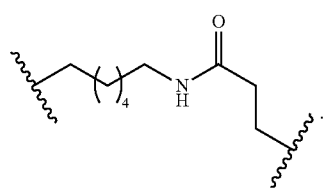

Embodiment 3. The conjugated antisense compound of any of embodiments 1179 to 1182 or 1688 to 1689, wherein the linker has a structure selected from among:

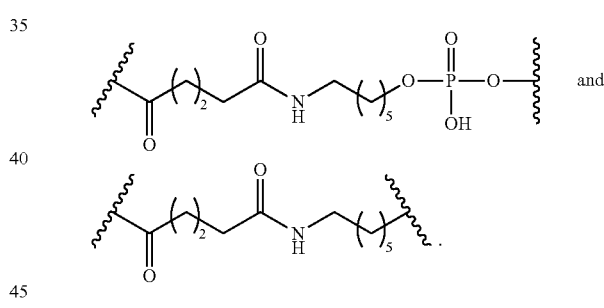

Embodiment 4. The conjugated antisense compound of any of embodiments 1179 to 1182 or 1688 to 1689, wherein the linker has a structure selected from among:

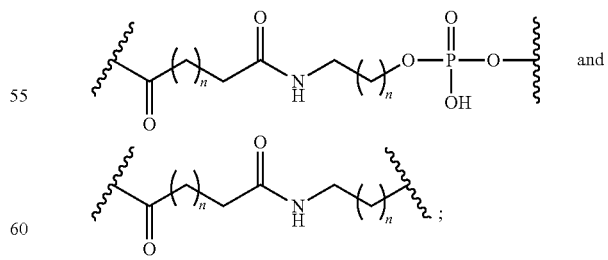

wherein each n is independently, 0, 1, 2, 3, 4, 5, 6, or 7.

Embodiment 5. The conjugated antisense compound of any of embodiments 1179 to 1182 or 1688 to 1689, wherein the linker has the structure:

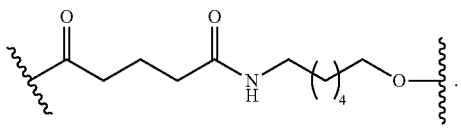

In embodiments having more than one of a particular variable (e.g., more than one "m" or "n"), unless otherwise indicated, each such particular variable is selected independently. Thus, for a structure having more than one n, each n is selected independently, so they may or may not be the same as one another.

DETAILED DESCRIPTION

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within +10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to PTP1B is an active pharmaceutical agent.

"Active target region" or "target region" means a region to which one or more active antisense compounds is targeted. "Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or inflammatory obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal "First Agent" means a therapeutic compound provided herein. For example, a first agent can be an antisense oligonucleotide targeting PTP1B. "Second agent" means a second therapeutic compound of the invention (e.g. a second antisense oligonucleotide targeting PTP1B) and/or a non-PTP1B therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Complementarity" means the capacity for pairing between nucleobases of a first nucleic acid and a second nucleic acid.

As used herein, "constrained ethyl nucleoside" or "cEt" means a nucleoside comprising a bicyclic sugar moiety comprising a 4'-CH($CH_3$)—O-2'bridge.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

As used herein, "furanosyl" means a structure comprising a 5-membered ring comprising four carbon atoms and one oxygen atom.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting an animal with metabolic" means identifying or selecting a subject having been diagnosed with a metabolic disease, or a metabolic disorder; or, identifying or selecting a subject having any symptom of a metabolic disease, including, but not limited to, metabolic syndrome, hyperglycemia, hypertriglyceridemia, hypertension increased insulin resistance, decreased insulin sensitivity, above normal body weight, and/or above normal body fat or any combination thereof. Such identification may be accomplished by any method, including but not limited to, standard clinical tests or assessments, such as measuring serum or circulating (plasma) blood-glucose, measuring serum or circulating (plasma) triglycerides, measuring blood-pressure, measuring body fat, measuring body weight, and the like.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

As used herein, "locked nucleic acid nucleoside" or "LNA" means a nucleoside comprising a bicyclic sugar moiety comprising a 4'-$CH_2$—O-2'bridge.

"Lipid-lowering therapy" or "lipid lowering agent" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-HDL-C, triglycerides, small dense LDL particles, and Lp(a) in a subject. Examples of lipid-lowering therapy include statins, fibrates, and MTP inhibitors.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disease" or "metabolic disorder" refers to a condition characterized by an alteration or disturbance in metabolic function. "Metabolic" and "metabolism" are terms well known in the art and generally include the whole range of biochemical processes that occur within a living organism. Metabolic diseases or disorders include, but are not limited to, obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

As used herein, "modified sugar moiety" means a substituted sugar moiety or a sugar surrogate.

As used herein, "MOE" means —OCH$_2$CH$_2$OCH$_3$.

"Motif" means the pattern of chemically distinct regions in an antisense compound.

"MTP inhibitor" means an agent inhibits the enzyme, microsomal triglyceride transfer protein.

"Naturally occurring internucleoside linkage" means a 3' to 5' phosphodiester linkage.

As used herein, "naturally occurring sugar moiety" means a ribofuranosyl as found in naturally occurring RNA or a deoxyribofuranosyl as found in naturally occurring DNA.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines "Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid. As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

"Nucleobase sequence" means the order of contiguous nucleobases independent of any sugar, linkage, or nucleobase modification.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside. As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to PTP1B is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Protein tyrosine phosphatase 1B" or "PTP1B" (also known as PTPN1; protein tyrosine phosphatase, non-receptor type 1; PTP-1B; RKPTP) means any nucleic acid or protein of PTP1B.

"PTP1B expression" means the level of mRNA transcribed from the gene encoding PTP or the level of protein translated from the mRNA. PTP1B expression can be determined by art known methods such as a Northern or Western blot.

"PTP1B nucleic acid" means any nucleic acid encoding PTP1B. For example, in certain embodiments, a PTP1B nucleic acid includes a DNA sequence encoding PTP1B, a RNA sequence transcribed from DNA encoding PTP1B (including genomic DNA comprising introns and exons), and a mRNA sequence encoding PTP1B. "PTP1B mRNA" means a mRNA encoding a PTP1B protein.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

As used herein, "sugar moiety" means a naturally occurring sugar moiety or a modified sugar moiety of a nucleoside.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates may also include more complex sugar replacements (e.g., the non-ring systems of peptide nucleic acid). Sugar surrogates include without limitation morpholines, cyclohexenyls and cyclohexitols.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to an animal to effect an alteration or improvement of a disease, disorder, or condition.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom. Phosphorus linking groups include without limitation groups having the formula:

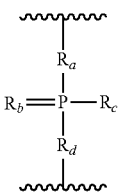

wherein:
$R_a$ and $R_d$ are each, independently, O, S, $CH_2$, NH, or $NJ_1$ wherein $J_1$ is $C_1$-$C_6$ alkyl or substituted $C_1$-$C_6$ alkyl;
$R_b$ is O or S;
$R_c$ is OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$J_1$ is $R_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI (—$CH_2$—N($CH_3$)—O—), amide-3 (—$CH_2$—C(=O)—N(H)—), amide-4 (—$CH_2$—N(H)—C(=O)—), formacetal (—O—$CH_2$—O—), and thioformacetal (—S—$CH_2$—O—). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and $CH_2$ component parts.

As used herein, "internucleoside neutral linking group" means a neutral linking group that directly links two nucleosides.

As used herein, "non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites. In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "GalNAc$_3$". In certain embodiments, the carbohydrate cluster portion comprises 4 GalNAc groups and is designated "GalNAc$_4$". Specific carbohydrate cluster portions (having specific tether, branching and conjugate linker groups) are described herein and designated by Roman numeral followed by subscript "a". Accordingly "GalNac3-1," refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

As used herein, "cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

As used herein, "cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

As used herein, "carbohydrate cluster" means a compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

As used herein "protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

As used herein, "single-stranded" means an oligomeric compound that is not hybridized to its complement and which lacks sufficient self-complementarity to form a stable self-duplex.

As used herein, "double stranded" means a pair of oligomeric compounds that are hybridized to one another or a single self-complementary oligomeric compound that forms a hairpin structure. In certain embodiments, a double-stranded oligomeric compound comprises a first and a second oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity includes modulation of the amount or activity of a target nucleic acid transcript (e.g.

mRNA). In certain embodiments, antisense activity includes modulation of the splicing of pre-mRNA.

As used herein, "RNase H based antisense compound" means an antisense compound wherein at least some of the antisense activity of the antisense compound is attributable to hybridization of the antisense compound to a target nucleic acid and subsequent cleavage of the target nucleic acid by RNase H.

As used herein, "RISC based antisense compound" means an antisense compound wherein at least some of the antisense activity of the antisense compound is attributable to the RNA Induced Silencing Complex (RISC).

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize to result in a desired antisense activity. Antisense oligonucleotides have sufficient complementarity to their target nucleic acids to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein the term "metabolic disorder" means a disease or condition principally characterized by dysregulation of metabolism—the complex set of chemical reactions associated with breakdown of food to produce energy.

As used herein, the term "cardiovascular disorder" means a disease or condition principally characterized by impaired function of the heart or blood vessels.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein, "prodrug" means an inactive or less active form of a compound which, when administered to a subject, is metabolized to form the active, or more active, compound (e.g., drug).

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(═N$R_{bb}$)N($R_{bb}$)($R_{cc}$)), amidinyl (—C(═N$R_{bb}$)N($R_{bb}$)($R_{cc}$) or —N($R_{bb}$)C(═N$R_{bb}$)($R_{aa}$)), thiol (—S$R_{bb}$), sulfinyl (—S(O)$R_{bb}$), sulfonyl (—S(O)$_2$$R_{bb}$) and sulfonamidyl (—S(O)$_2$N($R_{bb}$)($R_{cc}$) or —N($R_{bb}$)S—(O)$_2$$R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "conjugate compound" means any atoms, group of atoms, or group of linked atoms suitable for use as a conjugate group. In certain embodiments, conjugate compounds may possess or impart one or more properties, including, but not limited to pharmacodynamic, pharmacokinetic, binding, absorption, cellular distribution, cellular uptake, charge and/or clearance properties.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

B. Certain Compounds

In certain embodiments, the invention provides conjugated antisense compounds comprising antisense oligonucleotides and a conjugate.

a. Certain Antisense Oligonucleotides

In certain embodiments, the invention provides antisense oligonucleotides. Such antisense oligonucleotides comprise linked nucleosides, each nucleoside comprising a sugar moiety and a nucleobase. The structure of such antisense oligonucleotides may be considered in terms of chemical features (e.g., modifications and patterns of modifications) and nucleobase sequence (e.g., sequence of antisense oligonucleotide, identify and sequence of target nucleic acid).

i. Certain Chemistry Features

In certain embodiments, antisense oligonucleotide comprise one or more modification. In certain such embodiments, antisense oligonucleotides comprise one or more modified nucleosides and/or modified internucleoside linkages. In certain embodiments, modified nucleosides comprise a modified sugar moiety and/or modified nucleobase.

1. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$O CH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH (CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., J. Org. Chem., 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-$CH(CH_3)$—O-2') BNA (also referred to as constrained ethyl or cEt), (G) methylene-thio (4'-$CH_2$—S-2') BNA, (H) methylene-amino (4'-CH2-N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

(A)
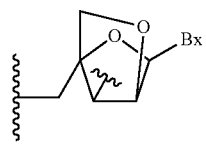

(B)
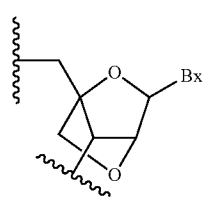

(C)
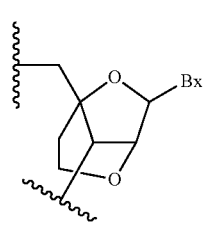

(D)
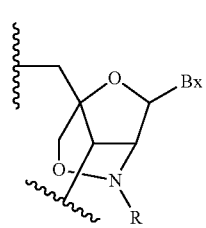

(E)
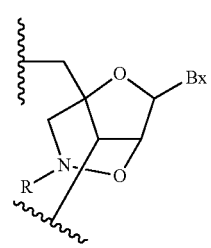

(F)
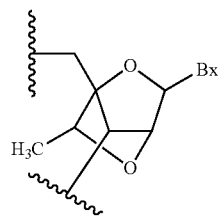

(G)
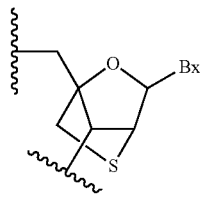

(H)
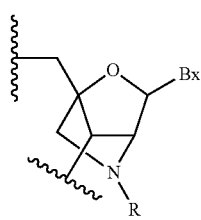

(I)
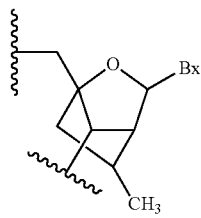

(J)
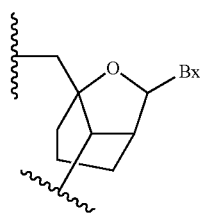

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. No. 12/129,154, U.S. Provisional Applications 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a morpholino. Morpholino compounds and their use in oligomeric compounds has been reported in numerous patents and published articles (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following structure:

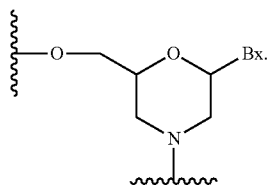

In certain embodiments, morpholinos may be modified, for example by adding or altering various substituent groups from the above morpholino structure. Such sugar surrogates are referred to herein as "modified morpholinos."

For another example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VI:

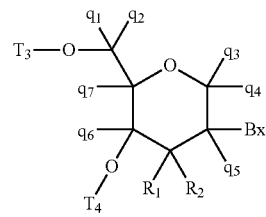

wherein independently for each of said at least one tetrahydropyran nucleoside analog of Formula VI:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VI are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

2. Certain Nucleobase Modifications

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

3. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (PO), phosphotriesters, methylphosphonates, phosphoramidate, and phosphorothioates (PS). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

4. Certain Motifs

In certain embodiments, antisense oligonucleotides comprise one or more modified nucleoside (e.g., nucleoside comprising a modified sugar and/or modified nucleobase) and/or one or more modified internucleoside linkage. The pattern of such modifications on an oligonucleotide is referred to herein as a motif. In certain embodiments, sugar, nucleobase, and linkage motifs are independent of one another.

a. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain 5'-Wings

In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

ii. Certain 3'-Wings

In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

iii. Certain Central Regions (gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleotides and a stretch of one or more interrupting modified nucleosides). In certain embodiments, no stretch of unmodified 2'-deoxynucleotides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

b. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 7 phosphorothioate internucleoside linkages. In certain embodiments, the oligonucleotide comprises at least 8 phosphorothioate internucleoside linkages. In certain embodiments, the oligonucleotide comprises at least 9 phosphorothioate internucleoside linkages. In certain embodiments, the oligonucleotide comprises at least 10 phosphorothioate internucleoside linkages. In certain embodiments, the oligonucleotide comprises at least 11 phosphorothioate internucleoside linkages. In certain embodiments, the oligonucleotide comprises at least 12 phosphorothioate internucleoside linkages. In certain embodiments, the oligonucleotide comprises at least 13 phosphorothioate internucleoside linkages. In certain embodiments, the oligonucleotide comprises at least 14 phosphorothioate internucleoside linkages.

In certain embodiments, the oligonucleotide comprises at least one block of at least 6 consecutive phosphorothioate internucleoside linkages. In certain embodiments, the oligonucleotide comprises at least one block of at least 7 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 9 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide. In certain embodiments, the oligonucleotide comprises less than 15 phosphorothioate internucleoside linkages. In certain embodiments, the oligonucleotide comprises less than 14 phosphorothioate internucleoside linkages. In certain embodiments, the oligonucleotide comprises less than 13 phosphorothioate internucleoside linkages. In certain embodiments, the oligonucleotide comprises less than 12 phosphorothioate internucleoside linkages. In certain embodiments, the oligonucleotide comprises less than 11 phosphorothioate internucleoside linkages. In certain embodiments, the oligonucleotide comprises less than 10 phosphorothioate internucleoside linkages. In certain embodiments, the oligonucleotide comprises less than 9 phosphorothioate internucleoside linkages. In certain embodiments, the oligonucleotide comprises less than 8 phosphorothioate internucleoside linkages. In certain embodiments, the oligonucleotide comprises less than 7 phosphorothioate internucleoside linkages. In certain embodiments, the oligonucleotide comprises less than 6 phosphorothioate internucleoside linkages. In certain embodiments, the oligonucleotide comprises less than 5 phosphorothioate internucleoside linkages.

c. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

In certain embodiments, chemical modifications to nucleobases comprise attachment of certain conjugate groups to nucleobases. In certain embodiments, each purine or each pyrimidine in an oligonucleotide may be optionally modified to comprise a conjugate group.

d. Certain Overall Lengths

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

5. Certain Antisense Oligonucleotide Chemistry Motifs

In certain embodiments, the chemical structural features of antisense oligonucleotides are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides.

In certain embodiments, the selection of internucleoside linkage and nucleoside modification are not independent of one another.

i. Certain Sequences and Targets

In certain embodiments, the invention provides antisense oligonucleotides having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessibility of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

In certain embodiments, a conjugate group comprises a cleavable moiety. In certain embodiments, a conjugate group comprises one or more cleavable bond. In certain embodiments, a conjugate group comprises a linker. In certain embodiments, a linker comprises a protein binding moiety. In certain embodiments, a conjugate group comprises a cell-targeting moiety (also referred to as a cell-targeting group). In certain embodiments a cell-targeting moiety comprises a branching group. In certain embodiments, a cell-targeting moiety comprises one or more tethers. In certain embodiments, a cell-targeting moiety comprises a carbohydrate or carbohydrate cluster.

ii. Certain Cleavable Moieties

In certain embodiments, a cleavable moiety is a cleavable bond. In certain embodiments, a cleavable moiety comprises a cleavable bond. In certain embodiments, the conjugate group comprises a cleavable moiety. In certain such embodiments, the cleavable moiety attaches to the antisense oligonucleotide. In certain such embodiments, the cleavable moiety attaches directly to the cell-targeting moiety. In certain such embodiments, the cleavable moiety attaches to the conjugate linker. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, the cleavable moiety is cleaved after the complex has been administered to an animal only after being internalized by a targeted cell. Inside the cell the cleavable moiety is cleaved thereby releasing the active antisense oligonucleotide. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

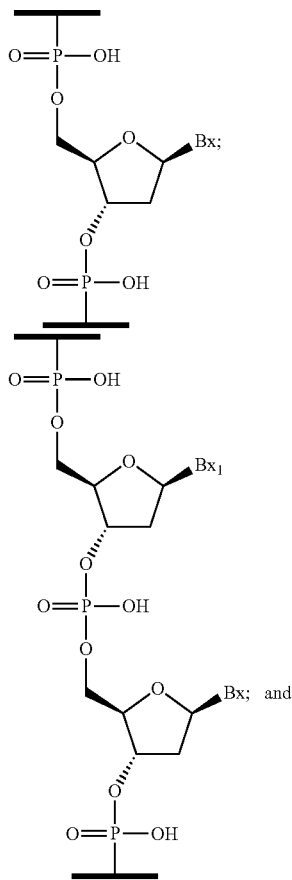

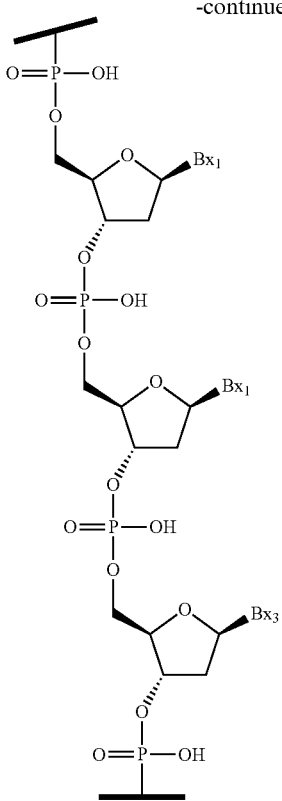

wherein each of Bx, Bx$_1$, Bx$_2$, and Bx$_3$ is independently a heterocyclic base moiety. In certain embodiments, the cleavable moiety has a structure selected from among the following:

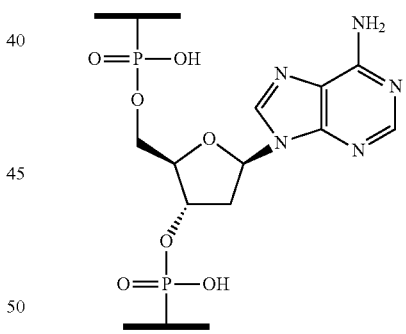

iii. Certain Linkers

In certain embodiments, the conjugate groups comprise a linker. In certain such embodiments, the linker is covalently bound to the cleavable moiety. In certain such embodiments, the linker is covalently bound to the antisense oligonucleotide. In certain embodiments, the linker is covalently bound to a cell-targeting moiety. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker includes multiple positions for attachment of tethered ligands and is not attached to a branching group. In certain embodiments, the linker further comprises one or more cleavable bond. In certain embodiments, the conjugate group does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl.

In certain embodiments, a linker has a structure selected from among:

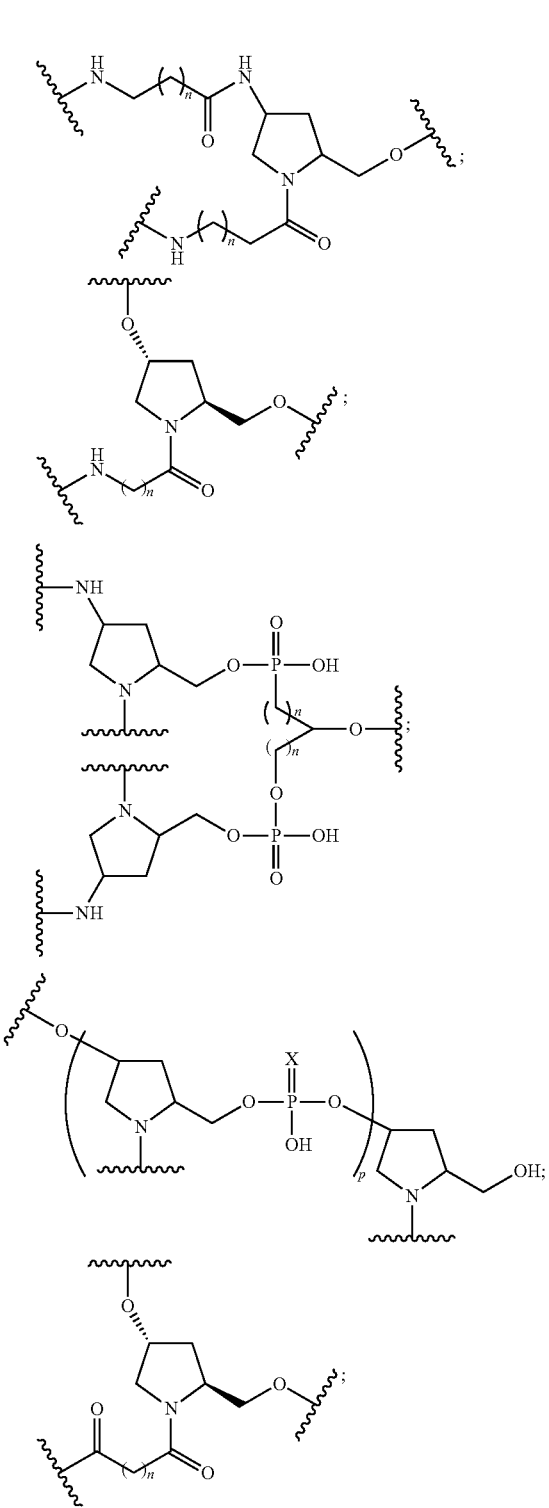

53
-continued
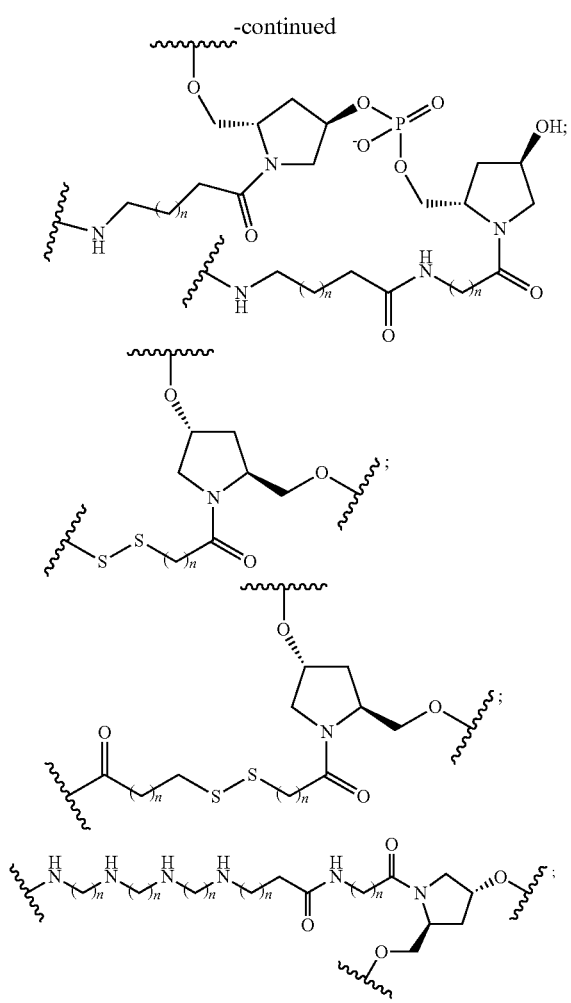
54
-continued
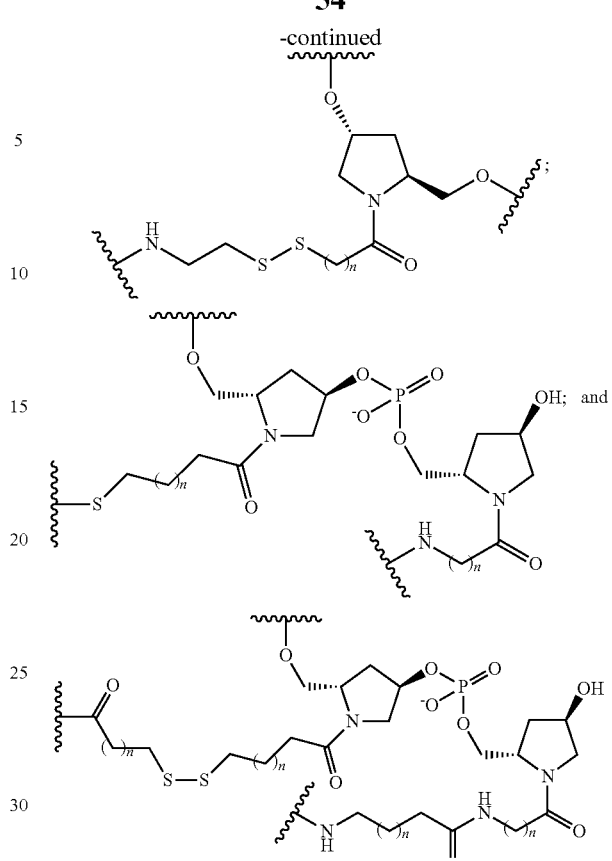
wherein each n is, independently, from 1 to 20; and p is from 1 to 6.
In certain embodiments, a linker has a structure selected from among:
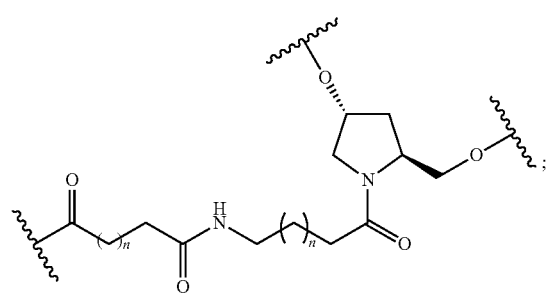
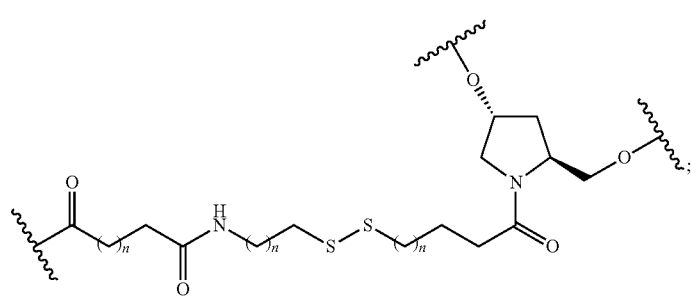

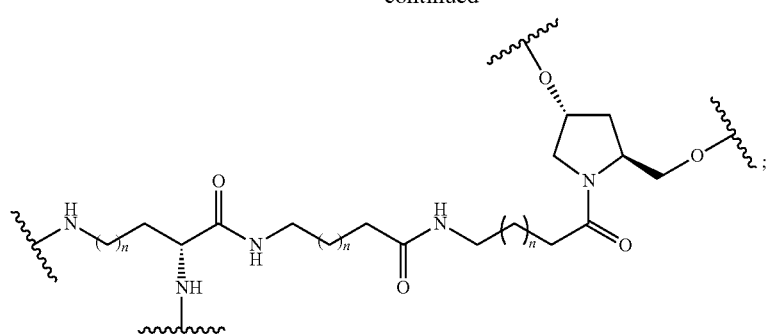
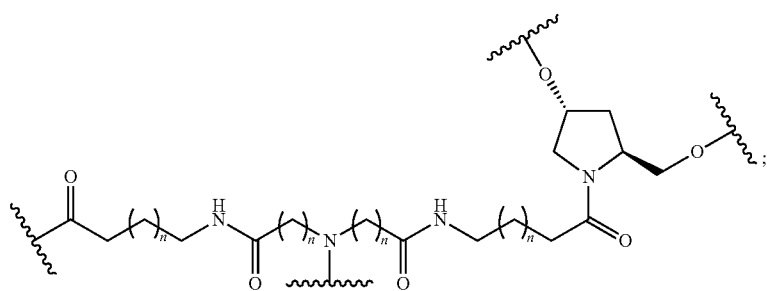
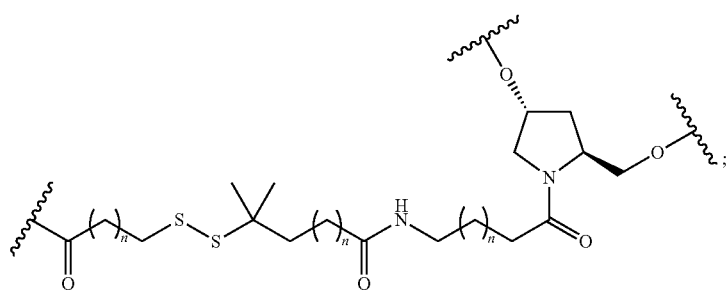
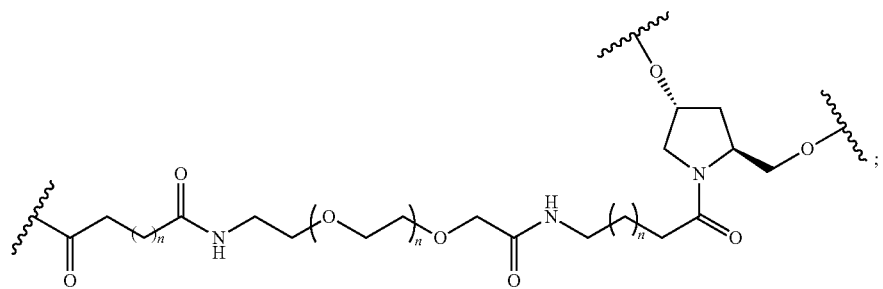
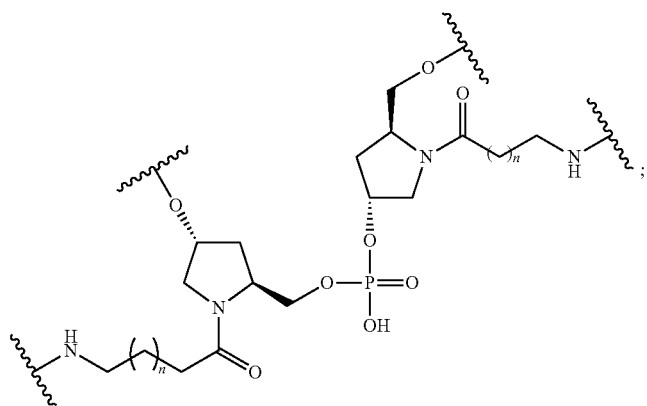

-continued
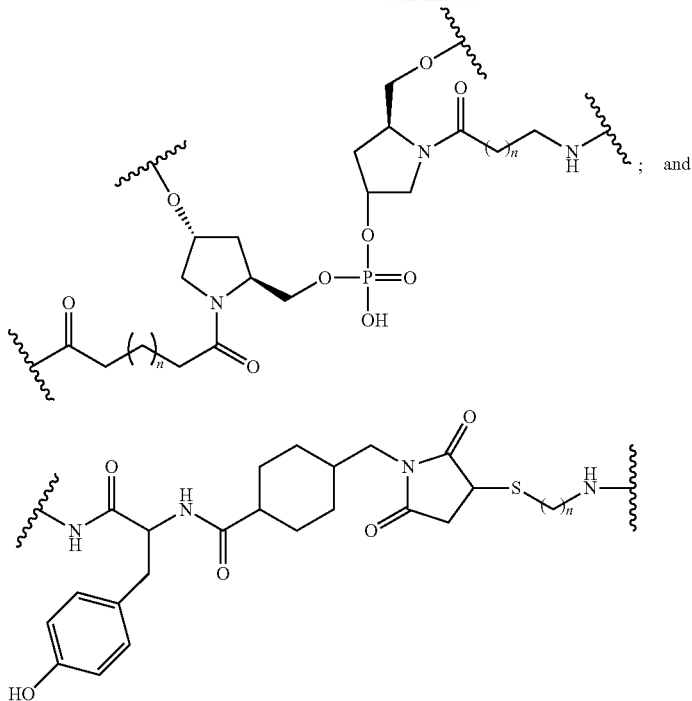
wherein each n is, independently, from 1 to 20.
In certain embodiments, a linker has a structure selected from among:
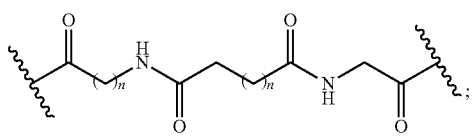
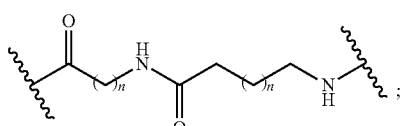
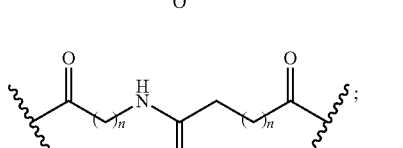
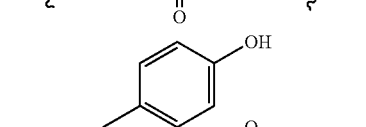
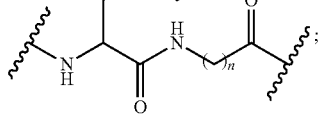
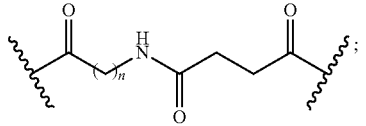
-continued
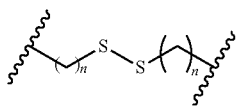
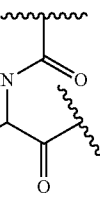
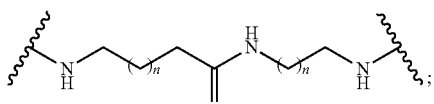
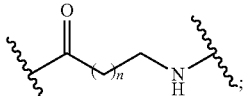
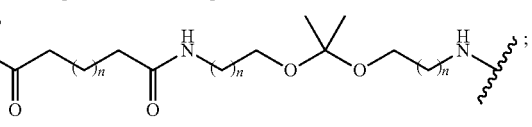
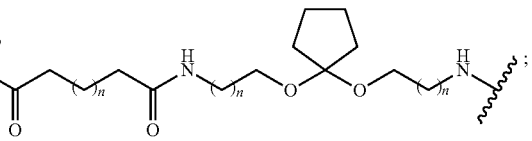
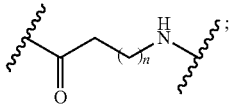

wherein n is from 1 to 20.

In certain embodiments, a linker has a structure selected from among:

wherein each L is, independently, a phosphorus linking group or a neutral linking group; and each n is, independently, from 1 to 20.

In certain embodiments, a linker has a structure selected from among:

61
-continued
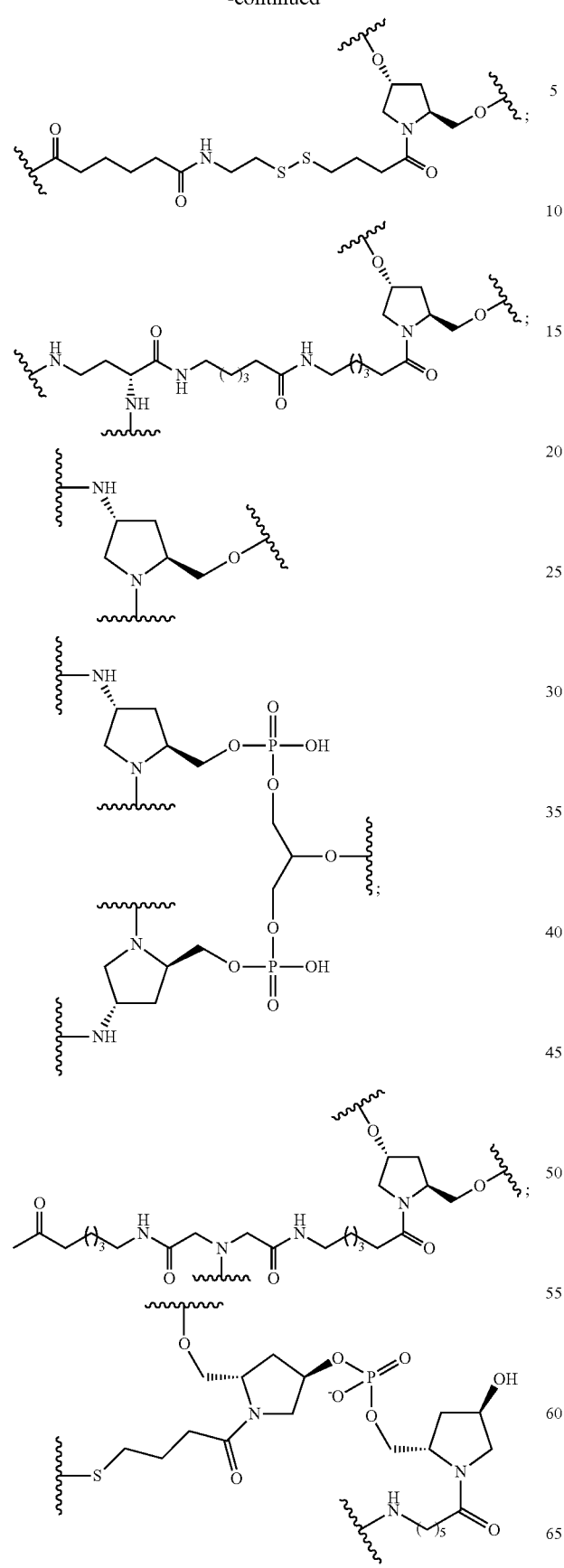
62
-continued
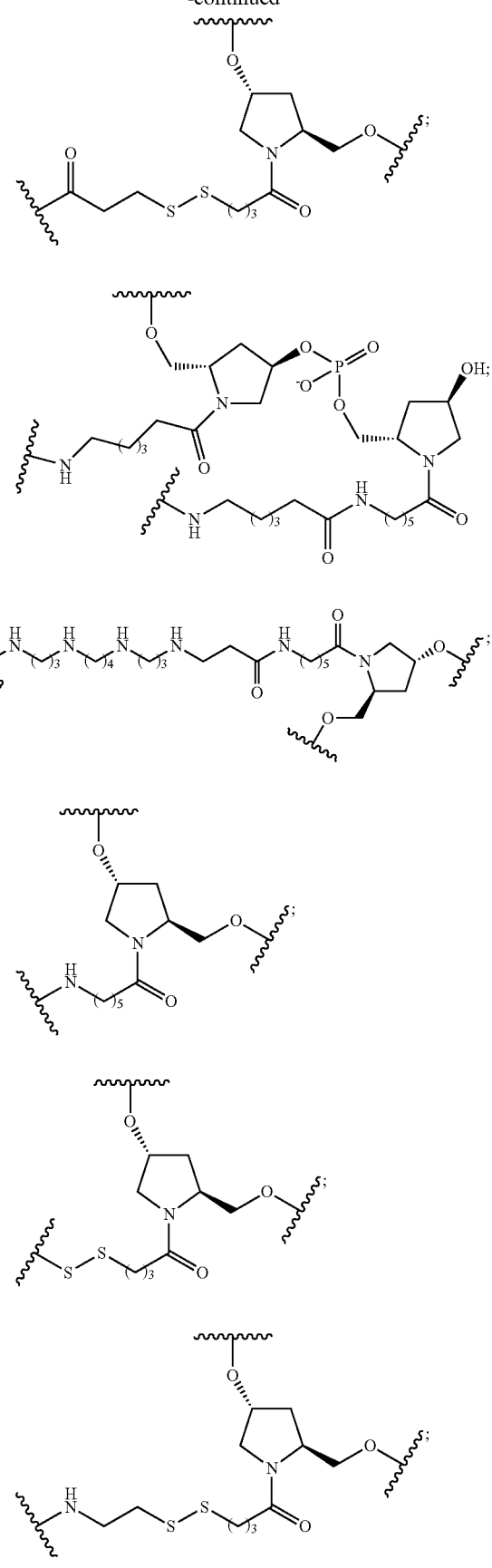

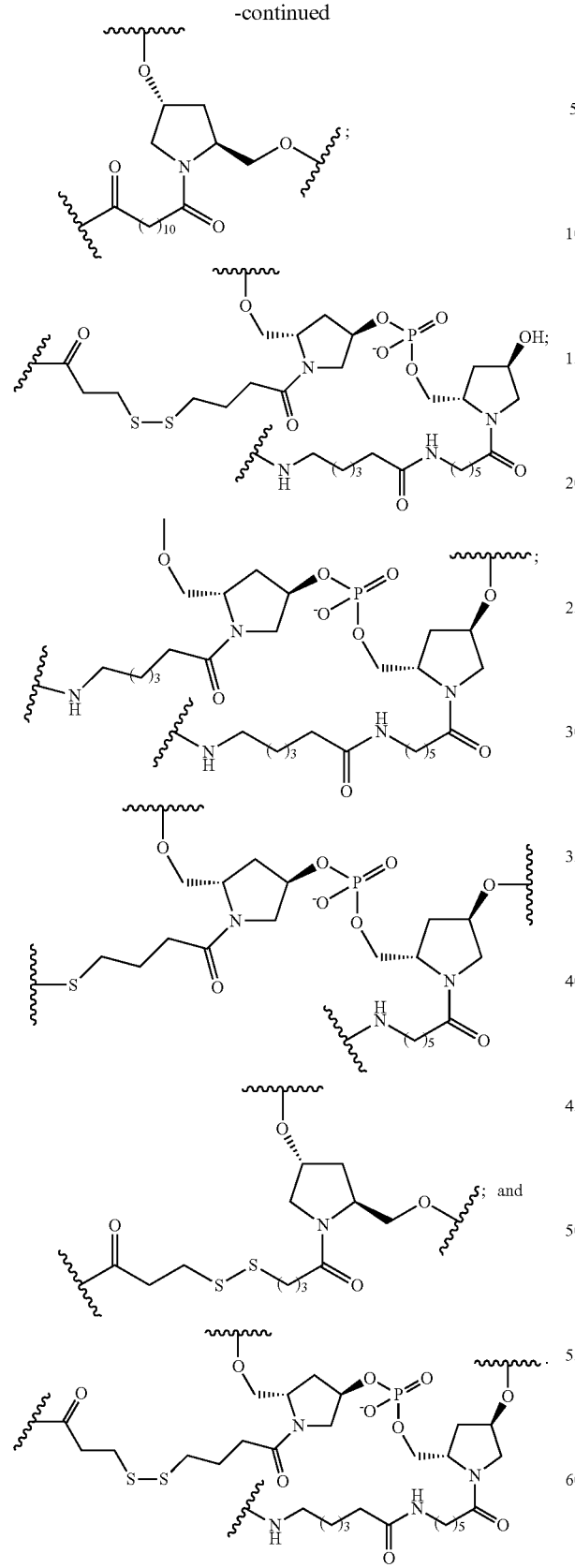
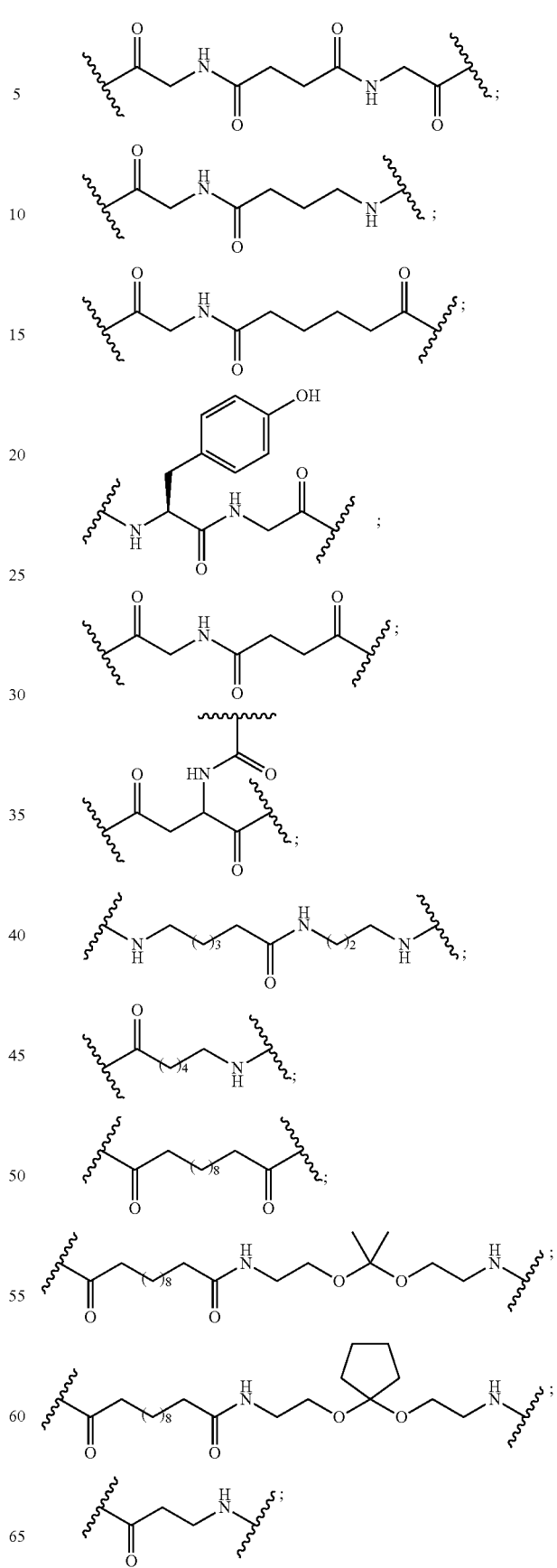
In certain embodiments, a linker has a structure selected from among:

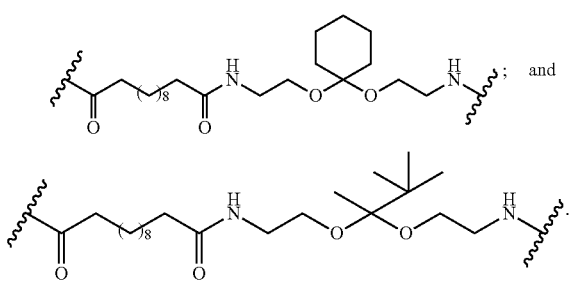
In certain embodiments, a linker has a structure selected from among:
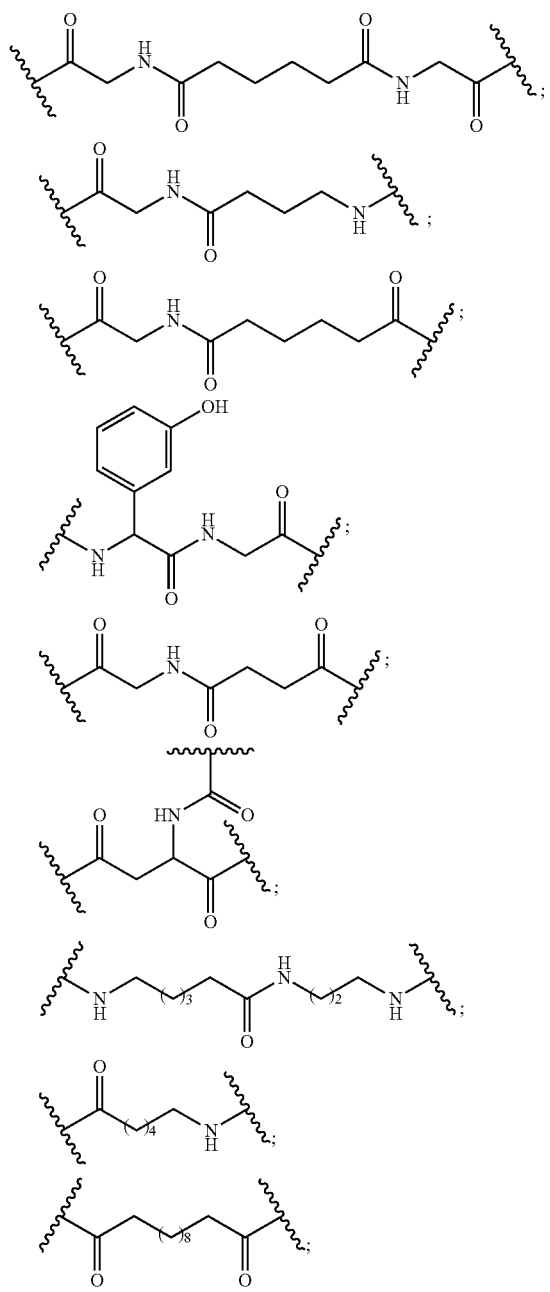
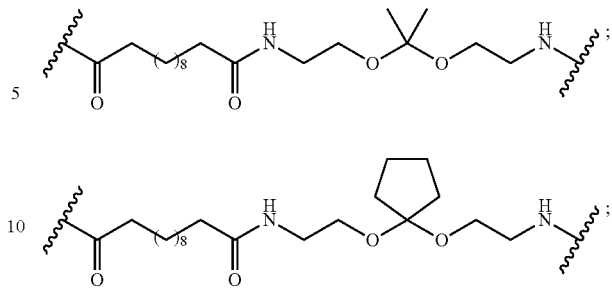
In certain embodiments, a linker has a structure selected from among:

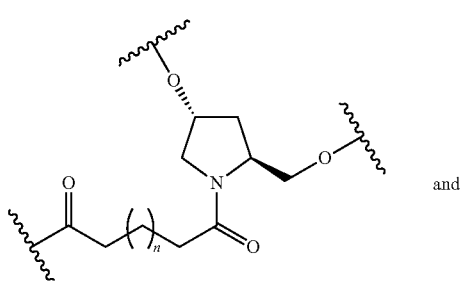

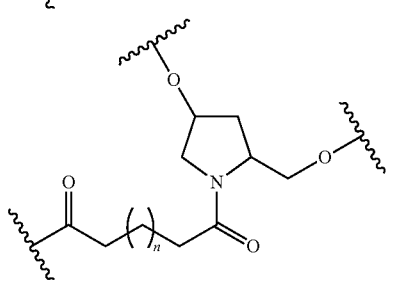

and wherein n is from 1 to 20.

In certain embodiments, a linker has a structure selected from among:

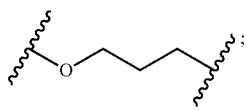;

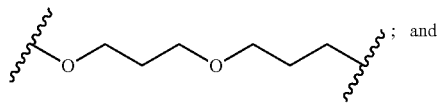; and

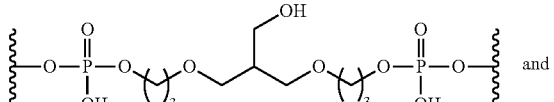.

In certain embodiments, a linker has a structure selected from among:

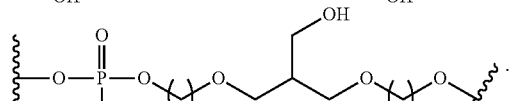 and

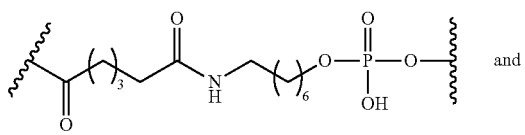.

In certain embodiments, a linker has a structure selected from among:

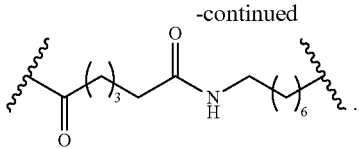 and

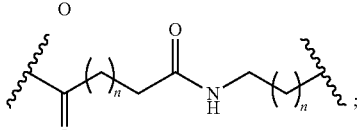.

In certain embodiments, the conjugate linker has the structure:

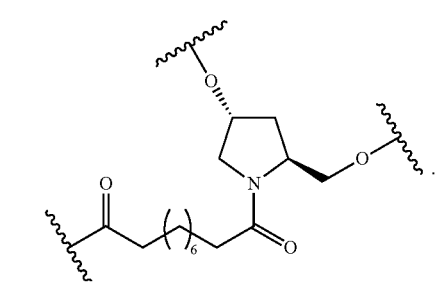.

In certain embodiments, the conjugate linker has the structure:

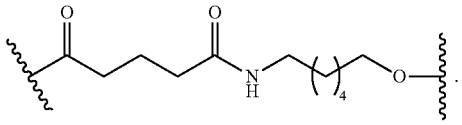.

In certain embodiments, a linker has a structure selected from among:

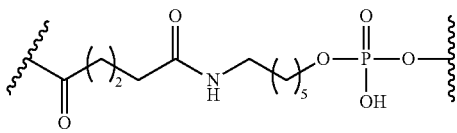 and

In certain embodiments, a linker has a structure selected from among:

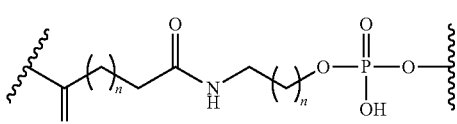 and wherein each n is independently, 0, 1, 2, 3, 4, 5, 6, or 7.

iv. Certain Cell-Targeting Moieties

In certain embodiments, conjugate groups comprise cell-targeting moieties. Certain such cell-targeting moieties increase cellular uptake of antisense compounds. In certain embodiments, cell-targeting moieties comprise a branching group, one or more tether, and one or more ligand. In certain embodiments, cell-targeting moieties comprise a branching group, one or more tether, one or more ligand and one or more cleavable bond.

1. Certain Branching Groups

In certain embodiments, the conjugate groups comprise a targeting moiety comprising a branching group and at least two tethered ligands. In certain embodiments, the branching group attaches the conjugate linker. In certain embodiments, the branching group attaches the cleavable moiety. In certain embodiments, the branching group attaches the antisense oligonucleotide. In certain embodiments, the branching group is covalently attached to the linker and each of the tethered ligands. In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the conjugate group does not include a branching group.

In certain embodiments, a branching group has a structure selected from among:

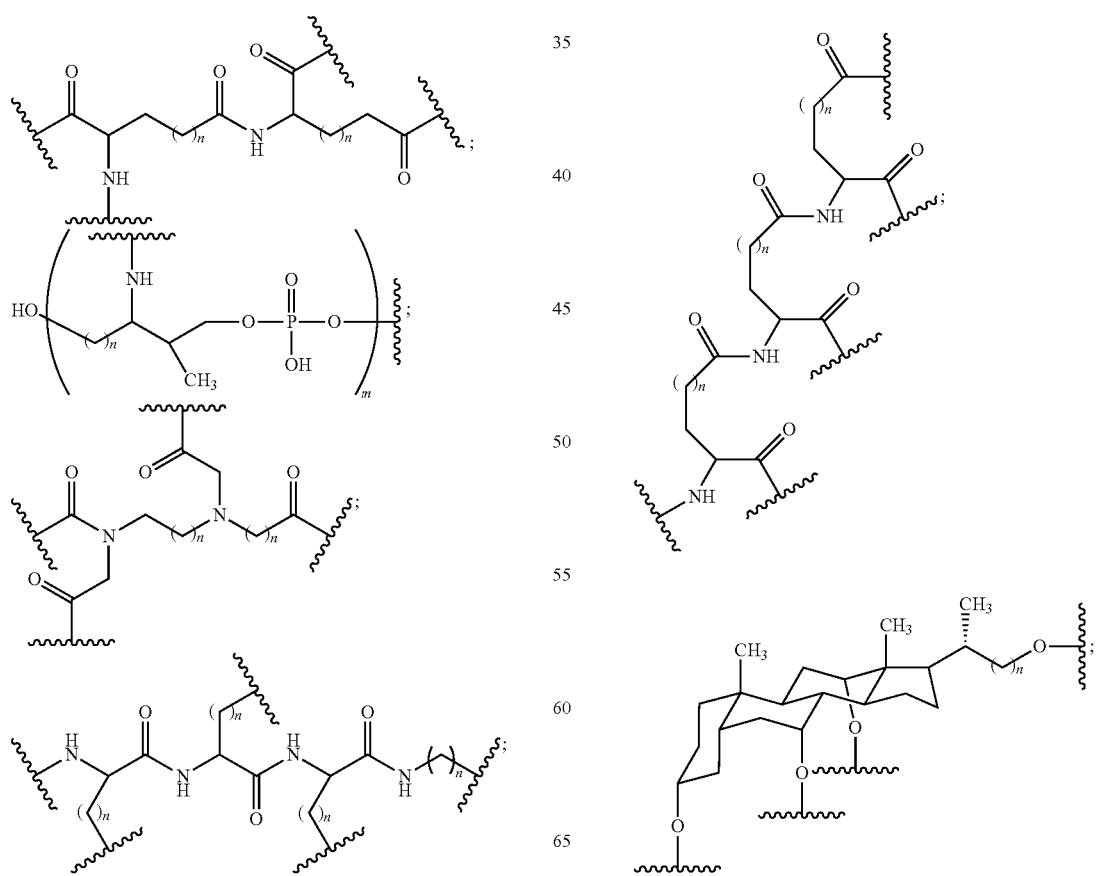

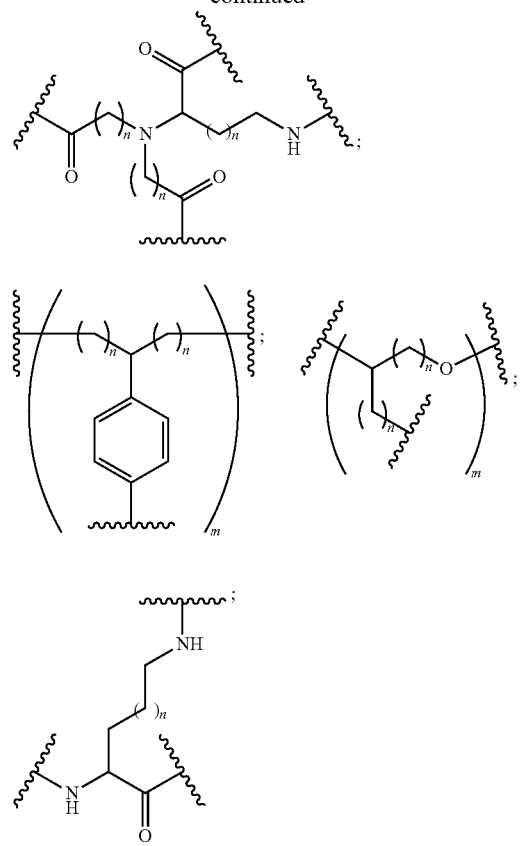

-continued
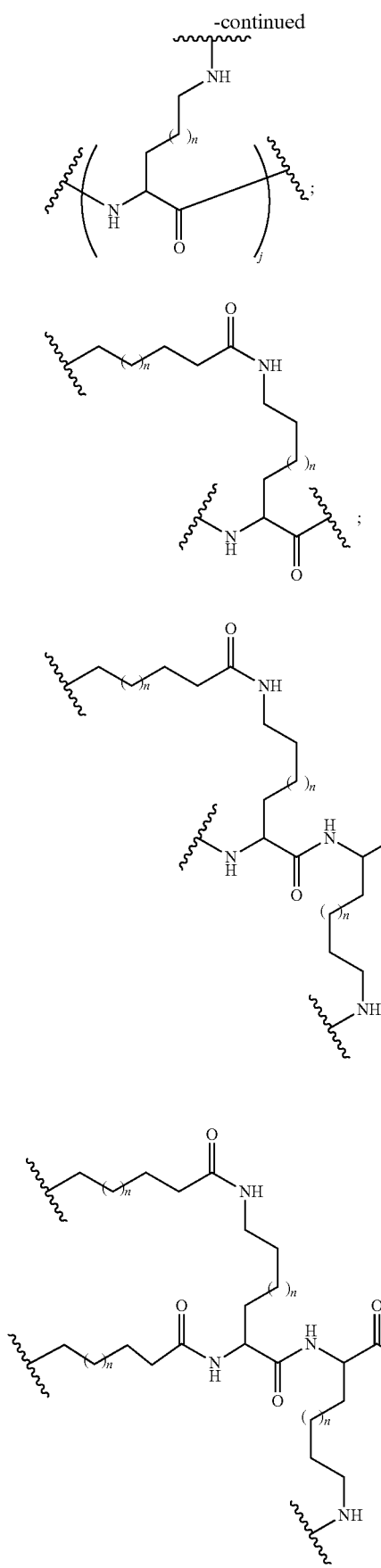
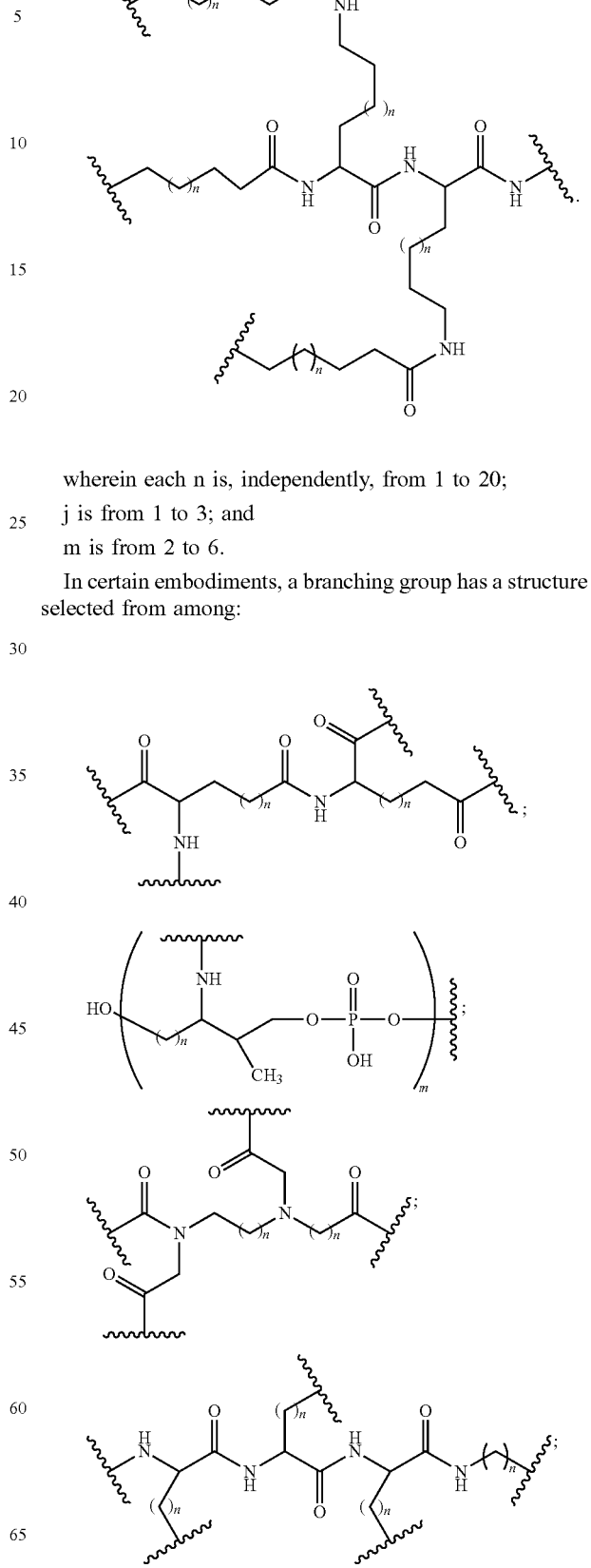
wherein each n is, independently, from 1 to 20;
j is from 1 to 3; and
m is from 2 to 6.
In certain embodiments, a branching group has a structure selected from among:

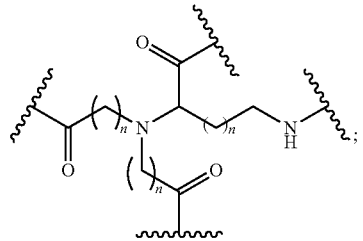
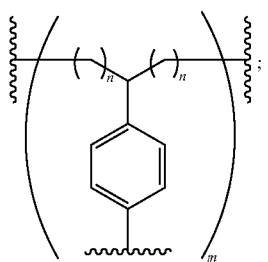 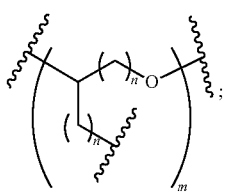
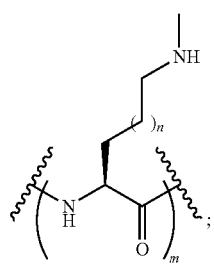
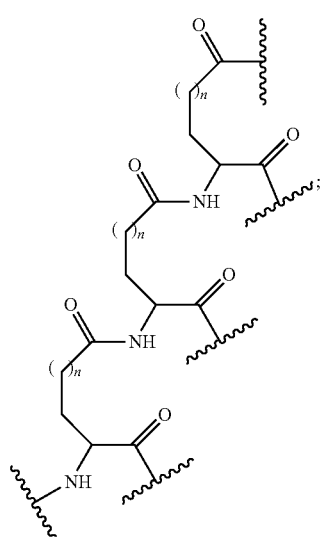
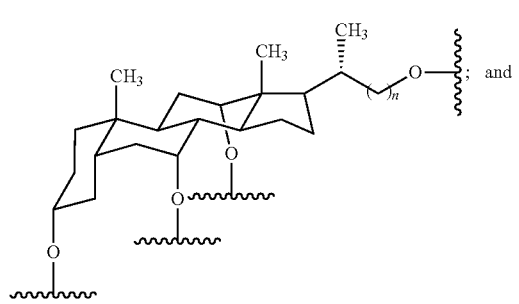
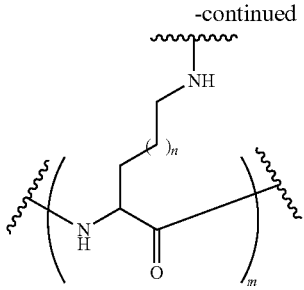
wherein each n is, independently, from 1 to 20; and m is from 2 to 6.
In certain embodiments, a branching group has a structure selected from among:
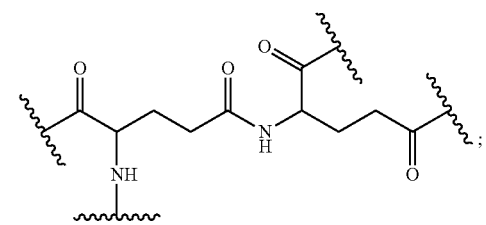
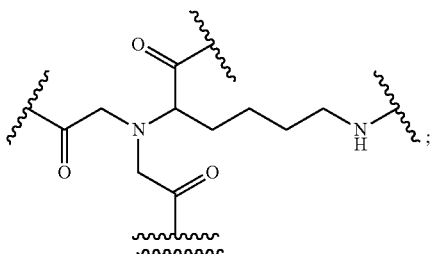
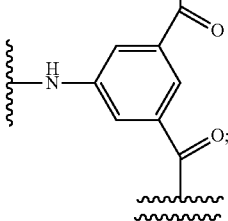
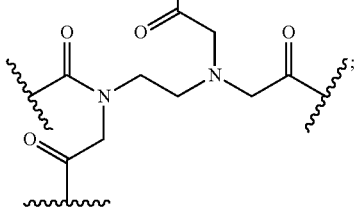
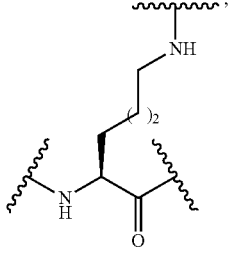

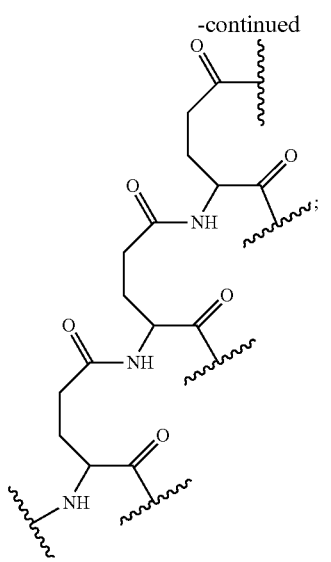
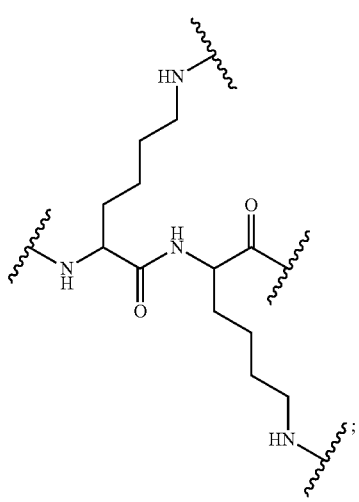
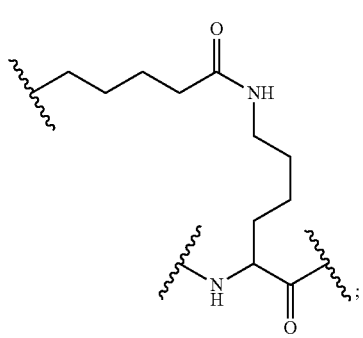
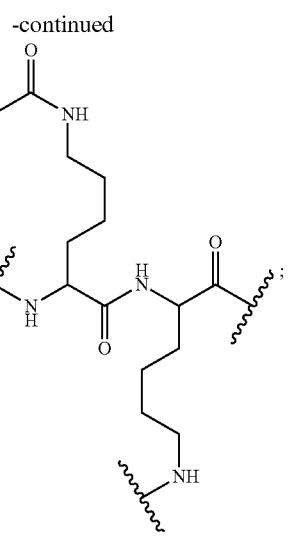
In certain embodiments, a branching group has a structure selected from among:

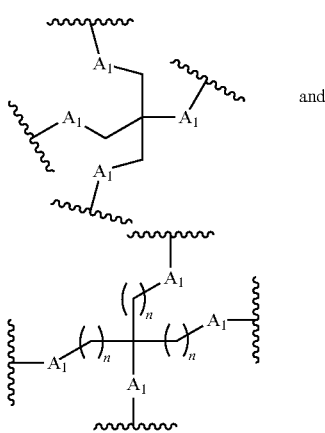

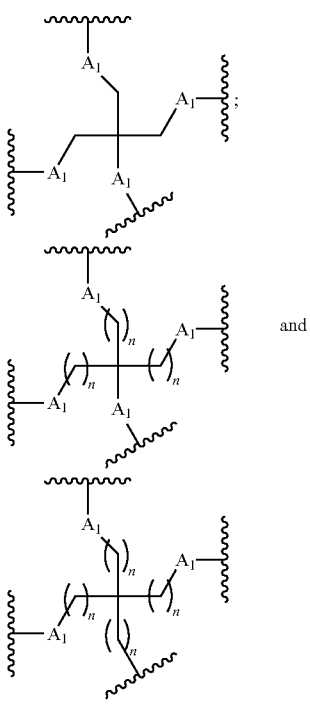

wherein each $A_1$ is independently, O, S, C=O or NH; and each n is, independently, from 1 to 20.

In certain embodiments, a branching group has a structure selected from among:

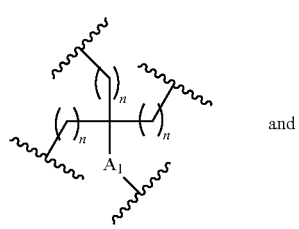

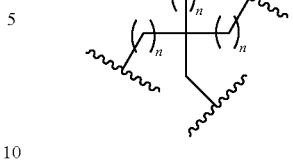

wherein $A_1$ is O, S, C=O or NH; and
each n is, independently, from 1 to 20.

In certain embodiments, a branching group has a structure selected from among:

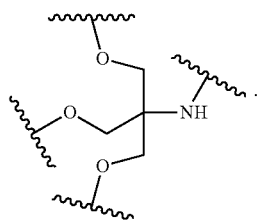 [SMILES: *NC(CO*)(CO*)CO*]

In certain embodiments, a branching group has a structure selected from among:

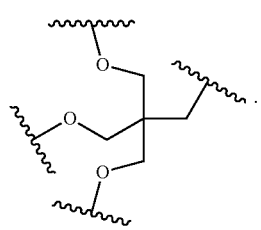 [SMILES: *CC(CO*)(CO*)CO*]

In certain embodiments, a branching group has a structure selected from among:

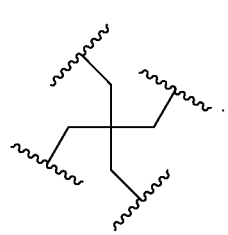 [SMILES: *CC(C*)(C*)C*]

2. Certain Tethers

In certain embodiments, conjugate groups comprise one or more tethers covalently attached to the branching group. In certain embodiments, conjugate groups comprise one or more tethers covalently attached to the linking group. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

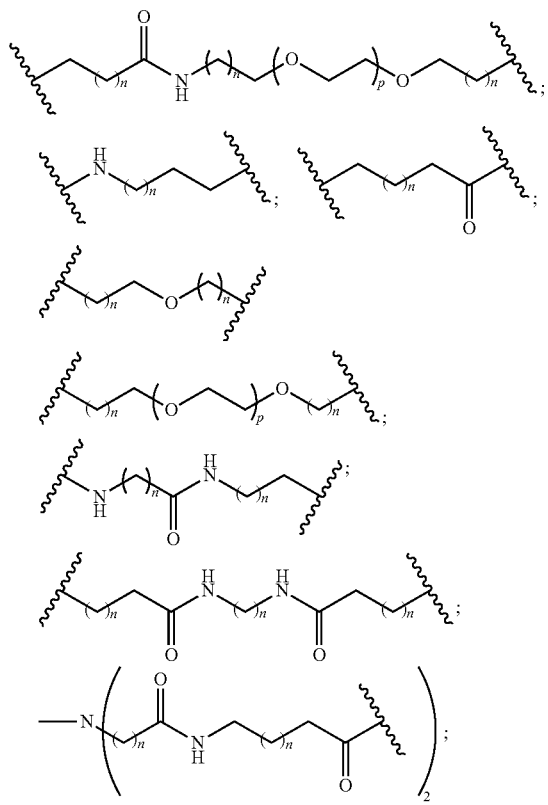

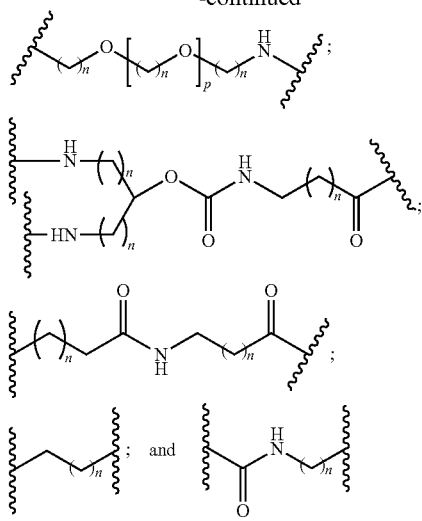

wherein each n is, independently, from 1 to 20; and each p is from 1 to about 6.

In certain embodiments, a tether has a structure selected from among:

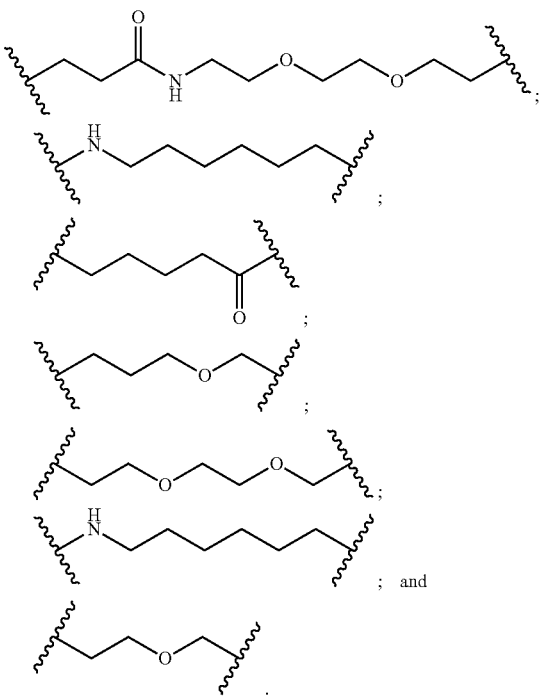

In certain embodiments, a tether has a structure selected from among:

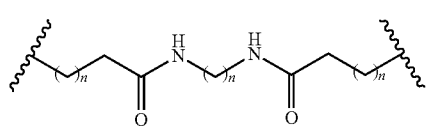

wherein each n is, independently, from 1 to 20.

In certain embodiments, a tether has a structure selected from among:

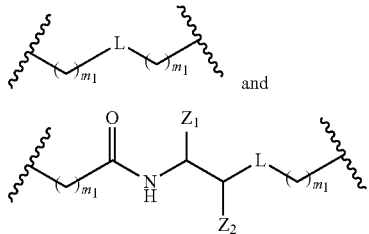

and wherein L is either a phosphorus linking group or a neutral linking group;

$Z_1$ is $C(=O)O—R_2$ $Z_2$ is H, $C_1$-$C_6$ alkyl or substituted $C_1$-$C_6$ alkyl;

$R_2$ is H, $C_1$-$C_6$ alkyl or substituted $C_1$-$C_6$ alkyl; and each $m_1$ is, independently, from 0 to 20 wherein at least one $m_1$ is greater than 0 for each tether.

In certain embodiments, a tether has a structure selected from among:

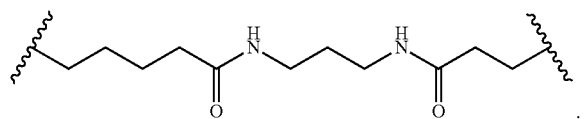 [SMILES: *CCCCC(=O)NCCCNC(=O)CC*]

In certain embodiments, a tether has a structure selected from among:

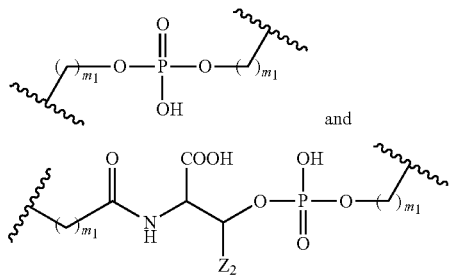

wherein $Z_2$ is H or $CH_3$; and each $m_1$ is, independently, from 0 to 20 wherein at least one $m_1$ is greater than 0 for each tether.

In certain embodiments, a tether has a structure selected from among:

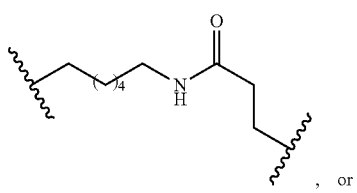

, or

;

wherein each n is independently, 0, 1, 2, 3, 4, 5, 6, or 7.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Ligands

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, "GalNac" or "Gal-NAc" refers to 2-(Acetylamino)-2-deoxy-D-galactopyranose, commonly referred to in the literature as N-acetyl galactosamine. In certain embodiments, "N-acetyl galactosamine" refers to 2-(Acetylamino)-2-deoxy-D-galactopyranose. In certain embodiments, "GalNac" or "Gal-NAc" refers to 2-(Acetylamino)-2-deoxy-D-galactopyranose. In certain embodiments, "GalNac" or "Gal-NAc" refers to 2-(Acetylamino)-2-deoxy-D-galactopyranose, which includes both the β-form: 2-(Acetylamino)-2-deoxy-β-D-galactopyranose and α-form: 2-(Acetylamino)-2-deoxy-D-galactopyranose. In certain embodiments, both the β-form: 2-(Acetylamino)-2-deoxy-β-D-galactopyranose and α-form: 2-(Acetylamino)-

2-deoxy-D-galactopyranose may be used interchangeably. Accordingly, in structures in which one form is depicted, these structures are intended to include the other form as well. For example, where the structure for an α-form: 2-(Acetylamino)-2-deoxy-D-galactopyranose is shown, this structure is intended to include the other form as well. In certain embodiments, In certain preferred embodiments, the β-form 2-(Acetylamino)-2-deoxy-D-galactopyranose is the preferred embodiment.

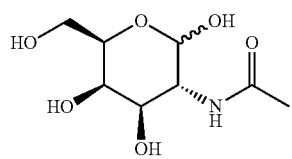

2-(Acetylamino)-2-deoxy-
D-galactopyranose

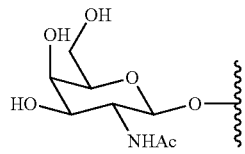

2-(Acetylamino)-2-deoxy-β-
D-galactopyranose

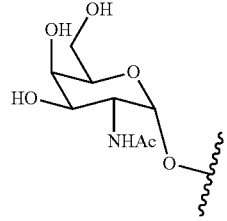

2-(Acetylamino)-2-deoxy-α-
D-galactopyranose

In certain embodiments one or more ligand has a structure selected from among:

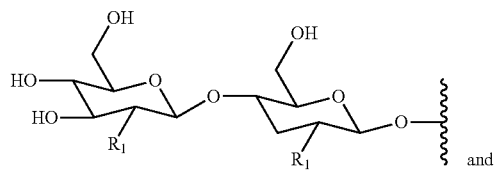

and

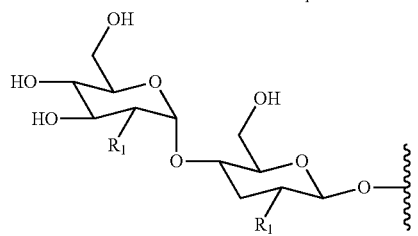

wherein each $R_1$ is selected from OH and NHCOOH.

In certain embodiments one or more ligand has a structure selected from among:

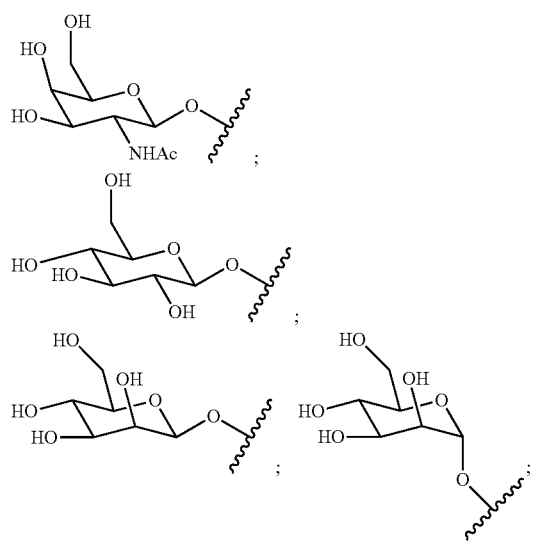

; and

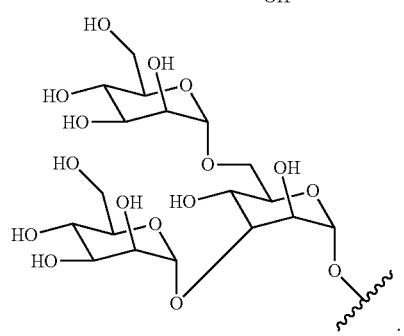

In certain embodiments one or more ligand has a structure selected from among:

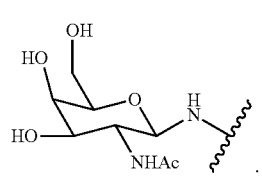

In certain embodiments one or more ligand has a structure selected from among:

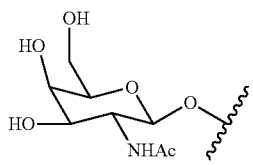

i. Certain Conjugates

In certain embodiments, conjugate groups comprise the structural features above. In certain such embodiments, conjugate groups have the following structure:

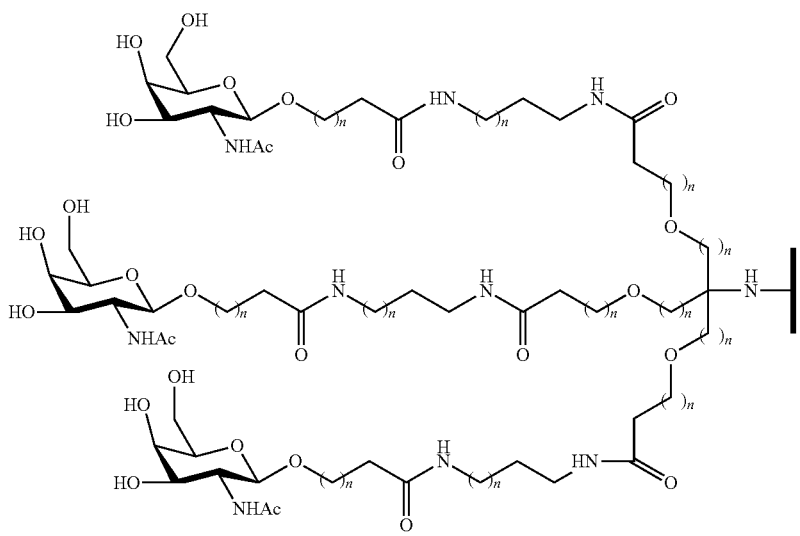

wherein each n is, independently, from 1 to 20.

In certain such embodiments, conjugate groups have the following structure:

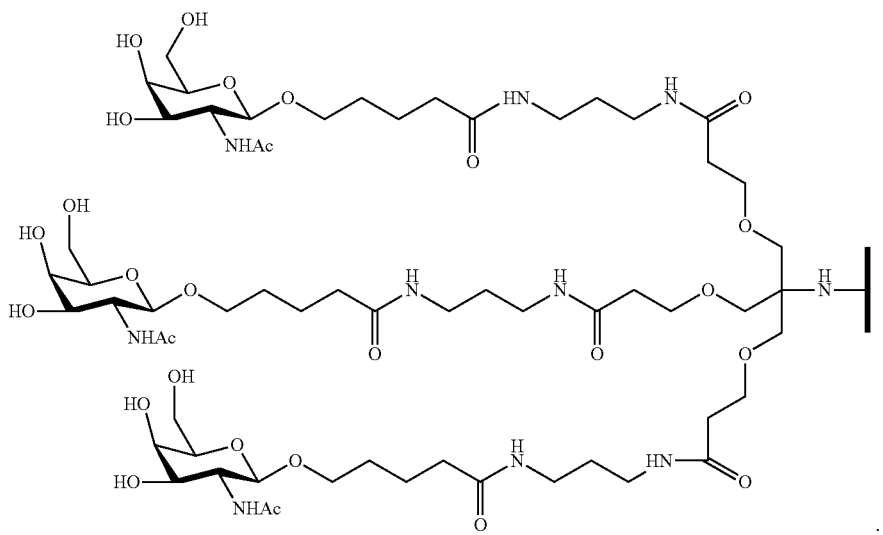

In certain such embodiments, conjugate groups have the following structure:
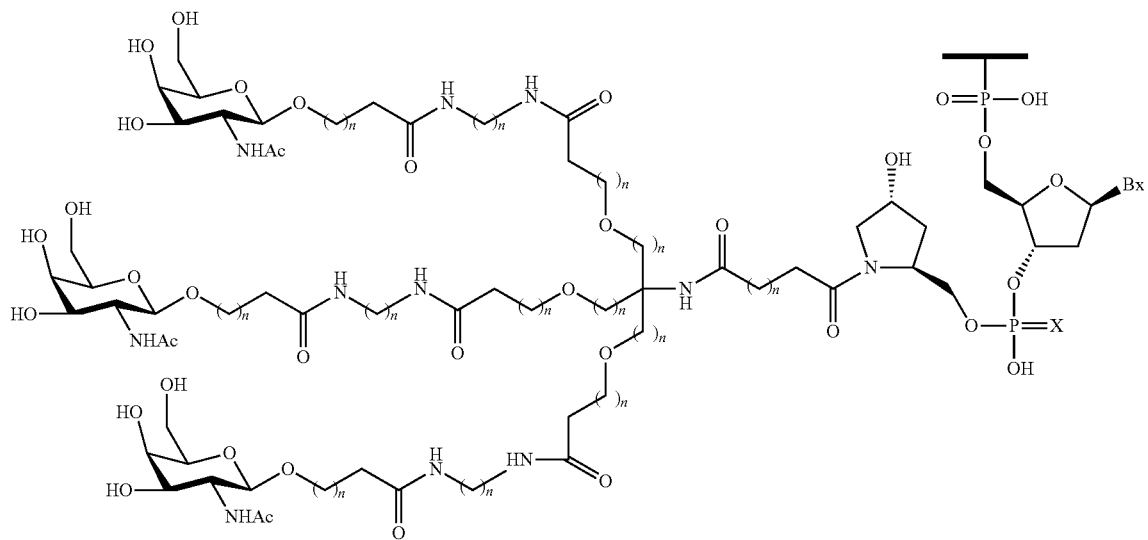
wherein each n is, independently, from 1 to 20;
Z is H or a linked solid support;
Q is an antisense compound;
X is O or S; and
Bx is a heterocyclic base moiety.
In certain such embodiments, conjugate groups have the following structure:
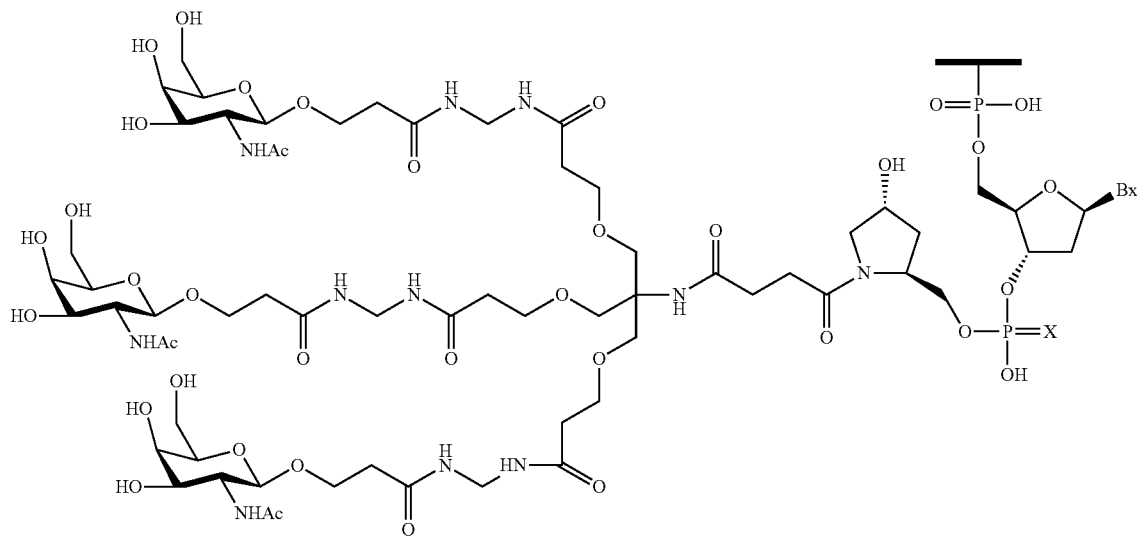

In certain such embodiments, conjugate groups have the following structure:
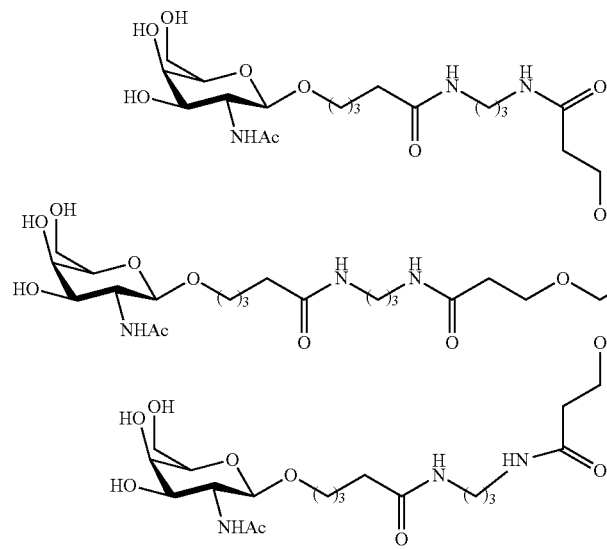
In certain such embodiments, conjugate groups have the following structure:
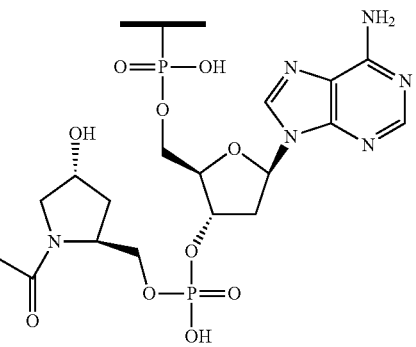
In certain such embodiments, conjugate groups have the following structure:
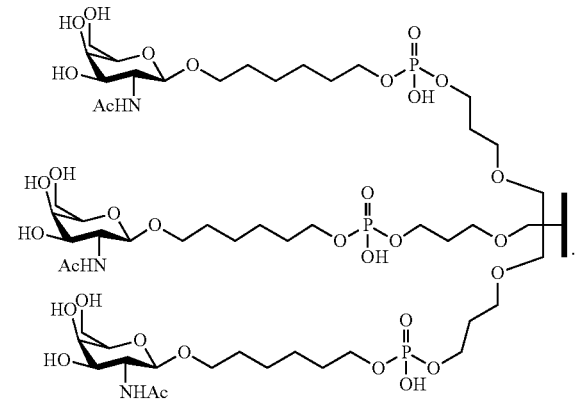
In certain such embodiments, conjugate groups have the following structure:
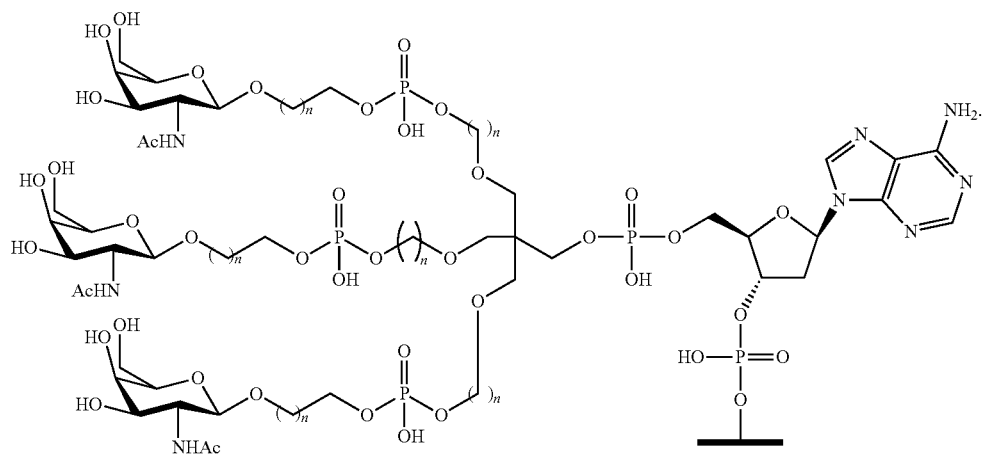

In certain such embodiments, conjugate groups have the following structure:
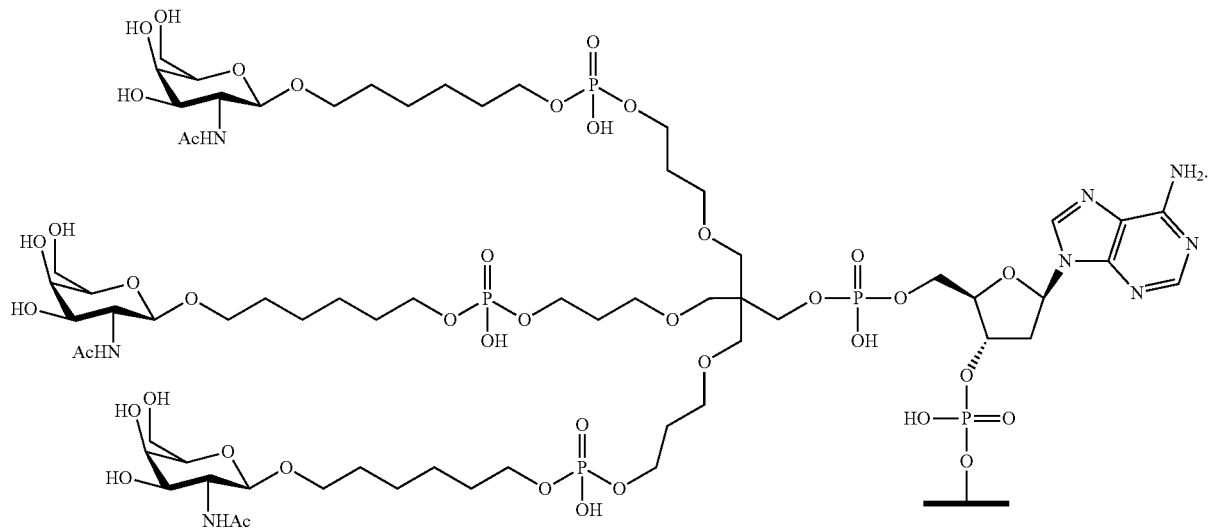
In certain such embodiments, conjugate groups have the following structure:
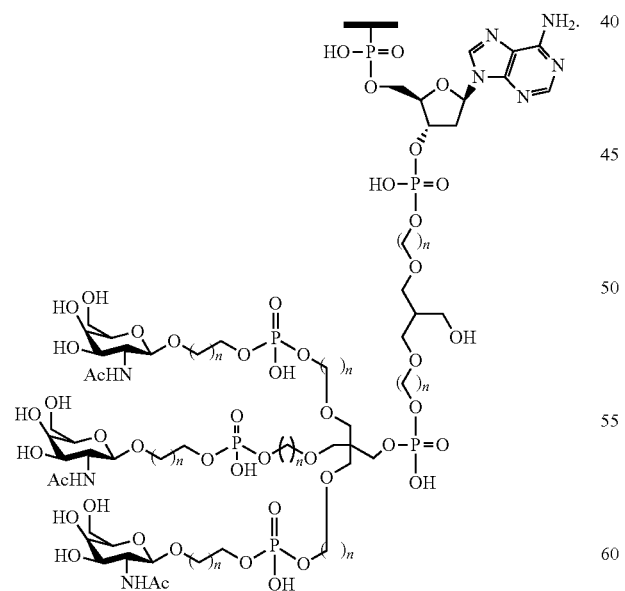
In certain such embodiments, conjugate groups have the following structure:

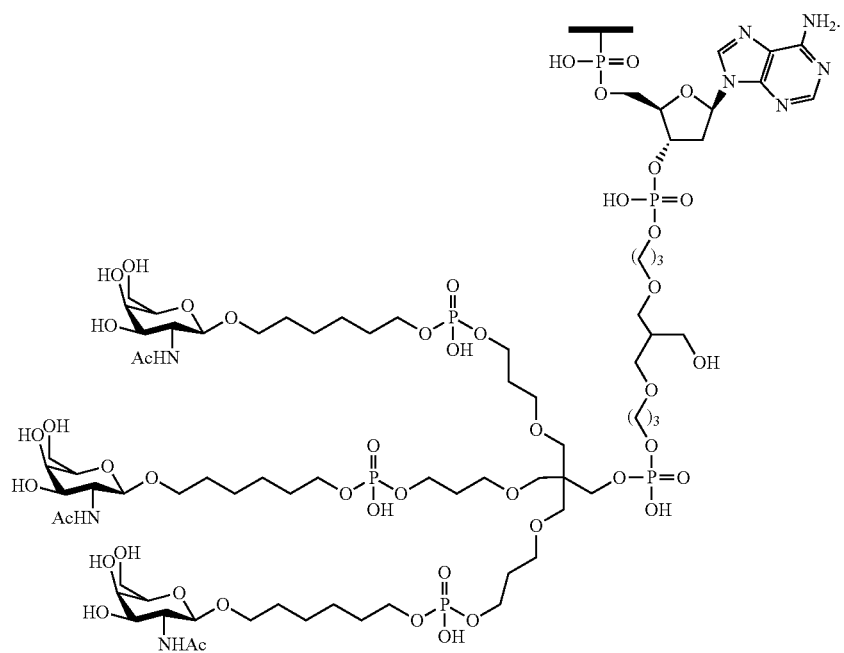
In certain embodiments, conjugates do not comprise a pyrrolidine.
In certain such embodiments, conjugate groups have the following structure:
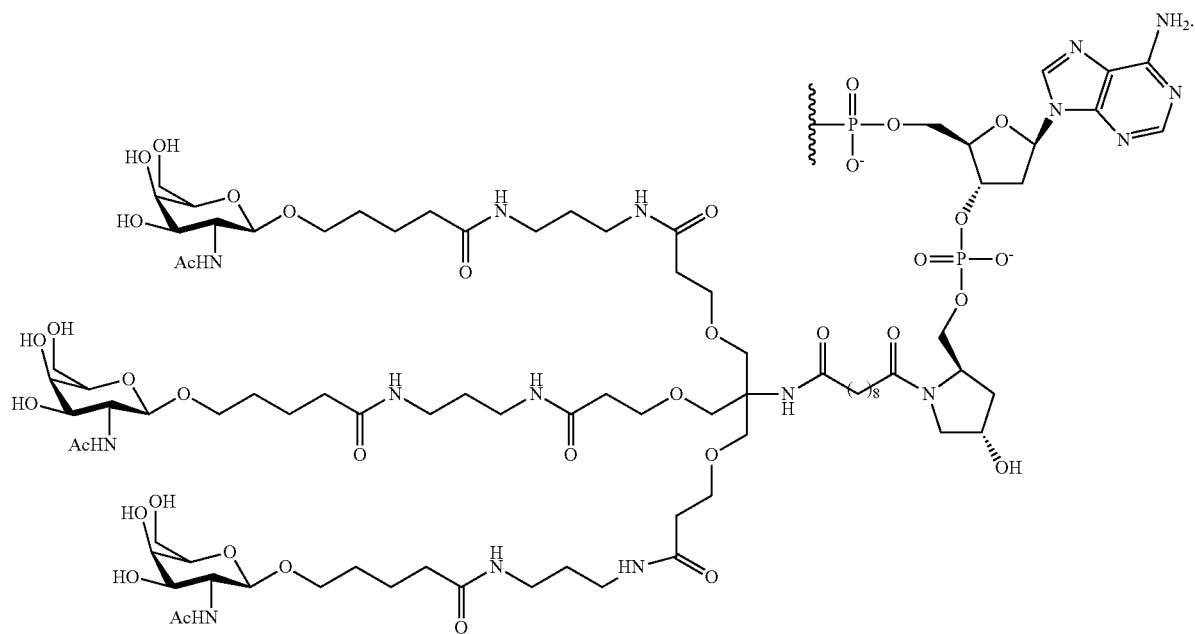
In certain such embodiments, conjugate groups have the following structure:

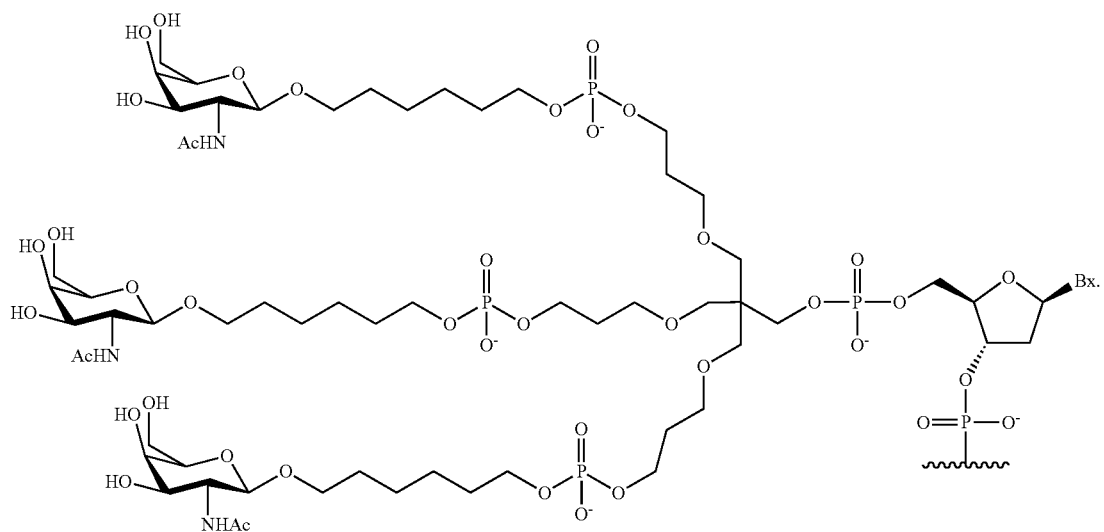
In certain such embodiments, conjugate groups have the following structure:
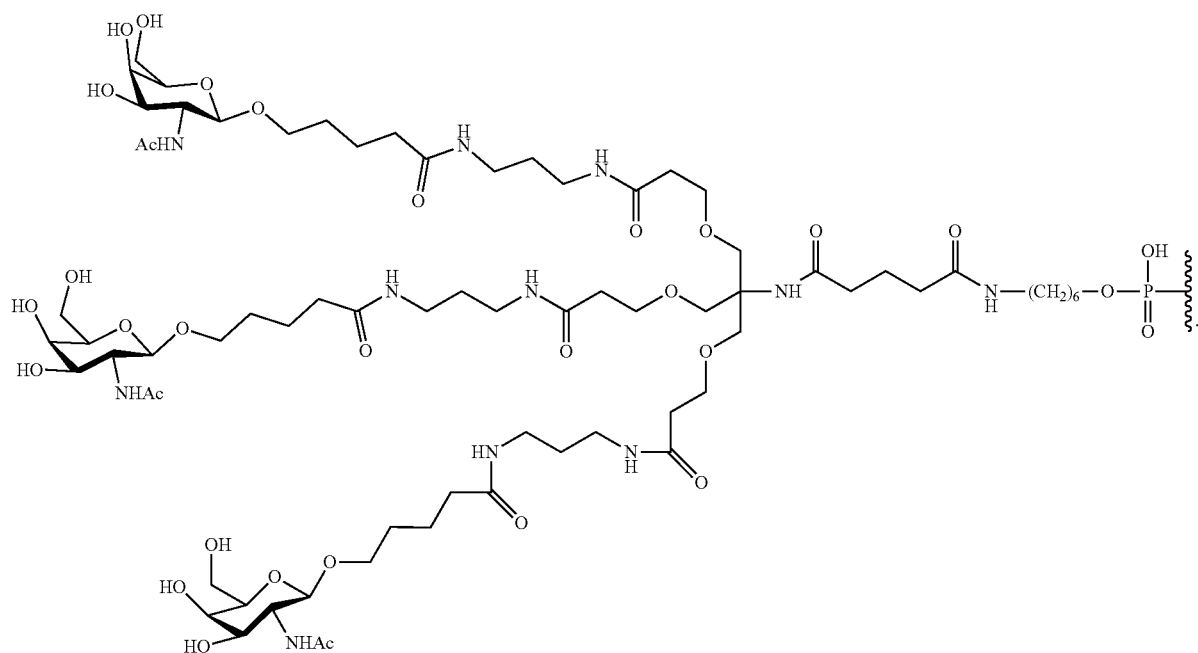
In certain such embodiments, conjugate groups have the following structure:

20
In certain such embodiments, conjugate groups have the following structure:
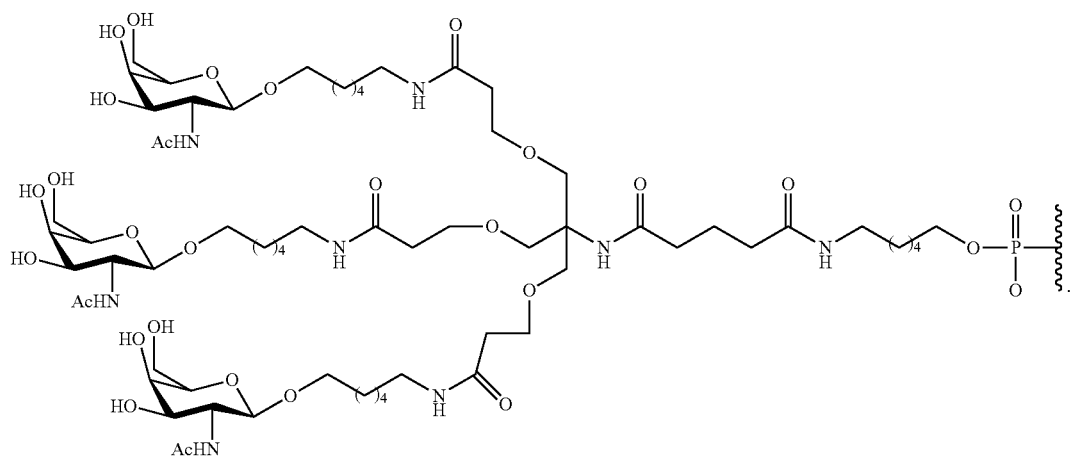
In certain such embodiments, conjugate groups have the following structure:
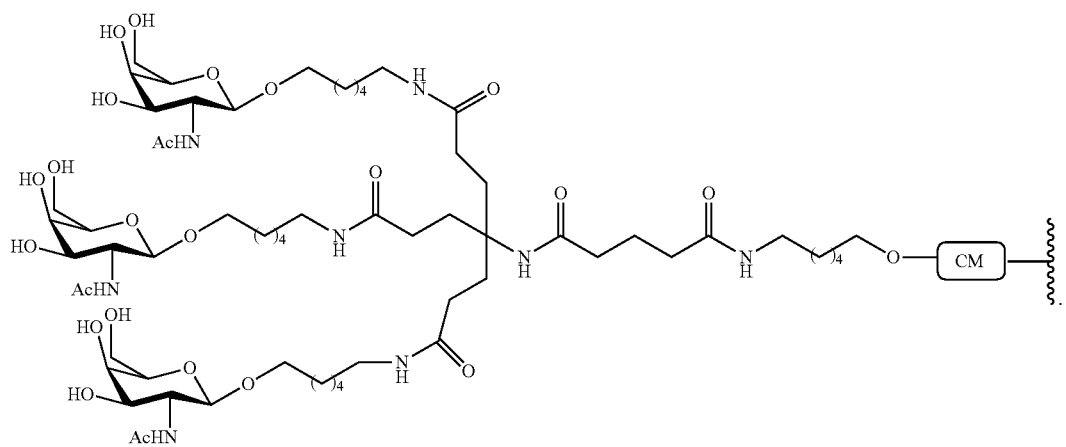
65
In certain such embodiments, conjugate groups have the following structure:

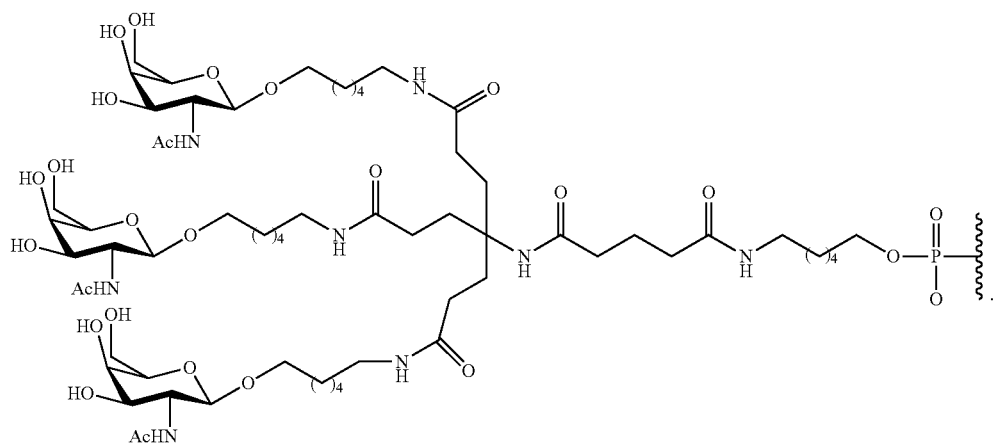
In certain such embodiments, conjugate groups have the following structure:
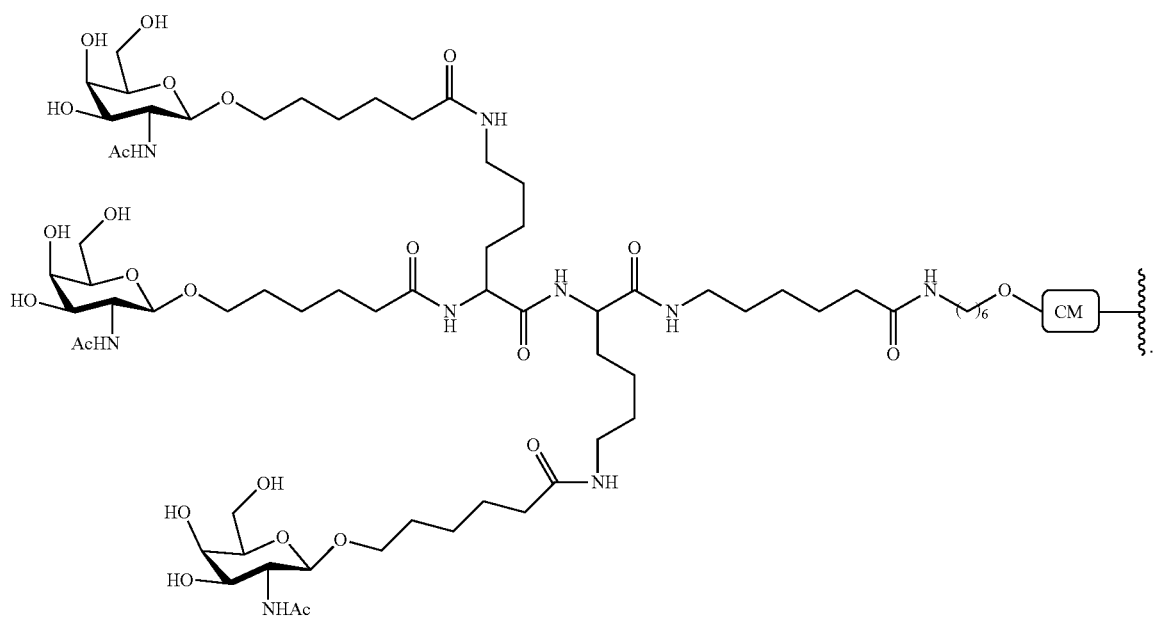
In certain such embodiments, conjugate groups have the following structure:

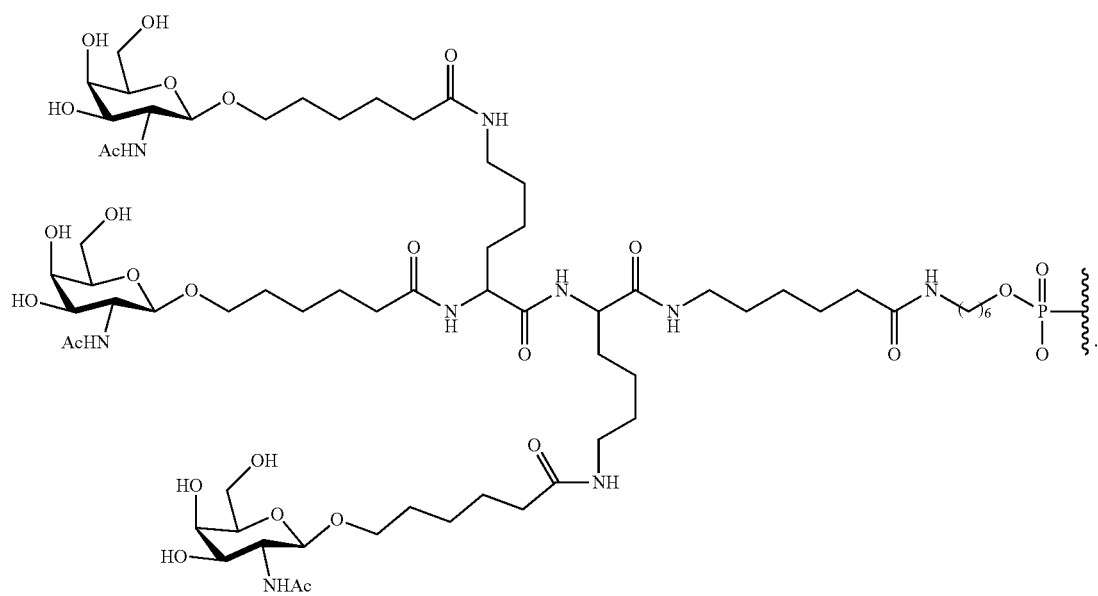
In certain such embodiments, conjugate groups have the following structure:
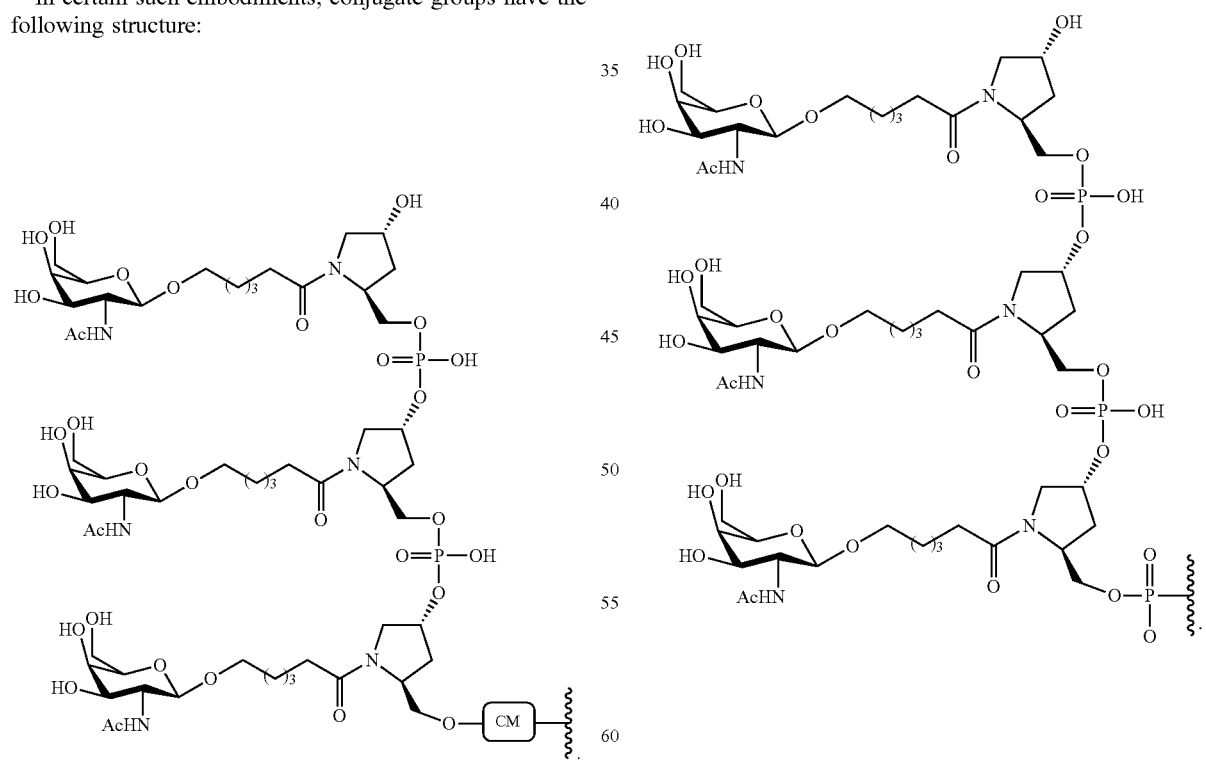
In certain such embodiments, conjugate groups have the following structure:
In certain embodiments, the cell-targeting moiety of the conjugate group has the following structure:

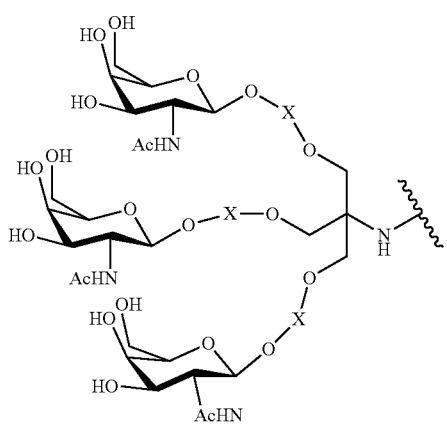

wherein X is a substituted or unsubstituted tether of six to eleven consecutively bonded atoms.

In certain embodiments, the cell-targeting moiety of the conjugate group has the following structure:

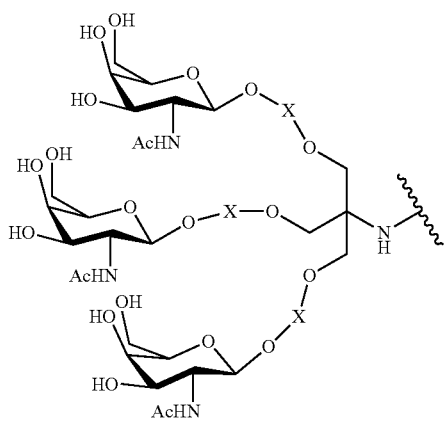

wherein X is a substituted or unsubstituted tether of ten consecutively bonded atoms.

In certain embodiments, the cell-targeting moiety of the conjugate group has the following structure:

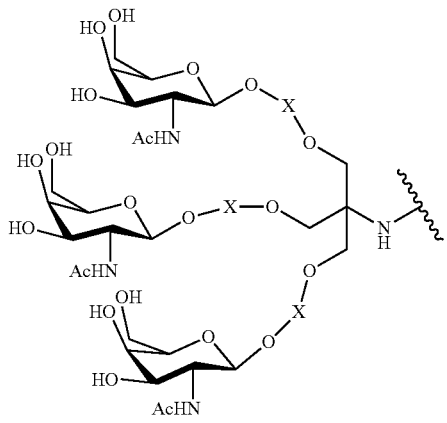

wherein X is a substituted or unsubstituted tether of four to eleven consecutively bonded atoms and wherein the tether comprises exactly one amide bond.

In certain embodiments, the cell-targeting moiety of the conjugate group has the following structure:

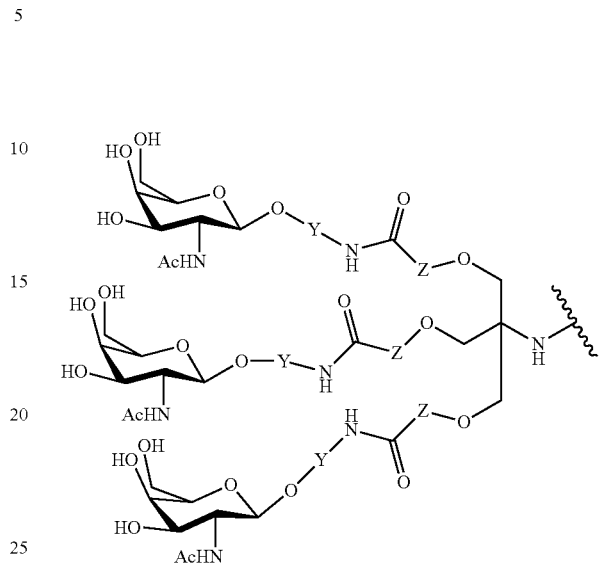

wherein Y and Z are independently selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

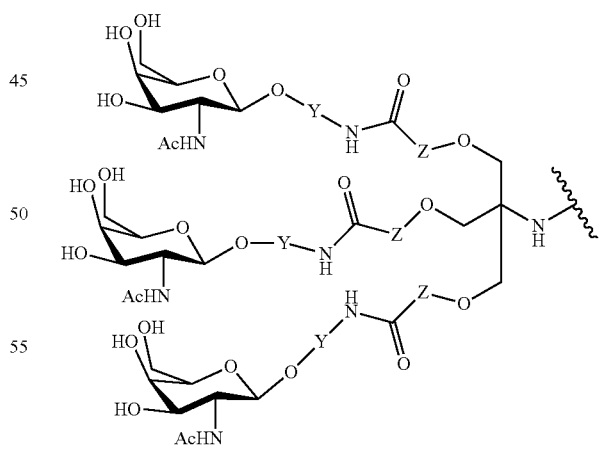

wherein Y and Z are independently selected from a $C_1$-$C_{12}$ substituted or unsubstituted alkyl group, or a group comprising exactly one ether or exactly two ethers, an amide, an amine, a piperidine, a phosphate, a phosphodiester, or a phosphorothioate.

In certain such embodiments, the cell-targeting moiety of the conjugate group has the following structure:

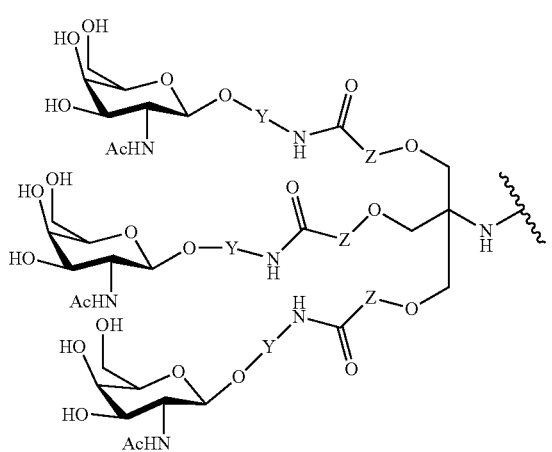

wherein Y and Z are independently selected from a $C_1$-$C_{12}$ substituted or unsubstituted alkyl group.

In certain such embodiments, the cell-targeting moiety of the conjugate group has the following structure:

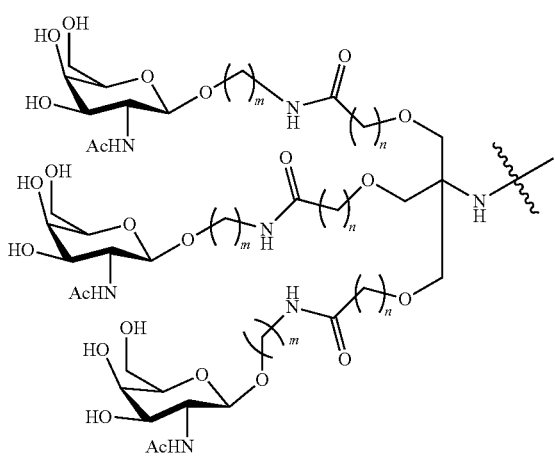

wherein m and n are independently selected from 1, 2, 3, 4, 5, 6, 7, 8, 9, 10, 11, and 12.

In certain such embodiments, the cell-targeting moiety of the conjugate group has the following structure:

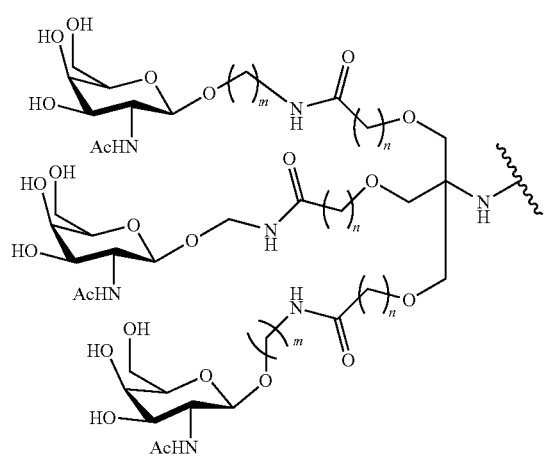

wherein m is 4, 5, 6, 7, or 8, and n is 1, 2, 3, or 4.

In certain embodiments, the cell-targeting moiety of the conjugate group has the following structure:

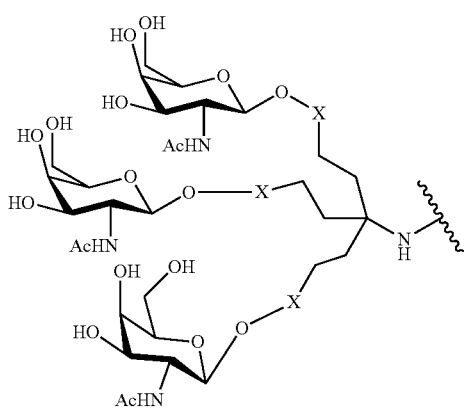

wherein X is a substituted or unsubstituted tether of four to thirteen consecutively bonded atoms, and wherein X does not comprise an ether group.

In certain embodiments, the cell-targeting moiety of the conjugate group has the following structure:

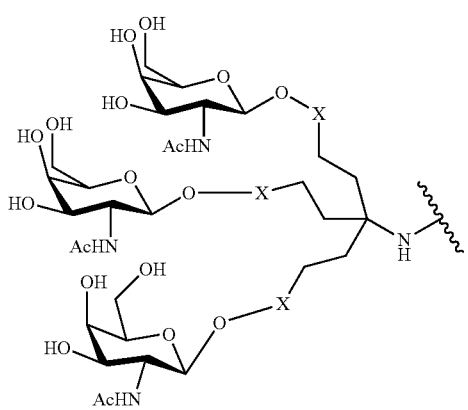

wherein X is a substituted or unsubstituted tether of eight consecutively bonded atoms, and wherein X does not comprise an ether group.

In certain embodiments, the cell-targeting moiety of the conjugate group has the following structure:

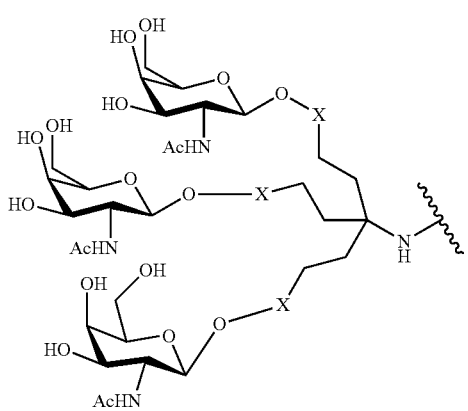

wherein X is a substituted or unsubstituted tether of four to thirteen consecutively bonded atoms, and wherein the tether comprises exactly one amide bond, and wherein X does not comprise an ether group.

In certain embodiments, the cell-targeting moiety of the conjugate group has the following structure:

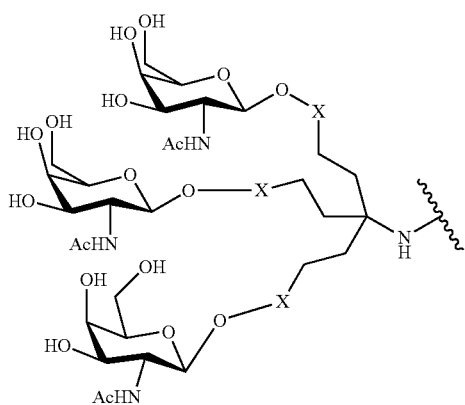

wherein X is a substituted or unsubstituted tether of four to thirteen consecutively bonded atoms and wherein the tether consists of an amide bond and a substituted or unsubstituted $C_2$-$C_{11}$ alkyl group.

In certain embodiments, the cell-targeting moiety of the conjugate group has the following structure:

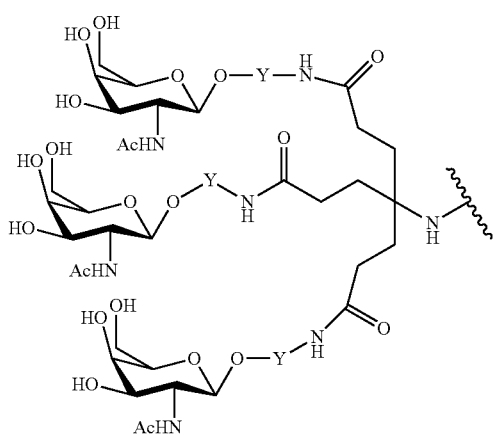

wherein Y is selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

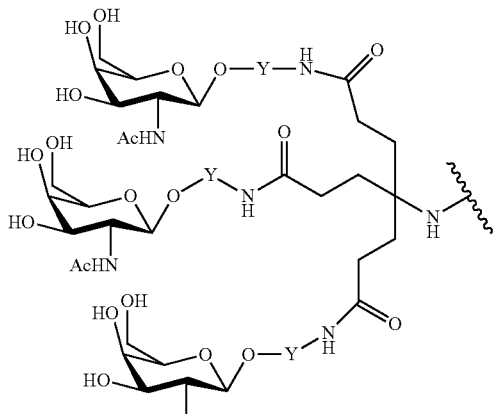

wherein Y is selected from a $C_1$-$C_{12}$ substituted or unsubstituted alkyl group, or a group comprising an ether, an amine, a piperidine, a phosphate, a phosphodiester, or a phosphorothioate.

In certain such embodiments, the cell-targeting moiety of the conjugate group has the following structure:

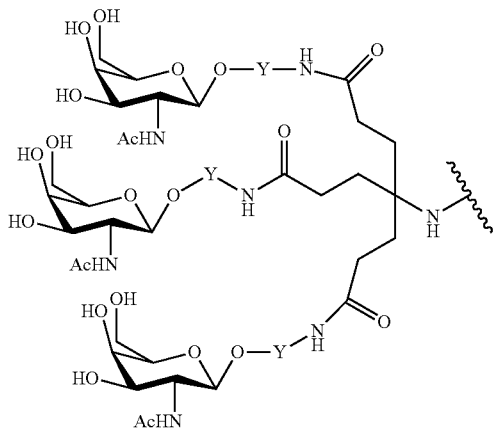

wherein Y is selected from a $C_1$-$C_{12}$ substituted or unsubstituted alkyl group.

In certain such embodiments, the cell-targeting moiety of the conjugate group has the following structure:

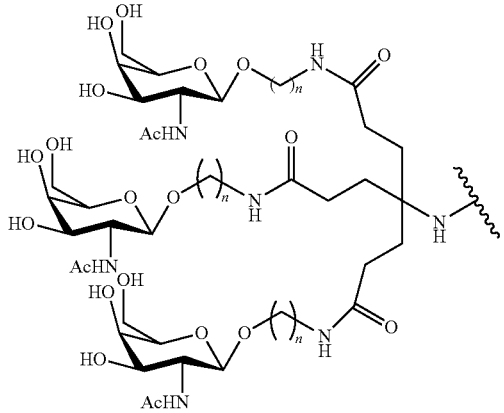

Wherein n is 1, 2, 3, 4, 5, 6, 7, 8, 9, 10, 11, or 12.

In certain embodiments, the cell-targeting moiety of the conjugate group has the following structure:

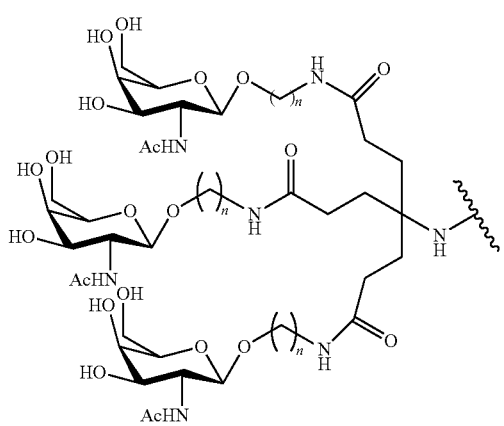

wherein n is 4, 5, 6, 7, or 8.

In certain embodiments, conjugates do not comprise a pyrrolidine.

b. Certain Conjugated Antisense Compounds

In certain embodiments, the conjugates are bound to a nucleoside of the antisense oligonucleotide at the 2', 3', of 5' position of the nucleoside. In certain embodiments, a conjugated antisense compound has the following structure:

$$A\text{-}B\text{-}C\text{-}D\text{-}(E\text{-}F)_q$$

wherein

A is the antisense oligonucleotide;

B is the cleavable moiety

C is the conjugate linker

D is the branching group each E is a tether;

each F is a ligand; and q is an integer between 1 and 5.

In certain embodiments, a conjugated antisense compound has the following structure:

$$A\text{-}C\text{-}D\text{-}(E\text{-}F)_q$$

wherein

A is the antisense oligonucleotide;

C is the conjugate linker

D is the branching group each E is a tether;

each F is a ligand; and q is an integer between 1 and 5.

In certain such embodiments, the conjugate linker comprises at least one cleavable bond.

In certain such embodiments, the branching group comprises at least one cleavable bond.

In certain embodiments each tether comprises at least one cleavable bond.

In certain embodiments, the conjugates are bound to a nucleoside of the antisense oligonucleotide at the 2', 3', of 5' position of the nucleoside.

In certain embodiments, a conjugated antisense compound has the following structure:

$$A\text{-}B\text{-}C\text{-}(E\text{-}F)_q$$

wherein

A is the antisense oligonucleotide;

B is the cleavable moiety

C is the conjugate linker each E is a tether;

each F is a ligand; and q is an integer between 1 and 5.

In certain embodiments, the conjugates are bound to a nucleoside of the antisense oligonucleotide at the 2', 3', of 5' position of the nucleoside. In certain embodiments, a conjugated antisense compound has the following structure:

$$A\text{-}C\text{-}(E\text{-}F)_q$$

wherein

A is the antisense oligonucleotide;

C is the conjugate linker each E is a tether;

each F is a ligand; and q is an integer between 1 and 5.

In certain embodiments, a conjugated antisense compound has the following structure:

$$A\text{-}B\text{-}D\text{-}(E\text{-}F)_q$$

wherein

A is the antisense oligonucleotide;

B is the cleavable moiety

D is the branching group each E is a tether;

each F is a ligand; and q is an integer between 1 and 5.

In certain embodiments, a conjugated antisense compound has the following structure:

$$A\text{-}D\text{-}(E\text{-}F)_q$$

wherein

A is the antisense oligonucleotide;

D is the branching group each E is a tether;

each F is a ligand; and q is an integer between 1 and 5.

In certain such embodiments, the conjugate linker comprises at least one cleavable bond.

In certain embodiments each tether comprises at least one cleavable bond.

In certain embodiments, a conjugated antisense compound has a structure selected from among the following:

111    112
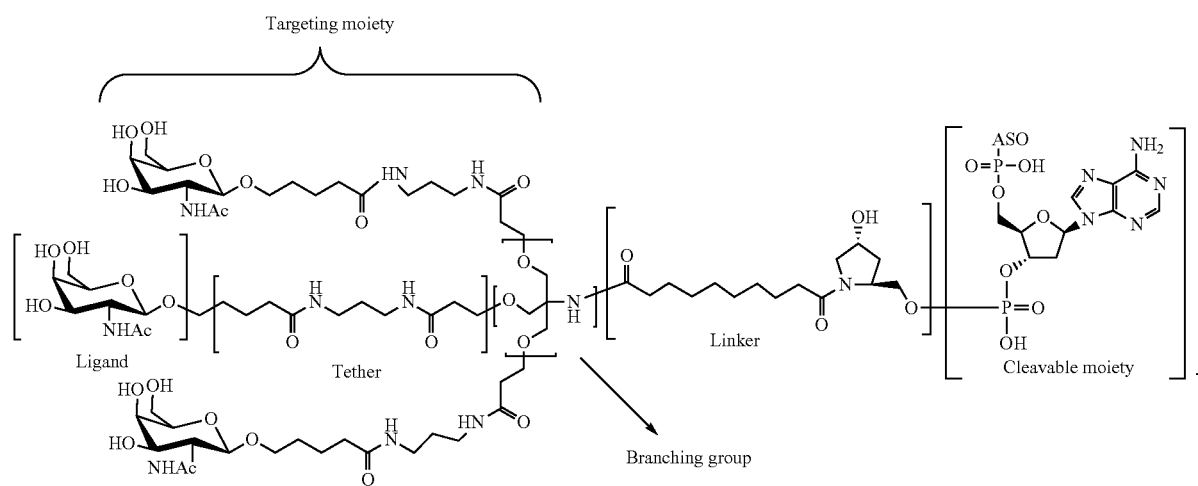
In certain embodiments, a conjugated antisense compound has a structure selected from among the following:
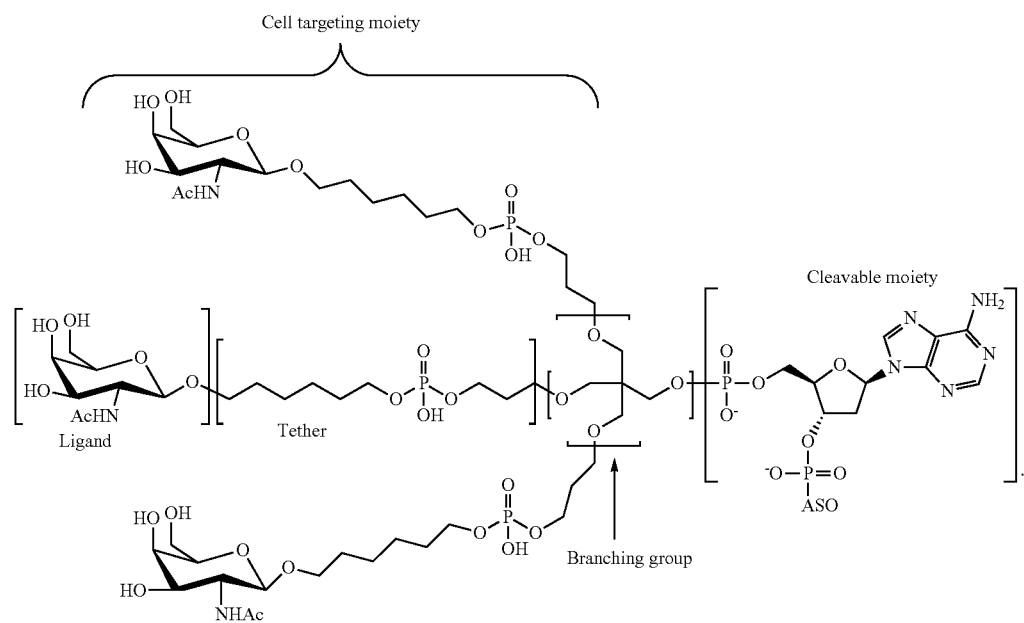
In certain embodiments, a conjugated antisense compound has a structure selected from among the following:

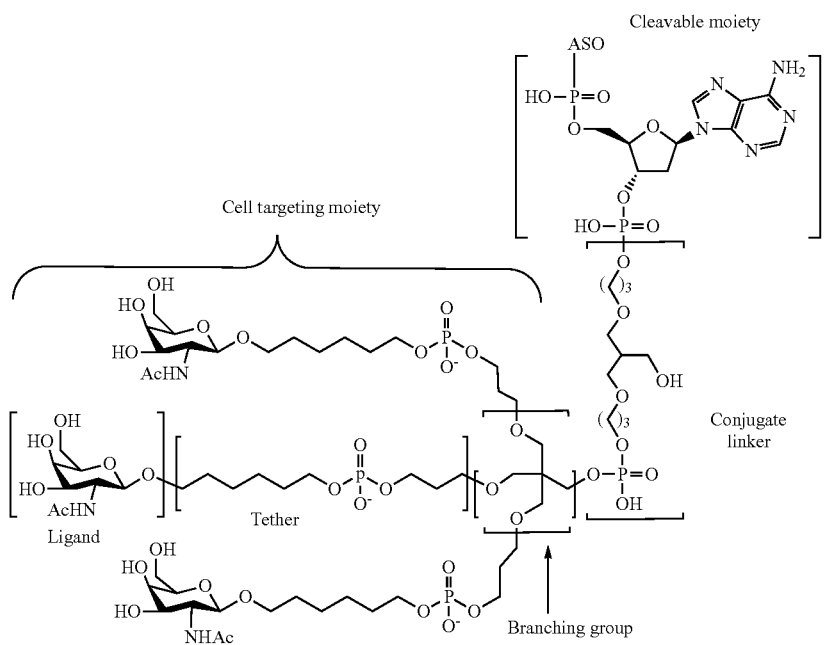

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906, 182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, Carbohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycobiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromb Vasc Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., *Bioorg Med Chem,* 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

C. Certain Uses And Features

In certain embodiments, conjugated antisense compounds exhibit potent target RNA reduction in vivo. In certain embodiments, unconjugated antisense compounds accumulate in the kidney. In certain embodiments, conjugated antisense compounds accumulate in the liver. In certain embodiments, conjugated antisense compounds are well tolerated. Such properties render conjugated antisense compounds particularly useful for inhibition of many target RNAs, including, but not limited to those involved in metabolic, cardiovascular and other diseases, disorders or conditions. Thus, provided herein are methods of treating such diseases, disorders or conditions by contacting liver tissues with the conjugated antisense compounds targeted to RNAs associated with such diseases, disorders or conditions. Thus, also provided are methods for ameliorating any of a variety of metabolic, cardiovascular and other diseases, disorders or conditions with the conjugated antisense compounds of the present invention.

In certain embodiments, conjugated antisense compounds are more potent than unconjugated counterpart at a particular tissue concentration. Without wishing to be bound by any theory or mechanism, in certain embodiments, the conjugate may allow the conjugated antisense compound to enter the cell more efficiently or to enter the cell more productively. For example, in certain embodiments conjugated antisense compounds may exhibit greater target reduction as compared to its unconjugated counterpart wherein both the conjugated antisense compound and its unconjugated counterpart are present in the tissue at the same concentrations. For example, in certain embodiments conjugated antisense compounds may exhibit greater target reduction as compared to its unconjugated counterpart wherein both the conjugated antisense compound and its unconjugated counterpart are present in the liver at the same concentrations.

Productive and non-productive uptake of oligonucleotides has been discussed previously (See e.g. Geary, R. S., E. Wancewicz, et al. (2009). "Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. 78(3): 284-91; & Koller, E., T. M. Vincent, et al. (2011). "Mechanisms of single-stranded phosphorothioate modified antisense oligonucleotide accumulation in hepatocytes." Nucleic Acids Res. 39(11): 4795-807). Conjugate groups described herein may improve productive uptake.

In certain embodiments, the conjugate groups described herein may further improve potency by increasing the affinity of the conjugated antisense compound for a particular type of cell or tissue. In certain embodiments, the conjugate groups described herein may further improve potency by increasing recognition of the conjugated antisense compound by one or more cell-surface receptors. In certain embodiments, the conjugate groups described herein may further improve potency by facilitating endocytosis of the conjugated antisense compound.

In certain embodiments, the cleavable moiety may further improve potency by allowing the conjugate to be cleaved from the antisense oligonucleotide after the conjugated antisense compound has entered the cell. Accordingly, in certain embodiments, conjugated antisense compounds can be administered at doses lower than would be necessary for unconjugated antisense oligonucleotides.

Phosphorothioate linkages have been incorporated into antisense oligonucleotides previously. Such phosphorothioate linkages are resistant to nucleases and so improve stability of the oligonucleotide. Further, phosphorothioate linkages also bind certain proteins, which results in accumulation of antisense oligonucleotide in the liver. Oligonucleotides with fewer phosphorothioate linkages accumulate less in the liver and more in the kidney (see, for example, Geary, R., "Pharmacokinetic Properties of 2'-O-(2-Methoxyethyl)-Modified Oligonucleotide Analogs in Rats," *Journal of Pharmacology and Experimental Therapeutics,* Vol. 296, No. 3, 890-897; & *Pharmacological Properties of 2'-O-Methoxyethyl Modified Oligonucleotides* in Antisense a Drug Technology, Chapter 10, Crooke, S. T., ed., 2008) In certain embodiments, oligonucleotides with fewer phosphorothioate internucleoside linkages and more phosphodiester internucleoside linkages accumulate less in the liver and more in the kidney. When treating diseases in the liver, this is undesirable for several reasons (1) less drug is getting to the site of desired action (liver); (2) drug is escaping into the urine; and (3) the kidney is exposed to relatively high concentration of drug which can result in toxicities in the kidney. Thus, for liver diseases, phosphorothioate linkages provide important benefits.

In certain embodiments, however, administration of oligonucleotides uniformly linked by phosphorothioate internucleoside linkages induces one or more proinflammatory reactions. (see for example: *J Lab Clin Med.* 1996 September; 128(3):329-38. "Amplification of antibody production by phosphorothioate oligodeoxynucleotides". Branda et al.; and see also for example: *Toxicologic Properties* in Antisense a Drug Technology, Chapter 12, pages 342-351, Crooke, S. T., ed., 2008). In certain embodiments, administration of oligonucleotides wherein most of the internucleoside linkages comprise phosphorothioate internucleoside linkages induces one or more proinflammatory reactions.

In certain embodiments, the degree of proinflammatory effect may depend on several variables (e.g. backbone modification, off-target effects, nucleobase modifications, and/or nucleoside modifications) see for example: *Toxico-* logic Properties in Antisense a Drug Technology, Chapter 12, pages 342-351, Crooke, S. T., ed., 2008). In certain embodiments, the degree of proinflammatory effect may be mitigated by adjusting one or more variables. For example the degree of proinflammatory effect of a given oligonucleotide may be mitigated by replacing any number of phosphorothioate internucleoside linkages with phosphodiester internucleoside linkages and thereby reducing the total number of phosphorothioate internucleoside linkages.

In certain embodiments, it would be desirable to reduce the number of phosphorothioate linkages, if doing so could be done without losing stability and without shifting the distribution from liver to kidney. For example, in certain embodiments, the number of phosphorothioate linkages may be reduced by replacing phosphorothioate linkages with phosphodiester linkages. In such an embodiment, the antisense compound having fewer phosphorothioate linkages and more phosphodiester linkages may induce less proinflammatory reactions or no proinflammatory reaction. Although the the antisense compound having fewer phosphorothioate linkages and more phosphodiester linkages may induce fewer proinflammatory reactions, the antisense compound having fewer phosphorothioate linkages and more phosphodiester linkages may not accumulate in the liver and may be less efficacious at the same or similar dose as compared to an antisense compound having more phosphorothioate linkages. In certain embodiments, it is therefore desirable to design an antisense compound that has a plurality of phosphodiester bonds and a plurality of phosphorothioate bonds but which also possesses stability and good distribution to the liver.

In certain embodiments, conjugated antisense compounds accumulate more in the liver and less in the kidney than unconjugated counterparts, even when some of the phosporothioate linkages are replaced with less proinflammatory phosphodiester internucleoside linkages. In certain embodiments, conjugated antisense compounds accumulate more in the liver and are not excreted as much in the urine compared to its unconjugated counterparts, even when some of the phosporothioate linkages are replaced with less proinflammatory phosphodiester internucleoside linkages. In certain embodiments, the use of a conjugate allows one to design more potent and better tolerated antisense drugs. Indeed, in certain embodiments, conjugated antisense compounds have larger therapeutic indexes than unconjugated counterparts. This allows the conjugated antisense compound to be administered at a higher absolute dose, because there is less risk of proinflammatory response and less risk of kidney toxicity. This higher dose, allows one to dose less frequently, since the clearance (metabolism) is expected to be similar. Further, because the compound is more potent, as described above, one can allow the concentration to go lower before the next dose without losing therapeutic activity, allowing for even longer periods between dosing.

In certain embodiments, the inclusion of some phosphorothioate linkages remains desirable. For example, the terminal linkages are vulnerable to exonucleases and so in certain embodiments, those linkages are phosphorothioate or other modified linkage. Internucleoside linkages linking two deoxynucleosides are vulnerable to endonucleases and so in certain embodiments those those linkages are phosphorothioate or other modified linkage. Internucleoside linkages between a modified nucleoside and a deoxynucleoside where the deoxynucleoside is on the 5' side of the linkage deoxynucleosides are vulnerable to endonucleases and so in certain embodiments those those linkages are phosphorothioate or other modified linkage. Internucleoside linkages between two modified nucleosides of certain types and between a deoxynucleoside and a modified nucleoside of certain type where the modified nucleoside is at the 5' side of the linkage are sufficiently resistant to nuclease digestion, that the linkage can be phosphodiester.

In certain embodiments, the antisense oligonucleotide of a conjugated antisense compound comprises fewer than 16 phosphorthioate linkages. In certain embodiments, the antisense oligonucleotide of a conjugated antisense compound comprises fewer than 15 phosphorthioate linkages. In certain embodiments, the antisense oligonucleotide of a conjugated antisense compound comprises fewer than 14 phosphorthioate linkages. In certain embodiments, the antisense oligonucleotide of a conjugated antisense compound comprises fewer than 13 phosphorthioate linkages. In certain embodiments, the antisense oligonucleotide of a conjugated antisense compound comprises fewer than 12 phosphorthioate linkages. In certain embodiments, the antisense oligonucleotide of a conjugated antisense compound comprises fewer than 11 phosphorthioate linkages. In certain embodiments, the antisense oligonucleotide of a conjugated antisense compound comprises fewer than 10 phosphorthioate linkages. In certain embodiments, the antisense oligonucleotide of a conjugated antisense compound comprises fewer than 9 phosphorthioate linkages. In certain embodiments, the antisense oligonucleotide of a conjugated antisense compound comprises fewer than 8 phosphorthioate linkages.

In certain embodiments, antisense compounds comprising one or more conjugate group described herein has increased activity and/or potency and/or tolerability compared to a parent antisense compound lacking such one or more conjugate group. Accordingly, in certain embodiments, attachment of such conjugate groups to an oligonucleotide is desirable. Such conjugate groups may be attached at the 5'-, and/or 3'-end of an oligonucleotide. In certain instances, attachment at the 5'-end is synthetically desirable. Typically, oligonucleotides are synthesized by attachment of the 3' terminal nucleoside to a solid support and sequential coupling of nucleosides from 3' to 5' using techniques that are well known in the art. Accordingly if a conjugate group is desired at the 3'-terminus, one may (1) attach the conjugate group to the 3'-terminal nucleoside and attach that conjugated nucleoside to the solid support for subsequent preparation of the oligonucleotide or (2) attach the conjugate group to the 3'-terminal nucleoside of a completed oligonucleotide after synthesis. Neither of these approaches is very efficient and thus both are costly. In particular, attachment of the conjugated nucleoside to the solid support, while demonstrated in the Examples herein, is an inefficient process. In certain embodiments, attaching a conjugate group to the 5'-terminal nucleoside is synthetically easier than attachment at the 3'-end. One may attach a non-conjugated 3' terminal nucleoside to the solid support and prepare the oligonucleotide using standard and well characterized reactions. One then needs only to attach a 5'nucleoside having a conjugate group at the final coupling step. In certain embodiments, this is more efficient than attaching a conjugated nucleoside directly to the solid support as is typically done to prepare a 3'-conjugated oligonucleotide. The Examples herein demonstrate attachment at the 5'-end. In addition, certain conjugate groups have synthetic advantages. For Example, certain conjugate groups comprising phosphorus linkage groups are synthetically simpler and more efficiently prepared than other conjugate groups, including conjugate groups reported previously (e.g., WO/2012/037254).

In certain embodiments, conjugated antisense compounds are administered to a subject. In such embodiments, antisense compounds comprising one or more conjugate group described herein has increased activity and/or potency and/or tolerability compared to a parent antisense compound lacking such one or more conjugate group. Without being bound by mechanism, it is believed that the conjugate group helps with distribution, delivery, and/or uptake into a target cell or tissue. In certain embodiments, once inside the target cell or tissue, it is desirable that all or part of the conjugate group to be cleaved to release the active oligonucleotide. In certain embodiments, it is not necessary that the entire conjugate group be cleaved from the oligonucleotide. For example, in Example 20 a conjugated oligonucleotide was administered to mice and a number of different chemical species, each comprising a different portion of the conjugate group remaining on the oligonucleotide, were detected (Table 10a). This conjugated antisense compound demonstrated good potency (Table 10). Thus, in certain embodiments, such metabolite profile of multiple partial cleavage of the conjugate group does not interfere with activity/potency. Nevertheless, in certain embodiments it is desirable that a prodrug (conjugated oligonucleotide) yield a single active compound. In certain instances, if multiple forms of the active compound are found, it may be necessary to determine relative amounts and activities for each one. In certain embodiments where regulatory review is required (e.g., USFDA or counterpart) it is desirable to have a single (or predominantly single) active species. In certain such embodiments, it is desirable that such single active species be the antisense oligonucleotide lacking any portion of the conjugate group. In certain embodiments, conjugate groups at the 5'-end are more likely to result in complete metabolism of the conjugate group. Without being bound by mechanism it may be that endogenous enzymes responsible for metabolism at the 5' end (e.g., 5' nucleases) are more active/efficient than the 3' counterparts. In certain embodiments, the specific conjugate groups are more amenable to metabolism to a single active species. In certain embodiments, certain conjugate groups are more amenable to metabolism to the oligonucleotide.

D. Antisense

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, antisense compounds comprise a portion having a nucleobase sequence at least 70% complementary to the nucleobase sequence of a target nucleic acid. In certain embodiments, antisense compounds comprise a portion having a nucleobase sequence at least 80% complementary to the nucleobase sequence of a target nucleic acid. In certain embodiments, antisense compounds comprise a portion having a nucleobase sequence at least 90% complementary to the nucleobase sequence of a target nucleic acid. In certain embodiments, antisense compounds comprise a portion having a nucleobase sequence at least 95% complementary to the nucleobase sequence of a target nucleic acid. In certain embodiments, antisense compounds comprise a portion having a nucleobase sequence at least 98% complementary to the nucleobase sequence of a target nucleic acid. In certain embodiments, antisense compounds comprise a portion having a nucleobase sequence that is 100% complementary to the nucleobase sequence of a target nucleic acid. In certain embodiments, antisense compounds are at least 70%, 80%, 90%, 95%, 98%, or 100% complementary to the nucleobase sequence of a target nucleic acid over the entire length of the antisense compound.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or polyadenylation of the target nucleic acid or of a nucleic acid with which the target nucleic acid may otherwise interact.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, oligonucleotides comprising conjugates described herein are RNAi compounds. In certain embodiments, oligomeric oligonucleotides comprising conjugates described herein are ssRNA compounds. In certain embodiments, oligonucleotides comprising conjugates described herein are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligonucleotides comprising conjugates described herein is the antisense strand in an siRNA compound. In certain embodiments, the oligonucleotides comprising conjugates described herein is the sense strand in an siRNA compound. In embodiments in which the conjugated oligomeric compound is double-stranded siRnA, the conjugate may be on the sense strand, the antisense strand or both the sense strand and the antisense strand.

D. Target Nucleic Acids, Regions and Segments

In certain embodiments, conjugated antisense compounds target any nucleic acid. In certain embodiments, the target nucleic acid encodes a target protein that is clinically relevant. In such embodiments, modulation of the target nucleic acid results in clinical benefit. Certain target nucleic acids include, but are not limited to, the target nucleic acids illustrated in Table 1.

TABLE 1

Certain Human Target Nucleic Acids

| Target | GENBANK ® Accession Number | SEQ ID NO |
|---|---|---|
| PTP1B | NM_002827.2 | 1 |
|  | NT_011362.9 truncated from nucleotides 14178000 to 14256000 | 2 |
| FGFR4 | NM_002011.3 | 3 |
|  | NT_023133.11 truncated from nucleosides 21323018 to 21335213 | 4 |
|  | AB209631.1 | 5 |
|  | NM_022963.2 | 6 |
| GCCR | the complement of GENBANK Accession No. NT_029289.10 truncated from nucleotides 3818000 to 3980000 | 7 |
| GCGR | NM_000160.3 | 8 |
|  | NW_926918.1 truncated from nucleotides 16865000 to 16885000 | 9 |
| Factor VII | NT_027140.6 truncated from nucleotides 1255000 to 1273000 | 10 |
|  | NM_019616.2 | 11 |
|  | DB184141.1 | 12 |
|  | NW_001104507.1 truncated from nucleotides 691000 to 706000 | 13 |
| Factor XI | NM_000128.3 | 14 |
|  | NT_022792.17, truncated from 19598000 to 19624000 | 15 |
|  | NM_028066.1 | 16 |
|  | NW_001118167.1 | 17 |

The targeting process usually includes determination of at least one target region, segment, or site within the target nucleic acid for the antisense interaction to occur such that the desired effect will result.

In certain embodiments, a target region is a structurally defined region of the nucleic acid. For example, in certain such embodiments, a target region may encompass a 3' UTR, a 5' UTR, an exon, an intron, a coding region, a translation initiation region, translation termination region, or other defined nucleic acid region or target segment.

In certain embodiments, a target segment is at least about an 8-nucleobase portion of a target region to which a conjugated antisense compound is targeted. Target segments can include DNA or RNA sequences that comprise at least 8 consecutive nucleobases from the 5'-terminus of one of the target segments (the remaining nucleobases being a consecutive stretch of the same DNA or RNA beginning immediately upstream of the 5'-terminus of the target segment and continuing until the DNA or RNA comprises about 8 to about 30 nucleobases). Target segments are also represented by DNA or RNA sequences that comprise at least 8 consecutive nucleobases from the 3'-terminus of one of the target segments (the remaining nucleobases being a consecutive stretch of the same DNA or RNA beginning immediately downstream of the 3'-terminus of the target segment and continuing until the DNA or RNA comprises about 8 to about 30 nucleobases). Target segments can also be represented by DNA or RNA sequences that comprise at least 8 consecutive nucleobases from an internal portion of the sequence of a target segment, and may extend in either or both directions until the conjugated antisense compound comprises about 8 to about 30 nucleobases.

In certain embodiments, antisense compounds targeted to the nucleic acids listed in Table 1 can be modified as described herein. In certain embodiments, the antisense compounds can have a modified sugar moiety, an unmodified sugar moiety or a mixture of modified and unmodified sugar moieties as described herein. In certain embodiments, the antisense compounds can have a modified internucleoside linkage, an unmodified internucleoside linkage or a mixture of modified and unmodified internucleoside linkages as described herein. In certain embodiments, the antisense compounds can have a modified nucleobase, an unmodified nucleobase or a mixture of modified and unmodified nucleobases as described herein. In certain embodiments, the antisense compounds can have a motif as described herein.

In certain embodiments, antisense compounds targeted to the nucleic acids listed in Table 1 can be conjugated as described herein.

1. Protein Tyrosine Phosphatase 1B (PTP1B)

Protein tyrosine phosphatase 1B (PTP1B) is a member of a family of PTPs (Barford, et al., Science 1994. 263: 1397-1404) and is a cytosolic enzyme (Neel and Tonks, Curr. Opin. Cell Biol. 1997. 9: 193-204). PTP1B is expressed ubiquitously including tissues that are key regulators of insulin metabolism such as liver, muscle and fat (Goldstein, Receptor 1993. 3: 1-15), where it is the main PTP enzyme.

PTP1B is considered to be a negative regulator of insulin signaling. PTP1B interacts with and dephosphorylates the insulin receptor, thus attenuating and potentially terminating the insulin signaling transduction (Goldstein et al., J. Biol. Chem. 2000. 275: 4383-4389). The physiological role of PTP1B in insulin signaling has been demonstrated in knockout mice models. Mice lacking the PTP1B gene were protected against insulin resistance and obesity (Elchebly et al., Science 1999. 283: 1544-1548). PTP1B-deficient mice had low adiposity, increased basal metabolic rate as well as total energy expenditure and were protected from diet-induced obesity. Insulin-stimulated glucose uptake was elevated in skeletal muscle, whereas adipose tissue was unaffected providing evidence that increased insulin sensitivity in PTP1B-deficient mice was tissue-specific (Klaman et al., Mol. Cell. Biol. 2000. 20: 5479-5489). These mice were phenotypically normal and were also resistant to diet-induced obesity, insulin resistance and had significantly lower triglyceride levels on a high-fat diet. Therefore, inhibition of PTP1B in patients suffering from Type II diabetes, metabolic syndrome, diabetic dyslipidemia, or related metabolic diseases would be beneficial.

Antisense inhibition of PTP1B provides a unique advantage over traditional small molecule inhibitors in that antisense inhibitors do not rely on competitive binding of the compound to the protein and inhibit activity directly by reducing the expression of PTP1B. Antisense technology is emerging as an effective means for reducing the expression of certain gene products and may therefore prove to be uniquely useful in a number of therapeutic, diagnostic, and research applications for the modulation of PTP1B.

There is a currently a lack of acceptable options for treating metabolic disorders. It is therefore an object herein to provide compounds and methods for the treatment of such diseases and disorder.

All documents, or portions of documents, cited in this application, including, but not limited to, patents, patent applications, articles, books, and treatises, are hereby expressly incorporated-by-reference for the portions of the document discussed herein, as well as in their entirety.

Certain Conjugated Antisense Compounds Targeted to a PTP1B Nucleic Acid

In certain embodiments, conjugated antisense compounds are targeted to a PTP1B nucleic acid having the sequence of GENBANK® Accession No. NM_002827.2, incorporated herein as SEQ ID NO: 1 or GENBANK Accession No. NT_011362.9 truncated from nucleotides 14178000 to Ser.

No. 14/256,000, incorporated herein as SEQ ID NO: 2. In certain such embodiments, a conjugated antisense compound targeted to SEQ ID NO: 1 is at least 90%, at least 95%, or 100% complementary to SEQ ID NOs: 1 and/or 2.

In certain embodiments, a conjugated antisense compound targeted to SEQ ID NO: 1 comprises an at least 8 consecutive nucleobase sequence of SEQ ID NO: 54. In certain embodiments, a conjugated antisense compound targeted to SEQ ID NO: 1 comprises a nucleobase sequence of SEQ ID NO: 54.

In certain embodiments, a conjugated antisense compound targeted to SEQ ID NO: 1 comprises an at least 8 consecutive nucleobase sequence of SEQ ID NO: 55. In certain embodiments, a conjugated antisense compound targeted to SEQ ID NO: 1 comprises a nucleobase sequence of SEQ ID NO: 55.

In certain embodiments, a conjugated antisense compound targeted to SEQ ID NO: 1 comprises an at least 8 consecutive nucleobase sequence of SEQ ID NO: 56. In certain embodiments, a conjugated antisense compound targeted to SEQ ID NO: 1 comprises a nucleobase sequence of SEQ ID NO: 56.

In certain embodiments, a conjugated antisense compound targeted to SEQ ID NO: 1 comprises an at least 8 consecutive nucleobase sequence of SEQ ID NO: 57. In certain embodiments, a conjugated antisense compound targeted to SEQ ID NO: 1 comprises a nucleobase sequence of SEQ ID NO: 57.

TABLE 2

Antisense Compounds targeted to PTP1B SEQ ID NO: 1

| ISIS No | Target Start Site | Sequence (5'-3') | Motif | SEQ ID NO |
|---|---|---|---|---|
| 142082 | 3291 | AAATGGTTTATTCCATGGCC | 5-10-5 MOE | 54 |
| 404173 | 3290 | AATGGTTTATTCCATGGCCA | 5-10-5 MOE | 55 |
| 409826 | 3287 | GGTTTATTCCATGGCCATTG | 5-10-5 MOE | 56 |
| 446431 | 3292 | AATGGTTTATTCCATGGC | 4-10-4 MOE | 57 |

In certain embodiments, a compound comprises or consists of ISIS 142082 and a conjugate group. ISIS 142082 is a modified oligonucleotide having the formula: Aes Aes Aes Tes Ges Gds Tds Tds Tds Ads Tds Tds mCds mCds Ads Tes Ges Ges mCes mCe, wherein,
  A=an adenine,
  mC=a 5'-methylcytosine
  G=a guanine,
  T=a thymine,
  e=a 2'-O-methoxyethyl modified nucleoside,
  d=a 2'-deoxynucleoside, and
  s=a phosphorothioate internucleoside linkage.

In certain embodiments, a compound comprises or consists of ISIS 404173 and a conjugate group. ISIS 404173 is a modified oligonucleotide having the formula: Aes Aes Tes Ges Ges Tds Tds Tds Ads Tds Tds mCds mCds Ads Tds Ges Ges mCes mCes Ae, wherein,
  A=an adenine,
  mC=a 5'-methylcytosine
  G=a guanine,
  T=a thymine,
  e=a 2'-O-methoxyethyl modified nucleoside,
  d=a 2'-deoxynucleoside, and
  s=a phosphorothioate internucleoside linkage.

In certain embodiments, a compound comprises or consists of ISIS 409826 and a conjugate group. ISIS 409826 is a modified oligonucleotide having the formula: Ges Ges Tes Tes Tes Ads Tds Tds mCds mCds Ads Tds Gds Gds mCds mCes Aes Tes Tes Ge, wherein,
  A=an adenine,
  mC=a 5'-methylcytosine
  G=a guanine,
  T=a thymine,
  e=a 2'-O-methoxyethyl modified nucleoside,
  d=a 2'-deoxynucleoside, and
  s=a phosphorothioate internucleoside linkage.

In certain embodiments, a compound comprises or consists of ISIS 446431 and a conjugate group. ISIS 446431 is a modified oligonucleotide having the formula: Aes Aes Tes Ges Gds Tds Tds Tds Ads Tds Tds mCds mCds Ads Tes Ges Ges mCe, wherein,
  A=an adenine,
  mC=a 5'-methylcytosine
  G=a guanine,
  T=a thymine,
  e=a 2'-O-methoxyethyl modified nucleoside,
  d=a 2'-deoxynucleoside, and
  s=a phosphorothioate internucleoside linkage.

In certain embodiments, a compound comprises an antisense oligonucleotide disclosed in U.S. Pat. No. 7,563,884 and WO 2007/131237, which is incorporated by reference in its entirety herein, and a conjugate group described herein. In certain embodiments, a compound comprises an antisense oligonucleotide having a nucleobase sequence of any of SEQ ID NOs 17-96 and 244-389 disclosed in U.S. Pat. No. 7,563,884 and a conjugate group described herein. In certain embodiments, a compound comprises an antisense oligonucleotide having a nucleobase sequence of any of SEQ ID NOs 886-1552 of SEQ ID Nos WO 2007/131237 and a conjugate group described herein. In certain embodiments, a compound comprises an antisense oligonucleotide disclosed in U.S. Pat. No. 7,563,884 and WO 2007/131237, which is incorporated by reference in its entirety herein, and a conjugate group described herein. In certain embodiments, a compound comprises an antisense oligonucleotide having a nucleobase sequence of any of SEQ ID NOs disclosed in U.S. Pat. No. 7,563,884 and WO 2007/131237 and a conjugate group described herein. The nucleobase sequences of all of the aforementioned referenced SEQ ID NOs are incorporated by reference herein.

PTP1B Therapeutic Indications

In certain embodiments, provided herein are methods of treating an individual comprising administering one or more conjugated pharmaceutical compositions as described herein. In certain embodiments, the individual has metabolic related disease.

As shown in the examples below, conjugated compounds targeted to PTP1B, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain. In certain of the experiments, the conjugated compounds reduced blood glucose levels, e.g., the animals continued to experience symptoms, but the symptoms were less severe compared to untreated animals. In other of the experiments, however, the conjugated compounds appear to reduce the symptoms of diabetes; e.g., animals treated for a longer period of time experienced less severe symptoms than those administered the compounds for a shorter period of time. In other of the experiments, however, the conjugated compounds appear to inhibit weight gain; e.g., animals treated for a longer period of time experienced less severe symptoms than those administered the compounds for a shorter period of time. In other of the experiments, however, the conjugated compounds appear to inhibit hypertriglyceridemia; e.g., animals treated for a longer period of time experienced less severe symptoms than those administered the compounds for a shorter period of time. The ability of the conjugated compounds exemplified below to restore function therefore demonstrates that symptoms of the disease may be reversed by treatment with a compound as described herein.

Diabetes mellitus is characterized by numerous physical and physiological symptoms. Any symptom known to one of skill in the art to be associated with Type 2 diabetes can be ameliorated or otherwise modulated as set forth above in the methods described above. In certain embodiments, the symptom is a physical symptom selected from the group consisting of increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums In certain embodiments, the symptom is a physiological symptom selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

Liu and Chernoff have shown that PTP1B binds to and serves as a substrate for the epidermal growth factor receptor (EGFR) (Liu and Chernoff, *Biochem. J.*, 1997, 327, 139-145). Furthermore, in A431 human epidermoid carcinoma cells, PT1B was found to be inactivated by the presence of $H_2O_2$ generated by the addition of EGF. These studies indicate that PTP1B can be negatively regulated by the oxidation state of the cell, which is often deregulated during tumorigenesis (Lee et al., *J. Biol. Chem.*, 1998, 273, 15366-15372).

Overexpression of PTP1B has been demonstrated in malignant ovarian cancers and this correlation was accompanied by a concomitant increase in the expression of the associated growth factor receptor (Wiener et al., *Am. J. Obstet. Gynecol.*, 1994, 170, 1177-1183).

PTP1B has been shown to suppress transformation in NIH3T3 cells induced by the neu oncogene (Brown-Shimer et al., *Cancer Res.*, 1992, 52, 478-482), as well as in rat 3Y1 fibroblasts induced by v-srk, v-src, and v-ras (Liu et al., *Mol. Cell. Biol.*, 1998, 18, 250-259) and rat-1 fibroblasts induced by bcr-abl (LaMontagne et al., *Proc. Natl. Acad. Sci. U.S.A*, 1998, 95, 14094-14099). It has also been shown that PTP1B promotes differentiation of K562 cells, a chronic myelogenous leukemia cell line, in a similar manner as does an inhibitor of the bcr-abl oncoprotein. These studies describe the possible role of PTP1B in controlling the pathogenesis of chronic myeloid leukemia (LaMontagne et al., *Proc. Natl. Acad. Sci. U.S.A*, 1998, 95, 14094-14099).

Accordingly, provided herein are methods for ameliorating a symptom associated with hyperproliferative disorders in a subject in need thereof. In certain embodiments, the hyperproliferative disorder is cancer. In certain embodiments, provided herein are methods for ameliorating a symptom associated with cancer. In certain embodiments, provided is a method for reducing the rate of onset of a symptom associated with hyperproliferative disorders. In certain embodiments, provided is a method for reducing the rate of onset of a symptom associated with cancer. In certain embodiments, provided is a method for reducing the severity of a symptom associated with hyperproliferative disorders. In certain embodiments, provided is a method for reducing the severity of a symptom associated with cancer. In such embodiments, the methods comprise administering to an individual in need thereof a therapeutically effective amount of a compound targeted to a PTP1B nucleic acid.

In certain embodiments, provided are methods of treating an individual comprising administering one or more conjugated pharmaceutical compositions as described herein. In certain embodiments, the individual has metabolic related disease.

In certain embodiments, administration of a conjugated antisense compound targeted to a PTP1B nucleic acid results in reduction of PTP1B expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising a conjugated antisense compound targeted to PTP1B are used for the preparation of a medicament for treating a patient suffering or susceptible to metabolic related disease.

In certain embodiments, the methods described herein include administering a compound comprising a conjugate group and a modified oligonucleotide having a contiguous nucleobases portion as described herein of a sequence recited in SEQ ID NOs: 54-57.

It will be understood that any of the compounds described herein can be used in the aforementioned methods and uses. For example, in certain embodiments a conjugated antisense compound targeted to a PTP1B nucleic acid in the aforementioned methods and uses can include, but is not limited to, a conjugated antisense compound targeted to SEQ ID NO: 1 comprising an at least 8 consecutive nucleobase sequence of any of SEQ ID NOs: 54-57; a conjugated antisense compound targeted to SEQ ID NO: 1 comprising a nucleobase sequence of any of SEQ ID NOs: 54-57; a compound comprising or consisting of ISIS 142082, ISIS 404173, ISIS 409826, or ISIS 446431 and a conjugate group; a compound comprising an antisense oligonucleotide disclosed in U.S. Pat. No. 7,563,884 and WO 2007/131237, which is incorporated by reference in its entirety herein, and a conjugate group; a compound comprising an antisense oligonucleotide having a nucleobase sequence of any of SEQ ID NOs 17-96 and 244-389 disclosed in U.S. Pat. No. 7,563,884 and a conjugate group described herein; or a compound comprising an antisense oligonucleotide having a nucleobase sequence of any of—SEQ ID NOs 886-1552 disclosed in WO 2007/131237 and a conjugate group described herein.

2. FGFR4

Obesity is considered a long-term metabolic disease. There are several serious medical sequelae related to obesity. There are over 1 billion overweight individuals worldwide with 100 million clinically obese. The increasing health care costs of treating obesity related diseases in the US alone are estimated at over $100 billion annually. Current methods for treating obesity include behavioral modification, diet, surgery (gastroplasty), administering pharmaceutical agents that block appetite stimulating signals or absorption of nutrients (fat), and administering agents that increase thermogenesis or fat metabolism. Some of these methods have disadvantages in that they rely on patient resolve, are invasive, or have unwanted side effects. An understanding of the mechanisms by which obesity is regulated may provide important therapeutic information.

Obesity is frequently associated with insulin resistance and together constitutes risk factors for later development of type 2 diabetes and cardiovascular diseases. Insulin resistance occurs well before development of type 2 diabetes, and insulin is overproduced to compensate for the insulin resistance and to maintain normal glucose levels. Type 2 diabetes ensues, as the pancreas can no longer produce enough insulin to maintain normal glucose levels. Early stages of type 2 diabetes are associated with elevated levels of insulin but as the disease progresses the pancreas may fail to produce insulin, resulting in increased blood glucose levels. Diabetes is a significant risk factor for both heart disease and stroke and is the leading cause of blindness and end-stage renal failure.

Diabetes is a disorder characterized by hyperglycemia due to deficient insulin action that may result from reduced insulin production or insulin resistance or both. Diabetes mellitus is a polygenic disorder affecting a significant portion of the people in the world. It is divided into two types. In type I diabetes, or insulin-dependent diabetes mellitus (IDDM), patients produce little or no insulin, the hormone that regulates glucose utilization. In type 2 diabetes, or noninsulin-dependent diabetes mellitus (NIDDM), patients often have plasma insulin levels that are the same compared to nondiabetic humans; however, these patients have developed a resistance to the insulin stimulating effect of glucose and lipid metabolism in the main insulin-sensitive tissues, i.e., muscle, liver and adipose tissues, and the plasma insulin levels are insufficient to overcome the pronounced insulin resistance. Additionally, glucotoxicity, which results from long-term hyperglycemia, induces tissue-dependent insulin resistance (Nawano et al., *Am. J. Physiol. Endocrinol. Metab.*, 278, E535-543) exacerbating the disease. Type 2 diabetes accounts for over 90% of all diabetes cases. It is a metabolic disorder characterized by hyperglycemia leading to secondary complications such as neuropathy, nephropathy, retinopathy, hypertriglyceridemia, obesity, and other cardiovascular diseases generally referred to as metabolic syndrome.

Metabolic syndrome is a combination of medical disorders that increase one's risk for cardiovascular disease and diabetes. The symptoms, including high blood pressure, high triglycerides, decreased HDL and obesity, tend to appear together in some individuals. Metabolic syndrome is known under various other names, such as (metabolic) syndrome X, insulin resistance syndrome or Reaven's syndrome.

Diabetes and obesity (sometimes now collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., *Physiol Res.*, 51, 85-91). Additionally, several compounds on the market for the treatment of diabetes are known to induce weight gain, a very undesirable side effect to the treatment of this disease. Therefore, a compound that has the potential to treat both diabetes and obesity would provide a significant improvement over current treatments.

Fibroblast growth factor receptor 4 (also known as FGF receptor-4, TKF; tyrosine kinase related to fibroblast growth factor receptor; hydroxyaryl-protein kinase; tyrosylprotein kinase; Fgfr4; FGFR-4; FGFR4; CD334, FGFR4_HUMAN and JTK2) has high affinity for the acidic and/or basic fibroblast growth factors. (Armstrong et al., *Genes Chromosomes Cancer*, 4, 94-98).

Although FGFRs generally have been shown to have wide distribution throughout the body, to date, FGFR4 has only been found in a few tissues. Among a wide variety of cells and tissues tested, including human lymphocytes and macrophages, FGFR4 was found to be expressed in the lung and in some tumors of lung origin as well as in malignancies not derived from lung tissues. (Holtrich et al., *Proc. Nat. Acad. Sci.*, 88, 10411-10415). FGFR4 has also been found to be expressed in the liver and in adipose tissues. (Patel et al., *JCEM*, 90(2), 1226-1232). FGFR4 has also been found to be expressed in certain carcinoma cell lines. (Bange et al., *Cancer Res.*, 62, 840-847).

Additionally, FGFR4 has been shown to play a role in systemic lipid and glucose homeostasis. FGFR4-deficient mice on a normal diet exhibited features of metabolic syndrome that include increase mass of insulin resistance, in addition to hypercholesterolemia. FGFR4 deficiency was shown to alleviate high-fat diet-induced fatty liver in a certain obese mouse model, which is also a correlate of metabolic syndrome. Restoration of FGFR4, specifically in hepatocytes of FGFR4 deficient mice, decrease plasma lipid level and restored the high fat diet-induced fatty liver but failed to restore glucose tolerance and sensitivity to insulin. (Huang et al., *Diabetes*, 56, 2501-2510).

Antisense inhibition of FGFR4 provides a unique advantage over traditional small molecule inhibitors in that antisense inhibitors do not rely on competitive binding of the compound to the protein and inhibit activity directly by reducing the expression of FGFR4. A representative United States patent that teaches FGFR4 antisense inhibitors includes US. Pat. Publication No. US2010/0292140, of which is herein incorporated by reference in its entirety. Antisense technology is emerging as an effective means for reducing the expression of certain gene products and may therefore prove to be uniquely useful in a number of therapeutic, diagnostic, and research applications for the modulation of FGFR4.

There is a currently a lack of acceptable options for treating metabolic disorders. It is therefore an object herein to provide compounds and methods for the treatment of such diseases and disorder. This invention relates to the discovery of novel, highly potent inhibitors of FGFR4 gene expression.

All documents, or portions of documents, cited in this application, including, but not limited to, patents, patent applications, articles, books, and treatises, are hereby expressly incorporated-by-reference for the portions of the document discussed herein, as well as in their entirety.

Certain Conjugated Antisense Compounds Targeted to a FGFR4 Nucleic Acid

In certain embodiments, conjugated antisense compounds are targeted to a FGFR4 nucleic acid having the sequence GENBANK Accession No. NM_002011.3 (incorporated herein as SEQ ID NO: 3), GENBANK Accession No: NT_023133.11 truncated from nucleosides 21323018 to 21335213 (incorporated herein as SEQ ID NO: 4); and GENBANK Accession No. AB209631.1 (incorporated herein as SEQ ID NO: 5); and GENBANK Accession No NM_022963.2 (incorporated herein as SEQ ID NO: 6). In certain such embodiments, a conjugated antisense compound targeted to SEQ ID NOs: 3-6 is at least 90%, at least 95%, or 100% complementary to SEQ ID NOs: 3-6.

In certain embodiments, a conjugated antisense compound targeted to SEQ ID NO: 3 comprises an at least 8 consecutive nucleobase sequence of any one of SEQ ID NOs: 58-65. In certain embodiments, a conjugated antisense compound targeted to SEQ ID NO: 3 comprises a nucleobase sequence of any one of SEQ ID NO: 12-19.

In certain embodiments, a conjugated antisense compound targeted to SEQ ID NO: 3 comprises an at least 8 consecutive nucleobase sequence of SEQ ID NO: 58. In certain embodiments, a conjugated antisense compound targeted to SEQ ID NO: 3 comprises a nucleobase sequence of SEQ ID NO: 59.

In certain embodiments, a conjugated antisense compound targeted to SEQ ID NO: 3 comprises an at least 8 consecutive nucleobase sequence of SEQ ID NO: 59. In certain embodiments, a conjugated antisense compound targeted to SEQ ID NO: 3 comprises a nucleobase sequence of SEQ ID NO: 59.

In certain embodiments, a conjugated antisense compound targeted to SEQ ID NO: 3 comprises an at least 8 consecutive nucleobase sequence of SEQ ID NO: 60. In certain embodiments, a conjugated antisense compound targeted to SEQ ID NO: 3 comprises a nucleobase sequence of SEQ ID NO: 60.

In certain embodiments, a conjugated antisense compound targeted to SEQ ID NO: 3 comprises an at least 8 consecutive nucleobase sequence of SEQ ID NO: 61. In certain embodiments, a conjugated antisense compound targeted to SEQ ID NO: 3 comprises a nucleobase sequence of SEQ ID NO: 61.

In certain embodiments, a conjugated antisense compound targeted to SEQ ID NO: 3 comprises an at least 8 consecutive nucleobase sequence of SEQ ID NO: 62. In certain embodiments, a conjugated antisense compound targeted to SEQ ID NO: 3 comprises a nucleobase sequence of SEQ ID NO: 62.

In certain embodiments, a conjugated antisense compound targeted to SEQ ID NO: 3 comprises an at least 8 consecutive nucleobase sequence of SEQ ID NO: 63. In certain embodiments, a conjugated antisense compound targeted to SEQ ID NO: 3 comprises a nucleobase sequence of SEQ ID NO: 63.

In certain embodiments, a conjugated antisense compound targeted to SEQ ID NO: 3 comprises an at least 8 consecutive nucleobase sequence of SEQ ID NO: 64. In certain embodiments, a conjugated antisense compound targeted to SEQ ID NO: 3 comprises a nucleobase sequence of SEQ ID NO: 64.

In certain embodiments, a conjugated antisense compound targeted to SEQ ID NO: 3 comprises an at least 8 consecutive nucleobase sequence of SEQ ID NO: 65. In certain embodiments, a conjugated antisense compound targeted to SEQ ID NO: 3 comprises a nucleobase sequence of SEQ ID NO: 65.

TABLE 3

Antisense Compounds targeted to FGFR4 SEQ ID NO: 3

| ISIS No | Target Start Site | Sequence (5'-3') | Motif | SEQ ID NO |
|---|---|---|---|---|
| 299005 | 192 | GGCACACTCAGCAGGACCCC | 5-10-5 MOE | 58 |
| 463588 | 191 | GCACACTCAGCAGGACCCCC | 5-10-5 MOE | 59 |
| 463589 | 193 | AGGCACACTCAGCAGGACCC | 5-10-5 MOE | 60 |
| 463690 | 369 | GCCAGGCGACTGCCCTCCTT | 5-10-5 MOE | 61 |
| 463691 | 370 | TGCCAGGCGACTGCCCTCCT | 5-10-5 MOE | 62 |
| 463835 | 788 | CGCTCTCCATCACGAGACTC | 5-10-5 MOE | 63 |
| 463837 | 790 | CACGCTCTCCATCACGAGAC | 5-10-5 MOE | 64 |
| 464225 | 2954 | CTTCCAGCTTCTCTGGGCTC | 5-10-5 MOE | 65 |

In certain embodiments, a compound comprises or consists of ISIS 299005 and a conjugate group. ISIS 299005 is a modified oligonucleotide having the formula: Ges Ges mCes Aes mCes Ads mCds Tds mCds Ads Gds mCds Ads Gds Gds Aes mCes mCes mCes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 463588 and a conjugate group. ISIS 463588 is a modified oligonucleotide having the formula: Ges mCes Aes mCes Aes mCds Tds mCds Ads Gds mCds Ads Gds Gds Ads mCes mCes mCes mCes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 463589 and a conjugate group. ISIS 463589 is a modified oligonucleotide having the formula: Aes Ges Ges mCes Aes mCds Ads mCds Tds mCds Ads Gds mCds Ads Gds Ges Aes mCes mCes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 463690 and a conjugate group. ISIS 463690 is a modified oligonucleotide having the formula: Ges mCes mCes Aes Ges Gds mCds Gds Ads mCds Tds Gds mCds mCds Tes mCes mCes Tes Te, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 463691 and a conjugate group. ISIS 463691 is a modified oligonucleotide having the formula: Tes Ges mCes mCes Aes Gds Gds mCds Gds Ads mCds Tds Gds mCds mCds mCes Tes mCes mCes Te, wherein A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 463835 and a conjugate group. ISIS 463835 is a modified oligonucleotide having the formula: mCes Ges mCes Tes mCes Tds mCds mCds Ads Tds mCds Ads mCds Gds Ads Ges Aes mCes Tes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 463837 and a conjugate group. ISIS 463837 is a modified oligonucleotide having the formula: mCes Aes mCes Ges mCes Tds mCds Tds mCds mCds Ads Tds mCds Ads mCds Ges Aes Ges Aes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 464225 and a conjugate group. ISIS 464225 is a modified oligonucleotide having the formula: mCes Tes Tes mCes mCes Ads Gds mCds Tds Tds mCds Tds mCds Tds Gds Ges Ges mCes Tes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises an antisense oligonucleotide disclosed in WO 2009/046141, which are incorporated by reference in their entireties herein, and a conjugate group. In certain embodiments, a compound comprises an antisense oligonucleotide having a nucleobase sequence of any of SEQ ID NOs 21-24, 28, 29, 36, 38, 39, 43, 48, 51, 54-56, 58-60, 64-66, 92-166 disclosed in WO 2009/046141 and a conjugate group described herein. In certain embodiments, a compound comprises an antisense oligonucleotide having a nucleobase sequence complementary to a preferred target segment of any of SEQ ID NOs 21-24, 28, 29, 36, 38, 39, 43, 48, 51, 54-56, 58-60, 64-66, 92-166 disclosed in WO 2009/046141 and a conjugate group described herein. The nucleobase sequences of all of the aforementioned referenced SEQ ID NOs are incorporated by reference herein.

FGFR4 Therapeutic Indications

In certain embodiments, provided herein are methods of treating an individual comprising administering one or more pharmaceutical compositions as described herein. In certain embodiments, the individual has a metabolic disease.

As shown in the examples below, conjugated compounds targeted to FGFR4, as described herein, have been shown to reduce the severity of physiological symptoms of a metabolic disease, including obesity or adiposity, metabolic syndrome, diabetes mellitus, insulin resistance, diabetic dyslipidemia, and hypertriglyceridemia. In certain of the experiments, the conjugated compounds reduced body weight, e.g., the animals continued to experience symptoms, but the symptoms were less severe compared to untreated animals. In certain of the experiments, the conjugated compounds reduced body fat, e.g., the animals continued to experience symptoms, but the symptoms were less severe compared to untreated animals. In certain of the experiments, the conjugated compounds reduced adipose tissue, e.g., the animals continued to experience symptoms, but the symptoms were less severe compared to untreated animals. In other of the experiments, however, the conjugated compounds appear to reduce the symptoms of obesity; e.g., animals treated for a longer period of time experienced less severe symptoms than those administered the compounds for a shorter period of time. In other of the experiments, however, the conjugated compounds appear to reduce the symptoms of diabetes; e.g., animals treated for a longer period of time experienced less severe symptoms than those administered the compounds for a shorter period of time. In other of the experiments, however, the conjugated compounds appear to inhibit weight gain; e.g., animals treated for a longer period of time experienced less severe symptoms than those administered the compounds for a shorter period of time. In other of the experiments, however, the conjugated compounds appear to reduce glucose levels; e.g., animals treated for a longer period of time experienced less severe symptoms than those administered the compounds for a shorter period of time. In other of the experiments, however, the conjugated compounds appear to increase fatty acid oxidation; e.g., animals treated for a longer period of time experienced less severe symptoms than those administered the compounds for a shorter period of time. The ability of the conjugated compounds exemplified below to restore function therefore demonstrates that symptoms of the disease may be reversed by treatment with a compound as described herein.

Obesity is characterized by numerous physical and physiological symptoms. Any symptom known to one of skill in the art to be associated with obesity can be ameliorated or otherwise modulated as set forth above in the methods described above. In certain embodiments, the symptom is a physical symptom selected from the group consisting of increased adipose tissue mass or weight, increased weight gain, increased fat pad weight, imbalance with caloric intake and energy expenditure, increase in body fat, increase in body mass, having a body mass index (BMI) of 30 or higher, increase in body frame, increased sweating, sleep apnea, difficulty in sleeping, inability to cope with sudden physical activity, lethargy, back and joint problems, increase in breathlessness, increase in breast region adiposity, increase in abdomen size or fat, extreme hunger, or extreme fatigue.

In certain embodiments, the symptom is a physiological symptom selected from the group consisting of high blood pressure, hypertension, high cholesterol levels, type 2 diabetes, stroke, cardiac insufficiency, heart disease, coronary artery obstruction, breast cancer in women, gastro-oesophageal reflux disease, hip and knee arthrosis, and reduced life expectancy.

In certain embodiments, the physical symptom is excess body weight. In certain embodiments, the symptom is excess fat mass. In certain embodiments, the symptom is a body mass index of 30 or higher. In certain embodiments, the symptom is breathlessness. In certain embodiments, the symptom is increased sweating. In certain embodiments, the symptom is sleep apnea. In certain embodiments, the symptom is difficulty in sleeping. In certain embodiments, the symptom is inability to cope with sudden physical activity. In certain embodiments, the symptom is lethargy. In certain embodiments, the symptom is back and joint problems.

In certain embodiments, the physiological symptom is high blood pressure. In certain embodiments, the symptom is hypertension. In certain embodiments, the symptom is high cholesterol levels. In certain embodiments, the symptom is type 2 diabetes. In certain embodiments, the symptom is stroke. In certain embodiments, the symptom is cardiac insufficiency. In certain embodiments, the symptom is heart disease. In certain embodiments, the symptom is coronary artery obstruction. In certain embodiments, the symptom is breast cancer in women. In certain embodiments, the symptom is gastro-oesophageal reflux disease. In certain embodiments, the symptom is hip and knee arthrosis. In certain embodiments, the symptom is reduced life expectancy.

Diabetes mellitus is characterized by numerous physical and physiological symptoms. Any symptom known to one of skill in the art to be associated with Type 2 diabetes can be ameliorated or otherwise modulated as set forth above in the methods described above. In certain embodiments, the symptom is a physical symptom selected from the group consisting of increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums In certain embodiments, the symptom is a physiological symptom selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical symptom is increased weight gain. In certain embodiments, the symptom is frequent urination. In certain embodiments, the symptom is unusual thirst. In certain embodiments, the symptom is extreme hunger. In certain embodiments, the symptom is extreme fatigue. In certain embodiments, the symptom is blurred vision. In certain embodiments, the symptom is frequent infections. In certain embodiments, the symptom is tingling or numbness at the extremities. In certain embodiments, the symptom is dry and itchy skin. In certain embodiments, the symptom is weight loss. In certain embodiments, the symptom is slow-healing sores. In certain embodiments, the symptom is swollen gums. In certain embodiments, the symptom is increased insulin resistance. In certain embodiments, the symptom is increased fat mass. In certain embodiments, the symptom is decreased metabolic rate. In certain embodiments, the symptom is decreased glucose clearance. In certain embodiments, the symptom is decreased glucose tolerance. In certain embodiments, the symptom is decreased insulin sensitivity. In certain embodiments, the symptom is decreased hepatic insulin sensitivity. In certain embodiments, the symptom is increased adipose tissue size and weight. In certain embodiments, the symptom is increased body fat. In certain embodiments, the symptom is increased body weight.

In certain embodiments, provided are methods of treating an individual comprising administering one or more pharmaceutical compositions as described herein. In certain embodiments, the individual has metabolic related disease.

In certain embodiments, administration of a conjugated antisense compound targeted to a FGFR4 nucleic acid results in reduction of FGFR4 expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising a conjugated antisense compound targeted to FGFR4 are used for the preparation of a medicament for treating a patient suffering or susceptible to a metabolic disease.

In certain embodiments, the methods described herein include administering a conjugated compound comprising a modified oligonucleotide having a contiguous nucleobases portion as described herein of a sequence recited in SEQ ID NO: 58-65.

It will be understood that any of the compounds described herein can be used in the aforementioned methods and uses. For example, in certain embodiments a conjugated antisense compound targeted to a FGFR4 nucleic acid in the aforementioned methods and uses can include, but is not limited to, a conjugated antisense compound targeted to SEQ ID NO: 3 comprising an at least 8 consecutive nucleobase sequence of any one of SEQ ID NOs: 58-65; a conjugated antisense compound targeted to SEQ ID NO: 3 comprising a nucleobase sequence of any one of SEQ ID NO: 58-65; a compound comprising or consisting of ISIS 299005, ISIS 463588, ISIS 463589, ISIS 463690, ISIS 463691, ISIS 463835, ISIS 463837, or ISIS 464225 and a conjugate group; a compound comprising an antisense oligonucleotide disclosed in WO 2009/046141, which are incorporated by reference in their entireties herein, and a conjugate group; a compound comprising an antisense oligonucleotide having a nucleobase sequence of any of SEQ ID NOs SEQ ID NOs 21-24, 28, 29, 36, 38, 39, 43, 48, 51, 54-56, 58-60, 64-66, 92-166 disclosed in WO 2009/046141 and a conjugate group described herein; or a compound comprising an antisense oligonucleotide having a nucleobase sequence complementary to a preferred target segment of any of SEQ ID NOs 21-24, 28, 29, 36, 38, 39, 43, 48, 51, 54-56, 58-60, 64-66, 92-166 disclosed in WO 2009/046141 and a conjugate group described herein. The nucleobase sequences of all of the aforementioned referenced SEQ ID NOs are incorporated by reference herein.

3. GCCR

Diabetes is a chronic metabolic disorder characterized by impaired insulin secretion and/or action. In type 2 diabetes (T2DM), insulin resistance leads to an inability of insulin to control the activity of gluconeogenic enzymes, and many subjects also exhibit inappropriate levels of circulating glucagon (GC) in the fasting and postprandial state. Glucagon is secreted from the α-cells of the pancreatic islets and regulates glucose homeostasis through modulation of hepatic glucose production (Quesada et al., J. Endocrinol. 2008. 199: 5-19).

Glucagon exerts its action on target tissues via the activation of glucocorticoid receptor (GCCR). The glucocorticoid receptor is a 62 kDa protein that is a member of the class B G-protein coupled family of receptors (Brubaker et al., Recept. Channels. 2002. 8: 179-88). GCCR activation leads to signal transduction by G proteins ($G_s\alpha$ and $G_q$), whereby $G_s\alpha$ activates adenylate cyclase, which causes cAMP production, resulting in an increase in levels of protein kinase A. GCCR signaling in the liver results in increased hepatic glucose production by induction of glycogenolysis and gluconeogenesis along with inhibition of glycogenesis (Jiang and Zhang. Am. J. Physiol. Endocrinol. Metab. 2003. 284: E671-E678). GCCR is also expressed in extrahepatic tissues, which includes heart, intestinal smooth muscle, kidney, brain, and adipose tissue (Hansen et al., Peptides. 1995. 16: 1163-1166).

Development of GCCR inhibitors have been hampered by the unfavorable side effects associated with systemic GCCR inhibition, including activation of the hypothalamic-pituitary adrenal (HPA) axis. Inhibition of GCCR activity in the brain can lead to an increase in circulating adrenocorticotropic hormone due to feedback regulation and a consequent increase in secretion of adrenal steroids (Philibert et al., Front. Horm. Res. 1991. 19: 1-17). This, in turn, can produce a myriad of negative chronic steroid-related side-effects. Other studies have demonstrated that specific inactivation of GCCR resulted in hypoglycemia upon prolonged fasting (Opherk et al., Mol. Endocronol. 2004. 18: 1346-1353).

It has previously been demonstrated in pre-clinical models that administration of GCCR antisense oligonucleotides results in tissue-specific accumulation and reduced GCCR expression in liver and adipose tissue (PCT Pub. No. WO2005/071080; PCT Pub. No. WO2007/035759) without affecting GCCR mRNA levels in the CNS or adrenal glands. Thus, antisense inhibition of GCCR mRNA expression has be shown to improve hyperglycemia and hyperlipidemia without activating the HPA axis. The present invention provides compositions and methods for modulating GCCR expression. Antisense compounds for modulating expression of GCCR are disclosed in the aforementioned published patent applications. However, there remains a need for additional improved compounds. The compounds and treatment methods described herein provide significant advantages over the treatments options currently available for GCCR related disorders. All documents, or portions of documents, cited in this application, including, but not limited to, patents, patent applications, articles, books, and treatises, are hereby expressly incorporated-by-reference for the portions of the document discussed herein, as well as in their entirety.

Certain Conjugated Antisense Compounds Targeted to a GCCR Nucleic Acid

In certain embodiments, conjugated antisense compounds are targeted to a GCCR nucleic acid having the sequence the complement of GENBANK Accession No. NT_029289.10 truncated from nucleotides 3818000 to U.S. Pat. No. 3,980,000 (incorporated herein as SEQ ID NO: 7). In certain such embodiments, a conjugated antisense compound targeted to SEQ ID NO: 7 is at least 90%, at least 95%, or 100% complementary to SEQ ID NO: 7.

In certain embodiments, a conjugated antisense compound targeted to SEQ ID NO: 7 comprises an at least 8 consecutive nucleobase sequence of any one of SEQ ID NOs: 66-77. In certain embodiments, a conjugated antisense compound targeted to SEQ ID NO: 7 comprises a nucleobase sequence of any one of SEQ ID NO: 66-77.

In certain embodiments, a conjugated antisense compound targeted to SEQ ID NO: 7 comprises an at least 8 consecutive nucleobase sequence of SEQ ID NO: 66. In certain embodiments, a conjugated antisense compound targeted to SEQ ID NO: 7 comprises a nucleobase sequence of SEQ ID NO: 66.

In certain embodiments, a conjugated antisense compound targeted to SEQ ID NO: 7 comprises an at least 8 consecutive nucleobase sequence of SEQ ID NO: 67. In certain embodiments, a conjugated antisense compound targeted to SEQ ID NO: 7 comprises a nucleobase sequence of SEQ ID NO: 67.

In certain embodiments, a conjugated antisense compound targeted to SEQ ID NO: 7 comprises an at least 8 consecutive nucleobase sequence of SEQ ID NO: 68. In certain embodiments, a conjugated antisense compound targeted to SEQ ID NO: 7 comprises a nucleobase sequence of SEQ ID NO: 68.

In certain embodiments, a conjugated antisense compound targeted to SEQ ID NO: 7 comprises an at least 8 consecutive nucleobase sequence of SEQ ID NO: 69. In certain embodiments, a conjugated antisense compound targeted to SEQ ID NO: 7 comprises a nucleobase sequence of SEQ ID NO: 69.

In certain embodiments, a conjugated antisense compound targeted to SEQ ID NO: 7 comprises an at least 8 consecutive nucleobase sequence of SEQ ID NO: 70. In certain embodiments, a conjugated antisense compound targeted to SEQ ID NO: 7 comprises a nucleobase sequence of SEQ ID NO: 70.

In certain embodiments, a conjugated antisense compound targeted to SEQ ID NO: 7 comprises an at least 8 consecutive nucleobase sequence of SEQ ID NO: 71. In certain embodiments, a conjugated antisense compound targeted to SEQ ID NO: 7 comprises a nucleobase sequence of SEQ ID NO: 71.

In certain embodiments, a conjugated antisense compound targeted to SEQ ID NO: 7 comprises an at least 8 consecutive nucleobase sequence of SEQ ID NO: 72. In certain embodiments, a conjugated antisense compound targeted to SEQ ID NO: 7 comprises a nucleobase sequence of SEQ ID NO: 72.

In certain embodiments, a conjugated antisense compound targeted to SEQ ID NO: 7 comprises an at least 8 consecutive nucleobase sequence of SEQ ID NO: 73. In certain embodiments, a conjugated antisense compound targeted to SEQ ID NO: 7 comprises a nucleobase sequence of SEQ ID NO: 73.

In certain embodiments, a conjugated antisense compound targeted to SEQ ID NO: 7 comprises an at least 8 consecutive nucleobase sequence of SEQ ID NO: 74. In certain embodiments, a conjugated antisense compound targeted to SEQ ID NO: 7 comprises a nucleobase sequence of SEQ ID NO: 74.

In certain embodiments, a conjugated antisense compound targeted to SEQ ID NO: 7 comprises an at least 8 consecutive nucleobase sequence of SEQ ID NO: 75. In certain embodiments, a conjugated antisense compound targeted to SEQ ID NO: 7 comprises a nucleobase sequence of SEQ ID NO: 75.

In certain embodiments, a conjugated antisense compound targeted to SEQ ID NO: 7 comprises an at least 8 consecutive nucleobase sequence of SEQ ID NO: 76. In certain embodiments, a conjugated antisense compound targeted to SEQ ID NO: 7 comprises a nucleobase sequence of SEQ ID NO: 76.

In certain embodiments, a conjugated antisense compound targeted to SEQ ID NO: 7 comprises an at least 8 consecutive nucleobase sequence of SEQ ID NO: 77. In certain embodiments, a conjugated antisense compound targeted to SEQ ID NO: 7 comprises a nucleobase sequence of SEQ ID NO: 77.

TABLE 4

Antisense Compounds targeted to GCCR SEQ ID NO: 7

| ISIS No | Target Start Site | Sequence (5'-3') | Motif | SEQ ID NO |
|---|---|---|---|---|
| 420470 | 57825 | GGTAGAAATATAGTTGTTCC | 5-10-5 MOE | 66 |
| 420476 | 59956 | TTCATGTGTCTGCATCATGT | 5-10-5 MOE | 67 |

TABLE 4-continued

Antisense Compounds targeted to GCCR SEQ ID NO: 7

| ISIS No | Target Start Site | Sequence (5'-3') | Motif | SEQ ID NO |
|---|---|---|---|---|
| 426115 | 65940 | GCAGCCATGGTGATCAGGAG | 5-10-5 MOE | 68 |
| 426130 | 63677 | GCATCCAGCGAGCACCAAAG | 5-10-5 MOE | 69 |
| 426168 | 76224 | GTCTGGATTACAGCATAAAC | 5-10-5 MOE | 70 |
| 426172 | 76229 | CCTTGGTCTGGATTACAGCA | 5-10-5 MOE | 71 |
| 426183 | 65938 | AGCCATGGTGATCAGGAGGC | 3-14-3 MOE | 72 |
| 426246 | 76225 | GGTCTGGATTACAGCATAAA | 3-14-3 MOE | 73 |
| 426261 | 65938 | AGCCATGGTGATCAGGAGGC | 2-13-5 MOE | 74 |
| 426262 | 65939 | CAGCCATGGTGATCAGGAGG | 2-13-5 MOE | 75 |
| 426267 | 95513 | GTGCTTGTCCAGGATGATGC | 2-13-5 MOE | 76 |
| 426325 | 76229 | CCTTGGTCTGGATTACAGCA | 2-13-5 MOE | 77 |

In certain embodiments, a compound comprises or consists of ISIS 420470 and a conjugate group. ISIS 420470 is a modified oligonucleotide having the formula: Ges Ges Tes Aes Ges Ads Ads Ads Tds Ads Tds Ads Gds Tds Tds Ges Tes Tes mCes mCe, wherein
A=an adenine,
mC=a 5'-methylctosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 420476 and a conjugate group. ISIS 420476 is a modified oligonucleotide having the formula: Tes Tes mCes Aes Tes Gds Tds Gds Tds mCds Tds Gds mCds Ads Tds mCes Aes Tes Ges Te, wherein
A=an adenine,
mC=a 5'-methylctosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426115 and a conjugate group. ISIS 426115 is a modified oligonucleotide having the formula: Ges mCes Aes Ges mCes mCds Ads Tds Gds Gds Tds Gds Ads Tds mCds Aes Ges Ges Aes Ge, wherein
A=an adenine,
mC=a 5'-methylcytosine
G=a guanine,
T=a thymine,
e=a 2'-O-methoxyethyl modified nucleoside.,
d=a 2'-deoxynucleoside., and
s=a phosphorothioate internucleoside linkage.

In certain embodiments, a compound comprises or consists of ISIS 426130 and a conjugate group. ISIS 426130 is a modified oligonucleotide having the formula: Ges mCes Aes Tes mCes mCds Ads Gds mCds Gds Ads Gds mCds Ads mCds mCes Aes Aes Aes Ge, wherein A=an adenine,
mC=a 5'-methylctosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426168 and a conjugate group. ISIS 426168 is a modified oligonucleotide having the formula: Ges Tes mCes Tes Ges Gds Ads Tds Tds Ads mCds Ads Gds mCds Ads Tes Aes Aes Aes mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426172 and a conjugate group. ISIS 426172 is a modified oligonucleotide having the formula: mCes mCes Tes Tes Ges Gds Tds mCds Tds Gds Gds Ads Tds Tds Ads mCes Aes Ges mCes Ae, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426183 and a conjugate group. ISIS 426183 is a modified oligonucleotide having the formula: Aes Ges mCes mCds Ads Tds Gds Gds Tds Gds Ads Tds mCds Ads Gds Gds Ads Ges Ges mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426246 and a conjugate group. ISIS 426246 is a modified oligonucleotide having the formula: Ges Ges Tes mCds Tds Gds Gds Ads Tds Tds Ads mCds Ads Gds mCds Ads Tds Aes Aes Ae, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426261 and a conjugate group. ISIS 426261 is a modified oligonucleotide having the formula: Aes Ges mCds mCds Ads Tds Gds Gds Tds Gds Ads Tds mCds Ads Gds Ges Aes Ges Ges mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 426262 and a conjugate group. ISIS 426262 is a modified oligonucleotide having the formula: mCes Aes Gds mCds mCds Ads Tds Gds Gds Tds Gds Ads Tds mCds Ads Ges Ges Aes Ges Ge, wherein
- A=an adenine,
- mC=a 5'-methylcytosine
- G=a guanine,
- T=a thymine,
- e=a 2'-O-methoxyethyl modified nucleoside.
- d=a 2'-deoxynucleoside, and
- s=a phosphorothioate internucleoside linkage.

In certain embodiments, a compound comprises or consists of ISIS 426267 and a conjugate group. ISIS 426267 is a modified oligonucleotide having the formula: Ges Tes Gds mCds Tds Tds Gds Tds mCds mCds Ads Gds Gds Ads Tds Ges Aes Tes Ges mCe, wherein
- A=an adenine,
- mC=a 5'-methylcytosine
- G=a guanine,
- T=a thymine,
- e=a 2'-O-methoxyethyl modified nucleoside.
- d=a 2'-deoxynucleoside, and
- s=a phosphorothioate internucleoside linkage.

In certain embodiments, a compound comprises or consists of ISIS 426325 and a conjugate group. ISIS 426325 is a modified oligonucleotide having the formula: mCes mCes Tds Tds Gds Gds Tds mCds Tds Gds Gds Ads Tds Tds Ads mCes Aes Ges mCes Ae, wherein
- A=an adenine,
- mC=a 5'-methylcytosine
- G=a guanine,
- T=a thymine,
- e=a 2'-O-methoxyethyl modified nucleoside.
- d=a 2'-deoxynucleoside, and
- s=a phosphorothioate internucleoside linkage.

In certain embodiments, a compound comprises an antisense oligonucleotide disclosed in WO 2005/071080, WO 2007/035759, or WO 2007/136988, which are incorporated by reference in their entireties herein, and a conjugate group. In certain embodiments, a compound comprises an antisense oligonucleotide having a nucleobase sequence of any of SEQ ID NOs 30-216, and 306-310 disclosed in WO 2005/071080 and a conjugate group described herein. In certain embodiments, a compound comprises an antisense oligonucleotide having a nucleobase sequence of any of SEQ ID NOs 26-113 disclosed in WO 2007/035759 and a conjugate group described herein. In certain embodiments, a compound comprises an antisense oligonucleotide having a nucleobase sequence of any of SEQ ID NOs 413-485 disclosed in WO 2007/136988 and a conjugate group described herein. In certain embodiments, a compound comprises an antisense oligonucleotide having a nucleobase sequence complementary to a preferred target segment of any of SEQ ID NOs 30-216, and 306-310 disclosed in WO 2005/071080, 26-113 disclosed in WO 2007/035759, and 413-485 disclosed in WO 2007/136988, and a conjugate group described herein. The nucleobase sequences of all of the aforementioned referenced SEQ ID NOs are incorporated by reference herein.

GCCR Therapeutic Indications

In certain embodiments, provided herein are methods of treating an individual comprising administering one or more pharmaceutical compositions as described herein. In certain embodiments, the individual has metabolic related disease. As shown in the examples below, conjugated compounds targeted to GCCR, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain e.g., the animals continued to experience symptoms, but the symptoms were less severe compared to untreated animals. In certain experiments, the conjugated compounds reduced blood glucose levels. In other experiments, the conjugated compounds reduce the symptoms of diabetes. In other experiments, the conjugated compounds inhibit weight gain. In other experiments, the conjugated compounds inhibit hypertriglyceridemia. In certain embodiments, the conjugated compounds restore function therefore demonstratingreversal of disease by treatment with a compound as described herein. In certain embodiments, animals treated for a longer period of time experience less severe symptoms than those administered the compounds for a shorter period of time.

Diabetes mellitus is characterized by numerous physical and physiological signs and/or symptoms. Any symptom known to one of skill in the art to be associated with Type 2 diabetes can be ameliorated or otherwise modulated as set forth above in the methods described above. In certain embodiments, the sign or symptom is a physical symptom such as increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums. In certain embodiments, the sign or symptom is a physiological symptom such as increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical sign or symptom is increased glucose levels. In certain embodiments, the sign or symptom is weight gain. In certain embodiments, the sign or symptom is frequent urination. In certain embodiments, the sign or symptom is unusual thirst. In certain embodiments, the sign or symptom is extreme hunger. In certain embodiments, the sign or symptom is extreme fatigue. In certain embodiments, the sign or symptom is blurred vision. In certain embodiments, the sign or symptom is frequent infections. In certain embodiments, the sign or symptom is tingling or numbness at the extremities. In certain embodiments, the sign or symptom is dry and itchy skin. In certain embodiments, the sign or symptom is weight loss. In certain embodiments, the sign or symptom is slow-healing sores. In certain embodiments, the sign or symptom is swollen gums. In certain embodiments, the sign or symptom is increased insulin resistance. In certain embodiments, the sign or symptom is increased glucose levels. In certain embodiments, the sign or symptom is increased fat mass. In certain embodiments, the sign or symptom is decreased metabolic rate. In certain embodiments, the sign or symptom is decreased glucose clearance. In certain embodiments, the sign or symptom is decreased glucose tolerance. In certain embodiments, the sign or symptom is decreased insulin sensitivity. In certain embodiments, the sign or symptom is decreased hepatic insulin sensitivity. In certain embodiments, the sign or symptom is increased adipose tissue size and weight.

In certain embodiments, the sign or symptom is increased body fat. In certain embodiments, the sign or symptom is increased body weight.

In certain embodiments, provided are methods of treating an individual comprising administering one or more pharmaceutical compositions as described herein. In certain embodiments, the individual has metabolic related disease.

In certain embodiments, administration of a conjugated antisense compound targeted to a GCCR nucleic acid results in reduction of GCCR expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising a conjugated antisense compound targeted to GCCR are used for the preparation of a medicament for treating a patient suffering or susceptible to metabolic related disease.

In certain embodiments, the methods described herein include administering a conjugated compound comprising a modified oligonucleotide having a contiguous nucleobases portion as described herein of a sequence recited in SEQ ID NO: 66-77.

It will be understood that any of the compounds described herein can be used in the aforementioned methods and uses. For example, in certain embodiments a conjugated antisense compound targeted to a GCCR nucleic acid in the aforementioned methods and uses can include, but is not limited to a conjugated antisense compound targeted to SEQ ID NO: 7 comprising an at least 8 consecutive nucleobase sequence of any one of SEQ ID NOs: 66-77; a conjugated antisense compound targeted to SEQ ID NO: 7 comprising a nucleobase sequence of any one of SEQ ID NO: 66-77; a compound comprising or consisting of ISIS 420470, ISIS 420476, ISIS 426115, ISIS 426130, ISIS 426168, ISIS 426172, ISIS 426183, ISIS 426246, ISIS 426262, ISIS 426267, or ISIS 426325 and a conjugate group: a compound comprising an antisense oligonucleotide disclosed in WO 2005/071080, WO 20071035759, or WO 2007/136988, which are incorporated by reference in their entireties herein, and a conjugate group; a compound comprising an antisense oligonucleotide having a nucleobase sequence of any of SEQ ID NOs 26-113 disclosed in WO 2007/035759 and a conjugate group described herein; a compound comprising an antisense oligonucleotide having a nucleobase sequence of any of SEQ ID NOs 26-113 disclosed in WO 2007/035759 and a conjugate group described herein; or a compound comprising an antisense oligonucleotide having a nucleobase sequence of any of SEQ ID NOs 413-485 disclosed in WO 2007/136988 and a conjugate group described herein; The nucleobase sequences of all of the aforementioned referenced SEQ ID NOs are incorporated by reference herein.

4. GCCR

Insulin and glucagon are two pancreatic hormones involved in regulating glucose homeostasis and metabolism. Glucagon is secreted from the α-cells of the pancreatic islets and regulates glucose homeostasis through modulation of hepatic glucose production (Quesada et al., J. Endocrinol. 2008. 199: 5-19). The main function of glucagon is to counteract the actions of insulin.

Dysregulation of glucose metabolism may be caused either by defective insulin secretion and/or action, or by impaired postprandial glucagon suppression (Shah et al., Am. J. Physiol. Endocrinol. Metab. 1999. 277: E283-E290). Inhibition of postprandial glucagon secretion in diabetic subjects has been shown to substantially reduce blood glucose, suggesting that glucagon contributes significantly to the hyperglycemia seen in subjects with type 2 diabetes mellitus (Shah et al., J. Clin. Endocrinol. Metab. 2000. 85: 4053-4059).

Type 2 diabetes is characterized by impaired insulin secretion and/or action, and many subjects also exhibit inappropriate levels of circulating glucagon in the fasting and postprandial state. An increase in the glucagon/insulin ratio is likely an important determinant of the hyperglycemia seen in type 2 diabetes patients (Baron et al., Diabetes. 1987. 36: 274-283). Lack of suppression of postprandial glucagon secretion in subjects with T2DM also plays an important role in the pathogenesis of postprandial hyperglycemia (Henkel et al., Metabolism. 2005. 54: 1168-1173).

Glucagon exerts its action on target tissues via the activation of its receptor, GCGR. The glucagon receptor is a 62 kDa protein that is a member of the class B G-protein coupled family of receptors (Brubaker et al., Recept. Channels. 2002. 8: 179-88). GCGR activation leads to signal transduction by G proteins ($G_s\alpha$ and $G_q$), whereby $G_s\alpha$ activates adenylate cyclase, which causes cAMP production, resulting in an increase in levels of protein kinase A. GCGR signaling in the liver results in increased hepatic glucose production by induction of glycogenolysis and gluconeogenesis along with inhibition of glycogenesis (Jiang and Zhang. Am. J. Physiol. Endocrinol. Metab. 2003. 284: E671-E678). GCGR is also expressed in extrahepatic tissues, which includes heart, intestinal smooth muscle, kidney, brain, and adipose tissue (Hansen et al., Peptides. 1995. 16: 1163-1166).

Antisense inhibition of GCGR provides a unique advantage over traditional small molecule inhibitors in that antisense inhibitors do not rely on competitive binding of the compound to the protein and inhibit activity directly by reducing the expression of GCGR. A representative United States patent that teaches GCGR antisense inhibitors includes U.S. Pat. No. 7,750,142, of which is herein incorporated by reference in its entirety. Antisense technology is emerging as an effective means for reducing the expression of certain gene products and may therefore prove to be uniquely useful in a number of therapeutic, diagnostic, and research applications for the modulation of GCGR.

There is a currently a lack of acceptable options for treating metabolic disorders. It is therefore an object herein to provide compounds and methods for the treatment of such diseases and disorder. This invention relates to the discovery of novel, highly potent inhibitors of GCGR gene expression. All documents, or portions of documents, cited in this application, including, but not limited to, patents, patent applications, articles, books, and treatises, are hereby expressly incorporated-by-reference for the portions of the document discussed herein, as well as in their entirety.

Certain Conjugated Antisense Compounds Targeted to a GCGR Nucleic Acid

In certain embodiments, conjugated antisense compounds are targeted to a GCGR nucleic acid having the sequence GENBANK Accession No. NM_000160.3 (incorporated herein as SEQ ID NO: 8) or GENBANK Accession No: NW_926918.1 truncated from nucleotides 16865000 to Ser. No. 16/885,000 (incorporated herein as SEQ ID NO: 9). In certain such embodiments, a conjugated antisense compound targeted to SEQ ID NOs: 8 and/or 9 is at least 90%, at least 95%, or 100% complementary to SEQ ID NOs: 8 and/or 9.

In certain embodiments, a conjugated antisense compound targeted to SEQ ID NO: 8 and/or 9 comprises an at least 8 consecutive nucleobase sequence of any one of SEQ ID NOs: 78-83. In certain embodiments, a conjugated antisense compound targeted to SEQ ID NO: 8 and/or 9 comprises a nucleobase sequence of any one of SEQ ID NO: 78-83.

In certain embodiments, a conjugated antisense compound targeted to SEQ ID NO: 8 comprises an at least 8 consecutive nucleobase sequence of SEQ ID NO: 78. In certain embodiments, a conjugated antisense compound targeted to SEQ ID NO: 8 comprises a nucleobase sequence of SEQ ID NO: 78.

In certain embodiments, a conjugated antisense compound targeted to SEQ ID NO: 9 comprises an at least 8 consecutive nucleobase sequence of SEQ ID NO: 79. In certain embodiments, a conjugated antisense compound targeted to SEQ ID NO: 9 comprises a nucleobase sequence of SEQ ID NO: 79.

In certain embodiments, a conjugated antisense compound targeted to SEQ ID NO: 9 comprises an at least 8 consecutive nucleobase sequence of SEQ ID NO: 80. In certain embodiments, a conjugated antisense compound targeted to SEQ ID NO: 9 comprises a nucleobase sequence of SEQ ID NO: 80.

In certain embodiments, a conjugated antisense compound targeted to SEQ ID NO: 9 comprises an at least 8 consecutive nucleobase sequence of SEQ ID NO: 81. In certain embodiments, a conjugated antisense compound targeted to SEQ ID NO: 9 comprises a nucleobase sequence of SEQ ID NO: 81.

In certain embodiments, a conjugated antisense compound targeted to SEQ ID NO: 8 and 9 comprises an at least 8 consecutive nucleobase sequence of SEQ ID NO: 82. In certain embodiments, a conjugated antisense compound targeted to SEQ ID NO: 8 and 9 comprises a nucleobase sequence of SEQ ID NO: 82.

In certain embodiments, a conjugated antisense compound targeted to SEQ ID NO: 9 comprises an at least 8 consecutive nucleobase sequence of SEQ ID NO: 83. In certain embodiments, a conjugated antisense compound targeted to SEQ ID NO: 9 comprises a nucleobase sequence of SEQ ID NO: 83.

TABLE 5

Antisense Compounds targeted to GCGR SEQ ID NOs: 8 and 9

| ISIS No | Target Start Site to SEQ ID NO: 8 | Target Start Site to SEQ ID NO: 9 | Sequence (5'-3') | Motif | SEQ ID NO |
|---|---|---|---|---|---|
| 325568 | 548 | n/a | GCACTTTGTGGTGCCAAGGC | 2-16-2 MOE | 78 |
| 398471 | n/a | 8133 | TCCACAGGCCACAGGTGGGC | 5-10-5 MOE | 79 |
| 448766 | n/a | 9804 | GCAAGGCTCGGTTGGGCTTC | 5-10-5 MOE | 80 |
| 449884 | n/a | 7270 7295 7319 7344 7368 7392 7416 7440 | GGTTCCCGAGGTGCCCA | 3-10-4 MOE | 81 |
| 459014 | 227 | 10718 | GGGCAATGCAGTCCTGG | 3-10-4 MOE | 82 |
| 459157 | n/a | 7267 7292 7316 7341 7365 7389 7437 | GGGTTCCCGAGGTGCCCAATG | 5-10-6 MOE | 83 |

In certain embodiments, a compound comprises or consists of ISIS 325568 and a conjugate group, ISIS 325568 is a modified oligonucleotide having the formula: Ges mCes Ads mCds Tds Tds Tcds Gds Tds Gds Gds Tds Gds mCds mCds Ads Ads Gds Ges mCe, wherein
A=an adenine,
mC=a 5-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 398471 and a conjugate group, ISIS 398471 is a modified oligonucleotide having the formula: Tee mCes mCes Aes mCes Ads Gds Gds mCds mCds Ads mCds Ads Gds Gds Tes Ges Ges Ges mCe, wherein
A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 448766 and a conjugate group, ISIS 448766 is a modified oligonucleotide having the formula: Ges mCes Aes Aes Ges Gds mCds Tds mCds Gds Gds Tds Tds Gds Gds Ges mCes Tes Tes mCe, wherein
A=an adenine,
mC=a 5'-methylcytosine
G=a guanine,
T=a thymine,
e=a 2'-O-methoxyethyl modified nucleoside.
d=a 2'-deoxynucleoside, and
s=a phosphorothioate internucleoside linkage.

In certain embodiments, a compound comprises or consists of ISIS 449884 and a conjugate group. ISIS 449884 is a modified oligonucleotide having the formula: Ges Ges Tes Tds mCds mCds mCds Gds Ads Gds Gds Tds Gds mCes mCes mCes Ae, wherein
A=an adenine,
mC=a 5'-methylcytosine
G=a guanine,
T=a thymine,
e=a 2'-O-methoxyethyl modified nucleoside.
d=a 2'-deoxynucleoside, and
s=a phosphorothioate internucleoside linkage.

In certain embodiments, a compound comprises or consists of ISIS 459014 and a conjugate group. ISIS 459014 is a modified oligonucleotide having the formula: Ges Ges Ges mCds Ads Ads Tds Gds mCds Ads Gds Tds mCds mCes Tes Ges Ge, wherein A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises or consists of ISIS 459157 and a conjugate group. ISIS 459157 is a modified oligonucleotide having the formula: Ges Ges Ges Tes Tes mCds mCds mCds Gds Ads Gds Gds Tds Gds mCds mCes mCes Aes Aes Tes Ge, wherein A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, a compound comprises an antisense oligonucleotide disclosed in U.S. Pat. No. 7,750,142, U.S. Pat. No. 7,399,853, WO 2007/035771, or WO 2007/134014, which are incorporated by reference in their entireties herein, and a conjugate group. In certain embodiments, a compound comprises an antisense oligonucleotide having a nucleobase sequence of any of SEQ ID NOs 20-399 disclosed in U.S. Pat. No. 7,750,142 and a conjugate group described herein. In certain embodiments, a compound comprises an antisense oligonucleotide having a nucleobase sequence of any of SEQ ID NOs 20-399 disclosed in U.S. Pat. No. 7,399,853 and a conjugate group described herein. In certain embodiments, a compound comprises an antisense oligonucleotide having a nucleobase sequence of any of SEQ ID NOs 2 disclosed in WO 2007/035771 and a conjugate group described herein. In certain embodiments, a compound comprises an antisense oligonucleotide having a nucleobase sequence of any of SEQ ID NOs: 486-680 disclosed in WO 2007/134014 and a conjugate group described herein. In certain embodiments, a compound comprises an antisense oligonucleotide having a nucleobase sequence complementary to a preferred target segment of any of SEQ ID NOs 20-399 of U.S. Pat. No. 7,750,142, SEQ ID NO: 20-399 of U.S. Pat. No. 7,399,853, SEQ ID NO 2 of WO 2007/035771, or SEQ ID NOs. 486-680 of WO 2007/134014, and a conjugate group described herein. The nucleobase sequences of all of the aforementioned referenced SEQ ID NOs are incorporated by reference herein.

GCGR Therapeutic Indications

In certain embodiments, provided herein are methods of treating an individual comprising administering one or more pharmaceutical compositions as described herein. In certain embodiments, the individual has metabolic related disease.

As shown in the examples below, conjugated compounds targeted to GCGR, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain. In certain of the experiments, the conjugated compounds reduced blood glucose levels, e.g., the animals continued to experience symptoms, but the symptoms were less severe compared to untreated animals. In other experiments, however, the conjugated compounds appear to reduce the symptoms of diabetes; e.g., animals treated for a longer period of time experienced less severe symptoms than those administered the compounds for a shorter period of time. In other experiments, however, the conjugated compounds appear to inhibit weight gain; e.g., animals treated for a longer period of time experienced less severe symptoms than those administered the compounds for a shorter period of time. In other experiments, however, the conjugated compounds appear to inhibit hypertriglyceridemia; e.g., animals treated for a longer period of time experienced less severe signs and/or symptoms than those administered the compounds for a shorter period of time. The ability of the conjugated compounds exemplified below to restore function therefore demonstrates that symptoms of the disease may be reversed by treatment with a compound as described herein.

Diabetes mellitus is characterized by numerous physical and physiological signs and/or symptoms. Any symptom known to one of skill in the art to be associated with Type 2 diabetes can be ameliorated or otherwise modulated as set forth above in the methods described above. In certain embodiments, the symptom or sign is a physical symptom or sign ssuch as increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums. In certain embodiments, the symptom or sign is a physiological symptom or sign selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical symptom or sign is increased glucose levels. In certain embodiments, the sign or symptom is weight gain. In certain embodiments, the symptom is frequent urination. In certain embodiments, the symptom is unusual thirst. In certain embodiments, the symptom is extreme hunger. In certain embodiments, the symptom is extreme fatigue. In certain embodiments, the symptom is blurred vision. In certain embodiments, the symptom is frequent infections. In certain embodiments, the symptom is tingling or numbness at the extremities. In certain embodiments, the symptom is dry and itchy skin. In certain embodiments, the sign or symptom is weight loss. In certain embodiments, the symptom is slow-healing sores. In certain embodiments, the symptom is swollen gums. In certain embodiments, the symptom or sign is increased insulin resistance. In certain embodiments, the symptom or sign is increased glucose levels. In certain embodiments, the symptom or sign is increased fat mass. In certain embodiments, the symptom or sign is decreased metabolic rate. In certain embodiments, the symptom o resign is decreased glucose clearance. In certain embodiments, the symptom or sign is decreased glucose tolerance. In certain embodiments, the symptom or sign is decreased insulin sensitivity. In certain embodiments, the symptom or sign is decreased hepatic insulin sensitivity. In certain embodiments, the symptom or sign is increased adipose tissue size and weight. In certain embodiments, the symptom or sign is increased body fat. In certain embodiments, the sign or symptom is increased body weight.

In certain embodiments, provided are methods of treating an individual comprising administering one or more pharmaceutical compositions as described herein. In certain embodiments, the individual has metabolic related disease.

In certain embodiments, administration of a conjugated antisense compound targeted to a GCGR nucleic acid results in reduction of GCGR expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising a conjugated antisense compound targeted to GCGR are used for the preparation of a medicament for treating a patient suffering or susceptible to metabolic related disease.

In certain embodiments, the methods described herein include administering a conjugated compound comprising a modified oligonucleotide having a contiguous nucleobases portion as described herein of a sequence recited in SEQ ID NO: 78-83.

It will be understood that any of the compounds described herein can be used in the aforementioned methods and uses. For example, in certain embodiments a conjugated antisense compound targeted to a GCGR nucleic acid in the aforementioned methods and uses can include, but is not limited to, a conjugated antisense compound targeted to SEQ ID NO: 8 and/or 9 comprising an at least 8 consecutive nucleobase sequence of any one of SEQ ID NOs: 78-83; a conjugated antisense compound targeted to SEQ ID NO: 8 and/or 9 comprising a nucleobase sequence of any one of SEQ ID NO: 78-83; a compound comprising or consisting of ISIS 325568, ISIS 398471, ISIS 448766, ISIS 449884, ISIS 459014, or ISIS 459157 and a conjugate group; a compound comprising an antisense oligonucleotide disclosed in U.S. Pat. No. 7,750,142; U.S. Pat. No. 7,399,853, WO 2007/035771, or WO 2007/134014, which are incorporated by reference in their entireties herein, and a conjugate group; The nucleobase sequences of all of the aforementioned referenced SEQ ID NOs are incorporated by reference herein.

4. 4. Coagulation Factor 7

The circulatory system requires mechanisms that prevent blood loss, as well as those that counteract inappropriate intravascular obstructions. Generally, coagulation comprises a cascade of reactions culminating in the conversion of soluble fibrinogen to an insoluble fibrin gel. The steps of the cascade involve the conversion of an inactive zymogen to an activated enzyme. The active enzyme then catalyzes the next step in the cascade.

Coagulation Cascade

The coagulation cascade may be initiated through two branches, the tissue factor pathway (also "extrinsic pathway"), which is the primary pathway, and the contact activation pathway (also "intrinsic pathway").

The tissue factor pathway is initiated by the cell surface receptor tissue factor (TF, also referred to as factor III), which is expressed constitutively by extravascular cells (pericytes, cardiomyocytes, smooth muscle cells, and keratinocytes) and expressed by vascular monocytes and endothelial cells upon induction by inflammatory cytokines or endotoxin. (Drake et al., *Am J Pathol* 1989, 134:1087-1097). TF is the high affinity cellular receptor for coagulation factor VIIa, a serine protease. In the absence of TF, VIIa has very low catalytic activity, and binding to TF is necessary to render VIIa functional through an allosteric mechanism. (Drake et al., *Am J Pathol* 1989, 134:1087-1097). The TF-VIIa complex activates factor X to Xa. Xa in turn associates with its co-factor factor Va into a prothrombinase complex which in turn activates prothrombin, (also known as factor II or factor 2) to thrombin (also known as factor IIa, or factor 2a). Thrombin activates platelets, converts fibrinogen to fibrin and promotes fibrin cross-linking by activating factor XIII, thus forming a stable plug at sites where TF is exposed on extravascular cells. In addition, thrombin reinforces the coagulation cascade response by activating factors V and VIII.

The contact activation pathway is triggered by activation of factor XII to XIIa. Factor XIIa converts XI to XIa, and XIa converts IX to IXa. IXa associates with its cofactor VIIIa to convert X to Xa. The two pathways converge at this point as factor Xa associates factor Va to activate prothrombin (factor II) to thrombin (factor IIa).

Inhibition of Coagulation

At least three mechanisms keep the coagulation cascade in check, namely the action of activated protein C, antithrombin, and tissue factor pathway inhibitor. Activated protein C is a serine protease that degrades cofactors Va and VIIIa. Protein C is activated by thrombin with thrombomodulin, and requires coenzyme Protein S to function. Antithrombin is a serine protease inhibitor (serpin) that inhibits serine proteases: thrombin, Xa, XIIa, XIa and IXa. Tissue factor pathway inhibitor inhibits the action of Xa and the TF-VIIa complex. (Schwartz A L et al., Trends Cardiovasc Med. 1997; 7:234-239.)

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year. (Adcock et al. American Journal of Clinical Pathology. 1997; 108:434-49). While most cases of thrombosis are due to acquired extrinsic problems, for example, surgery, cancer, immobility, some cases are due to a genetic predisposition, for example, antiphospholipid syndrome and the autosomal dominant condition, Factor V Leiden. (Bertina R M et al. *Nature* 1994; 369:64-67.)

Treatment

The most commonly used anticoagulants, warfarin, heparin, and low molecular weight heparin (LMWH) all possess significant drawbacks.

Warfarin is typically used to treat patients suffering from atrial fibrillation. The drug interacts with vitamin K-dependent coagulation factors which include factors II, VII, IX and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182.) Treatment with heparin may cause an immunological reaction that makes platelets aggregate within blood vessels that can lead to thrombosis. This side effect is known as heparin-induced thrombocytopenia (HIT) and requires patient monitoring. Prolonged treatment with heparin may also lead to osteoporosis. LMWH can also inhibit Factor 2, but to a lesser degree than unfractionated heparin (UFH). LMWH has been implicated in the development of HIT.

Thus, current anticoagulant agents lack predictability and specificity and, therefore, require careful patient monitoring to prevent adverse side effects, such as bleeding complications. There are currently no anticoagulants which target only the intrinsic or extrinsic pathway.

Antisense compounds targeting Factor VII have been previously disclosed in WO 2013/119979 and WO 2009/061851, each herein incorporated by reference in its entirety. Clinical studies are ongoing to assess the effect of antisense compounds targeting Factor VII in patients. However, there is still a need to provide patients with additional and more potent treatment options.

Certain Conjugated Antisense Compounds Targeted to a Factor VII Nucleic Acid

In certain embodiments, conjugated antisense compounds are targeted to a Factor VII nucleic acid having the sequence GENBANK Accession No. NT_027140.6 truncated from nucleotides 1255000 to 1273000, incorporated herein as SEQ ID NO: 10; GENBANK Accession No. NM_019616.2, incorporated herein as SEQ ID NO: 11; DB184141.1, designated herein as SEQ ID NO: 12; and GENBANK Accession No. NW_001104507.1 truncated from nucleotides 691000 to 706000, designated herein as SEQ ID NO: 13. In certain such embodiments, a conjugated antisense compound targeted to SEQ ID NO: 11 is at least 90%, at least 95%, or 100% complementary to SEQ ID NO: 11.

In certain embodiments, a conjugated antisense compound targeted to SEQ ID NO: 11 comprises an at least 8 consecutive nucleobase sequence of any one of SEQ ID NOs: 84-92. In certain embodiments, a conjugated antisense compound targeted to SEQ ID NO: 11 comprises a nucleobase sequence of any one of SEQ ID NO: 84-92.

In certain embodiments, a conjugated antisense compound targeted to SEQ ID NO: 11 comprises an at least 8 consecutive nucleobase sequence of SEQ ID NO: 84. In certain embodiments, a conjugated antisense compound targeted to SEQ ID NO: 11 comprises a nucleobase sequence of SEQ ID NO: 84.

In certain embodiments, a conjugated antisense compound targeted to SEQ ID NO: 11 comprises an at least 8 consecutive nucleobase sequence of SEQ ID NO: 85. In certain embodiments, a conjugated antisense compound targeted to SEQ ID NO: 11 comprises a nucleobase sequence of SEQ ID NO: 85.

In certain embodiments, a conjugated antisense compound targeted to SEQ ID NO: 11 comprises an at least 8 consecutive nucleobase sequence of SEQ ID NO: 86. In certain embodiments, a conjugated antisense compound targeted to SEQ ID NO: 11 comprises a nucleobase sequence of SEQ ID NO: 86.

In certain embodiments, a conjugated antisense compound targeted to SEQ ID NO: 11 comprises an at least 8 consecutive nucleobase sequence of SEQ ID NO: 87. In certain embodiments, a conjugated antisense compound targeted to SEQ ID NO: 11 comprises a nucleobase sequence of SEQ ID NO: 87.

In certain embodiments, a conjugated antisense compound targeted to SEQ ID NO: 11 comprises an at least 8 consecutive nucleobase sequence of SEQ ID NO: 88. In certain embodiments, a conjugated antisense compound targeted to SEQ ID NO: 11 comprises a nucleobase sequence of SEQ ID NO: 88.

In certain embodiments, a conjugated antisense compound targeted to SEQ ID NO: 11 comprises an at least 8 consecutive nucleobase sequence of SEQ ID NO: 89. In certain embodiments, a conjugated antisense compound targeted to SEQ ID NO: 11 comprises a nucleobase sequence of SEQ ID NO: 89.

In certain embodiments, a conjugated antisense compound targeted to SEQ ID NO: 11 comprises an at least 8 consecutive nucleobase sequence of SEQ ID NO: 90. In certain embodiments, a conjugated antisense compound targeted to SEQ ID NO: 11 comprises a nucleobase sequence of SEQ ID NO: 90.

TABLE 3

Antisense Compounds targeted to Factor VII SEQ ID NO: 11

| ISIS No | Target Start Site | Sequence (5'-3') | Motif | SEQ ID NO |
|---|---|---|---|---|
| 407935 | 15191 | ATGCATGGTGATGCTTCTGA | eeeeedddddddddeeeee | 84 |
| 473589 | 15128 | GCTAAACAACCGCCTT | kdkdkddddddddddee | 85 |
| 490279 | 1387 | CCCTCCTGTGCCTGGATGCT | eeeeedddddddddeeeee | 86 |
| 529804 | 15192 | CATGGTGATGCTTCTG | kdddddddddddkekee | 87 |
| 534796 | 15131 | AGAGCTAAACAACCGC | ekkddddddddddkke | 88 |
| 540162 | 2565; 2633; 2667 | ACTCCCGGGACACCCA | eekdddddddddddkke | 89 |
| 540175 | | GGACACCCACGCCCCC | | 90 |
| 540182 | | ACACCCTCGCCTCCGG | | 91 |
| 540191 | | GCCTCCGGAACACCCA | | 92 |

In certain embodiments, a compound comprises or consists of ISIS 420915 and a conjugate group. ISIS 407935 is a modified oligonucleotide having the formula: Aes Tes Ges mCes Aes Tds Gds Gds Tds Gds Ads Tds Gds mCds Tds Tes mCes Tes Ges Ae, wherein
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 304299 and a conjugate group. ISIS 473589 is a modified oligonucleotide having the formula: Gks mCds Tks Ads Aks Ads mCds Ads Ads mCds mCds Gds mCds mCds Tes Te; wherein,
each nucleobase is indicated according to the following:
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420921 and a conjugate group. ISIS 490279 is a modified oligonucleotide having the formula: mCes mCes mCes Tes mCes mCds Tds Gds Tds Gds mCds mCds Tds Gds Gds Aes Tes Ges mCes Te; wherein, each nucleobase is indicated according to the following:
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420922 and a conjugate group. ISIS 529804 is a modified oligonucleotide having the formula: mCks Ads Tds Gds Gds Tds Gds Ads Tds Gds mCds Tks Tes mCks Tes Ge, wherein
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420950 and a conjugate group. ISIS 534796 is a modified oligonucleotide having the formula: Aes Gks Aks Gds mCds Tds Ads Ads Ads mCds Ads Ads mCds mCks Gks mCe, wherein
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420955 and a conjugate group. ISIS 540162 is a modified oligonucleotide having the formula: Ges Aes Aes Tes Ges Tds Tds Tds Tds Ads Tds Tds Gds Tds mCds Tes mCes Tes Ges mCe, wherein
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420957 and a conjugate group. ISIS 540175 is a modified oligonucleotide having the formula: Ges Ges Aks mCds Ads mCds mCds mCds Ads mCds Gds mCds mCds mCks mCks mCe; wherein, each nucleobase is indicated according to the following:
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420959 and a conjugate group. ISIS 540182 is a modified oligonucleotide having the formula: Aes mCes Aks mCds mCds mCds Tds mCds Gds mCds mCds Tds mCds mCks Gks Ge, wherein
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises or consists of ISIS 420959 and a conjugate group. ISIS 540191 is a modified oligonucleotide having the formula: Ges mCes mCks Tds mCds mCds Gds Gds Ads Ads mCds Ads mCds mCks mCks Ae, wherein
A=adenine
T=thymine
G=guanine;
mC=5-methylcytosine; wherein
each sugar moiety is indicated according to the following:
k=cEt;
d=2'-deoxyribose;
e=2'-MOE; wherein
each internucleoside linkage is indicated according to the following:
s=phosphorothioate.

In certain embodiments, a compound comprises an antisense oligonucleotide disclosed in WO 2013/119979 and WO 2009/061851, which are incorporated by reference in their entireties herein. In certain embodiments, a compound comprises an antisense oligonucleotide having a nucleobase sequence of any of SEQ ID NOs 21-659 disclosed in WO 2013/119979 and a conjugate group described herein. In certain embodiments, a compound comprises an antisense oligonucleotide having a nucleobase sequence of any of SEQ ID NOs 4-159 and 168-611 disclosed in WO 2009/061851 and a conjugate group described herein. The nucleobase sequences of all of the aforementioned referenced SEQ ID NOs are incorporated by reference herein.

Factor VII Therapeutic Indications

In certain embodiments, provided herein are compounds and compositions as described herein for use in therapy.

In certain embodiments, provided herein are conjugated antisense compounds and compositions as described herein for use in treating, preventing, or slowing progression of a thromboembolic complication.

In certain embodiments, provided herein are conjugated antisense compounds and compositions as described herein for use in treating, preventing, or slowing progression of a hyperproliferative disorder.

In certain embodiments, provided herein are conjugated antisense compounds and compositions as described herein for use in treating, preventing, or slowing progression of an inflammatory condition.

In certain embodiments, the invention provides methods for using a conjugated antisense compound targeted to a Factor VII nucleic acid for modulating the expression of Factor VII in a subject. In certain embodiments, the expression of Factor VII is reduced.

In certain embodiments, the invention provides methods for using a conjugated antisense compound targeted to a Factor VII nucleic acid in a pharmaceutical composition for treating a subject. In certain embodiments, the subject has a Factor VII related disease, disorder or condition, or symptom thereof. In certain embodiments, the Factor VII related disease, disorder or condition is a thromboembolic complication, a hyperproliferative disorder or an inflammatory condition.

In certain embodiments, the invention provides methods for using a conjugated antisense compound targeted to a Factor VII nucleic acid in the preparation of a medicament.

In certain embodiments, the invention provides a conjugated antisense compound targeted to a Factor VII nucleic acid, or a pharmaceutically acceptable salt thereof, for use in therapy.

Certain embodiments provide a conjugated antisense compound targeted to a Factor VII nucleic acid for use in the treatment of a Factor VII related disease, disorder or condition, or symptom thereof. In certain embodiments, the Factor VII related disease, disorder or condition is a thromboembolic complication, a hyperproliferative disorder or an inflammatory condition.

In certain embodiments, provided herein are conjugated antisense compounds and compositions as described herein for use in treating, preventing, or slowing progression of a thromboembolic complication.

In certain embodiments, provided herein are conjugated antisense compounds and compositions as described herein for use in treating, preventing, or slowing progression of a hyperproliferative disorder.

In certain embodiments, provided herein are conjugated antisense compounds and compositions as described herein for use in treating, preventing, or slowing progression of an inflammatory condition.

It will be understood that any of the compounds described herein can be used in the aforementioned methods and uses. For example, in certain embodiments a conjugated antisense compound targeted to a Factor VII nucleic acid in the aforementioned methods and uses can include, but is not limited to, a conjugated antisense compound targeted to SEQ ID NO: 11 comprising an at least 8 consecutive nucleobase sequence of any one of SEQ ID NOs: 84-92: a conjugated antisense compound targeted to SEQ ID NO: 11 comprising a nucleobase sequence of any one of SEQ ID NO: 84-92: a compound comprising or consisting of ISIS 407935. ISIS 473589 ISIS 490279 ISIS 529804 ISIS 534796 ISIS 540162 ISIS 540175, ISIS 540182, or ISIS 540191 and a conjugate group; a compound comprising an antisense oligonucleotide disclosed in WO 2013/119979 and WO 2009/061851, which are incorporated by reference in their entireties herein, and a conjugate group; a compound comprising an antisense oligonucleotide having a nucleobase sequence of any of SEQ ID NOs 21-659 disclosed in WO 2013/119979 and a conjugate group described herein; an antisense oligonucleotide having a nucleobase sequence of any of SEQ ID NOs 4-159 and 168-611 disclosed in WO 2009/061851 and a conjugate group described herein. The nucleobase sequences of all of the aforementioned referenced SEQ ID NOs are incorporated by reference herein.

4. Coagulation Factor 11

The circulatory system requires mechanisms that prevent blood loss, as well as those that counteract inappropriate intravascular obstructions. Generally, coagulation comprises a cascade of reactions culminating in the conversion of soluble fibrinogen to an insoluble fibrin gel. The steps of the cascade involve the conversion of an inactive zymogen to an activated enzyme. The active enzyme then catalyzes the next step in the cascade.

Coagulation Cascade

The coagulation cascade may be initiated through two branches, the tissue factor pathway (also "extrinsic pathway"), which is the primary pathway, and the contact activation pathway (also "intrinsic pathway").

The tissue factor pathway is initiated by the cell surface receptor tissue factor (TF, also referred to as factor III), which is expressed constitutively by extravascular cells (pericytes, cardiomyocytes, smooth muscle cells, and keratinocytes) and expressed by vascular monocytes and endothelial cells upon induction by inflammatory cytokines or endotoxin. (Drake et al., *Am J Pathol* 1989, 134:1087-1097). TF is the high affinity cellular receptor for coagulation factor VIIa, a serine protease. In the absence of TF, VIIa has very low catalytic activity, and binding to TF is necessary to render VIIa functional through an allosteric mechanism. (Drake et al., *Am J Pathol* 1989, 134:1087-1097). The TF-VIIa complex activates factor X to Xa. Xa in turn associates with its co-factor factor Va into a prothrombinase complex which in turn activates prothrombin, (also known as factor II or factor 2) to thrombin (also known as factor IIa, or factor 2a). Thrombin activates platelets, converts fibrinogen to fibrin and promotes fibrin cross-linking by activating factor XIII, thus forming a stable plug at sites where TF is exposed on extravascular cells. In addition, thrombin reinforces the coagulation cascade response by activating factors V and VIII.

The contact activation pathway is triggered by activation of factor XII to XIIa. Factor XIIa converts XI to XIa, and XIa converts IX to IXa. IXa associates with its cofactor VIIIa to convert X to Xa. The two pathways converge at this point as factor Xa associates factor Va to activate prothrombin (factor II) to thrombin (factor IIa).

Inhibition of Coagulation.

At least three mechanisms keep the coagulation cascade in check, namely the action of activated protein C, antithrombin, and tissue factor pathway inhibitor. Activated protein C is a serine protease that degrades cofactors Va and VIIIa. Protein C is activated by thrombin with thrombomodulin, and requires coenzyme Protein S to function. Antithrombin is a serine protease inhibitor (serpin) that inhibits serine proteases: thrombin, Xa, XIIa, XIa and IXa. Tissue factor pathway inhibitor inhibits the action of Xa and the TF-VIIa complex. (Schwartz A L et al., *Trends Cardiovasc Med.* 1997; 7:234-239.)

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year. (Adcock et al. *American Journal of Clinical Pathology.* 1997; 108:434-49). While most cases of thrombosis are due to acquired extrinsic problems, for example, surgery, cancer, immobility, some cases are due to a genetic predisposition, for example, antiphospholipid syndrome and the autosomal dominant condition, Factor V Leiden. (Bertina R M et al. *Nature* 1994; 369:64-67.)

Treatment.

The most commonly used anticoagulants, warfarin, heparin, and low molecular weight heparin (LMWH) all possess significant drawbacks.

Warfarin is typically used to treat patients suffering from atrial fibrillation. The drug interacts with vitamin K-dependent coagulation factors which include factors II, VII, IX and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182.) Treatment with heparin may cause an immunological reaction that makes platelets aggregate within blood vessels that can lead to thrombosis. This side effect is known as heparin-induced thrombocytopenia (HIT) and requires patient monitoring. Prolonged treatment with heparin may also lead to osteoporosis. LMWH can also inhibit Factor 2, but to a lesser degree than unfractioned heparin (UFH). LMWH has been implicated in the development of HIT.

Thus, current anticoagulant agents lack predictability and specificity and, therefore, require careful patient monitoring to prevent adverse side effects, such as bleeding complications. There are currently no anticoagulants which target only the intrinsic or extrinsic pathway.

Antisense compounds targeting Factor XI have been previously disclosed in WO 2010/045509 and WO 2010/121074, each herein incorporated by reference in its entirety. Clinical studies are ongoing to assess the effect of antisense compounds targeting Factor XI in patients. However, there is still a need to provide patients with additional and more potent treatment options.

Certain Conjugated Antisense Compounds Targeted to a Factor XI Nucleic Acid

In certain embodiments, conjugated antisense compounds are targeted to a Factor XI nucleic acid having the sequence GENBANK Accession No. NM_000128.3 (incorporated herein as SEQ ID NO: 14), GENBANK Accession No. NT_022792.17, truncated from Ser. No. 19/598,000 to Ser. No. 19/624,000, (incorporated herein as SEQ ID NO: 15), GENBANK Accession No. NM_028066.1 (incorporated herein as SEQ ID NO: 16), exons 1-15 GENBANK Accession No. NW_001118167.1 (incorporated herein as SEQ ID NO: 17). In certain such embodiments, a conjugated antisense compound targeted to SEQ ID NO: 2 is at least 90%, at least 95%, or 100% complementary to SEQ ID NO: 2.

In certain embodiments, a conjugated antisense compound targeted to SEQ ID NO: 2 comprises an at least 8 consecutive nucleobase sequence of any one of SEQ ID NOs: 12-19. In certain embodiments, a conjugated antisense compound targeted to SEQ ID NO: 2 comprises a nucleobase sequence of any one of SEQ ID NO: 12-19.

In certain embodiments, a conjugated antisense compound targeted to SEQ ID NO: 14 comprises an at least 8 consecutive nucleobase sequence of SEQ ID NO: 93. In certain embodiments, a conjugated antisense compound targeted to SEQ ID NO: 14 comprises a nucleobase sequence of SEQ ID NO: 93.

In certain embodiments, a conjugated antisense compound targeted to SEQ ID NO: 14 comprises an at least 8 consecutive nucleobase sequence of SEQ ID NO: 94. In certain embodiments, a conjugated antisense compound targeted to SEQ ID NO: 14 comprises a nucleobase sequence of SEQ ID NO: 94:

In certain embodiments, a conjugated antisense compound targeted to SEQ ID NO: 14 comprises an at least 8 consecutive nucleobase sequence of SEQ ID NO: 95. In certain embodiments, a conjugated antisense compound targeted to SEQ ID NO: 14 comprises a nucleobase sequence of SEQ ID NO: 95.

In certain embodiments, a conjugated antisense compound targeted to SEQ ID NO: 14 comprises an at least 8 consecutive nucleobase sequence of SEQ ID NO: 96. In certain embodiments, a conjugated antisense compound targeted to SEQ ID NO: 14 comprises a nucleobase sequence of SEQ ID NO: 96.

In certain embodiments, a conjugated antisense compound targeted to SEQ ID NO: 14 comprises an at least 8 consecutive nucleobase sequence of SEQ ID NO: 97. In certain embodiments, a conjugated antisense compound targeted to SEQ ID NO: 14 comprises a nucleobase sequence of SEQ ID NO: 97.

In certain embodiments, a conjugated antisense compound targeted to SEQ ID NO: 14 comprises an at least 8 consecutive nucleobase sequence of SEQ ID NO: 98. In certain embodiments, a conjugated antisense compound targeted to SEQ ID NO: 14 comprises a nucleobase sequence of SEQ ID NO: 98.

In certain embodiments, a conjugated antisense compound targeted to SEQ ID NO: 14 comprises an at least 8 consecutive nucleobase sequence of SEQ ID NO: 99. In certain embodiments, a conjugated antisense compound targeted to SEQ ID NO: 14 comprises a nucleobase sequence of SEQ ID NO: 99.

In certain embodiments, a conjugated antisense compound targeted to SEQ ID NO: 14 comprises an at least 8 consecutive nucleobase sequence of SEQ ID NO: 100. In certain embodiments, a conjugated antisense compound targeted to SEQ ID NO: 14 comprises a nucleobase sequence of SEQ ID NO: 100.

TABLE 7

Antisense Compounds targeted to Factor 11 SEQ ID NO: 14-17

| ISIS No | Target Start Site | Sequence (5'-3') | Motif | SEQ ID NO |
|---|---|---|---|---|
| 416850 | | TGCACAGTTTCTGGCAGGCC | | 93 |
| 416858 | | ACGGCATTGGTGCACAGTTT | | 94 |
| 445522 | | GCACAGTTTCTGGCAGGC | | 95 |
| 445531 | | GGCATTGGTGCACAGTTT | | 96 |
| 449707 | | CACAGTTTCTGGCAGG | | 97 |
| 449708 | | ACAGTTTCTGGCAG | | 98 |
| 449709 | | GCACAGTTTCTGGCAGGC | | 99 |

TABLE 7 -continued

Antisense Compounds targeted to Factor 11
SEQ ID NO: 14-17

| ISIS No | Target Start Site | Sequence (5'-3') | Motif | SEQ ID NO |
|---|---|---|---|---|
| 449710 | | CACAGTTTCTGGCAGG | | 100 |
| 449711 | | ACAGTTTCTGGCAG | | 101 |

In certain embodiments, a compound comprises an antisense oligonucleotide disclosed in WO 2010/045509 and WO 2010/121074, which are incorporated by reference in their entireties herein, and a conjugate group. In certain embodiments, a compound comprises an antisense oligonucleotide having a nucleobase sequence of any of SEQ ID NOs 15-270 disclosed in WO 2010/045509 and a conjugate group described herein. In certain embodiments, a compound comprises an antisense oligonucleotide having a nucleobase sequence of any of SEQ ID NOs 15-270 disclosed in WO 2010/121074 and a conjugate group described herein. The nucleobase sequences of all of the aforementioned referenced SEQ ID NOs are incorporated by reference herein.

E. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water.

In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1

General Method for the Preparation of Phosphoramidites, Compounds 1, 1a and 2

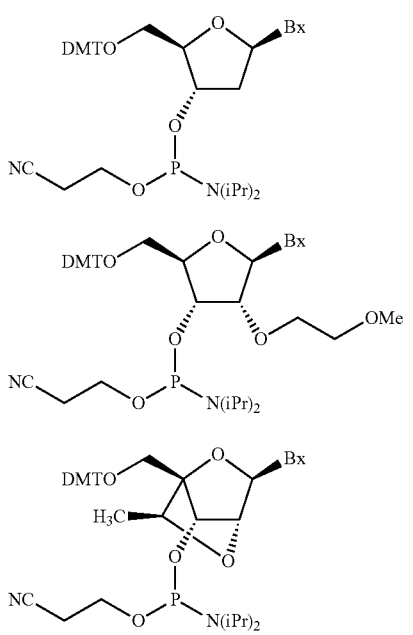

Bx is a heterocyclic base;

Compounds 1, 1a and 2 were prepared as per the procedures well known in the art as described in the specification herein (see Seth et al., Bioorg. Med. Chem., 2011, 21(4), 1122-1125, J. Org. Chem., 2010, 75(5), 1569-1581, Nucleic Acids Symposium Series, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2

Preparation of Compound 7

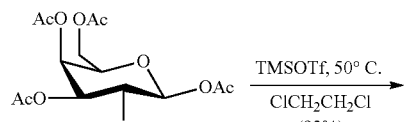

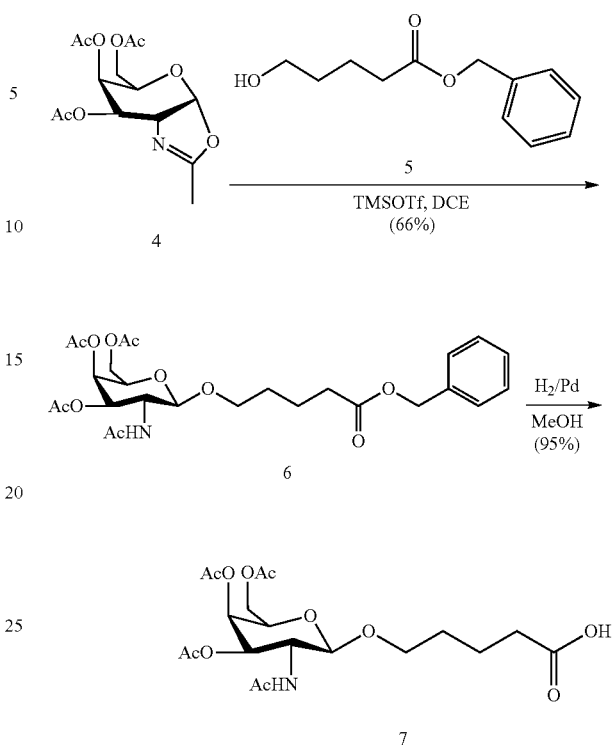

Compounds 3 (2-acetamido-1,3,4,6-tetra-O-acetyl-2-deoxy-β-D-galactopyranose or galactosamine pentaacetate) is commercially available. Compound 5 was prepared according to published procedures (Weber et al., *J. Med. Chem.*, 1991, 34, 2692).

Example 3

Preparation of Compound 11

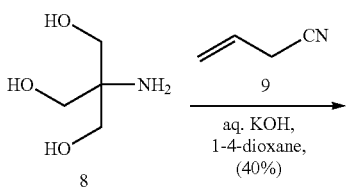

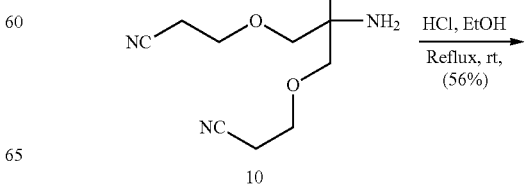

-continued
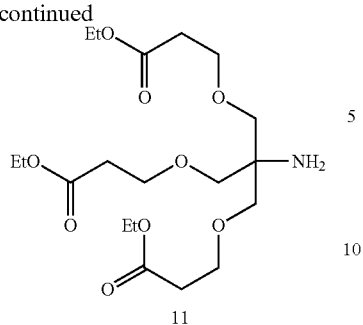
11
Compounds 8 and 9 are commercially available.
Example 4
Preparation of Compound 18
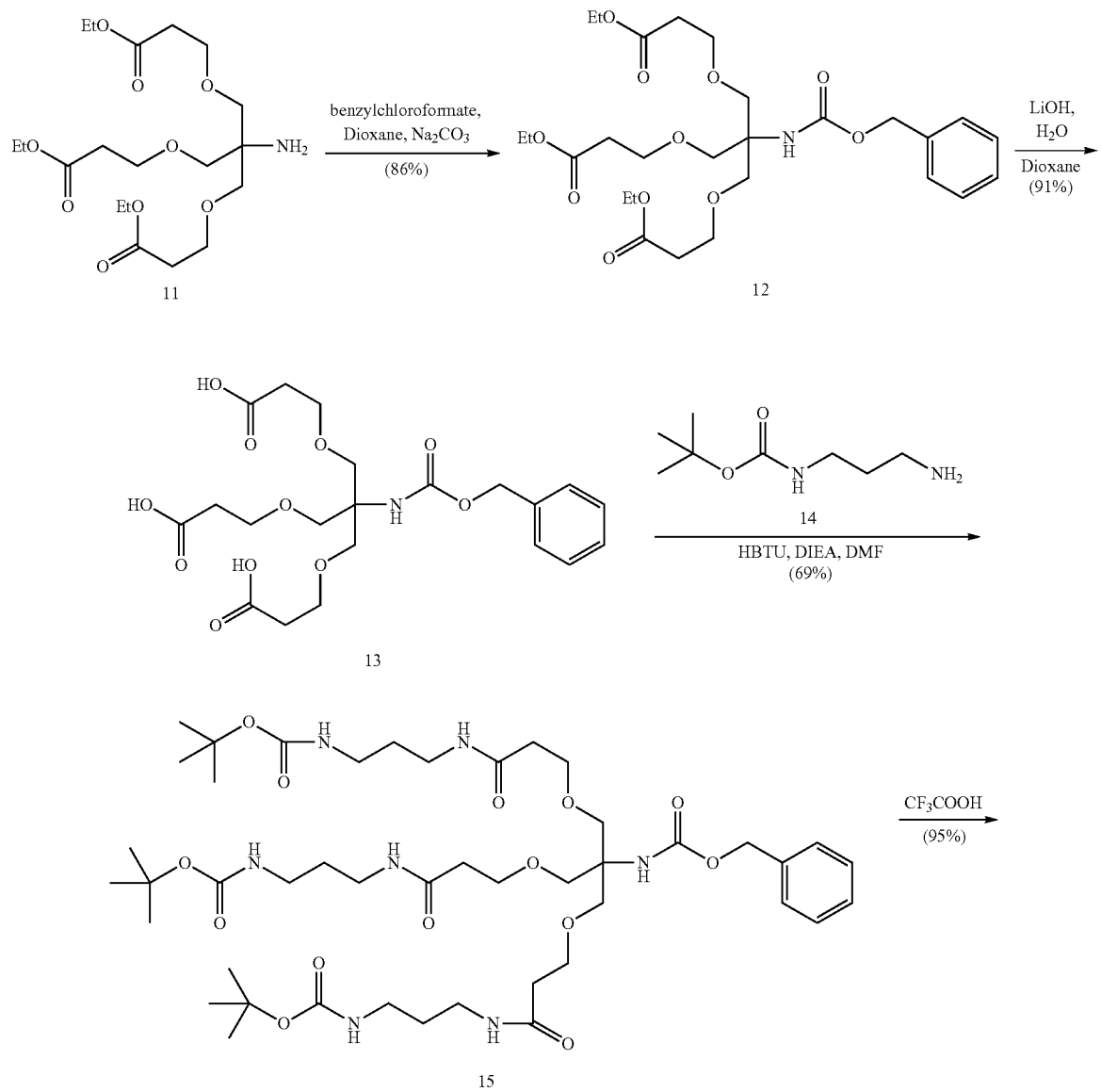

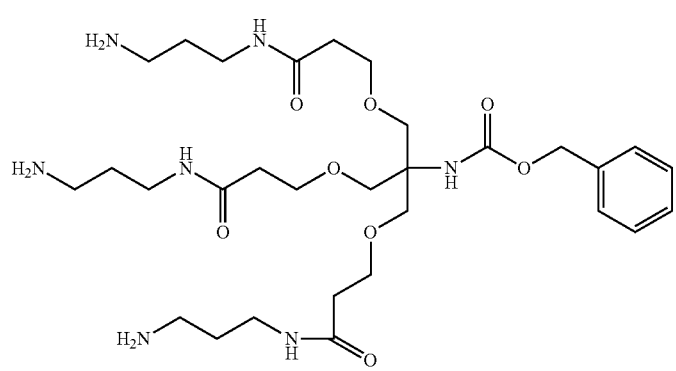
16
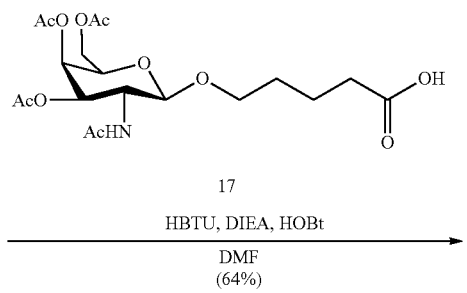
17
HBTU, DIEA, HOBt
DMF
(64%)
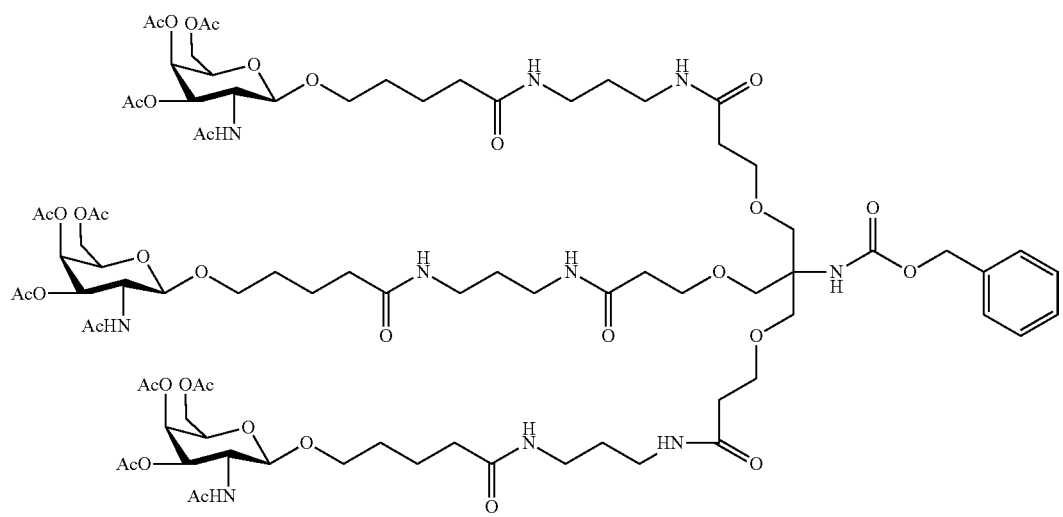
18
Compound 11 was prepared as per the procedures illustrated in Example 3. Compound 14 is commercially available. Compound 17 was prepared using similar procedures reported by Rensen et al., *J. Med. Chem.*, 2004, 47, 5798-5808.
Example 5
Preparation of Compound 23
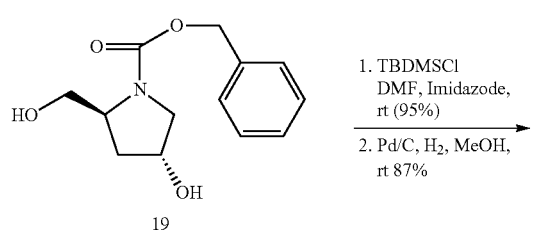
19
1. TBDMSCl
   DMF, Imidazode,
   rt (95%)
2. Pd/C, H₂, MeOH,
   rt 87%
-continued
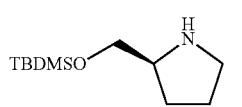
21
20
1. 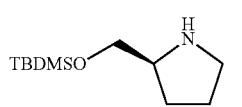 21
HBTU, DIEA
DMF, rt (65%)
2. TEA, 3HF, TEA, THF
(72%)
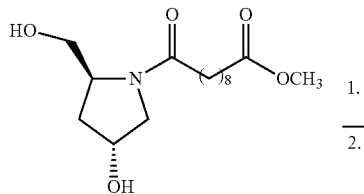
22
1. DMTCl, pyr,
   rt (75%)
2. LiOH, Dioxane
   (97%)

-continued
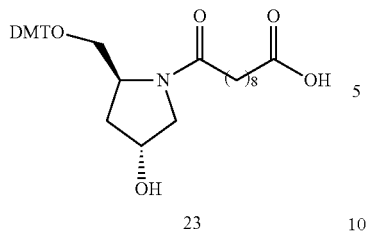
23
Compounds 19 and 21 are commercially available.
Example 6
Preparation of Compound 24
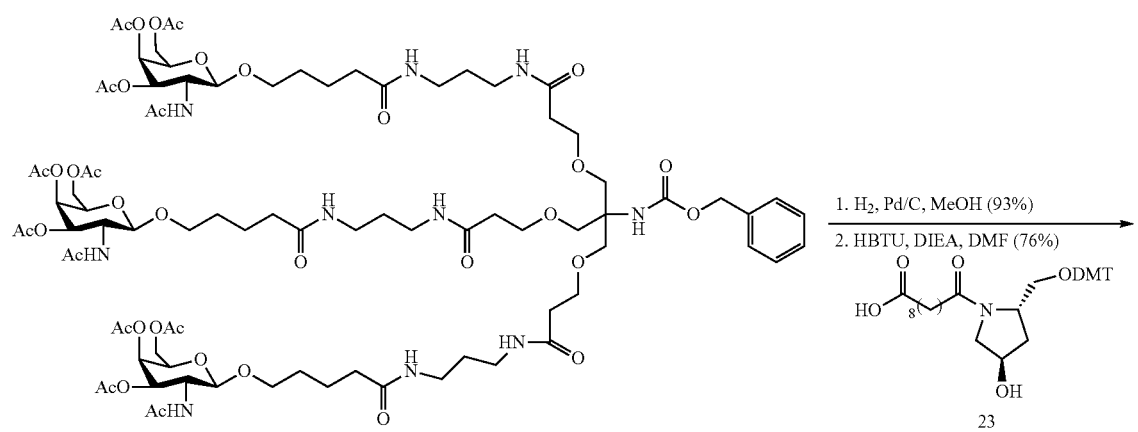
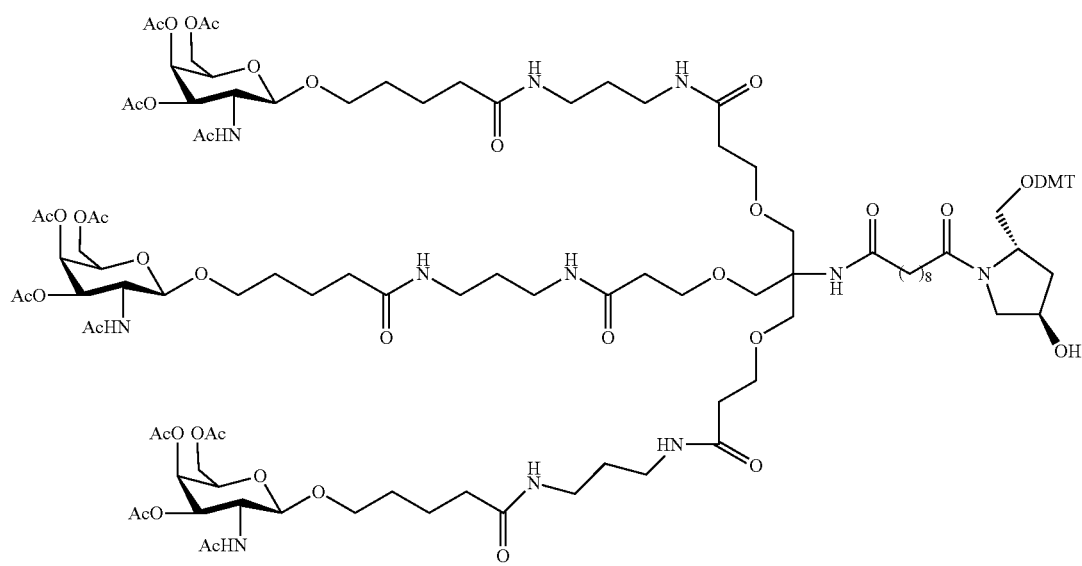
Compounds 18 and 23 were prepared as per the procedures illustrated in Examples 4 and 5.

Example 7
Preparation of Compound 25
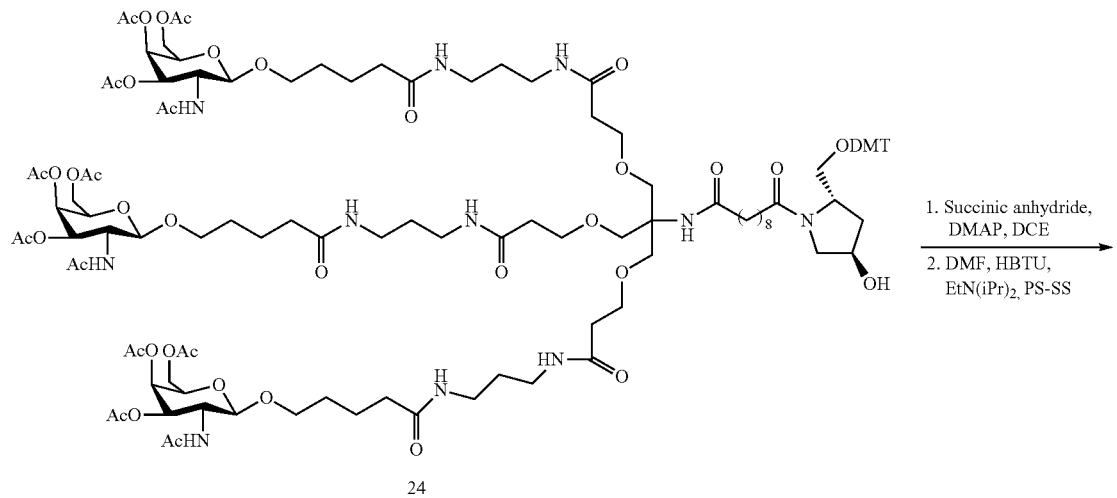
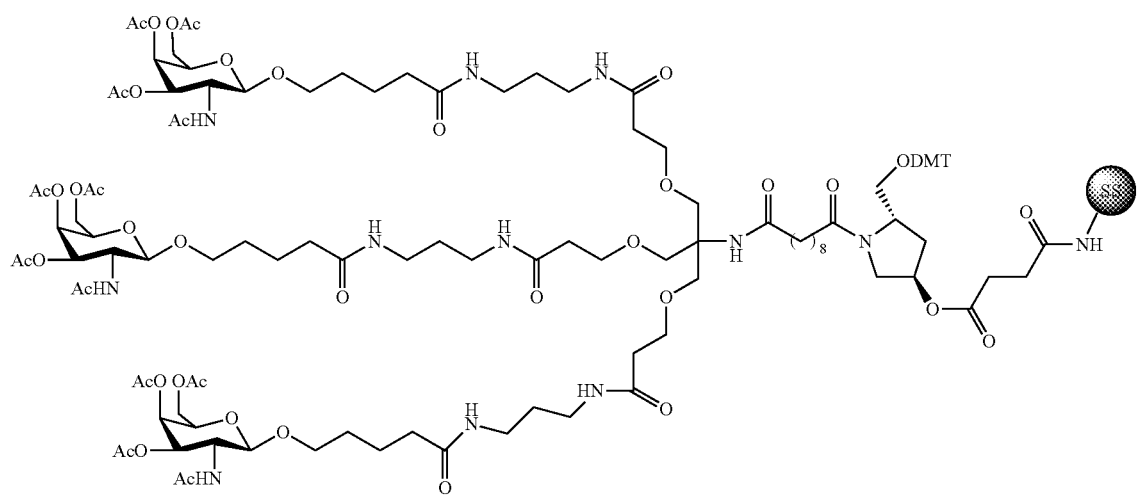
Compound 24 was prepared as per the procedures illustrated in Example 6.

Example 8
Preparation of Compound 26
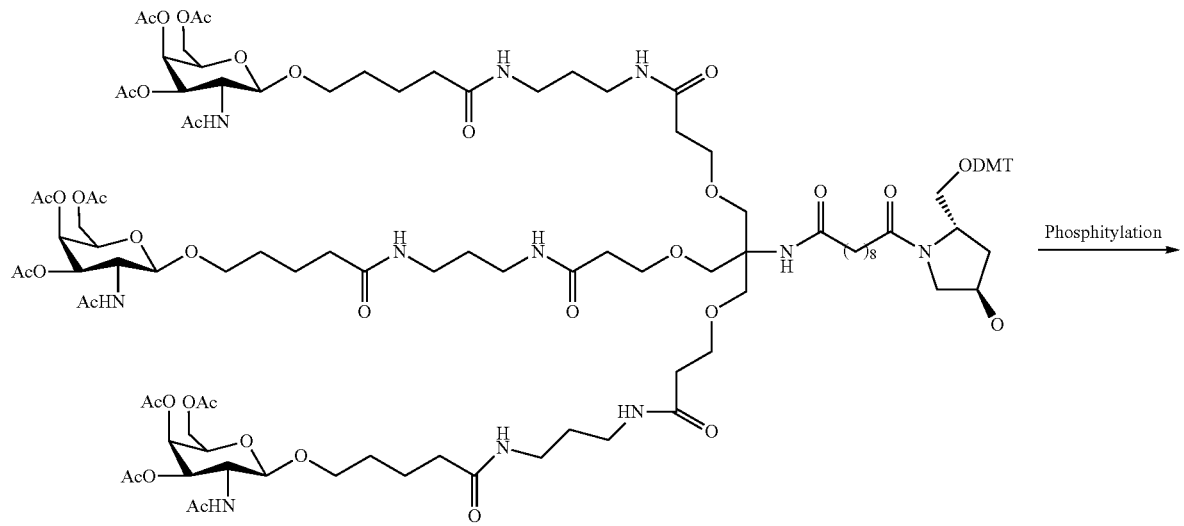
24
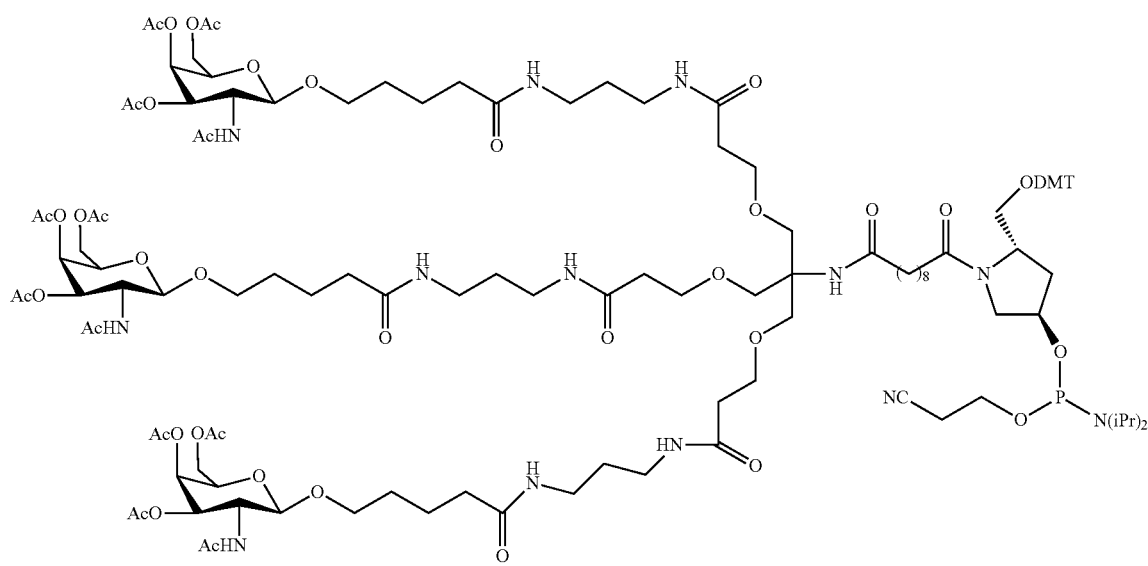
26
Compound 24 is prepared as per the procedures illustrated in Example 6.

Example 9
General Preparation of Conjugated ASOs Comprising GalNAc₃-1 at the 3' Terminus, Compound 29
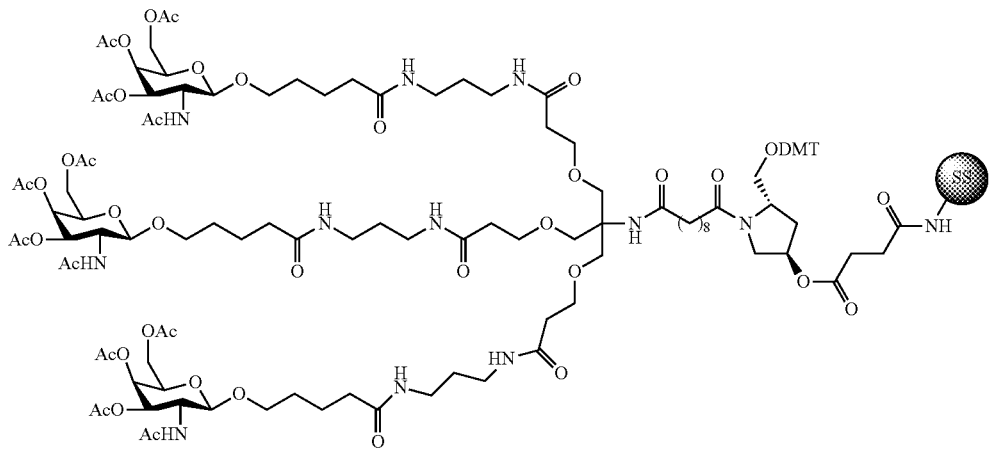
25
1. DCA, DCM
2. DCI, NMI, ACN
   Phosphoramidite
   building block 1
3. Capping
4. t-BuOOH
DNA/RNA automated synthesizer
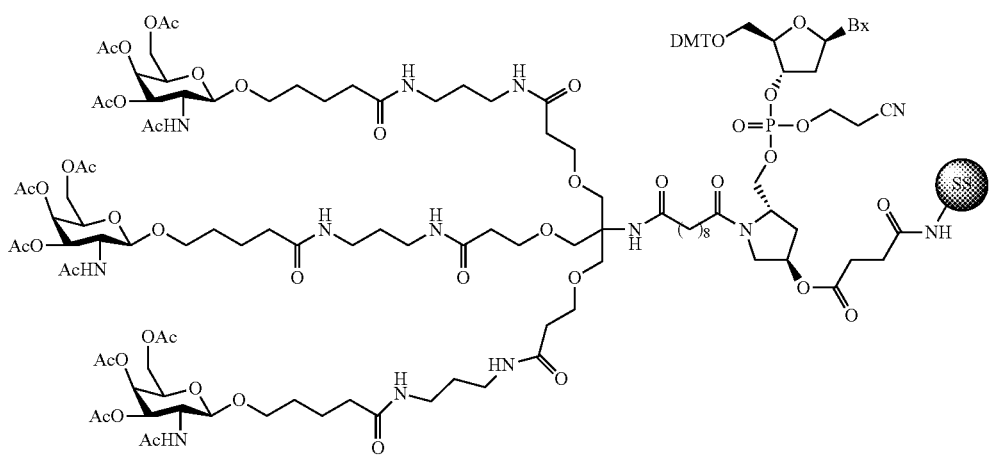
27
1. DCA, DCM
2. DCI, NMI, ACN
   Phosphoramidite
   building block 1a
3. Capping
4. t-BuOOH
DNA/RNA automated synthesizer -continued
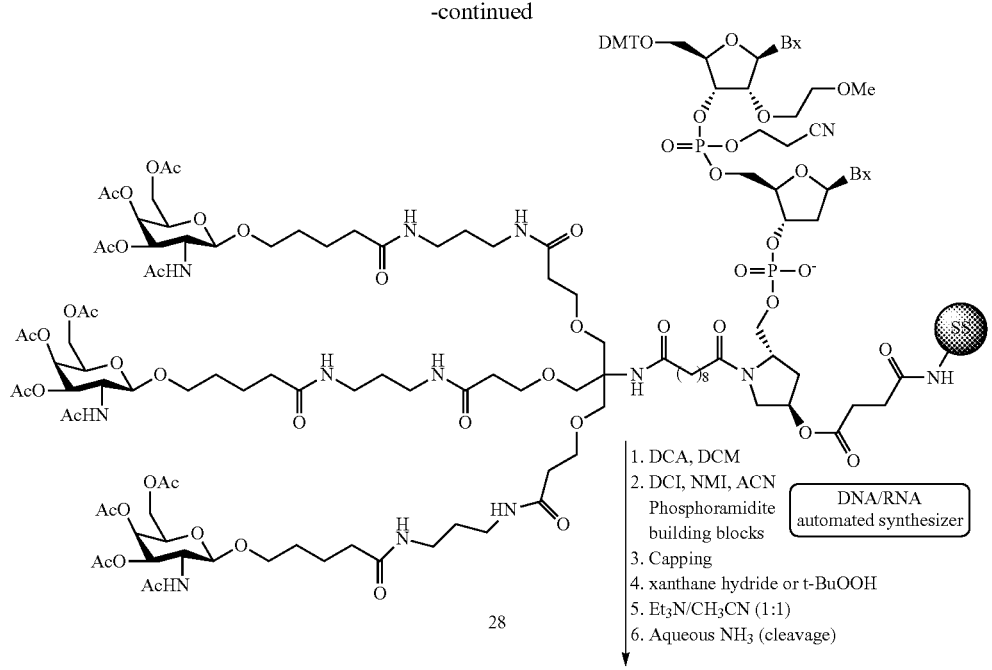
28
1. DCA, DCM
2. DCI, NMI, ACN
   Phosphoramidite building blocks
   DNA/RNA automated synthesizer
3. Capping
4. xanthane hydride or t-BuOOH
5. Et₃N/CH₃CN (1:1)
6. Aqueous NH₃ (cleavage)
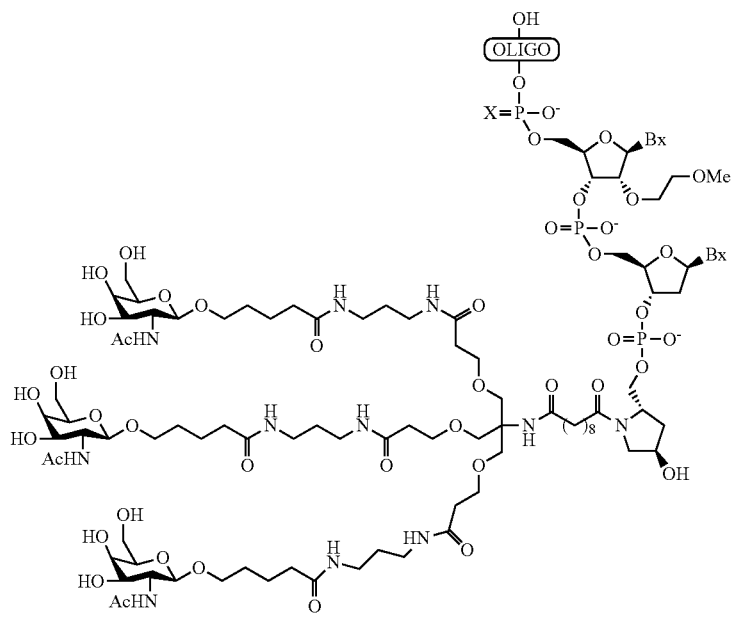
29
Bx = Heterocyclic base
X = O or S Wherein the protected GalNAc₃-1 has the structure:

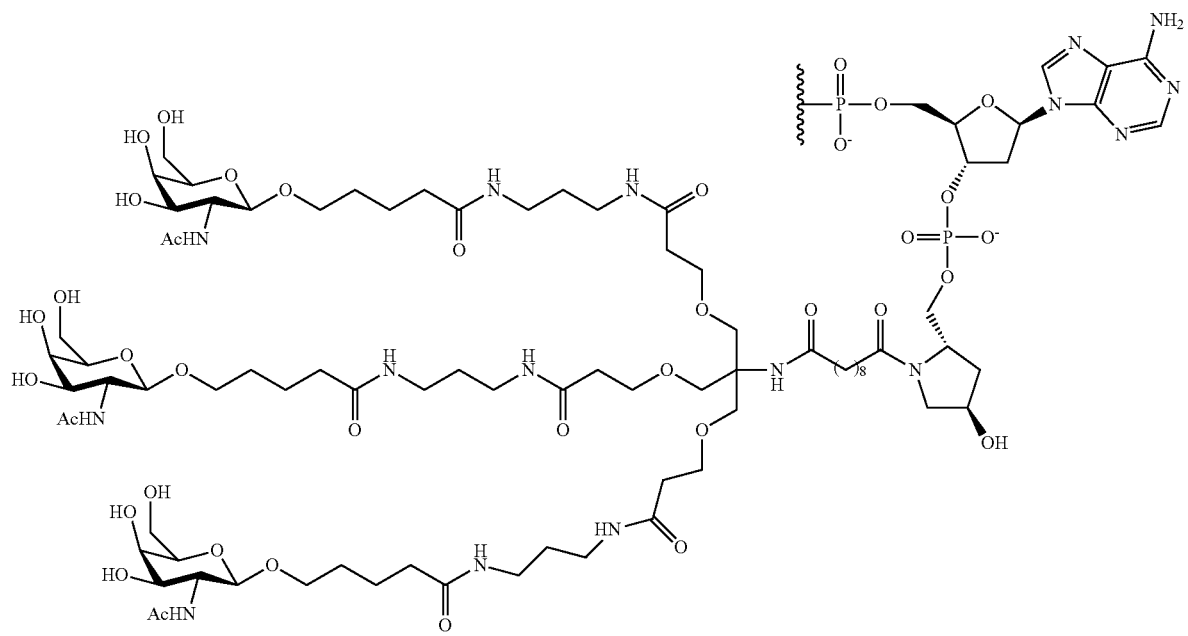

The GalNAc₃ cluster portion of the conjugate group GalNAc₃-1 (GalNAc₃-1$_a$) can be combined with any cleavable moiety to provide a variety of conjugate groups. Wherein GalNAc₃-1$_a$ has the formula:

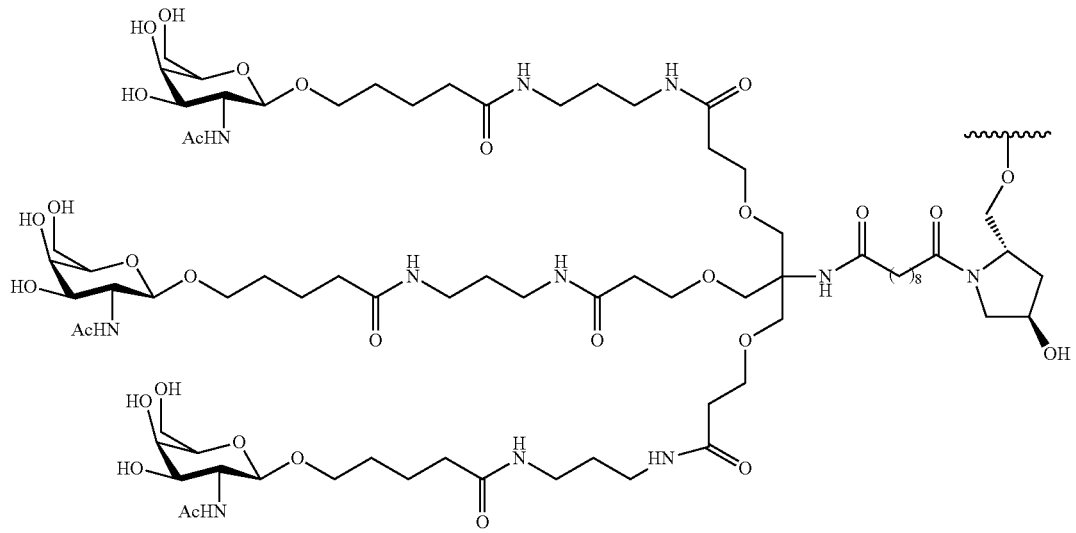

The solid support bound protected GalNAc₃-1, Compound 25, was prepared as per the procedures illustrated in Example 7. Oligomeric Compound 29 comprising GalNAc₃-1 at the 3' terminus was prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare oligomeric compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10
General Preparation Conjugated ASOs Comprising GalNAc₃-1 at the 5' Terminus, Compound 34
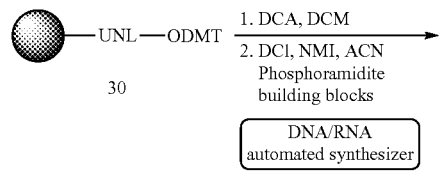
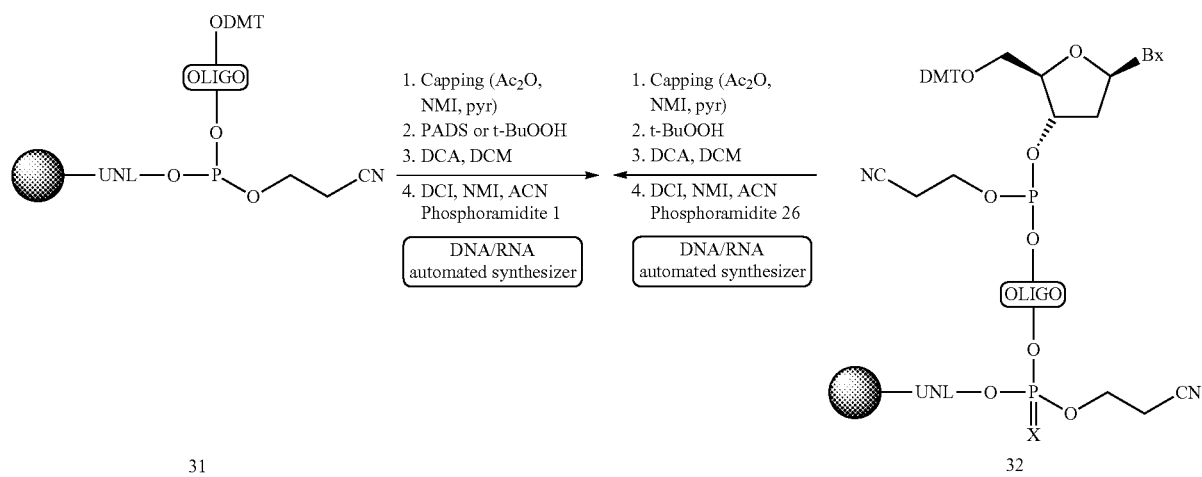
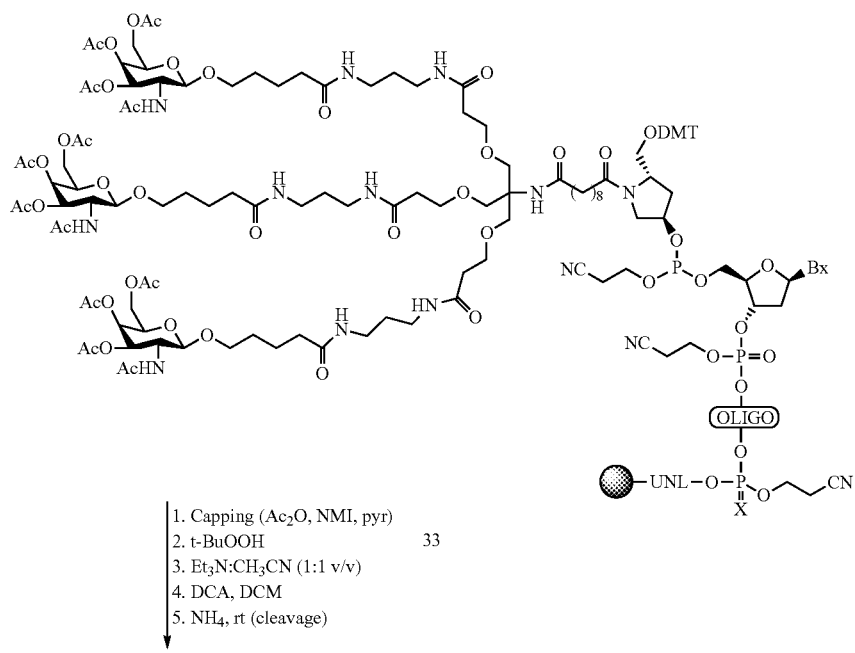

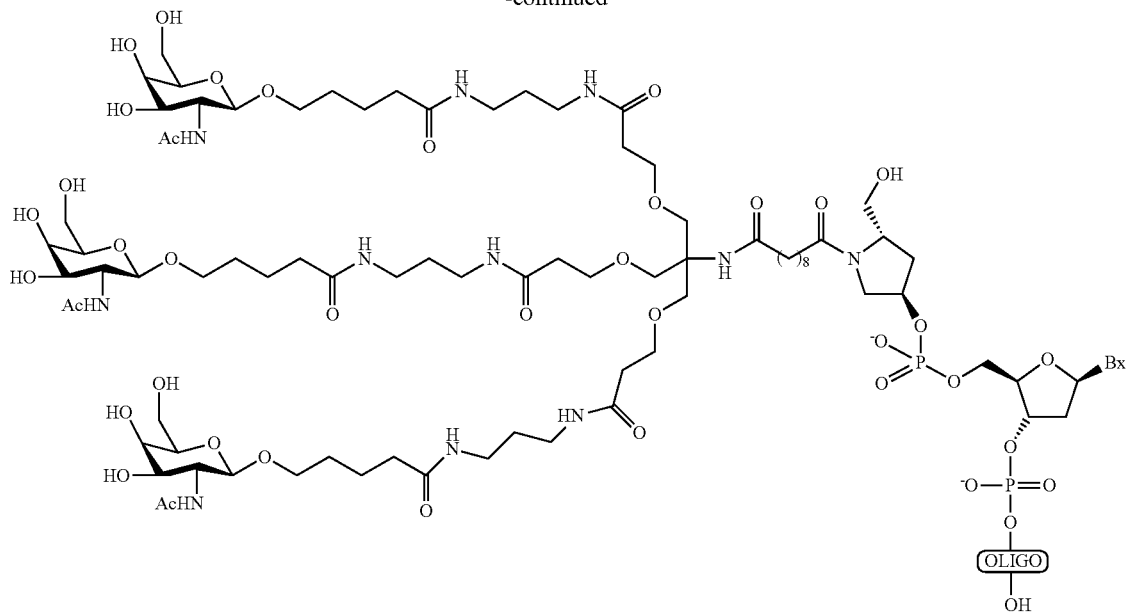

34

X = O, or S
Bx = Heterocylic base

The Unylinker™ 30 is commercially available. Oligomeric Compound 34 comprising a GalNAc$_3$-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare an oligomeric compound having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 11

Preparation of Compound 39

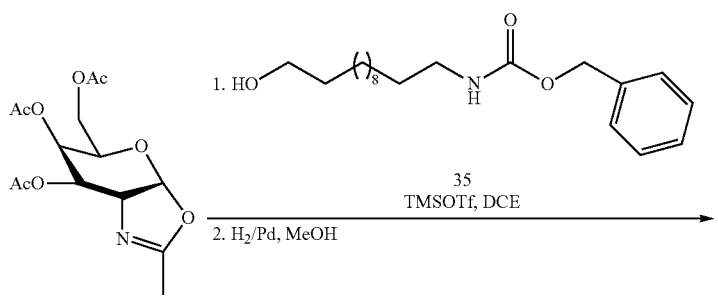

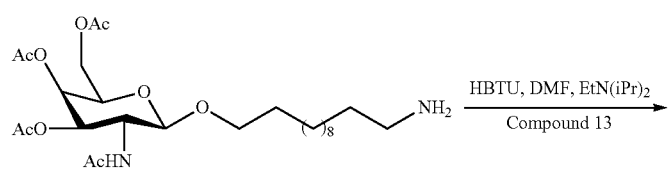

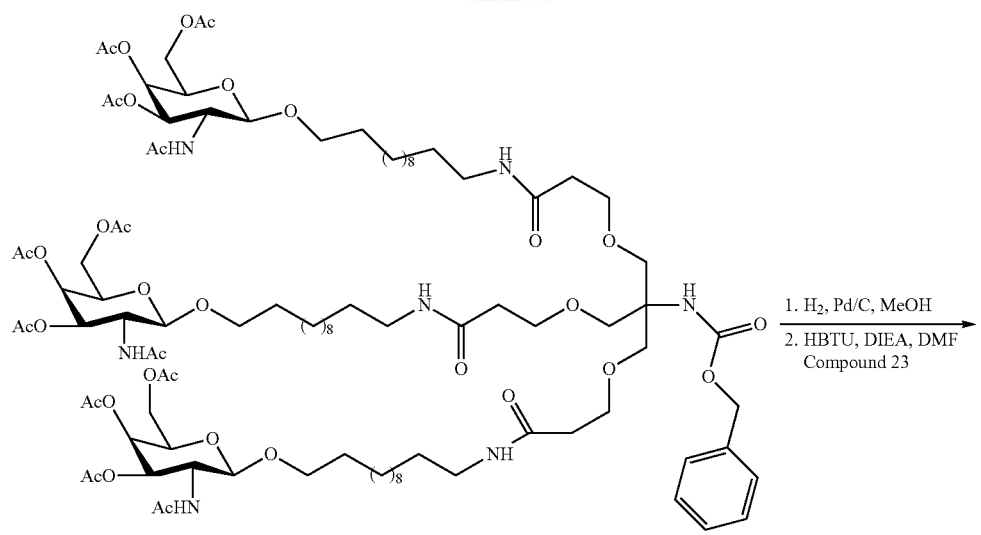
37
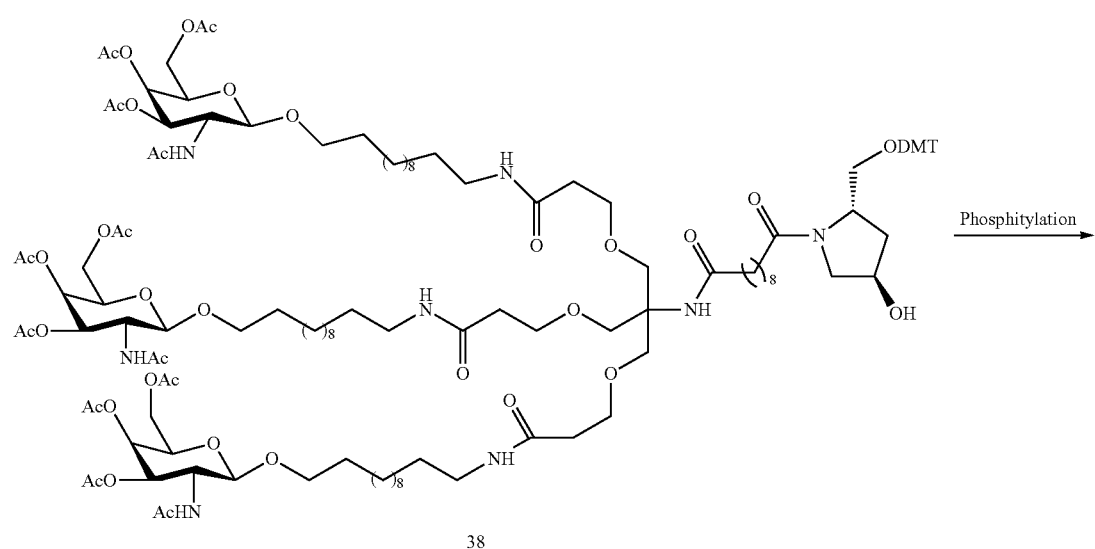
38
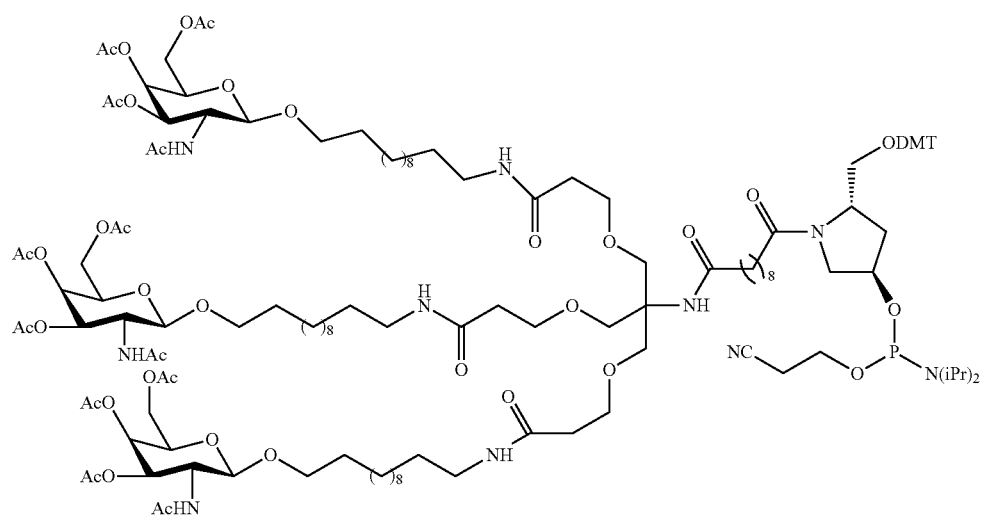
39

Compounds 4, 13 and 23 were prepared as per the procedures illustrated in Examples 2, 4, and 5. Compound 35 is prepared using similar procedures published in Rouchaud et al., *Eur. J. Org. Chem.*, 2011, 12, 2346-2353.
Example 12
Preparation of Compound 40
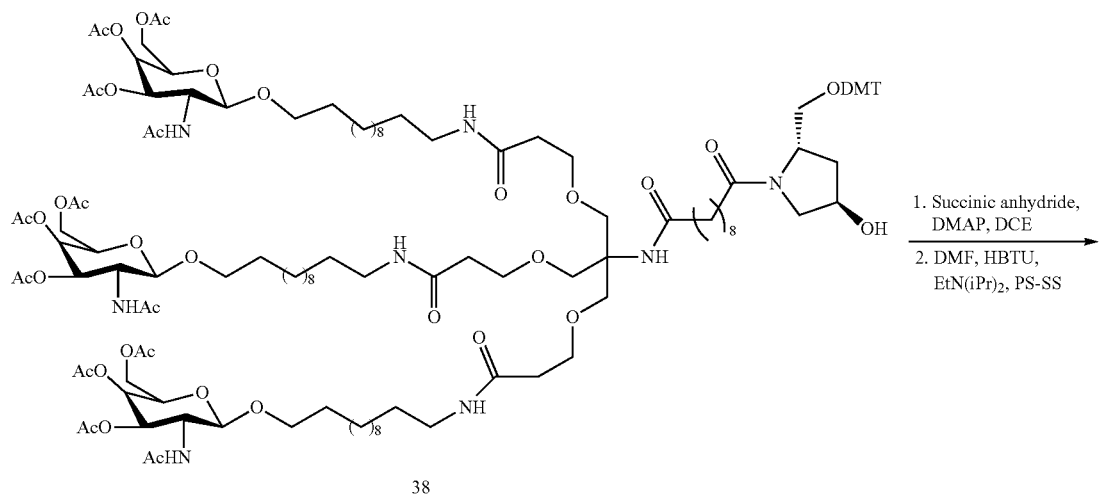
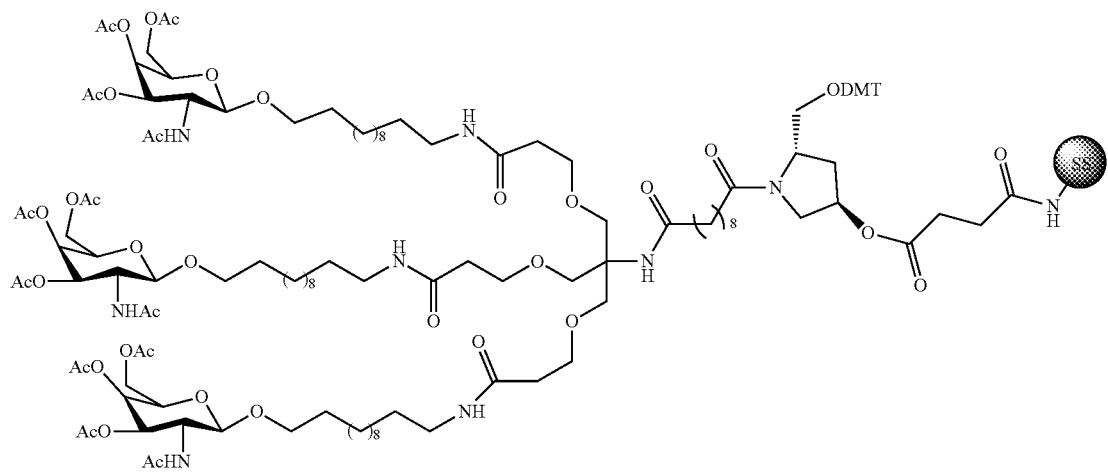
Compound 38 is prepared as per the procedures illustrated in Example 11.

Example 13
Preparation of Compound 44
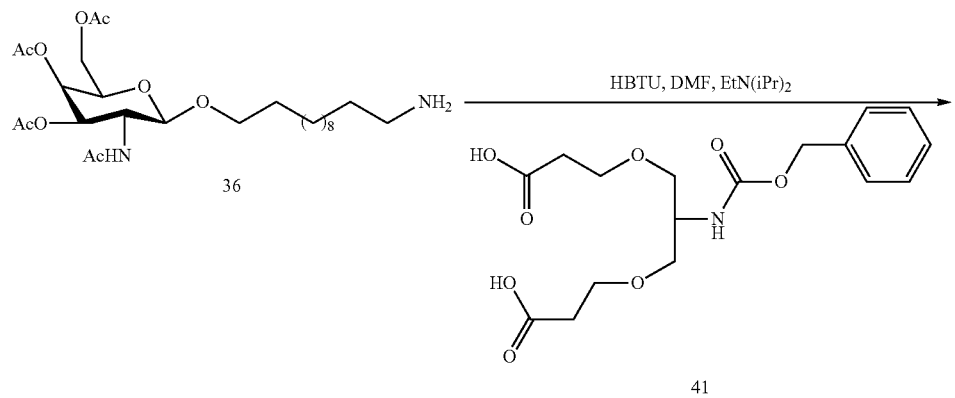
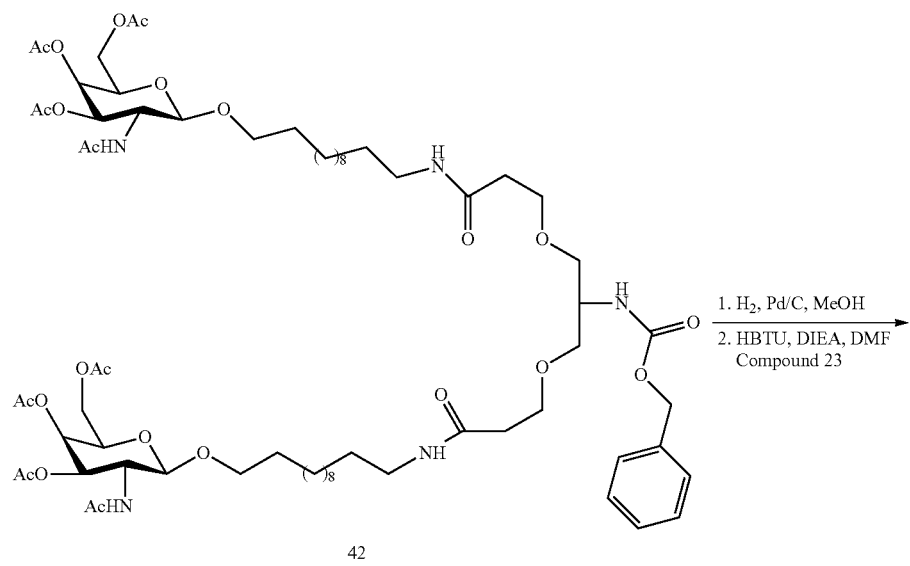
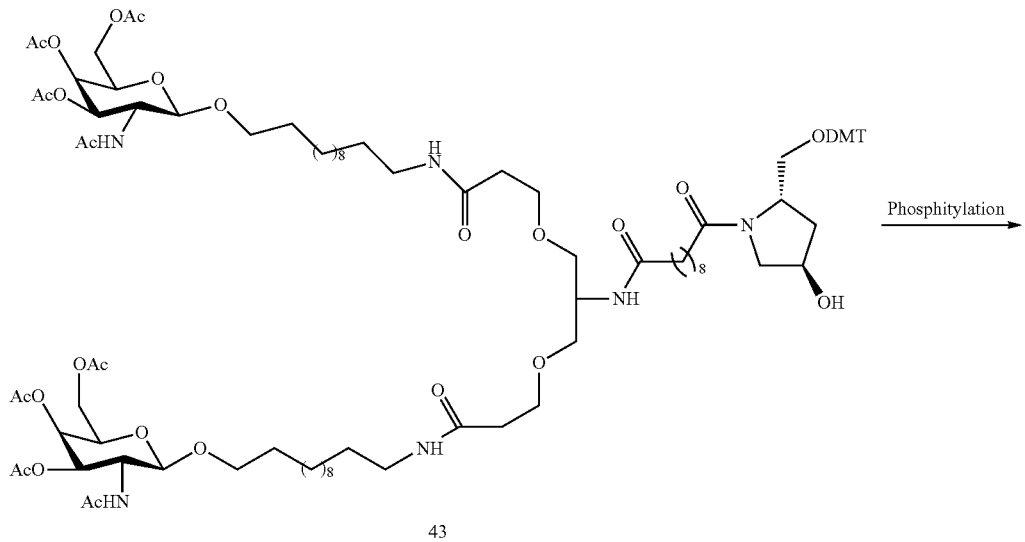

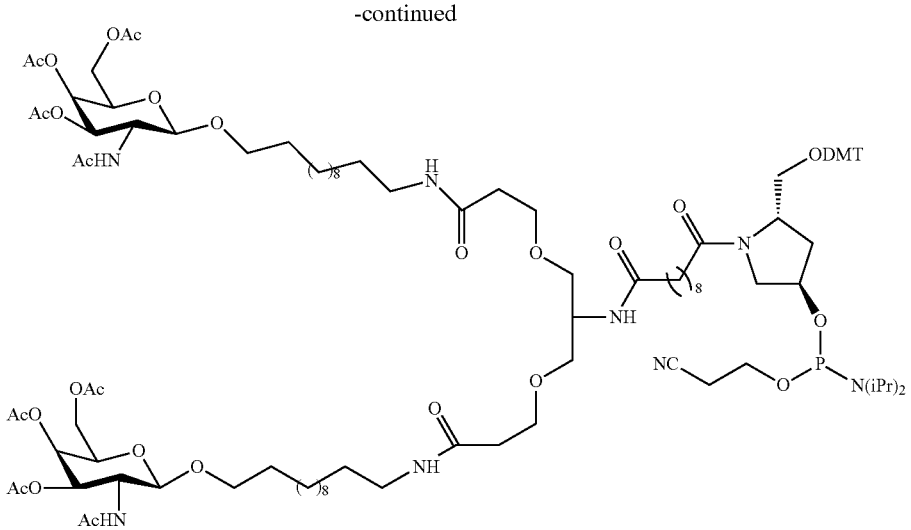
44
Compounds 23 and 36 are prepared as per the procedures illustrated in Examples 5 and 11. Compound 41 is prepared using similar procedures published in WO 2009082607.
Example 14
Preparation of Compound 45
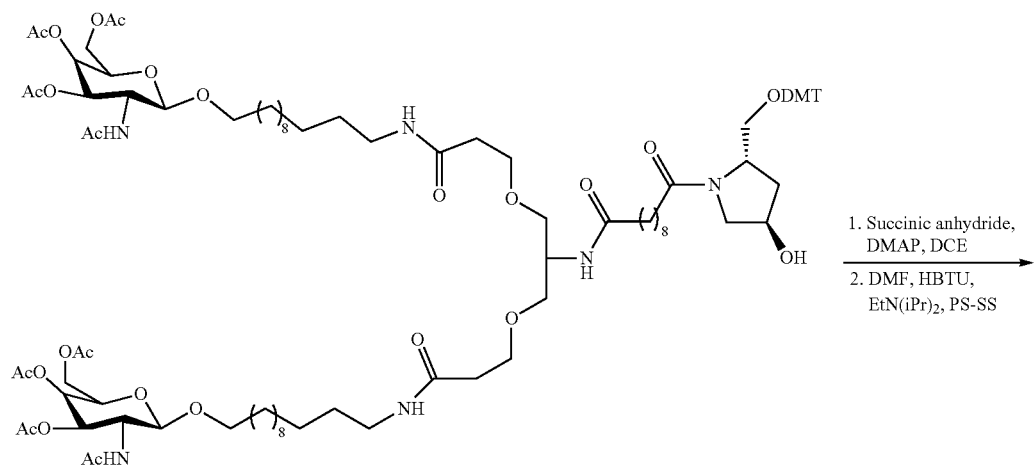

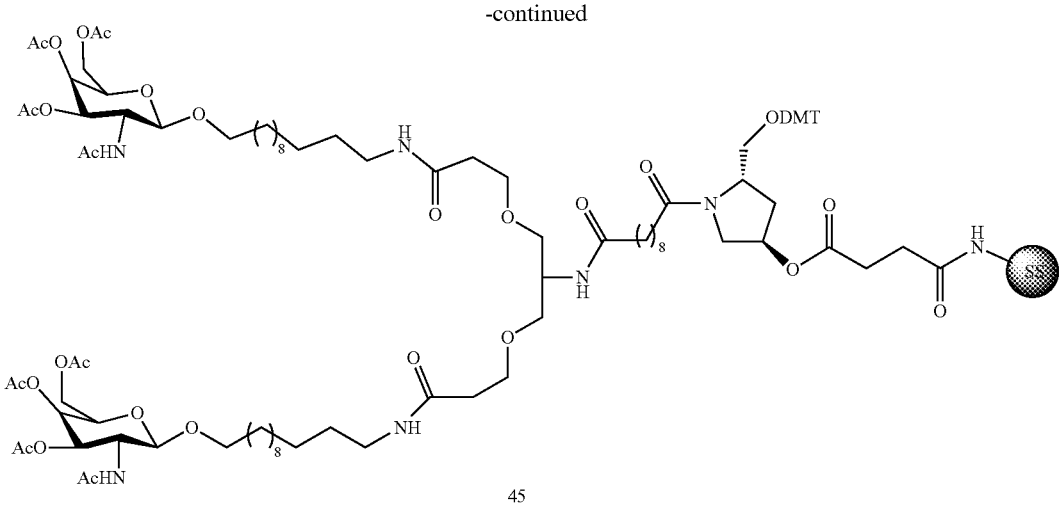
45
Compound 43 is prepared as per the procedures illustrated in Example 13.
Example 15
Preparation of Compound 47
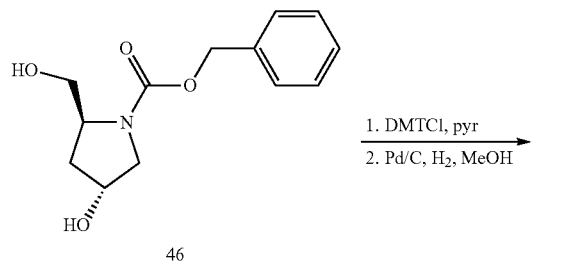
1. DMTCl, pyr
2. Pd/C, H₂, MeOH
Compound 46 is commercially available.
Example 16
Preparation of Compound 53
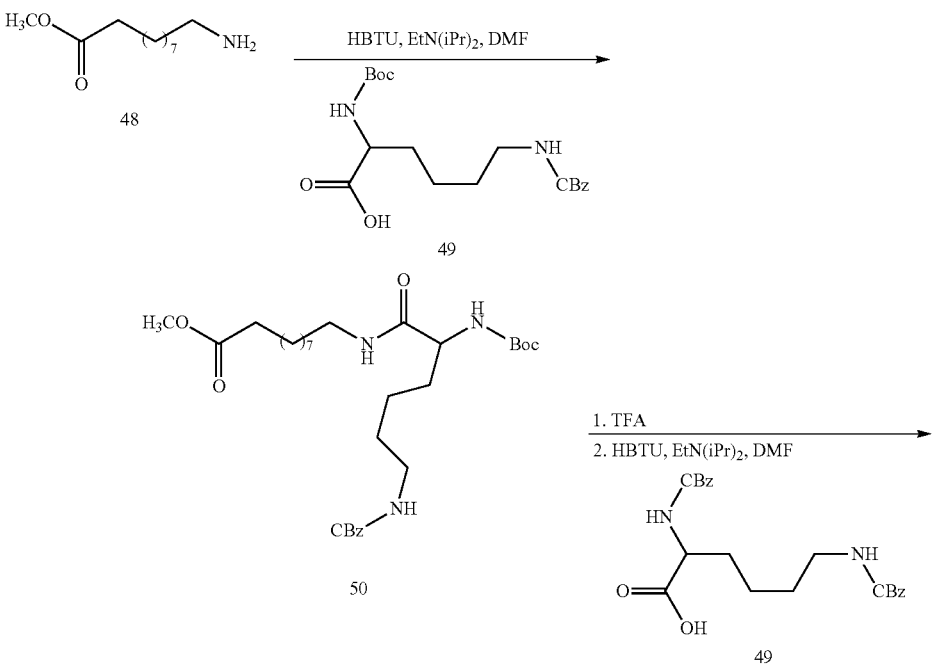

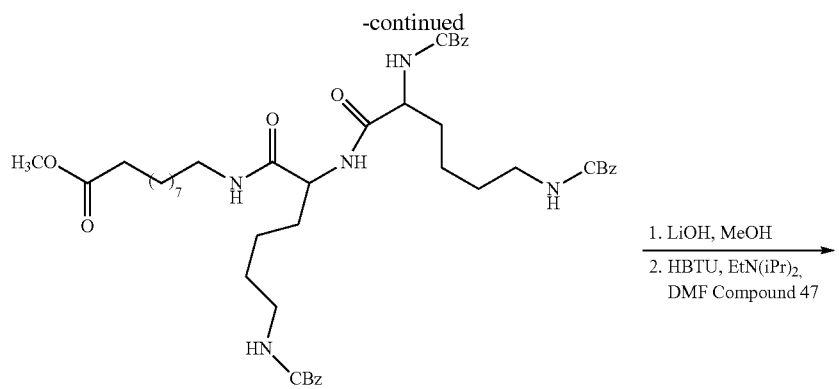
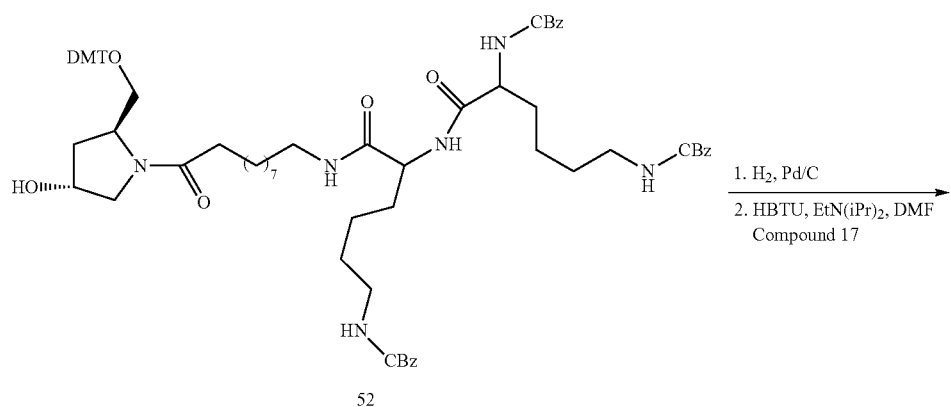
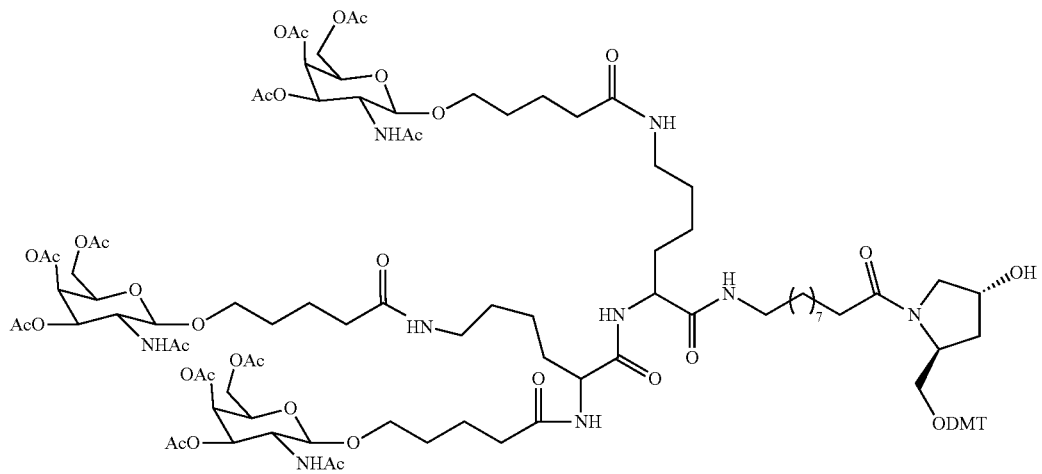
Compounds 48 and 49 are commercially available. Compounds 17 and 47 are prepared as per the procedures illustrated in Examples 4 and 15.

Example 17
Preparation of Compound 54
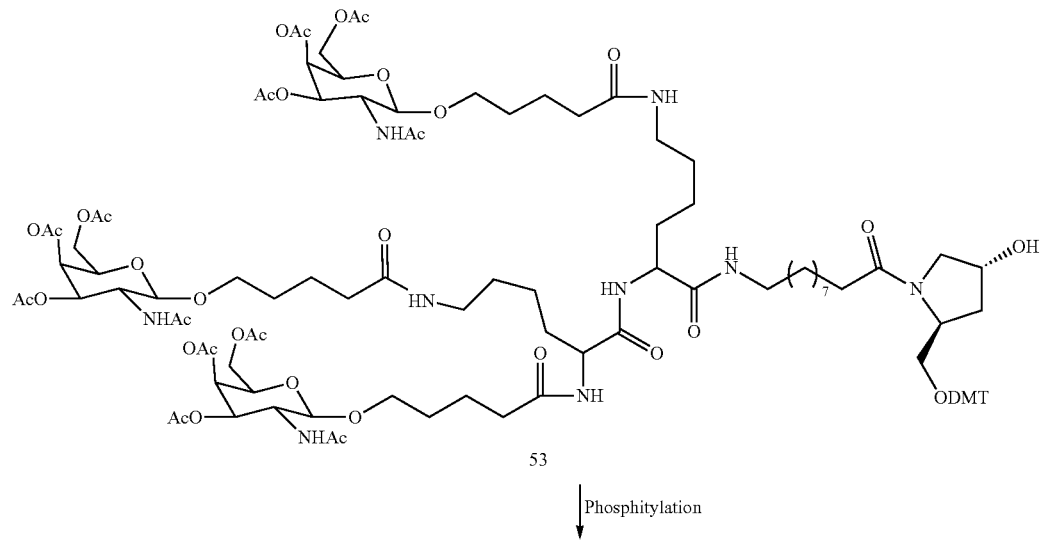
53
↓ Phosphitylation
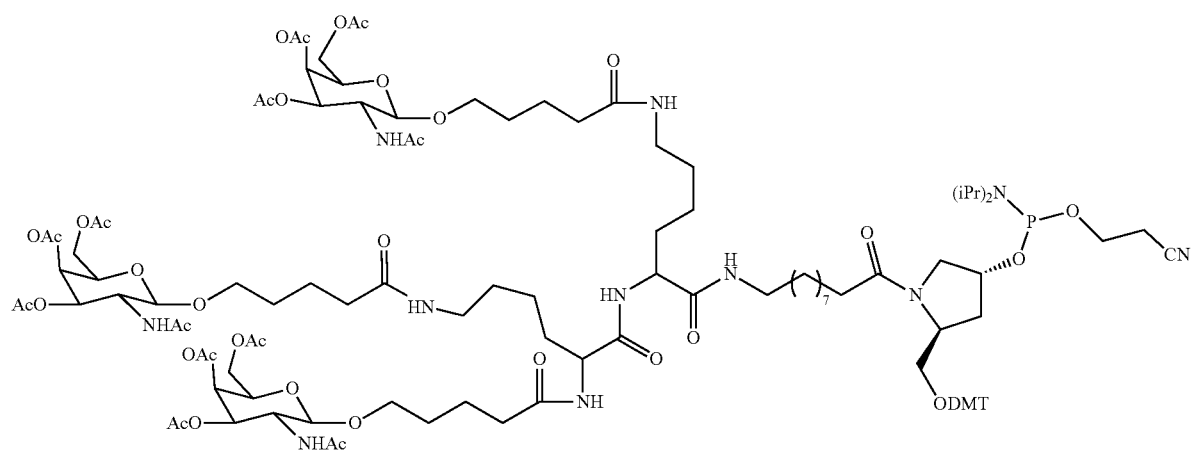
54
Compound 53 is prepared as per the procedures illustrated in Example 16.

Example 18

Preparation of Compound 55

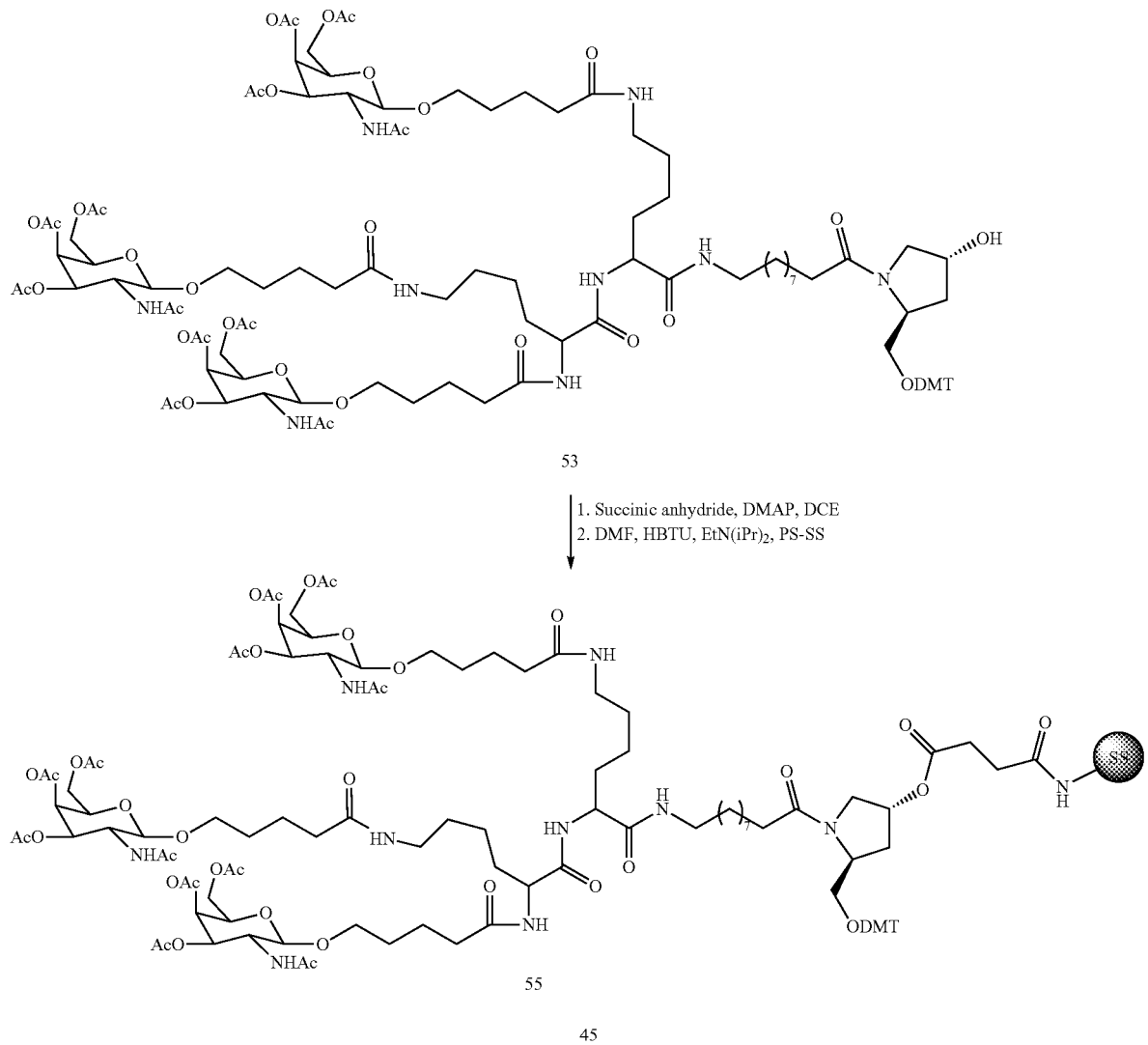

Compound 53 is prepared as per the procedures illustrated in Example 16.

Example 19

General Method for the Preparation of Conjugated ASOs Comprising GalNAc₃-1 at the 3' Position Via Solid Phase Techniques (Preparation of ISIS 647535, 647536 and 651900)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on an GalNAc₃-1 loaded VIMAD solid support (110 μmol/g, Guzaev et al., 2003) packed in the column. For the coupling step, the phosphoramidites were delivered 4 fold excess over the loading on the solid support and phosphoramidite condensation was carried out for 10 min. All other steps followed standard protocols supplied by the manufacturer. A solution of 6% dichloroacetic acid in toluene was used for removing dimethoxytrityl (DMT) group from 5'-hydroxyl group of the nucleotide. 4,5-Dicyanoimidazole (0.7 M) in anhydrous CH₃CN was used as activator during coupling step. Phosphorothioate linkages were introduced by sulfurization with 0.1 M solution of xanthane hydride in 1:1 pyridine/CH₃CN for a contact time of 3 minutes. A solution of 20% tert-butylhydroperoxide in CH₃CN containing 6% water was used as an oxidizing agent to provide phosphodiester internucleoside linkages with a contact time of 12 minutes.

After the desired sequence was assembled, the cyanoethyl phosphate protecting groups were deprotected using a 1:1 (v/v) mixture of triethylamine and acetonitrile with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 µm, 2.54×8 cm, A=100 mM ammonium acetate in 30% aqueous $CH_3CN$, B=1.5 M NaBr in A, O-40% of B in 60 min, flow 14 mL min-1, $\lambda$=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

Antisense oligonucleotides not comprising a conjugate were synthesized using standard oligonucleotide synthesis procedures well known in the art.

Using these methods, three separate antisense compounds targeting ApoC III were prepared. As summarized in Table 4, below, each of the three antisense compounds targeting ApoC III had the same nucleobase sequence; ISIS 304801 is a 5-10-5 MOE gapmer having all phosphorothioate linkages; ISIS 647535 is the same as ISIS 304801, except that it had a $GalNAc_3$-1 conjugated at its 3'end; and ISIS 647536 is the same as ISIS 647535 except that certain internucleoside linkages of that compound are phosphodiester linkages. As further summarized in Table 4, two separate antisense compounds targeting SRB-1 were synthesized. ISIS 440762 was a 2-10-2 cEt gapmer with all phosphorothioate internucleoside linkages; ISIS 651900 is the same as ISIS 440762, except that it included a $GalNAc_3$-1 at its 3'-end.

TABLE 4

Modified ASO targeting ApoC III and SRB-1

| ASO | Sequence (5' to 3') | Target | CalCd Mass | Observed Mass | SEQ ID No. |
|---|---|---|---|---|---|
| ISIS 304801 | $A_{es}G_{es}{}^mC_{es}T_{es}T_{es}{}^mC_{ds}$ $T_{ds}T_{ds}G_{ds}T_{ds}{}^mC_{ds}{}^mC_{ds}$ $A_{ds}G_{ds}{}^mC_{ds}T_{es}T_{es}$ $A_{es}T_e$ | ApoC III | 7165.4 | 7164.4 | 20 |
| ISIS 647535 | $A_{es}G_{es}{}^mC_{es}T_{es}T_{es}{}^mC_{ds}$ $T_{ds}T_{ds}G_{ds}T_{ds}{}^mC_{ds}{}^mC_{ds}$ $A_{ds}G_{ds}{}^mC_{ds}T_{es}T_{es}A_{es}$ $T_e\mathbf{A_{do}},\mathbf{\text{-GalNAc}_3\text{-1}_a}$ | ApoC III | 9239.5 | 9237.8 | 21 |
| ISIS 647536 | $A_{es}G_{eo}{}^mC_{eo}T_{eo}T_{eo}{}^mC_{ds}$ $T_{ds}T_{ds}G_{ds}T_{ds}{}^mC_{ds}{}^mC_{ds}$ $A_{ds}G_{ds}{}^mC_{ds}T_{eo}T_{eo}T_{es}A_{es}$ $T_e\mathbf{A_{do}},\mathbf{\text{-GalNAc}_3\text{-1}_a}$ | ApoC III | 9142.9 | 9140.8 | 21 |
| ISIS 440762 | $T_{ks}{}^mC_{ks}A_{ds}G_{ds}T_{ds}{}^mC_{ds}$ $A_{ds}T_{ds}G_{ds}A_{ds}{}^mC_{ds}T_{ds}$ $T_{ks}{}^mC_k$ | SRB-1 | 4647.0 | 4646.4 | 22 |
| ISIS 651900 | $T_{ks}{}^mC_{ks}A_{ds}G_{ds}T_{ds}{}^mC_{ds}$ $A_{ds}T_{ds}G_{ds}A_{ds}{}^mC_{ds}T_{ds}T_{ds}{}^m$ $C_k\mathbf{A_{do}},\mathbf{\text{-GalNAc}_3\text{-1}_a}$ | SRB-1 | 6721.1 | 6719.4 | 23 |

Subscripts: "e" indicates 2'-MOE modified nucleoside; "d" indicates β-D-2'-deoxyribonucleoside; "k" indicates 6'-(S)—$CH_3$ bicyclic nucleoside (e.g. cEt); "s" indicates phosphorothioate internucleoside linkages (PS); "o" indicates phosphodiester internucleoside linkages (PO); and "o" indicates —O—P(=O)(OH)—. Superscript "m" indicates 5-methylcytosines. "$GalNAc_3$-1" indicates a conjugate group having the structure shown previously in Example 9. Note that $GalNAc_3$-1 comprises a cleavable adenosine which links the ASO to remainder of the conjugate, which is designated "$GalNAc_3$-$1_a$." This nomenclature is used in the above table to show the full nucleobase sequence, including the adenosine, which is part of the conjugate. Thus, in the above table, the sequences could also be listed as ending with "$GalNAc_3$-1" with the "$A_{do}$" omitted. This convention of using the subscript "a" to indicate the portion of a conjugate group lacking a cleavable nucleoside or cleavable moiety is used throughout these Examples. This portion of a conjugate group lacking the cleavable moiety is referred to herein as a "cluster" or "conjugate cluster" or "$GalNAc_3$ cluster." In certain instances it is convenient to describe a conjugate group by separately providing its cluster and its cleavable moiety.

Example 20

Dose-Dependent Antisense Inhibition of Human ApoC III in huApoC III Transgenic Mice ISIS 304801 and ISIS 647535, each targeting human ApoC III and described above, were separately tested and evaluated in a dose-dependent study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once a week for two weeks with ISIS 304801 or 647535 at 0.08, 0.25. 0.75, 2.25 or 6.75 µmol/kg or with PBS as a control. Each treatment group consisted of 4 animals. Forty-eight hours after the administration of the last dose, blood was drawn from each mouse and the mice were sacrificed and tissues were collected.

ApoC III mRNA Analysis

ApoC III mRNA levels in the mice's livers were determined using real-time PCR and RIBOGREEN® RNA quantification reagent (Molecular Probes, Inc. Eugene, Oreg.) according to standard protocols. ApoC III mRNA levels were determined relative to total RNA (using Ribogreen), prior to normalization to PBS-treated control. The results below are presented as the average percent of ApoC III mRNA levels for each treatment group, normalized to PBS-treated control and are denoted as "% PBS". The half maximal effective dosage ($ED_{50}$) of each ASO is also presented in Table 5, below.

As illustrated, both antisense compounds reduced ApoC III RNA relative to the PBS control. Further, the antisense compound conjugated to $GalNAc_3$-1 (ISIS 647535) was substantially more potent than the antisense compound lacking the $GalNAc_3$-1 conjugate (ISIS 304801).

TABLE 5

Effect of ASO treatment on ApoC III mRNA levels in human ApoC III transgenic mice

| ASO | Dose (µmol/kg) | % PBS | $ED_{50}$ (µmol/kg) | 3' Conjugate | Internucleoside linkage/Length | SEQ ID No. |
|---|---|---|---|---|---|---|
| PBS | 0 | 100 | — | — | — | |
| ISIS 304801 | 0.08 | 95 | 0.77 | None | PS/20 | 20 |
| | 0.75 | 42 | | | | |
| | 2.25 | 32 | | | | |
| | 6.75 | 19 | | | | |

TABLE 5-continued

Effect of ASO treatment on ApoC III mRNA levels in human ApoC III transgenic mice

| ASO | Dose (µmol/kg) | % PBS | ED$_{50}$ (µmol/kg) | 3' Conjugate | Internucleoside linkage/Length | SEQ ID No. |
|---|---|---|---|---|---|---|
| ISIS 647535 | 0.08 | 50 | 0.074 | GalNAc$_3$-1 | PS/20 | 21 |
| | 0.75 | 15 | | | | |
| | 2.25 | 17 | | | | |
| | 6.75 | 8 | | | | |

ApoC III Protein Analysis (Turbidometric Assay)

Plasma ApoC III protein analysis was determined using procedures reported by Graham et al, *Circulation Research*, published online before print Mar. 29, 2013.

Approximately 100 µl of plasma isolated from mice was analyzed without dilution using an Olympus Clinical Analyzer and a commercially available turbidometric ApoC III assay (Kamiya, Cat#KAI-006, Kamiya Biomedical, Seattle, Wash.). The assay protocol was performed as described by the vendor.

As shown in the Table 6 below, both antisense compounds reduced ApoC III protein relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 6

Effect of ASO treatment on ApoC III plasma protein levels in human ApoC III transgenic mice

| ASO | Dose (µmol/kg) | % PBS | ED$_{50}$ (µmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 86 | 0.73 | None | PS/20 | 20 |
| | 0.75 | 51 | | | | |
| | 2.25 | 23 | | | | |
| | 6.75 | 13 | | | | |
| ISIS 647535 | 0.08 | 72 | 0.19 | GalNAc$_3$-1 | PS/20 | 21 |
| | 0.75 | 14 | | | | |
| | 2.25 | 12 | | | | |
| | 6.75 | 11 | | | | |

Plasma triglycerides and cholesterol were extracted by the method of Bligh and Dyer (Bligh, E. G. and Dyer, W. J. Can. J. Biochem. Physiol. 37: 911-917, 1959)(Bligh, E and Dyer, W, *Can J Biochem Physiol*, 37, 911-917, 1959)(Bligh, E and Dyer, W, *Can J Biochem Physiol*, 37, 911-917, 1959) and measured by using a Beckmann Coulter clinical analyzer and commercially available reagents.

The triglyceride levels were measured relative to PBS injected mice and are denoted as "% PBS". Results are presented in Table 7. As illustrated, both antisense compounds lowered triglyceride levels. Further, the antisense compound conjugated to GalNAc$_3$-1 (ISIS 647535) was substantially more potent than the antisense compound lacking the GalNAc$_3$-1 conjugate (ISIS 304801).

TABLE 7

Effect of ASO treatment on triglyceride levels in transgenic mice

| ASO | Dose (µmol/kg) | % PBS | ED$_{50}$ (µmol/kg) | 3' Conjugate | Internucleoside Linkage/Length | SEQ ID No. |
|---|---|---|---|---|---|---|
| PBS | 0 | 100 | — | — | — | |
| ISIS 304801 | 0.08 | 87 | 0.63 | None | PS/20 | 20 |
| | 0.75 | 46 | | | | |
| | 2.25 | 21 | | | | |
| | 6.75 | 12 | | | | |
| ISIS 647535 | 0.08 | 65 | 0.13 | GalNAc$_3$-1 | PS/20 | 21 |
| | 0.75 | 9 | | | | |
| | 2.25 | 8 | | | | |
| | 6.75 | 9 | | | | |

Plasma samples were analyzed by HPLC to determine the amount of total cholesterol and of different fractions of cholesterol (HDL and LDL). Results are presented in Tables 8 and 9. As illustrated, both antisense compounds lowered total cholesterol levels; both lowered LDL; and both raised HDL. Further, the antisense compound conjugated to GalNAc$_3$-1 (ISIS 647535) was substantially more potent than the antisense compound lacking the GalNAc$_3$-1 conjugate (ISIS 304801). An increase in HDL and a decrease in LDL levels is a cardiovascular beneficial effect of antisense inhibition of ApoC III.

TABLE 8

Effect of ASO treatment on total cholesterol levels in transgenic mice

| ASO | Dose (µmol/kg) | Total Cholesterol (mg/dL) | 3' Conjugate | Internucleoside Linkage/Length | SEQ ID No. |
|---|---|---|---|---|---|
| PBS | 0 | 257 | — | — | |
| ISIS 304801 | 0.08 | 226 | None | PS/20 | 20 |
| | 0.75 | 164 | | | |
| | 2.25 | 110 | | | |
| | 6.75 | 82 | | | |
| ISIS 647535 | 0.08 | 230 | GalNAc$_3$-1 | PS/20 | 21 |
| | 0.75 | 82 | | | |
| | 2.25 | 86 | | | |
| | 6.75 | 99 | | | |

TABLE 9

Effect of ASO treatment on HDL and LDL cholesterol levels in transgenic mice

| ASO | Dose (µmol/kg) | HDL (mg/dL) | LDL (mg/dL) | 3' Conjugate | Internucleoside Linkage/Length | SEQ ID No. |
|---|---|---|---|---|---|---|
| PBS | 0 | 17 | 28 | — | — | |
| ISIS 304801 | 0.08 | 17 | 23 | None | PS/20 | 32 |
| | 0.75 | 27 | 12 | | | |
| | 2.25 | 50 | 4 | | | |
| | 6.75 | 45 | 2 | | | |
| ISIS 647535 | 0.08 | 21 | 21 | GalNAc$_3$-1 | PS/20 | 111 |
| | 0.75 | 44 | 2 | | | |
| | 2.25 | 50 | 2 | | | |
| | 6.75 | 58 | 2 | | | |

Pharmacokinetics Analysis (PK)

The PK of the ASOs was also evaluated. Liver and kidney samples were minced and extracted using standard protocols. Samples were analyzed on MSD1 utilizing IP-HPLC-MS. The tissue level (µg/g) of full-length ISIS 304801 and 647535 was measured and the results are provided in Table 10. As illustrated, liver concentrations of total full-length antisense compounds were similar for the two antisense compounds. Thus, even though the GalNAc$_3$-1-conjugated antisense compound is more active in the liver (as demonstrated by the RNA and protein data above), it is not present at substantially higher concentration in the liver. Indeed, the calculated EC$_{50}$ (provided in Table 10) confirms that the observed increase in potency of the conjugated compound cannot be entirely attributed to increased accumulation. This result suggests that the conjugate improved potency by a mechanism other than liver accumulation alone, possibly by improving the productive uptake of the antisense compound into cells.

The results also show that the concentration of GalNAc$_3$-1 conjugated antisense compound in the kidney is lower than that of antisense compound lacking the GalNAc conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly, for non-kidney targets, kidney accumulation is undesired. These data suggest that GalNAc$_3$-1 conjugation reduces kidney accumulation.

Metabolites of ISIS 647535 were also identified and their masses were confirmed by high resolution mass spectrometry analysis. The cleavage sites and structures of the observed metabolites are shown below. The relative % of full length ASO was calculated using standard procedures and the results are presented in Table 10a. The major metabolite of ISIS 647535 was full-length ASO lacking the entire conjugate (i.e. ISIS 304801), which results from cleavage at cleavage site A, shown below. Further, additional metabolites resulting from other cleavage sites were also observed. These results suggest that introducing other cleavable bonds such as esters, peptides, disulfides, phosphoramidates or acyl-hydrazones between the GalNAc$_3$-1 sugar and the ASO, which can be cleaved by enzymes inside the cell, or which may cleave in the reductive environment of the cytosol, or which are labile to the acidic pH inside endosomes and lyzosomes, can also be useful.

TABLE 10

PK analysis of ASO treatment in transgenic mice

| ASO | Dose (µmol/kg) | Liver (µg/g) | Kidney (µg/g) | Liver EC$_{50}$ (µg/g) | 3' Conjugate | Internucleoside Linkage/Length | SEQ ID No. |
|---|---|---|---|---|---|---|---|
| ISIS 304801 | 0.1 | 5.2 | 2.1 | 53 | None | PS/20 | 20 |
|  | 0.8 | 62.8 | 119.6 |  |  |  |  |
|  | 2.3 | 142.3 | 191.5 |  |  |  |  |
|  | 6.8 | 202.3 | 337.7 |  |  |  |  |
| ISIS 647535 | 0.1 | 3.8 | 0.7 | 3.8 | GalNAc$_3$-1 | PS/20 | 21 |
|  | 0.8 | 72.7 | 34.3 |  |  |  |  |
|  | 2.3 | 106.8 | 111.4 |  |  |  |  |
|  | 6.8 | 237.2 | 179.3 |  |  |  |  |

TABLE 10a

Observed full length metabolites of ISIS 647535

| Metabolite | ASO | Cleavage site | Relative % |
|---|---|---|---|
| 1 | ISIS 304801 | A | 36.1 |
| 2 | ISIS 304801 + dA | B | 10.5 |
| 3 | ISIS 647535 minus [3 GalNAc] | C | 16.1 |
| 4 | ISIS 647535 minus [3 GalNAc + 1 5-hydroxypentanoic acid tether] | D | 17.6 |
| 5 | ISIS 647535 minus [2 GalNAc + 2 5-hydroxypentanoic acid tether] | D | 9.9 |
| 6 | ISIS 647535 minus [3 GalNAc + 3 5-hydroxypentanoic acid tether] | D | 9.8 |

Cleavage Sites

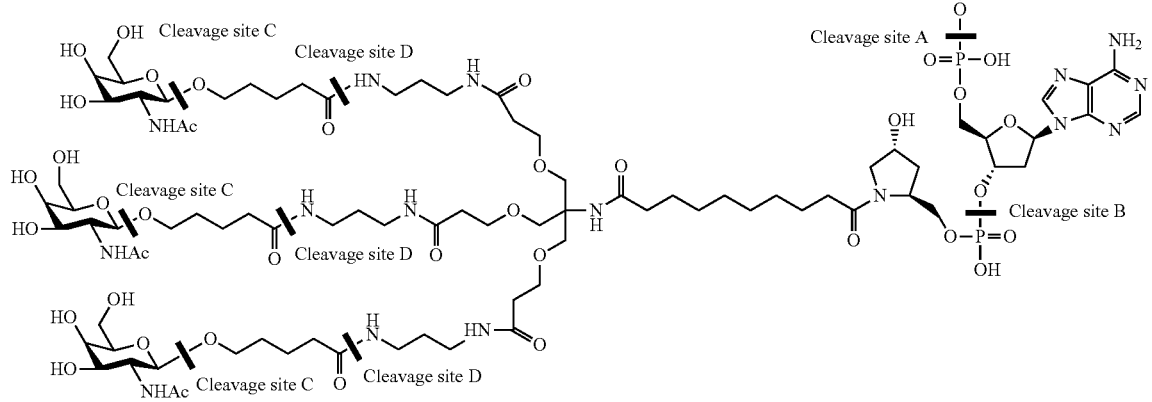

-continued
Metabolite 1
ASO 304801 OH
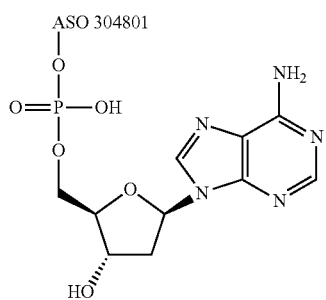
Metabolite 2
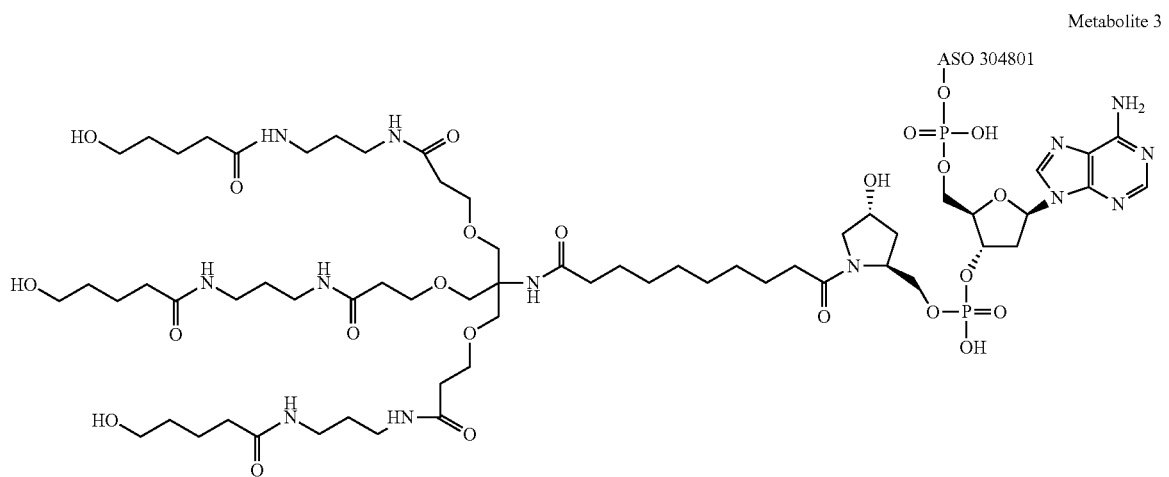
Metabolite 3
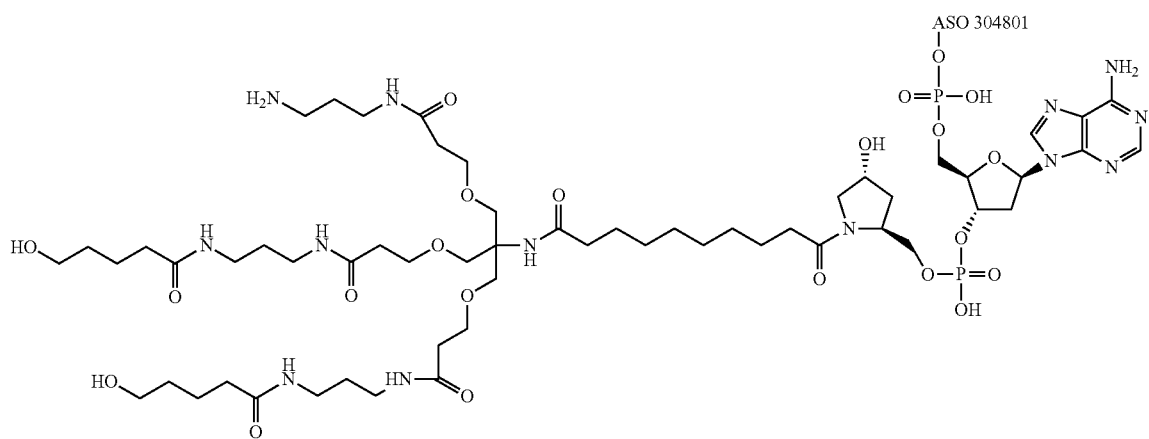
Metabolite 4

Metabolite 5

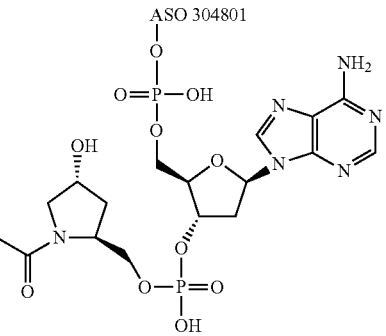
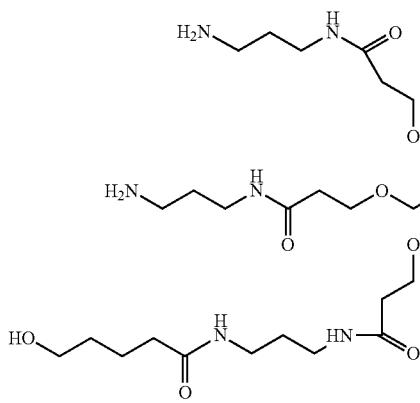

Metabolite 6

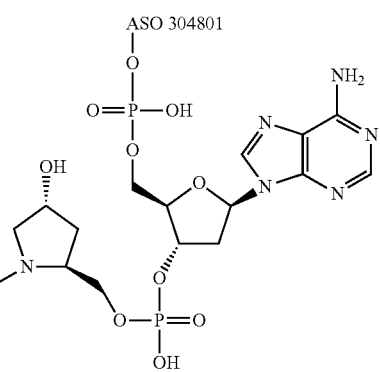
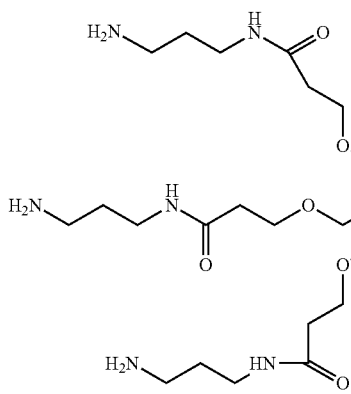

Example 21

Antisense Inhibition of Human ApoC III in Human ApoC III Transgenic Mice in Single Administration Study ISIS 304801, 647535 and 647536 each targeting human ApoC III and described in Table 4, were further evaluated in a single administration study for their ability to inhibit human ApoC III in human ApoC III transgenic mice.
Treatment Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once at the dosage shown below with ISIS 304801, 647535 or 647536 (described above) or with PBS treated control. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III mRNA and protein levels in the liver; plasma triglycerides; and cholesterol, including HDL and LDL fractions were assessed as described above (Example 20). Data from those analyses are presented in Tables 11-15, below. Liver transaminase levels, alanine aminotransferase (ALT) and aspartate aminotransferase (AST), in serum were measured relative to saline injected mice using standard protocols. The ALT and AST levels showed that the antisense compounds were well tolerated at all administered doses.

These results show improvement in potency for antisense compounds comprising a GalNAc$_3$-1 conjugate at the 3' terminus (ISIS 647535 and 647536) compared to the antisense compound lacking a GalNAc$_3$-1 conjugate (ISIS 304801). Further, ISIS 647536, which comprises a GalNAc$_3$-1 conjugate and some phosphodiester linkages was as potent as ISIS 647535, which comprises the same conjugate and all internucleoside linkages within the ASO are phosphorothioate.

TABLE 11

Effect of ASO treatment on ApoC III mRNA levels in human ApoC III transgenic mice

| ASO | Dose (mg/kg) | % PBS | ED$_{50}$ (mg/kg) | 3' Conjugate | Internucleoside linkage/Length | SEQ ID No. |
|---|---|---|---|---|---|---|
| PBS | 0 | 99 | — | — | — | |
| ISIS 304801 | 1 | 104 | 13.2 | None | PS/20 | 20 |
|  | 3 | 92 | | | | |
|  | 10 | 71 | | | | |
|  | 30 | 40 | | | | |
| ISIS 647535 | 0.3 | 98 | 1.9 | GalNAc$_3$-1 | PS/20 | 21 |
|  | 1 | 70 | | | | |
|  | 3 | 33 | | | | |
|  | 10 | 20 | | | | |
| ISIS 647536 | 0.3 | 103 | 1.7 | GalNAc$_3$-1 | PS/PO/20 | 21 |
|  | 1 | 60 | | | | |
|  | 3 | 31 | | | | |
|  | 10 | 21 | | | | |

TABLE 12

Effect of ASO treatment on ApoC III plasma protein levels in human ApoC III transgenic mice

| ASO | Dose (mg/kg) | % PBS | ED$_{50}$ (mg/kg) | 3' Conjugate | Internucleoside Linkage/Length | SEQ ID No. |
|---|---|---|---|---|---|---|
| PBS | 0 | 99 | — | — | — | |
| ISIS 304801 | 1 | 104 | 23.2 | None | PS/20 | 20 |
|  | 3 | 92 | | | | |
|  | 10 | 71 | | | | |
|  | 30 | 40 | | | | |
| ISIS 647535 | 0.3 | 98 | 2.1 | GalNAc$_3$-1 | PS/20 | 21 |
|  | 1 | 70 | | | | |
|  | 3 | 33 | | | | |
|  | 10 | 20 | | | | |
| ISIS 647536 | 0.3 | 103 | 1.8 | GalNAc$_3$-1 | PS/PO/20 | 21 |
|  | 1 | 60 | | | | |
|  | 3 | 31 | | | | |
|  | 10 | 21 | | | | |

TABLE 13

Effect of ASO treatment on triglyceride levels in transgenic mice

| ASO | Dose (mg/kg) | % PBS | ED$_{50}$ (mg/kg) | 3' Conjugate | Internucleoside Linkage/Length | SEQ ID No. |
|---|---|---|---|---|---|---|
| PBS | 0 | 98 | — | — | — | |
| ISIS 304801 | 1 | 80 | 29.1 | None | PS/20 | 20 |
|  | 3 | 92 | | | | |
|  | 10 | 70 | | | | |
|  | 30 | 47 | | | | |
| ISIS 647535 | 0.3 | 100 | 2.2 | GalNAc$_3$-1 | PS/20 | 21 |
|  | 1 | 70 | | | | |
|  | 3 | 34 | | | | |
|  | 10 | 23 | | | | |
| ISIS 647536 | 0.3 | 95 | 1.9 | GalNAc$_3$-1 | PS/PO/20 | 21 |
|  | 1 | 66 | | | | |
|  | 3 | 31 | | | | |
|  | 10 | 23 | | | | |

TABLE 14

Effect of ASO treatment on total cholesterol levels in transgenic mice

| ASO | Dose (mg/kg) | % PBS | 3' Conjugate | Internucleoside Linkage/Length | SEQ ID No. |
|---|---|---|---|---|---|
| PBS | 0 | 96 | — | — | |
| ISIS 304801 | 1 | 104 | None | PS/20 | 20 |
|  | 3 | 96 | | | |
|  | 10 | 86 | | | |
|  | 30 | 72 | | | |
| ISIS 647535 | 0.3 | 93 | GalNAc$_3$-1 | PS/20 | 21 |
|  | 1 | 85 | | | |
|  | 3 | 61 | | | |
|  | 10 | 53 | | | |
| ISIS 647536 | 0.3 | 115 | GalNAc$_3$-1 | PS/PO/20 | 21 |
|  | 1 | 79 | | | |
|  | 3 | 51 | | | |
|  | 10 | 54 | | | |

TABLE 15

Effect of ASO treatment on HDL and LDL cholesterol levels in transgenic mice

| ASO | Dose (mg/kg) | HDL % PBS | LDL % PBS | 3' Conjugate | Internucleoside Linkage/Length | SEQ ID No. |
|---|---|---|---|---|---|---|
| PBS | 0 | 131 | 90 | — | — | |
| ISIS 304801 | 1 | 130 | 72 | None | PS/20 | 20 |
|  | 3 | 186 | 79 | | | |
|  | 10 | 226 | 63 | | | |
|  | 30 | 240 | 46 | | | |
| ISIS 647535 | 0.3 | 98 | 86 | GalNAc$_3$-1 | PS/20 | 21 |
|  | 1 | 214 | 67 | | | |
|  | 3 | 212 | 39 | | | |
|  | 10 | 218 | 35 | | | |
| ISIS 647536 | 0.3 | 143 | 89 | GalNAc$_3$-1 | PS/PO/20 | 21 |
|  | 1 | 187 | 56 | | | |
|  | 3 | 213 | 33 | | | |
|  | 10 | 221 | 34 | | | |

These results confirm that the GalNAc$_3$-1 conjugate improves potency of an antisense compound. The results also show equal potency of a GalNAc$_3$-1 conjugated antisense compounds where the antisense oligonucleotides have mixed linkages (ISIS 647536 which has six phosphodiester linkages) and a full phosphorothioate version of the same antisense compound (ISIS 647535).

Phosphorothioate linkages provide several properties to antisense compounds. For example, they resist nuclease digestion and they bind proteins resulting in accumulation of compound in the liver, rather than in the kidney/urine. These are desirable properties, particularly when treating an indication in the liver. However, phosphorothioate linkages have also been associated with an inflammatory response. Accordingly, reducing the number of phosphorothioate linkages in a compound is expected to reduce the risk of inflammation, but also lower concentration of the compound in liver, increase concentration in the kidney and urine, decrease stability in the presence of nucleases, and lower overall potency. The present results show that a GalNAc$_3$-1 conjugated antisense compound where certain phosphorothioate linkages have been replaced with phosphodiester linkages is as potent against a target in the liver as a counterpart having full phosphorothioate linkages. Such compounds are expected to be less proinflammatory (See Example 24 describing an experiment showing reduction of PS results in reduced inflammatory effect).

Example 22

Effect of GalNAc₃-1 Conjugated Modified ASO Targeting SRB-1 In Vivo

ISIS 440762 and 651900, each targeting SRB-1 and described in Table 4 were evaluated in a dose-dependent study for their ability to inhibit SRB-1 in Balb/c mice.
Treatment Six week old male Balb/c mice (Jackson Laboratory, Bar Harbor, Me.) were injected subcutaneously once at the dosage shown below with ISIS 440762, 651900 or with PBS treated control. Each treatment group consisted of 4 animals. The mice were sacrificed 48 hours following the final administration to determine the SRB-1 mRNA levels in liver using real-time PCR and RIBOGREEN® RNA quantification reagent (Molecular Probes, Inc. Eugene, Oreg.) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS".

As illustrated in Table 16, both antisense compounds lowered SRB-1 mRNA levels. Further, the antisense compound comprising the GalNAc₃-1 conjugate (ISIS 651900) was substantially more potent than the antisense compound lacking the GalNAc₃-1 conjugate (ISIS 440762). These results demonstrate that the potency benefit of GalNAc₃-1 conjugates are observed using antisense oligonucleotides complementary to a different target and having different chemically modified nucleosides, in this instance modified nucleosides comprise constrained ethyl sugar moieties (a bicyclic sugar moiety).

TABLE 16

Effect of ASO treatment on SRB-1 mRNA levels in Balb/c mice

| ASO | Dose (mg/kg) | Liver % PBS | ED₅₀ (mg/kg) | 3' Conjugate | Internucleoside linkage/Length | SEQ ID No. |
|---|---|---|---|---|---|---|
| PBS | 0 | 100 | — | — | | |
| ISIS 440762 | 0.7 | 85 | 2.2 | None | PS/14 | 22 |
| | 2 | 55 | | | | |
| | 7 | 12 | | | | |
| | 20 | 3 | | | | |
| ISIS 651900 | 0.07 | 98 | 0.3 | GalNAc₃-1 | PS/14 | 23 |
| | 0.2 | 63 | | | | |
| | 0.7 | 20 | | | | |
| | 2 | 6 | | | | |
| | 7 | 5 | | | | |

Example 23

Human Peripheral Blood Mononuclear Cells (hPBMC) Assay Protocol

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat.#BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS ($Ca^{++}$, $Mg^{++}$ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 µl sample was pipette into a sample vial (Beckman Coulter) with 600 µl VersaLyse reagent (Beckman Coulter Cat#A09777) and was gently vortexed for 10-15 sec. The sample was allowed to incubate for 10 min at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to $1 \times 10^7$ live PBMC/ml in RPMI+ 10% FBS+pen/strep.

The cells were plated at $5 \times 10^5$ in 50 µl/well of 96-well tissue culture plate (Falcon Microtest). 50 µl/well of 2× concentration oligos/controls diluted in RPMI+10% FBS+pen/strep. was added according to experiment template (100 µl/well total). Plates were placed on the shaker and allowed to mix for approx. 1 min After being incubated for 24 hrs at 37° C.; 5% $CO_2$, the plates were centrifuged at 400×g for 10 minutes before removing the supernatant for MSD cytokine assay (i.e. human IL-6, IL-10, IL-8 and MCP-1).

Example 24

Evaluation of Proinflammatory Effects in hPBMC Assay for GalNAc₃-1 Conjugated ASOs The antisense oligonucleotides (ASOs) listed in Table 17 were evaluated for proinflammatory effect in hPBMC assay using the protocol described in Example 23. ISIS 353512 is an internal standard known to be a high responder for IL-6 release in the assay. The hPBMCs were isolated from fresh, volunteered donors and were treated with ASOs at 0, 0.0128, 0.064, 0.32, 1.6, 8, 40 and 200 µM concentrations. After a 24 hr treatment, the cytokine levels were measured.

The levels of IL-6 were used as the primary readout. The $EC_{50}$ and $E_{max}$ was calculated using standard procedures. Results are expressed as the average ratio of $E_{max}/EC_{50}$ from two donors and is denoted as "$E_{max}/EC_{50}$." The lower ratio indicates a relative decrease in the proinflammatory response and the higher ratio indicates a relative increase in the proinflammatory response.

With regard to the test compounds, the least proinflammatory compound was the PS/PO linked ASO (ISIS 616468). The GalNAc₃-1 conjugated ASO, ISIS 647535 was slightly less proinflammatory than its non-conjugated counterpart ISIS 304801. These results indicate that incorporation of some PO linkages reduces proinflammatory reaction and addition of a GalNAc₃-1 conjugate does not make a compound more proinflammatory and may reduce proinflammatory response. Accordingly, one would expect that an antisense compound comprising both mixed PS/PO linkages and a GalNAc₃-1 conjugate would produce lower proinflammatory responses relative to full PS linked antisense compound with or without a GalNAc₃-1 conjugate. These results show that GalNAc₃-1 conjugated antisense compounds, particularly those having reduced PS content are less proinflammatory.

Together, these results suggest that a GalNAc₃-1 conjugated compound, particularly one with reduced PS content, can be administered at a higher dose than a counterpart full PS antisense compound lacking a GalNAc₃-1 conjugate. Since half-life is not expected to be substantially different for these compounds, such higher administration would result in less frequent dosing. Indeed such administration could be even less frequent, because the GalNAc₃-1 conjugated compounds are more potent (See Examples 20-22) and re-dosing is necessary once the concentration of a compound has dropped below a desired level, where such desired level is based on potency.

TABLE 17

Modified ASOs

| ASO | Sequence (5' to 3') | Target | SEQ ID No. |
|---|---|---|---|
| ISIS 104838 | G$_{es}$$^m$C$_{es}$T$_{es}$G$_{es}$A$_{es}$T$_{ds}$T$_{ds}$A$_{ds}$G$_{ds}$A$_{ds}$G$_{ds}$ A$_{ds}$G$_{ds}$A$_{ds}$G$_{ds}$G$_{es}$T$_{es}$$^m$C$_{es}$$^m$C$_{es}$$^m$C$_{e}$ | TNFα | 24 |
| ISIS 353512 | T$_{es}$$^m$C$_{es}$$^m$C$_{es}$$^m$C$_{ds}$A$_{ds}$T$_{ds}$T$_{ds}$T$_{ds}$$^m$C$_{ds}$A$_{ds}$G$_{ds}$ G$_{ds}$A$_{ds}$G$_{ds}$A$_{ds}$$^m$C$_{ds}$$^m$C$_{ds}$T$_{es}$G$_{es}$G$_{e}$ | CRP | 25 |
| ISIS 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$ C$_{ds}$$^m$C$_{ds}$A$_{ds}$G$_{ds}$$^m$C$_{ds}$T$_{es}$T$_{es}$T$_{es}$A$_{es}$T$_{e}$ | ApoC III | 20 |
| ISIS 647535 | A$_{es}$G$_{es}$$^m$C$_{es}$T$_{es}$T$_{es}$$^m$C$_{ds}$T$_{ds}$T$_{ds}$G$_{ds}$T$_{ds}$$^m$ C$_{ds}$$^m$C$_{ds}$A$_{ds}$G$_{ds}$$^m$C$_{ds}$T$_{es}$T$_{es}$T$_{es}$A$_{es}$ T$_{eo}$A$_{do}$,-GalNAc₃-1$_a$ | ApoC III | 21 |
| ISIS 616468 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$ C$_{ds}$$^m$C$_{ds}$A$_{ds}$G$_{ds}$$^m$C$_{ds}$T$_{eo}$T$_{eo}$T$_{es}$A$_{es}$T$_{e}$ | ApoC III | 20 |

Subscripts: "e" indicates 2'-MOE modified nucleoside; "d" indicates β-D-2'-deoxyribonucleoside; "k" indicates 6'-(S)—CH₃ bicyclic nucleoside (e.g. cEt); "s" indicates phosphorothioate internucleoside linkages (PS); "o" indicates phosphodiester internucleoside linkages (PO); and "o" indicates —O—P(=O)(OH)—. Superscript "m" indicates 5-methylcytosines. "A$_{do}$GalNAc₃-1." indicates a conjugate having the structure GalNAc₃-1 shown in Example 9 attached to the 3'-end of the antisense oligonucleotide, as indicated.

TABLE 18

Proinflammatory Effect of ASOs targeting ApoC III in hPBMC assay

| ASO | EC$_{50}$ (μM) | E$_{max}$ (μM) | E$_{max}$/EC$_{50}$ | 3' Conjugate | Internucleoside Linkage/Length | SEQ ID No. |
|---|---|---|---|---|---|---|
| ISIS 353512 (high responder) | 0.01 | 265.9 | 26,590 | None | PS/20 | 25 |
| ISIS 304801 | 0.07 | 106.55 | 1,522 | None | PS/20 | 20 |
| ISIS 647535 | 0.12 | 138 | 1,150 | GalNAc₃-1 | PS/20 | 21 |
| ISIS 616468 | 0.32 | 71.52 | 224 | None | PS/PO/20 | 20 |

Example 25

Effect of GalNAc₃-1 Conjugated Modified ASO Targeting Human ApoC III In Vitro

ISIS 304801 and 647535 described above were tested in vitro. Primary hepatocyte cells from transgenic mice at a density of 25,000 cells per well were treated with 0.03, 0.08, 0.24, 0.74, 2.22, 6.67 and 20 μM concentrations of modified oligonucleotides. After a treatment period of approximately 16 hours, RNA was isolated from the cells and mRNA levels were measured by quantitative real-time PCR and the hApoC III mRNA levels were adjusted according to total RNA content, as measured by RIBOGREEN.

The IC$_{50}$ was calculated using the standard methods and the results are presented in Table 19. As illustrated, comparable potency was observed in cells treated with ISIS 647535 as compared to the control, ISIS 304801.

TABLE 19

Modified ASO targeting human ApoC III in primary hepatocytes

| ASO | IC$_{50}$ (μM) | 3' Conjugate | Internucleoside linkage/Length | SEQ ID No. |
|---|---|---|---|---|
| ISIS 304801 | 0.44 | None | PS/20 | 20 |
| ISIS 647535 | 0.31 | GalNAc₃-1 | PS/20 | 21 |

In this experiment, the large potency benefits of GalNAc₃-1 conjugation that are observed in vivo were not observed in vitro. Subsequent free uptake experiments in primary hepatocytes in vitro did show increased potency of oligonucleotides comprising various GalNAc conjugates relative to oligonucleotides that lacking the GalNAc conjugate. (see Examples 60, 82, and 92)

Example 26

Effect of PO/PS Linkages on ApoC III ASO Activity

Human ApoC III transgenic mice were injected intraperitoneally once at 25 mg/kg of ISIS 304801, or ISIS 616468 (both described above) or with PBS treated control once per week for two weeks. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III protein levels in the liver as described above (Example 20). Data from those analyses are presented in Table 20, below.

These results show reduction in potency for antisense compounds with PO/PS (ISIS 616468) in the wings relative to full PS (ISIS 304801).

TABLE 20

Effect of ASO treatment on ApoC III protein levels in human ApoC III transgenic mice

| ASO | Dose (mg/kg) | % PBS | 3' Conjugate | Internucleoside linkage/Length | SEQ ID No. |
|---|---|---|---|---|---|
| PBS | 0 | 99 | — | — | |
| ISIS 304801 | 25 mg/kg/wk for 2 wks | 24 | None | Full PS | 20 |
| ISIS 616468 | 25 mg/kg/wk for 2 wks | 40 | None | 14 PS/6 PO | 20 |

Example 27

Compound 56

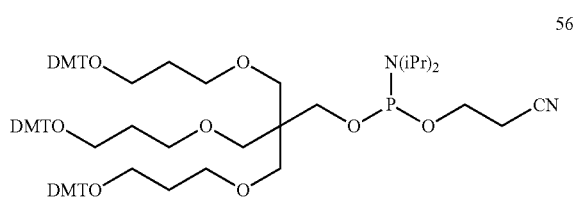

Compound 56 is commercially available from Glen Research or may be prepared according to published procedures reported by Shchepinov et al., *Nucleic Acids Research*, 1997, 25(22), 4447-4454.

Example 28

Preparation of Compound 60

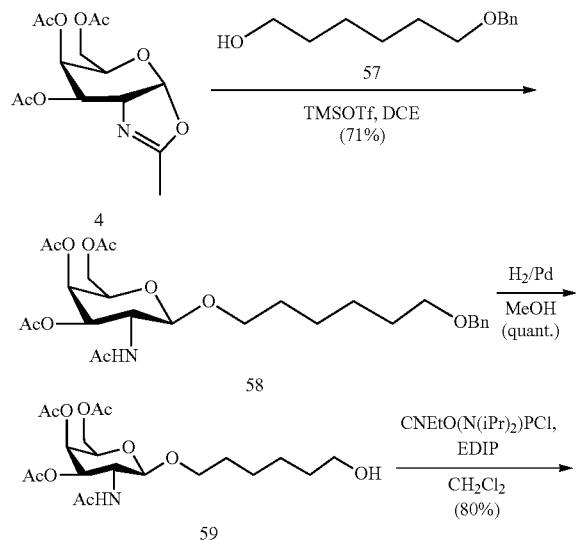

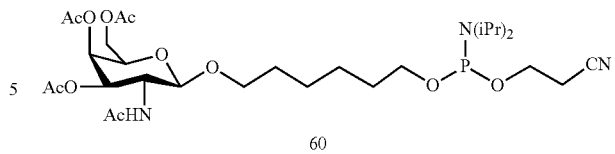

Compound 4 was prepared as per the procedures illustrated in Example 2. Compound 57 is commercially available. Compound 60 was confirmed by structural analysis.

Compound 57 is meant to be representative and not intended to be limiting as other monoprotected substituted or unsubstituted alkyl diols including but not limited to those presented in the specification herein can be used to prepare phosphoramidites having a predetermined composition.

Example 29

Preparation of Compound 63

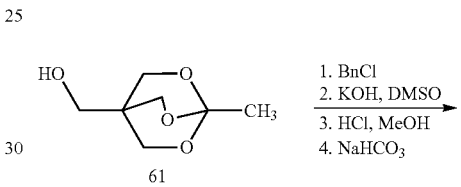

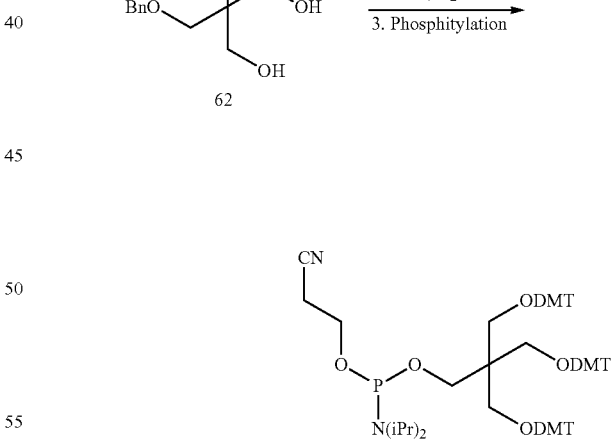

Compounds 61 and 62 are prepared using procedures similar to those reported by Tober et al., *Eur. J. Org. Chem.*, 2013, 3, 566-577; and Jiang et al., *Tetrahedron*, 2007, 63(19), 3982-3988.

Alternatively, Compound 63 is prepared using procedures similar to those reported in scientific and patent literature by Kim et al., *Synlett*, 2003, 12, 1838-1840; and Kim et al., published PCT International Application. WO 2004063208.

Example 30
Preparation of Compound 63b
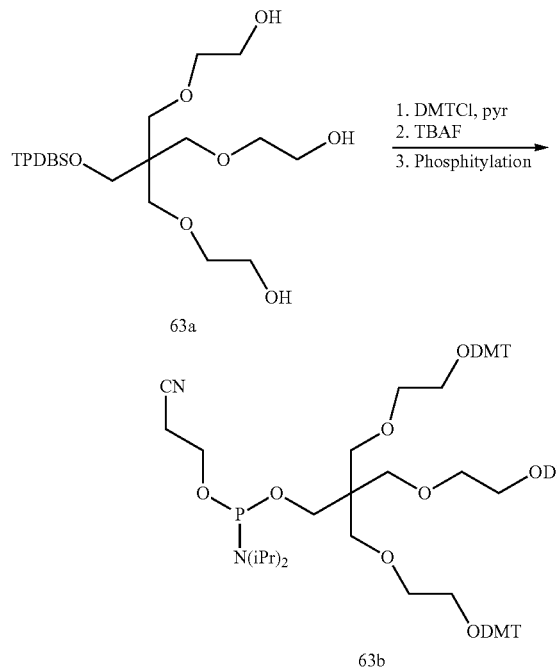
Compound 63a is prepared using procedures similar to those reported by Hanessian et al., *Canadian Journal of Chemistry*, 1996, 74(9), 1731-1737.
Example 31
Preparation of Compound 63d
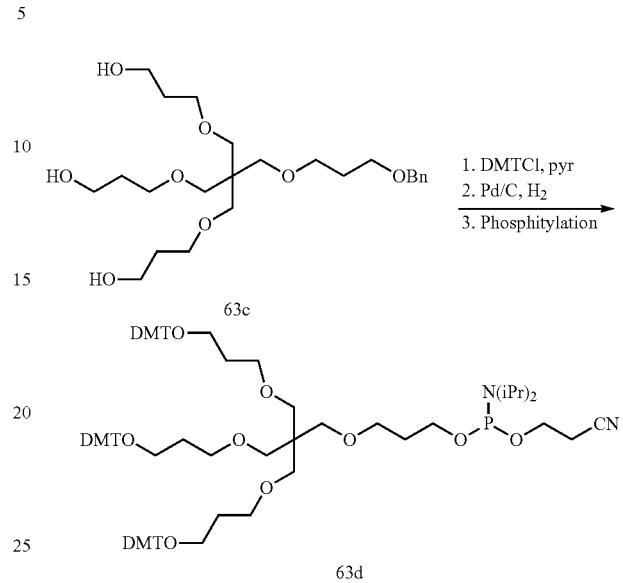
Compound 63c is prepared using procedures similar to those reported by Chen et al., *Chinese Chemical Letters*, 1998, 9(5), 451-453.
Example 32
Preparation of Compound 67
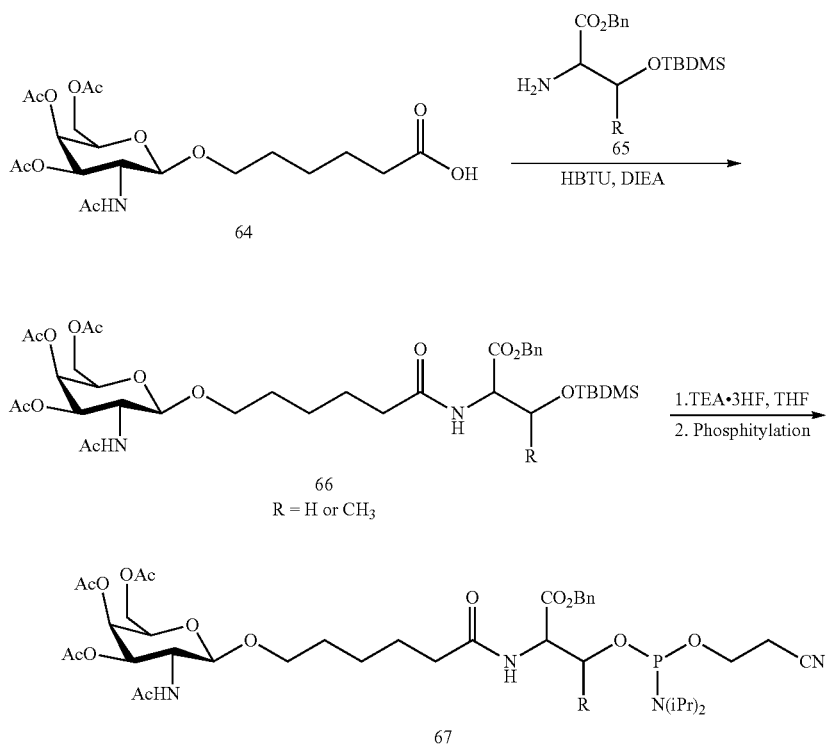

Compound 64 was prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 33

Preparation of Compound 70

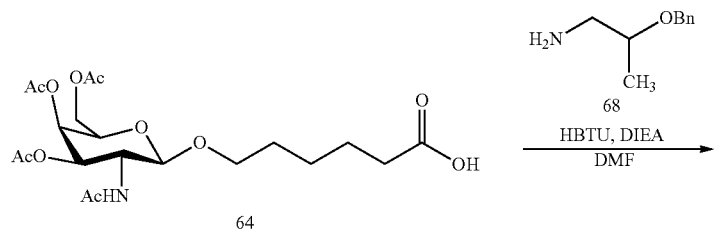

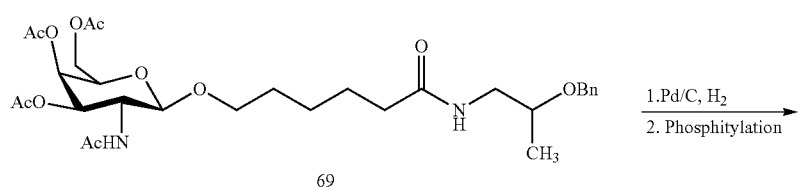

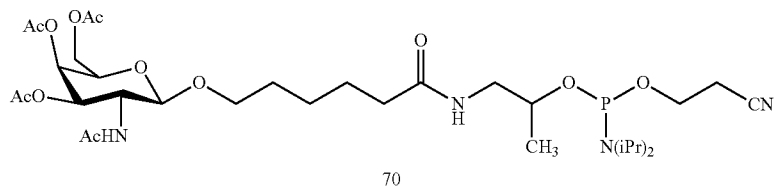

Compound 64 was prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 34

Preparation of Compound 75a

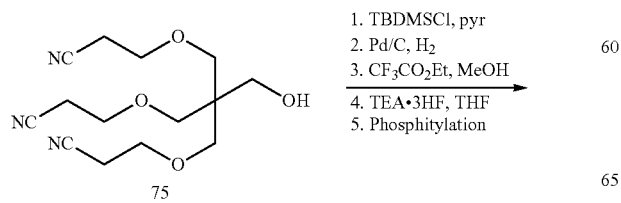

-continued

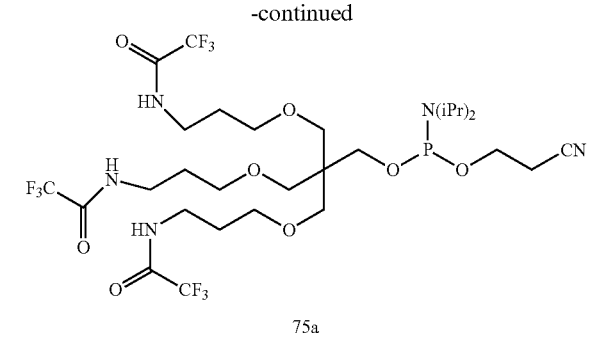

Compound 75 is prepared according to published procedures reported by Shchepinov et al., *Nucleic Acids Research*, 1997, 25(22), 4447-4454.

Example 35
Preparation of Compound 79
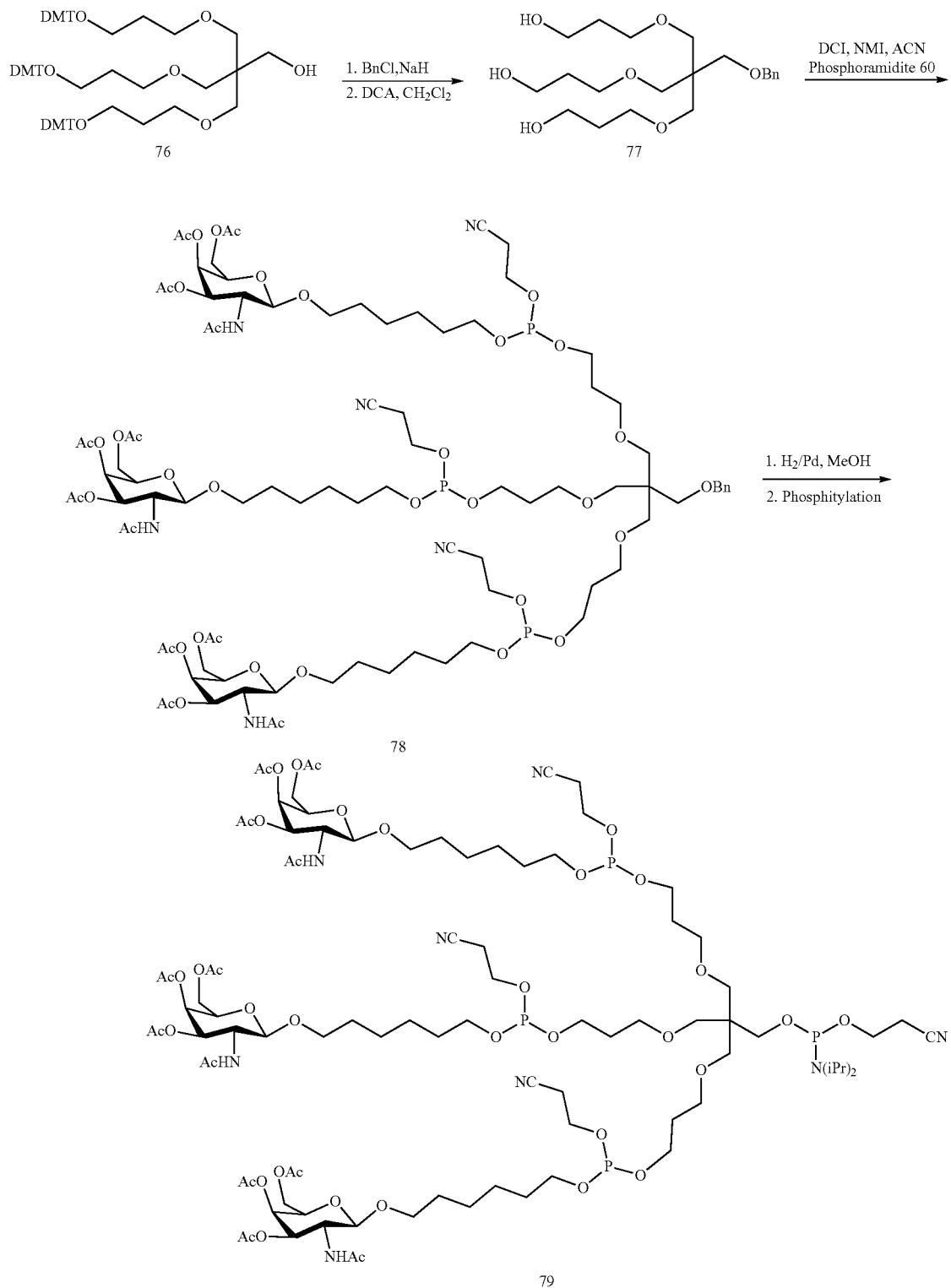
Compound 76 was prepared according to published procedures reported by Shchepinov et al., *Nucleic Acids Research*, 1997, 25(22), 4447-4454.

Example 36
Preparation of Compound 79a
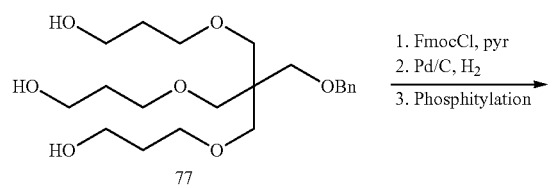
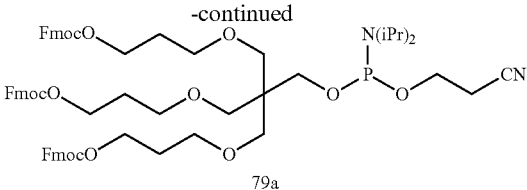
Compound 77 is prepared as per the procedures illustrated in Example 35.
Example 37
General Method for the Preparation of Conjugated Oligomeric Compound 82 Comprising a Phosphodiester Linked GalNAc$_3$-2 Conjugate at 5' Terminus Via Solid Support (Method I)
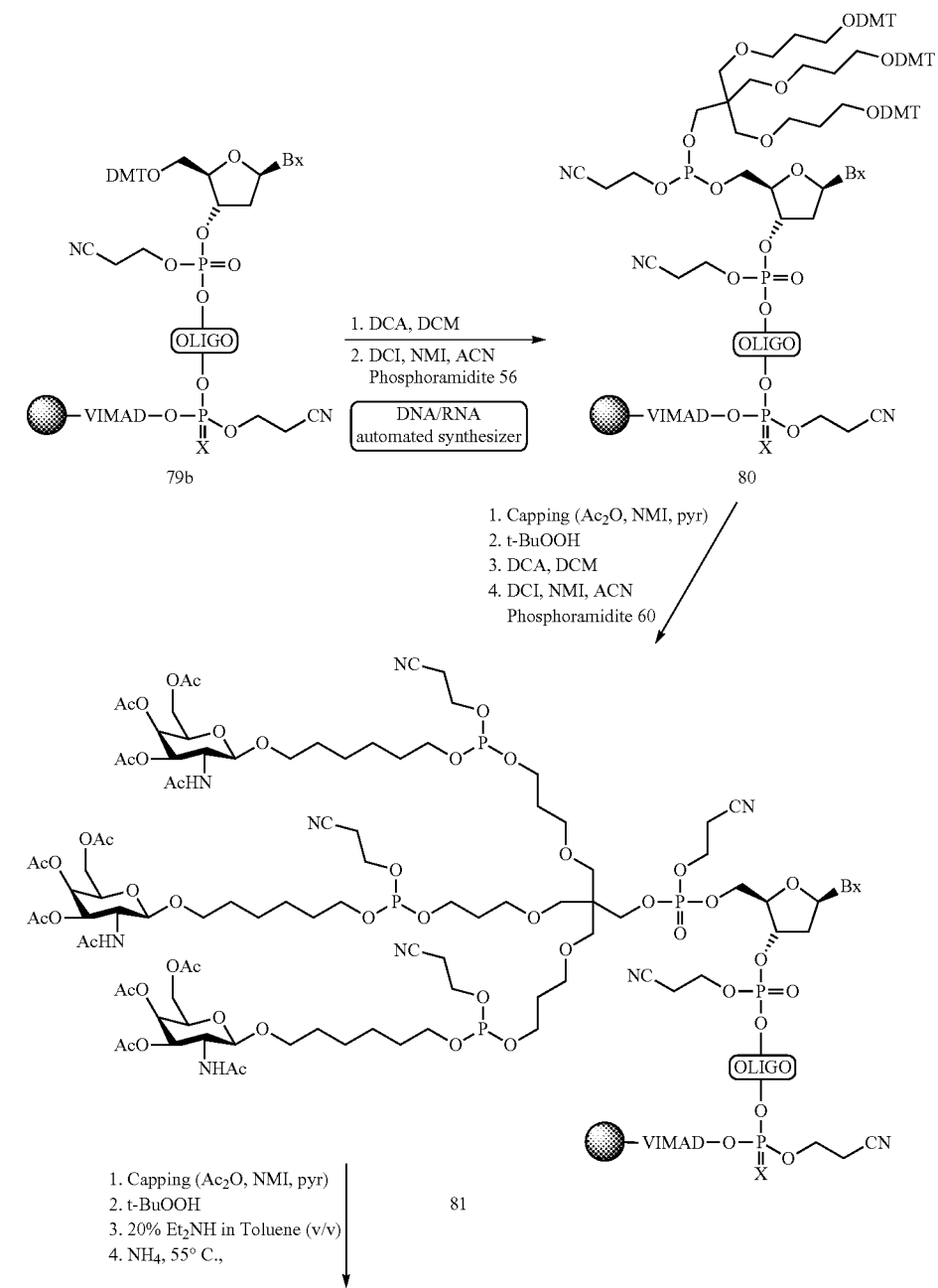

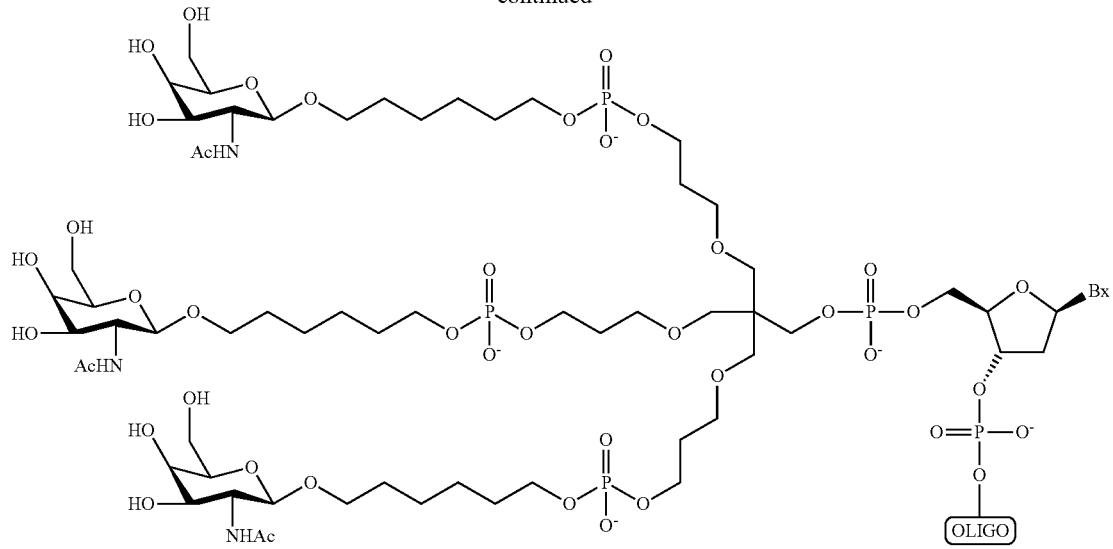
82
wherein GalNAc$_3$-2 has the structure:
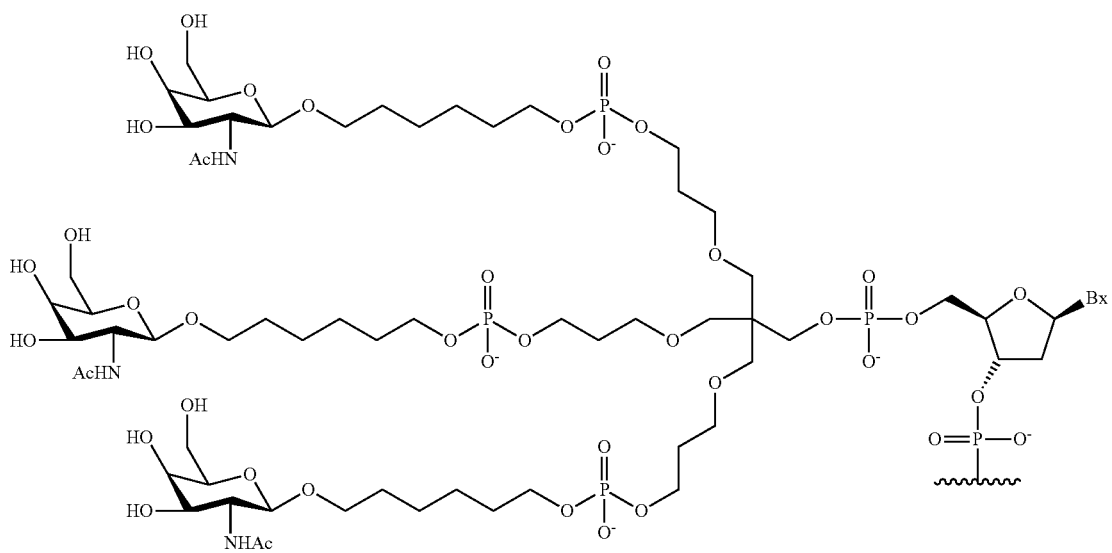
X = S⁻ or O⁻
Bx = Heterocylic base
The GalNAc$_3$ cluster portion of the conjugate group GalNAc$_3$-2 (GalNAc$_3$-2$_a$) can be combined with any cleavable moiety to provide a variety of conjugate groups. Wherein GalNAc$_3$-2$_a$ has the formula:

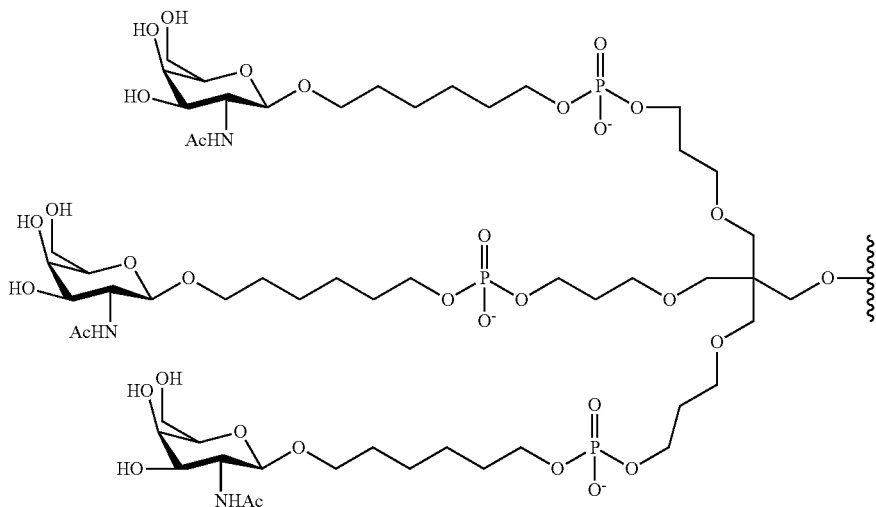

The VIMAD-bound oligomeric compound 79b was prepared using standard procedures for automated DNA/RNA synthesis (see Dupouy et al., *Angew. Chem. Int. Ed*, 2006, 45, 3623-3627). The phosphoramidite Compounds 56 and 60 were prepared as per the procedures illustrated in Examples 27 and 28, respectively. The phosphoramidites illustrated are meant to be representative and not intended to be limiting as other phosphoramidite building blocks including but not limited those presented in the specification herein can be used to prepare an oligomeric compound having a phosphodiester linked conjugate group at the 5' terminus. The order and quantity of phosphoramidites added to the solid support can be adjusted to prepare the oligomeric compounds as described herein having any predetermined sequence and composition.

Example 38

Alternative Method for the Preparation of Oligomeric Compound 82 Comprising a Phosphodiester Linked GalNAc$_3$-2 Conjugate at 5' Terminus (Method II)

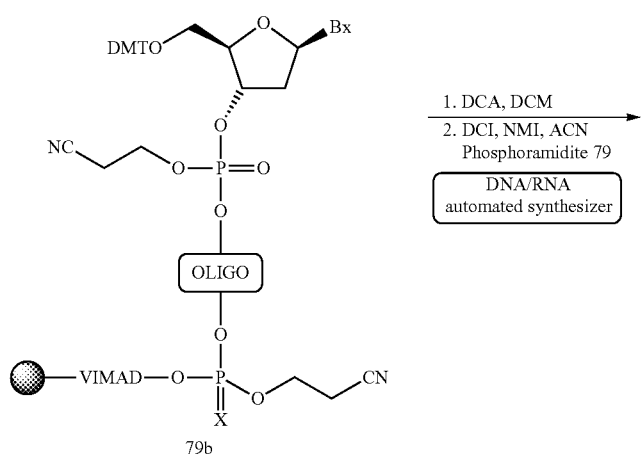

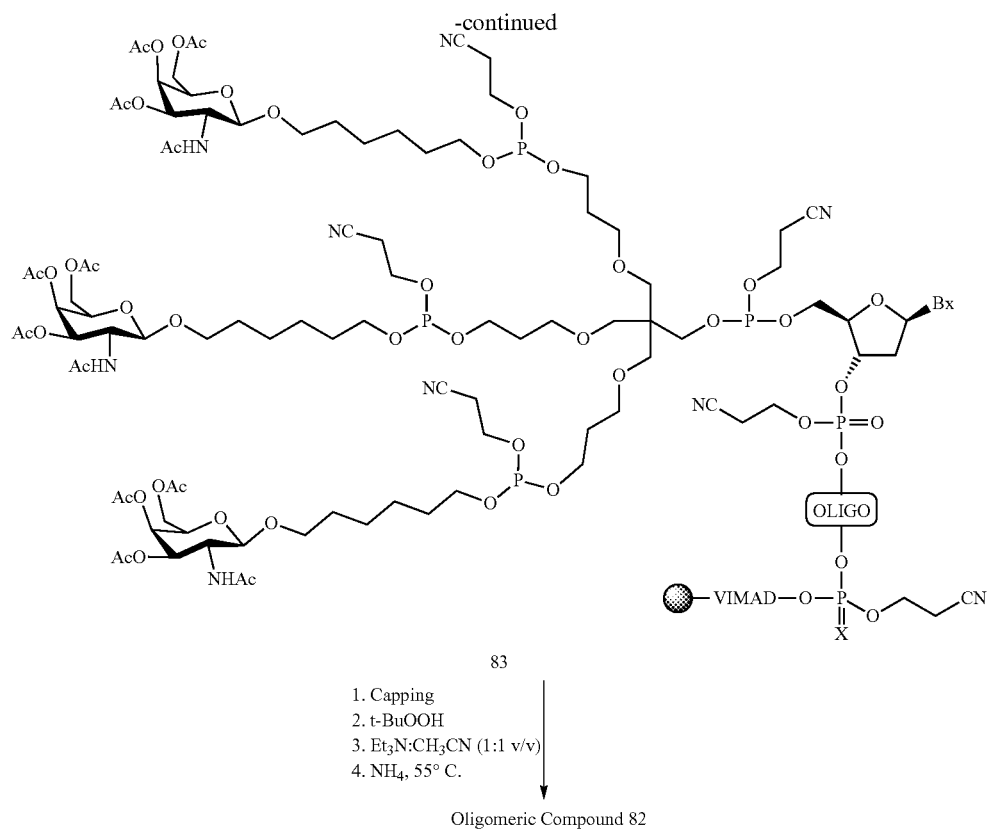

83

1. Capping
2. t-BuOOH
3. Et$_3$N:CH$_3$CN (1:1 v/v)
4. NH$_4$, 55° C.

Oligomeric Compound 82

X = S⁻ or O⁻
Bx = Heterocyclic base

The VIMAD-bound oligomeric compound 79b was prepared using standard procedures for automated DNA/RNA synthesis (see Dupouy et al., *Angew. Chem. Int. Ed*, 2006, 45, 3623-3627). The GalNAc$_3$-2 cluster phosphoramidite, Compound 79 was prepared as per the procedures illustrated in Example 35. This alternative method allows a one-step installation of the phosphodiester linked GalNAc$_3$-2 conjugate to the oligomeric compound at the final step of the synthesis. The phosphoramidites illustrated are meant to be representative and not intended to be limiting, as other phosphoramidite building blocks including but not limited to those presented in the specification herein can be used to prepare oligomeric compounds having a phosphodiester conjugate at the 5' terminus. The order and quantity of phosphoramidites added to the solid support can be adjusted to prepare the oligomeric compounds as described herein having any predetermined sequence and composition.

Example 39

General Method for the Preparation of Oligomeric Compound 83 h Comprising a GalNAc$_3$-3 Conjugate at the 5' Terminus (GalNAc$_3$-1 Modified for 5' End Attachment) Via Solid Support

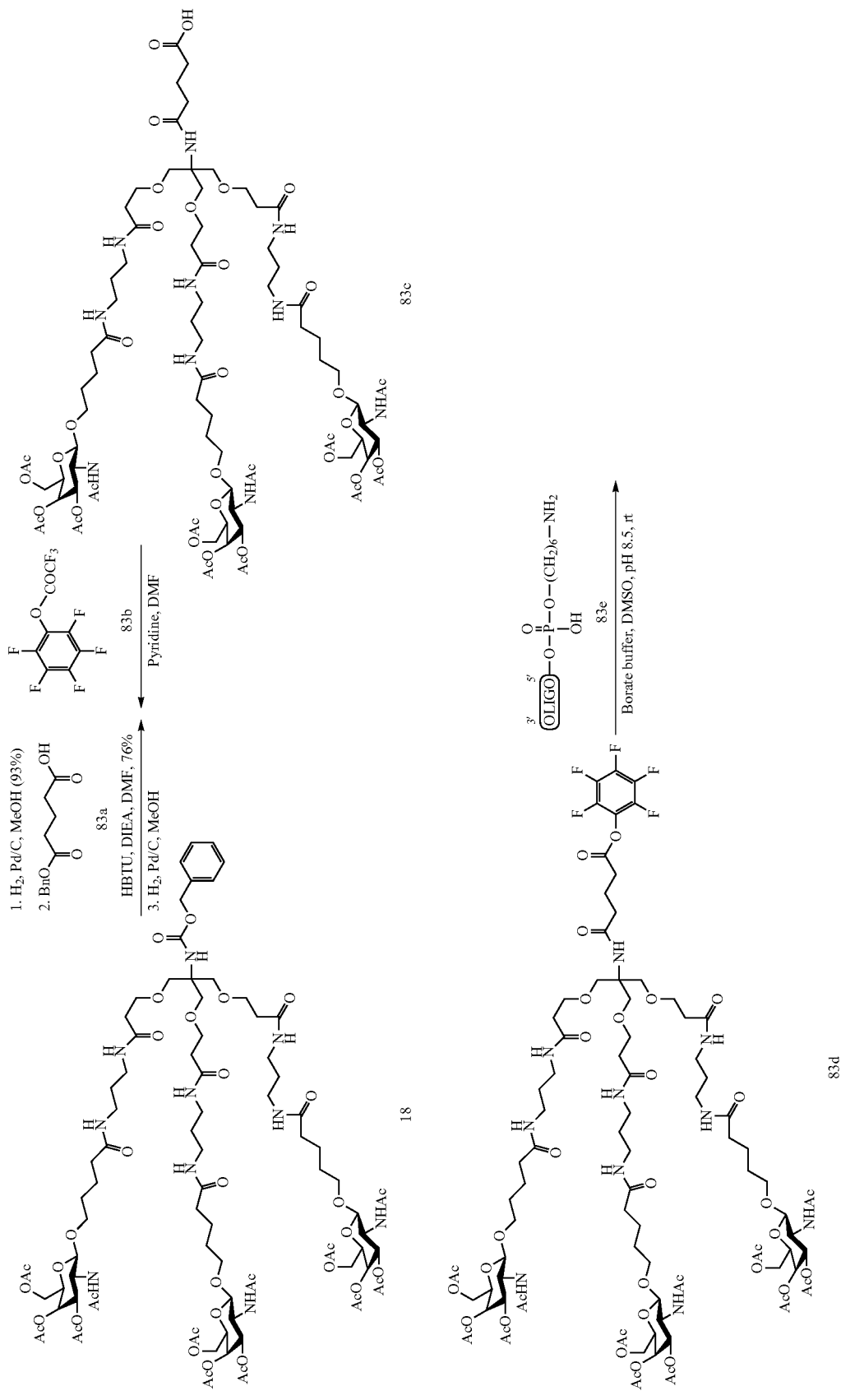

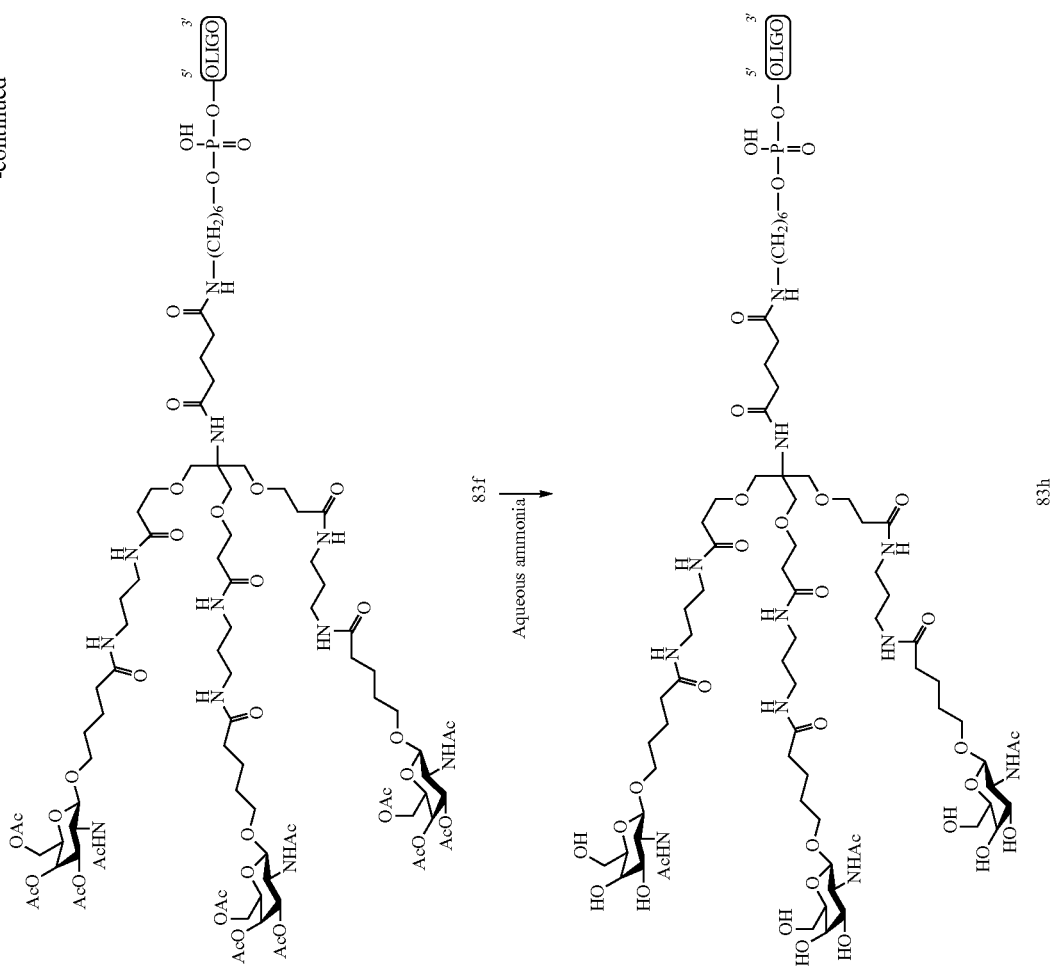

Compound 18 was prepared as per the procedures illustrated in Example 4. Compounds 83a and 83b are commercially available. Oligomeric Compound 83e comprising a phosphodiester linked hexylamine was prepared using standard oligonucleotide synthesis procedures. Treatment of the protected oligomeric compound with aqueous ammonia provided the 5'-GalNAc$_3$-3 conjugated oligomeric compound (83 h).

Wherein GalNAc$_3$-3 has the structure:

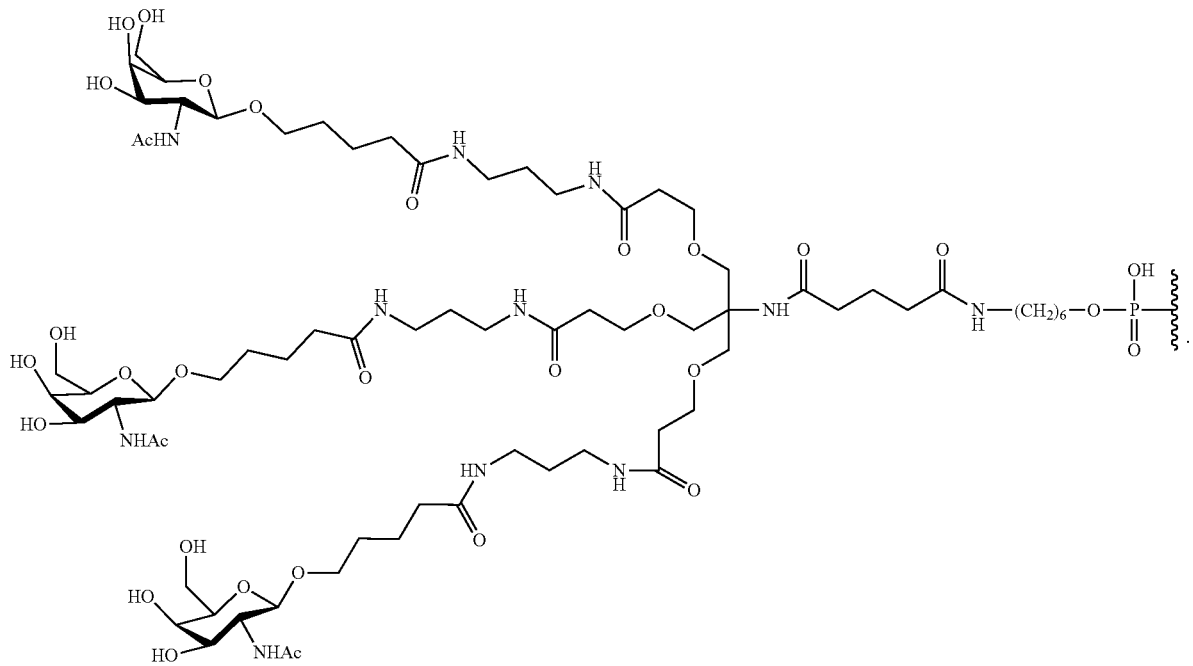

The GalNAc$_3$ cluster portion of the conjugate group GalNAc$_3$-3 (GalNAc$_3$-3$_a$) can be combined with any cleavable moiety to provide a variety of conjugate groups. Wherein GalNAc$_3$-3$_a$ has the formula:

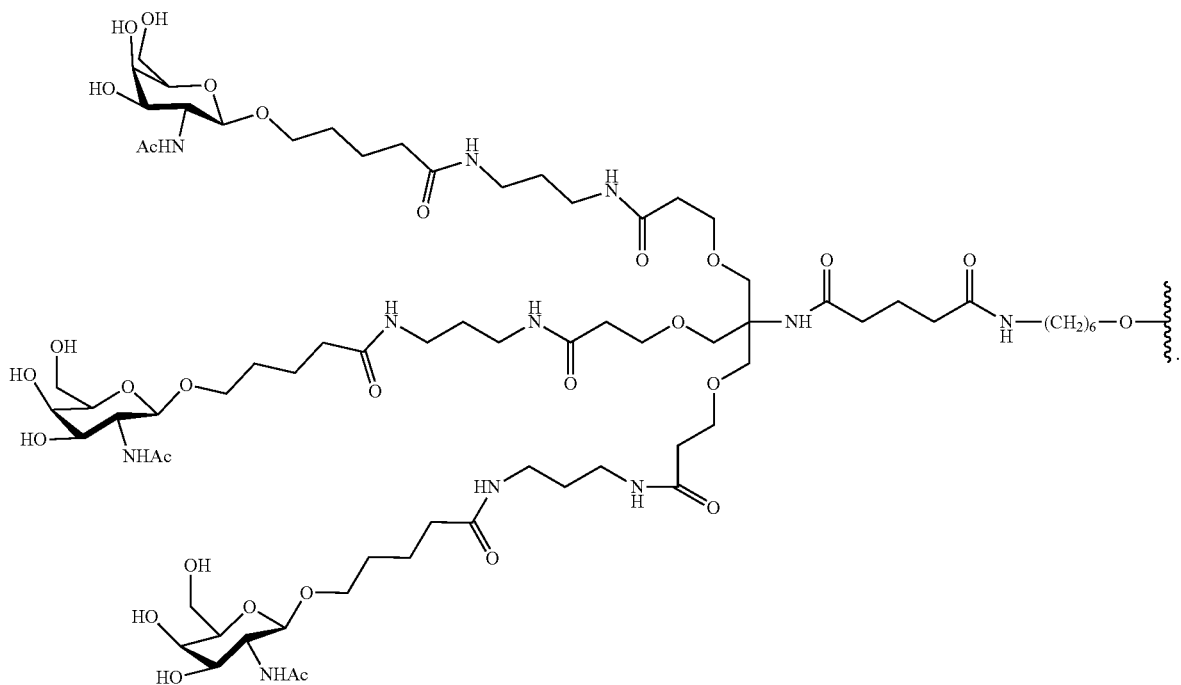

Example 40
General Method for the Preparation of Oligomeric Compound 89 Comprising a Phosphodiester Linked GalNAc$_3$-4 Conjugate at the 3' Terminus Via Solid Support
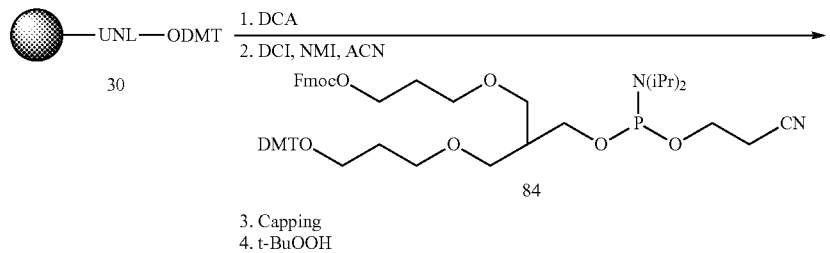
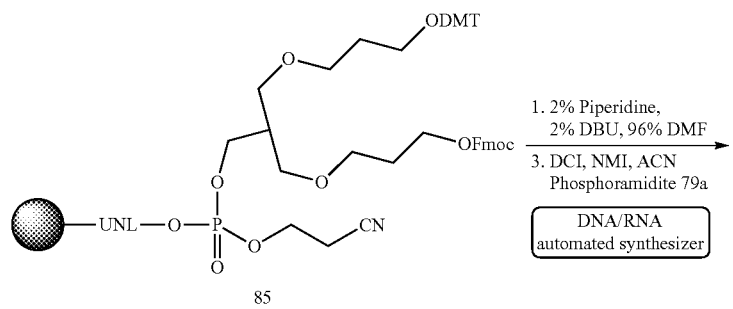
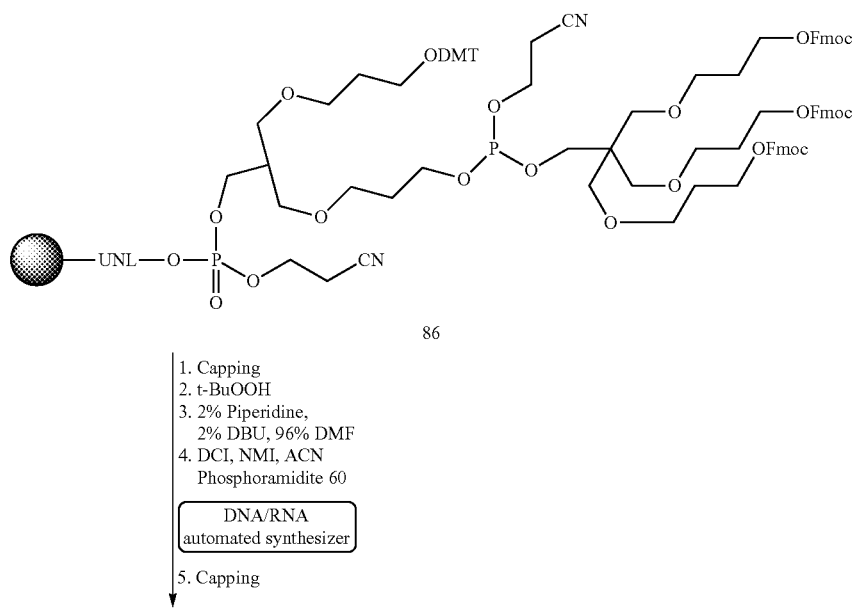

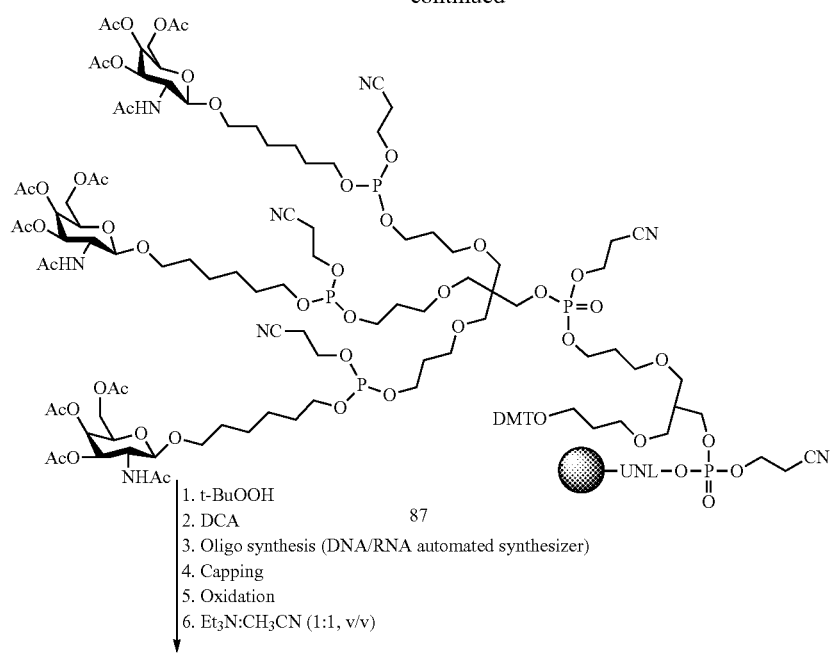
87
1. t-BuOOH
2. DCA
3. Oligo synthesis (DNA/RNA automated synthesizer)
4. Capping
5. Oxidation
6. Et₃N:CH₃CN (1:1, v/v)
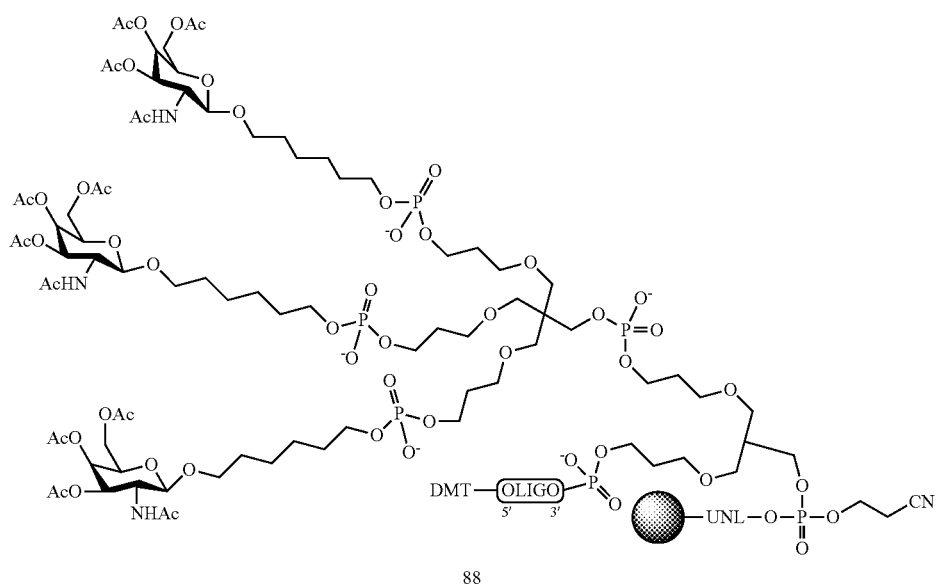
88
NH₄, 55° C.

-continued
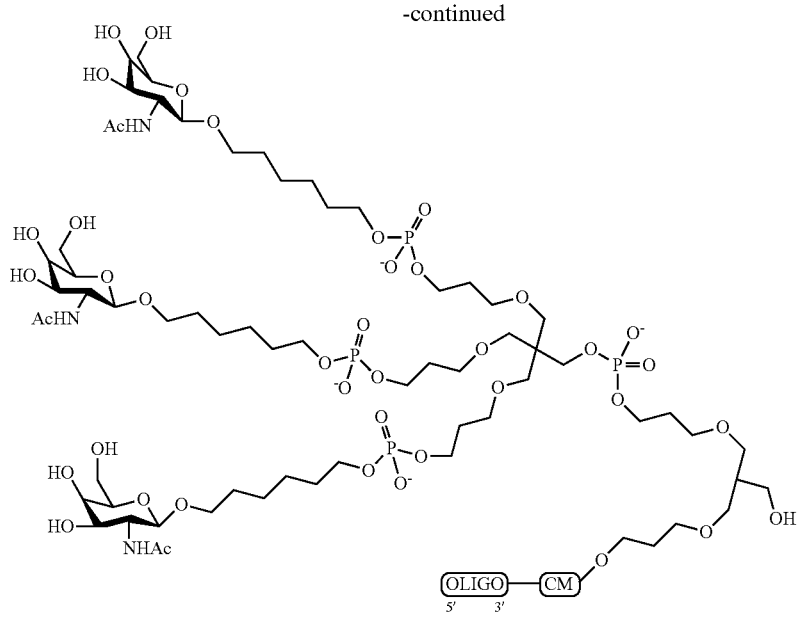
89
Wherein GalNAc₃-4 has the structure:
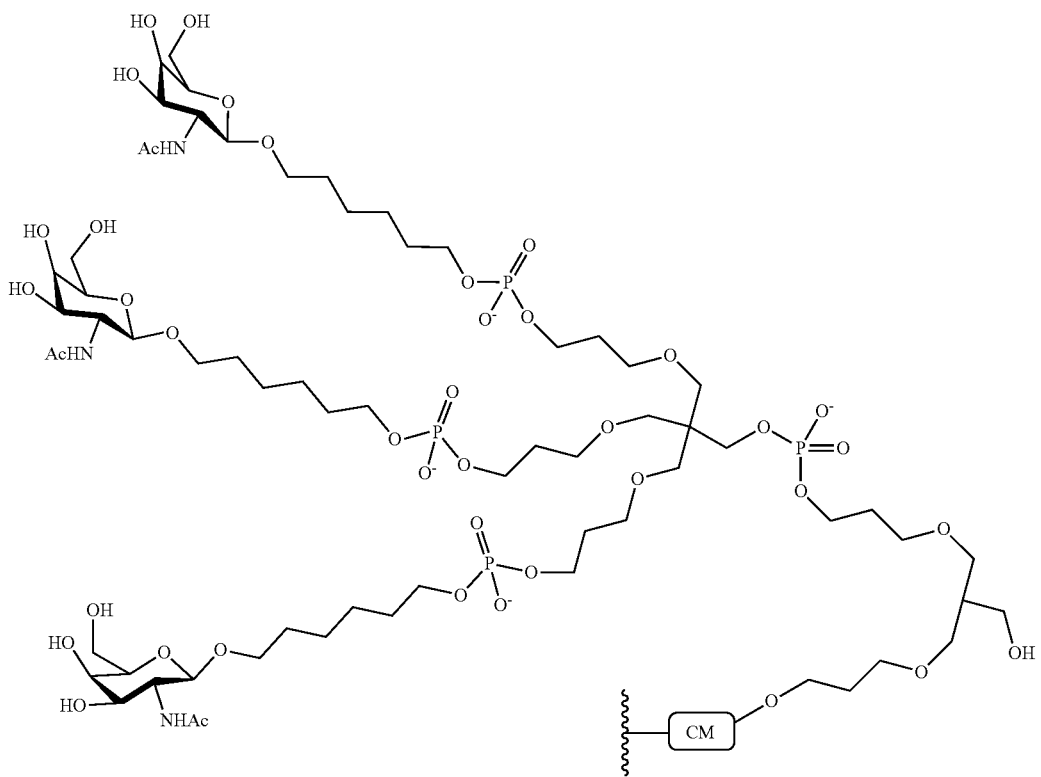
65
Wherein CM is a cleavable moiety. In certain embodiments, cleavable moiety is:

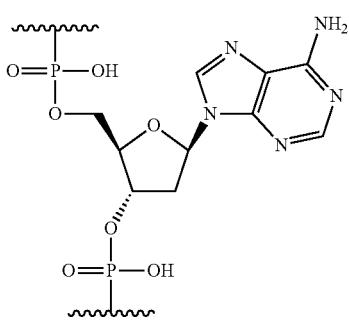 [SMILES: *P(=O)(O)OC[C@H]1O[C@@H](n2cnc3c(N)ncnc32)C[C@@H]1OP(*)(=O)O]

The GalNAc$_3$ cluster portion of the conjugate group GalNAc$_3$-4 (GalNAc$_3$-4$_a$) can be combined with any cleavable moiety to provide a variety of conjugate groups. Wherein GalNAc$_3$-4$_a$ has the formula:

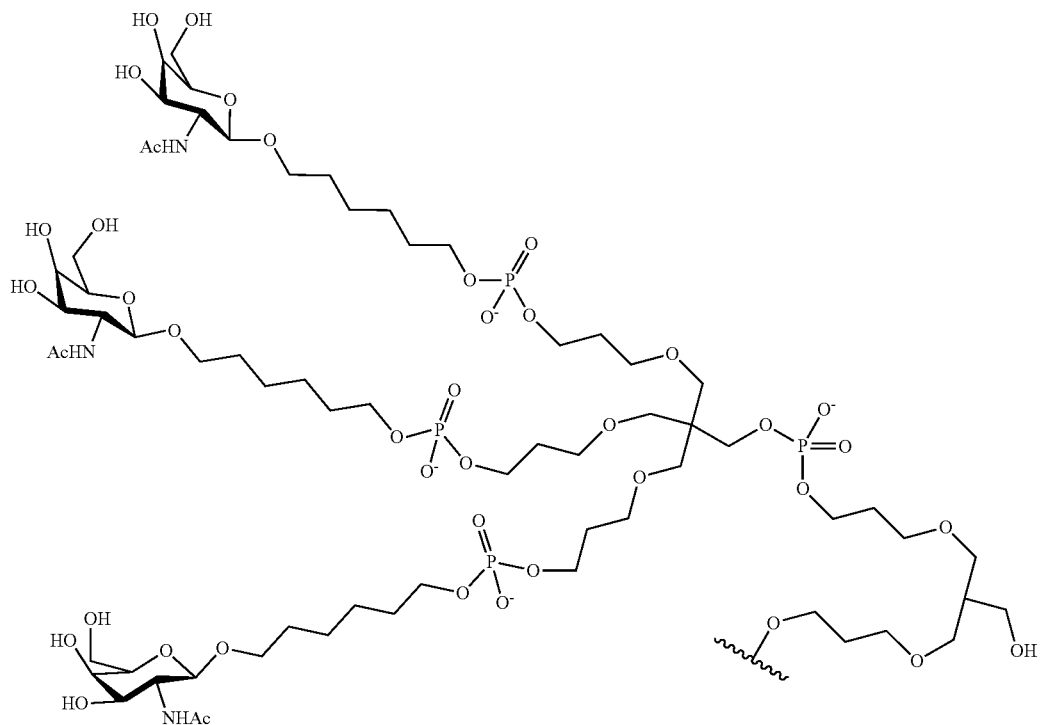

The protected Unylinker functionalized solid support Compound 30 is commercially available. Compound 84 is prepared using procedures similar to those reported in the literature (see Shchepinov et al., *Nucleic Acids Research*, 1997, 25(22), 4447-4454; Shchepinov et al., *Nucleic Acids Research*, 1999, 27, 3035-3041; and Hornet et al., *Nucleic Acids Research*, 1997, 25, 4842-4849).

The phosphoramidite building blocks, Compounds 60 and 79a are prepared as per the procedures illustrated in Examples 28 and 36. The phosphoramidites illustrated are meant to be representative and not intended to be limiting as other phosphoramidite building blocks can be used to prepare an oligomeric compound having a phosphodiester linked conjugate at the 3' terminus with a predetermined sequence and composition. The order and quantity of phosphoramidites added to the solid support can be adjusted to prepare the oligomeric compounds as described herein having any predetermined sequence and composition.

Example 41

General Method for the Preparation of ASOs Comprising a Phosphodiester Linked GalNAc$_3$-2 (See Example 37, Bx is Adenine) Conjugate at the 5' Position Via Solid Phase Techniques (Preparation of ISIS 661134)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. Phosphoramidite compounds 56 and 60 were used to synthesize the phosphodiester linked GalNAc$_3$-2 conjugate at the 5' terminus. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on VIMAD solid support (110 μmol/g, Guzaev et al., 2003) packed in the column. For the coupling step, the phosphoramidites were delivered at a 4 fold excess over the initial loading of the solid support and phosphoramidite coupling was carried out for 10 min. All other steps followed standard protocols supplied by the manufacturer. A solution of 6% dichloroacetic acid in toluene was used for removing the dimethoxytrityl (DMT) groups from 5'-hydroxyl groups of the nucleotide. 4,5-Dicyanoimidazole (0.7 M) in anhydrous CH$_3$CN was used as activator during the coupling step. Phosphorothioate linkages were introduced by sulfurization with 0.1 M solution of xanthane hydride in 1:1 pyridine/CH$_3$CN for a contact time of 3 minutes. A solution of 20% tert-butylhydroperoxide in CH$_3$CN containing 6% water was used as an oxidizing agent to provide phosphodiester internucleoside linkages with a contact time of 12 minutes.

After the desired sequence was assembled, the cyanoethyl phosphate protecting groups were deprotected using a 20% diethylamine in toluene (v/v) with a contact time of 45 minutes. The solid-support bound ASOs were suspended in aqueous ammonia (28-30 wt %) and heated at 55° C. for 6 h. The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min-1,λ=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

TABLE 21

ASO comprising a phosphodiester linked $GalNAc_3$-2 conjugate at the 5' position targeting SRB-1

| ISIS No. | Sequence (5' to 3') | CalCd Mass | Observed Mass | SEQ ID No. |
|---|---|---|---|---|
| 661134 | GalNAc$_3$-2$_a$-$_o$,A$_{es}$T$_{ks}$$^m$C$_{ks}$ A$_{ds}$G$_{ds}$T$_{ds}$$^m$C$_{ds}$A$_{ds}$T$_{ds}$G$_{ds}$ A$_{ds}$$^m$C$_{ds}$T$_{ds}$T$_{ks}$$^m$C$_k$ | 6482.2 | 6481.6 | 26 |

Subscripts: "e" indicates 2'-MOE modified nucleoside; "d" indicates β-D-2'-deoxyribonucleoside; "k" indicates 6'-(S)—$CH_3$ bicyclic nucleoside (e.g. cEt); "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of $GalNAc_3$-$2_a$ is shown in Example 37.

Example 42

General Method for the Preparation of ASOs Comprising a $GalNAc_3$-3 Conjugate at the 5' Position Via Solid Phase Techniques (Preparation of ISIS 661166)

The synthesis for ISIS 661166 was performed using similar procedures as illustrated in Examples 39 and 41.

ISIS 661166 is a 5-10-5 MOE gapmer, wherein the 5' position comprises a $GalNAc_3$-3 conjugate. The ASO was characterized by ion-pair-HPLC coupled MS analysis with Agilent 1100 MSD system.

TABLE 21a

ASO comprising a $GalNAc_3$-3 conjugate at the 5' position via a hexylamino phosphodiester linkage targeting Malat-1

| ISIS No. | Sequence (5' to 3') | Conjugate | Calcd Mass | Observed Mass | SEQ ID No. |
|---|---|---|---|---|---|
| 661166 | 5'-GalNAc$_3$-3$_{a-o}$, $^m$C$_{es}$G$_{es}$G$_{es}$T$_{es}$ G$_{es}$$^m$C$_{ds}$A$_{ds}$A$_{ds}$G$_{ds}$ G$_{ds}$$^m$C$_{ds}$T$_{dss}$T$_{ds}$A$_{ds}$ G$_{ds}$G$_{es}$A$_{es}$A$_e$T$_{es}$T$_e$ | 5'-GalNAc$_3$-3 | 8992.16 | 8990.51 | 27 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of "5'-$GalNAc_3$-3a" is shown in Example 39.

Example 43

Dose-Dependent Study of Phosphodiester Linked $GalNAc_3$-2 (See Examples 37 and 41, Bx is Adenine) at the 5' Terminus Targeting SRB-1 In Vivo ISIS 661134 (see Example 41) comprising a phosphodiester linked $GalNAc_3$-2 conjugate at the 5' terminus was tested in a dose-dependent study for antisense inhibition of SRB-1 in mice. Unconjugated ISIS 440762 and 651900 ($GalNAc_3$-1 conjugate at 3' terminus, see Example 9) were included in the study for comparison and are described previously in Table 4.

Treatment

Six week old male Balb/c mice (Jackson Laboratory, Bar Harbor, Me.) were injected subcutaneously once at the dosage shown below with ISIS 440762, 651900, 661134 or with PBS treated control. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The $ED_{50}$s were measured using similar methods as described previously and are presented below.

As illustrated in Table 22, treatment with antisense oligonucleotides lowered SRB-1 mRNA levels in a dose-dependent manner. Indeed, the antisense oligonucleotides comprising the phosphodiester linked $GalNAc_3$-2 conjugate at the 5' terminus (ISIS 661134) or the $GalNAc_3$-1 conjugate linked at the 3' terminus (ISIS 651900) showed substantial improvement in potency compared to the unconjugated antisense oligonucleotide (ISIS 440762). Further, ISIS 661134, which comprises the phosphodiester linked $GalNAc_3$-2 conjugate at the 5' terminus was equipotent compared to ISIS 651900, which comprises the $GalNAc_3$-1 conjugate at the 3' terminus.

TABLE 22

ASOs containing GalNAc$_3$-1 or GalNAc$_3$-2 targeting SRB-1

| ISIS No. | Dosage (mg/kg) | SRB-1 mRNA levels (% PBS) | ED$_{50}$ (mg/kg) | Conjugate | SEQ ID No. |
|---|---|---|---|---|---|
| PBS | 0 | 100 | — | — | |
| 440762 | 0.2 | 116 | 2.58 | No conjugate | 22 |
| | 0.7 | 91 | | | |
| | 2 | 69 | | | |
| | 7 | 22 | | | |
| | 20 | 5 | | | |
| 651900 | 0.07 | 95 | 0.26 | 3' GalNAc$_3$-1 | 23 |
| | 0.2 | 77 | | | |
| | 0.7 | 28 | | | |
| | 2 | 11 | | | |
| | 7 | 8 | | | |
| 661134 | 0.07 | 107 | 0.25 | 5' GalNAc$_3$-2 | 26 |
| | 0.2 | 86 | | | |
| | 0.7 | 28 | | | |
| | 2 | 10 | | | |
| | 7 | 6 | | | |

Structures for 3' GalNAc$_3$-1 and 5' GalNAc$_3$-2 were described previously in Examples 9 and 37.

Pharmacokinetics Analysis (PK)

The PK of the ASOs from the high dose group (7 mg/kg) was examined and evaluated in the same manner as illustrated in Example 20. Liver sample was minced and extracted using standard protocols. The full length metabolites of 661134 (5' GalNAc$_3$-2) and ISIS 651900 (3' GalNAc$_3$-1) were identified and their masses were confirmed by high resolution mass spectrometry analysis. The results showed that the major metabolite detected for the ASO comprising a phosphodiester linked GalNAc$_3$-2 conjugate at the 5' terminus (ISIS 661134) was ISIS 440762 (data not shown). No additional metabolites, at a detectable level, were observed. Unlike its counterpart, additional metabolites similar to those reported previously in Table 10a were observed for the ASO having the GalNAc$_3$-1 conjugate at the 3' terminus (ISIS 651900). These results suggest that having the phosphodiester linked GalNAc$_3$-1 or GalNAc$_3$-2 conjugate may improve the PK profile of ASOs without compromising their potency.

Example 44

Effect of PO/PS Linkages on Antisense Inhibition of ASOs Comprising GalNAc$_3$-1 Conjugate (See Example 9) at the 3' Terminus Targeting SRB-1

ISIS 655861 and 655862 comprising a GalNAc$_3$-1 conjugate at the 3' terminus each targeting SRB-1 were tested in a single administration study for their ability to inhibit SRB-1 in mice. The parent unconjugated compound, ISIS 353382 was included in the study for comparison.

The ASOs are 5-10-5 MOE gapmers, wherein the gap region comprises ten 2'-deoxyribonucleosides and each wing region comprises five 2'-MOE modified nucleosides. The ASOs were prepared using similar methods as illustrated previously in Example 19 and are described Table a 23, below.

TABLE 23

Modified ASOs comprising GalNAc$_3$-1 conjugate at the 3' terminus targeting SRB-1

| ISIS No. | Sequence (5' to 3') | Chemistry | SEQ ID No. |
|---|---|---|---|
| 353382 (parent) | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | Full PS no conjugate | 28 |
| 655861 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo}$A$_{do}$,-GalNAc$_3$-1$_a$ | Full PS with GalNAc$_3$-1 conjugate | 29 |
| 655862 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{eo}$T$_{es}$T$_{eo}$A$_{do}$,-GalNAc$_3$-1$_a$ | Mixed PS/PO with GalNAc$_3$-1 conjugate | 29 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(=O)(OH)—. Superscript "m" indicates 5-methylcytosines. The structure of "GalNAc$_3$-1" is shown in Example 9.

Treatment

Six week old male Balb/c mice (Jackson Laboratory, Bar Harbor, Me.) were injected subcutaneously once at the dosage shown below with ISIS 353382, 655861, 655862 or with PBS treated control. Each treatment group consisted of 4 animals. Prior to the treatment as well as after the last dose, blood was drawn from each mouse and plasma samples were analyzed. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are reported below.

As illustrated in Table 24, treatment with antisense oligonucleotides lowered SRB-1 mRNA levels in a dose-dependent manner compared to PBS treated control. Indeed, the antisense oligonucleotides comprising the GalNAc$_3$-1 conjugate at the 3' terminus (ISIS 655861 and 655862) showed substantial improvement in potency comparing to the unconjugated antisense oligonucleotide (ISIS 353382). Further, ISIS 655862 with mixed PS/PO linkages showed an improvement in potency relative to full PS (ISIS 655861).

TABLE 24

Effect of PO/PS linkages on antisense inhibition of ASOs comprising GalNAc$_3$-1 conjugate at 3' terminus targeting SRB-1

| ISIS No. | Dosage (mg/kg) | SRB-1 mRNA levels (% PBS) | ED$_{50}$ (mg/kg) | Chemistry | SEQ ID No. |
|---|---|---|---|---|---|
| PBS | 0 | 100 | — | — | |
| 353382 (parent) | 3 | 76.65 | 10.4 | Full PS without conjugate | 28 |
| | 10 | 52.40 | 10.4 | | |
| | 30 | 24.95 | | | |

TABLE 24-continued

Effect of PO/PS linkages on antisense inhibition of ASOs comprising GalNAc$_3$-1 conjugate at 3' terminus targeting SRB-1

| ISIS No. | Dosage (mg/kg) | SRB-1 mRNA levels (% PBS) | ED$_{50}$ (mg/kg) | Chemistry | SEQ ID No. |
|---|---|---|---|---|---|
| 655861 | 0.5 | 81.22 | 2.2 | Full PS with GalNAc$_3$-1 conjugate | 29 |
|  | 1.5 | 63.51 |  |  |  |
|  | 5 | 24.61 |  |  |  |
|  | 15 | 14.80 |  |  |  |
| 655862 | 0.5 | 69.57 | 1.3 | Mixed PS/PO with GalNAc$_3$-1 conjugate | 29 |
|  | 1.5 | 45.78 |  |  |  |
|  | 5 | 19.70 |  |  |  |
|  | 15 | 12.90 |  |  |  |

Liver transaminase levels, alanine aminotransferase (ALT) and aspartate aminotransferase (AST), in serum were measured relative to saline injected mice using standard protocols. Organ weights were also evaluated. The results demonstrated that no elevation in transaminase levels (Table 25) or organ weights (data not shown) were observed in mice treated with ASOs compared to PBS control. Further, the ASO with mixed PS/PO linkages (ISIS 655862) showed similar transaminase levels compared to full PS (ISIS 655861).

TABLE 25

Effect of PO/PS linkages on transaminase levels of ASOs comprising GalNAc$_3$-1 conjugate at 3' terminus targeting SRB-1

| ISIS No. | Dosage (mg/kg) | ALT (U/L) | AST (U/L) | Chemistry | SEQ ID No. |
|---|---|---|---|---|---|
| PBS | 0 | 28.5 | 65 | — |  |
| 353382 (parent) | 3 | 50.25 | 89 | Full PS without conjugate | 28 |
|  | 10 | 27.5 | 79.3 |  |  |
|  | 30 | 27.3 | 97 |  |  |
| 655861 | 0.5 | 28 | 55.7 | Full PS with GalNAc$_3$-1 | 29 |
|  | 1.5 | 30 | 78 |  |  |
|  | 5 | 29 | 63.5 |  |  |
|  | 15 | 28.8 | 67.8 |  |  |
| 655862 | 0.5 | 50 | 75.5 | Mixed PS/PO with GalNAc$_3$-1 | 29 |
|  | 1.5 | 21.7 | 58.5 |  |  |
|  | 5 | 29.3 | 69 |  |  |
|  | 15 | 22 | 61 |  |  |

Example 45

Preparation of PFP Ester, Compound 110a

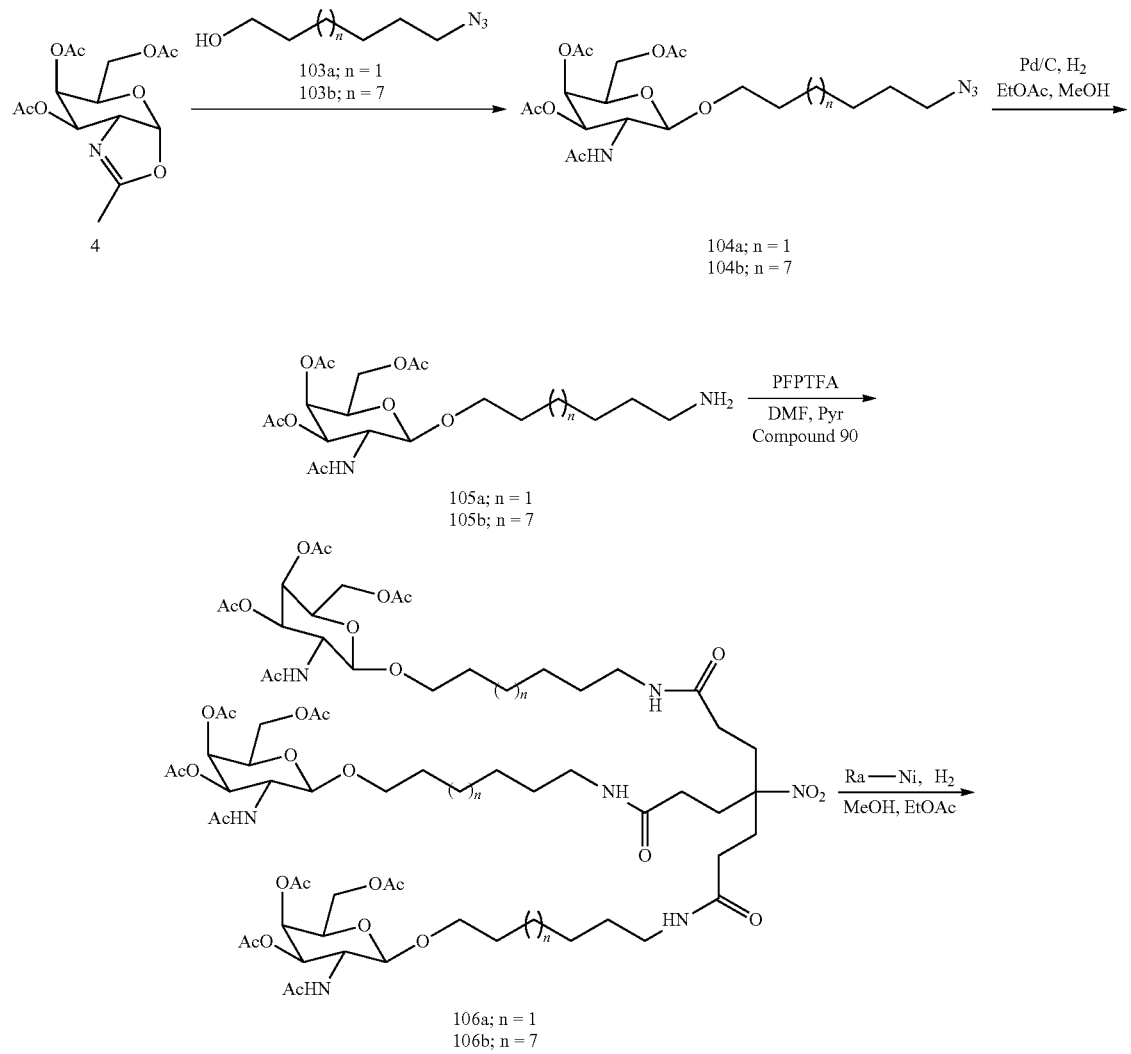

-continued
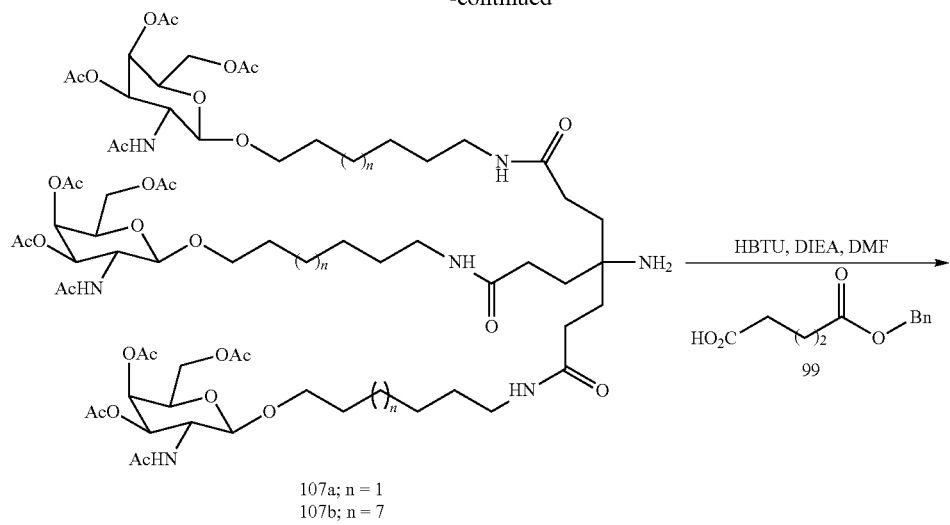
107a; n = 1
107b; n = 7
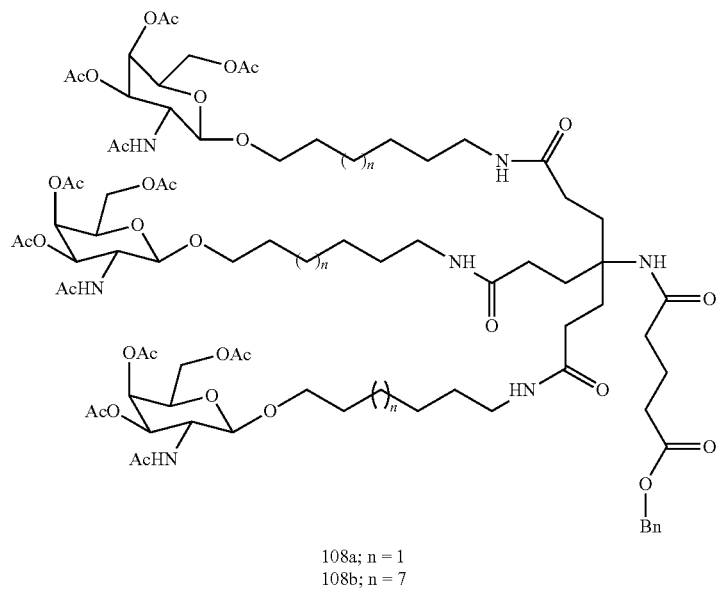
108a; n = 1
108b; n = 7
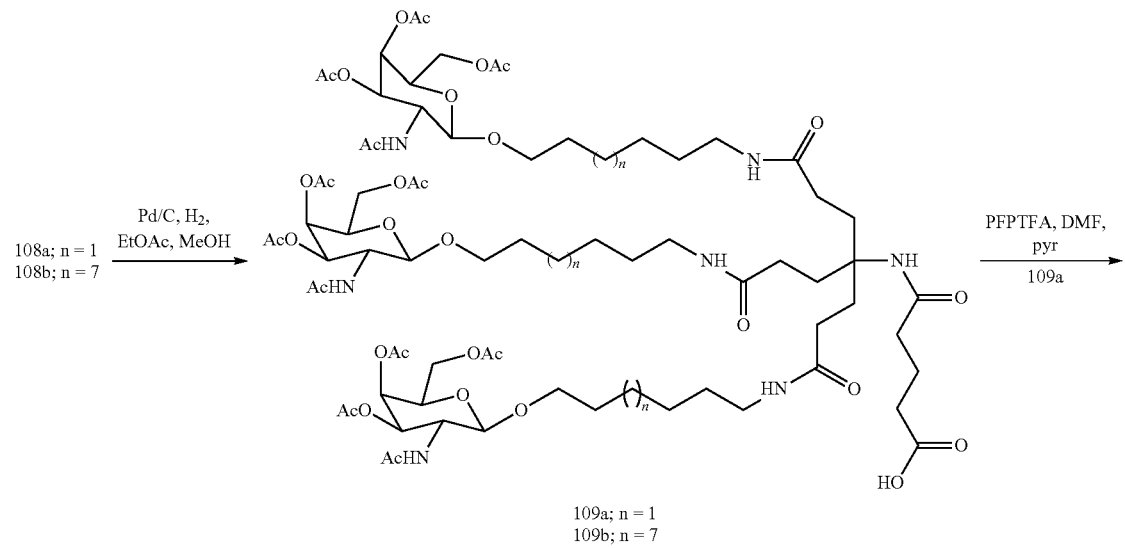
109a; n = 1
109b; n = 7

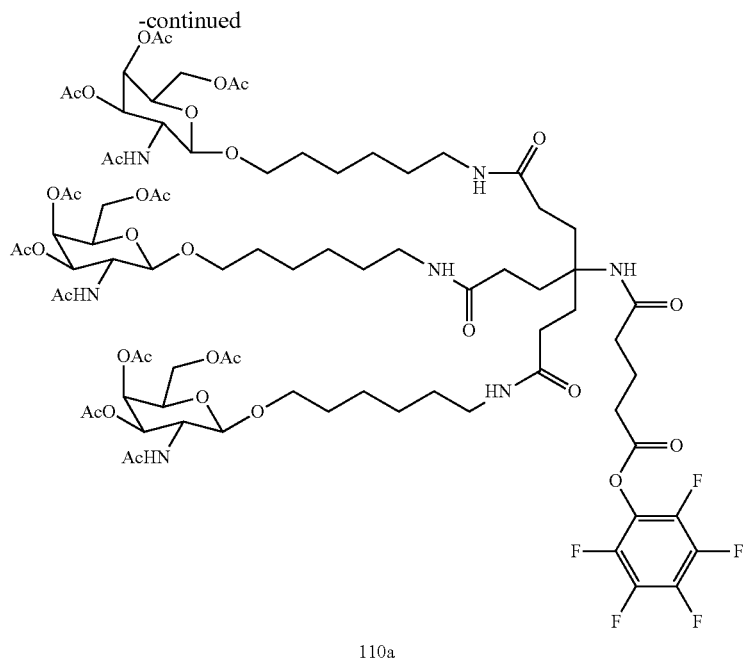

110a

Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%→10% methanol dichloromethane) to give compounds 104a and 104b in >80% yield. LCMS and proton NMR was consistent with the structure.

Compounds 104a and 104b were treated to the same conditions as for compounds 100a-d (Example 47), to give compounds 105a and 105b in >90% yield. LCMS and proton NMR was consistent with the structure.

Compounds 105a and 105b were treated, individually, with compound 90 under the same conditions as for compounds 901a-d, to give compounds 106a (80%) and 106b (20%). LCMS and proton NMR was consistent with the structure.

Compounds 106a and 106b were treated to the same conditions as for compounds 96a-d (Example 47), to give 107a (60%) and 107b (20%). LCMS and proton NMR was consistent with the structure.

Compounds 107a and 107b were treated to the same conditions as for compounds 97a-d (Example 47), to give compounds 108a and 108b in 40-60% yield. LCMS and proton NMR was consistent with the structure.

Compounds 108a (60%) and 108b (40%) were treated to the same conditions as for compounds 100a-d (Example 47), to give compounds 109a and 109b in >80% yields. LCMS and proton NMR was consistent with the structure.

Compound 109a was treated to the same conditions as for compounds 101a-d (Example 47), to give Compound 110a in 30-60% yield. LCMS and proton NMR was consistent with the structure. Alternatively, Compound 110b can be prepared in a similar manner starting with Compound 109b.

Example 46

General Procedure for Conjugation with PFP Esters (Oligonucleotide 111); Preparation of ISIS 666881 (GalNAc$_3$-10)

A 5'-hexylamino modified oligonucleotide was synthesized and purified using standard solid-phase oligonucleotide procedures. The 5'-hexylamino modified oligonucleotide was dissolved in 0.1 M sodium tetraborate, pH 8.5 (200 μL) and 3 equivalents of a selected PFP esterified GalNAc$_3$ cluster dissolved in DMSO (50 μL) was added. If the PFP ester precipitated upon addition to the ASO solution DMSO was added until all PFP ester was in solution. The reaction was complete after about 16 h of mixing at room temperature. The resulting solution was diluted with water to 12 mL and then spun down at 3000 rpm in a spin filter with a mass cut off of 3000 Da. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligonucleotide was purified and desalted by RP-HPLC and lyophilized to provide the GalNAc$_3$ conjugated oligonucleotide.

110a

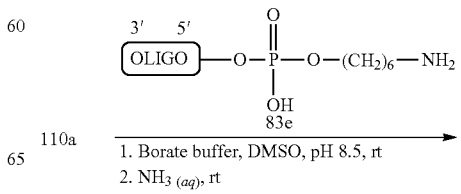

1. Borate buffer, DMSO, pH 8.5, rt
2. NH$_3$ $_{(aq)}$, rt

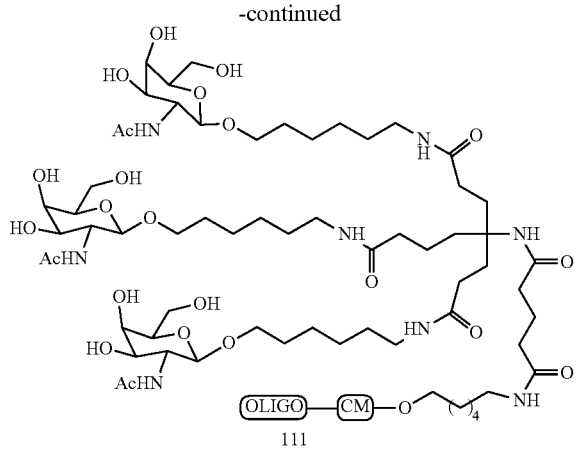

111

Oligonucleotide 111 is conjugated with GalNAc$_3$-10. The GalNAc$_3$ cluster portion of the conjugate group GalNAc$_3$-10 (GalNAc$_3$-10$_a$) can be combined with any cleavable moiety to provide a variety of conjugate groups. In certain embodiments, the cleavable moiety is —P(=O)(OH)-A$_d$-P(=O)(OH)— as shown in the oligonucleotide (ISIS 666881) synthesized with GalNAc$_3$-10 below. The structure of GalNAc$_3$-10 (GalNAc$_3$-10$_a$-CM-) is shown below:

additional DMSO (600 μL) to fully dissolve the PFP ester. The reaction was complete after 16 h of mixing at room temperature. The solution was diluted with water to 12 mL total volume and spun down at 3000 rpm in a spin filter with a mass cut off of 3000 Da. This process was repeated twice to remove small molecule impurities. The solution was lyophilized to dryness and redissolved in concentrated aqueous ammonia with mixing at room temperature for 2.5 h followed by concentration in vacuo to remove most of the ammonia. The conjugated oligonucleotide was purified and desalted by RP-HPLC and lyophilized to give ISIS 666881 in 90% yield by weight (42 mg, 4.7 μmol).

| GalNAc$_3$-10 conjugated oligonucleotide | | | |
|---|---|---|---|
| ASO | Sequence (5' to 3') | 5' group | SEQ ID No. |
| ISIS 660254 | NH$_2$(CH$_2$)$_6$-$_o$A$_{do}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | Hexylamine | 30 |
| ISIS 666881 | GalNAc$_3$-10$_a$-$_o$,A$_d$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-10 | 30 |

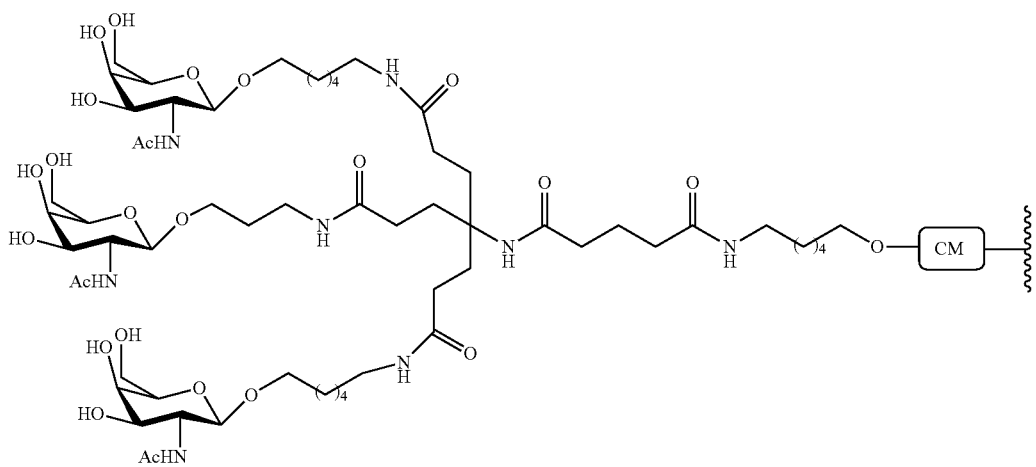

Following this general procedure ISIS 666881 was prepared. 5'-hexylamino modified oligonucleotide, ISIS 660254, was synthesized and purified using standard solid-phase oligonucleotide procedures. ISIS 660254 (40 mg, 5.2 μmol) was dissolved in 0.1 M sodium tetraborate, pH 8.5 (200 μL) and 3 equivalents PFP ester (Compound 110a) dissolved in DMSO (50 μL) was added. The PFP ester precipitated upon addition to the ASO solution requiring Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Example 47
Preparation of Oligonucleotide 102 Comprising GalNAc₃-8
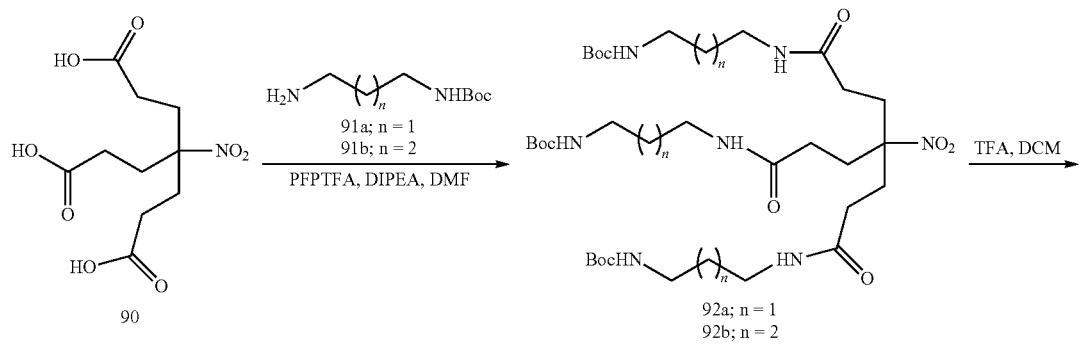
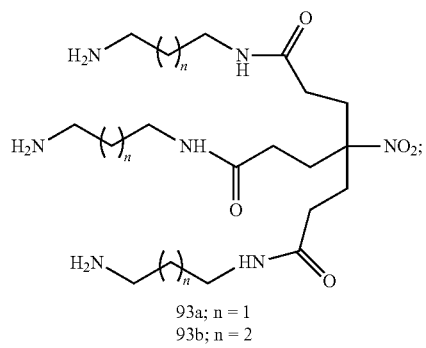
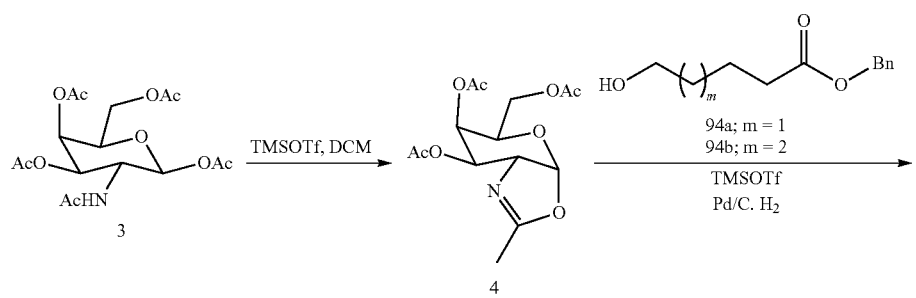
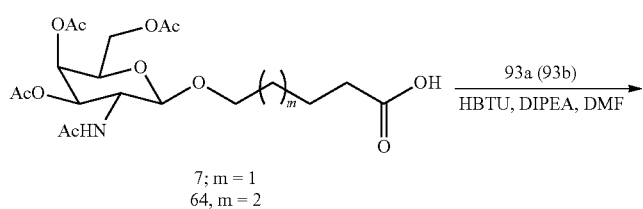

-continued
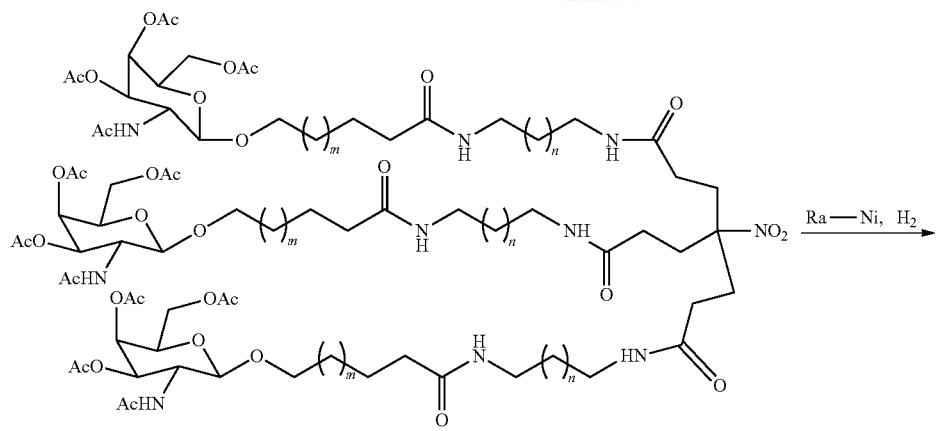
96a; n = 1, m = 1
96b; n = 1, m = 2
96c; n = 2, m = 1
96d; n = 2, m = 2
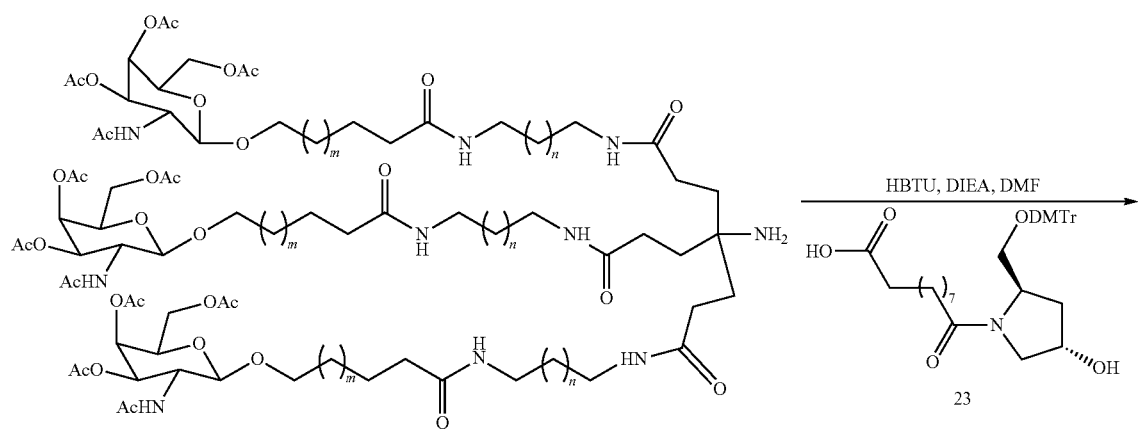
97a; n = 1, m = 1
97b; n = 1, m = 2
97c; n = 2, m = 1
97d; n = 2, m = 2
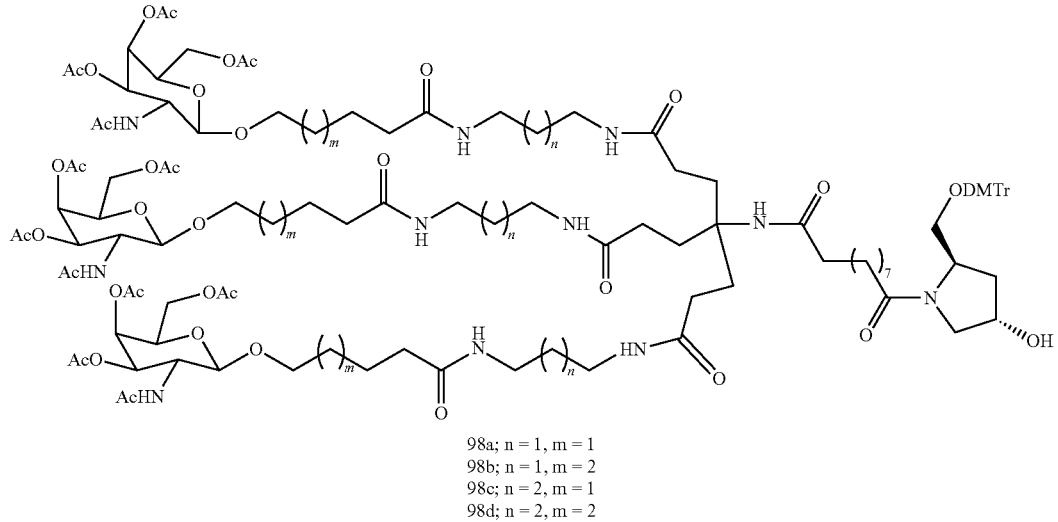
98a; n = 1, m = 1
98b; n = 1, m = 2
98c; n = 2, m = 1
98d; n = 2, m = 2

-continued
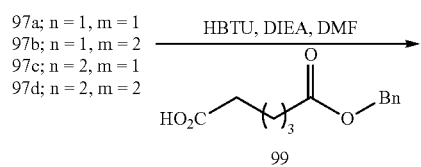
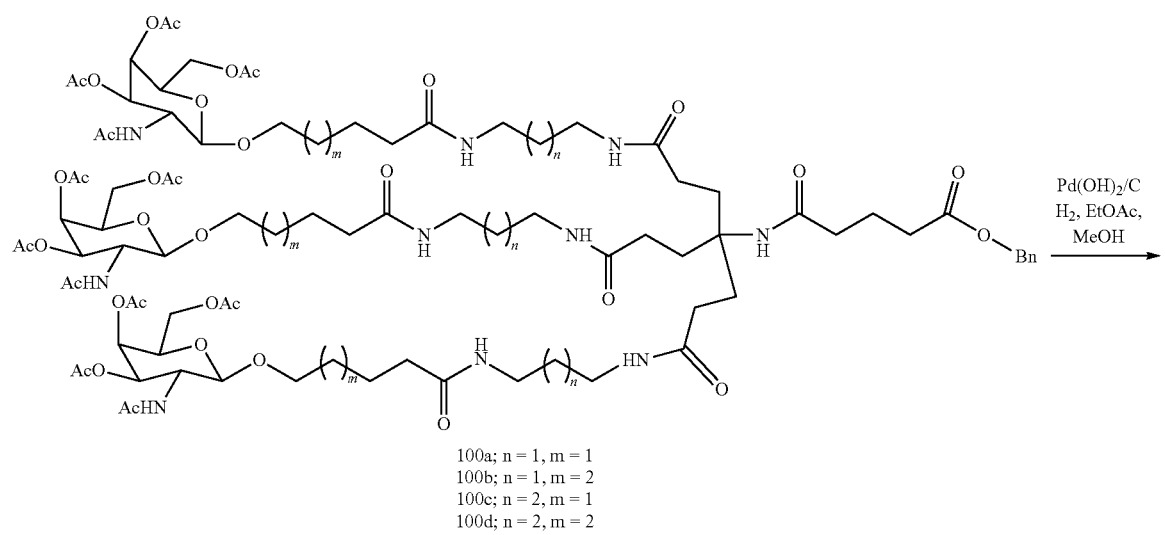
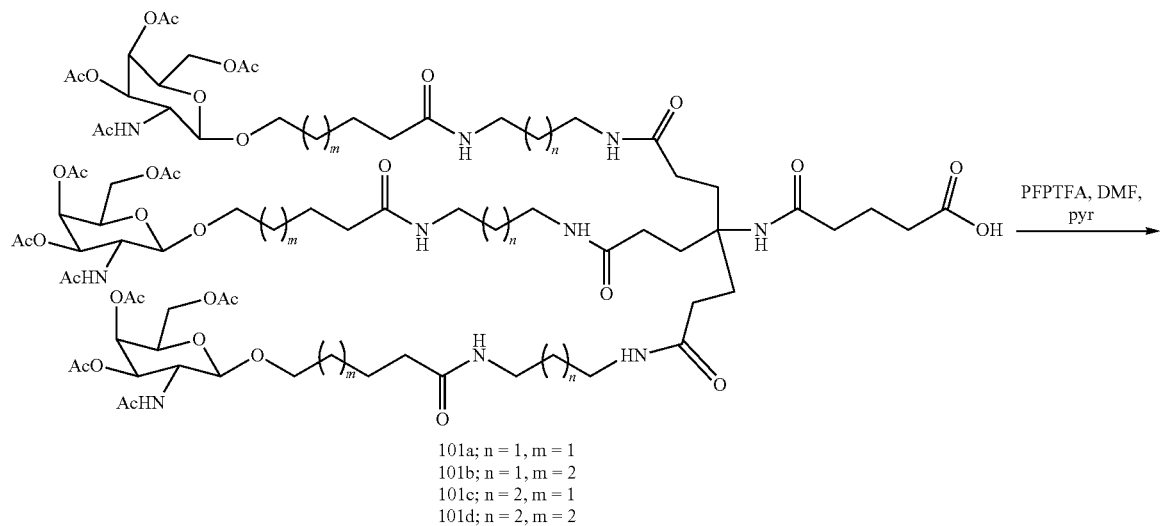

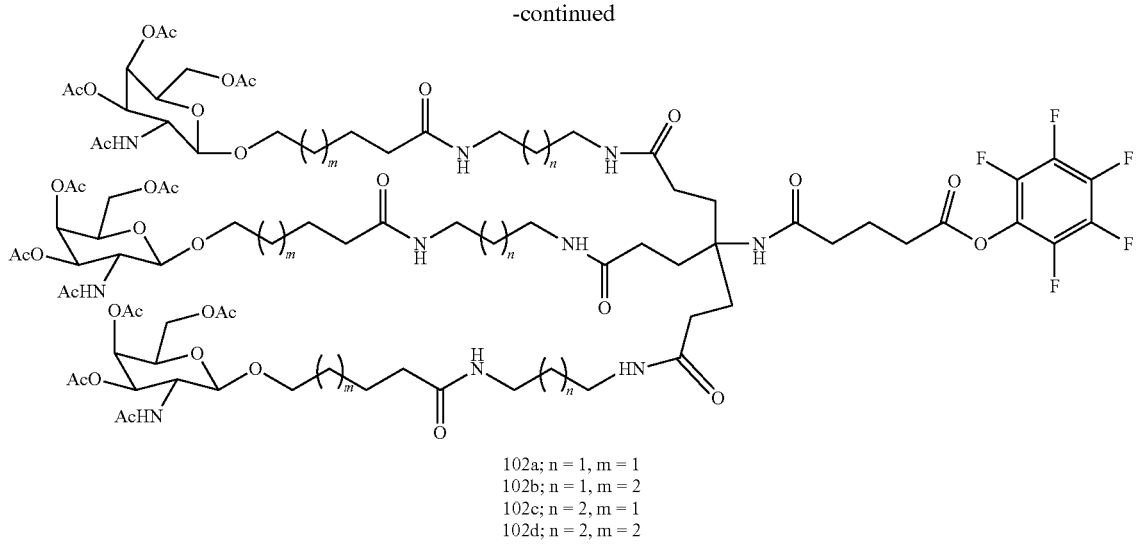

102a; n = 1, m = 1
102b; n = 1, m = 2
102c; n = 2, m = 1
102d; n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→10% methanol dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%→20% methanol/dichloromethane) to give compounds 100a-d in 40-60% yield. LCMS and proton NMR was consistent with the structure.

Compounds 100a-d (0.16 mmoles), individually, were hydrogenated over 10% Pd(OH)$_2$/C for 3 hours in methanol/ethyl acetate (1:1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%→5% methanol dichloromethane) to give compounds 102a-d in an approximate 80% yield. LCMS and proton NMR were consistent with the structure.

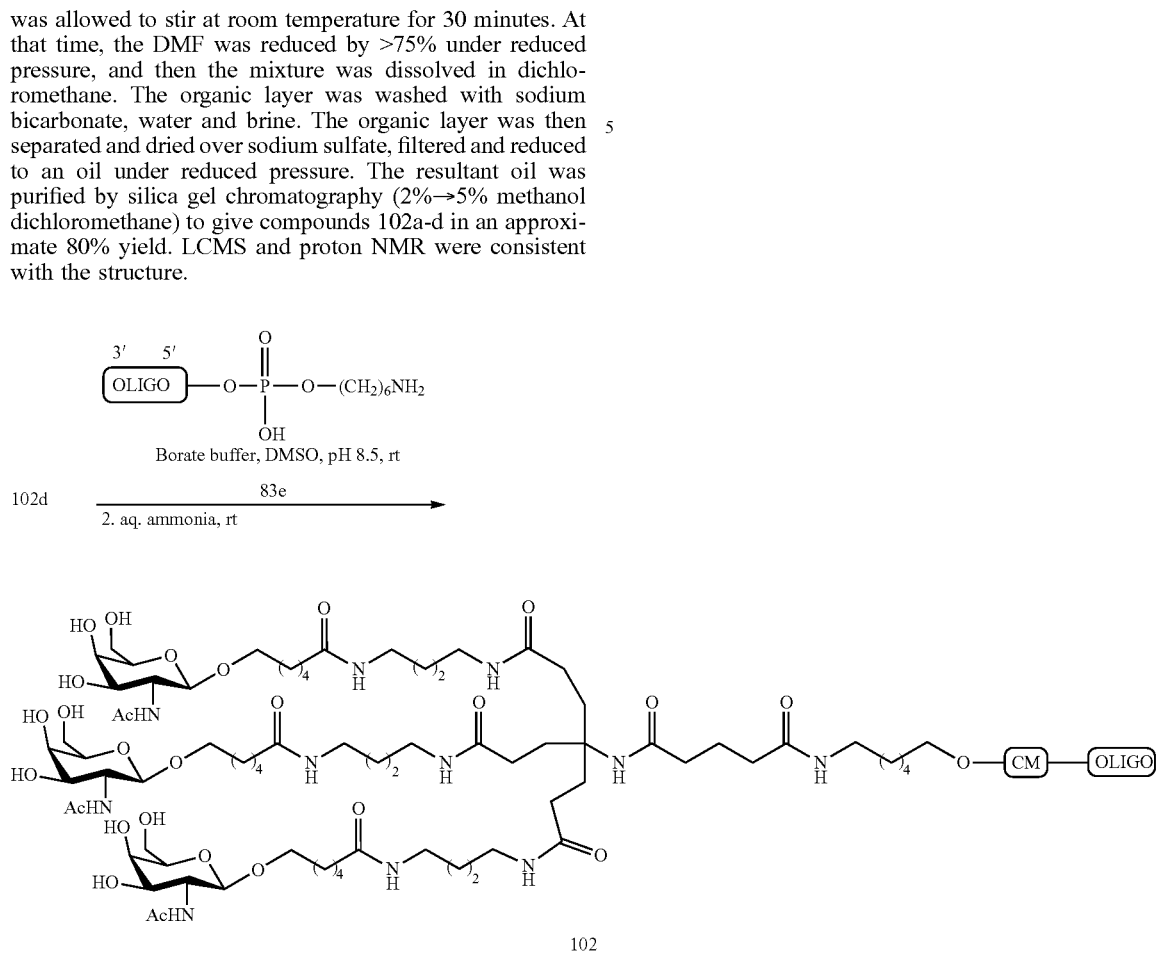

Oligomeric Compound 102, comprising a GalNAc$_3$-8 conjugate group, was prepared using the general procedures illustrated in Example 46. The GalNAc$_3$ cluster portion of the conjugate group GalNAc$_3$-8 (GalNAc$_3$-8$_a$) can be combined with any cleavable moiety to provide a variety of conjugate groups. In a preferred embodiment, the cleavable moiety is —P(=O)(OH)-A$_d$-P(=O)(OH)—.

The structure of GalNAc$_3$-8 (GalNAc$_3$-8$_a$-CM-) is shown below:

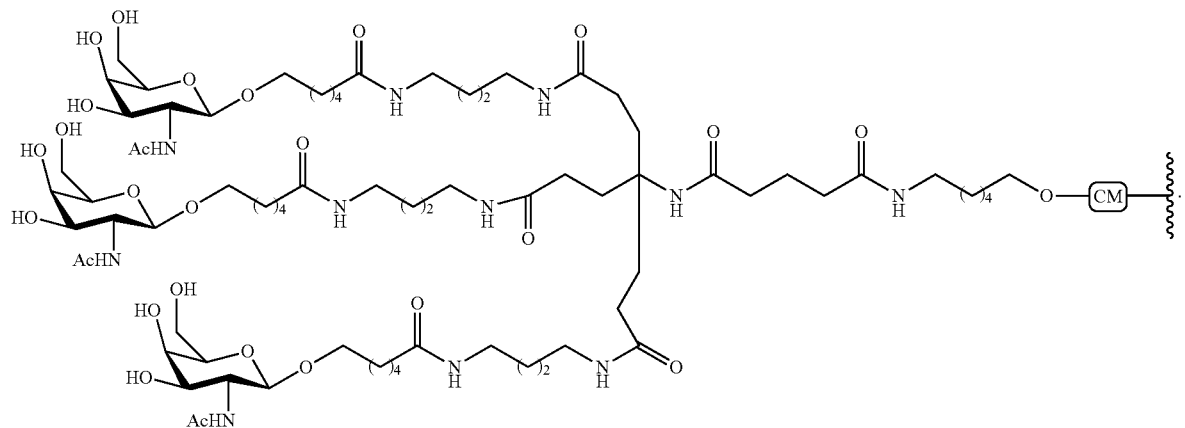

Example 48
Preparation of Oligonucleotide 119 Comprising GalNAc₃-7
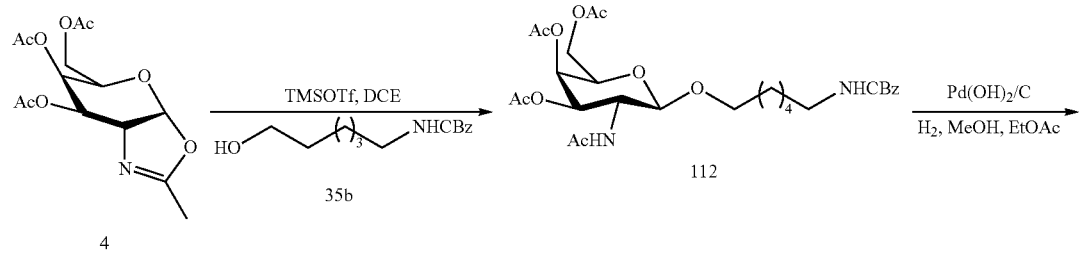
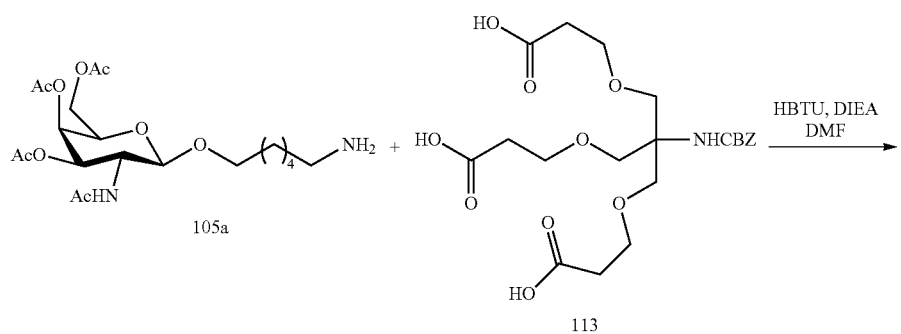
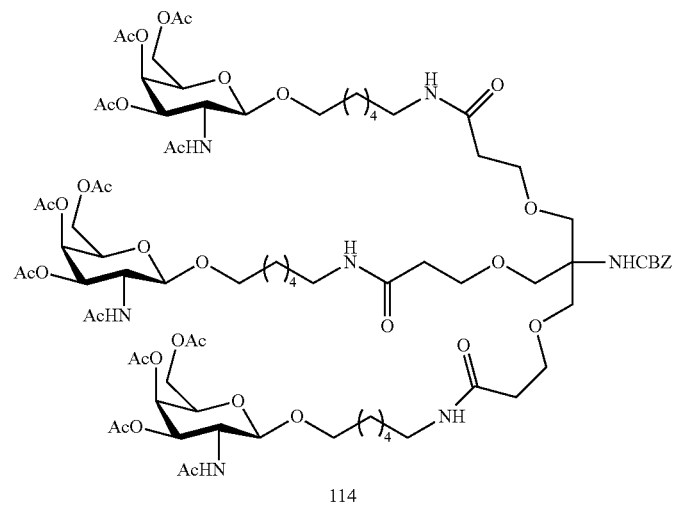
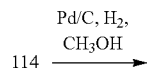

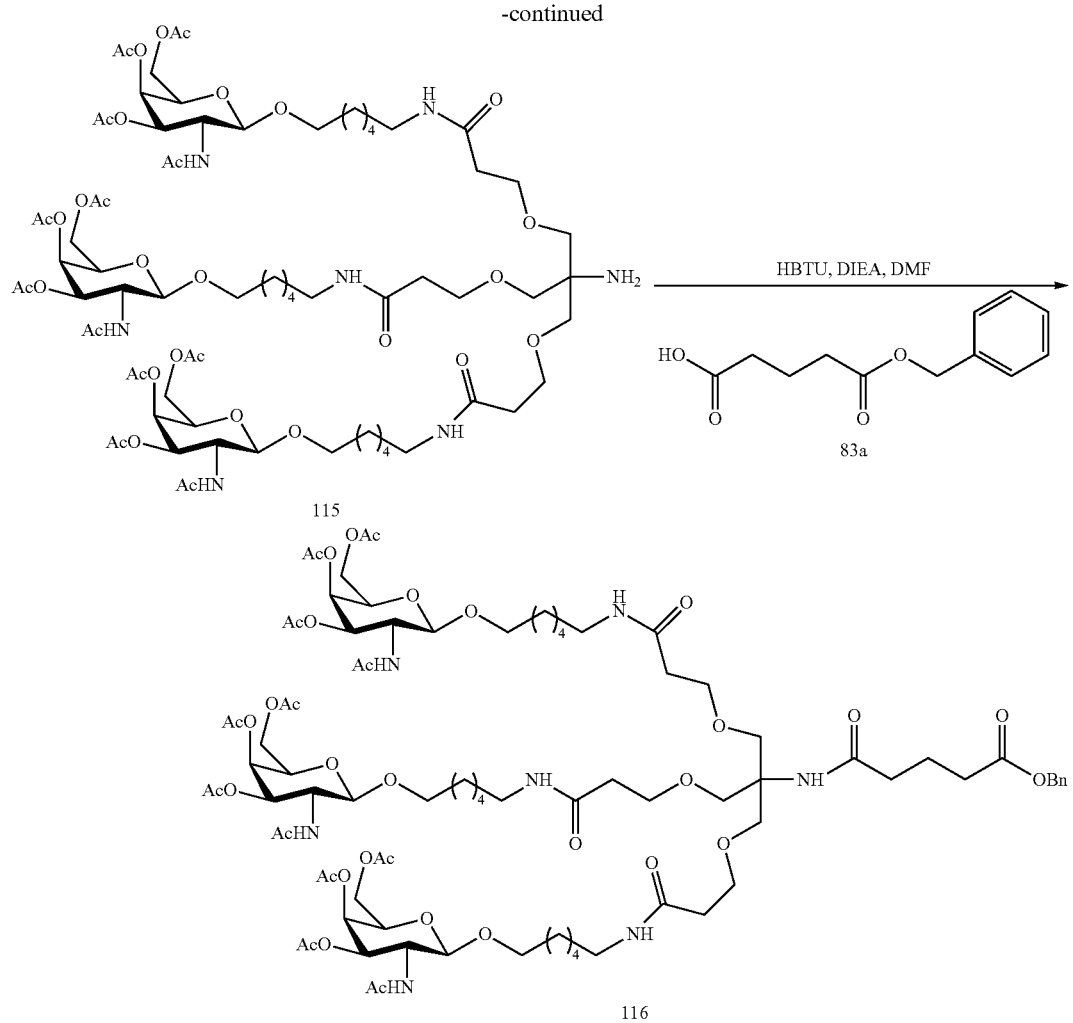

Compound 112 was synthesized following the procedure described in the literature (*J. Med. Chem.* 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in $CH_2Cl_2$ (100 mL) and washed with aqueous saturated $NaHCO_3$ solution (100 mL) and brine (100 mL). The organic phase was separated, dried ($Na_2SO_4$), filtered and evaporated. The residue was purified by silica gel column chromatography and eluted with 10 to 20% MeOH in dichloromethane to yield Compound 114 (1.45 g, 30%). The structure was confirmed by LCMS and $^1H$ NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1H$ NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min To this a solution of Compound 115 (1.22 g, 0.75 mmol) in anhydrous DMF was added and the reaction was stirred at room temperature for 6 h. The solvent was removed under reduced pressure and the residue was dissolved in $CH_2Cl_2$. The organic layer was washed aqueous saturated $NaHCO_3$ solution and brine and dried over anhydrous $Na_2SO_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1H$ NMR analysis.

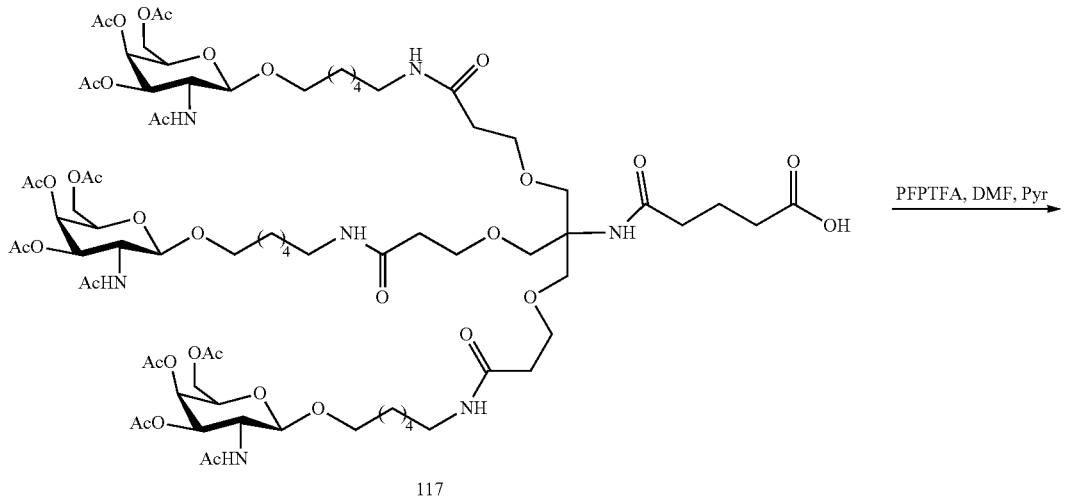

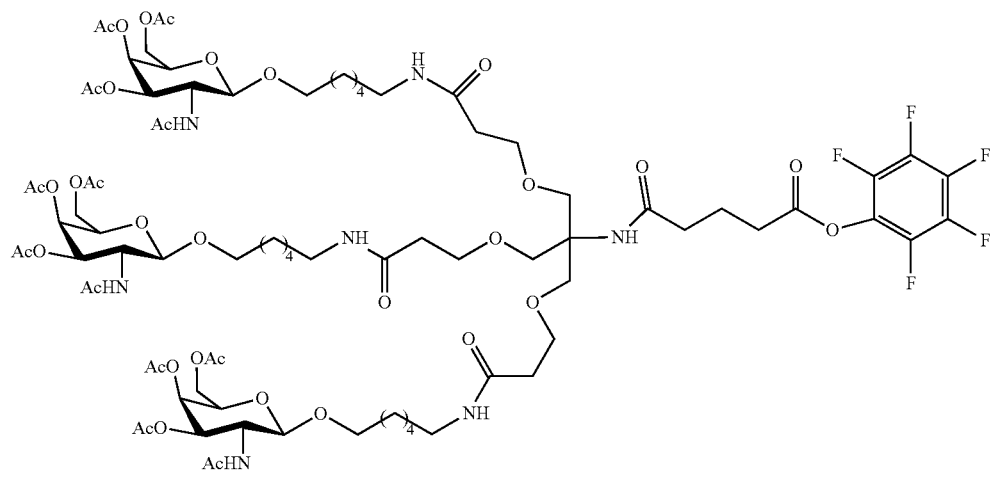

Compound 116 (0.74 g, 0.4 mmol) was dissolved in 1:1 methanol/ethyl acetate (5 mL/5 mL). Palladium on carbon (wet, 0.074 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and $^1$H NMR analysis.

Compound 117 (0.63 g, 0.36 mmol) was dissolved in anhydrous DMF (3 mL). To this solution N,N-Diisopropylethylamine (70 μL, 0.4 mmol) and pentafluorophenyl trifluoroacetate (72 μL, 0.42 mmol) were added. The reaction mixture was stirred at room temperature for 12 h and poured into a aqueous saturated NaHCO$_3$ solution. The mixture was extracted with dichloromethane, washed with brine and dried over anhydrous Na$_2$SO$_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^1$H and $^1$H and $^{19}$F NMR.

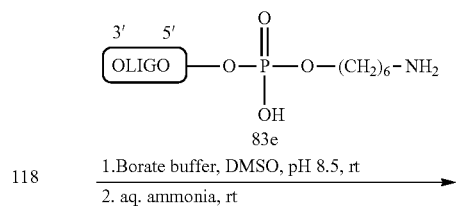

118

1. Borate buffer, DMSO, pH 8.5, rt
2. aq. ammonia, rt
→

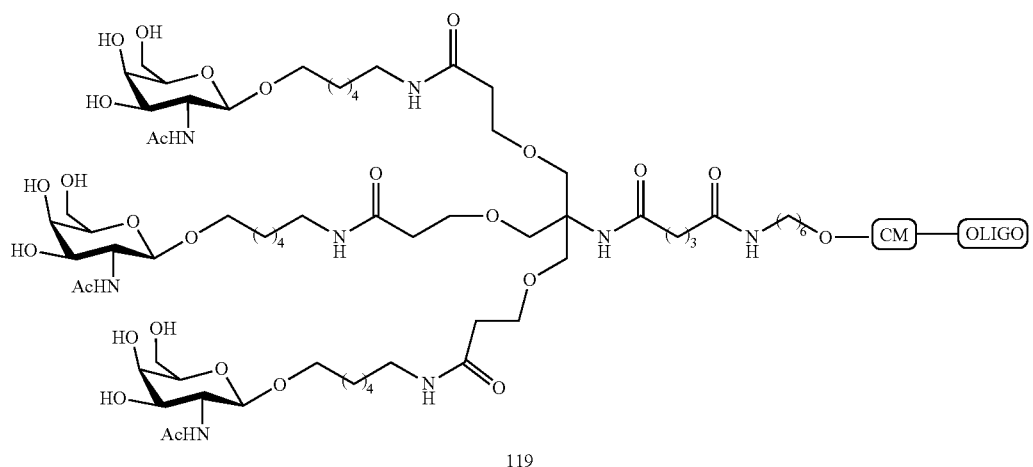

119

Oligomeric Compound 119, comprising a GalNAc$_3$-7 conjugate group, was prepared using the general procedures illustrated in Example 46. The GalNAc$_3$ cluster portion of the conjugate group GalNAc$_3$-7 (GalNAc$_3$-7$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-7 (GalNAc$_3$-7$_a$-CM-) is shown below:

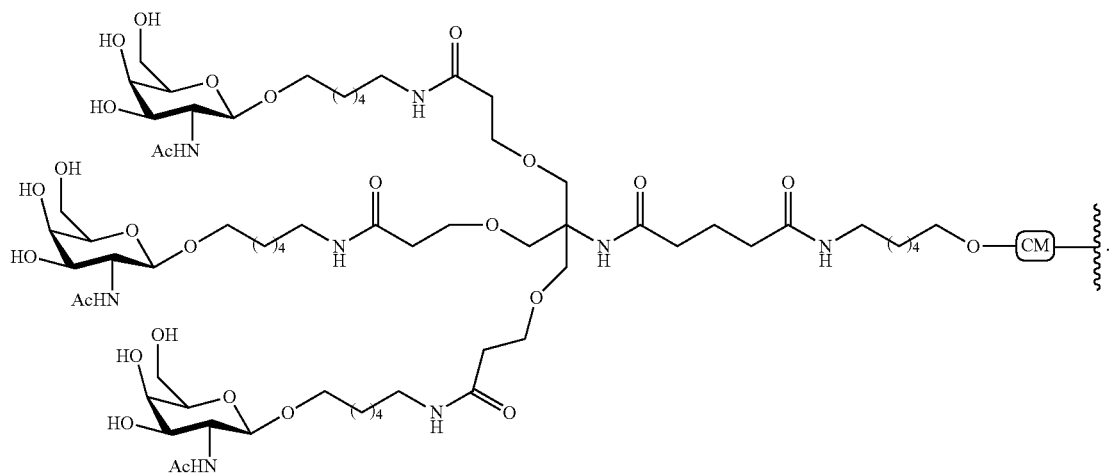

Example 49

Preparation of Oligonucleotide 132 Comprising GalNAc$_3$-5

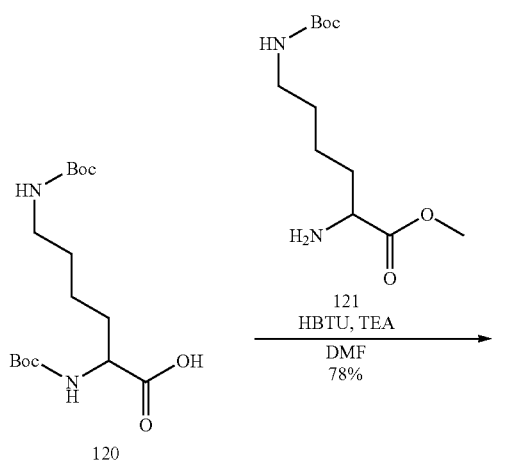

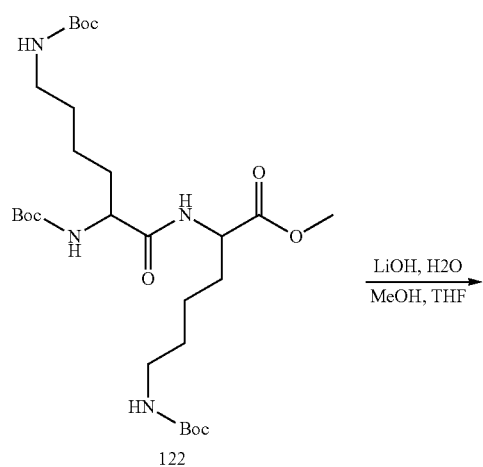

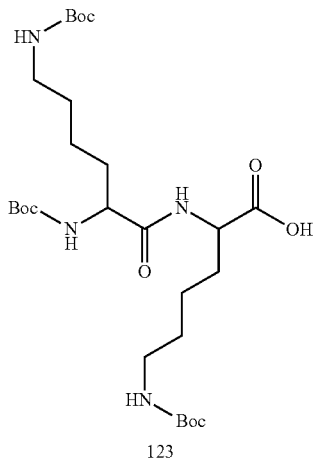

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC (ethyl acetate:hexane; 1:1; Rf=0.47). The solvent was removed under reduced pressure. The residue was taken up in EtOAc (300 mL) and washed with 1M NaHSO$_4$ (3×150 mL), aqueous saturated NaHCO$_3$ solution (3×150 mL) and brine (2×100 mL). Organic layer was dried with Na$_2$SO$_4$. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and $^1$H NMR analysis. Mass m/z 589.3 [M+H]$^+$.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min and monitored by TLC (EtOAc:hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried (Na$_2$SO$_4$), filtered and evaporated to yield Compound 123 (8.42 g). Residual salt is the likely cause of excess mass. LCMS is consistent with structure. Product was used without any further purification. M.W.cal:574.36; M.W.fd:575.3 [M+H]$^+$.

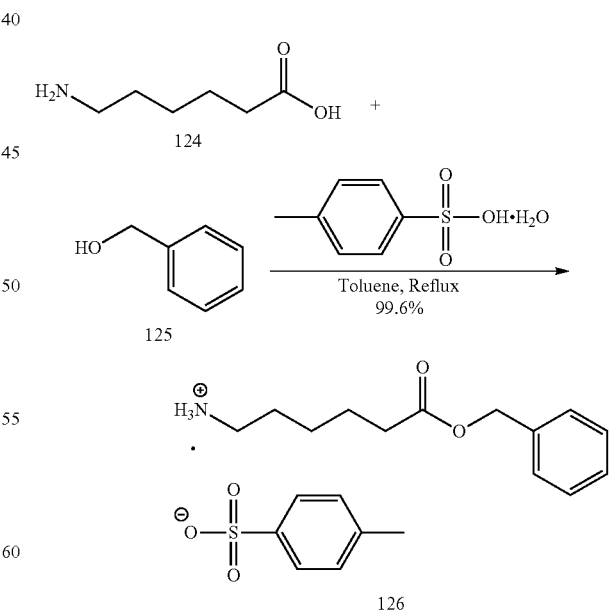

Compound 126 was synthesized following the procedure described in the literature (*J. Am. Chem. Soc.* 2011, 133, 958-963).

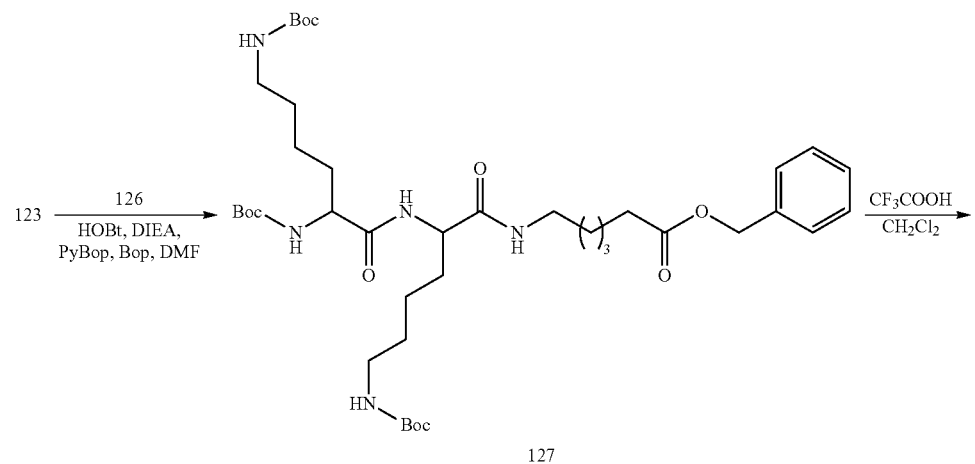
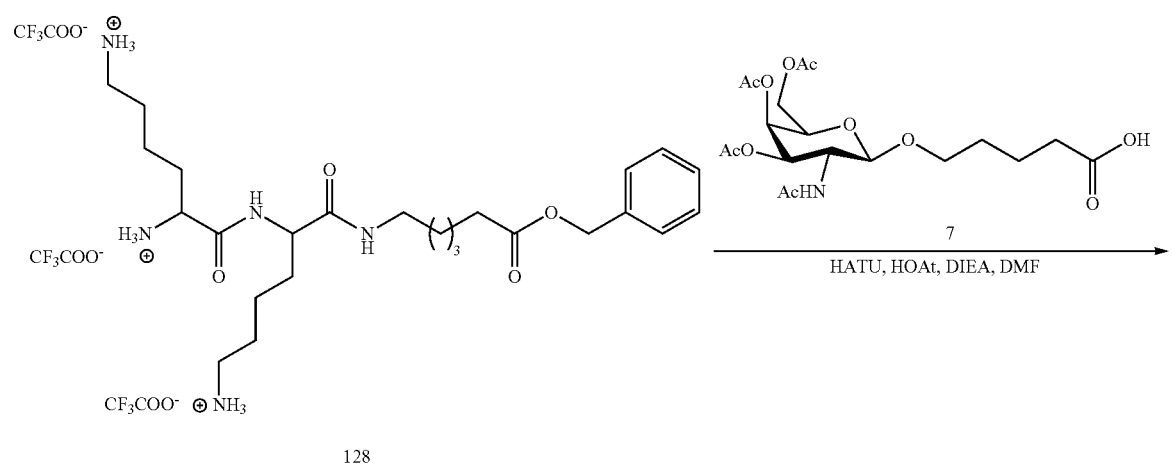
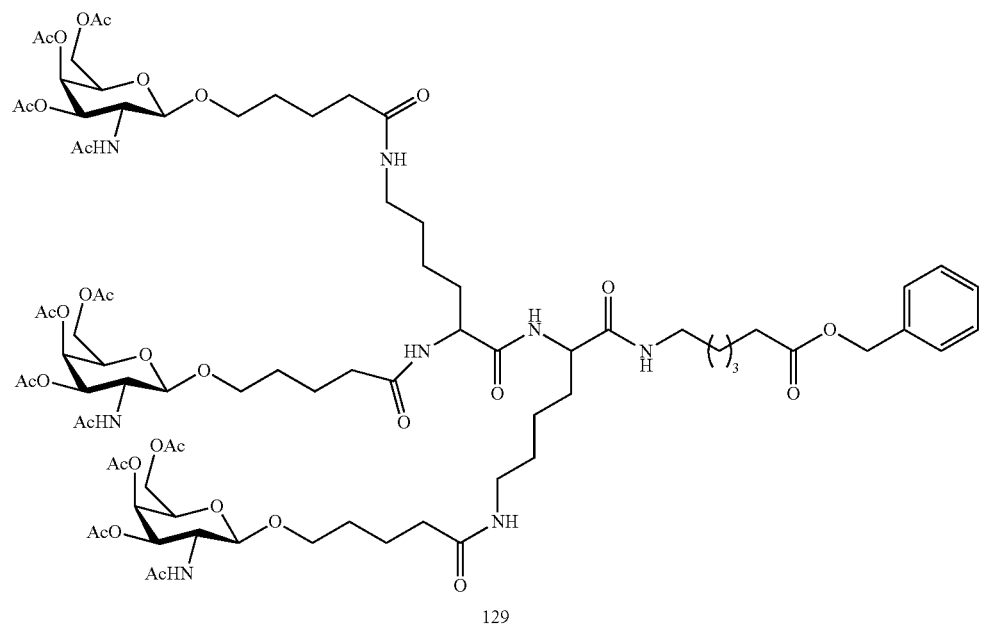

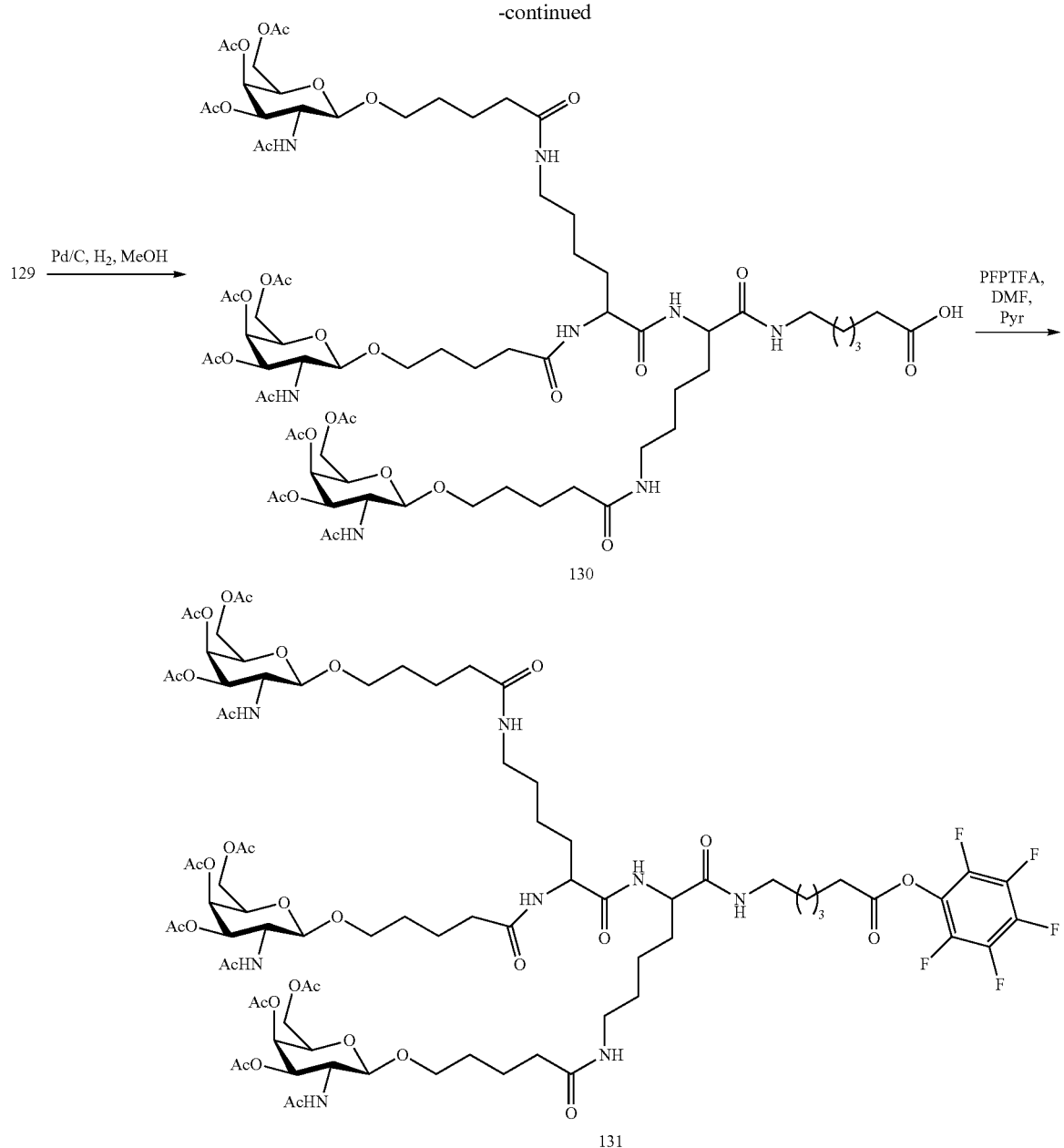

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM:MeOH:AA; 89:10:1). The reaction mixture was concentrated under reduced pressure. The residue was dissolved in EtOAc (200 mL) and washed with 1 M NaHSO$_4$ (3×100 mL), aqueous saturated NaHCO$_3$ (3×100 mL) and brine (2×100 mL). The organic phase separated dried (Na$_2$SO$_4$), filtered and concentrated. The residue was purified by silica gel column chromatography with a gradient of 50% hexanes/EtOAC to 100% EtOAc to yield Compound 127 (9.4 g) as a white foam. LCMS and $^1$H NMR were consistent with structure. Mass m/z 778.4 [M+H]$^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1$H NMR were consistent with structure. Mass m/z 478.2 [M+H]$^+$.

Compound 7 (0.43 g, 0.963 mmol), HATU (0.35 g, 0.91 mmol), and HOAt (0.035 g, 0.26 mmol) were combined together and dried for 4 h over P$_2$O$_5$ under reduced pressure in a round bottom flask and then dissolved in anhydrous DMF (1 mL) and stirred for 5 min To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC (7% MeOH/DCM). The reaction mixture was concentrated under reduced pressure. The residue was dissolved in DCM (30 mL) and washed with 1 M NaHSO$_4$ (3×20 mL), aqueous saturated NaHCO$_3$ (3×20 mL) and brine (3×20 mL). The organic phase was separated, dried over Na$_2$SO$_4$, filtered and concentrated. The residue was purified by silica gel column chromatography using 5-15% MeOH in dichloromethane to yield Compound 129 (96.6 mg). LC MS and $^1$H NMR are consistent with structure. Mass m/z 883.4 [M+2H]$^+$.

To a 10 mL pointed round bottom flask were added compound 130 (75.8 mg, 0.046 mmol), 0.37 M pyridine/DMF (200 µL) and a stir bar. To this solution was added 0.7 M pentafluorophenyl trifluoroacetate/DMF (100 µL) drop wise with stirring. The reaction was completed after 1 h as determined by LC MS. The solvent was removed under reduced pressure and the residue was dissolved in CHCl$_3$ (~10 mL). The organic layer was partitioned against NaHSO$_4$ (1 M, 10 mL), aqueous saturated NaHCO$_3$ (10 mL) and brine (10 mL) three times each. The organic phase separated and dried over Na$_2$SO$_4$, filtered and concentrated to yield Compound 131 (77.7 mg). LCMS is consistent with structure. Used without further purification. Mass m/z 921.3 [M+2H]$^+$.

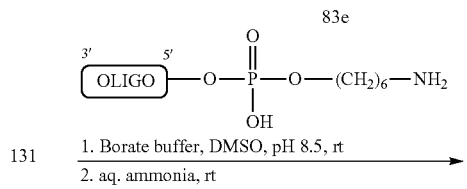

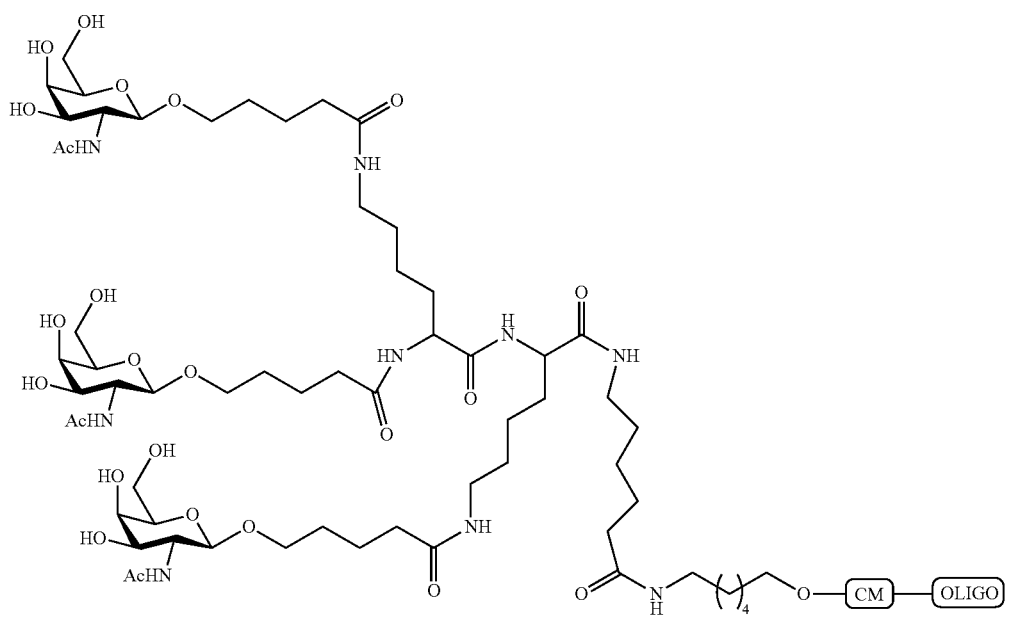

Compound 129 (0.09 g, 0.051 mmol) was dissolved in methanol (5 mL) in 20 mL scintillation vial. To this was added a small amount of 10% Pd/C (0.015 mg) and the reaction vessel was flushed with H$_2$ gas. The reaction mixture was stirred at room temperature under H$_2$ atmosphere for 18 h. The reaction mixture was filtered through a pad of Celite and the Celite pad was washed with methanol. The filtrate washings were pooled together and concentrated under reduced pressure to yield Compound 130 (0.08 g). LCMS and $^1$H NMR were consistent with structure. The product was used without further purification. Mass m/z 838.3 [M+2H]$^+$.

Oligomeric Compound 132, comprising a GalNAc$_3$-5 conjugate group, was prepared using the general procedures illustrated in Example 46. The GalNAc$_3$ cluster portion of the conjugate group GalNAc$_3$-5 (GalNAc$_3$-5$_a$) can be combined with any cleavable moiety to provide a variety of conjugate groups. In certain embodiments, the cleavable moiety is —P(=O)(OH)-A$_d$-P(=O)(OH)—.

The structure of GalNAc$_3$-5 (GalNAc$_3$-5$_a$-CM-) is shown below:

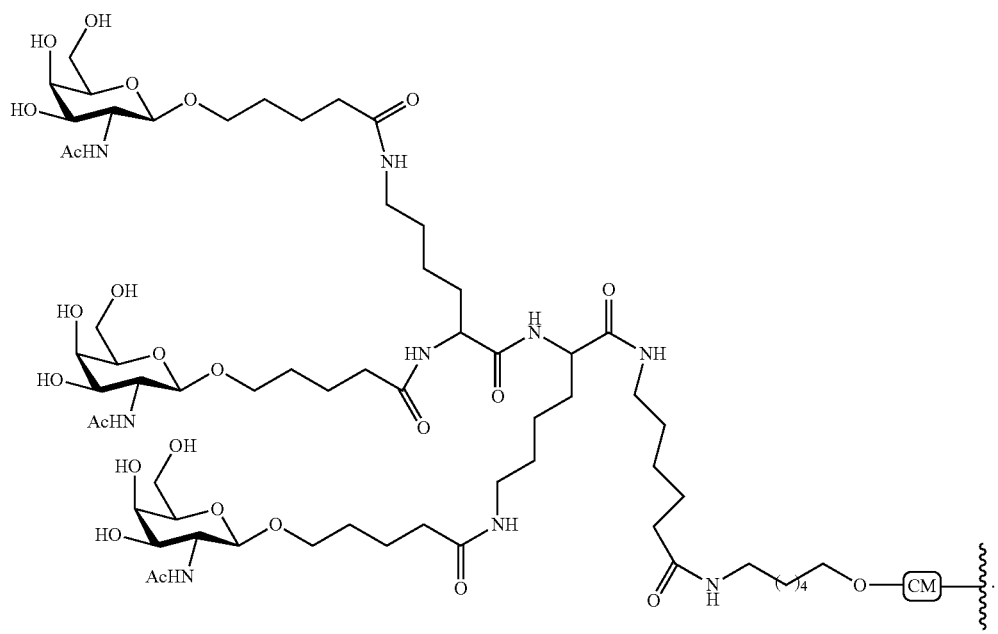
Example 50
Preparation of Oligonucleotide 144 Comprising GalNAc$_4$-11
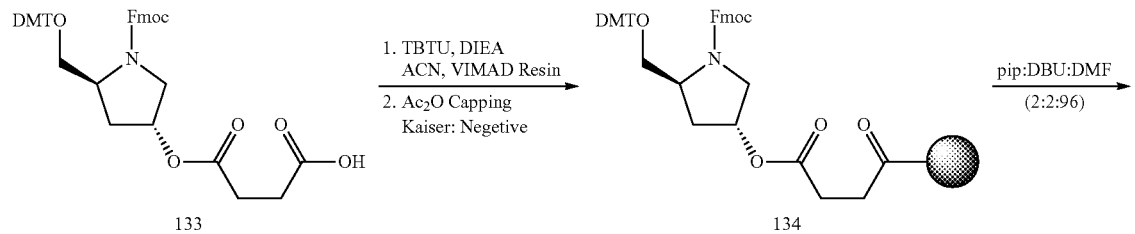
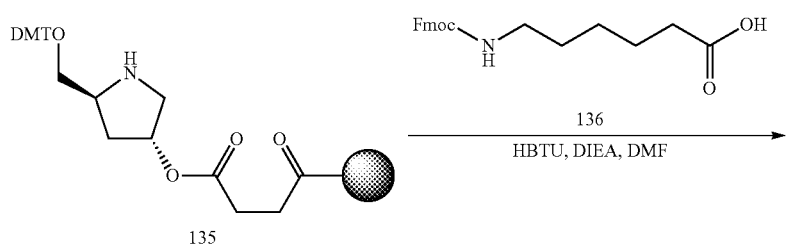

-continued
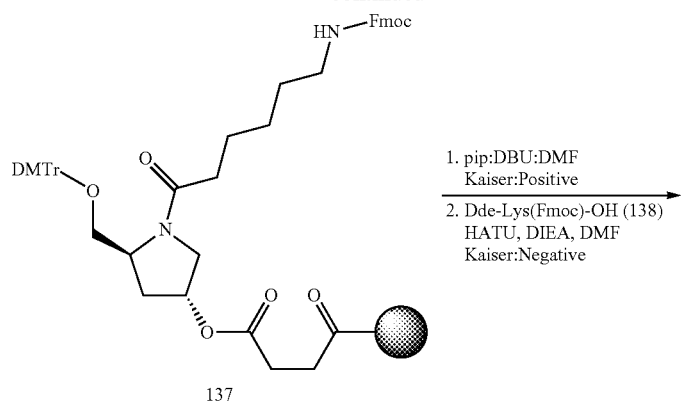
137
1. pip:DBU:DMF
   Kaiser:Positive
2. Dde-Lys(Fmoc)-OH (138)
   HATU, DIEA, DMF
   Kaiser:Negative
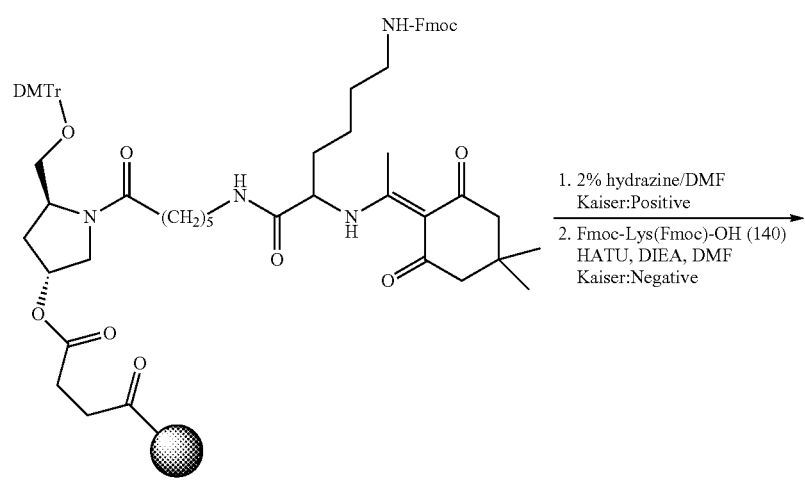
139
1. 2% hydrazine/DMF
   Kaiser:Positive
2. Fmoc-Lys(Fmoc)-OH (140)
   HATU, DIEA, DMF
   Kaiser:Negative -continued
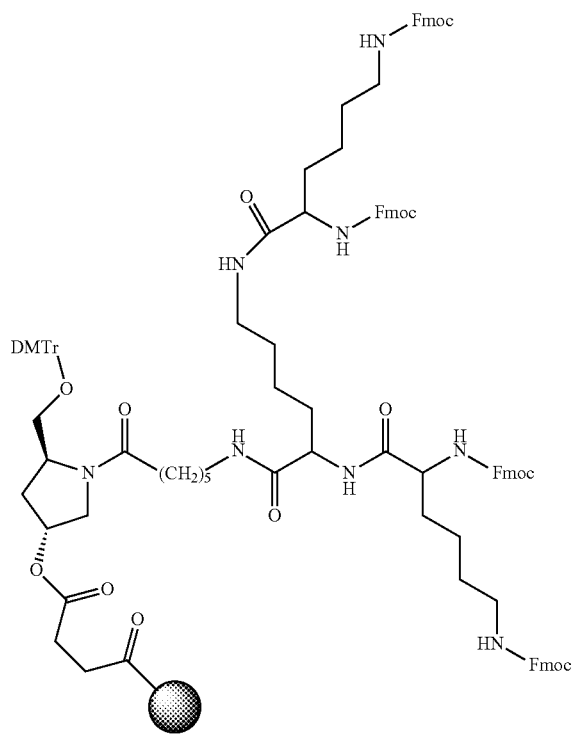
141
141 →
1. pip:DBU:DMF
   Kaiser:Positive
2. 7, HATU, DIEA, DMF
   Kaiser:Negative
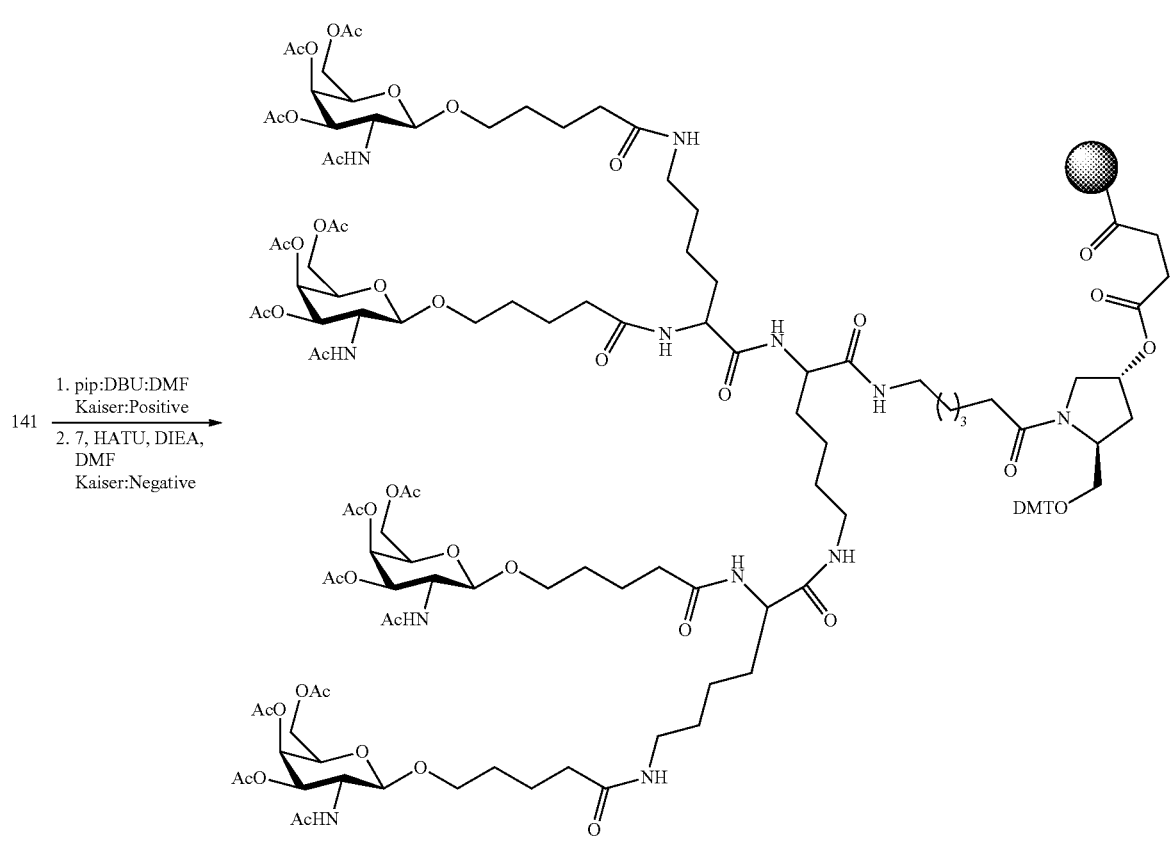
142

Synthesis of Compound 134. To a Merrifield flask was added aminomethyl VIMAD resin (2.5 g, 450 µmol/g) that was washed with acetonitrile, dimethylformamide, dichloromethane and acetonitrile. The resin was swelled in acetonitrile (4 mL). Compound 133 was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 µmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m/z 1063.8 [M+2H]$^+$.

The solid support bound compound 142 was synthesized using solid phase peptide synthesis methods.

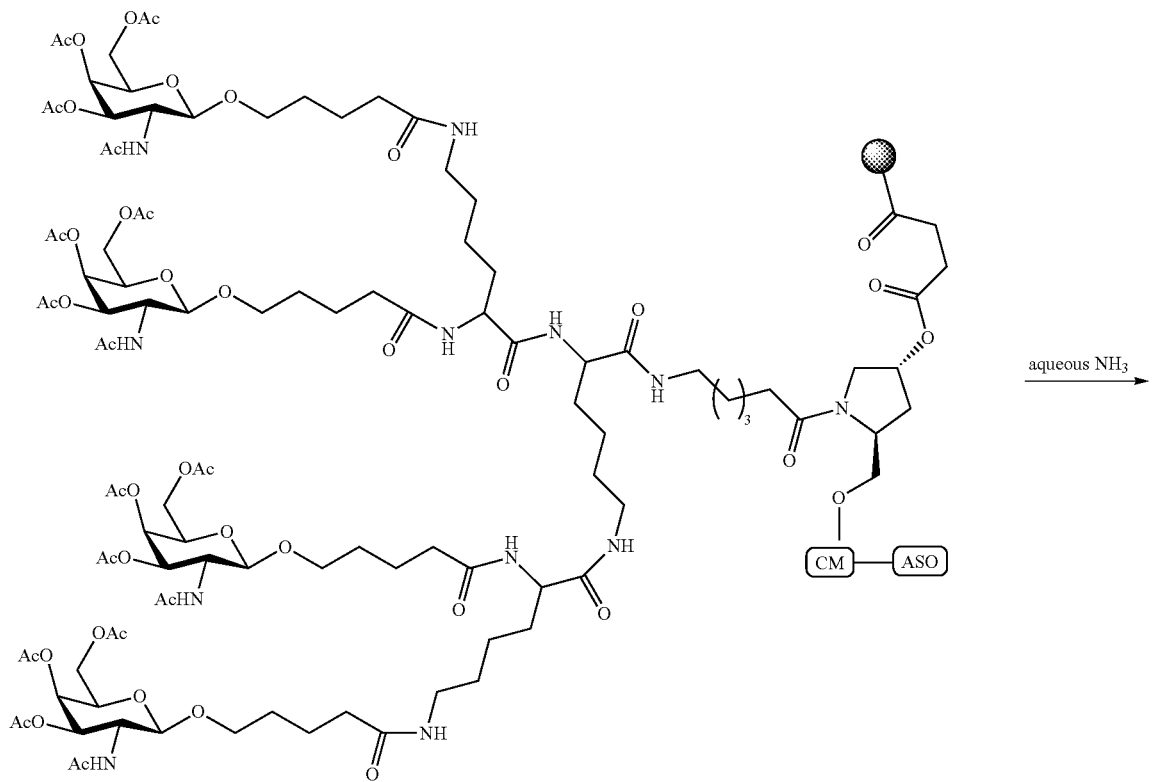

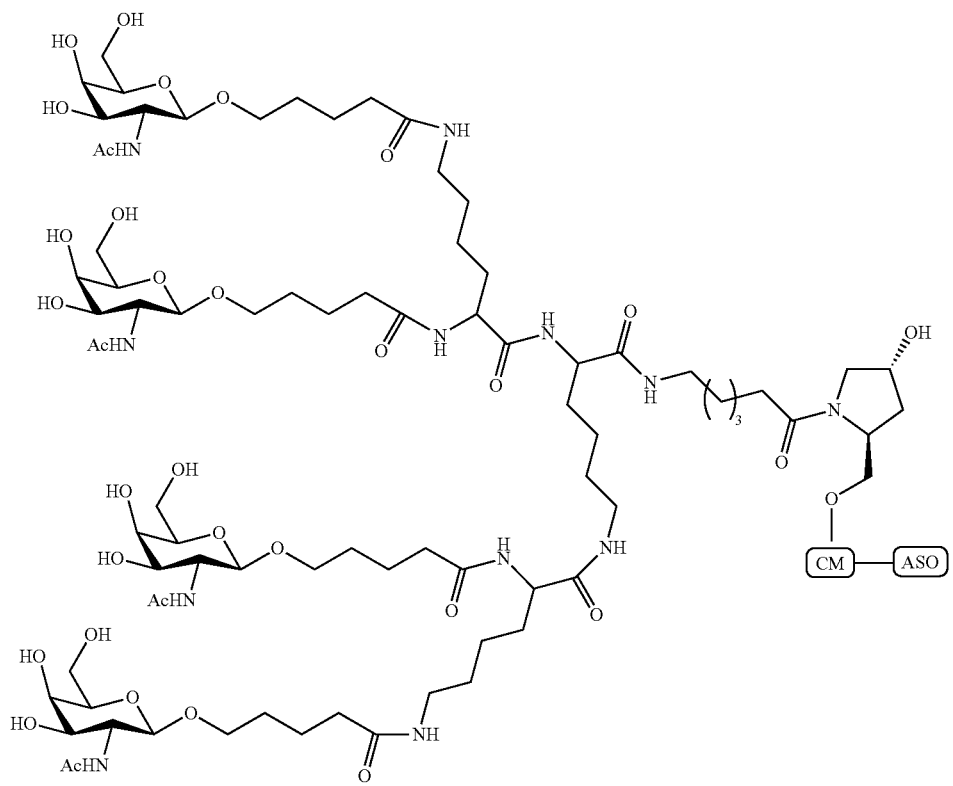

144

The solid support bound compound 143 was synthesized using standard solid phase synthesis on a DNA synthesizer.

The solid support bound compound 143 was suspended in aqueous ammonia (28-30 wt %) and heated at 55° C. for 16 h. The solution was cooled and the solid support was filtered. The filtrate was concentrated and the residue dissolved in water and purified by HPLC on a strong anion exchange column. The fractions containing full length compound 144 were pooled together and desalted. The resulting GalNAc$_4$-11 conjugated oligomeric compound was analyzed by LC-MS and the observed mass was consistent with structure.

The GalNAc$_4$ cluster portion of the conjugate group GalNAc$_4$-11 (GalNAc$_4$-11$_a$) can be combined with any cleavable moiety to provide a variety of conjugate groups. In certain embodiments, the cleavable moiety is —P(=O)(OH)-A$_d$-P(=O)(OH)—.

The structure of GalNAc$_4$-11 (GalNAc$_4$-11$_a$-CM) is shown below:

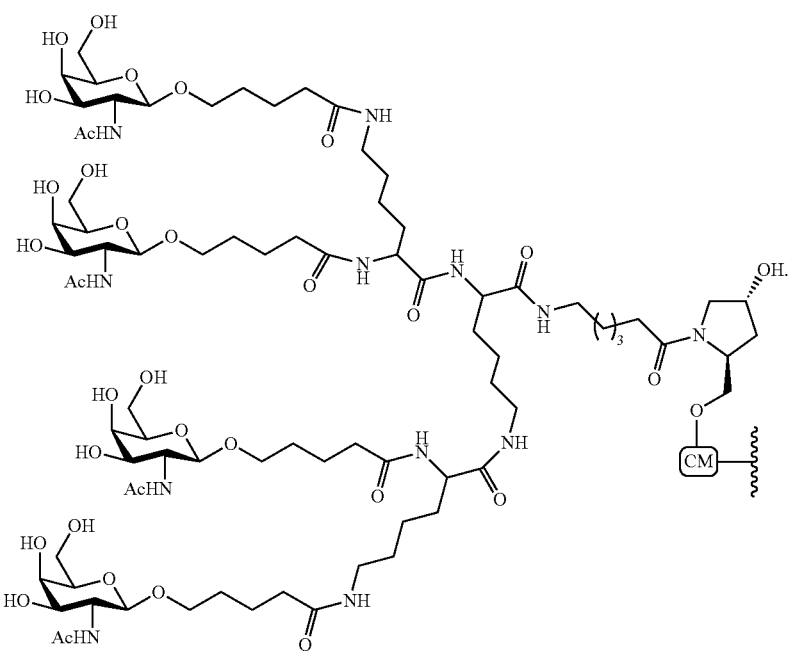
Example 51
Preparation of Oligonucleotide 155 Comprising GalNAc$_3$-6
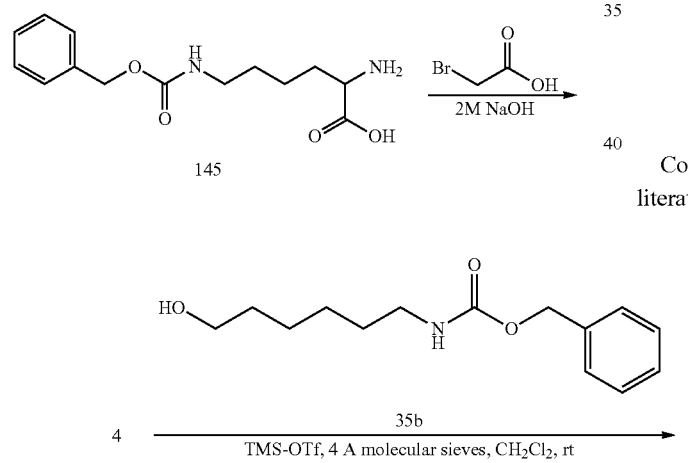
-continued
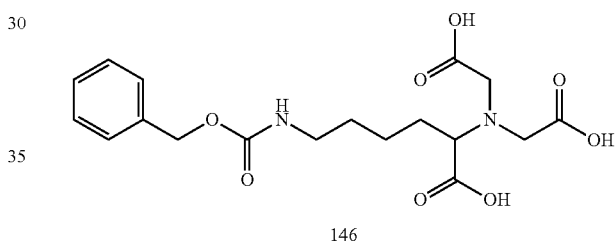
Compound 146 was synthesized as described in the literature (*Analytical Biochemistry* 1995, 229, 54-60).
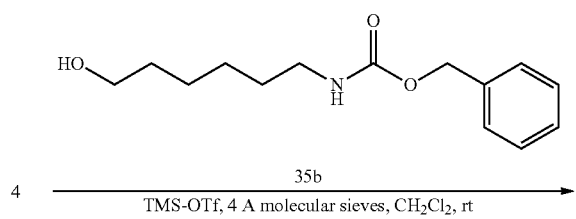
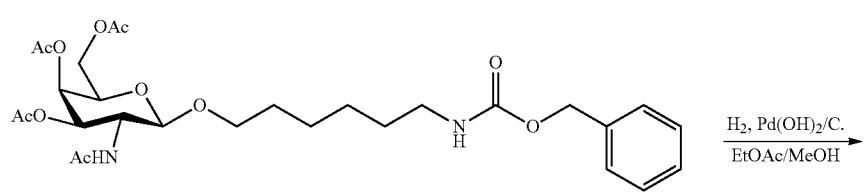

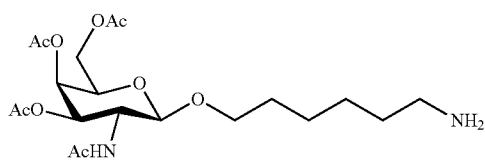

105a

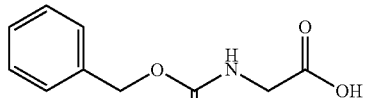

147

→ HTBU, DIEA, DMF, rt

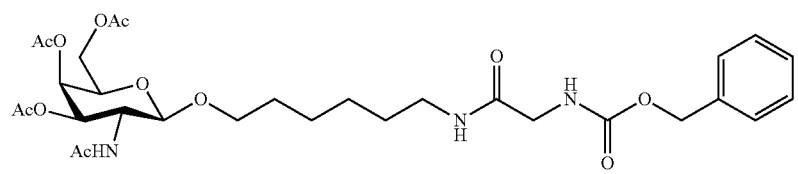

148

→ H₂, Pd(OH)₂/C., EtOAc/MeOH

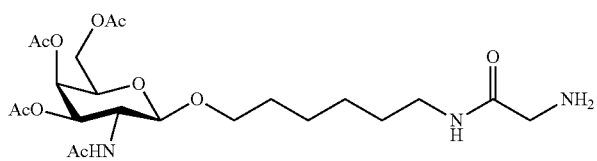

149

Compound 4 (15 g, 45.55 mmol) and compound 35b (14.3 grams, 57 mmol) were dissolved in CH$_2$Cl$_2$ (200 ml). Activated molecular sieves (4 Å. 2 g, powdered) were added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous NaHCO$_3$ (500 ml) and crushed ice (~150 g). The organic layer was separated, washed with brine, dried over MgSO$_4$, filtered, and was concentrated to an orange oil under reduced pressure. The crude material was purified by silica gel column chromatography and eluted with 2-10% MeOH in CH$_2$Cl$_2$ to yield Compound 112 (16.53 g, 63%). LCMS and $^1$H NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled through the solution for 30 minutes. Upon completion (TLC 10% MeOH in CH$_2$Cl$_2$, and LCMS), the catalyst was removed by filtration through a pad of celite. The filtrate was concentrated by rotary evaporation, and was dried briefly under high vacuum to yield Compound 105a (3.28 g). LCMS and 1H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous NaHCO$_3$ and brine. The organics phase was separated, dried (MgSO$_4$), filtered, and concentrated to an orange syrup. The crude material was purified by column chromatography 2-5% MeOH in CH$_2$Cl$_2$ to yield Compound 148 (3.44 g, 73%). LCMS and $^1$H NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

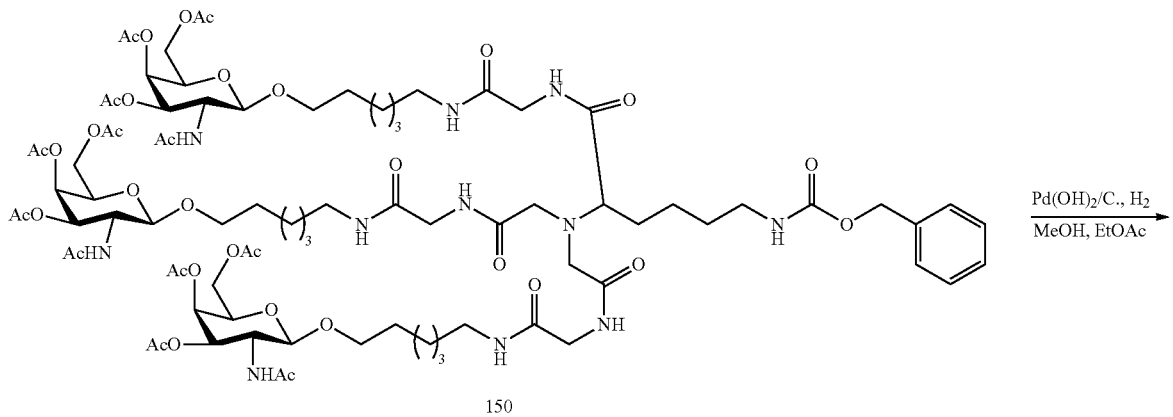

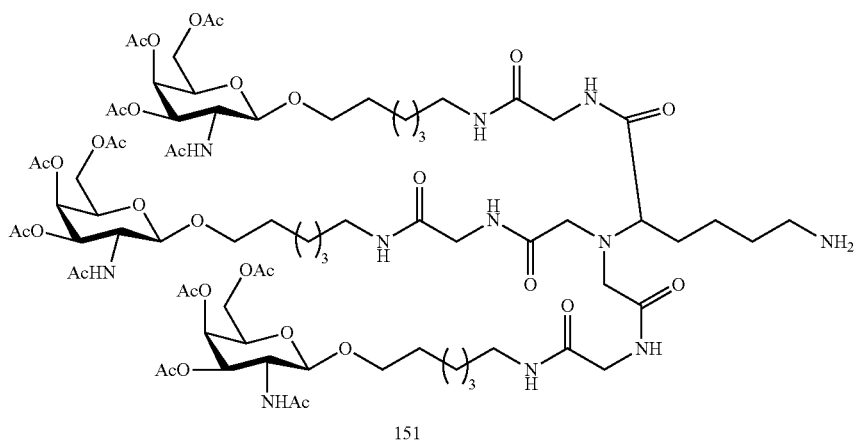

Compound 146 (0.68 g, 1.73 mmol) was dissolved in dry DMF (20 ml). To this DIEA (450 μL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous NaHCO$_3$, followed by brine. The organic phase was separated, dried over MgSO$_4$, filtered, and concentrated. The residue was purified by silica gel column chromatography and eluted with 2-10% MeOH in CH$_2$Cl$_2$ to yield Compound 150 (0.62 g, 20%). LCMS and $^1$H NMR were consistent with the desired product.

Compound 150 (0.62 g) was dissolved in 1:1 MeOH/EtOAc (5 L). The reaction mixture was purged by bubbling a stream of argon through the solution for 15 minutes. Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

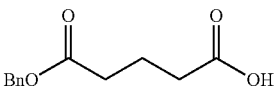

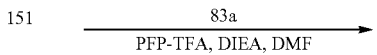

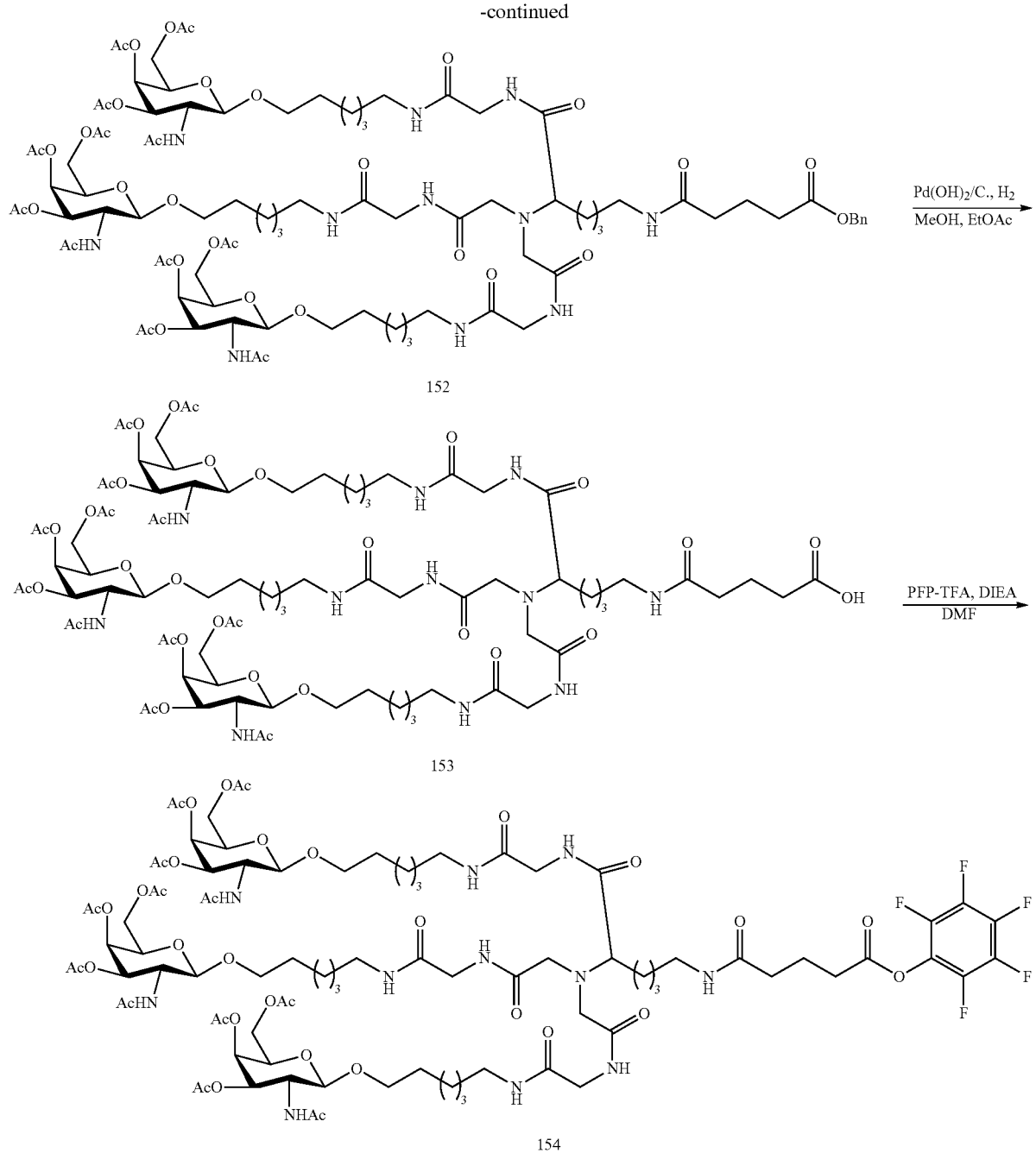

Compound 83a (0.11 g, 0.33 mmol) was dissolved in anhydrous DMF (5 mL) and N,N-Diisopropylethylamine (75 μL, 1 mmol) and PFP-TFA (90 μL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~30 min Upon completion, the majority of the solvent was removed under reduced pressure. The residue was diluted with $CH_2Cl_2$ and washed with aqueous saturated $NaHCO_3$, followed by brine. The organic phase separated, dried over $MgSO_4$, filtered, and concentrated to an orange syrup. The residue was purified by silica gel column chromatography (2-10% MeOH in $CH_2Cl_2$) to yield Compound 152 (0.35 g, 55%). LCMS and $^1H$ NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 μL, 0.37 mmol) and PFP-TFA (35 μL, 0.28 mmol) were added. The reaction mixture was stirred under nitrogen for ~30 min. The reaction mixture turned magenta upon contact, and gradually turned orange. The pH of the reaction mixture was maintained at pH=9-10 by adding more N,-Diisopropylethylamine. The progress of the reaction was monitored by TLC and LCMS. Upon completion, the majority of the solvent was removed under reduced pressure. The residue was diluted with $CH_2Cl_2$ (50 mL), and washed with saturated aqueous $NaHCO_3$, followed by brine. The organic layer was dried over $MgSO_4$, filtered, and concentrated to an orange syrup. The residue was purified by column chromatography and eluted with 2-10% MeOH in $CH_2Cl_2$ to yield Compound 154 (0.29 g, 79%). LCMS and $^1H$ NMR were consistent with the desired product.

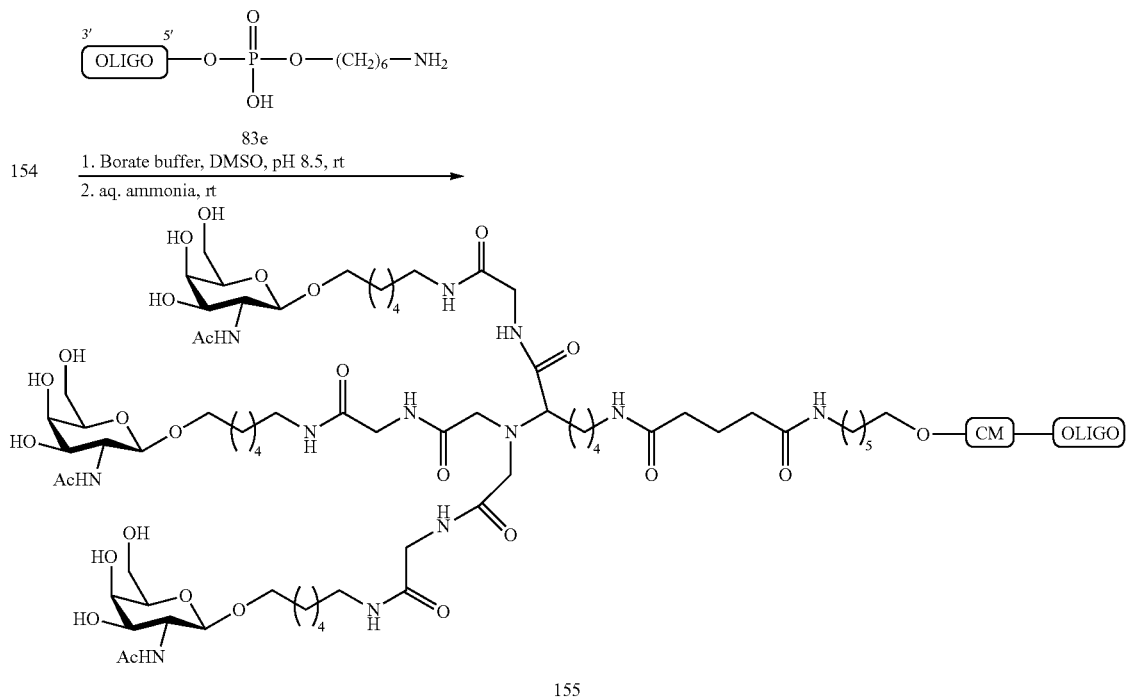

Oligomeric Compound 155, comprising a $GalNAc_3$-6 conjugate group, was prepared using the general procedures illustrated in Example 46. The $GalNAc_3$ cluster portion of the conjugate group $GalNAc_3$-6 ($GalNAc_3$-$6_a$) can be combined with any cleavable moiety to provide a variety of conjugate groups. In certain embodiments, the cleavable moiety is —P(=O)(OH)-$A_d$-P(=O)(OH)—.

The structure of $GalNAc_3$-6 ($GalNAc_3$-$6_a$-CM-) is shown below:

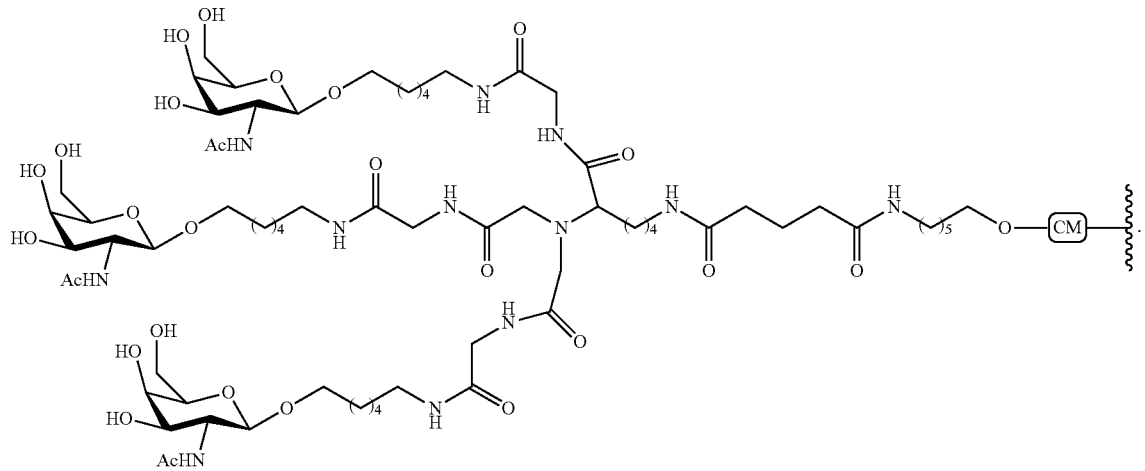

Example 52

Preparation of Oligonucleotide 160 Comprising GalNAc₃-9

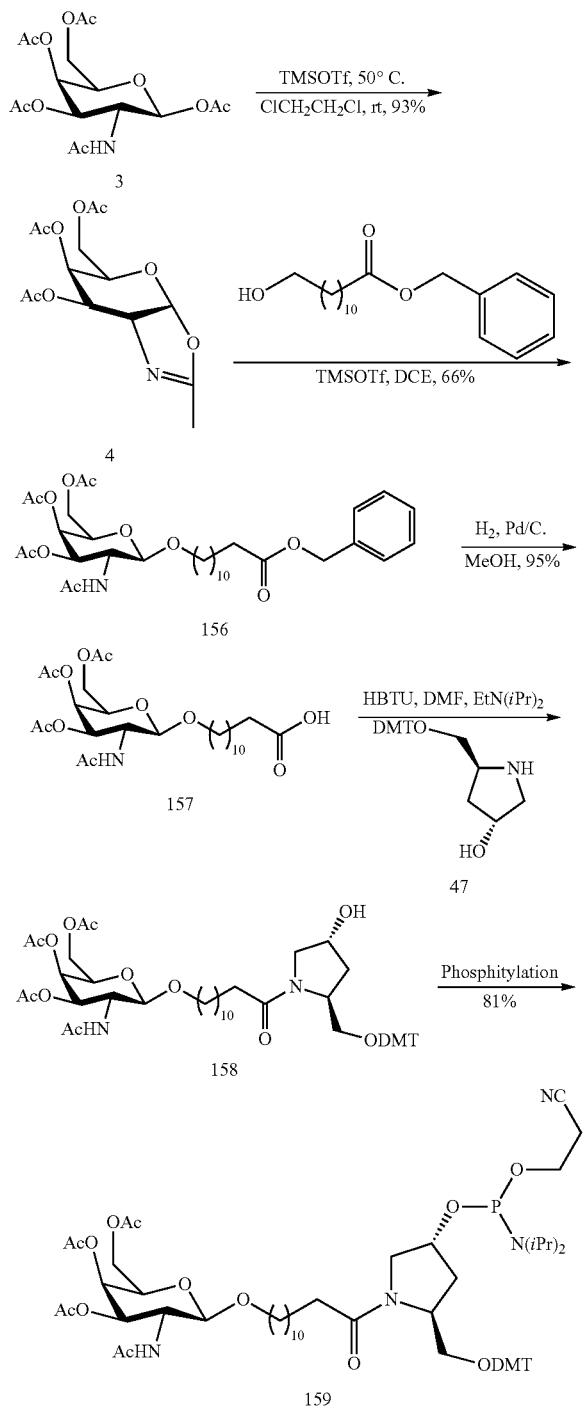

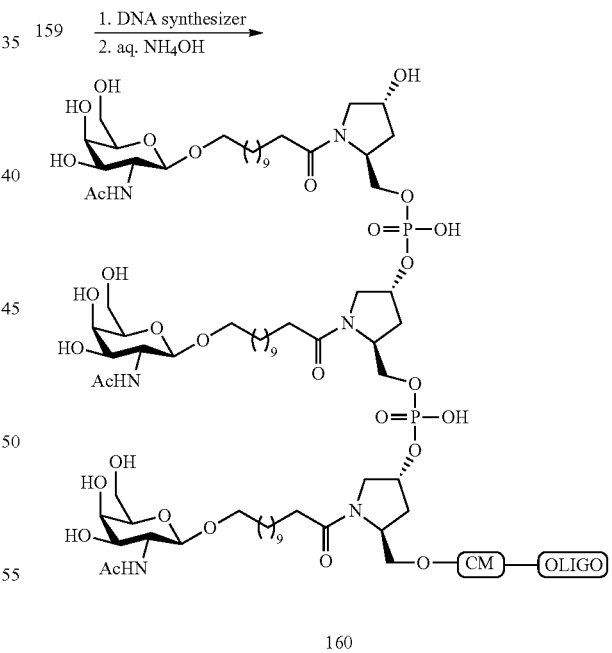

Compound 156 was synthesized following the procedure described in the literature (*J. Med. Chem.* 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m/z 544.1 [M−H]⁻.

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated NaHCO₃ aqueous solution. The mixture was extracted with ethyl acetate and the organic layer was washed with brine and dried (Na₂SO₄), filtered and evaporated. The residue obtained was purified by silica gel column chromatography and eluted with 50% ethyl acetate in hexane to yield compound 158 (8.25 g, 73.3%). The structure was confirmed by MS and ¹H NMR analysis.

Compound 158 (7.2 g, 7.61 mmol) was dried over P₂O₅ under reduced pressure. The dried compound was dissolved in anhydrous DMF (50 mL). To this 1H-tetrazole (0.43 g, 6.09 mmol) and N-methylimidazole (0.3 mL, 3.81 mmol) and 2-cyanoethyl-N,N,N',N'-tetraisopropyl phosphorodiamidite (3.65 mL, 11.50 mmol) were added. The reaction mixture was stirred t under an argon atmosphere for 4 h. The reaction mixture was diluted with ethyl acetate (200 mL). The reaction mixture was washed with saturated NaHCO₃ and brine. The organic phase was separated, dried (Na₂SO₄), filtered and evaporated. The residue was purified by silica gel column chromatography and eluted with 50-90% ethyl acetate in hexane to yield Compound 159 (7.82 g, 80.5%). The structure was confirmed by LCMS and ³¹P NMR analysis.

Oligomeric Compound 160, comprising a GalNAc₃-9 conjugate group, was prepared using standard oligonucleotide synthesis procedures. Three units of compound 159 were coupled to the solid support, followed by nucleotide phosphoramidites. Treatment of the protected oligomeric compound with aqueous ammonia yielded compound 160. The GalNAc₃ cluster portion of the conjugate group GalNAc₃-9 (GalNAc₃-9ₐ) can be combined with any cleavable moiety to provide a variety of conjugate groups. In certain embodiments, the cleavable moiety is —P(=O)(OH)-A$_d$-P(=O)(OH)—. The structure of GalNAc$_3$-9 (GalNAc$_3$-9$_a$-CM) is shown below:
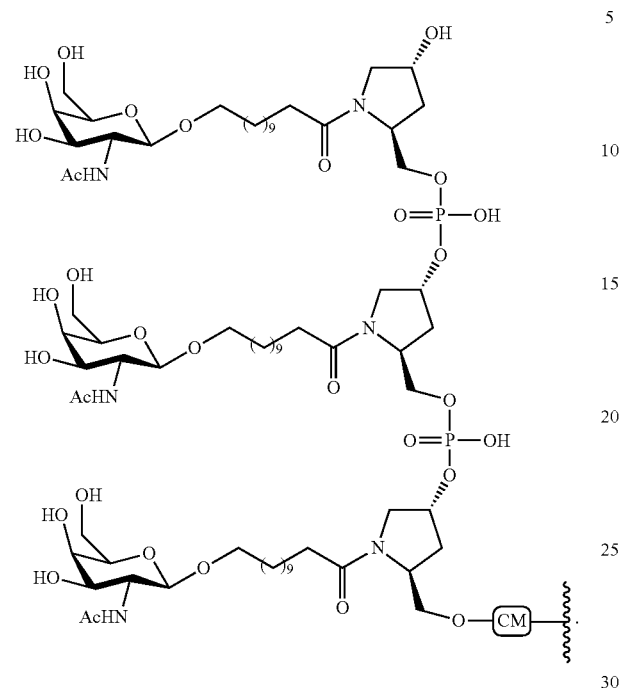
Example 53
Alternate Procedure for Preparation of Compound 18 (GalNAc$_3$-1a and GalNAc$_3$-3a)
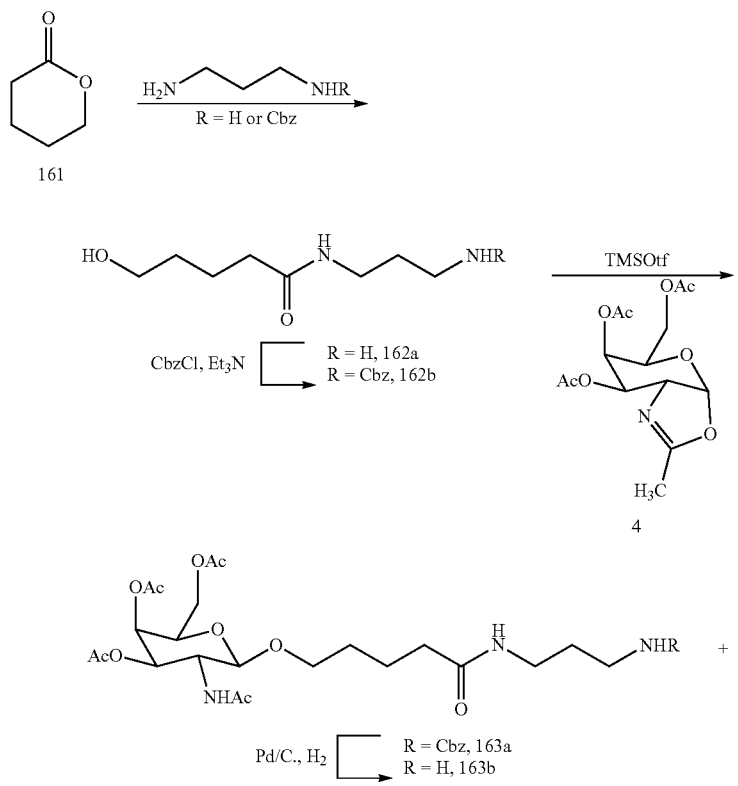

-continued

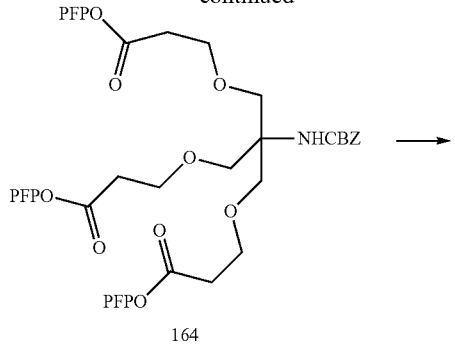
164

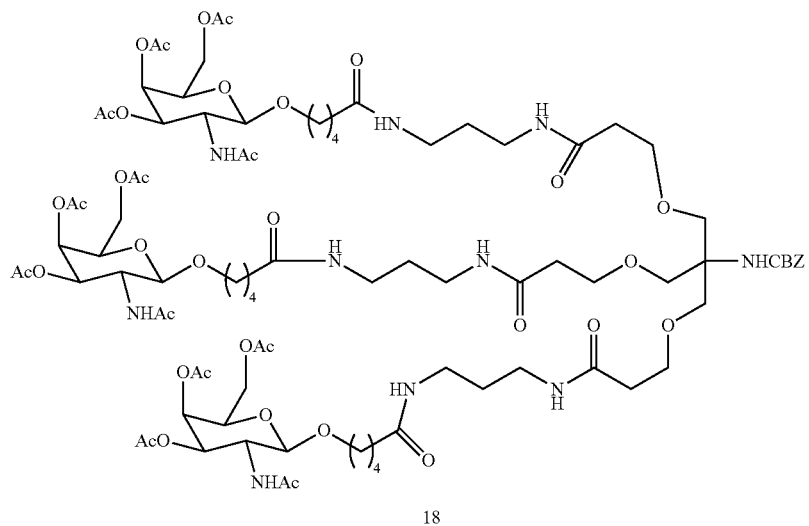
18

Lactone 161 was reacted with diamino propane (3-5 eq) or Mono-Boc protected diamino propane (1 eq) to provide alcohol 162a or 162b. When unprotected propanediamine was used for the above reaction, the excess diamine was removed by evaporation under high vacuum and the free amino group in 162a was protected using CbzCl to provide 162b as a white solid after purification by column chromatography. Alcohol 162b was further reacted with compound 4 in the presence of TMSOTf to provide 163a which was converted to 163b by removal of the Cbz group using catalytic hydrogenation. The pentafluorophenyl (PFP) ester 164 was prepared by reacting triacid 113 (see Example 48) with PFPTFA (3.5 eq) and pyridine (3.5 eq) in DMF (0.1 to 0.5 M). The triester 164 was directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 54

Alternate Procedure for Preparation of Compound 18 (GalNAc$_3$-1a and GalNAc$_3$-3a)

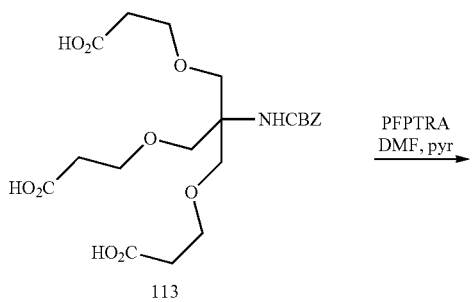
113 →[PFPTRA, DMF, pyr]

-continued

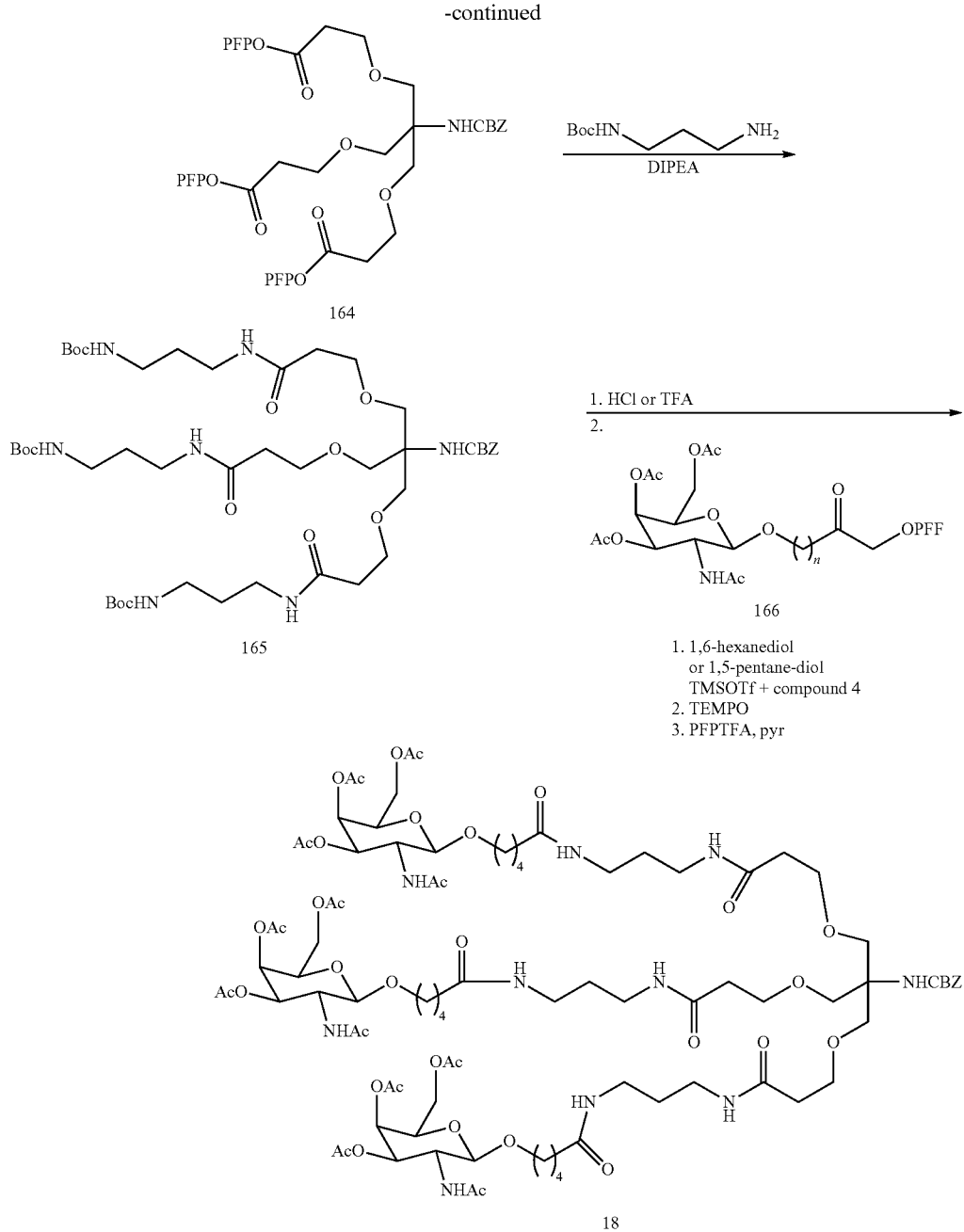

The triPFP ester 164 was prepared from acid 113 using the procedure outlined in example 53 above and reacted with mono-Boc protected diamine to provide 165 in essentially quantitative yield. The Boc groups were removed with hydrochloric acid or trifluoroacetic acid to provide the triamine which was reacted with the PFP activated acid 166 in the presence of a suitable base such as DIPEA to provide Compound 18.

The PFP protected Gal-NAc acid 166 was prepared from the corresponding acid by treatment with PFPTFA (1-1.2 eq) and pyridine (1-1.2 eq) in DMF. The precursor acid in turn was prepared from the corresponding alcohol by oxidation using TEMPO (0.2 eq) and BAIB in acetonitrile and water. The precursor alcohol was prepared from sugar intermediate 4 by reaction with 1,6-hexanediol (or 1,5-pentanediol or other diol for other n values) (2-4 eq) and TMSOTf using conditions described previously in example 47.

Example 55

Dose-Dependent Study of Oligonucleotides Comprising Either a 3' or 5'-Conjugate Group (Comparison of GalNAc$_3$-1, 3, 8 and 9) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at either the 3' or 5' terminus of the respective oligonucleotide by a phosphodiester linked 2'-deoxyadenosine nucleoside (cleavable moiety).

TABLE 26

Modified ASO targeting SRB-1

| ASO | Sequence (5' to 3') | Motif | Conjugate | SEQ ID No. |
|---|---|---|---|---|
| ISIS 353382 (parent) | $G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}T_e$ | 5/10/5 | none | 28 |
| ISIS 655861 | $G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}T_{eo}$ $A_{do}, \text{-GalNAc}_3\text{-}1_a$ | 5/10/5 | GalNAc$_3$-1 | 29 |
| ISIS 664078 | $G_{es}{}^mC_{es}T_{es}T_{es}{}^mC_{ess}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}T_e$ $A_{do}, \text{-GalNAc}_3\text{-}9_a$ | 5/10/5 | GalNAc$_3$-3 | 29 |
| ISIS 661161 | $\text{GalNAc}_3\text{-}3_a\text{-}_o, A_{do}$ $G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}T_e$ | 5/10/5 | GalNAc$_3$-3 | 30 |
| ISIS 665001 | $\text{GalNAc}_3\text{-}8_a\text{-}_o, A_{do}$ $G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}T_e$ | 5/10/5 | GalNAc$_3$-8 | 30 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-9 was shown previously in Example 52. The structure of GalNAc$_3$-3 was shown previously in Example 39. The structure of GalNAc$_3$-8 was shown previously in Example 47.

Treatment

Six week old male Balb/c mice (Jackson Laboratory, Bar Harbor, Me.) were injected subcutaneously once at the dosage shown below with ISIS 353382, 655861, 664078, 661161, 665001 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 27, treatment with antisense oligonucleotides lowered SRB-1 mRNA levels in a dose-dependent manner. Indeed, the antisense oligonucleotides comprising the phosphodiester linked GalNAc$_3$-1 and GalNAc$_3$-9 conjugates at the 3' terminus (ISIS 655861 and ISIS 664078) and the GalNAc$_3$-3 and GalNAc$_3$-8 conjugates linked at the 5' terminus (ISIS 661161 and ISIS 665001) showed substantial improvement in potency compared to the unconjugated antisense oligonucleotide (ISIS 353382). Furthermore, ISIS 664078, comprising a GalNAc$_3$-9 conjugate at the 3' terminus was essentially equipotent compared to ISIS 655861, which comprises a GalNAc$_3$-1 conjugate at the 3' terminus. The 5' conjugated antisense oligonucleotides, ISIS 661161 and ISIS 665001, comprising a GalNAc$_3$-3 or GalNAc$_3$-9, respectively, had increased potency compared to the 3' conjugated antisense oligonucleotides (ISIS 655861 and ISIS 664078).

TABLE 27

ASOs containing GalNAc$_3$-1, 3, 8 or 9 targeting SRB-1

| ISIS No. | Dosage (mg/kg) | SRB-1 mRNA (% Saline) | Conjugate |
|---|---|---|---|
| Saline | n/a | 100 | |
| 353382 | 3 | 88 | none |
| | 10 | 68 | |
| | 30 | 36 | |
| 655861 | 0.5 | 98 | GalNac$_3$-1 (3') |
| | 1.5 | 76 | |
| | 5 | 31 | |
| | 15 | 20 | |
| 664078 | 0.5 | 88 | GalNac$_3$-9 (3') |
| | 1.5 | 85 | |
| | 5 | 46 | |
| | 15 | 20 | |
| 661161 | 0.5 | 92 | GalNac$_3$-3 (5') |
| | 1.5 | 59 | |
| | 5 | 19 | |
| | 15 | 11 | |
| 665001 | 0.5 | 100 | GalNac$_3$-8 (5') |
| | 1.5 | 73 | |
| | 5 | 29 | |
| | 15 | 13 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in the table below.

TABLE 28

| ISIS No. | Dosage mg/kg | ALT | AST | Total Bilirubin | BUN | Conjugate |
|---|---|---|---|---|---|---|
| Saline | | 24 | 59 | 0.1 | 37.52 | |
| 353382 | 3 | 21 | 66 | 0.2 | 34.65 | none |
| | 10 | 22 | 54 | 0.2 | 34.2 | |
| | 30 | 22 | 49 | 0.2 | 33.72 | |
| 655861 | 0.5 | 25 | 62 | 0.2 | 30.65 | GalNac$_3$-1 (3') |
| | 1.5 | 23 | 48 | 0.2 | 30.97 | |
| | 5 | 28 | 49 | 0.1 | 32.92 | |
| | 15 | 40 | 97 | 0.1 | 31.62 | |
| 664078 | 0.5 | 40 | 74 | 0.1 | 35.3 | GalNac$_3$-9 (3') |
| | 1.5 | 47 | 104 | 0.1 | 32.75 | |
| | 5 | 20 | 43 | 0.1 | 30.62 | |
| | 15 | 38 | 92 | 0.1 | 26.2 | |
| 661161 | 0.5 | 101 | 162 | 0.1 | 34.17 | GalNac$_3$-3 (5') |
| | 1.5 g | 42 | 100 | 0.1 | 33.37 | |
| | 5 g | 23 | 99 | 0.1 | 34.97 | |
| | 15 | 53 | 83 | 0.1 | 34.8 | |
| 665001 | 0.5 | 28 | 54 | 0.1 | 31.32 | GalNac$_3$-8 (5') |
| | 1.5 | 42 | 75 | 0.1 | 32.32 | |
| | 5 | 24 | 42 | 0.1 | 31.85 | |
| | 15 | 32 | 67 | 0.1 | 31. | |

Example 56

Dose-Dependent Study of Oligonucleotides Comprising Either a 3' or 5'-Conjugate Group (Comparison of GalNAc$_3$-1, 2, 3, 5, 6, 7 and 10) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at the 5' terminus of the respective oligonucleotide by a phosphodiester linked 2'-deoxyadenosine nucleoside (cleavable moiety) except for ISIS 655861 which had the GalNAc$_3$ conjugate group attached at the 3' terminus.

TABLE 29

Modified ASO targeting SRB-1

| ASO | Sequence (5' to 3') | Motif | Conjugate | SEQ ID No. |
|---|---|---|---|---|
| ISIS 353382 (parent) | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{e}$ | 5/10/5 | no conjugate | 28 |
| ISIS 655861 | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{eo}$ GalNAc$_3$-1$_a$ | 5/10/5 | GalNAc$_3$-1 | 29 |
| ISIS 664507 | GalNAc$_3$-2$_a$-$_o$,A$_{do}$G$_{es}$$^m$ C$_{es}$T$_{es}$T$_{es}$$^m$C$_{es}$A$_{ds}$G$_{ds}$T$_{ds}$$^m$ C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_{e}$ | 5/10/5 | GalNAc$_3$-2 | 30 |
| ISIS 661161 | GalNAc$_3$-3$_a$-$_o$,A$_{do}$ G$_{es}$$^m$C$_{es}$T$_{es}$T$_{es}$$^m$C$_{es}$A$_{ds}$G$_{ds}$ T$_{ds}$mC$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{e}$ | 5/10/5 | GalNAc$_3$-3 | 30 |
| ISIS 666224 | GalNAc$_3$-5$_a$-$_o$,A$_{do}$G$_{es}$$^m$ C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{e}$ | 5/10/5 | GalNAc$_3$-5 | 30 |
| ISIS 666961 | GalNAc$_3$-6$_a$-$_o$,A$_{do}$G$_{es}$$^m$ C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{e}$ | 5/10/5 | GalNAc$_3$-6 | 30 |
| ISIS 666981 | GalNAc$_3$-7$_a$-$_o$,A$_{do}$G$_{es}$$^m$ C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{e}$ | 5/10/5 | GalNAc$_3$-7 | 30 |
| ISIS 666881 | GalNAc$_3$-10$_a$-$_o$,A$_{do}$G$_{es}$$^m$ C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_{e}$ | 5/10/5 | GalNAc$_3$-10 | 30 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-2$_a$ was shown previously in Example 37. The structure of GalNAc$_3$-3$_a$ was shown previously in Example 39. The structure of GalNAc$_3$-5$_a$ was shown previously in Example 49. The structure of GalNAc$_3$-6$_a$ was shown previously in Example 51. The structure of GalNAc$_3$-7$_a$ was shown previously in Example 48. The structure of GalNAc$_3$-10$_a$ was shown previously in Example 46.

Treatment

Six week old male Balb/c mice (Jackson Laboratory, Bar Harbor, Me.) were injected subcutaneously once at the dosage shown below with ISIS 353382, 655861, 664507, 661161, 666224, 666961, 666981, 666881 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 30, treatment with antisense oligonucleotides lowered SRB-1 mRNA levels in a dose-dependent manner Indeed, the conjugated antisense oligonucleotides showed substantial improvement in potency compared to the unconjugated antisense oligonucleotide (ISIS 353382). The 5' conjugated antisense oligonucleotides showed a slight increase in potency compared to the 3' conjugated antisense oligonucleotide.

TABLE 30

| ISIS No. | Dosage (mg/kg) | SRB-1 mRNA (% Saline) | Conjugate |
|---|---|---|---|
| Saline | n/a | 100.0 | |
| 353382 | 3 | 96.0 | none |
| | 10 | 73.1 | |
| | 30 | 36.1 | |
| 655861 | 0.5 | 99.4 | GalNac$_3$-1 (3') |
| | 1.5 | 81.2 | |
| | 5 | 33.9 | |
| | 15 | 15.2 | |
| 664507 | 0.5 | 102.0 | GalNac$_3$-2 (5') |
| | 1.5 | 73.2 | |
| | 5 | 31.3 | |
| | 15 | 10.8 | |
| 661161 | 0.5 | 90.7 | GalNac$_3$-3 (5') |
| | 1.5 | 67.6 | |
| | 5 | 24.3 | |
| | 15 | 11.5 | |
| 666224 | 0.5 | 96.1 | GalNac$_3$-5 (5') |
| | 1.5 | 61.6 | |
| | 5 | 25.6 | |
| | 15 | 11.7 | |
| 666961 | 0.5 | 85.5 | GalNac$_3$-6 (5') |
| | 1.5 | 56.3 | |
| | 5 | 34.2 | |
| | 15 | 13.1 | |
| 666981 | 0.5 | 84.7 | GalNac$_3$-7 (5') |
| | 1.5 | 59.9 | |
| | 5 | 24.9 | |
| | 15 | 8.5 | |
| 666881 | 0.5 | 100.0 | GalNac$_3$-10 (5') |
| | 1.5 | 65.8 | |
| | 5 | 26.0 | |
| | 15 | 13.0 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 31 below.

TABLE 31

| ISIS No. | Dosage mg/kg | ALT | AST | Total Bilirubin | BUN | Conjugate |
|---|---|---|---|---|---|---|
| Saline | | 26 | 57 | 0.2 | 27 | |
| 353382 | 3 | 25 | 92 | 0.2 | 27 | none |
| | 10 | 23 | 40 | 0.2 | 25 | |
| | 30 | 29 | 54 | 0.1 | 28 | |
| 655861 | 0.5 | 25 | 71 | 0.2 | 34 | GalNac$_3$-1 (3') |
| | 1.5 | 28 | 60 | 0.2 | 26 | |
| | 5 | 26 | 63 | 0.2 | 28 | |
| | 15 | 25 | 61 | 0.2 | 28 | |
| 664507 | 0.5 | 25 | 62 | 0.2 | 25 | GalNac$_3$-2 (5') |
| | 1.5 | 24 | 49 | 0.2 | 26 | |
| | 5 | 21 | 50 | 0.2 | 26 | |
| | 15 | 59 | 84 | 0.1 | 22 | |
| 661161 | 0.5 | 20 | 42 | 0.2 | 29 | GalNac$_3$-3 (5') |
| | 1.5 g | 37 | 74 | 0.2 | 25 | |
| | 5 g | 28 | 61 | 0.2 | 29 | |
| | 15 | 21 | 41 | 0.2 | 25 | |
| 666224 | 0.5 | 34 | 48 | 0.2 | 21 | GalNac$_3$-5 (5') |
| | 1.5 | 23 | 46 | 0.2 | 26 | |
| | 5 | 24 | 47 | 0.2 | 23 | |
| | 15 | 32 | 49 | 0.1 | 26 | |
| 666961 | 0.5 | 17 | 63 | 0.2 | 26 | GalNac$_3$-6 (5') |
| | 1.5 | 23 | 68 | 0.2 | 26 | |
| | 5 | 25 | 66 | 0.2 | 26 | |
| | 15 | 29 | 107 | 0.2 | 28 | |
| 666981 | 0.5 | 24 | 48 | 0.2 | 26 | GalNac$_3$-7 (5') |
| | 1.5 | 30 | 55 | 0.2 | 24 | |

TABLE 31-continued

| ISIS No. | Dosage mg/kg | ALT | AST | Total Bilirubin | BUN | Conjugate |
|---|---|---|---|---|---|---|
| | 5 | 46 | 74 | 0.1 | 24 | |
| | 15 | 29 | 58 | 0.1 | 26 | |
| 666881 | 0.5 | 20 | 65 | 0.2 | 27 | GalNac$_3$-10 (5') |
| | 1.5 | 23 | 59 | 0.2 | 24 | |
| | 5 | 45 | 70 | 0.2 | 26 | |
| | 15 | 21 | 57 | 0.2 | 24 | |

Example 57

Duration of Action Study of Oligonucleotides Comprising a 3'-Conjugate Group Targeting ApoC III In Vivo Mice were injected once with the doses indicated below and monitored over the course of 42 days for ApoC-III and plasma triglycerides (Plasma TG) levels. The study was performed using 3 transgenic mice that express human APOC-III in each group.

TABLE 32

| Modified ASO targeting ApoC III | | | |
|---|---|---|---|
| ASO | Sequence (5' to 3') | Linkages | SEQ ID No. |
| ISIS 304801 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_{e}$ | PS | 20 |
| ISIS 647535 | A$_{es}$G$_{es}$$^m$C$_{es}$T$_{es}$T$_{es}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{es}$T$_{es}$T$_{es}$A$_{es}$T$_{eo}$A$_{do}$, -GalNAc$_3$-1$_a$ | PS | 21 |
| ISIS 647536 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{eo}$T$_{eo}$T$_{eo}$A$_{es}$T$_{eo}$A$_{do}$, -GalNAc$_3$-1$_a$ | PO/PS | 21 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9.

TABLE 33

| ApoC III mRNA (% Saline on Day 1) and Plasma TG Levels (% Saline on Day 1) | | | | | | | |
|---|---|---|---|---|---|---|---|
| ASO | Dose | Target | Day 3 | Day 7 | Day 14 | Day 35 | Day 42 |
| Saline | 0 mg/kg | ApoC-III | 98 | 100 | 100 | 95 | 116 |
| ISIS 304801 | 30 mg/kg | ApoC-III | 28 | 30 | 41 | 65 | 74 |
| ISIS 647535 | 10 mg/kg | ApoC-III | 16 | 19 | 25 | 74 | 94 |
| ISIS 647536 | 10 mg/kg | ApoC-III | 18 | 16 | 17 | 35 | 51 |
| Saline | 0 mg/kg | Plasma TG | 121 | 130 | 123 | 105 | 109 |
| ISIS 304801 | 30 mg/kg | Plasma TG | 34 | 37 | 50 | 69 | 69 |
| ISIS 647535 | 10 mg/kg | Plasma TG | 18 | 14 | 24 | 18 | 71 |
| ISIS 647536 | 10 mg/kg | Plasma TG | 21 | 19 | 15 | 32 | 35 |

As can be seen in the table above the duration of action increased with addition of the 3'-conjugate group compared to the unconjugated oligonucleotide. There was a further increase in the duration of action for the conjugated mixed PO/PS oligonucleotide 647536 as compared to the conjugated full PS oligonucleotide 647535.

Example 58

Dose-Dependent Study of Oligonucleotides Comprising a 3'-Conjugate Group (Comparison of GalNAc$_3$-1 and GalNAc$_4$-11) Targeting SRB-1 In Vivo The oligonucleotides listed below were tested in a dose-dependent study for antisense inhibition of SRB-1 in mice. Unconjugated ISIS 440762 was included as an unconjugated standard. Each of the conjugate groups were attached at the 3' terminus of the respective oligonucleotide by a phosphodiester linked 2'-deoxyadenosine nucleoside cleavable moiety.

The structure of GalNAc$_3$-1$_a$ was shown previously in Example 9. The structure of GalNAc$_3$-11$_a$ was shown previously in Example 50.

Treatment

Six week old male Balb/c mice (Jackson Laboratory, Bar Harbor, Me.) were injected subcutaneously once at the dosage shown below with ISIS 440762, 651900, 663748 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 34, treatment with antisense oligonucleotides lowered SRB-1 mRNA levels in a dose-dependent manner. The antisense oligonucleotides comprising the phosphodiester linked GalNAc$_3$-1 and GalNAc$_4$-11 conjugates at the 3' terminus (ISIS 651900 and ISIS 663748) showed substantial improvement in potency compared to the unconjugated antisense oligonucleotide (ISIS 440762). The two conjugated oligonucleotides, GalNAc$_3$-1 and GalNAc$_4$-11, were equipotent.

TABLE 34

Modified ASO targeting SRB-1

| ASO | Sequence (5' to 3') | Dose mg/kg | % Saline control | SEQ ID No. |
|---|---|---|---|---|
| Saline | | | 100 | |
| ISIS 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | 0.6 | 73.45 | 22 |
| | | 2 | 59.66 | |
| | | 6 | 23.50 | |
| ISIS 651900 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$A$_{do}$, -GalNAc$_3$-1$_a$ | 0.2 | 62.75 | 23 |
| | | 0.6 | 29.14 | |
| | | 2 | 8.61 | |
| | | 6 | 5.62 | |
| ISIS 663748 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$A$_{do}$, -GalNAc$_4$-11$_a$ | 0.2 | 63.99 | 23 |
| | | 0.6 | 33.53 | |
| | | 2 | 7.58 | |
| | | 6 | 5.52 | |

Capital letters indicate the nucleobase for each nucleoside and $^m$C indicates a 5-methyl cytosine. Subscripts: "e" indicates a 2'-MOE modified nucleoside; "k" indicates 6'-(S)—CH$_3$ bicyclic nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 35 below.

TABLE 35

| ISIS No. | Dosage mg/kg | ALT | AST | Total Bilirubin | BUN | Conjugate |
|---|---|---|---|---|---|---|
| Saline | | 30 | 76 | 0.2 | 40 | |
| 440762 | 0.60 | 32 | 70 | 0.1 | 35 | none |
| | 2 | 26 | 57 | 0.1 | 35 | |
| | 6 | 31 | 48 | 0.1 | 39 | |
| 651900 | 0.2 | 32 | 115 | 0.2 | 39 | GalNAc$_3$-1 (3') |
| | 0.6 | 33 | 61 | 0.1 | 35 | |
| | 2 | 30 | 50 | 0.1 | 37 | |
| | 6 | 34 | 52 | 0.1 | 36 | |
| 663748 | 0.2 | 28 | 56 | 0.2 | 36 | GalNAc$_4$-11 (3') |
| | 0.6 | 34 | 60 | 0.1 | 35 | |
| | 2 | 44 | 62 | 0.1 | 36 | |
| | 6 | 38 | 71 | 0.1 | 33 | |

Example 59

Effects of GalNAc$_3$-1 Conjugated ASOs Targeting FXI In Vivo

The oligonucleotides listed below were tested in a multiple dose study for antisense inhibition of FXI in mice. ISIS 404071 was included as an unconjugated standard. Each of the conjugate groups was attached at the 3' terminus of the respective oligonucleotide by a phosphodiester linked 2'-deoxyadenosine nucleoside cleavable moiety.

TABLE 36

Modified ASOs targeting FXI

| ASO | Sequence (5' to 3') | Linkages | SEQ ID No. |
|---|---|---|---|
| ISIS 404071 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{es}$G$_{es}$A$_{es}$G$_{e}$ | PS | 31 |
| ISIS 656172 | T$_{es}$G$_{es}$G$_{es}$T$_{es}$A$_{es}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{es}$G$_{es}$A$_{es}$G$_{es}$G$_{e}$A$_{do}$, -GalNAc$_3$-1$_a$ | PS | 32 |
| ISIS 656173 | T$_{es}$G$_{eo}$G$_{eo}$T$_{eo}$A$_{eo}$A$_{ds}$T$_{ds}$$^m$C$_{ds}$$^m$C$_{ds}$A$_{ds}$$^m$C$_{ds}$T$_{ds}$T$_{ds}$T$_{ds}$$^m$C$_{ds}$A$_{eo}$G$_{eo}$A$_{es}$G$_{es}$G$_{e}$A$_{do}$, -GalNAc$_3$-1$_a$ | PO/PS | 32 |

Capital letters indicate the nucleobase for each nucleoside and $^m$C indicates a 5-methyl cytosine.

Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9.

Treatment

Six week old male Balb/c mice (Jackson Laboratory, Bar Harbor, Me.) were injected subcutaneously twice a week for 3 weeks at the dosage shown below with ISIS 404071, 656172, 656173 or with PBS treated control. Each treatment group consisted of 4 animals. The mice were sacrificed 72 hours following the final administration to determine the liver FXI mRNA levels using real-time PCR and RIBOGREEN® RNA quantification reagent (Molecular Probes, Inc. Eugene, Oreg.) according to standard protocols. Plasma FXI protein levels were also measured using ELISA. FXI mRNA levels were determined relative to total RNA (using RIBOGREEN®), prior to normalization to PBS-treated control. The results below are presented as the average percent of FXI mRNA levels for each treatment group. The data was normalized to PBS-treated control and is denoted as "% PBS". The $ED_{50}$s were measured using similar methods as described previously and are presented below.

TABLE 37

Factor XI mRNA (% Saline)

| ASO | Dose mg/kg | % Control | Conjugate | Linkages |
|---|---|---|---|---|
| Saline | | 100 | none | |
| ISIS 404071 | 3 | 92 | none | PS |
| | 10 | 40 | | |
| | 30 | 15 | | |
| ISIS 656172 | 0.7 | 74 | GalNac₃-1 | PS |
| | 2 | 33 | | |
| | 6 | 9 | | |
| ISIS 656173 | 0.7 | 49 | GalNac₃-1 | PO/PS |
| | 2 | 22 | | |
| | 6 | 1 | | |

TABLE 37a

Factor XI protein (% Saline)

| ASO | Dose mg/kg | Protein (% Control) | Conjugate | Linkages |
|---|---|---|---|---|
| Saline | | 100 | none | |
| ISIS 404071 | 3 | 127 | none | PS |
| | 10 | 32 | | |
| | 30 | 3 | | |
| ISIS 656172 | 0.7 | 70 | GalNac₃-1 | PS |
| | 2 | 23 | | |
| | 6 | 1 | | |
| ISIS 656173 | 0.7 | 45 | GalNac₃-1 | PO/PS |
| | 2 | 6 | | |
| | 6 | 0 | | |

Liver transaminase levels, alanine aminotransferase (ALT) and aspartate aminotransferase (AST), in serum were measured relative to saline injected mice using standard protocols. Total bilirubin, total albumin, CRE and BUN were also evaluated. The change in body weights was evaluated with no significant change from the saline group. ALTs, ASTs, total bilirubin and BUN values are shown in the table below.

TABLE 38

| ISIS No. | Dosage mg/kg | ALT | AST | Total Albumin | Total Bilirubin | CRE | BUN | Conjugate |
|---|---|---|---|---|---|---|---|---|
| Saline | | 71.8 | 84.0 | 3.1 | 0.2 | 0.2 | 22.9 | |
| 404071 | 3 | 152.8 | 176.0 | 3.1 | 0.3 | 0.2 | 23.0 | none |
| | 10 | 73.3 | 121.5 | 3.0 | 0.2 | 0.2 | 21.4 | |
| | 30 | 82.5 | 92.3 | 3.0 | 0.2 | 0.2 | 23.0 | |
| 656172 | 0.7 | 62.5 | 111.5 | 3.1 | 0.2 | 0.2 | 23.8 | GalNac₃-1 (3') |
| | 2 | 33.0 | 51.8 | 2.9 | 0.2 | 0.2 | 22.0 | |
| | 6 | 65.0 | 71.5 | 3.2 | 0.2 | 0.2 | 23.9 | |
| 656173 | 0.7 | 54.8 | 90.5 | 3.0 | 0.2 | 0.2 | 24.9 | GalNac₃-1 (3') |
| | 2 | 85.8 | 71.5 | 3.2 | 0.2 | 0.2 | 21.0 | |
| | 6 | 114.0 | 101.8 | 3.3 | 0.2 | 0.2 | 22.7 | |

As illustrated in Table 37, treatment with antisense oligonucleotides lowered FXI mRNA levels in a dose-dependent manner. The oligonucleotides comprising a 3'-GalNAc₃-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

As illustrated in Table 37a, treatment with antisense oligonucleotides lowered FXI protein levels in a dose-dependent manner. The oligonucleotides comprising a 3'-GalNAc₃-1 conjugate group showed substantial improvement in potency compared to the unconjugated antisense oligonucleotide (ISIS 404071). Between the two conjugated oligonucleotides an improvement in potency was further provided by substituting some of the PS linkages with PO (ISIS 656173).

Example 60

Effects of Conjugated ASOs Targeting SRB-1 In Vitro

The oligonucleotides listed below were tested in a multiple dose study for antisense inhibition of SRB-1 in primary mouse hepatocytes. ISIS 353382 was included as an unconjugated standard. Each of the conjugate groups were attached at the 3' or 5' terminus of the respective oligonucleotide by a phosphodiester linked 2'-deoxyadenosine nucleoside cleavable moiety.

TABLE 39

Modified ASO targeting SRB-1

| ASO | Sequence (5' to 3') | Motif | Conjugate | SEQ ID No. |
|---|---|---|---|---|
| ISIS 353382 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | 5/10/5 | none | 28 |

TABLE 39-continued

Modified ASO targeting SRB-1

| ASO | Sequence (5' to 3') | Motif | Conjugate | SEQ ID No. |
|---|---|---|---|---|
| ISIS 655861 | $G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}$ $T_{eo}\mathbf{A_{do}},\mathbf{-GalNAc_3-1_a}$ | 5/10/5 | GalNAc$_3$-1 | 29 |
| ISIS 655862 | $G_{es}{}^mC_{eo}T_{eo}T_{eo}{}^mC_{eo}A_{ds}G_{ds}$ $T_{ds}{}^mC_{ds}A_{ds}T_{ds}G_{ds}A_{ds}{}^mC_{ds}$ $T_{ds}T_{eo}{}^mC_{eo}{}^mC_{es}T_{es}$ $T_{eo}\mathbf{A_{do}},\mathbf{-GalNAc_3-1_a}$ | 5/10/5 | GalNAc$_3$-1 | 29 |
| ISIS 661161 | $\mathbf{GalNAc_3\text{-}3_{a\text{-}o}},\mathbf{A_{do}}G_{es}$ ${}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}T_e$ | 5/10/5 | GalNAc$_3$-3 | 30 |
| ISIS 665001 | $\mathbf{GalNAc_3\text{-}8_{a\text{-}o}},\mathbf{A_{do}}G_{es}$ ${}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}$ $T_{es}{}^mC_{es}{}^mC_{es}T_{es}T_e$ | 5/10/5 | GalNAc$_3$-8 | 30 |
| ISIS 664078 | $G_{es}{}^mC_{es}T_{es}T_{es}{}^mC_{es}A_{ds}G_{ds}$ $T_{ds}{}^mC_{ds}A_{ds}T_{ds}G_{ds}A_{ds}{}^mC_{ds}$ $T_{ds}T_{es}{}^mC_{es}{}^mC_{es}T_{es}$ $T_{eo}\mathbf{A_{do}},\mathbf{-GalNAc_3-9_a}$ | 5/10/5 | GalNAc$_3$-9 | 29 |
| ISIS 666961 | $\mathbf{GalNAc_3\text{-}6_{a\text{-}o}},\mathbf{A_{do}}G_{es}$ ${}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}$ $T_{es}{}^mC_{es}{}^mC_{es}T_{es}T_e$ | 5/10/5 | GalNAc$_3$-6 | 30 |
| ISIS 664507 | $\mathbf{GalNAc_3\text{-}2_{a\text{-}o}},\mathbf{A_{do}}G_{es}$ ${}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}$ $T_{es}{}^mC_{es}{}^mC_{es}T_{es}T_e$ | 5/10/5 | GalNAc$_3$-2 | 30 |
| ISIS 666881 | $\mathbf{GalNAc_3\text{-}10_{a\text{-}o}},\mathbf{A_{do}}G_{es}$ ${}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}$ $T_{es}{}^mC_{es}{}^mC_{es}T_{es}T_e$ | 5/10/5 | GalNAc$_3$-10 | 30 |
| ISIS 666224 | $\mathbf{GalNAc_3\text{-}5_{a\text{-}o}},\mathbf{A_{do}}G_{es}$ ${}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}$ $T_{es}{}^mC_{es}{}^mC_{es}T_{es}T_e$ | 5/10/5 | GalNAc$_3$-5 | 30 |
| ISIS 666981 | $\mathbf{GalNAc_3\text{-}7_{a\text{-}o}},\mathbf{A_{do}}G_{es}$ ${}^mC_{es}T_{es}T_{es}{}^mC_{es}A_{ds}G_{ds}T_{ds}$ ${}^mC_{ds}A_{ds}T_{ds}G_{ds}A_{ds}{}^mC_{ds}T_{ds}$ $T_{es}{}^mC_{es}{}^mC_{es}T_{es}T_e$ | 5/10/5 | GalNAc$_3$-7 | 30 |

Capital letters indicate the nucleobase for each nucleoside and $^mC$ indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-1$_a$ was shown previously in Example 9. The structure of GalNAc$_3$-3a was shown previously in Example 39. The structure of GalNAc$_3$-8a was shown previously in Example 47. The structure of GalNAc$_3$-9a was shown previously in Example 52. The structure of GalNAc$_3$-6a was shown previously in Example 51. The structure of GalNAc$_3$-2a was shown previously in Example 37. The structure of GalNAc$_3$-10a was shown previously in Example 46. The structure of GalNAc$_3$-5a was shown previously in Example 49. The structure of GalNAc$_3$-7a was shown previously in Example 48.

Treatment

The oligonucleotides listed above were tested in vitro in primary mouse hepatocyte cells plated at a density of 25,000 cells per well and treated with 0.03, 0.08, 0.24, 0.74, 2.22, 6.67 or 20 nM modified oligonucleotide. After a treatment period of approximately 16 hours, RNA was isolated from the cells and mRNA levels were measured by quantitative real-time PCR and the SRB-1 mRNA levels were adjusted according to total RNA content, as measured by RIBOGREEN®.

The IC$_{50}$ was calculated using standard methods and the results are presented in Table 40. The results show that, under free uptake conditions in which no reagents or electroporation techniques are used to artificially promote entry of the oligonucleotides into cells, the oligonucleotides comprising a GalNAc conjugate were significantly more potent in hepatocytes than the parent oligonucleotide (ISIS 353382) that does not comprise a GalNAc conjugate.

TABLE 40

| ASO | IC$_{50}$ (nM) | Internucleoside linkages | Conjugate | SEQ ID No. |
|---|---|---|---|---|
| ISIS 353382 | 190$^a$ | PS | none | 28 |
| ISIS 655861 | 11$^a$ | PS | GalNac$_3$-1 | 29 |
| ISIS 655862 | 3 | PO/PS | GalNac$_3$-1 | 29 |
| ISIS 661161 | 15$^a$ | PS | GalNac$_3$-3 | 30 |
| ISIS 665001 | 20 | PS | GalNac$_3$-8 | 30 |
| ISIS 664078 | 55 | PS | GalNac$_3$-9 | 29 |
| ISIS 666961 | 22$^a$ | PS | GalNac$_3$-6 | 30 |
| ISIS 664507 | 30 | PS | GalNac$_3$-2 | 30 |
| ISIS 666881 | 30 | PS | GalNac$_3$-10 | 30 |
| ISIS 666224 | 30$^a$ | PS | GalNac$_3$-5 | 30 |
| ISIS 666981 | 40 | PS | GalNac$_3$-7 | 30 |

$^a$Average of multiple runs.

Example 61

Preparation of Oligomeric Compound 175 Comprising GalNAc$_3$-12

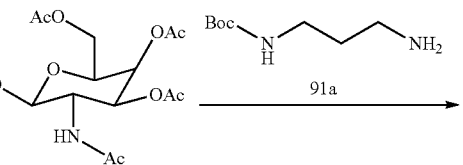

166

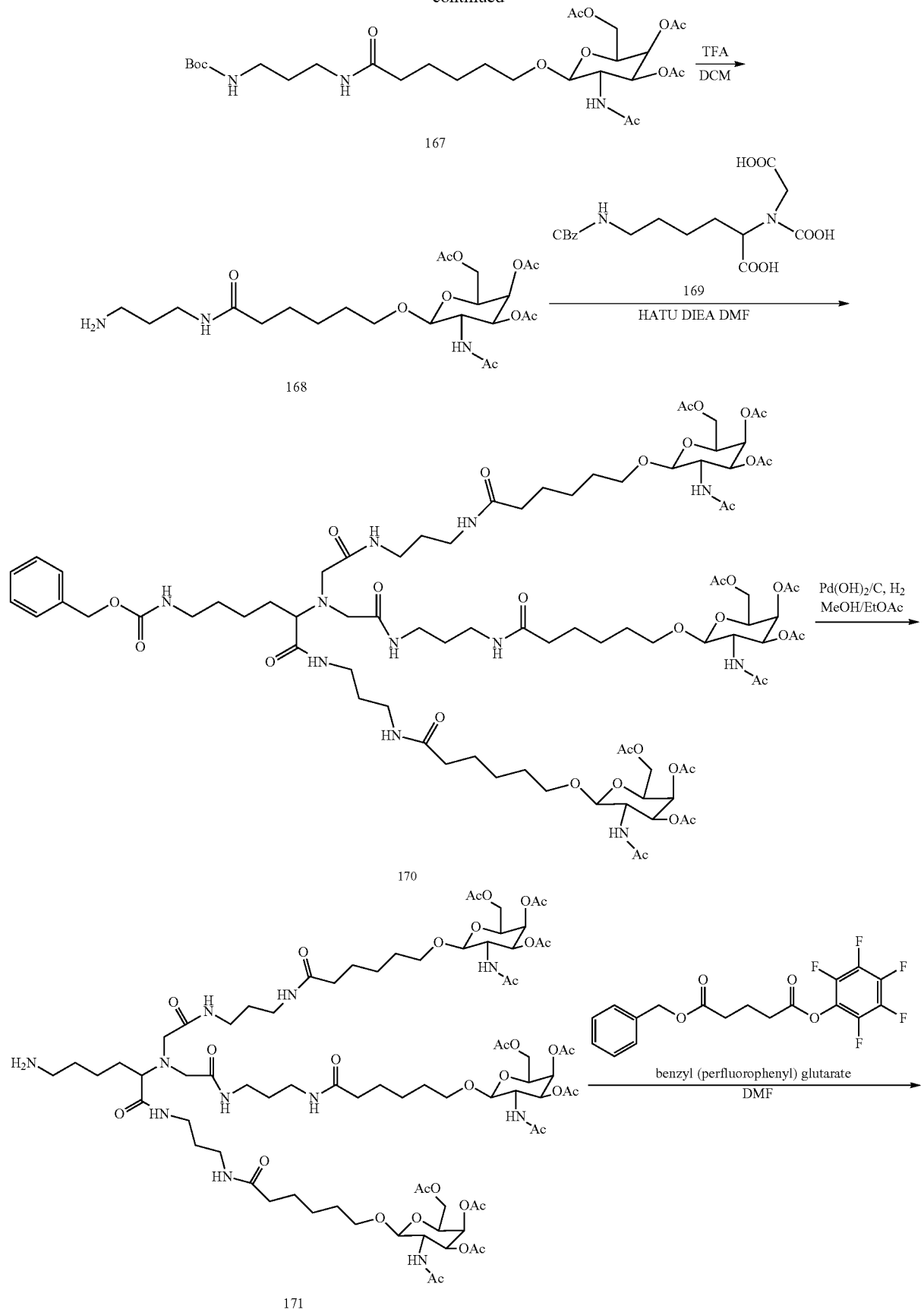

-continued
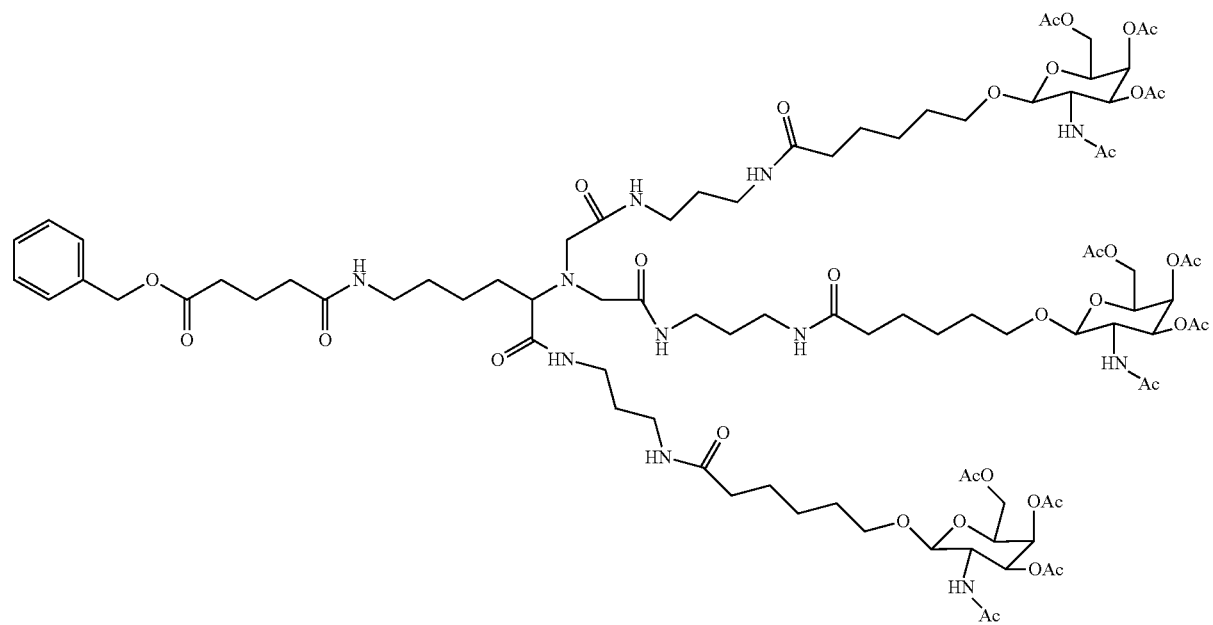
172
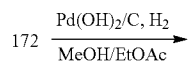
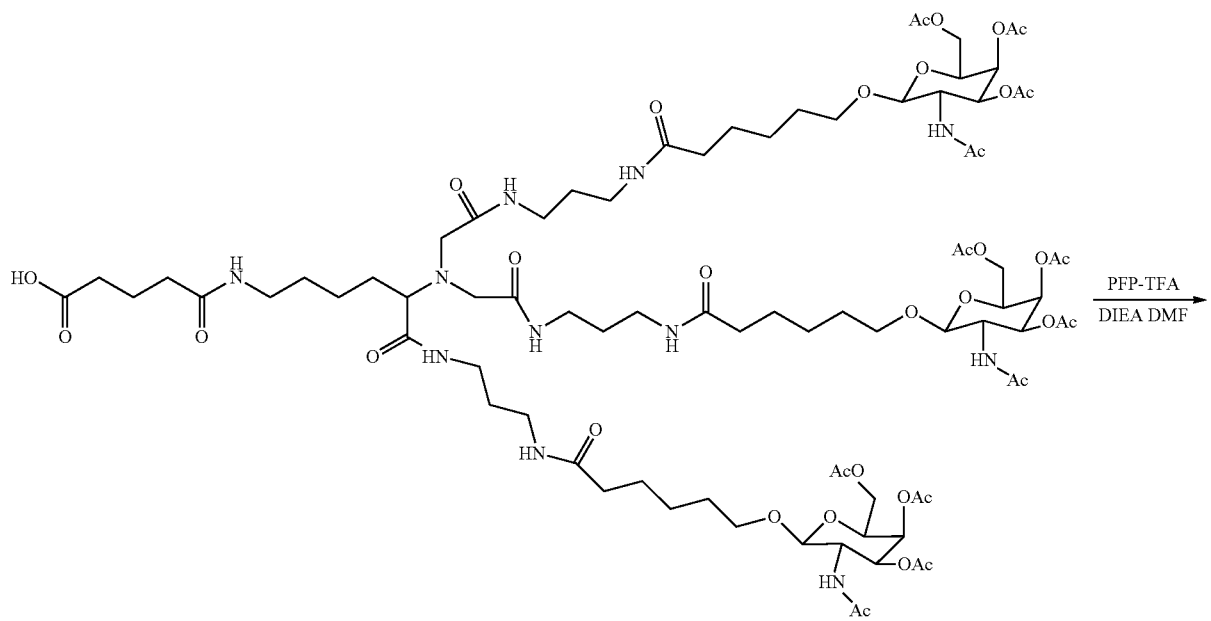
173

-continued

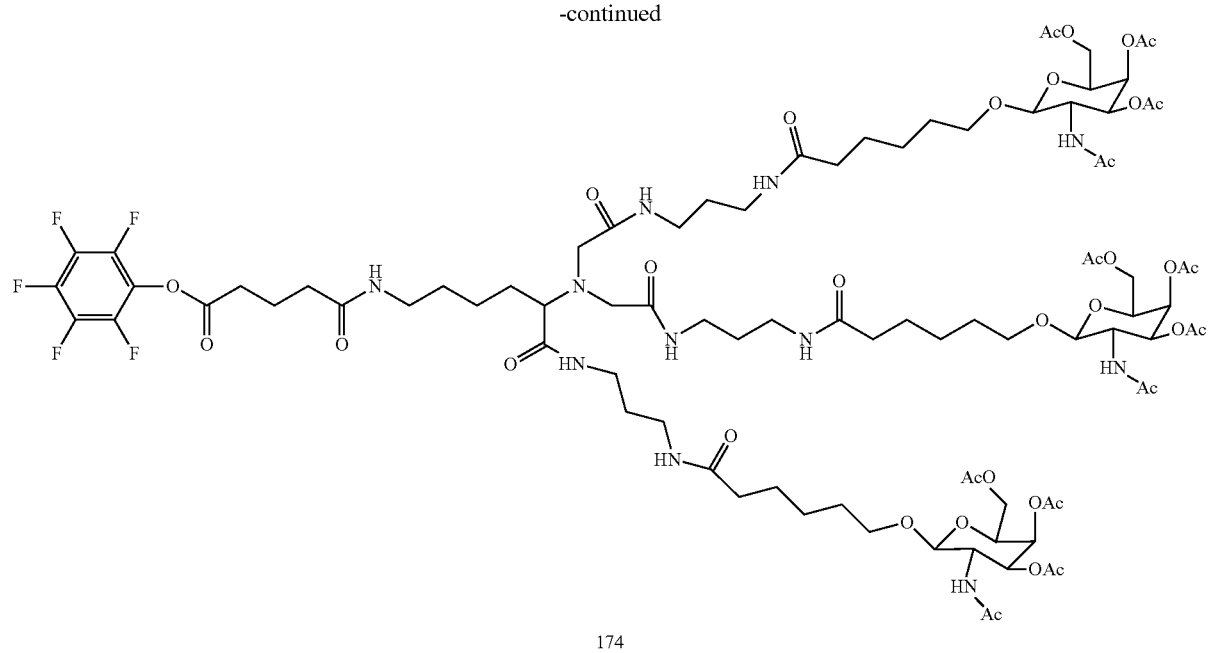

174

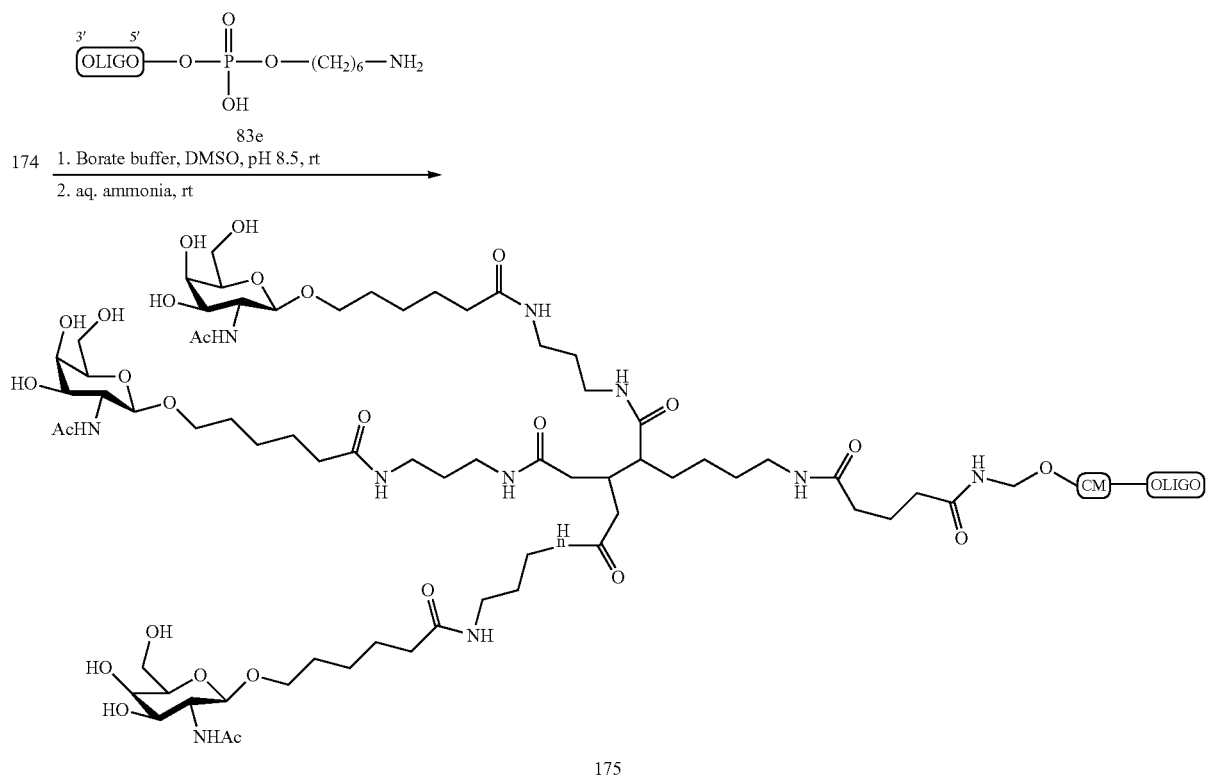

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Oligomeric compound 175, comprising a GalNAc$_3$-12 conjugate group, was prepared from compound 174 using the general procedures illustrated in Example 46. The GalNAc$_3$ cluster portion of the conjugate group GalNAc$_3$-12 (GalNAc$_3$-12$_a$) can be combined with any cleavable moiety to provide a variety of conjugate groups. In a certain embodiments, the cleavable moiety is —P(=O)(OH)-A$_d$-P(=O)(OH)—. The structure of GalNAc$_3$-12 (GalNAc$_3$-12$_a$-CM-) is shown below:

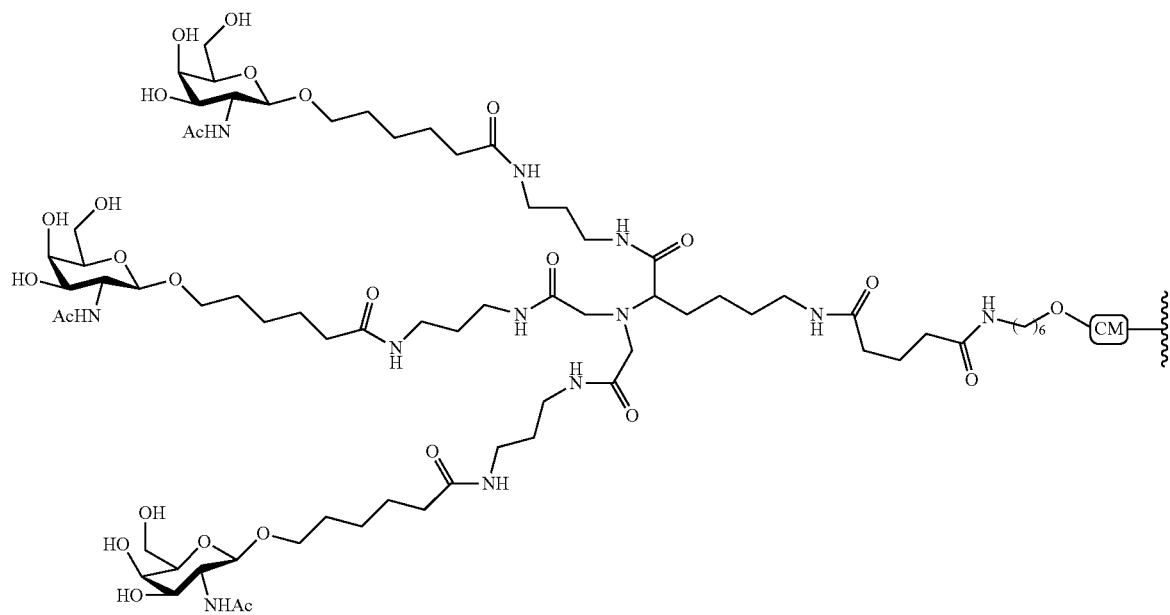
Example 62
Preparation of Oligomeric Compound 180
Comprising GalNAc$_3$-13
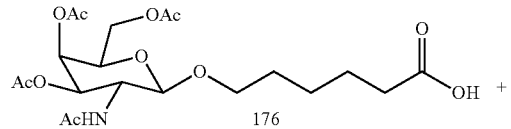
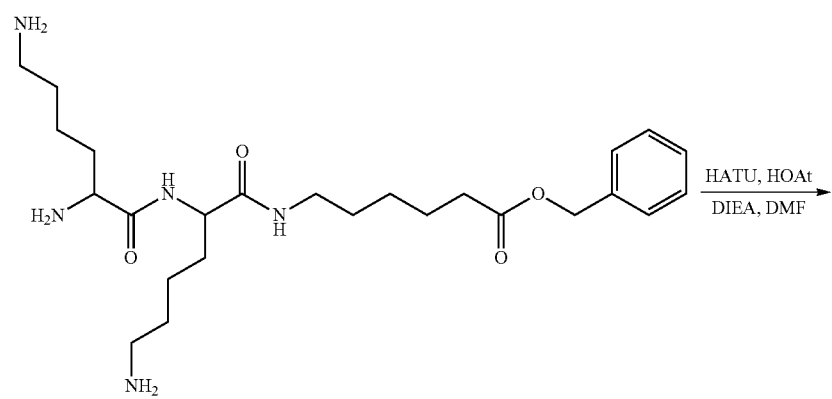

-continued
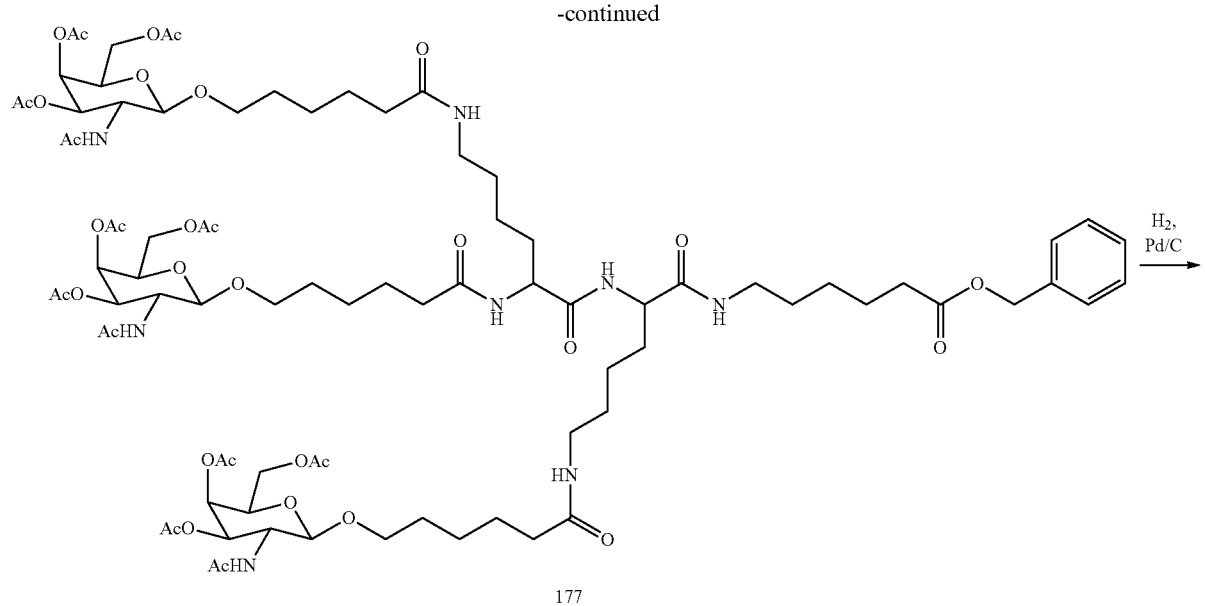
177
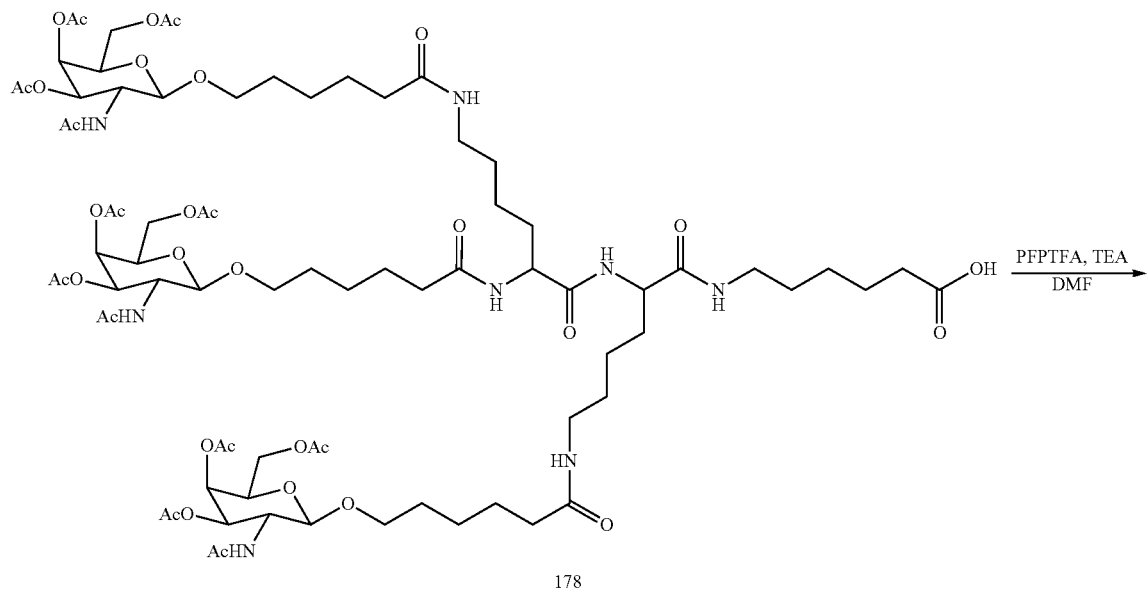
178
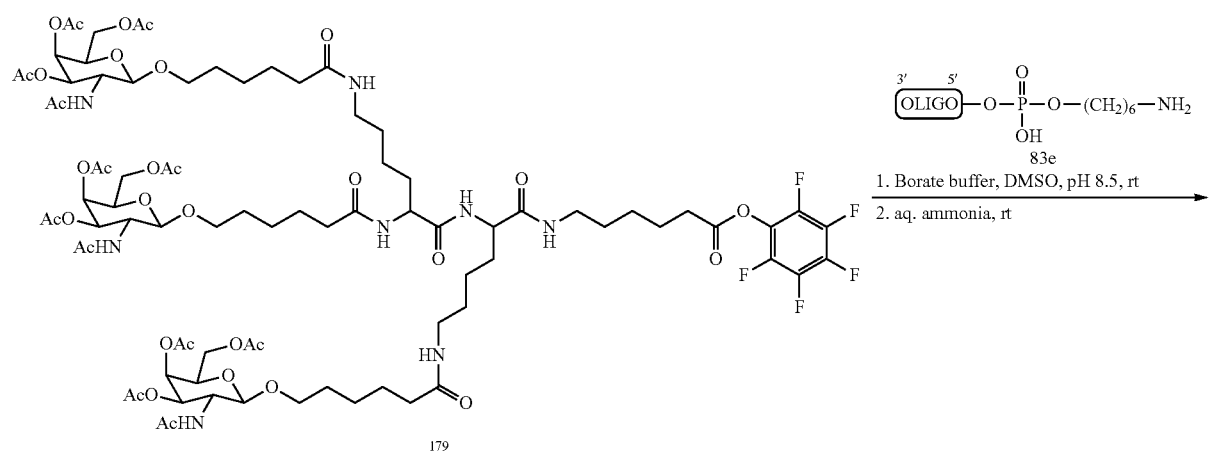
179

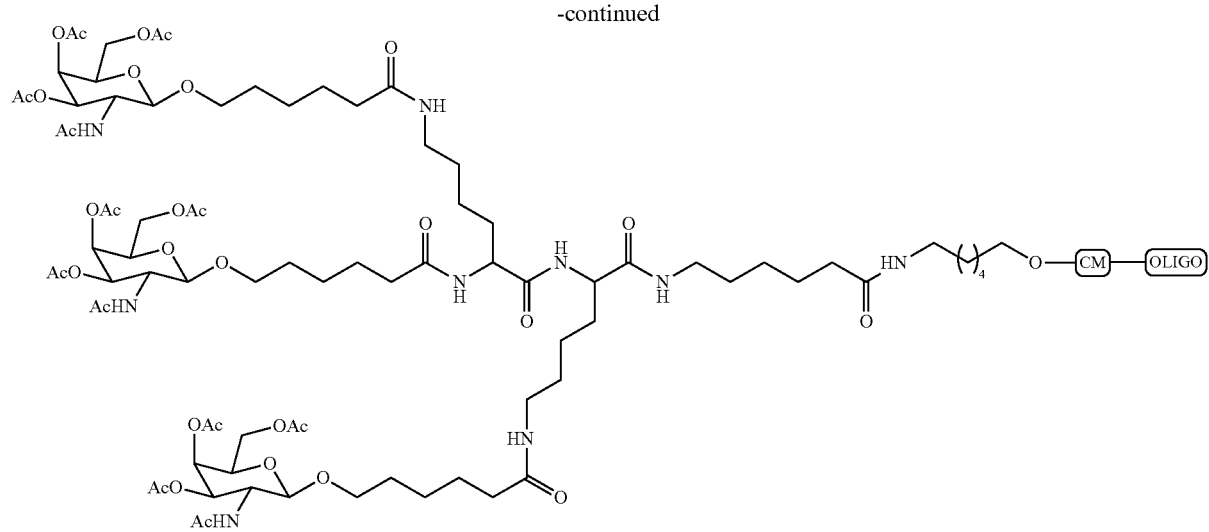

180

Compound 176 was prepared using the general procedure shown in Example 2. Oligomeric compound 180, comprising a GalNAc$_3$-13 conjugate group, was prepared from compound 177 using the general procedures illustrated in Example 49. The GalNAc$_3$ cluster portion of the conjugate group GalNAc$_3$-13 (GalNAc$_3$-13$_a$) can be combined with any cleavable moiety to provide a variety of conjugate groups. In a certain embodiments, the cleavable moiety is —P(=O)(OH)-A$_d$-P(=O)(OH)—. The structure of Gal-NAc$_3$-13 (GalNAc$_3$-13$_a$-CM-) is shown below:

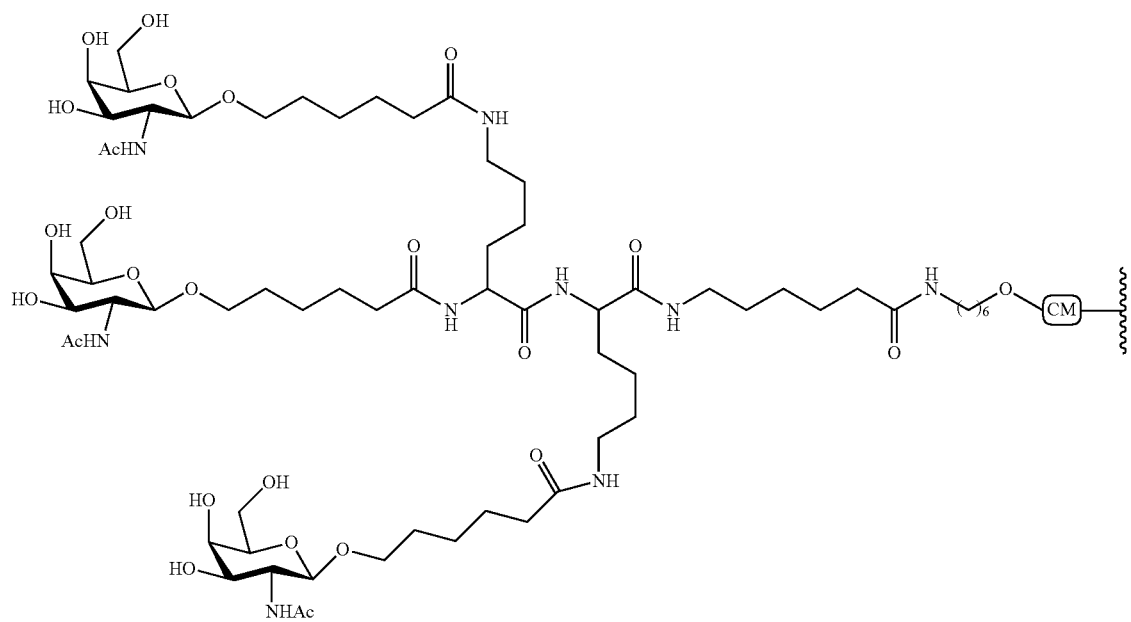

Example 63
Preparation of Oligomeric Compound 188 Comprising GalNAc$_3$-14
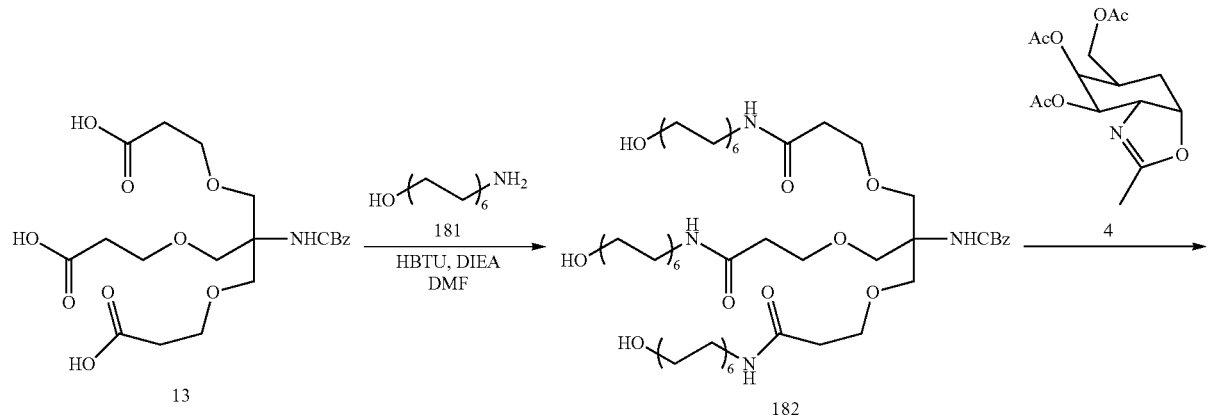
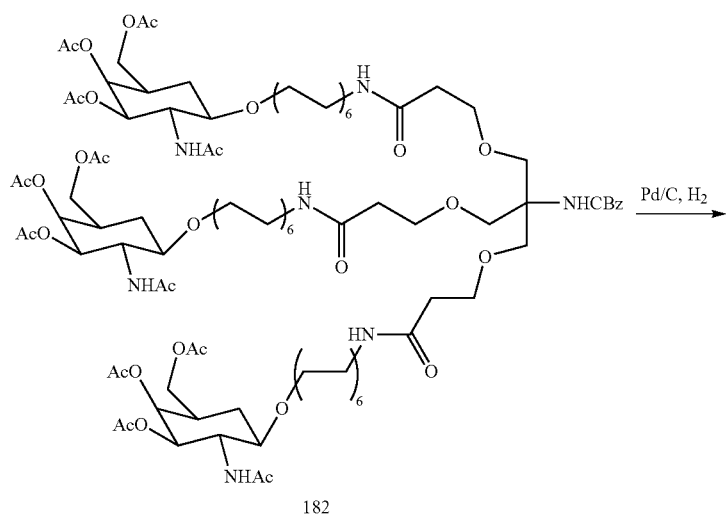
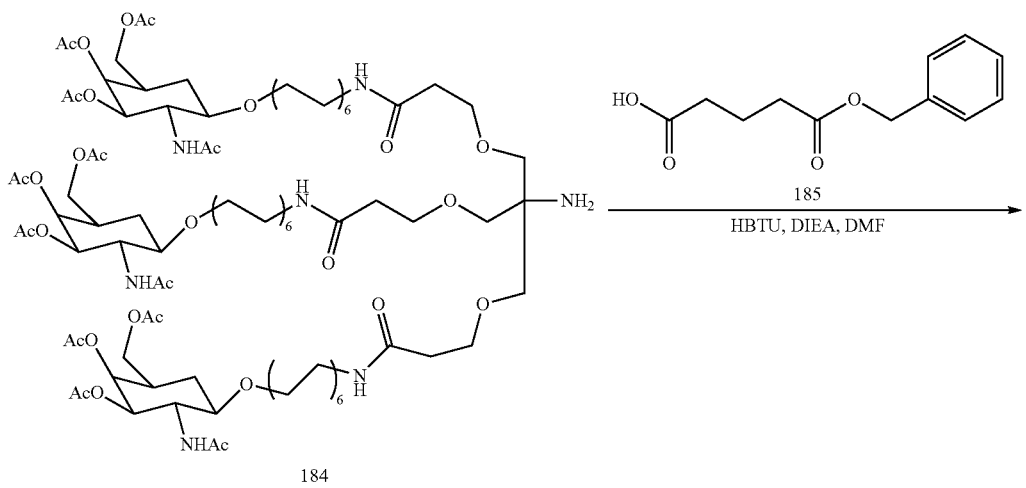

-continued
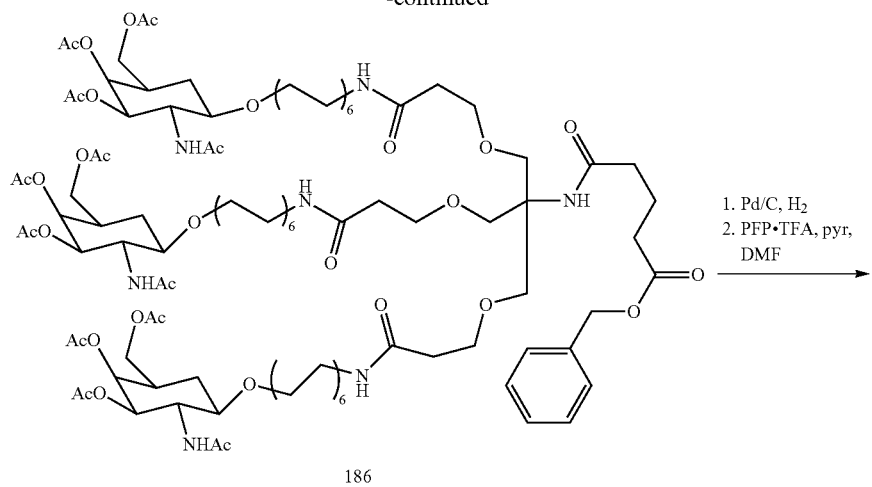
186
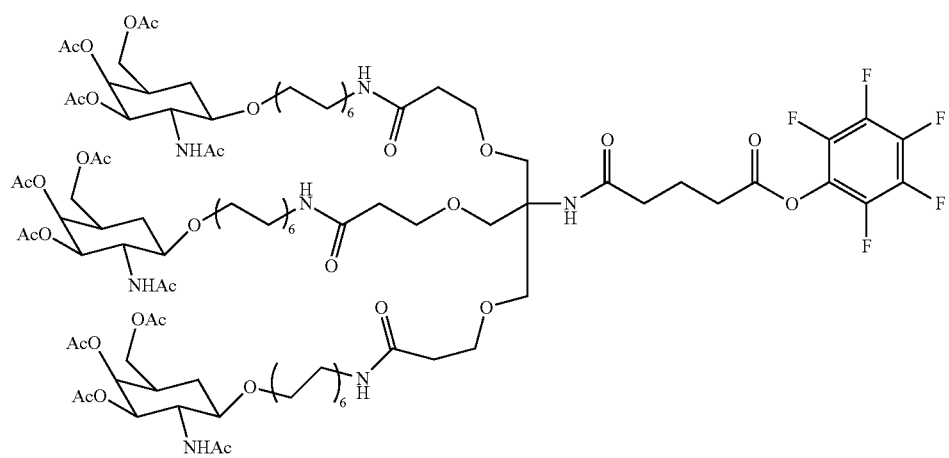
187
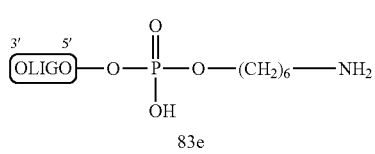
83e
187 $\xrightarrow{\text{1. Borate buffer, DMSO, pH 8.5, rt}}_{\text{2. aq. ammonia, rt}}$
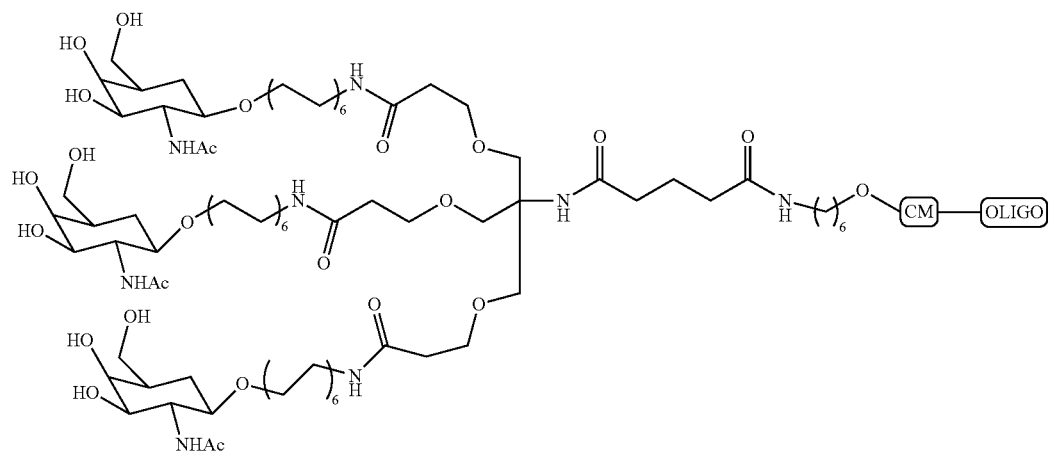
188

Compounds 181 and 185 are commercially available. Oligomeric compound 188, comprising a GalNAc$_3$-14 conjugate group, was prepared from compound 187 using the general procedures illustrated in Example 46. The GalNAc$_3$ cluster portion of the conjugate group GalNAc$_3$-14 (GalNAc$_3$-14$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-14 (GalNAc$_3$-14$_a$-CM-) is shown below:

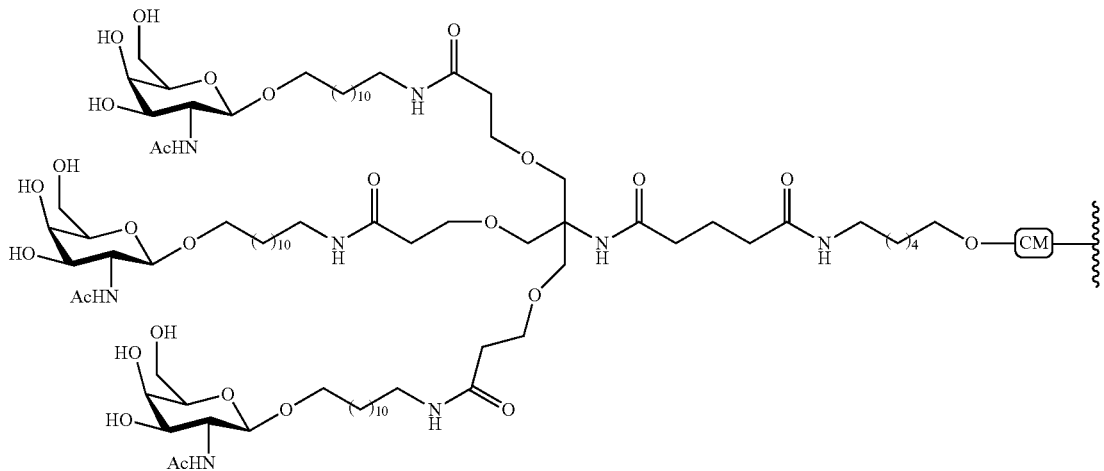

Example 64

Preparation of Oligomeric Compound 197 Comprising GalNAc$_3$-15

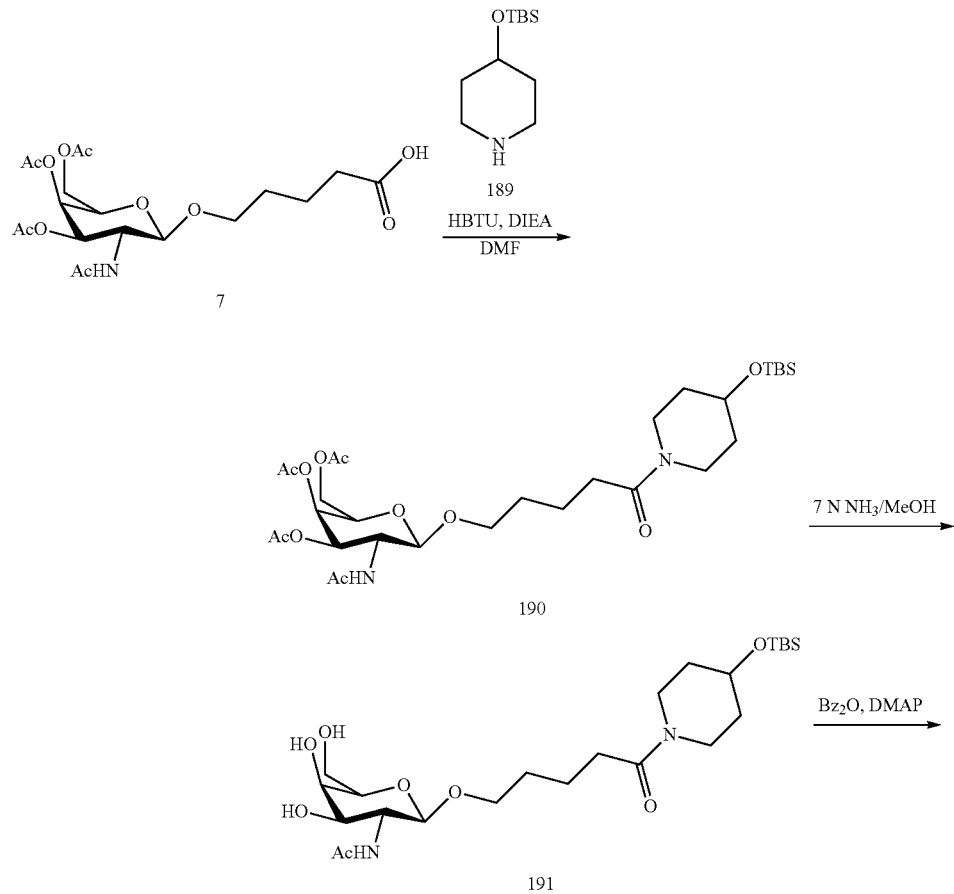

-continued
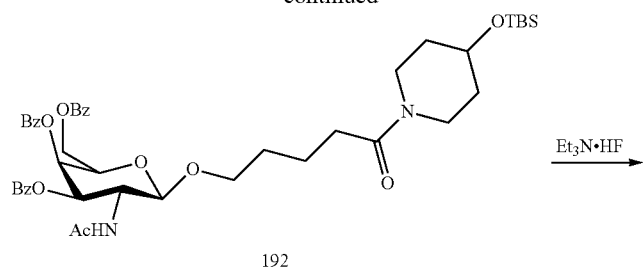
192
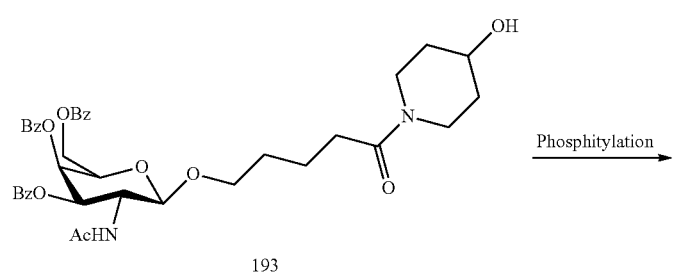
193
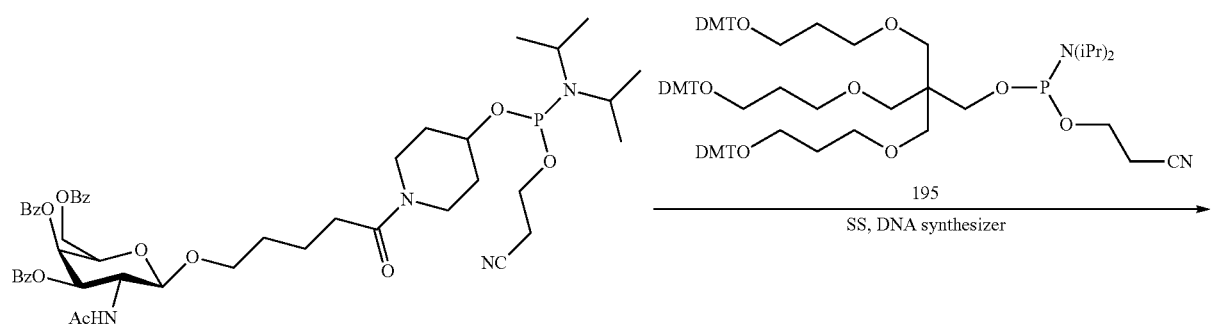
194
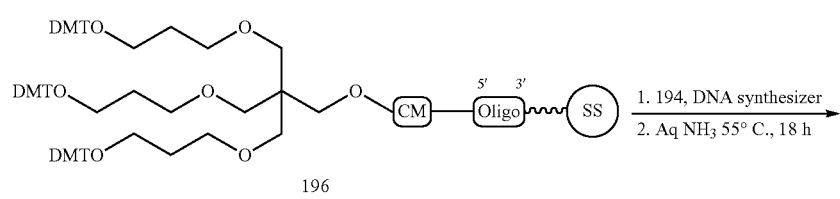
196
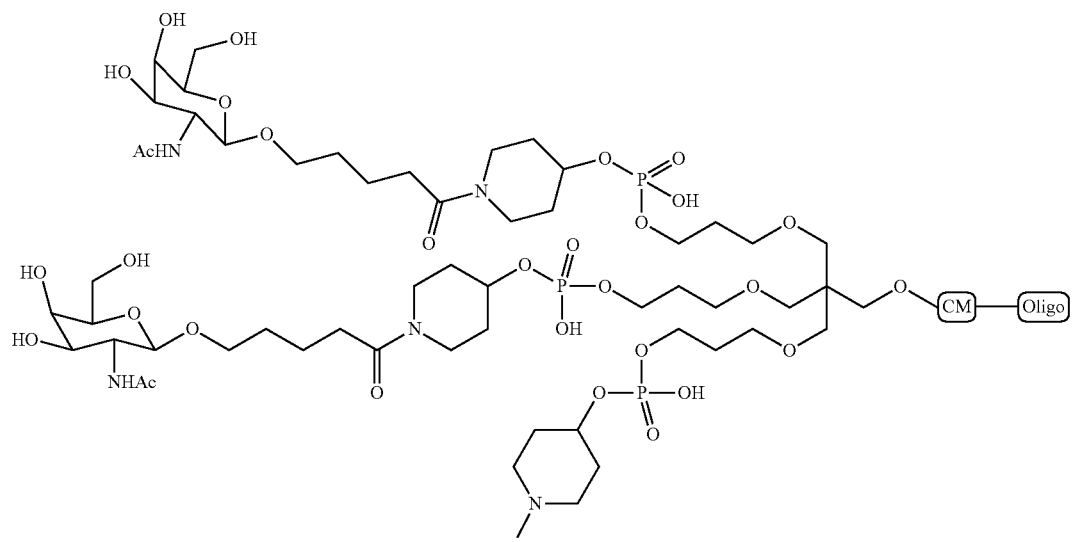

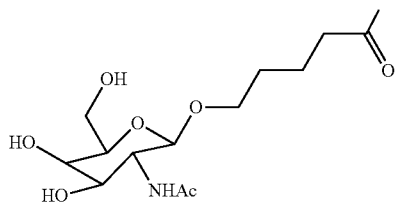

197

Compound 189 is commercially available. Compound 195 was prepared using the general procedure shown in Example 31. Oligomeric compound 197, comprising a GalNAc₃-15 conjugate group, was prepared from compounds 194 and 195 using standard oligonucleotide synthesis procedures. The GalNAc₃ cluster portion of the conjugate group GalNAc₃-15 (GalNAc₃-15$_a$) can be combined with any cleavable moiety to provide a variety of conjugate groups. In certain embodiments, the cleavable moiety is —P(=O)(OH)-A$_d$-P(=O)(OH)—. The structure of GalNAc₃-15 (GalNAc₃-15$_a$-CM-) is shown below:

TABLE 41

Modified ASOs targeting SRB-1

| ISIS No. | Sequences (5' to 3') | Conjugate | SEQ ID No. |
|---|---|---|---|
| 353382 | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | none | 28 |

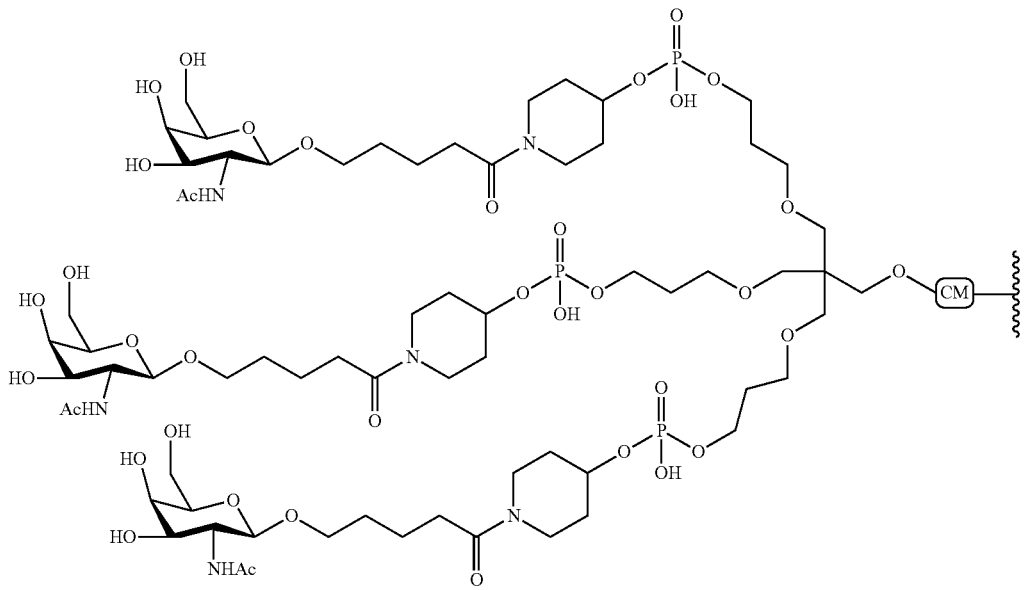

Example 65

Dose-Dependent Study of Oligonucleotides Comprising a 5'-Conjugate Group (Comparison of GalNAc₃-3, 12, 13, 14, and 15) Targeting SRB-1 In Vivo The oligonucleotides listed below were tested in a dose-dependent study for antisense inhibition of SRB-1 in mice. Unconjugated ISIS 353382 was included as a standard. Each of the GalNAc₃ conjugate groups was attached at the 5' terminus of the respective oligonucleotide by a phosphodiester linked 2'-deoxyadenosine nucleoside (cleavable moiety).

TABLE 41-continued

Modified ASOs targeting SRB-1

| ISIS No. | Sequences (5' to 3') | Conjugate | SEQ ID No. |
|---|---|---|---|
| 661161 | GalNAc₃-3$_a$-$_o$,A$_{ds}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | GalNAc₃-3 | 30 |
| 671144 | GalNAc₃-12$_a$-$_o$,A$_{ds}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | GalNAc₃-12 | 30 |

TABLE 41-continued

Modified ASOs targeting SRB-1

| ISIS No. | Sequences (5' to 3') | Conjugate | SEQ ID No. |
|---|---|---|---|
| 670061 | GalNAc$_3$-13$_a$-$_o'$A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | GalNAc$_3$-13 | 30 |
| 671261 | GalNAc$_3$-14$_a$-$_o'$A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | GalNAc$_3$-14 | 30 |
| 671262 | GalNAc$_3$-15$_a$-$_o'$A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | GalNAc$_3$-15 | 30 |

Capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-3$_a$ was shown previously in Example 39. The structure of GalNAc$_3$-12a was shown previously in Example 61. The structure of GalNAc$_3$-13a was shown previously in Example 62. The structure of GalNAc$_3$-14a was shown previously in Example 63. The structure of GalNAc$_3$-15a was shown previously in Example 64.

Treatment

Six to eight week old C57bl6 mice (Jackson Laboratory, Bar Harbor, Me.) were injected subcutaneously once or twice at the dosage shown below with ISIS 353382, 661161, 671144, 670061, 671261, 671262, or with saline. Mice that were dosed twice received the second dose three days after the first dose. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 42, treatment with antisense oligonucleotides lowered SRB-1 mRNA levels in a dose-dependent manner. No significant differences in target knockdown were observed between animals that received a single dose and animals that received two doses (see ISIS 353382 dosages 30 and 2×15 mg/kg; and ISIS 661161 dosages 5 and 2×2.5 mg/kg). The antisense oligonucleotides comprising the phosphodiester linked GalNAc$_3$-3, 12, 13, 14, and 15 conjugates showed substantial improvement in potency compared to the unconjugated antisense oligonucleotide (ISIS 335382).

TABLE 42

SRB-1 mRNA (% Saline)

| ISIS No. | Dosage (mg/kg) | SRB-1 mRNA (% Saline) | ED$_{50}$ (mg/kg) | Conjugate |
|---|---|---|---|---|
| Saline | n/a | 100.0 | n/a | n/a |
| 353382 | 3 | 85.0 | 22.4 | none |
|  | 10 | 69.2 |  |  |
|  | 30 | 34.2 |  |  |
|  | 2 × 15 | 36.0 |  |  |
| 661161 | 0.5 | 87.4 | 2.2 | GalNAc$_3$-3 |
|  | 1.5 | 59.0 |  |  |
|  | 5 | 25.6 |  |  |
|  | 2 × 2.5 | 27.5 |  |  |
|  | 15 | 17.4 |  |  |
| 671144 | 0.5 | 101.2 | 3.4 | GalNAc$_3$-12 |
|  | 1.5 | 76.1 |  |  |
|  | 5 | 32.0 |  |  |
|  | 15 | 17.6 |  |  |
| 670061 | 0.5 | 94.8 | 2.1 | GalNAc$_3$-13 |
|  | 1.5 | 57.8 |  |  |
|  | 5 | 20.7 |  |  |
|  | 15 | 13.3 |  |  |
| 671261 | 0.5 | 110.7 | 4.1 | GalNAc$_3$-14 |
|  | 1.5 | 81.9 |  |  |
|  | 5 | 39.8 |  |  |
|  | 15 | 14.1 |  |  |
| 671262 | 0.5 | 109.4 | 9.8 | GalNAc$_3$-15 |
|  | 1.5 | 99.5 |  |  |
|  | 5 | 69.2 |  |  |
|  | 15 | 36.1 |  |  |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 43 below.

TABLE 43

| ISIS No. | Dosage (mg/kg) | ALT (U/L) | AST (U/L) | Total Bilirubin (mg/dL) | BUN (mg/dL) | Conjugate |
|---|---|---|---|---|---|---|
| Saline | n/a | 28 | 60 | 0.1 | 39 | n/a |
| 353382 | 3 | 30 | 77 | 0.2 | 36 | none |
|  | 10 | 25 | 78 | 0.2 | 36 |  |
|  | 30 | 28 | 62 | 0.2 | 35 |  |
|  | 2 × 15 | 22 | 59 | 0.2 | 33 |  |
| 661161 | 0.5 | 39 | 72 | 0.2 | 34 | GalNac$_3$-3 |
|  | 1.5 | 26 | 50 | 0.2 | 33 |  |
|  | 5 | 41 | 80 | 0.2 | 32 |  |
|  | 2 × 2.5 | 24 | 72 | 0.2 | 28 |  |
|  | 15 | 32 | 69 | 0.2 | 36 |  |
| 671144 | 0.5 | 25 | 39 | 0.2 | 34 | GalNac$_3$-12 |
|  | 1.5 | 26 | 55 | 0.2 | 28 |  |
|  | 5 | 48 | 82 | 0.2 | 34 |  |
|  | 15 | 23 | 46 | 0.2 | 32 |  |
| 670061 | 0.5 | 27 | 53 | 0.2 | 33 | GalNac$_3$-13 |
|  | 1.5 | 24 | 45 | 0.2 | 35 |  |
|  | 5 | 23 | 58 | 0.1 | 34 |  |
|  | 15 | 24 | 72 | 0.1 | 31 |  |
| 671261 | 0.5 | 69 | 99 | 0.1 | 33 | GalNac$_3$-14 |
|  | 1.5 | 34 | 62 | 0.1 | 33 |  |
|  | 5 | 43 | 73 | 0.2 | 32 |  |
|  | 15 | 32 | 53 | 0.2 | 30 |  |
| 671262 | 0.5 | 24 | 51 | 0.2 | 29 | GalNac$_3$-15 |
|  | 1.5 | 32 | 62 | 0.1 | 31 |  |
|  | 5 | 30 | 76 | 0.2 | 32 |  |
|  | 15 | 31 | 64 | 0.1 | 32 |  |

Example 66

Effect of Various Cleavable Moieties on Antisense Inhibition In Vivo by Oligonucleotides Targeting SRB-1 Comprising a 5'-GalNAc₃ Cluster The oligonucleotides listed below were tested in a dose-dependent study for antisense inhibition of SRB-1 in mice. Each of the GalNAc₃ conjugate groups was attached at the 5' terminus of the respective oligonucleotide by a phosphodiester linked nucleoside (cleavable moiety (CM)).

TABLE 44

Modified ASOs targeting SRB-1

| ISIS No. | Sequences (5' to 3') | GalNAc₃ Cluster | CM | SEQ ID No. |
|---|---|---|---|---|
| 661161 | GalNAc₃-3ₐ-ₒ,Aₔ$G_{es}$ $^mC_{es}T_{es}T_{es}{}^mC_{es}A_{ds}G_{ds}T_{ds}$ $^mC_{ds}A_{ds}T_{ds}G_{ds}A_{ds}{}^mC_{ds}T_{ds}$ $T_{es}{}^mC_{es}{}^mC_{es}T_{es}T_e$ | GalNAc₃-3a | $A_d$ | 30 |
| 670699 | GalNAc₃-3ₐ-ₒ,$T_{do}G_{es}$ $^mC_{eo}T_{eo}T_{eo}{}^mC_{eo}A_{ds}G_{ds}T_{ds}$ $^mC_{ds}A_{ds}T_{ds}G_{ds}A_{ds}{}^mC_{ds}T_{ds}$ $T_{eo}{}^mC_{eo}{}^mC_{es}T_{es}T_e$ | GalNAc₃-3a | $T_d$ | 33 |
| 670700 | GalNAc₃-3ₐ-ₒ,$A_{do}G_{es}$ $^mC_{eo}T_{eo}T_{eo}{}^mC_{eo}A_{ds}G_{ds}T_{ds}$ $^mC_{ds}A_{ds}T_{ds}G_{ds}A_{ds}{}^mC_{ds}T_{ds}$ $T_{eo}{}^mC_{eo}{}^mC_{es}T_{es}T_e$ | GalNAc₃-3a | $A_e$ | 30 |
| 670701 | GalNAc₃-3ₐ-ₒ,$T_{do}G_{es}$ $^mC_{eo}T_{eo}T_{eo}{}^mC_{eo}A_{ds}G_{ds}T_{ds}$ $^mC_{ds}A_{ds}T_{ds}G_{ds}A_{ds}{}^mC_{ds}T_{ds}$ $T_{eo}{}^mC_{eo}{}^mC_{es}T_{es}T_e$ | GalNac₃-3a | $T_e$ | 33 |
| 671165 | GalNAc₃-13ₐ-ₒ,$A_{do}G_{es}$ $^mC_{eo}T_{eo}T_{eo}{}^mC_{eo}A_{ds}G_{ds}T_{ds}$ $^mC_{ds}A_{ds}T_{ds}G_{ds}A_{ds}{}^mC_{ds}T_{ds}$ $T_{eo}{}^mC_{eo}{}^mC_{es}T_{es}T_e$ | GalNAc₃-13a | $A_d$ | 30 |

Capital letters indicate the nucleobase for each nucleoside and $^mC$ indicates a 5-methyl cytosine.
Subscripts:
"e" indicates a 2'-MOE modified nucleoside;
"d" indicates a β-D-2'-deoxyribonucleoside;
"s" indicates a phosphorothioate internucleoside linkage (PS);
"o" indicates a phosphodiester internucleoside linkage (PO);
and "o'" indicates -O-P(=O)(OH)-.
Conjugate groups are in bold.

The structure of GalNAc₃-3ₐ was shown previously in Example 39. The structure of GalNAc₃-13a was shown previously in Example 62.

Treatment

Six to eight week old C57bl6 mice (Jackson Laboratory, Bar Harbor, Me.) were injected subcutaneously once at the dosage shown below with ISIS 661161, 670699, 670700, 670701, 671165, or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 45, treatment with antisense oligonucleotides lowered SRB-1 mRNA levels in a dose-dependent manner. The antisense oligonucleotides comprising various cleavable moieties all showed similar potencies.

TABLE 45

SRB-1 mRNA (% Saline)

| ISIS No. | Dosage (mg/kg) | SRB-1 mRNA (% Saline) | GalNAc₃ Cluster | CM |
|---|---|---|---|---|
| Saline | n/a | 100.0 | n/a | n/a |
| 661161 | 0.5 | 87.8 | GalNAc₃-3a | $A_d$ |
|  | 1.5 | 61.3 |  |  |
|  | 5 | 33.8 |  |  |
|  | 15 | 14.0 |  |  |
| 670699 | 0.5 | 89.4 | GalNAc₃-3a | $T_d$ |
|  | 1.5 | 59.4 |  |  |
|  | 5 | 31.3 |  |  |
|  | 15 | 17.1 |  |  |
| 670700 | 0.5 | 79.0 | GalNAc₃-3a | $A_e$ |
|  | 1.5 | 63.3 |  |  |
|  | 5 | 32.8 |  |  |
|  | 15 | 17.9 |  |  |
| 670701 | 0.5 | 79.1 | GalNAc₃-3a | $T_e$ |
|  | 1.5 | 59.2 |  |  |
|  | 5 | 35.8 |  |  |
|  | 15 | 17.7 |  |  |
| 671165 | 0.5 | 76.4 | GalNAc₃-13a | $A_d$ |
|  | 1.5 | 43.2 |  |  |
|  | 5 | 22.6 |  |  |
|  | 15 | 10.0 |  |  |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 46 below.

TABLE 46

| ISIS No. | Dosage (mg/kg) | ALT (U/L) | AST (U/L) | Total Bilirubin (mg/dL) | BUN (mg/dL) | GalNAc₃ Cluster | CM |
|---|---|---|---|---|---|---|---|
| Saline | n/a | 24 | 64 | 0.2 | 31 | n/a | n/a |
| 661161 | 0.5 | 25 | 64 | 0.2 | 31 | GalNac₃-3a | $A_d$ |
|  | 1.5 | 24 | 50 | 0.2 | 32 |  |  |
|  | 5 | 26 | 55 | 0.2 | 28 |  |  |
|  | 15 | 27 | 52 | 0.2 | 31 |  |  |
| 670699 | 0.5 | 42 | 83 | 0.2 | 31 | GalNac₃-3a | $T_d$ |
|  | 1.5 | 33 | 58 | 0.2 | 32 |  |  |
|  | 5 | 26 | 70 | 0.2 | 29 |  |  |
|  | 15 | 25 | 67 | 0.2 | 29 |  |  |
| 670700 | 0.5 | 40 | 74 | 0.2 | 27 | GalNac₃-3a | $A_e$ |
|  | 1.5 | 23 | 62 | 0.2 | 27 |  |  |
|  | 5 | 24 | 49 | 0.2 | 29 |  |  |
|  | 15 | 25 | 87 | 0.1 | 25 |  |  |

TABLE 46-continued
| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| 670701 | 0.5 | 30 | 77 | 0.2 | 27 | GalNac$_3$-3a | $T_e$ |
|  | 1.5 | 22 | 55 | 0.2 | 30 |  |  |
|  | 5 | 81 | 101 | 0.2 | 25 |  |  |
|  | 15 | 31 | 82 | 0.2 | 24 |  |  |
| 671165 | 0.5 | 44 | 84 | 0.2 | 26 | GalNac$_3$-13a | $A_d$ |
|  | 1.5 | 47 | 71 | 0.1 | 24 |  |  |
|  | 5 | 33 | 91 | 0.2 | 26 |  |  |
|  | 15 | 33 | 56 | 0.2 | 29 |  |  |
Example 67
Preparation of Oligomeric Compound 199 Comprising GalNAc$_3$-16
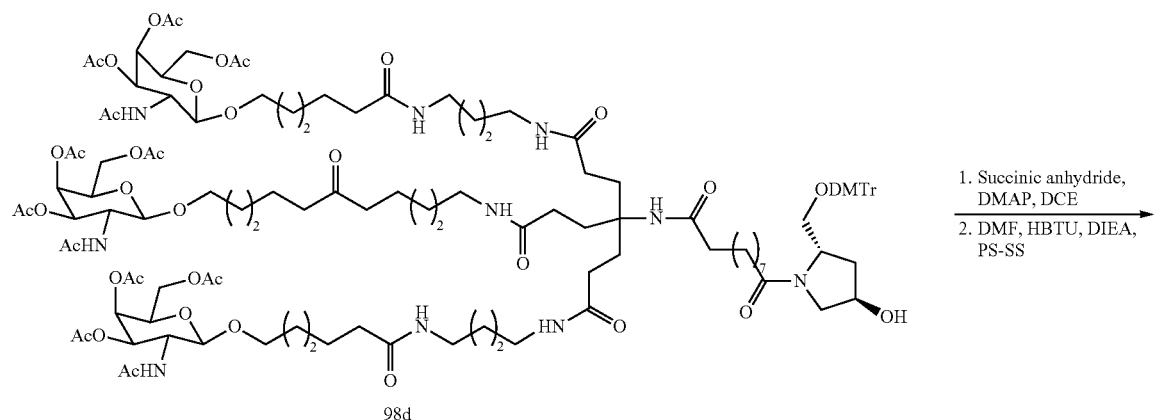
98d
1. Succinic anhydride, DMAP, DCE
2. DMF, HBTU, DIEA, PS-SS
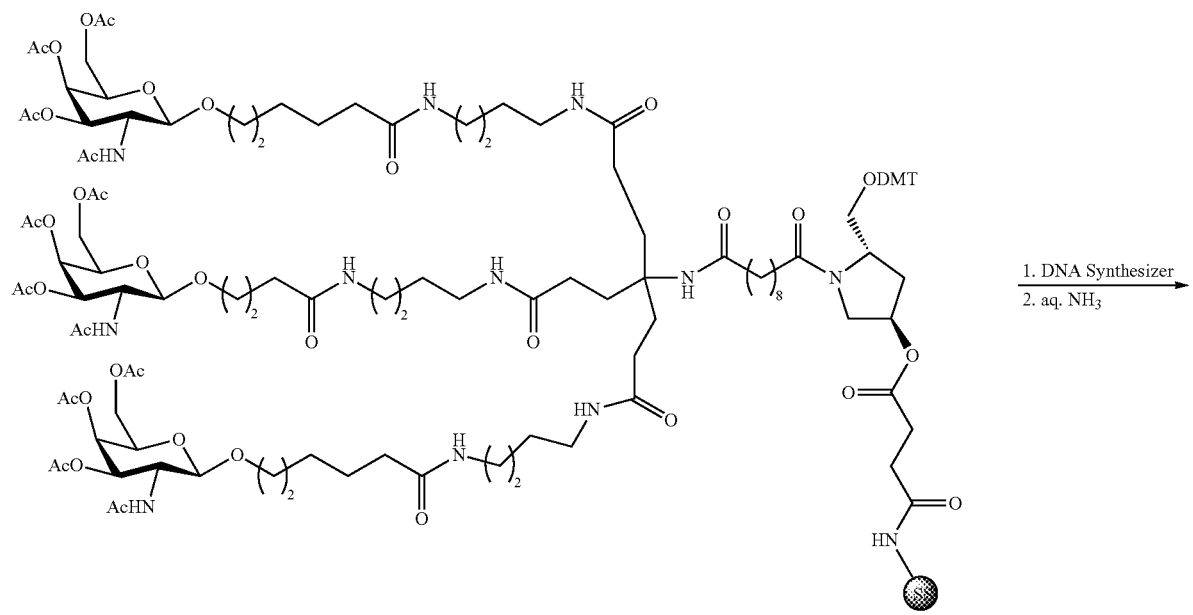
1. DNA Synthesizer
2. aq. NH$_3$
198

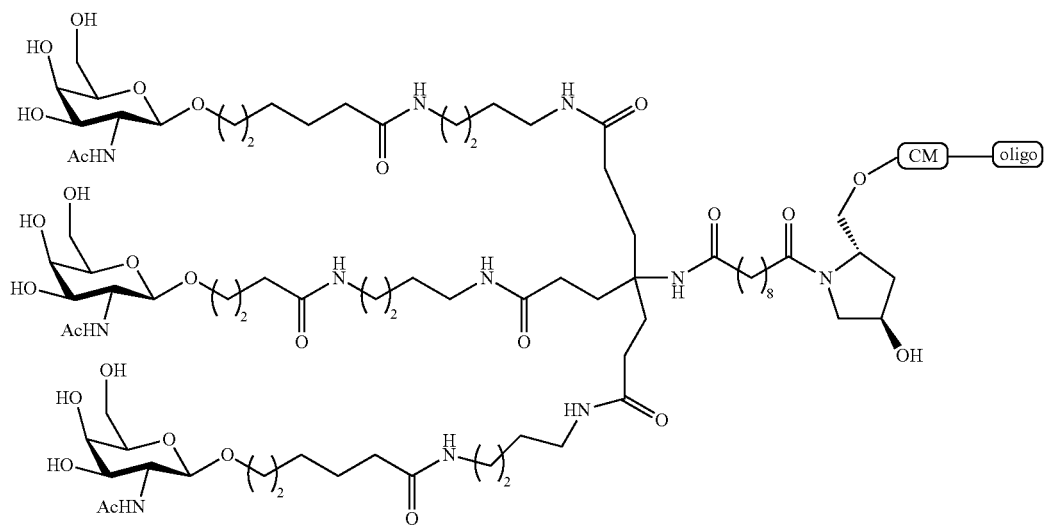

199

Oligomeric compound 199, comprising a GalNAc$_3$-16 conjugate group, is prepared using the general procedures illustrated in Examples 7 and 9. The GalNAc$_3$ cluster portion of the conjugate group GalNAc$_3$-16 (GalNAc$_3$-16$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-16 (GalNAc$_3$-16$_a$-CM-) is shown below:

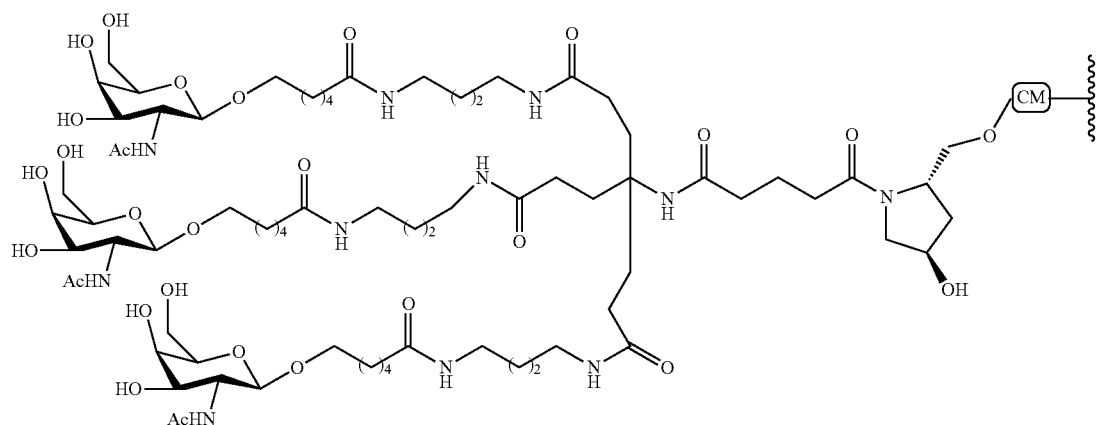

Example 68

Preparation of Oligomeric Compound 200 Comprising GalNAc$_3$-17

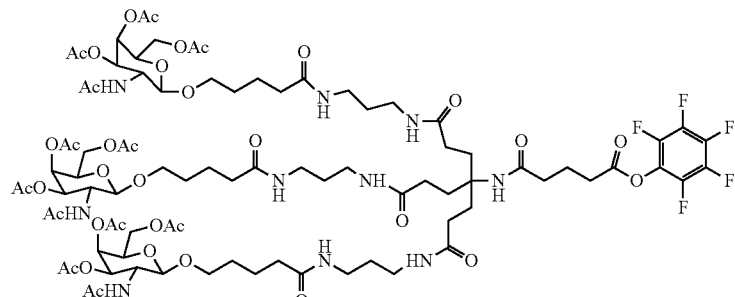

102a

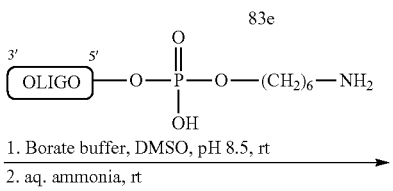

1. Borate buffer, DMSO, pH 8.5, rt
2. aq. ammonia, rt

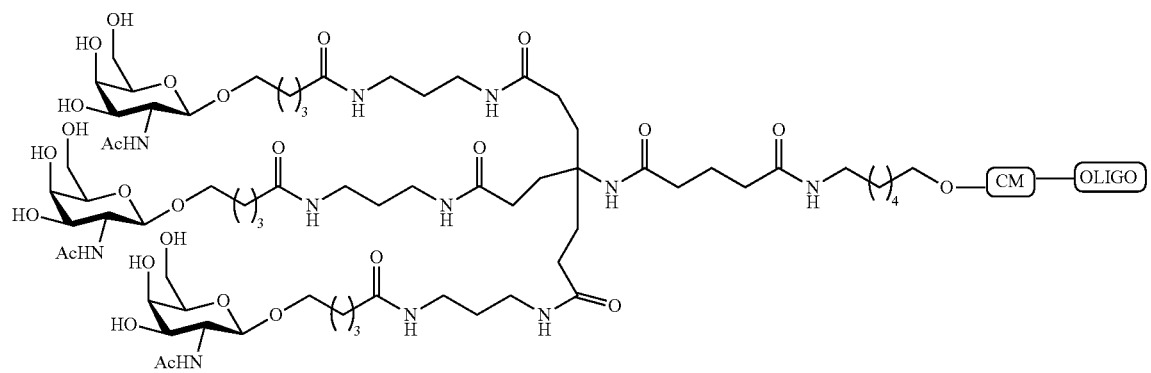

200

Oligomeric compound 200, comprising a GalNAc$_3$-17 conjugate group, was prepared using the general procedures illustrated in Example 46. The GalNAc$_3$ cluster portion of the conjugate group GalNAc$_3$-17 (GalNAc$_3$-17$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-17 (GalNAc$_3$-17$_a$-CM-) is shown below:

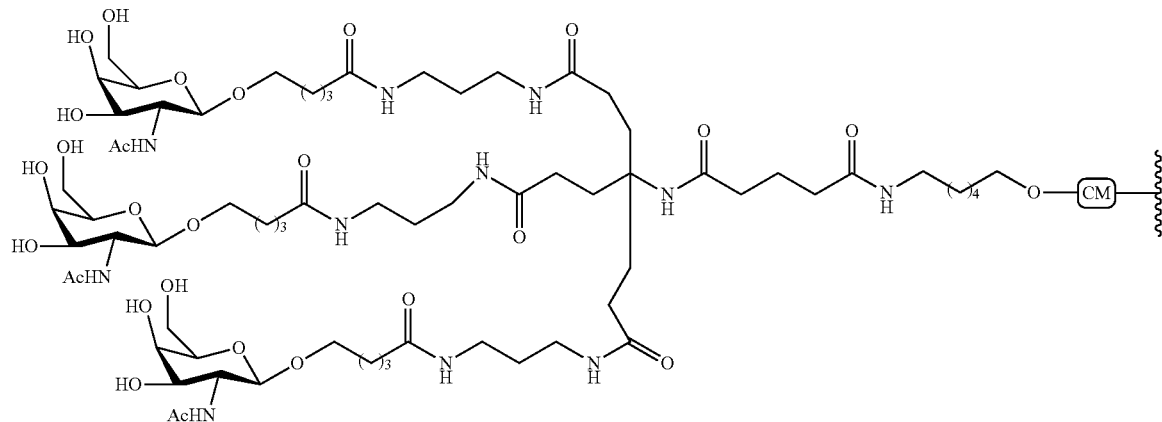

Example 69

Preparation of Oligomeric Compound 201 Comprising GalNAc₃-18

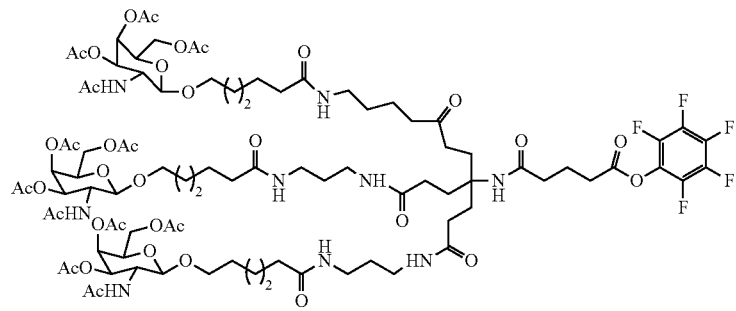

102b

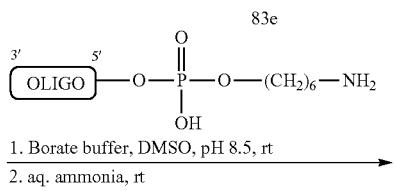

1. Borate buffer, DMSO, pH 8.5, rt
2. aq. ammonia, rt

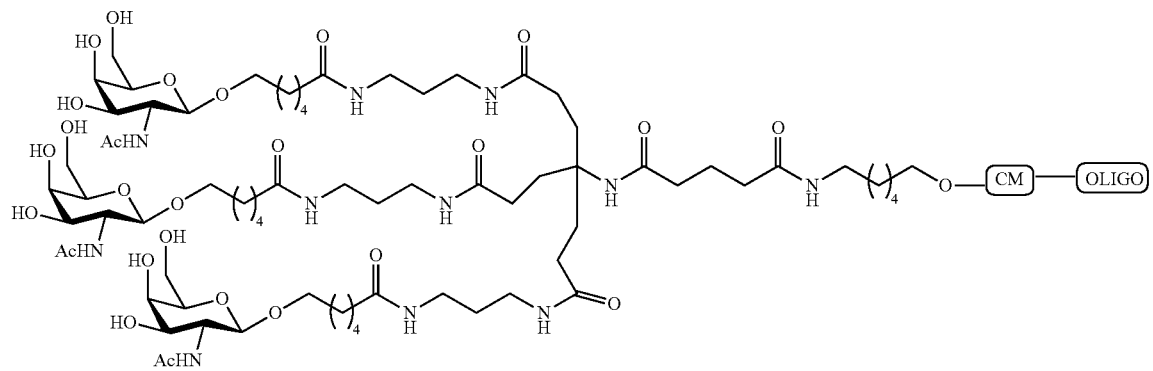

201

Oligomeric compound 201, comprising a GalNAc₃-18 conjugate group, was prepared using the general procedures illustrated in Example 46. The GalNAc₃ cluster portion of the conjugate group GalNAc₃-18 (GalNAc₃-18$_a$) can be combined with any cleavable moiety to provide a variety of conjugate groups. In certain embodiments, the cleavable moiety is —P(=O)(OH)-A$_d$-P(=O)(OH)—. The structure of GalNAc₃-18 (GalNAc₃-18$_a$-CM-) is shown below:

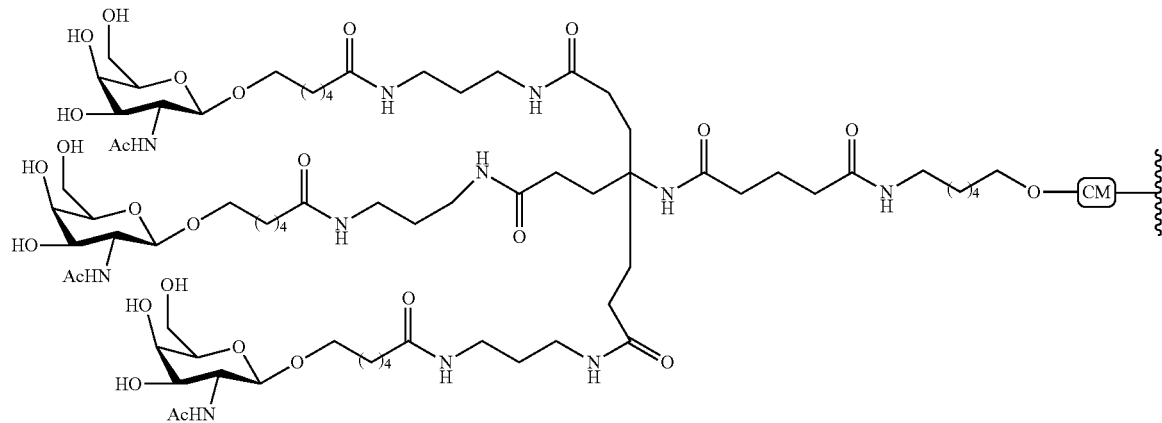

Example 70
Preparation of Oligomeric Compound 204 Comprising GalNAc$_3$-19
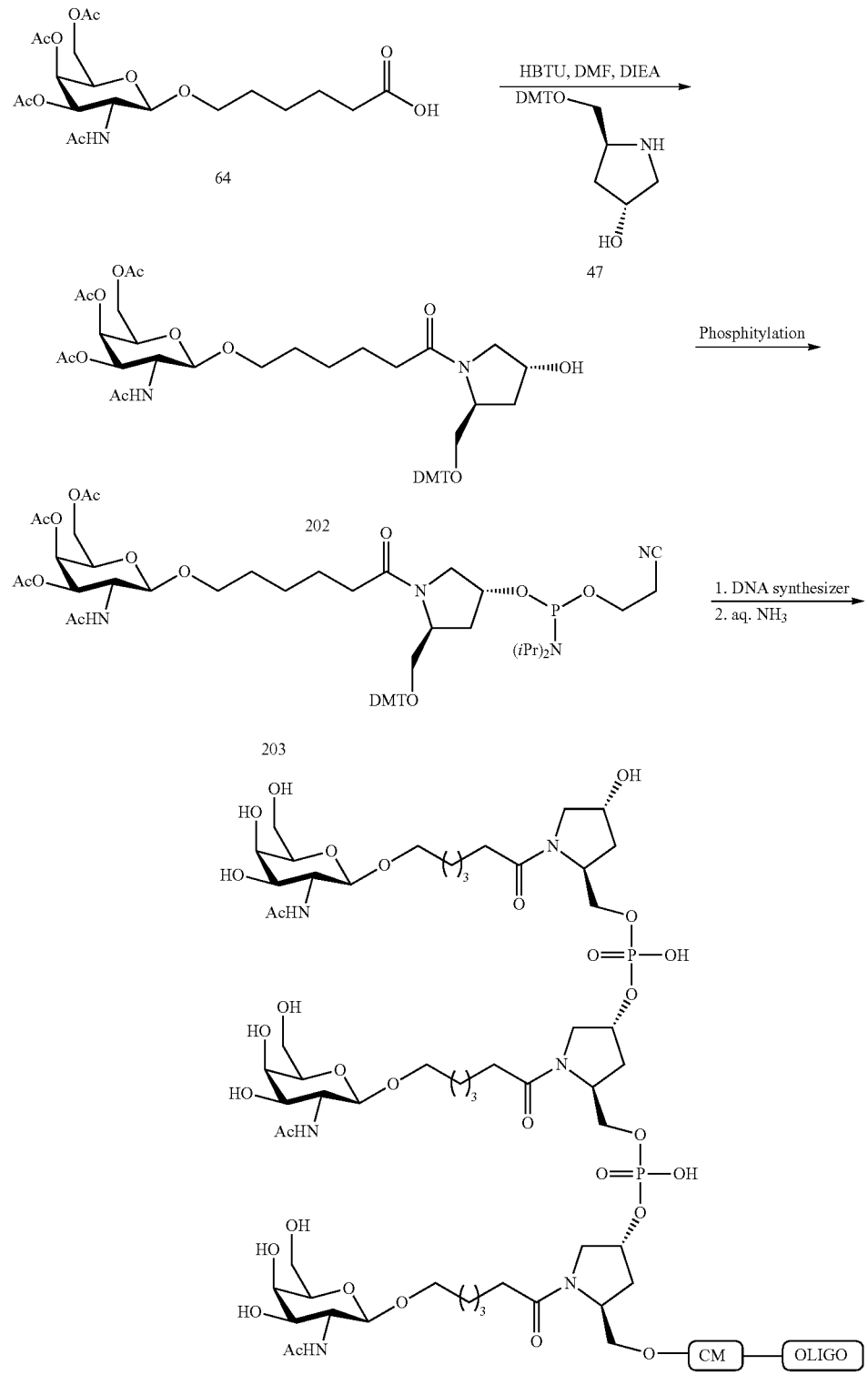

Oligomeric compound 204, comprising a GalNAc$_3$-19 conjugate group, was prepared from compound 64 using the general procedures illustrated in Example 52. The GalNAc$_3$ cluster portion of the conjugate group GalNAc$_3$-19 (GalNAc$_3$-19$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-19 (GalNAc$_3$-19$_a$-CM-) is shown below:

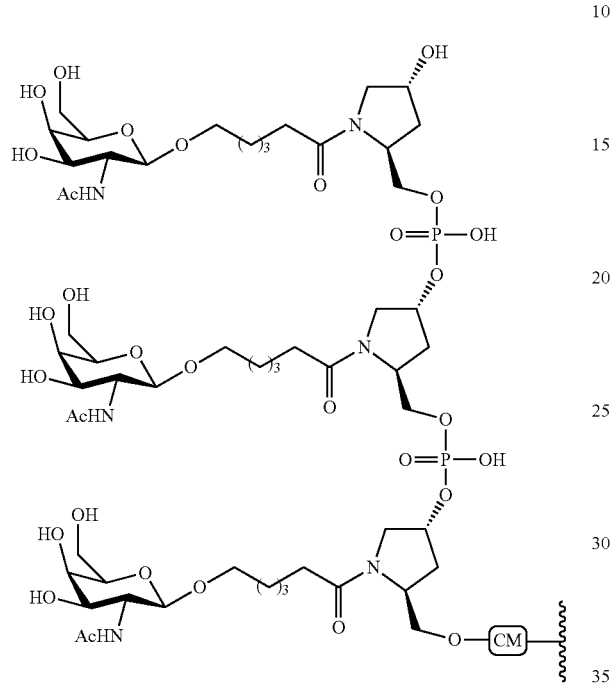

Example 71

Preparation of Oligomeric Compound 210 Comprising GalNAc$_3$-20

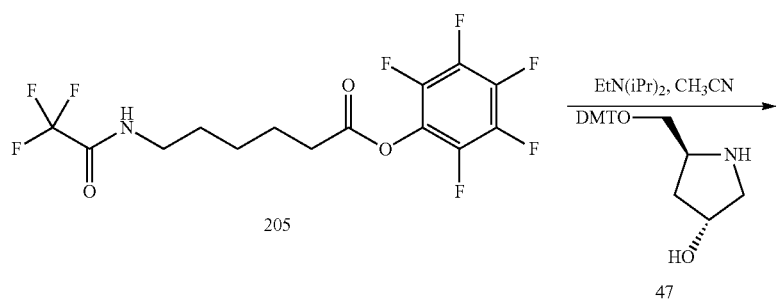

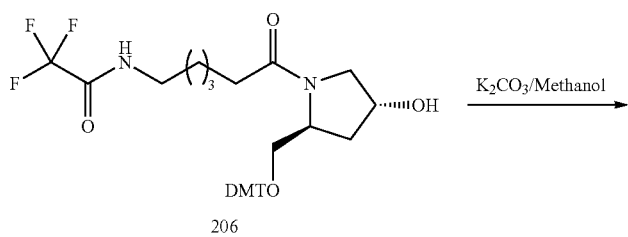

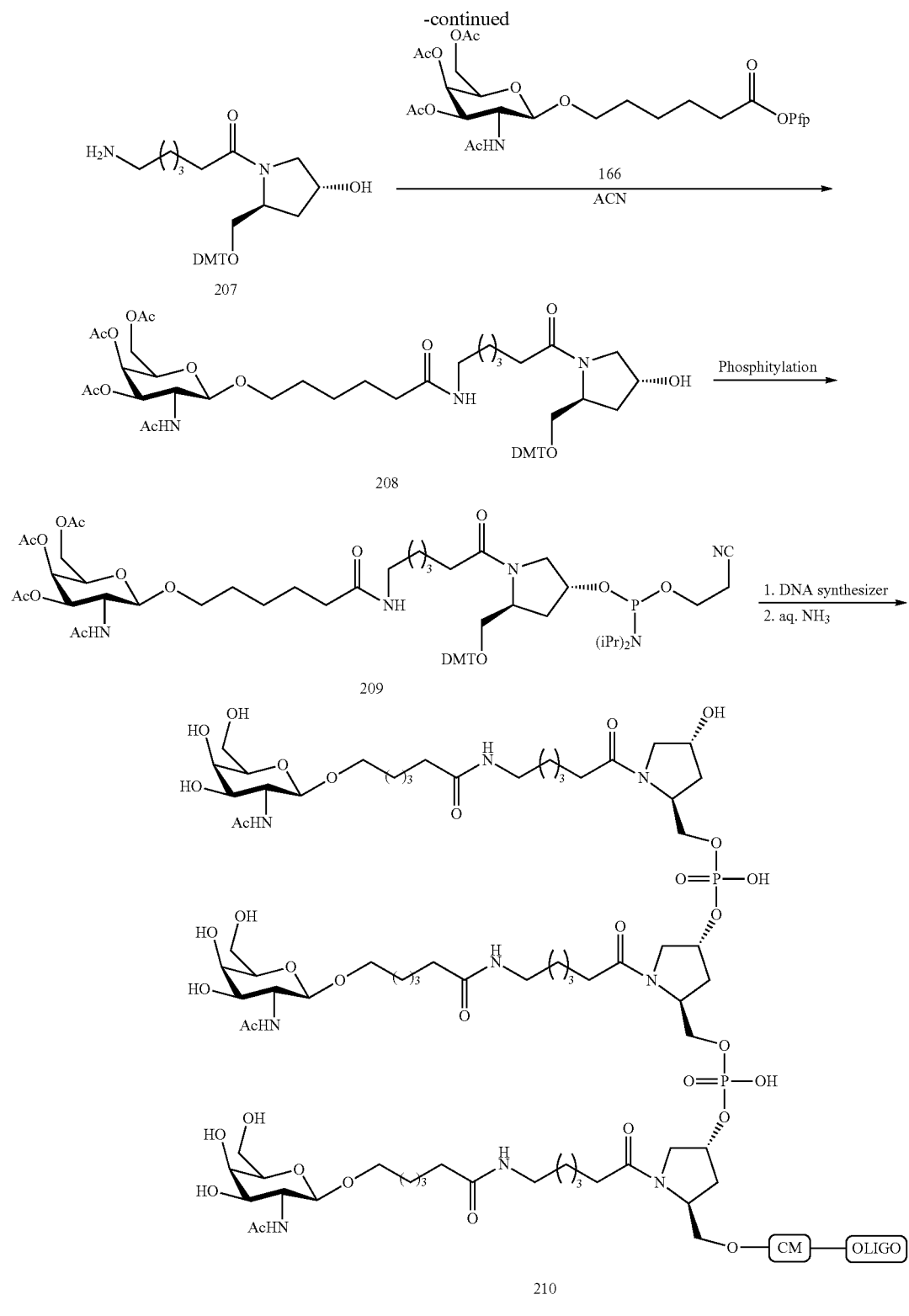

Compound 205 was prepared by adding PFP-TFA and DIEA to 6-(2,2,2-trifluoroacetamido)hexanoic acid in acetonitrile, which was prepared by adding triflic anhydride to 6-aminohexanoic acid. The reaction mixture was heated to 80° C., then lowered to rt. Oligomeric compound 210, comprising a GalNAc$_3$-20 conjugate group, was prepared from compound 208 using the general procedures illustrated in Example 52. The GalNAc$_3$ cluster portion of the conjugate group GalNAc$_3$-20 (GalNAc$_3$-20$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-20 (GalNAc$_3$-20$_a$-CM-) is shown below:

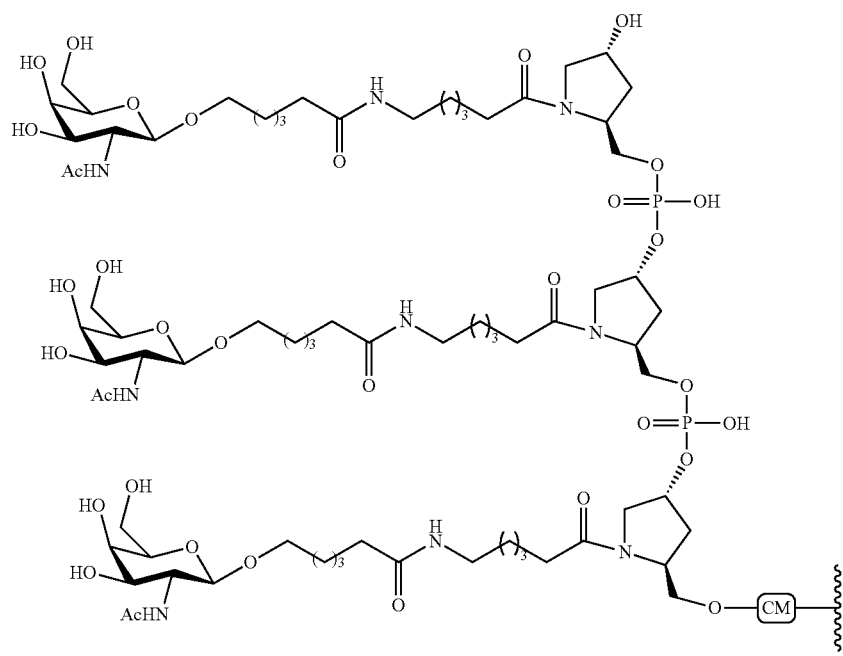
Example 72
Preparation of Oligomeric Compound 215 Comprising GalNAc$_3$-21
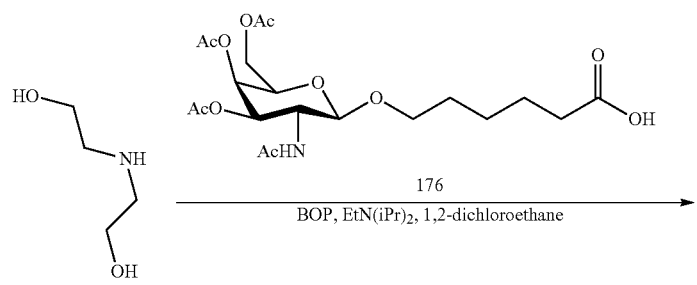
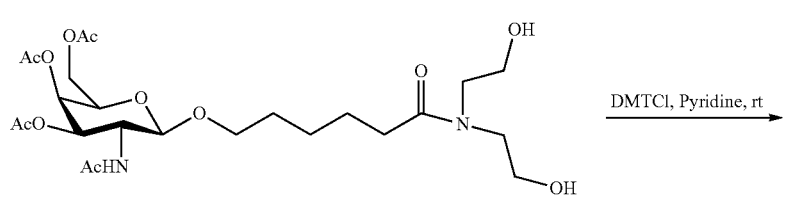

-continued
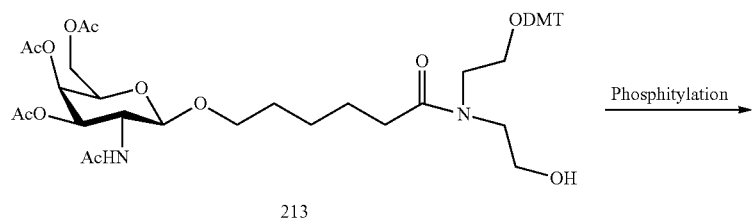
213
Phosphitylation →
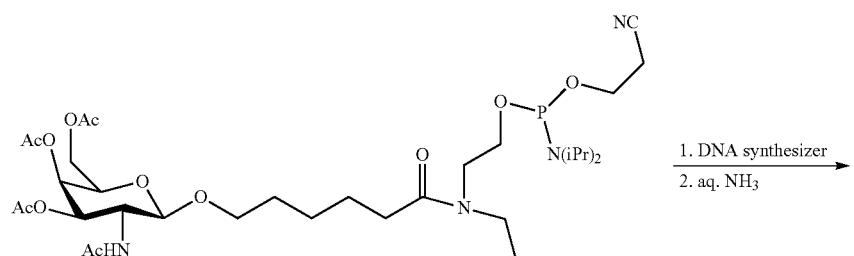
214
1. DNA synthesizer
2. aq. NH₃ →
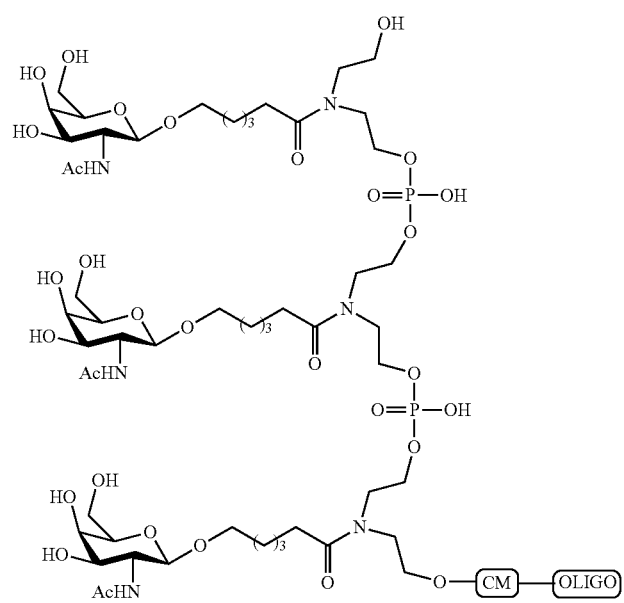
215

Compound 211 is commercially available. Oligomeric compound 215, comprising a GalNAc$_3$-21 conjugate group, was prepared from compound 213 using the general procedures illustrated in Example 52. The GalNAc$_3$ cluster portion of the conjugate group GalNAc$_3$-21 (GalNAc$_3$-21$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-21 (GalNAc$_3$-21$_a$-CM-) is shown below:

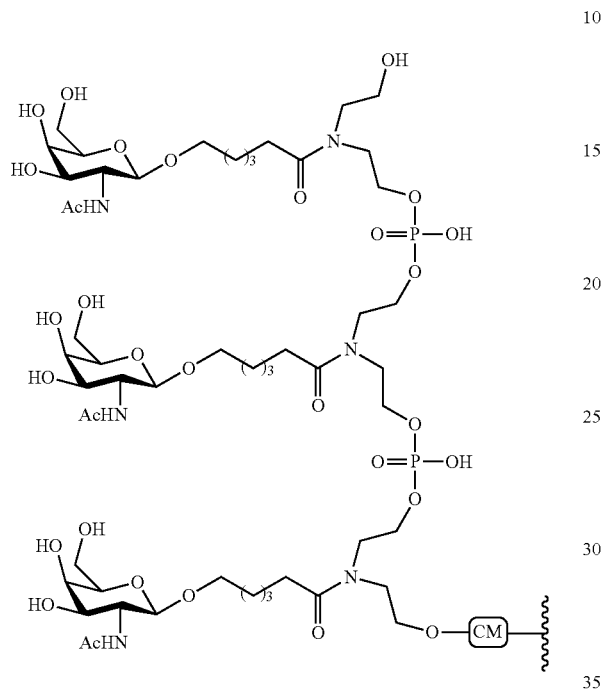

Example 73

Preparation of Oligomeric Compound 221 Comprising GalNAc$_3$-22

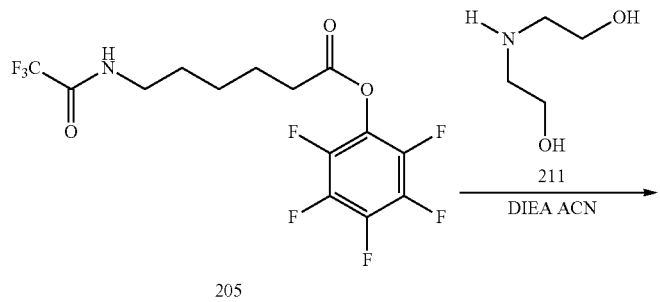

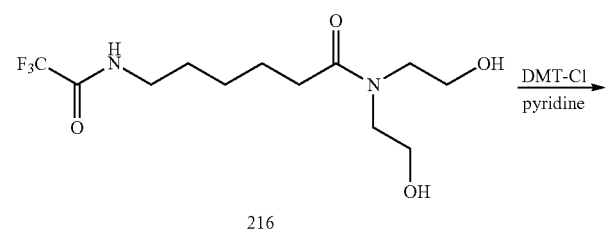

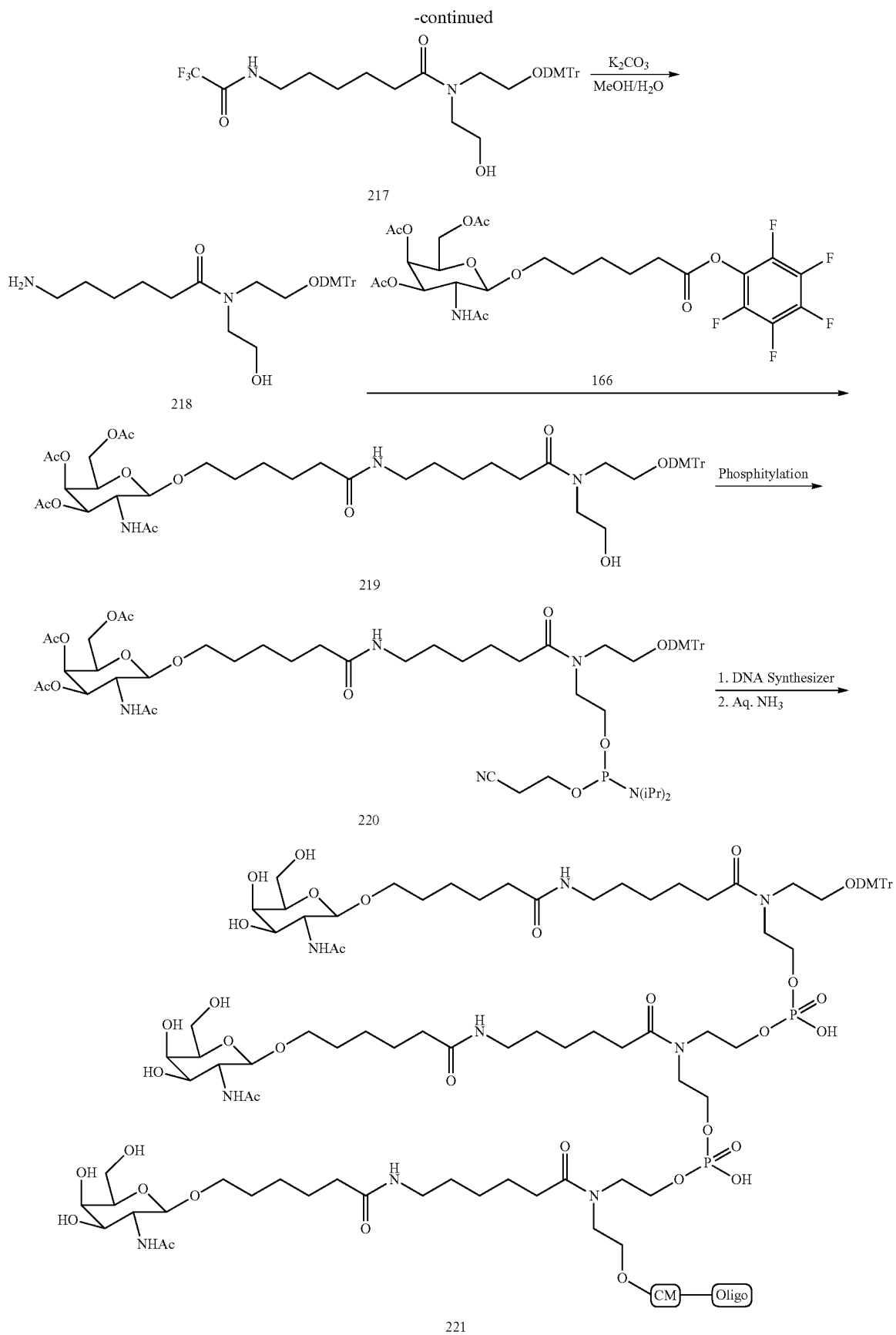

Compound 220 was prepared from compound 219 using diisopropylammonium tetrazolide. Oligomeric compound 221, comprising a GalNAc$_3$-21 conjugate group, is prepared from compound 220 using the general procedure illustrated in Example 52. The GalNAc$_3$ cluster portion of the conjugate group GalNAc$_3$-22 (GalNAc$_3$-22$_a$) can be combined with any cleavable moiety to provide a variety of conjugate groups. In certain embodiments, the cleavable moiety is —P(=O)(OH)-A$_d$-P(=O)(OH)—. The structure of GalNAc$_3$-22 (GalNAc$_3$-22$_a$-CM-) is shown below:

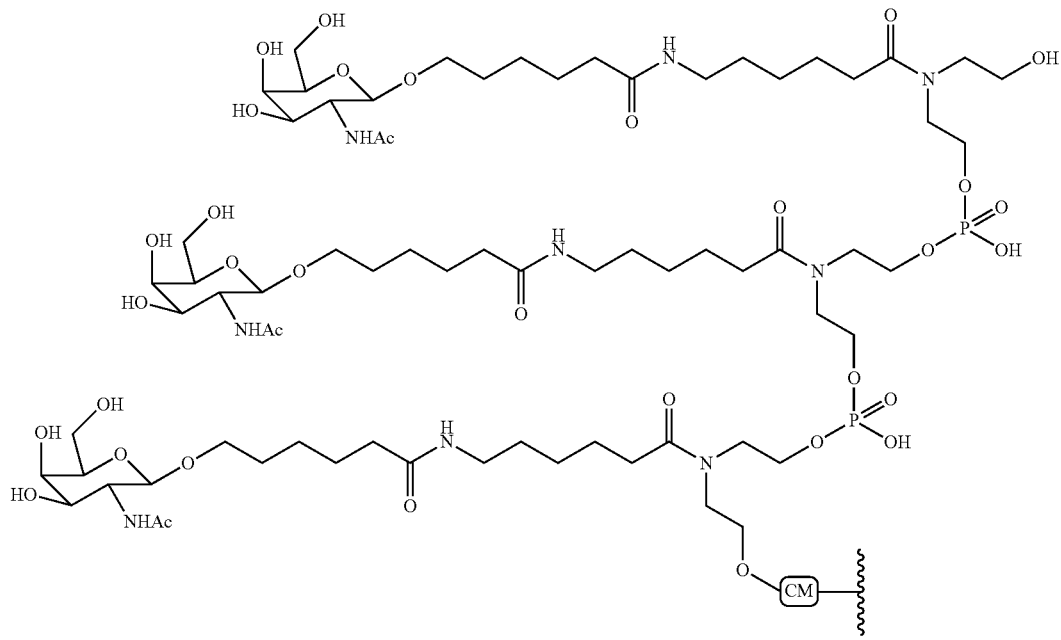

Example 74

Effect of Various Cleavable Moieties on Antisense Inhibition In Vivo by Oligonucleotides Targeting SRB-1 Comprising a 5'-GalNAc$_3$ Conjugate The oligonucleotides listed below were tested in a dose-dependent study for antisense inhibition of SRB-1 in mice. Each of the GalNAc$_3$ conjugate groups was attached at the 5' terminus of the respective oligonucleotide.

TABLE 47

Modified ASOs targeting SRB-1

| ISIS No. | Sequences (5' to 3') | GalNAc$_3$ Cluster | CM | SEQ ID No. |
|---|---|---|---|---|
| 353382 | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | n/a | n/a | 28 |
| 661161 | GalNAc$_3$-3$_a$-$_o$,A$_{ds}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | GalNAc$_3$-3a | A$_d$ | 30 |
| 666904 | GalNAc$_3$-3$_{a-o}$,G$_{es}$$^m$C$_{es}$ T$_{es}$T$_{es}$$^m$C$_{es}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{es}$ $^m$C$_{es}$$^m$C$_{es}$T$_{es}$T$_e$ | GalNAc$_3$-3a | PO | 28 |
| 675441 | GalNAc$_3$-17$_a$-$_o$,A$_{do}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | GalNAc$_3$-17a | A$_d$ | 30 |
| 675442 | GalNAc$_3$-18$_a$-$_o$,A$_{do}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | GalNAc$_3$-18a | A$_d$ | 30 |

In all tables, capital letters indicate the nucleobase for each nucleoside and $^m$C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—. Conjugate groups are in bold.

The structure of GalNAc$_3$-3$_a$ was shown previously in Example 39. The structure of GalNAc$_3$-17a was shown previously in Example 68, and the structure of GalNAc$_3$-18a was shown in Example 69.

Treatment

Six to eight week old C57BL/6 mice (Jackson Laboratory, Bar Harbor, Me.) were injected subcutaneously once at the dosage shown below with an oligonucleotide listed in Table 47 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 48, treatment with antisense oligonucleotides lowered SRB-1 mRNA levels in a dose-dependent manner. The antisense oligonucleotides comprising a GalNAc conjugate showed similar potencies and were significantly more potent than the parent oligonucleotide lacking a GalNAc conjugate.

TABLE 48

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 353382 | 3 | 79.38 | n/a | n/a |
|  | 10 | 68.67 |  |  |
|  | 30 | 40.70 |  |  |
| 661161 | 0.5 | 79.18 | GalNAc$_3$-3a | A$_d$ |
|  | 1.5 | 75.96 |  |  |
|  | 5 | 30.53 |  |  |
|  | 15 | 12.52 |  |  |
| 666904 | 0.5 | 91.30 | GalNAc$_3$-3a | PO |
|  | 1.5 | 57.88 |  |  |
|  | 5 | 21.22 |  |  |
|  | 15 | 16.49 |  |  |
| 675441 | 0.5 | 76.71 | GalNAc$_3$-17a | A$_d$ |
|  | 1.5 | 63.63 |  |  |
|  | 5 | 29.57 |  |  |
|  | 15 | 13.49 |  |  |
| 675442 | 0.5 | 95.03 | GalNAc$_3$-18a | A$_d$ |
|  | 1.5 | 60.06 |  |  |
|  | 5 | 31.04 |  |  |
|  | 15 | 19.40 |  |  |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group (data not shown). ALTs, ASTs, total bilirubin and BUN values are shown in Table 49 below.

TABLE 49

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 26 | 59 | 0.16 | 42 | n/a | n/a |
| 353382 | 3 | 23 | 58 | 0.18 | 39 | n/a | n/a |
|  | 10 | 28 | 58 | 0.16 | 43 |  |  |
|  | 30 | 20 | 48 | 0.12 | 34 |  |  |
| 661161 | 0.5 | 30 | 47 | 0.13 | 35 | GalNac$_3$-3a | A$_d$ |
|  | 1.5 | 23 | 53 | 0.14 | 37 |  |  |
|  | 5 | 26 | 48 | 0.15 | 39 |  |  |
|  | 15 | 32 | 57 | 0.15 | 42 |  |  |
| 666904 | 0.5 | 24 | 73 | 0.13 | 36 | GalNac$_3$-3a | PO |
|  | 1.5 | 21 | 48 | 0.12 | 32 |  |  |
|  | 5 | 19 | 49 | 0.14 | 33 |  |  |
|  | 15 | 20 | 52 | 0.15 | 26 |  |  |
| 675441 | 0.5 | 42 | 148 | 0.21 | 36 | GalNac$_3$-17a | A$_d$ |
|  | 1.5 | 60 | 95 | 0.16 | 34 |  |  |
|  | 5 | 27 | 75 | 0.14 | 37 |  |  |
|  | 15 | 24 | 61 | 0.14 | 36 |  |  |
| 675442 | 0.5 | 26 | 65 | 0.15 | 37 | GalNac$_3$-18a | A$_d$ |
|  | 1.5 | 25 | 64 | 0.15 | 43 |  |  |
|  | 5 | 27 | 69 | 0.15 | 37 |  |  |
|  | 15 | 30 | 84 | 0.14 | 37 |  |  |

Example 75

Pharmacokinetic Analysis of Oligonucleotides Comprising a 5'-Conjugate Group

The PK of the ASOs in Tables 41, 44 and 47 above was evaluated using liver samples that were obtained following the treatment procedures described in Examples 65, 66, and 74. The liver samples were minced and extracted using standard protocols and analyzed by IP-HPLC-MS alongside an internal standard. The combined tissue level (µg/g) of all metabolites was measured by integrating the appropriate UV peaks, and the tissue level of the full-length ASO missing the conjugate ("parent," which is Isis No. 353382 in this case) was measured using the appropriate extracted ion chromatograms (EIC).

TABLE 50

PK Analysis in Liver

| ISIS No. | Dosage (mg/kg) | Total Tissue Level by UV (µg/g) | Parent ASO Tissue Level by EIC (µg/g) | GalNAc$_3$ Cluster | CM |
|---|---|---|---|---|---|
| 353382 | 3 | 8.9 | 8.6 | n/a | n/a |
|  | 10 | 22.4 | 21.0 |  |  |
|  | 30 | 54.2 | 44.2 |  |  |
| 661161 | 5 | 32.4 | 20.7 | GalNAc$_3$-3a | A$_d$ |
|  | 15 | 63.2 | 44.1 |  |  |
| 671144 | 5 | 20.5 | 19.2 | GalNAc$_3$-12a | A$_d$ |
|  | 15 | 48.6 | 41.5 |  |  |
| 670061 | 5 | 31.6 | 28.0 | GalNAc$_3$-13a | A$_d$ |
|  | 15 | 67.6 | 55.5 |  |  |
| 671261 | 5 | 19.8 | 16.8 | GalNAc$_3$-14a | A$_d$ |
|  | 15 | 64.7 | 49.1 |  |  |
| 671262 | 5 | 18.5 | 7.4 | GalNAc$_3$-15a | A$_d$ |
|  | 15 | 52.3 | 24.2 |  |  |
| 670699 | 5 | 16.4 | 10.4 | GalNAc$_3$-3a | T$_d$ |
|  | 15 | 31.5 | 22.5 |  |  |

TABLE 50-continued

PK Analysis in Liver

| ISIS No. | Dosage (mg/kg) | Total Tissue Level by UV (µg/g) | Parent ASO Tissue Level by EIC (µg/g) | GalNAc$_3$ Cluster | CM |
|---|---|---|---|---|---|
| 670700 | 5 | 19.3 | 10.9 | GalNAc$_3$-3a | A$_e$ |
| | 15 | 38.1 | 20.0 | | |
| 670701 | 5 | 21.8 | 8.8 | GalNAc$_3$-3a | T$_e$ |
| | 15 | 35.2 | 16.1 | | |
| 671165 | 5 | 27.1 | 26.5 | GalNAc$_3$-13a | A$_d$ |
| | 15 | 48.3 | 44.3 | | |
| 666904 | 5 | 30.8 | 24.0 | GalNAc$_3$-3a | PO |
| | 15 | 52.6 | 37.6 | | |
| 675441 | 5 | 25.4 | 19.0 | GalNAc$_3$-17a | A$_d$ |
| | 15 | 54.2 | 42.1 | | |
| 675442 | 5 | 22.2 | 20.7 | GalNAc$_3$-18a | A$_d$ |
| | 15 | 39.6 | 29.0 | | |

The results in Table 50 above show that there were greater liver tissue levels of the oligonucleotides comprising a GalNAc$_3$ conjugate group than of the parent oligonucleotide that does not comprise a GalNAc$_3$ conjugate group (ISIS 353382) 72 hours following oligonucleotide administration, particularly when taking into consideration the differences in dosing between the oligonucleotides with and without a GalNAc$_3$ conjugate group. Furthermore, by 72 hours, 40-98% of each oligonucleotide comprising a GalNAc$_3$ conjugate group was metabolized to the parent compound, indicating that the GalNAc$_3$ conjugate groups were cleaved from the oligonucleotides.

Example 76

Preparation of Oligomeric Compound 230 Comprising GalNAc$_3$-23

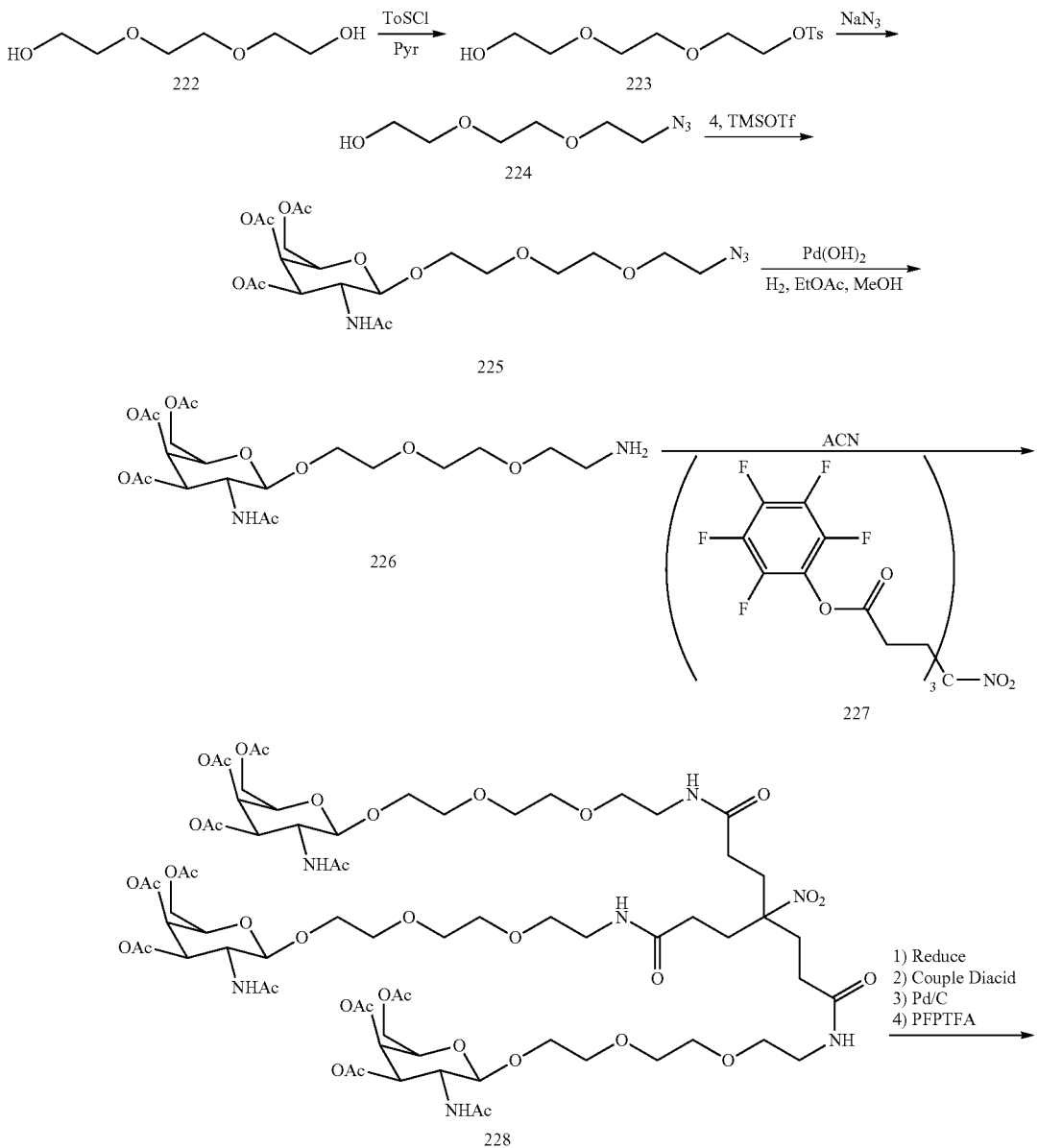

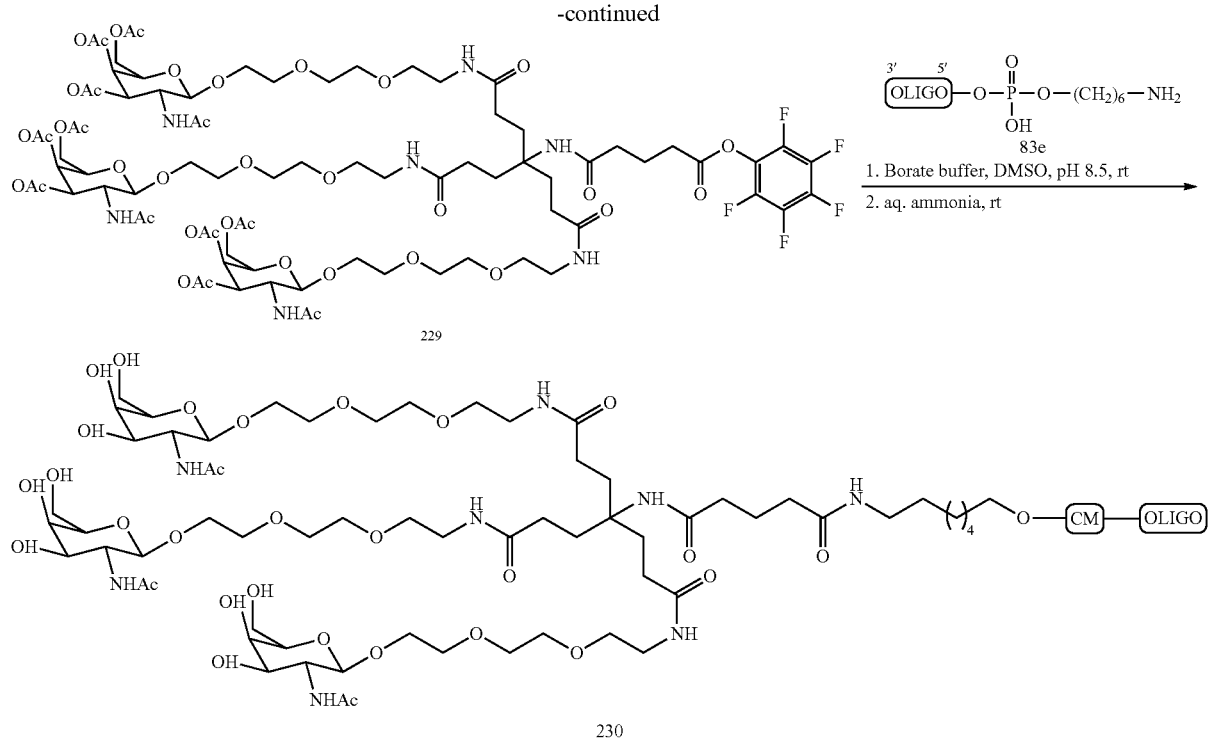

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. $NaHCO_3$, brine, and dried over $Na_2SO_4$. The ethyl acetate was concentrated to dryness and purified by column chromatography, eluted with EtOAc/hexanes (1:1) followed by 10% methanol in $CH_2Cl_2$ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO (100 mL) at room temperature for 17 hours. The reaction mixture was then poured onto water, and extracted with EtOAc. The organic layer was washed with water three times and dried over $Na_2SO_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4 A molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. $NaHCO_3$, water, brine, and dried over $Na_2SO_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over $Na_2SO_4$. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 µl, 1.6 mmol) in DMF (5 mL). After 16 hours, the DMF was removed under reduced pressure at 65° C. to an oil, and the oil was dissolved in dichloromethane. The organic layer was washed with sat. $NaHCO_3$, brine, and dried over $Na_2SO_4$. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 µl, 0.66 mmol) was added and the reaction was purged with argon.

Pentaflourotriflouro acetate (46.39 μl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with 1N NaHSO$_4$, brine, saturated sodium bicarbonate and brine again. The organics were dried over Na$_2$SO$_4$, filtered, and were concentrated to dryness to give 225 mg of compound 229 as a brittle yellow foam. LCMS and NMR were consistent with the structure.

Oligomeric compound 230, comprising a GalNAc$_3$-23 conjugate group, was prepared from compound 229 using the general procedure illustrated in Example 46. The GalNAc$_3$ cluster portion of the GalNAc$_3$-23 conjugate group (GalNAc$_3$-23$_a$) can be combined with any cleavable moiety to provide a variety of conjugate groups. The structure of GalNAc$_3$-23 (GalNAc$_3$-23$_a$-CM) is shown below:

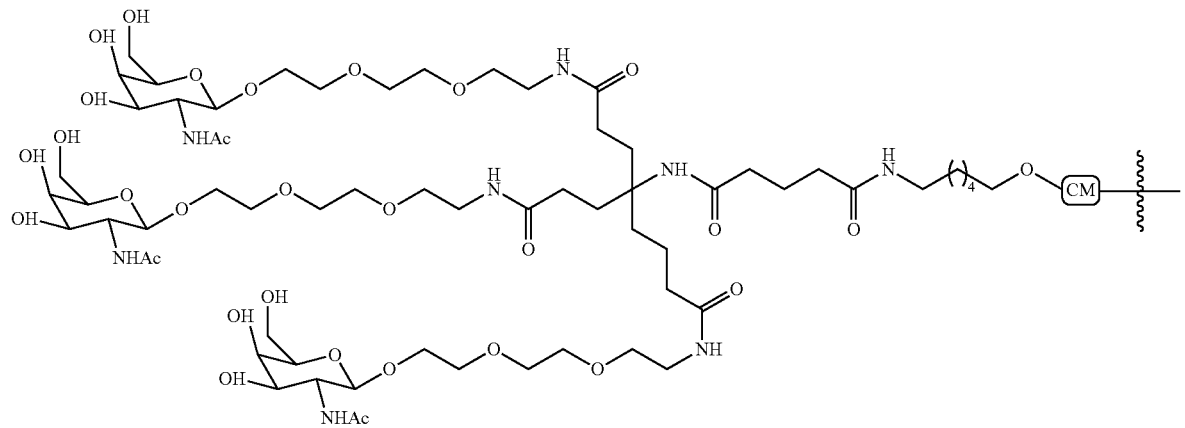

Example 77

Antisense Inhibition In Vivo by Oligonucleotides Targeting SRB-1 Comprising a GalNAc$_3$ Conjugate The oligonucleotides listed below were tested in a dose-dependent study for antisense inhibition of SRB-1 in mice.

TABLE 51

Modified ASOs targeting SRB-1

| ISIS No. | Sequences (5' to 3') | GalNAc$_3$ Cluster | CM | SEQ ID No. |
|---|---|---|---|---|
| 661161 | GalNAc$_3$-3$_a$-$_o$,A$_{do}$<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_e$ | GalNAc$_3$-3a | A$_d$ | 30 |
| 666904 | GalNAc$_3$-3$_a$-$_o$,<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_e$ | GalNAc$_3$-3a | PO | 28 |
| 673502 | GalNAc$_3$-10$_a$-$_o$,A$_{do}$<br>G$_{es}$$^m$C$_{eo}$T$_{eo}$T$_{eo}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{eo}$$^m$C$_{eo}$$^m$C$_{es}$T$_{es}$T$_e$ | GalNAc$_3$-10a | A$_d$ | 30 |
| 677844 | GalNAc$_3$-9$_a$-$_o$,A$_{do}$<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_e$ | GalNAc$_3$-9a | A$_d$ | 30 |
| 677843 | GalNAc$_3$-23$_a$-$_o$,A$_{do}$<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_e$ | GalNAc$_3$-23a | A$_d$ | 30 |
| 655861 | G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_{eo}$<br>A$_{do}$,-GalNAc$_3$-1$_a$ | GalNAc$_3$-1a | A$_d$ | 29 |
| 677841 | G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_{eo}$<br>A$_{do}$,-GalNAc$_3$-19$_a$ | GalNAc$_3$-19a | A$_d$ | 29 |
| 677842 | G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_{eo}$<br>A$_{do}$,-GalNAc$_3$-20$_a$ | GalNAc$_3$-20a | A$_d$ | 29 |

The structure of GalNAc$_3$-1$_a$ was shown previously in Example 9, GalNAc$_3$-3$_a$ was shown in Example 39, GalNAc$_3$-9a was shown in Example 52, GalNAc$_3$-10a was shown in Example 46, GalNAc$_3$-19$_a$ was shown in Example 70, GalNAc$_3$-20$_a$ was shown in Example 71, and GalNAc$_3$-23$_a$ was shown in Example 76.

Treatment

Six to eight week old C57BL/6 mice (Jackson Laboratory, Bar Harbor, Me.) were each injected subcutaneously once at a dosage shown below with an oligonucleotide listed in Table 51 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, Oreg.) according to standard protocols. The results below are presented as the average percent of SRB-1 mRNA levels for each treatment group, normalized to the saline control.

As illustrated in Table 52, treatment with antisense oligonucleotides lowered SRB-1 mRNA levels in a dose-dependent manner.

TABLE 52

SRB-1 mRNA (% Saline)

| ISIS No. | Dosage (mg/kg) | SRB-1 mRNA (% Saline) | GalNAc$_3$ Cluster | CM |
|---|---|---|---|---|
| Saline | n/a | 100.0 | n/a | n/a |
| 661161 | 0.5 | 89.18 | GalNAc$_3$-3a | A$_d$ |
|  | 1.5 | 77.02 |  |  |
|  | 5 | 29.10 |  |  |
|  | 15 | 12.64 |  |  |
| 666904 | 0.5 | 93.11 | GalNAc$_3$-3a | PO |
|  | 1.5 | 55.85 |  |  |
|  | 5 | 21.29 |  |  |
|  | 15 | 13.43 |  |  |
| 673502 | 0.5 | 77.75 | GalNAc$_3$-10a | A$_d$ |
|  | 1.5 | 41.05 |  |  |
|  | 5 | 19.27 |  |  |
|  | 15 | 14.41 |  |  |
| 677844 | 0.5 | 87.65 | GalNAc$_3$-9a | A$_d$ |
|  | 1.5 | 93.04 |  |  |
|  | 5 | 40.77 |  |  |
|  | 15 | 16.95 |  |  |
| 677843 | 0.5 | 102.28 | GalNAc$_3$-23a | A$_d$ |
|  | 1.5 | 70.51 |  |  |
|  | 5 | 30.68 |  |  |
|  | 15 | 13.26 |  |  |
| 655861 | 0.5 | 79.72 | GalNAc$_3$-1a | A$_d$ |
|  | 1.5 | 55.48 |  |  |
|  | 5 | 26.99 |  |  |
|  | 15 | 17.58 |  |  |
| 677841 | 0.5 | 67.43 | GalNAc$_3$-19a | A$_d$ |
|  | 1.5 | 45.13 |  |  |
|  | 5 | 27.02 |  |  |
|  | 15 | 12.41 |  |  |
| 677842 | 0.5 | 64.13 | GalNAc$_3$-20a | A$_d$ |
|  | 1.5 | 53.56 |  |  |
|  | 5 | 20.47 |  |  |
|  | 15 | 10.23 |  |  |

Liver transaminase levels, alanine aminotransferase (ALT) and aspartate aminotransferase (AST), in serum were also measured using standard protocols. Total bilirubin and BUN were also evaluated. Changes in body weights were evaluated, with no significant change from the saline group (data not shown). ALTs, ASTs, total bilirubin and BUN values are shown in Table 53 below.

TABLE 53

| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| Saline | n/a | 21 | 45 | 0.13 | 34 | n/a | n/a |
| 661161 | 0.5 | 28 | 51 | 0.14 | 39 | GalNac$_3$-3a | A$_d$ |
|  | 1.5 | 23 | 42 | 0.13 | 39 |  |  |
|  | 5 | 22 | 59 | 0.13 | 37 |  |  |
|  | 15 | 21 | 56 | 0.15 | 35 |  |  |
| 666904 | 0.5 | 24 | 56 | 0.14 | 37 | GalNac$_3$-3a | PO |
|  | 1.5 | 26 | 68 | 0.15 | 35 |  |  |
|  | 5 | 23 | 77 | 0.14 | 34 |  |  |
|  | 15 | 24 | 60 | 0.13 | 35 |  |  |
| 673502 | 0.5 | 24 | 59 | 0.16 | 34 | GalNac$_3$-10a | A$_d$ |
|  | 1.5 | 20 | 46 | 0.17 | 32 |  |  |
|  | 5 | 24 | 45 | 0.12 | 31 |  |  |
|  | 15 | 24 | 47 | 0.13 | 34 |  |  |
| 677844 | 0.5 | 25 | 61 | 0.14 | 37 | GalNac$_3$-9a | A$_d$ |
|  | 1.5 | 23 | 64 | 0.17 | 33 |  |  |
|  | 5 | 25 | 58 | 0.13 | 35 |  |  |
|  | 15 | 22 | 65 | 0.14 | 34 |  |  |
| 677843 | 0.5 | 53 | 53 | 0.13 | 35 | GalNac$_3$-23a | A$_d$ |
|  | 1.5 | 25 | 54 | 0.13 | 34 |  |  |
|  | 5 | 21 | 60 | 0.15 | 34 |  |  |
|  | 15 | 22 | 43 | 0.12 | 38 |  |  |
| 655861 | 0.5 | 21 | 48 | 0.15 | 33 | GalNac$_3$-1a | A$_d$ |
|  | 1.5 | 28 | 54 | 0.12 | 35 |  |  |
|  | 5 | 22 | 60 | 0.13 | 36 |  |  |
|  | 15 | 21 | 55 | 0.17 | 30 |  |  |
| 677841 | 0.5 | 32 | 54 | 0.13 | 34 | GalNac$_3$-19a | A$_d$ |
|  | 1.5 | 24 | 56 | 0.14 | 34 |  |  |
|  | 5 | 23 | 92 | 0.18 | 31 |  |  |
|  | 15 | 24 | 58 | 0.15 | 31 |  |  |
| 677842 | 0.5 | 23 | 61 | 0.15 | 35 | GalNac$_3$-20a | A$_d$ |
|  | 1.5 | 24 | 57 | 0.14 | 34 |  |  |
|  | 5 | 41 | 62 | 0.15 | 35 |  |  |
|  | 15 | 24 | 37 | 0.14 | 32 |  |  |

Example 78

Antisense Inhibition In Vivo by Oligonucleotides Targeting Angiotensinogen Comprising a GalNAc$_3$ Conjugate The oligonucleotides listed below were tested in a dose-dependent study for antisense inhibition of Angiotensinogen (AGT) in normotensive Sprague Dawley rats.

TABLE 54

Modified ASOs targeting AGT

| ISIS No. | Sequences (5' to 3') | GalNAc$_3$ Cluster | CM | SEQ ID No. |
|---|---|---|---|---|
| 552668 | $^mC_{es}A_{es}{}^mC_{es}T_{es}G_{es}A_{ds}T_{ds}$ $T_{ds}T_{ds}T_{ds}T_{ds}G_{ds}{}^mC_{ds}{}^mC_{ds}$ $^mC_{ds}A_{es}G_{es}G_{es}A_{es}T_e$ | n/a | n/a | 34 |
| 669509 | $^mC_{es}A_{es}{}^mC_{es}T_{es}G_{es}A_{ds}T_{ds}$ $T_{ds}T_{ds}T_{ds}T_{ds}G_{ds}{}^mC_{ds}{}^mC_{ds}$ $^mC_{ds}A_{es}G_{es}G_{es}A_{es}T_{eo}$ A$_{do}$,-GalNAc$_3$-1$_a$ | GalNAc$_3$-1$_a$ | A$_d$ | 35 |

The structure of GalNAc$_3$-1$_a$ was shown previously in Example 9.

Treatment

Six week old, male Sprague Dawley rats were each injected subcutaneously once per week at a dosage shown below, for a total of three doses, with an oligonucleotide listed in Table 54 or with PBS. Each treatment group consisted of 4 animals. The rats were sacrificed 72 hours following the final dose. AGT liver mRNA levels were measured using real-time PCR and RIBOGREEN® RNA quantification reagent (Molecular Probes, Inc. Eugene, Oreg.) according to standard protocols. AGT plasma protein levels were measured using the Total Angiotensinogen ELISA (Catalog #JP27412, IBL International, Toronto, ON) with plasma diluted 1:20,000. The results below are presented as the average percent of AGT mRNA levels in liver or AGT protein levels in plasma for each treatment group, normalized to the PBS control.

As illustrated in Table 55, treatment with antisense oligonucleotides lowered AGT liver mRNA and plasma protein levels in a dose-dependent manner, and the oligonucleotide comprising a GalNAc conjugate was significantly more potent than the parent oligonucleotide lacking a GalNAc conjugate.

TABLE 55

AGT liver mRNA and plasma protein levels

| ISIS No. | Dosage (mg/kg) | AGT liver mRNA (% PBS) | AGT plasma protein (% PBS) | GalNAc$_3$ Cluster | CM |
|---|---|---|---|---|---|
| PBS | n/a | 100 | 100 | n/a | n/a |
| 552668 | 3 | 95 | 122 | n/a | n/a |
|  | 10 | 85 | 97 |  |  |
|  | 30 | 46 | 79 |  |  |
|  | 90 | 8 | 11 |  |  |
| 669509 | 0.3 | 95 | 70 | GalNAc$_3$-1a | A$_d$ |
|  | 1 | 95 | 129 |  |  |
|  | 3 | 62 | 97 |  |  |
|  | 10 | 9 | 23 |  |  |

Liver transaminase levels, alanine aminotransferase (ALT) and aspartate aminotransferase (AST), in plasma and body weights were also measured at time of sacrifice using standard protocols. The results are shown in Table 56 below.

TABLE 56

Liver transaminase levels and rat body weights

| ISIS No. | Dosage (mg/kg) | ALT (U/L) | AST (U/L) | Body Weight (% of baseline) | GalNAc$_3$ Cluster | CM |
|---|---|---|---|---|---|---|
| PBS | n/a | 51 | 81 | 186 | n/a | n/a |
| 552668 | 3 | 54 | 93 | 183 | n/a | n/a |
|  | 10 | 51 | 93 | 194 |  |  |
|  | 30 | 59 | 99 | 182 |  |  |
|  | 90 | 56 | 78 | 170 |  |  |
| 669509 | 0.3 | 53 | 90 | 190 | GalNAc$_3$-1a | A$_d$ |
|  | 1 | 51 | 93 | 192 |  |  |
|  | 3 | 48 | 85 | 189 |  |  |
|  | 10 | 56 | 95 | 189 |  |  |

Example 79

Duration of Action In Vivo of Oligonucleotides Targeting APOC-III Comprising a GalNAc$_3$ Conjugate The oligonucleotides listed in Table 57 below were tested in a single dose study for duration of action in mice.

TABLE 57

Modified ASOs targeting APOC-III

| ISIS No. | Sequences (5' to 3') | GalNAc$_3$ Cluster | CM | SEQ ID No. |
|---|---|---|---|---|
| 304801 | $A_{es}G_{es}{}^mC_{es}T_{es}T_{es}{}^mC_{ds}T_{ds}$ $T_{ds}G_{ds}T_{ds}{}^mC_{ds}{}^mC_{ds}A_{ds}G_{ds}$ $^mC_{ds}T_{es}T_{es}T_{es}A_{es}T_e$ | n/a | n/a | 20 |
| 647535 | $A_{es}G_{es}{}^mC_{es}T_{es}T_{es}{}^mC_{ds}T_{ds}$ $T_{ds}G_{ds}T_{ds}{}^mC_{ds}{}^mC_{ds}A_{ds}G_{ds}$ $^mC_{ds}T_{es}T_{es}T_{es}A_{es}T_{eo}$ A$_{do}$,-GalNAc$_3$-1$_a$ | GalNAc$_3$-1a | A$_d$ | 21 |
| 663083 | GalNAc$_3$-3$_a$-$_o$,A$_{do}$ $A_{es}G_{es}{}^mC_{es}T_{es}T_{es}{}^mC_{ds}T_{ds}$ $T_{ds}G_{ds}T_{ds}{}^mC_{ds}{}^mC_{ds}A_{ds}G_{ds}$ $^mC_{ds}T_{es}T_{es}T_{es}A_{es}T_e$ | GalNAc$_3$-3a | A$_d$ | 36 |
| 674449 | GalNAc$_3$-7$_a$-$_o$,A$_{do}$ $A_{es}G_{es}{}^mC_{es}T_{es}T_{es}{}^mC_{ds}T_{ds}$ $T_{ds}G_{ds}T_{ds}{}^mC_{ds}{}^mC_{ds}A_{ds}G_{ds}$ $^mC_{ds}T_{es}T_{es}T_{es}A_{es}T_e$ | GalNAc$_3$-7a | A$_d$ | 36 |
| 674450 | GalNAc$_3$-10$_a$-$_o$,A$_{do}$ $A_{es}G_{es}{}^mC_{es}T_{es}T_{es}{}^mC_{ds}T_{ds}$ $T_{ds}G_{ds}T_{ds}{}^mC_{ds}{}^mC_{ds}A_{ds}G_{ds}$ $^mC_{ds}T_{es}T_{es}T_{es}A_{es}T_e$ | GalNAc$_3$-10 a | A$_d$ | 36 |
| 674451 | GalNAc$_3$-13$_a$-$_o$,A$_{do}$ $A_{es}G_{es}{}^mC_{es}T_{es}T_{es}{}^mC_{ds}T_{ds}$ $T_{ds}G_{ds}T_{ds}{}^mC_{ds}{}^mC_{ds}A_{ds}G_{ds}$ $^mC_{ds}T_{es}T_{es}T_{es}A_{es}T_e$ | GalNAc$_3$-13a | A$_d$ | 36 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six to eight week old transgenic mice that express human APOC-III were each injected subcutaneously once with an oligonucleotide listed in Table 57 or with PBS. Each treatment group consisted of 3 animals. Blood was drawn before dosing to determine baseline and at 72 hours, 1 week, 2 weeks, 3 weeks, 4 weeks, 5 weeks, and 6 weeks following the dose. Plasma triglyceride and APOC-III protein levels were measured as described in Example 20. The results below are presented as the average percent of plasma triglyceride and APOC-III levels for each treatment group, normalized to baseline levels, showing that the oligonucleotides comprising a GalNAc conjugate group exhibited a longer duration of action than the parent oligonucleotide without a conjugate group (ISIS 304801) even though the dosage of the parent was three times the dosage of the oligonucleotides comprising a GalNAc conjugate group.

TABLE 58

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc$_3$ Cluster | CM |
|---|---|---|---|---|---|---|
| PBS | n/a | 3 | 97 | 102 | n/a | n/a |
|  |  | 7 | 101 | 98 |  |  |
|  |  | 14 | 108 | 98 |  |  |
|  |  | 21 | 107 | 107 |  |  |
|  |  | 28 | 94 | 91 |  |  |
|  |  | 35 | 88 | 90 |  |  |
|  |  | 42 | 91 | 105 |  |  |
| 304801 | 30 | 3 | 40 | 34 | n/a | n/a |
|  |  | 7 | 41 | 37 |  |  |
|  |  | 14 | 50 | 57 |  |  |
|  |  | 21 | 50 | 50 |  |  |
|  |  | 28 | 57 | 73 |  |  |
|  |  | 35 | 68 | 70 |  |  |
|  |  | 42 | 75 | 93 |  |  |
| 647535 | 10 | 3 | 36 | 37 | GalNAc$_3$-1a | A$_d$ |
|  |  | 7 | 39 | 47 |  |  |
|  |  | 14 | 40 | 45 |  |  |
|  |  | 21 | 41 | 41 |  |  |
|  |  | 28 | 42 | 62 |  |  |
|  |  | 35 | 69 | 69 |  |  |
|  |  | 42 | 85 | 102 |  |  |
| 663083 | 10 | 3 | 24 | 18 | GalNAc$_3$-3a | A$_d$ |
|  |  | 7 | 28 | 23 |  |  |
|  |  | 14 | 25 | 27 |  |  |
|  |  | 21 | 28 | 28 |  |  |
|  |  | 28 | 37 | 44 |  |  |
|  |  | 35 | 55 | 57 |  |  |
|  |  | 42 | 60 | 78 |  |  |
| 674449 | 10 | 3 | 29 | 26 | GalNAc$_3$-7a | A$_d$ |
|  |  | 7 | 32 | 31 |  |  |
|  |  | 14 | 38 | 41 |  |  |
|  |  | 21 | 44 | 44 |  |  |
|  |  | 28 | 53 | 63 |  |  |
|  |  | 35 | 69 | 77 |  |  |
|  |  | 42 | 78 | 99 |  |  |
| 674450 | 10 | 3 | 33 | 30 | GalNAc$_3$-10a | A$_d$ |
|  |  | 7 | 35 | 34 |  |  |
|  |  | 14 | 31 | 34 |  |  |
|  |  | 21 | 44 | 44 |  |  |
|  |  | 28 | 56 | 61 |  |  |
|  |  | 35 | 68 | 70 |  |  |
|  |  | 42 | 83 | 95 |  |  |
| 674451 | 10 | 3 | 35 | 33 | GalNAc$_3$-13a | A$_d$ |
|  |  | 7 | 24 | 32 |  |  |
|  |  | 14 | 40 | 34 |  |  |
|  |  | 21 | 48 | 48 |  |  |
|  |  | 28 | 54 | 67 |  |  |
|  |  | 35 | 65 | 75 |  |  |
|  |  | 42 | 74 | 97 |  |  |

Example 80

Antisense Inhibition In Vivo by Oligonucleotides Targeting Alpha-1 Antitrypsin (A1AT) Comprising a GalNAc$_3$ Conjugate The oligonucleotides listed in Table 59 below were tested in a study for dose-dependent inhibition of A1AT in mice.

TABLE 59

Modified ASOs targeting A1AT

| ISIS No. | Sequences (5' to 3') | GalNAc$_3$ Cluster | CM | SEQ ID No. |
|---|---|---|---|---|
| 476366 | A$_{es}$$^m$C$_{es}$$^m$C$_{es}$$^m$C$_{es}$A$_{es}$A$_{ds}$T$_{ds}$ T$_{ds}$$^m$C$_{ds}$A$_{ds}$G$_{ds}$A$_{ds}$A$_{ds}$G$_{ds}$ G$_{ds}$A$_{es}$A$_{es}$G$_{es}$G$_{es}$A$_{e}$ | n/a | n/a | 37 |
| 656326 | A$_{es}$$^m$C$_{es}$$^m$C$_{es}$$^m$C$_{es}$A$_{es}$A$_{ds}$T$_{ds}$ T$_{ds}$$^m$C$_{ds}$A$_{ds}$G$_{ds}$A$_{ds}$A$_{ds}$G$_{ds}$ G$_{ds}$A$_{es}$A$_{es}$G$_{eo}$G$_{es}$A$_{eo}$ A$_{do}$,-GalNAc$_3$-1$_a$ | GalNAc$_3$-1a | A$_d$ | 38 |
| 678381 | GalNAc$_3$-3$_a$-$_o$,A$_{do}$A$_{es}$ $^m$C$_{es}$$^m$C$_{es}$$^m$C$_{es}$A$_{es}$A$_{ds}$T$_{ds}$ T$_{ds}$$^m$C$_{ds}$A$_{ds}$G$_{ds}$A$_{ds}$A$_{ds}$ G$_{ds}$G$_{ds}$A$_{es}$A$_{es}$G$_{es}$G$_{es}$A$_{e}$ | GalNAc$_3$-3a | A$_d$ | 39 |
| 678382 | GalNAc$_3$-7$_a$-$_o$,A$_{do}$A$_{es}$ G$_{es}$G$_{es}$A$_{e}$$^m$C$_{es}$$^m$C$_{es}$$^m$C$_{es}$ A$_{es}$A$_{ds}$T$_{ds}$T$_{ds}$$^m$C$_{ds}$A$_{ds}$G$_{ds}$ A$_{ds}$A$_{ds}$G$_{ds}$G$_{ds}$A$_{es}$A$_{es}$ | GalNAc$_3$-7a | A$_d$ | 39 |
| 678383 | GalNAc$_3$-10$_a$-$_o$,A$_{do}$ A$_{es}$$^m$C$_{es}$$^m$C$_{es}$$^m$C$_{es}$A$_{es}$A$_{ds}$ T$_{ds}$T$_{ds}$$^m$C$_{ds}$A$_{ds}$G$_{ds}$A$_{ds}$A$_{ds}$ G$_{ds}$G$_{ds}$A$_{es}$A$_{es}$G$_{es}$G$_{es}$A$_{e}$ | GalNAc$_3$-10a | A$_d$ | 39 |
| 678384 | GalNAc$_3$-13$_a$-$_o$,A$_{do}$ A$_{es}$$^m$C$_{es}$$^m$C$_{es}$$^m$C$_{es}$A$_{es}$A$_{ds}$ T$_{ds}$T$_{ds}$$^m$C$_{ds}$A$_{ds}$G$_{ds}$A$_{ds}$A$_{ds}$ G$_{ds}$G$_{ds}$A$_{es}$A$_{es}$ G$_{es}$G$_{es}$A$_{e}$ | GalNAc$_3$-13a | A$_d$ | 39 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six week old, male C57BL/6 mice (Jackson Laboratory, Bar Harbor, Me.) were each injected subcutaneously once per week at a dosage shown below, for a total of three doses, with an oligonucleotide listed in Table 59 or with PBS. Each treatment group consisted of 4 animals. The mice were sacrificed 72 hours following the final administration. A1AT liver mRNA levels were determined using real-time PCR and RIBOGREEN® RNA quantification reagent (Molecular Probes, Inc. Eugene, Oreg.) according to standard protocols. A1AT plasma protein levels were determined using the Mouse Alpha 1-Antitrypsin ELISA (catalog #41-A1AMS-E01, Alpco, Salem, N.H.). The results below are presented as the average percent of A1AT liver mRNA and plasma protein levels for each treatment group, normalized to the PBS control.

As illustrated in Table 60, treatment with antisense oligonucleotides lowered A1AT liver mRNA and A1AT plasma protein levels in a dose-dependent manner. The oligonucleotides comprising a GalNAc conjugate were significantly more potent than the parent (ISIS 476366).

TABLE 60

A1AT liver mRNA and plasma protein levels

| ISIS No. | Dosage (mg/kg) | A1AT liver mRNA (% PBS) | A1AT plasma protein (% PBS) | GalNAc$_3$ Cluster | CM |
|---|---|---|---|---|---|
| PBS | n/a | 100 | 100 | n/a | n/a |
| 476366 | 5 | 86 | 78 | n/a | n/a |
|  | 15 | 73 | 61 |  |  |
|  | 45 | 30 | 38 |  |  |
| 656326 | 0.6 | 99 | 90 | GalNAc$_3$-1a | A$_d$ |
|  | 2 | 61 | 70 |  |  |
|  | 6 | 15 | 30 |  |  |
|  | 18 | 6 | 10 |  |  |
| 678381 | 0.6 | 105 | 90 | GalNAc$_3$-3a | A$_d$ |
|  | 2 | 53 | 60 |  |  |
|  | 6 | 16 | 20 |  |  |
|  | 18 | 7 | 13 |  |  |
| 678382 | 0.6 | 90 | 79 | GalNAc$_3$-7a | A$_d$ |
|  | 2 | 49 | 57 |  |  |
|  | 6 | 21 | 27 |  |  |
|  | 18 | 8 | 11 |  |  |
| 678383 | 0.6 | 94 | 84 | GalNAc$_3$-10a | A$_d$ |
|  | 2 | 44 | 53 |  |  |
|  | 6 | 13 | 24 |  |  |
|  | 18 | 6 | 10 |  |  |
| 678384 | 0.6 | 106 | 91 | GalNAc$_3$-13a | A$_d$ |
|  | 2 | 65 | 59 |  |  |
|  | 6 | 26 | 31 |  |  |
|  | 18 | 11 | 15 |  |  |

Liver transaminase and BUN levels in plasma were measured at time of sacrifice using standard protocols. Body weights and organ weights were also measured. The results are shown in Table 61 below. Body weight is shown as % relative to baseline. Organ weights are shown as % of body weight relative to the PBS control group.

TABLE 61

| ISIS No. | Dosage (mg/kg) | ALT (U/L) | AST (U/L) | BUN (mg/dL) | Body weight (% baseline) | Liver weight (Rel % BW) | Kidney weight (Rel % BW) | Spleen weight (Rel % BW) |
|---|---|---|---|---|---|---|---|---|
| PBS | n/a | 25 | 51 | 37 | 119 | 100 | 100 | 100 |
| 476366 | 5 | 34 | 68 | 35 | 116 | 91 | 98 | 106 |
|  | 15 | 37 | 74 | 30 | 122 | 92 | 101 | 128 |
|  | 45 | 30 | 47 | 31 | 118 | 99 | 108 | 123 |
| 656326 | 0.6 | 29 | 57 | 40 | 123 | 100 | 103 | 119 |
|  | 2 | 36 | 75 | 39 | 114 | 98 | 111 | 106 |
|  | 6 | 32 | 67 | 39 | 125 | 99 | 97 | 122 |
|  | 18 | 46 | 77 | 36 | 116 | 102 | 109 | 101 |
| 678381 | 0.6 | 26 | 57 | 32 | 117 | 93 | 109 | 110 |
|  | 2 | 26 | 52 | 33 | 121 | 96 | 106 | 125 |
|  | 6 | 40 | 78 | 32 | 124 | 92 | 106 | 126 |
|  | 18 | 31 | 54 | 28 | 118 | 94 | 103 | 120 |
| 678382 | 0.6 | 26 | 42 | 35 | 114 | 100 | 103 | 103 |
|  | 2 | 25 | 50 | 31 | 117 | 91 | 104 | 117 |
|  | 6 | 30 | 79 | 29 | 117 | 89 | 102 | 107 |
|  | 18 | 65 | 112 | 31 | 120 | 89 | 104 | 113 |
| 678383 | 0.6 | 30 | 67 | 38 | 121 | 91 | 100 | 123 |
|  | 2 | 33 | 53 | 33 | 118 | 98 | 102 | 121 |
|  | 6 | 32 | 63 | 32 | 117 | 97 | 105 | 105 |
|  | 18 | 36 | 68 | 31 | 118 | 99 | 103 | 108 |
| 678384 | 0.6 | 36 | 63 | 31 | 118 | 98 | 103 | 98 |
|  | 2 | 32 | 61 | 32 | 119 | 93 | 102 | 114 |
|  | 6 | 34 | 69 | 34 | 122 | 100 | 100 | 96 |
|  | 18 | 28 | 54 | 30 | 117 | 98 | 101 | 104 |

Example 81

Duration of Action In Vivo of Oligonucleotides Targeting A1AT Comprising a GalNAc$_3$ Cluster The oligonucleotides listed in Table 59 were tested in a single dose study for duration of action in mice.

Treatment

Six week old, male C57BL/6 mice were each injected subcutaneously once with an oligonucleotide listed in Table 59 or with PBS. Each treatment group consisted of 4 animals. Blood was drawn the day before dosing to determine baseline and at 5, 12, 19, and 25 days following the dose. Plasma A1AT protein levels were measured via ELISA (see Example 80). The results below are presented as the average percent of plasma A1AT protein levels for each treatment group, normalized to baseline levels. The results show that the oligonucleotides comprising a GalNAc conjugate were more potent and had longer duration of action than the parent lacking a GalNAc conjugate (ISIS 476366). Furthermore, the oligonucleotides comprising a 5'-GalNAc conjugate (ISIS 678381, 678382, 678383, and 678384) were generally even more potent with even longer duration of action than the oligonucleotide comprising a 3'-GalNAc conjugate (ISIS 656326).

TABLE 62

Plasma A1AT protein levels in mice

| ISIS No. | Dosage (mg/kg) | Time point (days post-dose) | A1AT (% baseline) | GalNAc$_3$ Cluster | CM |
|---|---|---|---|---|---|
| PBS | n/a | 5 | 93 | n/a | n/a |
| | | 12 | 93 | | |
| | | 19 | 90 | | |
| | | 25 | 97 | | |
| 476366 | 100 | 5 | 38 | n/a | n/a |
| | | 12 | 46 | | |
| | | 19 | 62 | | |
| | | 25 | 77 | | |
| 656326 | 18 | 5 | 33 | GalNAc$_3$-1a | A$_d$ |
| | | 12 | 36 | | |
| | | 19 | 51 | | |
| | | 25 | 72 | | |
| 678381 | 18 | 5 | 21 | GalNAc$_3$-3a | A$_d$ |
| | | 12 | 21 | | |
| | | 19 | 35 | | |
| | | 25 | 48 | | |
| 678382 | 18 | 5 | 21 | GalNAc$_3$-7a | A$_d$ |
| | | 12 | 21 | | |
| | | 19 | 39 | | |
| | | 25 | 60 | | |
| 678383 | 18 | 5 | 24 | GalNAc$_3$-10a | A$_d$ |
| | | 12 | 21 | | |
| | | 19 | 45 | | |
| | | 25 | 73 | | |
| 678384 | 18 | 5 | 29 | GalNAc$_3$-13a | A$_d$ |
| | | 12 | 34 | | |
| | | 19 | 57 | | |
| | | 25 | 76 | | |

Example 82

Antisense Inhibition In Vitro by Oligonucleotides Targeting SRB-1 Comprising a GalNAc$_3$ Conjugate Primary mouse liver hepatocytes were seeded in 96 well plates at 15,000 cells/well 2 hours prior to treatment. The oligonucleotides listed in Table 63 were added at 2, 10, 50, or 250 nM in Williams E medium and cells were incubated overnight at 37° C. in 5% CO$_2$. Cells were lysed 16 hours following oligonucleotide addition, and total RNA was purified using RNease 3000 BioRobot (Qiagen). SRB-1 mRNA levels were determined using real-time PCR and RIBOGREEN® RNA quantification reagent (Molecular Probes, Inc. Eugene, Oreg.) according to standard protocols. IC$_{50}$ values were determined using Prism 4 software (Graph-Pad). The results show that oligonucleotides comprising a variety of different GalNAc conjugate groups and a variety of different cleavable moieties are significantly more potent in an in vitro free uptake experiment than the parent oligonucleotides lacking a GalNAc conjugate group (ISIS 353382 and 666841).

TABLE 63

Inhibition of SRB-1 expression in vitro

| ISIS No. | Sequence (5' to 3') | Linkages | GalNAc cluster | CM | IC$_{50}$ (nM) | SEQ ID No. |
|---|---|---|---|---|---|---|
| 353382 | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | PS | n/a | n/a | 250 | 28 |
| 655861 | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$ T$_e$A$_{do}$,-GalNAc$_3$-1$_a$ | PS | GalNAc$_3$-1$_a$ | A$_d$ | 40 | 29 |
| 661161 | GalNAc$_3$-3$_a$-$_o$,A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | PS | GalNAc$_3$-3$_a$ | A$_d$ | 40 | 30 |
| 661162 | GalNAc$_3$-3$_a$-$_o$,A$_{do}$G$_{es}$ $^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_e$ | PO/PS | GalNAc$_3$-3$_a$ | A$_d$ | 8 | 30 |
| 664078 | G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$ T$_e$A$_{do}$,-GalNAc$_3$-9$_a$ | PS | GalNAc$_3$-9$_a$ | A$_d$ | 20 | 29 |
| 665001 | GalNAc$_3$-8$_a$-$_o$,A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | PS | GalNAc$_3$-8$_a$ | A$_d$ | 70 | 30 |
| 666224 | GalNAc$_3$-5$_a$-$_o$,A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | PS | GalNAc$_3$-5$_a$ | A$_d$ | 80 | 30 |

TABLE 63-continued

Inhibition of SRB-1 expression in vitro

| ISIS No. | Sequence (5' to 3') | Link-ages | GalNAc cluster | CM | IC$_{50}$ (nM) | SEQ ID No. |
|---|---|---|---|---|---|---|
| 666841 | G$_{es}$$^m$C$_{eo}$T$_{eo}$T$_{eo}$$^m$C$_{eo}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{eo}$$^m$C$_{eo}$$^m$C$_{es}$T$_{es}$T$_e$ | PO/PS | n/a | n/a | >250 | 28 |
| 666881 | GalNAc$_3$-10$_a$-$_o$,A$_{eo}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | PS | GalNAc$_3$-10$_a$ | A$_d$ | 30 | 30 |
| 666904 | GalNAc$_3$-3$_a$-$_o$,G$_{es}$$^m$C$_{es}$ T$_{es}$T$_{es}$$^m$C$_{es}$A$_{ds}$G$_{ds}$T$_{ds}$$^m$C$_{ds}$ A$_{ds}$T$_{ds}$G$_{ds}$A$_{ds}$$^m$C$_{ds}$T$_{ds}$T$_{es}$ $^m$C$_{es}$$^m$C$_{es}$T$_{es}$T$_e$ | PS | GalNAc$_3$-3$_a$ | PO | 9 | 28 |
| 666924 | GalNAc$_3$-3$_a$-$_o$,T$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | PS | GalNAc$_3$-3$_a$ | T$_d$ | 15 | 33 |
| 666961 | GalNAc$_3$-6$_a$-$_o$,A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | PS | GalNAc$_3$-6$_a$ | A$_d$ | 150 | 30 |
| 666981 | GalNAc$_3$-7$_a$-$_o$,A$_{do}$G$_{es}$ $^m$C$_{es}$T$_{es}$T$_{es}$$^m$C$_{es}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{es}$$^m$C$_{es}$$^m$C$_{es}$T$_{es}$T$_e$ | PS | GalNAc$_3$-7$_a$ | A$_d$ | 20 | 30 |
| 670061 | GalNAc$_3$-13$_a$-$_o$,A$_{eo}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | PS | GalNAc$_3$-13$_a$ | A$_d$ | 30 | 30 |
| 670699 | GalNAc$_3$-3$_a$-$_o$,T$_{do}$G$_{es}$ $^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_e$ | PO/PS | GalNAc$_3$-3$_a$ | T$_d$ | 15 | 33 |
| 670700 | GalNAc$_3$-3$_a$-$_o$,A$_{eo}$G$_{es}$ $^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_e$ | PO/PS | GalNAc$_3$-3$_a$ | A$_e$ | 30 | 30 |
| 670701 | GalNAc$_3$-3$_a$-$_o$,T$_{eo}$G$_{es}$ $^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_e$ | PO/PS | GalNAc$_3$-3$_a$ | T$_e$ | 25 | 33 |
| 671144 | GalNAc$_3$-12$_a$-$_o$,A$_{eo}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | PS | GalNAc$_3$-12$_a$ | A$_d$ | 40 | 30 |
| 671165 | GalNAc$_3$-13$_a$-$_o$,A$_{eo}$ G$_{es}$$^m$C$_{eo}$T$_{eo}$T$_{eo}$$^m$C$_{eo}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{eo}$$^m$C$_{eo}$$^m$C$_{es}$T$_{es}$T$_e$ | PO/PS | GalNAc$_3$-13$_a$ | A$_d$ | 8 | 30 |
| 671261 | GalNAc$_3$-14$_a$-$_o$,A$_{eo}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | PS | GalNAc$_3$-14$_a$ | A$_d$ | >250 | 30 |
| 671262 | GalNAc$_3$-15$_a$-$_o$,A$_{eo}$ G$_{es}$$^m$C$_{es}$T$_{es}$T$_{es}$$^m$C$_{es}$A$_{ds}$G$_{ds}$ T$_{ds}$$^m$C$_{ds}$A$_{ds}$T$_{ds}$G$_{ds}$A$_{ds}$$^m$C$_{ds}$ T$_{ds}$T$_{es}$$^m$C$_{es}$$^m$C$_{es}$T$_{es}$T$_e$ | PS | GalNAc$_3$-15$_a$ | A$_d$ | >250 | 30 |
| 673501 | GalNAc$_3$-7$_a$-$_o$,A$_{eo}$G$_{es}$ $^m$C$_{eo}$T$_{eo}$T$_{eo}$$^m$C$_{eo}$A$_{ds}$G$_{ds}$T$_{ds}$ $^m$C$_{ds}$A$_{ds}$T$_{ds}$G$_{ds}$A$_{ds}$$^m$C$_{ds}$T$_{ds}$ T$_{eo}$$^m$C$_{eo}$$^m$C$_{es}$T$_{es}$T$_e$ | PO/PS | GalNAc$_3$-7$_a$ | A$_d$ | 30 | 30 |

TABLE 63-continued

Inhibition of SRB-1 expression in vitro

| ISIS No. | Sequence (5' to 3') | Linkages | GalNAc cluster | CM | IC$_{50}$ (nM) | SEQ ID No. |
|---|---|---|---|---|---|---|
| 673502 | GalNAc$_3$-10$_a$-$_o$,A$_{do}$<br>G$_{es}$$^m$C$_{eo}$T$_{eo}$T$_{eo}$$^m$C$_{eo}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{eo}$$^m$C$_{eo}$$^m$C$_{es}$T$_{es}$T$_{e}$ | PO/PS | GalNAc$_3$-10$_a$ | A$_d$ | 8 | 30 |
| 675441 | GalNAc$_3$-17$_a$-$_o$,A$_{do}$<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_{e}$ | PS | GalNac$_3$-17$_a$ | A$_d$ | 30 | 30 |
| 675442 | GalNAc$_3$-18$_a$-$_o$,A$_{do}$<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_{e}$ | PS | GalNAc$_3$-18$_a$ | A$_d$ | 20 | 30 |
| 677841 | G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$<br>T$_{e}$A$_{do}$,-GalNAc$_3$-19$_a$ | PS | GalNAc$_3$-19$_a$ | A$_d$ | 40 | 29 |
| 677842 | G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$<br>T$_{e}$A$_{do}$,-GalNAc$_3$-20$_a$ | PS | GalNAc$_3$-20$_a$ | A$_d$ | 30 | 29 |
| 677843 | GalNAc$_3$-23$_a$-$_o$,A$_{do}$<br>G$_{es}$$^m$C$_{es}$T$_{es}$T$_{es}$$^m$C$_{es}$A$_{ds}$G$_{ds}$<br>T$_{ds}$$^m$C$_{ds}$A$_{ds}$T$_{ds}$G$_{ds}$A$_{ds}$$^m$C$_{ds}$<br>T$_{ds}$T$_{es}$$^m$C$_{es}$$^m$C$_{es}$T$_{es}$T$_{e}$ | PS | GalNAc$_3$-23$_a$ | A$_d$ | 40 | 30 |

The structure of GalNAc$_3$-1$_a$ was shown previously in Example 9, GalNAc$_3$-3$_a$ was shown in Example 39, GalNAc$_3$-5$_a$ was shown in Example 49, GalNAc$_3$-6$_a$ was shown in Example 51, GalNAc$_3$-17$_a$ was shown in Example 48, GalNAc$_3$-8$_a$ was shown in Example 47, GalNAc$_3$-9$_a$ was shown in Example 52, GalNAc$_3$-10$_a$ was shown in Example 46, GalNAc$_3$-12$_a$ was shown in Example 61, GalNAc$_3$-13$_a$ was shown in Example 62, GalNAc$_3$-14$_a$ was shown in Example 63, GalNAc$_3$-15$_a$ was shown in Example 64, GalNAc$_3$-17$_a$ was shown in Example 68, GalNAc$_3$-18$_a$ was shown in Example 69, GalNAc$_3$-19$_a$ was shown in Example 70, GalNAc$_3$-20$_a$ was shown in Example 71, and GalNAc$_3$-23$_a$ was shown in Example 76.

Example 83

Antisense Inhibition In Vivo by Oligonucleotides Targeting Factor XI Comprising a GalNAc$_3$ Cluster The oligonucleotides listed in Table 64 below were tested in a study for dose-dependent inhibition of Factor XI in mice.

TABLE 64

Modified oligonucleotides targeting Factor XI

| ISIS No. | Sequence (5' to 3') | GalNAc cluster | CM | SEQ ID No. |
|---|---|---|---|---|
| 404071 | T$_{es}$G$_{es}$G$_{es}$T$_{es}$A$_{es}$A$_{ds}$T$_{ds}$<br>$^m$C$_{ds}$$^m$C$_{ds}$A$_{ds}$$^m$C$_{ds}$T$_{ds}$T$_{ds}$<br>T$_{ds}$$^m$C$_{ds}$A$_{es}$A$_{es}$G$_{es}$G$_{e}$ | n/a | n/a | 31 |
| 656173 | T$_{es}$G$_{eo}$G$_{eo}$T$_{eo}$A$_{eo}$A$_{ds}$T$_{ds}$<br>$^m$C$_{ds}$$^m$C$_{ds}$A$_{ds}$$^m$C$_{ds}$T$_{ds}$T$_{ds}$<br>T$_{ds}$$^m$C$_{ds}$A$_{eo}$G$_{eo}$A$_{es}$G$_{es}$<br>G$_{es}$A$_{do}$,-GalNAc$_3$-1$_a$ | GalNAc$_3$-1$_a$ | A$_d$ | 32 |
| 663086 | GalNAc$_3$-3$_a$-$_o$,A$_{do}$T$_{es}$<br>G$_{eo}$G$_{eo}$T$_{eo}$A$_{eo}$A$_{ds}$T$_{ds}$$^m$C$_{ds}$<br>$^m$C$_{ds}$A$_{ds}$$^m$C$_{ds}$T$_{ds}$T$_{ds}$T$_{ds}$<br>$^m$C$_{ds}$A$_{eo}$G$_{eo}$A$_{es}$G$_{es}$G$_{e}$ | GalNAc$_3$-3$_a$ | A$_d$ | 40 |
| 678347 | GalNAc$_3$-7$_a$-$_o$,A$_{do}$T$_{es}$<br>G$_{eo}$G$_{eo}$T$_{eo}$A$_{eo}$A$_{ds}$T$_{ds}$$^m$C$_{ds}$<br>$^m$C$_{ds}$A$_{ds}$$^m$C$_{ds}$T$_{ds}$T$_{ds}$T$_{ds}$<br>$^m$C$_{ds}$A$_{eo}$G$_{eo}$A$_{es}$G$_{es}$G$_{e}$ | GalNAc$_3$-7$_a$ | A$_d$ | 40 |
| 678348 | GalNAc$_3$-10$_a$-$_o$,A$_{do}$<br>T$_{es}$G$_{eo}$G$_{eo}$T$_{eo}$A$_{eo}$A$_{ds}$T$_{ds}$<br>$^m$C$_{ds}$$^m$C$_{ds}$A$_{ds}$$^m$C$_{ds}$T$_{ds}$T$_{ds}$<br>T$_{ds}$$^m$C$_{ds}$A$_{eo}$G$_{eo}$A$_{es}$G$_{es}$G$_{e}$ | GalNAc$_3$-10$_a$ | A$_d$ | 40 |
| 678349 | GalNAc$_3$-13$_a$-$_o$,A$_{do}$<br>T$_{es}$G$_{eo}$G$_{eo}$T$_{eo}$A$_{eo}$A$_{ds}$T$_{ds}$<br>$^m$C$_{ds}$$^m$C$_{ds}$A$_{ds}$$^m$C$_{ds}$T$_{ds}$T$_{ds}$<br>T$_{ds}$$^m$C$_{ds}$A$_{eo}$G$_{eo}$A$_{es}$G$_{es}$G$_{e}$ | GalNAc$_3$-13$_a$ | A$_d$ | 40 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six to eight week old mice were each injected subcutaneously once per week at a dosage shown below, for a total of three doses, with an oligonucleotide listed below or with PBS. Each treatment group consisted of 4 animals. The mice were sacrificed 72 hours following the final dose. Factor XI liver mRNA levels were measured using real-time PCR and normalized to cyclophilin according to standard protocols. Liver transaminases, BUN, and bilirubin were also measured. The results below are presented as the average percent for each treatment group, normalized to the PBS control.

As illustrated in Table 65, treatment with antisense oligonucleotides lowered Factor XI liver mRNA in a dose-dependent manner. The results show that the oligonucleotides comprising a GalNAc conjugate were more potent than the parent lacking a GalNAc conjugate (ISIS 404071). Furthermore, the oligonucleotides comprising a 5'-GalNAc conjugate (ISIS 663086, 678347, 678348, and 678349) were even more potent than the oligonucleotide comprising a 3'-GalNAc conjugate (ISIS 656173).

more potent with an even longer duration of action than the oligonucleotide comprising a 3'-GalNAc conjugate (ISIS 656173).

TABLE 66

Plasma Factor XI protein levels in mice

| ISIS No. | Dosage (mg/kg) | Time point (days post-dose) | Factor XI (% baseline) | GalNAc$_3$ Cluster | CM | SEQ ID No. |
|---|---|---|---|---|---|---|
| PBS | n/a | 3 | 123 | n/a | n/a | n/a |
|  |  | 10 | 56 |  |  |  |
|  |  | 17 | 100 |  |  |  |

TABLE 65

Factor XI liver mRNA, liver transaminase, BUN, and bilirubin levels

| ISIS No. | Dosage (mg/kg) | Factor XI mRNA (% PBS) | ALT (U/L) | AST (U/L) | BUN (mg/dL) | Bilirubin (mg/dL) | GalNAc$_3$ Cluster | SEQ ID No. |
|---|---|---|---|---|---|---|---|---|
| PBS | n/a | 100 | 63 | 70 | 21 | 0.18 | n/a | n/a |
| 404071 | 3 | 65 | 41 | 58 | 21 | 0.15 | n/a | 31 |
|  | 10 | 33 | 49 | 53 | 23 | 0.15 |  |  |
|  | 30 | 17 | 43 | 57 | 22 | 0.14 |  |  |
| 656173 | 0.7 | 43 | 90 | 89 | 21 | 0.16 | GalNAc$_3$-1a | 32 |
|  | 2 | 9 | 36 | 58 | 26 | 0.17 |  |  |
|  | 6 | 3 | 50 | 63 | 25 | 0.15 |  |  |
| 663086 | 0.7 | 33 | 91 | 169 | 25 | 0.16 | GalNAc$_3$-3a | 40 |
|  | 2 | 7 | 38 | 55 | 21 | 0.16 |  |  |
|  | 6 | 1 | 34 | 40 | 23 | 0.14 |  |  |
| 678347 | 0.7 | 35 | 28 | 49 | 20 | 0.14 | GalNAc$_3$-7a | 40 |
|  | 2 | 10 | 180 | 149 | 21 | 0.18 |  |  |
|  | 6 | 1 | 44 | 76 | 19 | 0.15 |  |  |
| 678348 | 0.7 | 39 | 43 | 54 | 21 | 0.16 | GalNAc$_3$-10a | 40 |
|  | 2 | 5 | 38 | 55 | 22 | 0.17 |  |  |
|  | 6 | 2 | 25 | 38 | 20 | 0.14 |  |  |
| 678349 | 0.7 | 34 | 39 | 46 | 20 | 0.16 | GalNAc$_3$-13a | 40 |
|  | 2 | 8 | 43 | 63 | 21 | 0.14 |  |  |
|  | 6 | 2 | 28 | 41 | 20 | 0.14 |  |  |

Example 84

Duration of Action In Vivo of Oligonucleotides Targeting Factor XI Comprising a GalNAc$_3$ Conjugate The oligonucleotides listed in Table 64 were tested in a single dose study for duration of action in mice.
Treatment Six to eight week old mice were each injected subcutaneously once with an oligonucleotide listed in Table 64 or with PBS. Each treatment group consisted of 4 animals. Blood was drawn by tail bleeds the day before dosing to determine baseline and at 3, 10, and 17 days following the dose. Plasma Factor XI protein levels were measured by ELISA using Factor XI capture and biotinylated detection antibodies from R & D Systems, Minneapolis, Minn. (catalog #AF2460 and #BAF2460, respectively) and the OptEIA Reagent Set B (Catalog #550534, BD Biosciences, San Jose, Calif.). The results below are presented as the average percent of plasma Factor XI protein levels for each treatment group, normalized to baseline levels. The results show that the oligonucleotides comprising a GalNAc conjugate were more potent with longer duration of action than the parent lacking a GalNAc conjugate (ISIS 404071). Furthermore, the oligonucleotides comprising a 5'-GalNAc conjugate (ISIS 663086, 678347, 678348, and 678349) were even TABLE 66-continued Plasma Factor XI protein levels in mice

| ISIS No. | Dosage (mg/kg) | Time point (days post-dose) | Factor XI (% baseline) | GalNAc$_3$ Cluster | CM | SEQ ID No. |
|---|---|---|---|---|---|---|
| 404071 | 30 | 3 | 11 | n/a | n/a | 31 |
|  |  | 10 | 47 |  |  |  |
|  |  | 17 | 52 |  |  |  |
| 656173 | 6 | 3 | 1 | GalNAc$_3$-1a | $A_d$ | 32 |
|  |  | 10 | 3 |  |  |  |
|  |  | 17 | 21 |  |  |  |
| 663086 | 6 | 3 | 1 | GalNAc$_3$-3a | $A_d$ | 40 |
|  |  | 10 | 2 |  |  |  |
|  |  | 17 | 9 |  |  |  |
| 678347 | 6 | 3 | 1 | GalNAc$_3$-7a | $A_d$ | 40 |
|  |  | 10 | 1 |  |  |  |
|  |  | 17 | 8 |  |  |  |
| 678348 | 6 | 3 | 1 | GalNAc$_3$-10a | $A_d$ | 40 |
|  |  | 10 | 1 |  |  |  |
|  |  | 17 | 6 |  |  |  |
| 678349 | 6 | 3 | 1 | GalNAc$_3$-13a | $A_d$ | 40 |
|  |  | 10 | 1 |  |  |  |
|  |  | 17 | 5 |  |  |  |

Example 85

Antisense Inhibition In Vivo by Oligonucleotides Targeting SRB-1 Comprising a GalNAc$_3$ Conjugate Oligonucleotides listed in Table 63 were tested in a dose-dependent study for antisense inhibition of SRB-1 in mice.

Treatment

Six to eight week old C57BL/6 mice were each injected subcutaneously once per week at a dosage shown below, for a total of three doses, with an oligonucleotide listed in Table 63 or with saline. Each treatment group consisted of 4 animals. The mice were sacrificed 48 hours following the final administration to determine the SRB-1 mRNA levels using real-time PCR and RIBOGREEN® RNA quantification reagent (Molecular Probes, Inc. Eugene, Oreg.) according to standard protocols. The results below are presented as the average percent of liver SRB-1 mRNA levels for each treatment group, normalized to the saline control.

As illustrated in Tables 67 and 68, treatment with antisense oligonucleotides lowered SRB-1 mRNA levels in a dose-dependent manner

TABLE 67

SRB-1 mRNA in liver

| ISIS No. | Dosage (mg/kg) | SRB-1 mRNA (% Saline) | GalNAc$_3$ Cluster | CM |
|---|---|---|---|---|
| Saline | n/a | 100 | n/a | n/a |
| 655861 | 0.1 | 94 | GalNAc$_3$-1a | A$_d$ |
|  | 0.3 | 119 |  |  |
|  | 1 | 68 |  |  |
|  | 3 | 32 |  |  |
| 661161 | 0.1 | 120 | GalNAc$_3$-3a | A$_d$ |
|  | 0.3 | 107 |  |  |
|  | 1 | 68 |  |  |
|  | 3 | 26 |  |  |
| 666881 | 0.1 | 107 | GalNAc$_3$-10a | A$_d$ |
|  | 0.3 | 107 |  |  |
|  | 1 | 69 |  |  |
|  | 3 | 27 |  |  |
| 666981 | 0.1 | 120 | GalNAc$_3$-7a | A$_d$ |
|  | 0.3 | 103 |  |  |
|  | 1 | 54 |  |  |
|  | 3 | 21 |  |  |
| 670061 | 0.1 | 118 | GalNAc$_3$-13a | A$_d$ |
|  | 0.3 | 89 |  |  |
|  | 1 | 52 |  |  |
|  | 3 | 18 |  |  |
| 677842 | 0.1 | 119 | GalNAc$_3$-20a | A$_d$ |
|  | 0.3 | 96 |  |  |
|  | 1 | 65 |  |  |
|  | 3 | 23 |  |  |

TABLE 68

SRB-1 mRNA in liver

| ISIS No. | Dosage (mg/kg) | SRB-1 mRNA (% Saline) | GalNAc$_3$ Cluster | CM |
|---|---|---|---|---|
| 661161 | 0.1 | 107 | GalNAc$_3$-3a | A$_d$ |
|  | 0.3 | 95 |  |  |
|  | 1 | 53 |  |  |
|  | 3 | 18 |  |  |
| 677841 | 0.1 | 110 | GalNAc$_3$-19a | A$_d$ |
|  | 0.3 | 88 |  |  |
|  | 1 | 52 |  |  |
|  | 3 | 25 |  |  |

Liver transaminase levels, total bilirubin, BUN, and body weights were also measured using standard protocols. Average values for each treatment group are shown in Table 69 below.

TABLE 69

| ISIS No. | Dosage (mg/kg) | ALT (U/L) | AST (U/L) | Bilirubin (mg/dL) | BUN (mg/dL) | Body Weight (% baseline) | GalNAc$_3$ Cluster | CM |
|---|---|---|---|---|---|---|---|---|
| Saline | n/a | 19 | 39 | 0.17 | 26 | 118 | n/a | n/a |
| 655861 | 0.1 | 25 | 47 | 0.17 | 27 | 114 | GalNAc$_3$-1a | A$_d$ |
|  | 0.3 | 29 | 56 | 0.15 | 27 | 118 |  |  |
|  | 1 | 20 | 32 | 0.14 | 24 | 112 |  |  |
|  | 3 | 27 | 54 | 0.14 | 24 | 115 |  |  |
| 661161 | 0.1 | 35 | 83 | 0.13 | 24 | 113 | GalNAc$_3$-3a | A$_d$ |
|  | 0.3 | 42 | 61 | 0.15 | 23 | 117 |  |  |
|  | 1 | 34 | 60 | 0.18 | 22 | 116 |  |  |
|  | 3 | 29 | 52 | 0.13 | 25 | 117 |  |  |
| 666881 | 0.1 | 30 | 51 | 0.15 | 23 | 118 | GalNAc$_3$-10a | A$_d$ |
|  | 0.3 | 49 | 82 | 0.16 | 25 | 119 |  |  |
|  | 1 | 23 | 45 | 0.14 | 24 | 117 |  |  |
|  | 3 | 20 | 38 | 0.15 | 21 | 112 |  |  |
| 666981 | 0.1 | 21 | 41 | 0.14 | 22 | 113 | GalNAc$_3$-7a | A$_d$ |
|  | 0.3 | 29 | 49 | 0.16 | 24 | 112 |  |  |
|  | 1 | 19 | 34 | 0.15 | 22 | 111 |  |  |
|  | 3 | 77 | 78 | 0.18 | 25 | 115 |  |  |
| 670061 | 0.1 | 20 | 63 | 0.18 | 24 | 111 | GalNAc$_3$-13a | A$_d$ |
|  | 0.3 | 20 | 57 | 0.15 | 21 | 115 |  |  |
|  | 1 | 20 | 35 | 0.14 | 20 | 115 |  |  |
|  | 3 | 27 | 42 | 0.12 | 20 | 116 |  |  |
| 677842 | 0.1 | 20 | 38 | 0.17 | 24 | 114 | GalNAc$_3$-20a | A$_d$ |
|  | 0.3 | 31 | 46 | 0.17 | 21 | 117 |  |  |
|  | 1 | 22 | 34 | 0.15 | 21 | 119 |  |  |
|  | 3 | 41 | 57 | 0.14 | 23 | 118 |  |  |

Example 86

Antisense Inhibition In Vivo by Oligonucleotides Targeting TTR Comprising a GalNAc$_3$ Cluster Oligonucleotides listed in Table 70 below were tested in a dose-dependent study for antisense inhibition of human transthyretin (TTR) in transgenic mice that express the human TTR gene.

In Tables 71-74, "BL" indicates baseline, measurements that were taken just prior to the first dose. As illustrated in Tables 71 and 72, treatment with antisense oligonucleotides lowered TTR expression levels in a dose-dependent manner. The oligonucleotides comprising a GalNAc conjugate were more potent than the parent lacking a GalNAc conjugate (ISIS 420915). Furthermore, the oligonucleotides comprising a GalNAc conjugate and mixed PS/PO internucleoside linkages were even more potent than the oligonucleotide comprising a GalNAc conjugate and full PS linkages.

TABLE 70

Oligonucleotides targeting human TTR

| Isis No. | Sequence 5' to 3' | Linkages | GalNAc cluster | CM | SEQ ID No. |
|---|---|---|---|---|---|
| 420915 | T$_{es}$$^m$C$_{es}$T$_{es}$T$_{es}$G$_{es}$G$_{ds}$T$_{ds}$T$_{ds}$A$_{ds}$$^m$C$_{ds}$ A$_{ds}$T$_{ds}$G$_{ds}$A$_{ds}$A$_{ds}$A$_{es}$T$_{es}$$^m$C$_{es}$$^m$C$_{es}$$^m$C$_{e}$ | PS | n/a | n/a | 41 |
| 660261 | T$_{es}$$^m$C$_{es}$T$_{es}$T$_{es}$G$_{es}$G$_{ds}$T$_{ds}$T$_{ds}$A$_{ds}$$^m$C$_{ds}$ A$_{ds}$T$_{ds}$G$_{ds}$A$_{ds}$A$_{ds}$A$_{es}$T$_{es}$$^m$C$_{es}$$^m$C$_{es}$ $^m$C$_{e}$A$_{do}$,-GalNAc$_3$-1$_a$ | PS | GalNAc$_3$-1a | A$_d$ | 42 |
| 682883 | GalNAc$_3$-3$_{a-o}$,T$_{es}$$^m$C$_{eo}$T$_{eo}$T$_{eo}$G$_{eo}$ G$_{ds}$T$_{ds}$T$_{ds}$A$_{ds}$$^m$C$_{ds}$A$_{ds}$T$_{ds}$G$_{ds}$A$_{ds}$A$_{ds}$ A$_{eo}$T$_{eo}$$^m$C$_{es}$$^m$C$_{es}$$^m$C$_{e}$ | PS/PO | GalNAc$_3$-3a | PO | 74 |
| 682884 | GalNAc$_3$-7$_{a-o}$,T$_{es}$$^m$C$_{eo}$T$_{eo}$T$_{eo}$G$_{eo}$ G$_{ds}$T$_{ds}$T$_{ds}$A$_{ds}$$^m$C$_{ds}$A$_{ds}$T$_{ds}$G$_{ds}$A$_{ds}$A$_{ds}$ A$_{eo}$T$_{eo}$$^m$C$_{es}$$^m$C$_{es}$$^m$C$_{e}$ | PS/PO | GalNAc$_3$-7a | PO | 41 |
| 682885 | GalNAc$_3$-10$_{a-o}$,T$_{es}$$^m$C$_{eo}$T$_{eo}$T$_{eo}$ G$_{eo}$G$_{ds}$T$_{ds}$T$_{ds}$A$_{ds}$$^m$C$_{ds}$A$_{ds}$T$_{ds}$G$_{ds}$A$_{ds}$ A$_{ds}$A$_{eo}$T$_{eo}$$^m$C$_{es}$$^m$C$_{es}$$^m$C$_{e}$ | PS/PO | GalNAc$_3$-10a | PO | 41 |
| 682886 | GalNAc$_3$-13$_{a-o}$,T$_{es}$$^m$C$_{eo}$T$_{eo}$T$_{eo}$ G$_{eo}$G$_{ds}$T$_{ds}$T$_{ds}$A$_{ds}$$^m$C$_{ds}$A$_{ds}$T$_{ds}$G$_{ds}$A$_{ds}$ A$_{ds}$A$_{eo}$T$_{eo}$$^m$C$_{es}$$^m$C$_{es}$$^m$C$_{e}$ | PS/PO | GalNAc$_3$-13a | PO | 41 |
| 684057 | T$_{es}$$^m$C$_{eo}$T$_{eo}$T$_{eo}$G$_{eo}$G$_{ds}$T$_{ds}$T$_{ds}$A$_{ds}$ $^m$C$_{ds}$A$_{ds}$T$_{ds}$G$_{ds}$A$_{ds}$A$_{ds}$A$_{eo}$T$_{eo}$$^m$C$_{es}$ $^m$C$_{es}$$^m$C$_{e}$A$_{do}$,-GalNAc$_3$-19$_a$ | PS/PO | GalNAc$_3$-19a | A$_d$ | 42 |

Treatment

Eight week old TTR transgenic mice were each injected subcutaneously once per week for three weeks, for a total of three doses, with an oligonucleotide and dosage listed in the tables below or with PBS. Each treatment group consisted of 4 animals. The mice were sacrificed 72 hours following the final administration. Tail bleeds were performed at various time points throughout the experiment, and plasma TTR protein, ALT, and AST levels were measured and reported in Tables 72-74. After the animals were sacrificed, plasma ALT, AST, and human TTR levels were measured, as were body weights, organ weights, and liver human TTR mRNA levels. TTR protein levels were measured using a clinical analyzer (AU480, Beckman Coulter, Calif.). Real-time PCR and RIBOGREEN® RNA quantification reagent (Molecular Probes, Inc. Eugene, Oreg.) were used according to standard protocols to determine liver human TTR mRNA levels. The results presented in Tables 71-74 are the average values for each treatment group. The mRNA levels are the average values relative to the average for the PBS group. Plasma protein levels are the average values relative to the average value for the PBS group at baseline. Body weights are the average percent weight change from baseline until sacrifice for each individual treatment group. Organ weights shown are normalized to the animal's body weight, and the average normalized organ weight for each treatment group is then presented relative to the average normalized organ weight for the PBS group.

The legend for Table 72 can be found in Example 74. The structure of GalNAc$_3$-1 was shown in Example 9. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62. The structure of GalNAc$_3$-19$_a$ was shown in Example 70.

TABLE 71

Antisense inhibition of human TTR in vivo

| Isis No. | Dosage (mg/kg) | TTR mRNA (% PBS) | Plasma TTR protein (% PBS) | GalNAc cluster | CM | SEQ ID No. |
|---|---|---|---|---|---|---|
| PBS | n/a | 100 | 100 | n/a | n/a | |
| 420915 | 6 | 99 | 95 | n/a | n/a | 41 |
| | 20 | 48 | 65 | | | |
| | 60 | 18 | 28 | | | |
| 660261 | 0.6 | 113 | 87 | GalNAc$_3$-1a | A$_d$ | 42 |
| | 2 | 40 | 56 | | | |
| | 6 | 20 | 27 | | | |
| | 20 | 9 | 11 | | | |

TABLE 72

Antisense inhibition of human TTR in vivo

| Isis No. | Dosage (mg/kg) | TTR mRNA (% PBS) | Plasma TTR protein (% PBS at BL) | | | | GalNAc cluster | CM | SEQ ID No. |
|---|---|---|---|---|---|---|---|---|---|
| | | | BL | Day 3 | Day 10 | Day 17 (After sac) | | | |
| PBS | n/a | 100 | 100 | 96 | 90 | 114 | n/a | n/a | |
| 420915 | 6 | 74 | 106 | 86 | 76 | 83 | n/a | n/a | 41 |
| | 20 | 43 | 102 | 66 | 61 | 58 | | | |
| | 60 | 24 | 92 | 43 | 29 | 32 | | | |
| 682883 | 0.6 | 60 | 88 | 73 | 63 | 68 | GalNAc$_3$-3a | PO | 41 |
| | 2 | 18 | 75 | 38 | 23 | 23 | | | |
| | 6 | 10 | 80 | 35 | 11 | 9 | | | |
| 682884 | 0.6 | 56 | 88 | 78 | 63 | 67 | GalNAc$_3$-7a | PO | 41 |
| | 2 | 19 | 76 | 44 | 25 | 23 | | | |
| | 6 | 15 | 82 | 35 | 21 | 24 | | | |
| 682885 | 0.6 | 60 | 92 | 77 | 68 | 76 | GalNAc$_3$-10a | PO | 41 |
| | 2 | 22 | 93 | 58 | 32 | 32 | | | |
| | 6 | 17 | 85 | 37 | 25 | 20 | | | |
| 682886 | 0.6 | 57 | 91 | 70 | 64 | 69 | GalNAc$_3$-13a | PO | 41 |
| | 2 | 21 | 89 | 50 | 31 | 30 | | | |
| | 6 | 18 | 102 | 41 | 24 | 27 | | | |
| 684057 | 0.6 | 53 | 80 | 69 | 56 | 62 | GalNAc$_3$-19a | A$_d$ | 42 |
| | 2 | 21 | 92 | 55 | 34 | 30 | | | |
| | 6 | 11 | 82 | 50 | 18 | 13 | | | |

TABLE 73

Transaminase levels, body weight changes, and relative organ weights

| Isis No. | Dosage (mg/kg) | ALT (U/L) | | | | AST (U/L) | | | | Body (% BL) | Liver (% PBS) | Spleen (% PBS) | Kidney (% PBS) | SEQ ID No. |
|---|---|---|---|---|---|---|---|---|---|---|---|---|---|---|
| | | BL | Day 3 | Day 10 | Day 17 | BL | Day 3 | Day 10 | Day 17 | | | | | |
| PBS | n/a | 33 | 34 | 33 | 24 | 58 | 62 | 67 | 52 | 105 | 100 | 100 | 100 | n/a |
| 420915 | 6 | 34 | 33 | 27 | 21 | 64 | 59 | 73 | 47 | 115 | 99 | 89 | 91 | 41 |
| | 20 | 34 | 30 | 28 | 19 | 64 | 54 | 56 | 42 | 111 | 97 | 83 | 89 | |
| | 60 | 34 | 35 | 31 | 24 | 61 | 58 | 71 | 58 | 113 | 102 | 98 | 95 | |
| 660261 | 0.6 | 33 | 38 | 28 | 26 | 70 | 71 | 63 | 59 | 111 | 96 | 99 | 92 | 42 |
| | 2 | 29 | 32 | 31 | 34 | 61 | 60 | 68 | 61 | 118 | 100 | 92 | 90 | |
| | 6 | 29 | 29 | 28 | 34 | 58 | 59 | 70 | 90 | 114 | 99 | 97 | 95 | |
| | 20 | 33 | 32 | 28 | 33 | 64 | 54 | 68 | 95 | 114 | 101 | 106 | 92 | |

TABLE 74

Transaminase levels, body weight changes, and relative organ weights

| Isis No. | Dosage (mg/kg) | ALT (U/L) | | | | AST (U/L) | | | | Body (% BL) | Liver (% PBS) | Spleen (% PBS) | Kidney (% PBS) | SEQ ID No. |
|---|---|---|---|---|---|---|---|---|---|---|---|---|---|---|
| | | BL | Day 3 | Day 10 | Day 17 | BL | Day 3 | Day 10 | Day 17 | | | | | |
| PBS | n/a | 32 | 34 | 37 | 41 | 62 | 78 | 76 | 77 | 104 | 100 | 100 | 100 | n/a |
| 420915 | 6 | 32 | 30 | 34 | 34 | 61 | 71 | 72 | 66 | 102 | 103 | 102 | 105 | 41 |
| | 20 | 41 | 34 | 37 | 33 | 80 | 76 | 63 | 54 | 106 | 107 | 135 | 101 | |
| | 60 | 36 | 30 | 32 | 34 | 58 | 81 | 57 | 60 | 106 | 105 | 104 | 99 | |
| 682883 | 0.6 | 32 | 35 | 38 | 40 | 53 | 81 | 74 | 76 | 104 | 101 | 112 | 95 | 41 |
| | 2 | 38 | 39 | 42 | 43 | 71 | 84 | 70 | 77 | 107 | 98 | 116 | 99 | |
| | 6 | 35 | 35 | 41 | 38 | 62 | 79 | 103 | 65 | 105 | 103 | 143 | 97 | |
| 682884 | 0.6 | 33 | 32 | 35 | 34 | 70 | 74 | 75 | 67 | 101 | 100 | 130 | 99 | 41 |
| | 2 | 31 | 32 | 38 | 38 | 63 | 77 | 66 | 55 | 104 | 103 | 122 | 100 | |
| | 6 | 38 | 32 | 36 | 34 | 65 | 85 | 80 | 62 | 99 | 105 | 129 | 95 | |
| 682885 | 0.6 | 39 | 26 | 37 | 35 | 63 | 63 | 77 | 59 | 100 | 109 | 109 | 112 | 41 |
| | 2 | 30 | 26 | 38 | 40 | 54 | 56 | 71 | 72 | 102 | 98 | 111 | 102 | |
| | 6 | 27 | 27 | 34 | 35 | 46 | 52 | 56 | 64 | 102 | 98 | 113 | 96 | |
| 682886 | 0.6 | 30 | 40 | 34 | 36 | 58 | 87 | 54 | 61 | 104 | 99 | 120 | 101 | 41 |
| | 2 | 27 | 26 | 34 | 36 | 51 | 55 | 55 | 69 | 103 | 91 | 105 | 92 | |
| | 6 | 40 | 28 | 34 | 37 | 107 | 54 | 61 | 69 | 109 | 100 | 102 | 99 | |

TABLE 74-continued

Transaminase levels, body weight changes, and relative organ weights

| Isis No. | Dosage (mg/kg) | ALT (U/L) | | | | AST (U/L) | | | | Body (% BL) | Liver (% PBS) | Spleen (% PBS) | Kidney (% PBS) | SEQ ID No. |
|---|---|---|---|---|---|---|---|---|---|---|---|---|---|---|
| | | BL | Day 3 | Day 10 | Day 17 | BL | Day 3 | Day 10 | Day 17 | | | | | |
| 684057 | 0.6 | 35 | 26 | 33 | 39 | 56 | 51 | 51 | 69 | 104 | 99 | 110 | 102 | 42 |
| | 2 | 33 | 32 | 31 | 40 | 54 | 57 | 56 | 87 | 103 | 100 | 112 | 97 | |
| | 6 | 39 | 33 | 35 | 40 | 67 | 52 | 55 | 92 | 98 | 104 | 121 | 108 | |

Example 87

Duration of Action In Vivo by Single Closes of Oligonucleotides Targeting TTR Comprising a GalNAc$_3$ Cluster ISIS numbers 420915 and 660261 (see Table 70) were tested in a single dose study for duration of action in mice. ISIS numbers 420915, 682883, and 682885 (see Table 70) were also tested in a single dose study for duration of action in mice.

Treatment

Eight week old, male transgenic mice that express human TTR were each injected subcutaneously once with 100 mg/kg ISIS No. 420915 or 13.5 mg/kg ISIS No. 660261. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 75

Plasma TTR protein levels

| ISIS No. | Dosage (mg/kg) | Time point (days post-dose) | TTR (% baseline) | GalNAc$_3$ Cluster | CM | SEQ ID No. |
|---|---|---|---|---|---|---|
| 420915 | 100 | 3 | 30 | n/a | n/a | 41 |
| | | 7 | 23 | | | |
| | | 10 | 35 | | | |
| | | 17 | 53 | | | |
| | | 24 | 75 | | | |
| | | 39 | 100 | | | |
| 660261 | 13.5 | 3 | 27 | GalNAc$_3$-1a | A$_d$ | 42 |
| | | 7 | 21 | | | |
| | | 10 | 22 | | | |
| | | 17 | 36 | | | |
| | | 24 | 48 | | | |
| | | 39 | 69 | | | |

Treatment

Female transgenic mice that express human TTR were each injected subcutaneously once with 100 mg/kg ISIS No. 420915, 10.0 mg/kg ISIS No. 682883, or 10.0 mg/kg 682885. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 76

Plasma TTR protein levels

| ISIS No. | Dosage (mg/kg) | Time point (days post-dose) | TTR (% baseline) | GalNAc$_3$ Cluster | CM | SEQ ID No. |
|---|---|---|---|---|---|---|
| 420915 | 100 | 3 | 48 | n/a | n/a | 41 |
| | | 7 | 48 | | | |
| | | 10 | 48 | | | |
| | | 17 | 66 | | | |
| | | 31 | 80 | | | |
| 682883 | 10.0 | 3 | 45 | GalNAc$_3$-3a | PO | 41 |
| | | 7 | 37 | | | |
| | | 10 | 38 | | | |
| | | 17 | 42 | | | |
| | | 31 | 65 | | | |
| 682885 | 10.0 | 3 | 40 | GalNAc$_3$-10a | PO | 41 |
| | | 7 | 33 | | | |
| | | 10 | 34 | | | |
| | | 17 | 40 | | | |
| | | 31 | 64 | | | |

The results in Tables 75 and 76 show that the oligonucleotides comprising a GalNAc conjugate are more potent with a longer duration of action than the parent oligonucleotide lacking a conjugate (ISIS 420915).

Example 88

Splicing Modulation In Vivo by Oligonucleotides Targeting SMN Comprising a GalNAc$_3$ Conjugate The oligonucleotides listed in Table 77 were tested for splicing modulation of human survival of motor neuron (SMN) in mice.

TABLE 77

Modified ASOs targeting SMN

| ISIS. No. | Sequences (5'-3') | GalNAc$_3$ Cluster | CM | SEQ ID No. |
|---|---|---|---|---|
| 387954 | A$_{es}$T$_{es}$T$_{es}$$^m$C$_{es}$A$_{es}$$^m$C$_{es}$T$_{es}$T$_{es}$T$_{es}$$^m$C$_{es}$A$_{es}$T$_{es}$A$_{es}$A$_{es}$T$_{es}$G$_{es}$$^m$C$_{es}$T$_{es}$G$_{es}$G$_e$ | n/a | n/a | 43 |
| 699819 | GalNAc$_3$-7$_a$-$_o$, A$_{es}$T$_{es}$T$_{es}$$^m$C$_{es}$A$_{es}$$^m$C$_{es}$T$_{es}$T$_{es}$T$_{es}$$^m$C$_{es}$A$_{es}$T$_{es}$A$_{es}$A$_{es}$T$_{es}$G$_{es}$$^m$C$_{es}$T$_{es}$G$_{es}$G$_e$ | GalNAc$_3$-7a | PO | 43 |

TABLE 77-continued

Modified ASOs targeting SMN

| ISIS. No. | Sequences (5'-3') | GalNAc$_3$ Cluster | CM | SEQ ID No. |
|---|---|---|---|---|
| 699821 | GalNAc$_3$-7$_a$-$_o$, A$_{es}$T$_{eo}$T$_{eo}$$^m$G$_{eo}$A$_{eo}$$^m$C$_{eo}$T$_{eo}$T$_{eo}$T$_{eo}$$^m$ C$_{eo}$A$_{eo}$T$_{eo}$A$_{eo}$A$_{eo}$T$_{eo}$G$_{eo}$$^m$C$_{eo}$T$_{es}$G$_{es}$G$_{e}$ | GalNAc$_3$-7a | PO | 43 |
| 700000 | A$_{es}$T$_{es}$T$_{es}$$^m$C$_{es}$A$_{es}$$^m$C$_{es}$T$_{es}$T$_{es}$T$_{es}$$^m$C$_{es}$A$_{es}$T$_{es}$A$_{es}$A$_{es}$ T$_{es}$G$_{es}$$^m$C$_{es}$T$_{es}$G$_{es}$G$_{eo}$A$_{do}$, -GalNAc$_3$-1$_a$ | GalNAc$_3$-1a | A$_d$ | 44 |
| 703421 | X-ATT$^m$CA$^m$CTTT$^m$CATAATG$^m$CTGG | n/a | n/a | 43 |
| 703422 | GalNAc$_3$-7$_b$-X-ATT$^m$CA$^m$CTTT$^m$CATAATG$^m$CTCG | GalNAc$_3$-7b | n/a | 43 |

The structure of GalNAc$_3$-7$_a$ was shown previously in Example 48. "X" indicates a 5' primary amine generated by Gene Tools (Philomath, Oreg.), and GalNAc$_3$-7$_b$ indicates the structure of GalNAc$_3$-7$_a$ lacking the —NH—C$_6$—O portion of the linker as shown below:

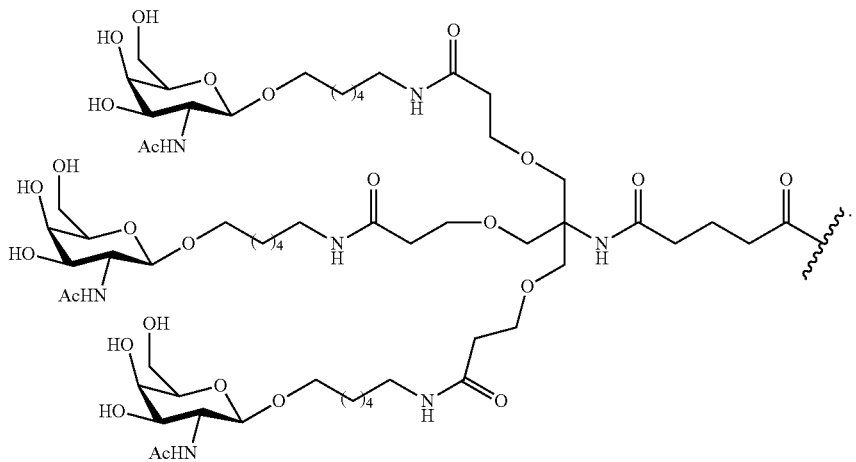

ISIS numbers 703421 and 703422 are morpholino oligonucleotides, wherein each nucleotide of the two oligonucleotides is a morpholino nucleotide.

Treatment

Six week old transgenic mice that express human SMN were injected subcutaneously once with an oligonucleotide listed in Table 78 or with saline. Each treatment group consisted of 2 males and 2 females. The mice were sacrificed 3 days following the dose to determine the liver human SMN mRNA levels both with and without exon 7 using real-time PCR according to standard protocols. Total RNA was measured using Ribogreen reagent. The SMN mRNA levels were normalized to total mRNA, and further normalized to the averages for the saline treatment group. The resulting average ratios of SMN mRNA including exon 7 to SMN mRNA missing exon 7 are shown in Table 78. The results show that fully modified oligonucleotides that modulate splicing and comprise a GalNAc conjugate are significantly more potent in altering splicing in the liver than the parent oligonucleotides lacking a GlaNAc conjugate. Furthermore, this trend is maintained for multiple modification chemistries, including 2'-MOE and morpholino modified oligonucleotides.

TABLE 78

Effect of oligonucleotides targeting human SMN in vivo

| ISIS No. | Dose (mg/kg) | +Exon 7/-Exon 7 | GalNAc$_3$ Cluster | CM | SEQ ID No. |
|---|---|---|---|---|---|
| Saline | n/a | 1.00 | n/a | n/a | n/a |
| 387954 | 32 | 1.65 | n/a | n/a | 43 |
| 387954 | 288 | 5.00 | n/a | n/a | 43 |
| 699819 | 32 | 7.84 | GalNAc$_3$-7a | PO | 43 |
| 699821 | 32 | 7.22 | GalNAc$_3$-7a | PO | 43 |
| 700000 | 32 | 6.91 | GalNAc$_3$-1a | A$_d$ | 44 |
| 703421 | 32 | 1.27 | n/a | n/a | 43 |
| 703422 | 32 | 4.12 | GalNAc$_3$-7b | n/a | 43 |

Example 89

Antisense Inhibition In Vivo by Oligonucleotides Targeting Apolipoprotein A (Apo(a)) Comprising a GalNAc$_3$ Conjugate The oligonucleotides listed in Table 79 below were tested in a study for dose-dependent inhibition of Apo(a) in transgenic mice.

Treatment

Eight week old, female C57BL/6 mice (Jackson Laboratory, Bar Harbor, Me.) were each injected subcutaneously once per week at a dosage shown below, for a total of six doses, with an oligonucleotide listed in Table 79 or with PBS. Each treatment group consisted of 3-4 animals. Tail bleeds were performed the day before the first dose and weekly following each dose to determine plasma Apo(a) protein levels. The mice were sacrificed two days following the final administration. Apo(a) liver mRNA levels were determined using real-time PCR and RIBOGREEN® RNA quantification reagent (Molecular Probes, Inc. Eugene, Oreg.) according to standard protocols. Apo(a) plasma protein levels were determined using ELISA, and liver transaminase levels were determined. The mRNA and plasma protein results in Table 80 are presented as the treatment group average percent relative to the PBS treated group. Plasma protein levels were further normalized to the baseline (BL) value for the PBS group. Average absolute transaminase levels and body weights (% relative to baseline averages) are reported in Table 81.

As illustrated in Table 80, treatment with the oligonucleotides lowered Apo(a) liver mRNA and plasma protein levels in a dose-dependent manner. Furthermore, the oligonucleotide comprising the GalNAc conjugate was significantly more potent with a longer duration of action than the parent oligonucleotide lacking a GalNAc conjugate. As illustrated in Table 81, transaminase levels and body weights were unaffected by the oligonucleotides, indicating that the oligonucleotides were well tolerated.

TABLE 80

Apo(a) liver mRNA and plasma protein levels

| ISIS No. | Dosage (mg/kg) | Apo(a) mRNA (% PBS) | Apo(a) plasma protein (% PBS) | | | | | |
|---|---|---|---|---|---|---|---|---|
| | | | BL | Week 1 | Week 2 | Week 3 | Week 4 | Week 5 | Week 6 |
| PBS | n/a | 100 | 100 | 120 | 119 | 113 | 88 | 121 | 97 |
| 494372 | 3 | 80 | 84 | 89 | 91 | 98 | 87 | 87 | 79 |
| | 10 | 30 | 87 | 72 | 76 | 71 | 57 | 59 | 46 |
| | 30 | 5 | 92 | 54 | 28 | 10 | 7 | 9 | 7 |
| 681257 | 0.3 | 75 | 79 | 76 | 89 | 98 | 71 | 94 | 78 |
| | 1 | 19 | 79 | 88 | 66 | 60 | 54 | 32 | 24 |
| | 3 | 2 | 82 | 52 | 17 | 7 | 4 | 6 | 5 |
| | 10 | 2 | 79 | 17 | 6 | 3 | 2 | 4 | 5 |

TABLE 79

Modified ASOs targeting Apo(a)

| ISIS No. | Sequences (5' to 3') | GalNAc$_3$ Cluster | CM | SEQ ID No. |
|---|---|---|---|---|
| 494372 | T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_{e}$ | n/a | n/a | 53 |
| 681257 | GalNAc$_3$-7$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_{e}$ | GalNAc$_3$-7a | PO | 53 |

The structure of GalNAc$_3$-7$_a$ was shown in Example 48.

TABLE 81

| ISIS No. | Dosage (mg/kg) | ALT (U/L) | AST (U/L) | Body weight (% baseline) |
|---|---|---|---|---|
| PBS | n/a | 37 | 54 | 103 |
| 494372 | 3 | 28 | 68 | 106 |
| | 10 | 22 | 55 | 102 |
| | 30 | 19 | 48 | 103 |
| 681257 | 0.3 | 30 | 80 | 104 |
| | 1 | 26 | 47 | 105 |
| | 3 | 29 | 62 | 102 |
| | 10 | 21 | 52 | 107 |

Example 90

Antisense Inhibition In Vivo by Oligonucleotides Targeting TTR Comprising a GalNAc$_3$ Cluster Oligonucleotides listed in Table 82 below were tested in a dose-dependent study for antisense inhibition of human transthyretin (TTR) in transgenic mice that express the human TTR gene.

Treatment

TTR transgenic mice were each injected subcutaneously once per week for three weeks, for a total of three doses, with an oligonucleotide and dosage listed in Table 83 or with PBS. Each treatment group consisted of 4 animals. Prior to the first dose, a tail bleed was performed to determine plasma TTR protein levels at baseline (BL). The mice were sacrificed 72 hours following the final administration. TTR protein levels were measured using a clinical analyzer (AU480, Beckman Coulter, Calif.). Real-time PCR and RIBOGREEN® RNA quantification reagent (Molecular Probes, Inc. Eugene, Oreg.) were used according to standard protocols to determine liver human TTR mRNA levels. The results presented in Table 83 are the average values for each treatment group. The mRNA levels are the average values relative to the average for the PBS group. Plasma protein levels are the average values relative to the average value for the PBS group at baseline. "BL" indicates baseline, measurements that were taken just prior to the first dose. As illustrated in Table 83, treatment with antisense oligonucleotides lowered TTR expression levels in a dose-dependent manner. The oligonucleotides comprising a GalNAc conjugate were more potent than the parent lacking a GalNAc conjugate (ISIS 420915), and oligonucleotides comprising a phosphodiester or deoxyadenosine cleavable moiety showed significant improvements in potency compared to the parent lacking a conjugate (see ISIS numbers 682883 and 666943 vs 420915 and see Examples 86 and 87).

TABLE 82

Oligonucleotides targeting human TTR

| Isis No. | Sequence 5' to 3' | Linkages | GalNAc cluster | CM | SEQ ID No. |
|---|---|---|---|---|---|
| 420915 | $T_{es}{}^mC_{es}T_{es}T_{es}G_{es}G_{ds}T_{ds}T_{ds}A_{ds}{}^mC_{ds}A_{ds}T_{ds}G_{ds}A_{ds}A_{ds}A_{es}T_{es}{}^mC_{es}{}^mC_{es}{}^mC_e$ | PS | n/a | n/a | 41 |
| 682883 | GalNAc$_3$-3$_{a-o}$/$T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-3a | PO | 41 |
| 666943 | GalNAc$_3$-3$_{a-o}$/$A_{do}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-3a | A$_d$ | 45 |
| 682887 | GalNAc$_3$-7$_{a-o}$/$A_{do}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-7a | A$_d$ | 45 |
| 682888 | GalNAc$_3$-10$_{a-o}$/$A_{do}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-10a | A$_d$ | 45 |
| 682889 | GalNAc$_3$-13$_{a-o}$/$A_{do}T_{es}{}^mC_{eo}T_{eo}T_{eo}G_{eo}G_{ds}T_{ds}T_{ds}A_{ds}{}^mC_{ds}A_{ds}T_{ds}G_{ds}A_{ds}A_{ds}A_{eo}T_{eo}{}^mC_{es}{}^mC_{es}{}^mC_e$ | PS/PO | GalNAc$_3$-13a | A$_d$ | 45 |

The legend for Table 82 can be found in Example 74. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62.

TABLE 83

Antisense inhibition of human TTR in vivo

| Isis No. | Dosage (mg/kg) | TTR mRNA (% PBS) | TTR protein (% BL) | GalNAc cluster | CM |
|---|---|---|---|---|---|
| PBS | n/a | 100 | 124 | n/a | n/a |
| 420915 | 6 | 69 | 114 | n/a | n/a |
|  | 20 | 71 | 86 |  |  |
|  | 60 | 21 | 36 |  |  |
| 682883 | 0.6 | 61 | 73 | GalNAc$_3$-3a | PO |
|  | 2 | 23 | 36 |  |  |
|  | 6 | 18 | 23 |  |  |
| 666943 | 0.6 | 74 | 93 | GalNAc$_3$-3a | A$_d$ |
|  | 2 | 33 | 57 |  |  |
|  | 6 | 17 | 22 |  |  |
| 682887 | 0.6 | 60 | 97 | GalNAc$_3$-7a | A$_d$ |
|  | 2 | 36 | 49 |  |  |
|  | 6 | 12 | 19 |  |  |
| 682888 | 0.6 | 65 | 92 | GalNAc$_3$-10a | A$_d$ |
|  | 2 | 32 | 46 |  |  |
|  | 6 | 17 | 22 |  |  |

TABLE 83-continued

Antisense inhibition of human TTR in vivo

| Isis No. | Dosage (mg/kg) | TTR mRNA (% PBS) | TTR protein (% BL) | GalNAc cluster | CM |
|---|---|---|---|---|---|
| 682889 | 0.6 | 72 | 74 | GalNAc$_3$-13a | A$_d$ |
|  | 2 | 38 | 45 |  |  |
|  | 6 | 16 | 18 |  |  |

Example 91

Antisense Inhibition In Vivo by Oligonucleotides Targeting Factor VII Comprising a GalNAc$_3$ Conjugate in Non-Human Primates Oligonucleotides listed in Table 84 below were tested in a non-terminal, dose escalation study for antisense inhibition of Factor VII in monkeys.

Treatment

Non-naïve monkeys were each injected subcutaneously on days 0, 15, and 29 with escalating doses of an oligonucleotide listed in Table 84 or with PBS. Each treatment group consisted of 4 males and 1 female. Prior to the first dose and at various time points thereafter, blood draws were performed to determine plasma Factor VII protein levels. Factor VII protein levels were measured by ELISA. The results presented in Table 85 are the average values for each treatment group relative to the average value for the PBS group at baseline (BL), the measurements taken just prior to the first dose. As illustrated in Table 85, treatment with antisense oligonucleotides lowered Factor VII expression levels in a dose-dependent manner, and the oligonucleotide comprising the GalNAc conjugate was significantly more potent in monkeys compared to the oligonucleotide lacking a GalNAc conjugate.

TABLE 84

Oligonucleotides targeting Factor VII

| Isis No. | Sequence 5' to 3' | Linkages | GalNAc cluster | CM | SEQ ID No. |
|---|---|---|---|---|---|
| 407935 | $A_{es}T_{es}G_{es}{}^mC_{es}A_{es}T_{ds}G_{ds}G_{ds}T_{ds}G_{ds}A_{ds}T_{ds}G_{ds}{}^mC_{ds}T_{ds}T_{es}{}^mC_{es}T_{es}G_{es}A_e$ | PS | n/a | n/a | 46 |
| 686892 | GalNAc$_3$-10$_{a-o}$, $A_{es}T_{es}G_{es}{}^mC_{es}A_{es}T_{ds}G_{ds}G_{ds}T_{ds}G_{ds}A_{ds}T_{ds}G_{ds}{}^mC_{ds}T_{ds}T_{es}{}^mC_{es}T_{es}G_{es}A_e$ | PS | GalNAc$_3$-10a | PO | 46 |

The legend for Table 84 can be found in Example 74. The structure of GalNAc$_3$-10$_a$ was shown in Example 46.

TABLE 85

Factor VII plasma protein levels

| ISIS No. | Day | Dose (mg/kg) | Factor VII (% BL) |
|---|---|---|---|
| 407935 | 0 | n/a | 100 |
|  | 15 | 10 | 87 |
|  | 22 | n/a | 92 |
|  | 29 | 30 | 77 |
|  | 36 | n/a | 46 |
|  | 43 | n/a | 43 |
| 686892 | 0 | 3 | 100 |
|  | 15 | 10 | 56 |
|  | 22 | n/a | 29 |
|  | 29 | 30 | 19 |
|  | 36 | n/a | 15 |
|  | 43 | n/a | 11 |

Example 92

Antisense Inhibition in Primary Hepatocytes by Antisense Oligonucleotides Targeting Apo-CIII Comprising a GalNAc$_3$ Conjugate Primary mouse hepatocytes were seeded in 96-well plates at 15,000 cells per well, and the oligonucleotides listed in Table 86, targeting mouse ApoC-III, were added at 0.46, 1.37, 4.12, or 12.35, 37.04, 111.11, or 333.33 nM or 1.00 µM. After incubation with the oligonucleotides for 24 hours, the cells were lysed and total RNA was purified using RNeasy (Qiagen). ApoC-III mRNA levels were determined using real-time PCR and RIBOGREEN® RNA quantification reagent (Molecular Probes, Inc.) according to standard protocols. IC$_{50}$ values were determined using Prism 4 software (GraphPad). The results show that regardless of whether the cleavable moiety was a phosphodiester or a phosphodiester-linked deoxyadenosine, the oligonucleotides comprising a GalNAc conjugate were significantly more potent than the parent oligonucleotide lacking a conjugate.

TABLE 86

Inhibition of mouse APOC-III expression in mouse primary hepatocytes

| ISIS No. | Sequence (5' to 3') | CM | IC$_{50}$ (nM) | SEQ ID No. |
|---|---|---|---|---|
| 440670 | ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | n/a | 13.20 | 47 |
| 661180 | ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_{es}G_{es}{}^mC_{es}A_{eo}A_{do}$-GalNAc$_3$-1$_a$ | A$_d$ | 1.40 | 48 |
| 680771 | GalNAc$_3$-3$_{a-o}$, ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 0.70 | 47 |
| 680772 | GalNAc$_3$-7$_{a-o}$, ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 1.70 | 47 |
| 680773 | GalNAc$_3$-10$_{a-o}$, ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 2.00 | 47 |
| 680774 | GalNAc$_3$-13$_{a-o}$, ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | PO | 1.50 | 47 |
| 681272 | GalNAc$_3$-3$_{a-o}$, ${}^mC_{es}A_{eo}G_{eo}{}^mC_{es}T_{eo}T_{ds}T_{ds}A_{ds}T_{ds}T_{ds}A_{ds}G_{ds}G_{ds}G_{ds}A_{ds}{}^mC_{eo}A_{eo}G_{es}{}^mC_{es}A_e$ | PO | <0.46 | 47 |
| 681273 | GalNAc$_3$-3$_a$-$_o$, A$_{do}$ ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_e$ | A$_d$ | 1.10 | 49 |
| 683733 | ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}A_{eo}A_{do}$-GalNAc$_3$-19$_a$ | A$_d$ | 2.50 | 48 |

The structure of GalNAc$_3$-1$_a$ was shown previously in Example 9, GalNAc$_3$-3$_a$ was shown in Example 39, GalNAc$_3$-7$_a$ was shown in Example 48, GalNAc$_3$-10$_a$ was shown in Example 46, GalNAc$_3$-13$_a$ was shown in Example 62, and GalNAc$_3$-19$_a$ was shown in Example 70.

Example 93

Antisense Inhibition In Vivo by Oligonucleotides Targeting SRB-1 Comprising Mixed Wings and a 5'-GalNAc$_3$ Conjugate The oligonucleotides listed in Table 87 were tested in a dose-dependent study for antisense inhibition of SRB-1 in mice.

TABLE 87

Modified ASOs targeting SRB-1

| ISIS No. | Sequences (5' to 3') | GalNAc$_3$ Cluster | CM | SEQ ID No. |
|---|---|---|---|---|
| 449093 | T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_k$ | n/a | n/a | 50 |
| 699806 | GalNAc$_3$-3$_{a\text{-}o}$/T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_k$ | GalNAc$_3$-3a | PO | 50 |
| 699807 | GalNAc$_3$-7$_{a\text{-}o}$/T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_k$ | GalNAc$_3$-7a | PO | 50 |
| 699809 | GalNAc$_3$-7$_{a\text{-}o}$/T$_{ks}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_e$ | GalNAc$_3$-7a | PO | 50 |
| 699811 | GalNAc$_3$-7$_{a\text{-}o}$/T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_k$ | GalNAc$_3$-7a | PO | 50 |
| 699813 | GalNAc$_3$-7$_{a\text{-}o}$/T$_{ks}$T$_{ds}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ds}$$^m$C$_k$ | GalNAc$_3$-7a | PO | 50 |
| 699815 | GalNAc$_3$-7$_{a\text{-}o}$/T$_{es}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_{ks}$$^m$C$_e$ | GalNAc$_3$-7a | PO | 50 |

The structure of GalNAc$_3$-3$_a$ was shown previously in Example 39, and the structure of GalNAc$_3$-7a was shown previously in Example 48. Subscripts: "e" indicates 2'-MOE modified nucleoside; "d" indicates β-D-2'-deoxyribonucleoside; "k" indicates 6'-(S)—CH$_3$ bicyclic nucleoside (cEt); "s" indicates phosphorothioate internucleoside linkages (PS); "o" indicates phosphodiester internucleoside linkages (PO). Supersript "m" indicates 5-methylcytosines.

Treatment

Six to eight week old C57BL/6 mice (Jackson Laboratory, Bar Harbor, Me.) were injected subcutaneously once at the dosage shown below with an oligonucleotide listed in Table 87 or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The results are presented as the average percent of SRB-1 mRNA levels for each treatment group relative to the saline control group. As illustrated in Table 88, treatment with antisense oligonucleotides lowered SRB-1 mRNA levels in a dose-dependent manner, and the gapmer oligonucleotides comprising a GalNAc conjugate and having wings that were either full cEt or mixed sugar modifications were significantly more potent than the parent oligonucleotide lacking a conjugate and comprising full cEt modified wings.

Body weights, liver transaminases, total bilirubin, and BUN were also measured, and the average values for each treatment group are shown in Table 88. Body weight is shown as the average percent body weight relative to the baseline body weight (% BL) measured just prior to the oligonucleotide dose.

TABLE 88

SRB-1 mRNA, ALT, AST, BUN, and total bilirubin levels and body weights

| ISIS No. | Dosage (mg/kg) | SRB-1 mRNA (% PBS) | ALT (U/L) | AST (U/L) | Bil | BUN | Body weight (% BL) |
|---|---|---|---|---|---|---|---|
| PBS | n/a | 100 | 31 | 84 | 0.15 | 28 | 102 |
| 449093 | 1 | 111 | 18 | 48 | 0.17 | 31 | 104 |
|  | 3 | 94 | 20 | 43 | 0.15 | 26 | 103 |
|  | 10 | 36 | 19 | 50 | 0.12 | 29 | 104 |
| 699806 | 0.1 | 114 | 23 | 58 | 0.13 | 26 | 107 |
|  | 0.3 | 59 | 21 | 45 | 0.12 | 27 | 108 |
|  | 1 | 25 | 30 | 61 | 0.12 | 30 | 104 |
| 699807 | 0.1 | 121 | 19 | 41 | 0.14 | 25 | 100 |
|  | 0.3 | 73 | 23 | 56 | 0.13 | 26 | 105 |
|  | 1 | 24 | 22 | 69 | 0.14 | 25 | 102 |
| 699809 | 0.1 | 125 | 23 | 57 | 0.14 | 26 | 104 |
|  | 0.3 | 70 | 20 | 49 | 0.10 | 25 | 105 |
|  | 1 | 33 | 34 | 62 | 0.17 | 25 | 107 |
| 699811 | 0.1 | 123 | 48 | 77 | 0.14 | 24 | 106 |
|  | 0.3 | 94 | 20 | 45 | 0.13 | 25 | 101 |
|  | 1 | 66 | 57 | 104 | 0.14 | 24 | 107 |
| 699813 | 0.1 | 95 | 20 | 58 | 0.13 | 28 | 104 |
|  | 0.3 | 98 | 22 | 61 | 0.17 | 28 | 105 |
|  | 1 | 49 | 19 | 47 | 0.11 | 27 | 106 |
| 699815 | 0.1 | 93 | 30 | 79 | 0.17 | 25 | 105 |
|  | 0.3 | 64 | 30 | 61 | 0.12 | 26 | 105 |
|  | 1 | 24 | 18 | 41 | 0.14 | 25 | 106 |

Example 94

Antisense Inhibition In Vivo by Oligonucleotides Targeting SRB-1 Comprising 2'-Sugar Modifications and a 5'-GalNAc$_3$ Conjugate The oligonucleotides listed in Table 89 were tested in a dose-dependent study for antisense inhibition of SRB-1 in mice.

TABLE 89

Modified ASOs targeting SRB-1

| ISIS No. | Sequences (5' to 3') | GalNAc$_3$ Cluster | CM | SEQ ID No. |
|---|---|---|---|---|
| 353382 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | n/a | n/a | 28 |
| 700989 | G$_{ms}$C$_{ms}$U$_{ms}$U$_{ms}$C$_{ms}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$U$_{ms}$C$_{ms}$C$_{ms}$U$_{ms}$U$_m$ | n/a | n/a | 51 |
| 666904 | GalNAc$_3$-3$_{a-o'}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_e$ | GalNAc$_3$-3a | PO | 28 |
| 700991 | GalNAc$_3$-7$_a$-$_o$G$_{ms}$C$_{ms}$U$_{ms}$U$_{ms}$C$_{ms}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$U$_{ms}$C$_{ms}$C$_{ms}$U$_{ms}$U$_m$ | GalNAc$_3$-7a | PO | 51 |

Subscript "m" indicates a 2'-O-methyl modified nucleoside. See Example 74 for complete table legend. The structure of GalNAc$_3$-3$_a$ was shown previously in Example 39, and the structure of GalNAc$_3$-7a was shown previously in Example 48.

Treatment

The study was completed using the protocol described in Example 93. Results are shown in Table 90 below and show that both the 2'-MOE and 2'-OMe modified oligonucleotides comprising a GalNAc conjugate were significantly more potent than the respective parent oligonucleotides lacking a conjugate. The results of the body weights, liver transaminases, total bilirubin, and BUN measurements indicated that the compounds were all well tolerated.

TABLE 90

SRB-1 mRNA

| ISIS No. | Dosage (mg/kg) | SRB-1 mRNA (% PBS) |
|---|---|---|
| PBS | n/a | 100 |
| 353382 | 5 | 116 |
|  | 15 | 58 |
|  | 45 | 27 |
| 700989 | 5 | 120 |
|  | 15 | 92 |
|  | 45 | 46 |
| 666904 | 1 | 98 |
|  | 3 | 45 |
|  | 10 | 17 |
| 700991 | 1 | 118 |
|  | 3 | 63 |
|  | 10 | 14 |

Example 95

Antisense Inhibition In Vivo by Oligonucleotides Targeting SRB-1 Comprising Bicyclic Nucleosides and a 5'-GalNAc$_3$ Conjugate The oligonucleotides listed in Table 91 were tested in a dose-dependent study for antisense inhibition of SRB-1 in mice.

TABLE 91

Modified ASOs targeting SRB-1

| ISIS No. | Sequences (5' to 3') | GalNAc$_3$ Cluster | CM | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | n/a | 22 |
| 666905 | GalNAc$_3$-3$_{a-o'}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-3$_a$ | PO | 22 |
| 699782 | GalNAc$_3$-7$_{a-o'}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-7$_a$ | PO | 22 |
| 699783 | GalNAc$_3$-3$_{a-o'}$T$_{ls}$$^m$C$_{ls}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ls}$$^m$C$_l$ | GalNAc$_3$-3$_a$ | PO | 22 |
| 653621 | T$_{ls}$C$_{ls}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ls}$$^m$C$_l$A$_{do'}$-GalNAc$_3$-1$_a$ | GalNAc$_3$-1$_a$ | A$_d$ | 23 |

TABLE 91-continued

Modified ASOs targeting SRB-1

| ISIS No. | Sequences (5' to 3') | GalNAc₃ Cluster | CM | SEQ ID No |
|---|---|---|---|---|
| 439879 | T$_{gs}$$^m$C$_{gs}$A$_{ds}$G$_{ds}$T$_{ds}$$^m$C$_{ds}$A$_{ds}$T$_{d}$G$_{ds}$A$_{ds}$$^m$C$_{ds}$T$_{ds}$T$_{gs}$$^m$C$_{g}$ | n/a | n/a | 22 |
| 699789 | GalNAc₃-3$_a$-$_o$,T$_{gs}$$^m$C$_{gs}$A$_{ds}$G$_{ds}$T$_{ds}$$^m$C$_{ds}$A$_{ds}$T$_{d}$G$_{ds}$A$_{ds}$$^m$C$_{ds}$T$_{ds}$T$_{gs}$$^m$C$_{g}$ | GalNAc₃-3$_a$ | PO | 22 |

Subscript "g" indicates a fluoro-HNA nucleoside, subscript "l" indicates a locked nucleoside comprising a 2'-O—CH₂-4' bridge. See the Example 74 table legend for other abbreviations. The structure of GalNAc₃-1$_a$ was shown previously in Example 9, the structure of GalNAc₃-3$_a$ was shown previously in Example 39, and the structure of GalNAc₃-7a was shown previously in Example 48.

Treatment

The study was completed using the protocol described in Example 93. Results are shown in Table 92 below and show that oligonucleotides comprising a GalNAc conjugate and various bicyclic nucleoside modifications were significantly more potent than the parent oligonucleotide lacking a conjugate and comprising bicyclic nucleoside modifications. Furthermore, the oligonucleotide comprising a GalNAc conjugate and fluoro-HNA modifications was significantly more potent than the parent lacking a conjugate and comprising fluoro-HNA modifications. The results of the body weights, liver transaminases, total bilirubin, and BUN measurements indicated that the compounds were all well tolerated.

TABLE 92

SRB-1 mRNA, ALT, AST, BUN, and total bilirubin levels and body weights

| ISIS No. | Dosage (mg/kg) | SRB-1 mRNA (% PBS) |
|---|---|---|
| PBS | n/a | 100 |
| 440762 | 1 | 104 |
|  | 3 | 65 |
|  | 10 | 35 |

TABLE 92-continued

SRB-1 mRNA, ALT, AST, BUN, and total bilirubin levels and body weights

| ISIS No. | Dosage (mg/kg) | SRB-1 mRNA (% PBS) |
|---|---|---|
| 666905 | 0.1 | 105 |
|  | 0.3 | 56 |
|  | 1 | 18 |
| 699782 | 0.1 | 93 |
|  | 0.3 | 63 |
|  | 1 | 15 |
| 699783 | 0.1 | 105 |
|  | 0.3 | 53 |
|  | 1 | 12 |
| 653621 | 0.1 | 109 |
|  | 0.3 | 82 |
|  | 1 | 27 |
| 439879 | 1 | 96 |
|  | 3 | 77 |
|  | 10 | 37 |
| 699789 | 0.1 | 82 |
|  | 0.3 | 69 |
|  | 1 | 26 |

Example 96

Plasma Protein Binding of Antisense Oligonucleotides Comprising a GalNAc₃ Conjugate Group Oligonucleotides listed in Table 57 targeting ApoC-III and oligonucleotides in Table 93 targeting Apo(a) were tested in an ultra-filtration assay in order to assess plasma protein binding.

TABLE 93

Modified oligonucleotides targeting Apo(a)

| ISIS No. | Sequences (5' to 3') | GalNAc₃ Cluster | CM | SEQ ID No |
|---|---|---|---|---|
| 494372 | T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_{e}$ | n/a | n/a | 53 |
| 693401 | T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{eo}$T$_{es}$T$_{es}$$^m$C$_{e}$ | n/a | n/a | 53 |
| 681251 | GalNAc₃-7$_a$-$_o$,T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{es}$G$_{es}$T$_{es}$T$_{es}$$^m$C$_{e}$ | GalNAc₃-7$_a$ | PO | 53 |
| 681257 | GalNAc₃-7$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$T$_{ds}$G$_{ds}$$^m$C$_{ds}$T$_{ds}$T$_{eo}$G$_{eo}$T$_{es}$T$_{es}$$^m$C$_{e}$ | GalNAc₃-7$_a$ | PO | 53 |

See the Example 74 for table legend. The structure of GalNAc$_3$-7a was shown previously in Example 48.

Ultrafree-MC ultrafiltration units (30,000 NMWL, low-binding regenerated cellulose membrane, Millipore, Bedford, Mass.) were pre-conditioned with 300 μL of 0.5% Tween 80 and centrifuged at 2000 g for 10 minutes, then with 300 μL of a 300 μg/mL solution of a control oligonucleotide in H$_2$O and centrifuged at 2000 g for 16 minutes. In order to assess non-specific binding to the filters of each test oligonucleotide from Tables 57 and 93 to be used in the studies, 300 μL of a 250 ng/mL solution of oligonucleotide in H$_2$O at pH 7.4 was placed in the pre-conditioned filters and centrifuged at 2000 g for 16 minutes. The unfiltered and filtered samples were analyzed by an ELISA assay to determine the oligonucleotide concentrations. Three replicates were used to obtain an average concentration for each sample. The average concentration of the filtered sample relative to the unfiltered sample is used to determine the percent of oligonucleotide that is recovered through the filter in the absence of plasma (% recovery).

Frozen whole plasma samples collected in K3-EDTA from normal, drug-free human volunteers, cynomolgus monkeys, and CD-1 mice, were purchased from Bioreclamation LLC (Westbury, N.Y.). The test oligonucleotides were added to 1.2 mL aliquots of plasma at two concentrations (5 and 150 μg/mL). An aliquot (300 μL) of each spiked plasma sample was placed in a pre-conditioned filter unit and incubated at 37° C. for 30 minutes, immediately followed by centrifugation at 2000 g for 16 minutes. Aliquots of filtered and unfiltered spiked plasma samples were analyzed by an ELISA to determine the oligonucleotide concentration in each sample. Three replicates per concentration were used to determine the average percentage of bound and unbound oligonucleotide in each sample. The average concentration of the filtered sample relative to the concentration of the unfiltered sample is used to determine the percent of oligonucleotide in the plasma that is not bound to plasma proteins (% unbound). The final unbound oligonucleotide values are corrected for non-specific binding by dividing the % unbound by the % recovery for each oligonucleotide. The final % bound oligonucleotide values are determined by subtracting the final % unbound values from 100. The results are shown in Table 94 for the two concentrations of oligonucleotide tested (5 and 150 μg/mL) in each species of plasma. The results show that GalNAc conjugate groups do not have a significant impact on plasma protein binding. Furthermore, oligonucleotides with full PS internucleoside linkages and mixed PO/PS linkages both bind plasma proteins, and those with full PS linkages bind plasma proteins to a somewhat greater extent than those with mixed PO/PS linkages.

TABLE 94

Percent of modified oligonucleotide bound to plasma proteins

| ISIS No. | Human plasma | | Monkey plasma | | Mouse plasma | |
|---|---|---|---|---|---|---|
| | 5 μg/mL | 150 μg/mL | 5 μg/mL | 150 μg/mL | 5 μg/mL | 150 μg/mL |
| 304801 | 99.2 | 98.0 | 99.8 | 99.5 | 98.1 | 97.2 |
| 663083 | 97.8 | 90.9 | 99.3 | 99.3 | 96.5 | 93.0 |
| 674450 | 96.2 | 97.0 | 98.6 | 94.4 | 94.6 | 89.3 |
| 494372 | 94.1 | 89.3 | 98.9 | 97.5 | 97.2 | 93.6 |
| 693401 | 93.6 | 89.9 | 96.7 | 92.0 | 94.6 | 90.2 |
| 681251 | 95.4 | 93.9 | 99.1 | 98.2 | 97.8 | 96.1 |
| 681257 | 93.4 | 90.5 | 97.6 | 93.7 | 95.6 | 92.7 |

Example 97

Modified Oligonucleotides Targeting TTR Comprising a GalNAc$_3$ Conjugate Group

The oligonucleotides shown in Table 95 comprising a GalNAc conjugate were designed to target TTR.

TABLE 95

Modified oligonucleotides targeting TTR

| ISIS No. | Sequences (5' to 3') | GalNAc$_3$ Cluster | CM | SEQ ID No |
|---|---|---|---|---|
| 666941 | GalNAc$_3$-3$_{a-o}$,A$_{do}$T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$ G$_{ds}$A$_{ds}$A$_{ds}$A$_{es}$T$_{es}$$^m$C$_{es}$$^m$C$_{es}$$^m$C$_{e}$ | GalNAc$_3$-3 | A$_d$ | 45 |
| 666942 | T$_{es}$$^m$C$_{eo}$T$_{eo}$T$_{eo}$G$_{eo}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{eo}$T$_{eo}$$^m$C$_{es}$$^m$C$_{es}$$^m$C$_{e}$A$_{do}$,-GalNAc$_3$-3$_a$ | GalNAc$_3$-1 | A$_d$ | 42 |
| 682876 | GalNAc$_3$-3$_{a-o}$,T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$ A$_{ds}$A$_{ds}$A$_{es}$T$_{es}$$^m$C$_{es}$$^m$C$_{es}$$^m$C$_{e}$ | GalNAc$_3$-3 | PO | 41 |
| 682877 | GalNAc$_3$-7$_{a-o}$,T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$ A$_{ds}$A$_{ds}$A$_{es}$T$_{es}$$^m$C$_{es}$$^m$C$_{es}$$^m$C$_{e}$ | GalNAc$_3$-7 | PO | 41 |
| 682878 | GalNAc$_3$-10$_{a-o}$,T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$ A$_{ds}$A$_{ds}$A$_{es}$T$_{es}$$^m$C$_{es}$$^m$C$_{es}$$^m$C$_{e}$ | GalNAc$_3$-10 | PO | 41 |

TABLE 95-continued

Modified oligonucleotides targeting TTR

| ISIS No. | Sequences (5' to 3') | GalNAc₃ Cluster | CM | SEQ ID No |
|---|---|---|---|---|
| 682879 | GalNAc₃-13$_{a-o}$,T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$ A$_{ds}$A$_{ds}$A$_{es}$T$_{es}$$^m$C$_{es}$$^m$C$_{es}$$^m$C$_{e}$ | GalNAc₃-13 | PO | 41 |
| 682880 | GalNAc₃-7$_{a-o}$,A$_{do}$T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$ G$_{ds}$A$_{ds}$A$_{ds}$A$_{es}$T$_{es}$$^m$C$_{es}$$^m$C$_{es}$$^m$C$_{e}$ | GalNAc₃-7 | A$_d$ | 45 |
| 682881 | GalNAc₃-10$_{a-o}$,A$_{do}$T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$ G$_{ds}$A$_{ds}$A$_{ds}$A$_{es}$T$_{es}$$^m$C$_{es}$$^m$C$_{es}$$^m$C$_{e}$ | GalNAc₃-10 | A$_d$ | 45 |
| 682882 | GalNAc₃-13$_{a-o}$,A$_{do}$T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$ G$_{ds}$A$_{ds}$A$_{ds}$A$_{es}$T$_{es}$$^m$C$_{es}$$^m$C$_{es}$$^m$C$_{e}$ | GalNAc₃-13 | A$_d$ | 45 |
| 684056 | T$_{es}$$^m$C$_{es}$T$_{es}$T$_{es}$G$_{es}$G$_{ds}$T$_{ds}$T$_{ds}$A$_{ds}$$^m$C$_{ds}$A$_{ds}$T$_{ds}$G$_{ds}$A$_{ds}$A$_{ds}$A$_{es}$T$_{es}$$^m$C$_{es}$$^m$ C$_{es}$$^m$C$_{e}$A$_{do}$,-GalNAc₃-19$_a$ | GalNAc₃-19 | A$_d$ | 42 |

The legend for Table 95 can be found in Example 74. The structure of GalNAc₃-1 was shown in Example 9. The structure of GalNAc₃-3$_a$ was shown in Example 39. The structure of GalNAc₃-7$_a$ was shown in Example 48. The structure of GalNAc₃-10$_a$ was shown in Example 46. The structure of GalNAc₃-13$_a$ was shown in Example 62. The structure of GalNAc₃-19$_a$ was shown in Example 70.

Example 98

Evaluation of Pro-Inflammatory Effects of Oligonucleotides Comprising a GalNAc Conjugate in hPMBC Assay The oligonucleotides listed in Table 96 and were tested for pro-inflammatory effects in an hPMBC assay as described in Examples 23 and 24. (See Tables 17, 70, 82, and 95 for descriptions of the oligonucleotides.) ISIS 353512 is a high responder used as a positive control, and the other oligonucleotides are described in Tables 70, 82, and 95. The results shown in Table 96 were obtained using blood from one volunteer donor. The results show that the oligonucleotides comprising mixed PO/PS internucleoside linkages produced significantly lower pro-inflammatory responses compared to the same oligonucleotides having full PS linkages. Furthermore, the GalNAc conjugate group did not have a significant effect in this assay.

TABLE 96

| ISIS No. | E$_{max}$/EC$_{50}$ | GalNAc₃ cluster | Linkages | CM |
|---|---|---|---|---|
| 353512 | 3630 | n/a | PS | n/a |
| 420915 | 802 | n/a | PS | n/a |
| 682881 | 1311 | GalNAc₃-10 | PS | A$_d$ |
| 682888 | 0.26 | GalNAc₃-10 | PO/PS | A$_d$ |
| 684057 | 1.03 | GalNAc₃-19 | PO/PS | A$_d$ |

Example 99

Binding Affinities of Oligonucleotides Comprising a GalNAc Conjugate for the Asialoglycoprotein Receptor The binding affinities of the oligonucleotides listed in Table 97 (see Table 63 for descriptions of the oligonucleotides) for the asialoglycoprotein receptor were tested in a competitive receptor binding assay. The competitor ligand, α1-acid glycoprotein (AGP), was incubated in 50 mM sodium acetate buffer (pH 5) with 1 U neuraminidase-agarose for 16 hours at 37° C., and >90% desialylation was confirmed by either sialic acid assay or size exclusion chromatography (SEC). Iodine monochloride was used to iodinate the AGP according to the procedure by Atsma et al. (see J Lipid Res. 1991 January; 32(1):173-81.) In this method, desialylated α1-acid glycoprotein (de-AGP) was added to 10 mM iodine chloride, Na$^{125}$I, and 1 M glycine in 0.25 M NaOH. After incubation for 10 minutes at room temperature, $^{125}$I-labeled de-AGP was separated from free $^{125}$I by concentrating the mixture twice utilizing a 3 KDM-WCO spin column. The protein was tested for labeling efficiency and purity on a HPLC system equipped with an Agilent SEC-3 column (7.8×300 mm) and a β-RAM counter. Competition experiments utilizing $^{125}$I-labeled de-AGP and various GalNAc-cluster containing ASOs were performed as follows. Human HepG2 cells (10$^6$ cells/ml) were plated on 6-well plates in 2 ml of appropriate growth media. MEM media supplemented with 10% fetal bovine serum (FBS), 2 mM L-Glutamine and 10 mM HEPES was used. Cells were incubated 16-20 hours @ 37° C. with 5% and 10% CO$_2$ respectively. Cells were washed with media without FBS prior to the experiment. Cells were incubated for 30 min @37° C. with 1 ml competition mix containing appropriate growth media with 2% FBS, 10$^{-8}$ M $^{125}$I-labeled de-AGP and GalNAc-cluster containing ASOs at concentrations ranging from 10$^{-11}$ to 10$^{-5}$ M. Non-specific binding was determined in the presence of 10$^{-2}$ M GalNAc sugar. Cells were washed twice with media without FBS to remove unbound $^{125}$I-labeled de-AGP and competitor GalNAc ASO. Cells were lysed using Qiagen's RLT buffer containing 1% β-mercaptoethanol. Lysates were transferred to round bottom assay tubes after a brief 10 min freeze/thaw cycle and assayed on a γ-counter. Non-specific binding was subtracted before dividing $^{125}$I protein counts by the value of the lowest GalNAc-ASO concentration counts. The inhibition curves were fitted according to a single site competition binding equation using a nonlinear regression algorithm to calculate the binding affinities (K$_D$'s).

The results in Table 97 were obtained from experiments performed on five different days. Results for oligonucleotides marked with superscript "a" are the average of experiments run on two different days. The results show that the oligonucleotides comprising a GalNAc conjugate group on the 5'-end bound the asialoglycoprotein receptor on human HepG2 cells with 1.5 to 16-fold greater affinity than the oligonucleotides comprising a GalNAc conjugate group on the 3'-end.

TABLE 97

Asialoglycoprotein receptor binding assay results

| ISIS No. | GalNAc conjugate | Oligonucleotide end to which GalNAc conjugate is attached | $K_D$ (nM) |
|---|---|---|---|
| 661161[a] | GalNAc$_3$-3 | 5' | 3.7 |
| 666881[a] | GalNAc$_3$-10 | 5' | 7.6 |
| 666981 | GalNAc$_3$-7 | 5' | 6.0 |
| 670061 | GalNAc$_3$-13 | 5' | 7.4 |
| 655861[a] | GalNAc$_3$-1 | 3' | 11.6 |
| 677841[a] | GalNAc$_3$-19 | 3' | 60.8 |

Example 100

Antisense Inhibition In Vivo by Oligonucleotides Comprising a GalNAc Conjugate Group Targeting Apo(a) In Vivo The oligonucleotides listed in Table 98a below were tested in a single dose study for duration of action in mice.

TABLE 98a

Modified ASOs targeting APO(a)

| ISIS No. | Sequences (5' to 3') | GalNAc$_3$ Cluster | CM | SEQ ID No. |
|---|---|---|---|---|
| 681251 | GalNAc$_3$-7$_a$-$_o$,T$_{es}$G$_{es}$$^m$C$_{es}$T$_{es}$$^m$C$_{es}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{es}$G$_{es}$T$_{es}$T$_{es}$$^m$C$_e$ | GalNAc$_3$-7a | PO | 53 |
| 681257 | GalNAc$_3$-7$_a$-$_o$,T$_{es}$G$_{eo}$$^m$C$_{eo}$T$_{eo}$$^m$C$_{eo}$$^m$C$_{ds}$G$_{ds}$T$_{ds}$T$_{ds}$G$_{ds}$G$_{ds}$ T$_{ds}$G$_{ds}$$^m$C$_{ds}$T$_{ds}$T$_{eo}$G$_{eo}$T$_{es}$T$_{es}$$^m$C$_e$ | GalNAc$_3$-7a | PO | 53 |

The structure of GalNAc$_3$-7$_a$ was shown in Example 48.

Treatment

Female transgenic mice that express human Apo(a) were each injected subcutaneously once per week, for a total of 6 doses, with an oligonucleotide and dosage listed in Table 98b or with PBS. Each treatment group consisted of 3 animals. Blood was drawn the day before dosing to determine baseline levels of Apo(a) protein in plasma and at 72 hours, 1 week, and 2 weeks following the first dose. Additional blood draws will occur at 3 weeks, 4 weeks, 5 weeks, and 6 weeks following the first dose. Plasma Apo(a) protein levels were measured using an ELISA. The results in Table 98b are presented as the average percent of plasma Apo(a) protein levels for each treatment group, normalized to baseline levels (% BL), The results show that the oligonucleotides comprising a GalNAc conjugate group exhibited potent reduction in Apo(a) expression. This potent effect was observed for the oligonucleotide that comprises full PS internucleoside linkages and the oligonucleotide that comprises mixed PO and PS linkages.

TABLE 98b

Apo(a) plasma protein levels

| ISIS No. | Dosage (mg/kg) | Apo(a) at 72 hours (% BL) | Apo(a) at 1 week (% BL) | Apo(a) at 3 weeks (% BL) |
|---|---|---|---|---|
| PBS | n/a | 116 | 104 | 107 |
| 681251 | 0.3 | 97 | 108 | 93 |
|  | 1.0 | 85 | 77 | 57 |
|  | 3.0 | 54 | 49 | 11 |
|  | 10.0 | 23 | 15 | 4 |
| 681257 | 0.3 | 114 | 138 | 104 |
|  | 1.0 | 91 | 98 | 54 |
|  | 3.0 | 69 | 40 | 6 |
|  | 10.0 | 30 | 21 | 4 |

Example 101

Antisense Inhibition by Oligonucleotides Comprising a GalNAc Cluster Linked Via a Stable Moiety The oligonucleotides listed in Table 99 were tested for inhibition of mouse APOC-III expression in vivo. C57Bl/6 mice were each injected subcutaneously once with an oligonucleotide listed in Table 99 or with PBS. Each treatment group consisted of 4 animals. Each mouse treated with ISIS 440670 received a dose of 2, 6, 20, or 60 mg/kg. Each mouse treated with ISIS 680772 or 696847 received 0.6, 2, 6, or 20 mg/kg. The GalNAc conjugate group of ISIS 696847 is linked via a stable moiety, a phosphorothioate linkage instead of a readily cleavable phosphodiester containing linkage. The animals were sacrificed 72 hours after the dose. Liver APOC-III mRNA levels were measured using real-time PCR. APOC-III mRNA levels were normalized to cyclophilin mRNA levels according to standard protocols. The results are presented in Table 99 as the average percent of APOC-III mRNA levels for each treatment group relative to the saline control group. The results show that the oligonucleotides comprising a GalNAc conjugate group were significantly more potent than the oligonucleotide lacking a conjugate group. Furthermore, the oligonucleotide comprising a GalNAc conjugate group linked to the oligonucleotide via a cleavable moiety (ISIS 680772) was even more potent than the oligonucleotide comprising a GalNAc conjugate group linked to the oligonucleotide via a stable moiety (ISIS 696847).

TABLE 99

Modified oligonucleotides targeting mouse APOC-III

| ISIS No. | Sequences (5' to 3') | CM | Dosage (mg/kg) | APOC-III mRNA (% PBS) | SEQ ID No. |
|---|---|---|---|---|---|
| 440670 | $^mC_{es}A_{es}G_{es}{}^mC_{es}T_{es}T_{ds}T_{ds}A_{ds}T_{ds}A_{ds}G_{ds}G_{ds}G_{ds}A_{ds}{}^mC_{es}A_{es}G_{es}{}^mC_{es}A_e$ | n/a | 2<br>6<br>20<br>60 | 92<br>86<br>59<br>37 | 47 |
| 680772 | GalNAc$_3$-7$_a$-$_o$,$^mC_{es}A_{es}G_{es}{}^mC_{es}T_{es}T_{ds}T_{ds}A_{ds}T_{ds}T_{ds}$$A_{ds}G_{ds}G_{ds}G_{ds}A_{ds}{}^mC_{es}A_{es}G_{es}{}^mC_{es}A_e$ | PO | 0.6<br>2<br>6<br>20 | 79<br>58<br>31<br>13 | 47 |
| 696847 | GalNAc$_3$-7$_a$-$_s$,$^mC_{es}A_{es}G_{es}{}^mC_{es}T_{es}T_{ds}T_{ds}A_{ds}T_{ds}T_{ds}$$A_{ds}G_{ds}G_{ds}G_{ds}A_{ds}{}^mC_{es}A_{es}G_{es}{}^mC_{es}A_e$ | n/a (PS) | 0.6<br>2<br>6<br>20 | 83<br>73<br>40<br>28 | 47 |

The structure of GalNAc$_3$-7$_a$ was shown in Example 48.

Example 102

Distribution in Liver of Antisense Oligonucleotides Comprising a GalNAc Conjugate The liver distribution of ISIS 353382 (see Table 23) that does not comprise a GalNAc conjugate and ISIS 655861 (see Table 23) that does comprise a GalNAc conjugate was evaluated. Male balb/c mice were subcutaneously injected once with ISIS 353382 or 655861 at a dosage listed in Table 100. Each treatment group consisted of 3 animals except for the 18 mg/kg group for ISIS 655861, which consisted of 2 animals. The animals were sacrificed 48 hours following the dose to determine the liver distribution of the oligonucleotides. In order to measure the number of antisense oligonucleotide molecules per cell, a Ruthenium (II) tris-bipyridine tag (MSD TAG, Meso Scale Discovery) was conjugated to an oligonucleotide probe used to detect the antisense oligonucleotides. The results presented in Table 100 are the average concentrations of oligonucleotide for each treatment group in units of millions of oligonucleotide molecules per cell. The results show that at equivalent doses, the oligonucleotide comprising a GalNAc conjugate was present at higher concentrations in the total liver and in hepatocytes than the oligonucleotide that does not comprise a GalNAc conjugate. Furthermore, the oligonucleotide comprising a GalNAc conjugate was present at lower concentrations in non-parenchymal liver cells than the oligonucleotide that does not comprise a GalNAc conjugate. And while the concentrations of ISIS 655861 in hepatocytes and non-parenchymal liver cells were similar per cell, the liver is approximately 80% hepatocytes by volume. Thus, the majority of the ISIS 655861 oligonucleotide that was present in the liver was found in hepatocytes, whereas the majority of the ISIS 353382 oligonucleotide that was present in the liver was found in non-parenchymal liver cells.

TABLE 100

| ISIS No. | Dosage (mg/kg) | Concentration in whole liver (molecules * $10^{\wedge}6$ per cell) | Concentration in hepatocytes (molecules * $10^{\wedge}6$ per cell) | Concentration in non-parenchymal liver cells (molecules * $10^{\wedge}6$ per cell) |
|---|---|---|---|---|
| 353382 | 3 | 9.7 | 1.2 | 37.2 |
|  | 10 | 17.3 | 4.5 | 34.0 |
|  | 20 | 23.6 | 6.6 | 65.6 |
|  | 30 | 29.1 | 11.7 | 80.0 |
|  | 60 | 73.4 | 14.8 | 98.0 |
|  | 90 | 89.6 | 18.5 | 119.9 |
| 655861 | 0.5 | 2.6 | 2.9 | 3.2 |
|  | 1 | 6.2 | 7.0 | 8.8 |
|  | 3 | 19.1 | 25.1 | 28.5 |
|  | 6 | 44.1 | 48.7 | 55.0 |
|  | 18 | 76.6 | 82.3 | 77.1 |

Example 103

Duration of Action In Vivo of Oligonucleotides Targeting APOC-III Comprising a GalNAc$_3$ Conjugate The oligonucleotides listed in Table 101 below were tested in a single dose study for duration of action in mice.

TABLE 101

Modified ASOs targeting APOC-III

| ISIS No. | Sequences (5' to 3') | GalNAc$_3$ Cluster | CM | SEQ ID No. |
|---|---|---|---|---|
| 304801 | $A_{es}G_{es}{}^mC_{es}T_{es}T_{es}{}^mC_{ds}T_{ds}T_{ds}G_{ds}T_{ds}{}^mC_{ds}{}^mC_{ds}A_{ds}G_{ds}{}^mC_{ds}T_{es}T_{es}T_{es}A_{es}T_e$ | n/a | n/a | 20 |
| 663084 | GalNAc$_3$-3$_a$-$_o$,$A_{do}$ $A_{es}G_{eo}{}^mC_{eo}T_{eo}T_{eo}{}^mC_{ds}T_{ds}T_{ds}G_{ds}T_{ds}{}^mC_{ds}{}^mC_{ds}$$A_{ds}G_{ds}{}^mC_{ds}T_{eo}T_{eo}T_{es}A_{es}T_e$ | GalNAc$_3$-3a | $A_d$ | 36 |

TABLE 101-continued

Modified ASOs targeting APOC-III

| ISIS No. | Sequences (5' to 3') | GalNAc$_3$ Cluster | CM | SEQ ID No. |
|---|---|---|---|---|
| 679241 | A$_{es}$G$_{eo}$$^m$C$_{eo}$T$_{eo}$T$_{eo}$$^m$C$_{ds}$T$_{ds}$T$_{ds}$G$_{ds}$T$_{ds}$$^m$C$_{ds}$$^m$C$_{ds}$A$_{ds}$G$_{ds}$$^m$C$_{ds}$T$_{eo}$T$_{eo}$T$_{es}$A$_{es}$T$_{eo}$A$_{do}$, -GalNAc$_3$-19$_a$ | GalNAc$_3$-19a | A$^d$ | 21 |

The structure of GalNAc$_3$-3$_a$ was shown in Example 39, and GalNAc$_3$-19$_a$ was shown in Example 70.

Treatment

Female transgenic mice that express human APOC-III were each injected subcutaneously once with an oligonucleotide listed in Table 101 or with PBS. Each treatment group consisted of 3 animals. Blood was drawn before dosing to determine baseline and at 3, 7, 14, 21, 28, 35, and 42 days following the dose. Plasma triglyceride and APOC-III protein levels were measured as described in Example 20. The results in Table 102 are presented as the average percent of plasma triglyceride and APOC-III levels for each treatment group, normalized to baseline levels. A comparison of the results in Table 58 of example 79 with the results in Table 102 below show that oligonucleotides comprising a mixture of phosphodiester and phosphorothioate internucleoside linkages exhibited increased duration of action than equivalent oligonucleotides comprising only phosphorothioate internucleoside linkages.

TABLE 102

Plasma triglyceride and APOC-III protein levels in transgenic mice

| ISIS No. | Dosage (mg/kg) | Time point (days post-dose) | Triglycerides (% baseline) | APOC-III protein (% baseline) | GalNAc$_3$ Cluster | CM |
|---|---|---|---|---|---|---|
| PBS | n/a | 3 | 96 | 101 | n/a | n/a |
| | | 7 | 88 | 98 | | |
| | | 14 | 91 | 103 | | |
| | | 21 | 69 | 92 | | |
| | | 28 | 83 | 81 | | |
| | | 35 | 65 | 86 | | |
| | | 42 | 72 | 88 | | |
| 304801 | 30 | 3 | 42 | 46 | n/a | n/a |
| | | 7 | 42 | 51 | | |
| | | 14 | 59 | 69 | | |
| | | 21 | 67 | 81 | | |
| | | 28 | 79 | 76 | | |
| | | 35 | 72 | 95 | | |
| | | 42 | 82 | 92 | | |
| 663084 | 10 | 3 | 35 | 28 | GalNAc$_3$-3a | A$_d$ |
| | | 7 | 23 | 24 | | |
| | | 14 | 23 | 26 | | |
| | | 21 | 23 | 29 | | |
| | | 28 | 30 | 22 | | |
| | | 35 | 32 | 36 | | |
| | | 42 | 37 | 47 | | |
| 679241 | 10 | 3 | 38 | 30 | GalNAc$_3$-19a | A$_d$ |
| | | 7 | 31 | 28 | | |
| | | 14 | 30 | 22 | | |
| | | 21 | 36 | 34 | | |
| | | 28 | 48 | 34 | | |
| | | 35 | 50 | 45 | | |
| | | 42 | 72 | 64 | | |

Example 104

Synthesis of Oligonucleotides Comprising a 5'-GalNAc$_2$ Conjugate

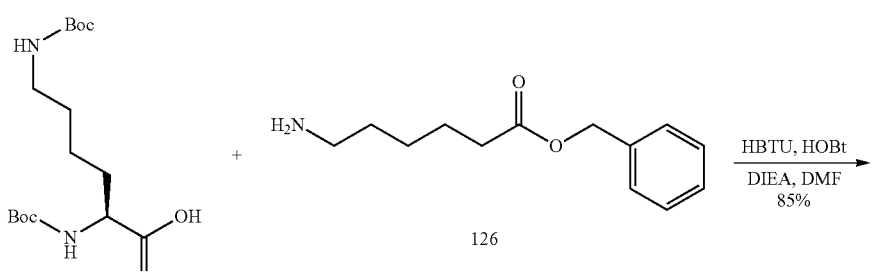

-continued
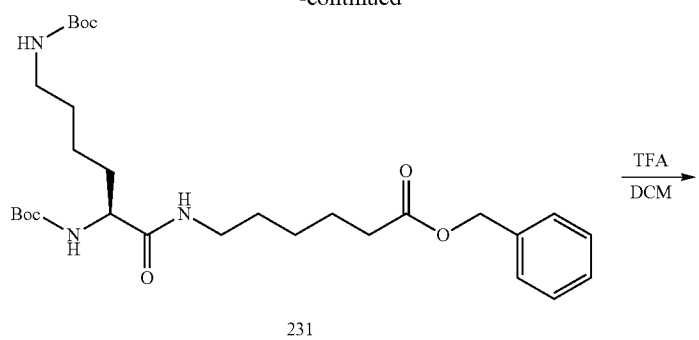
231
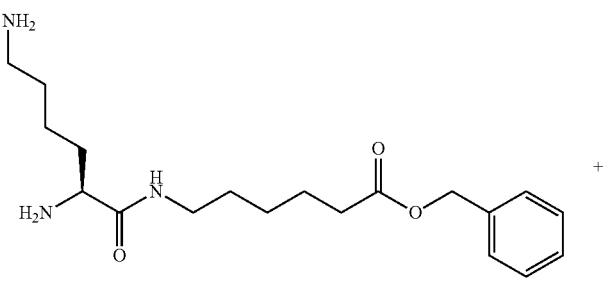
232
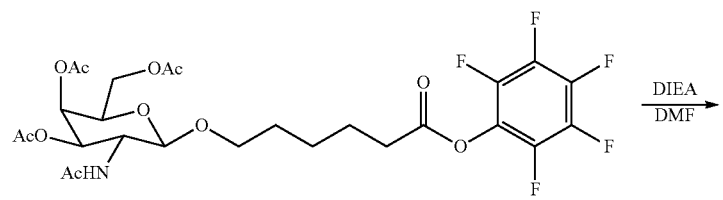
166
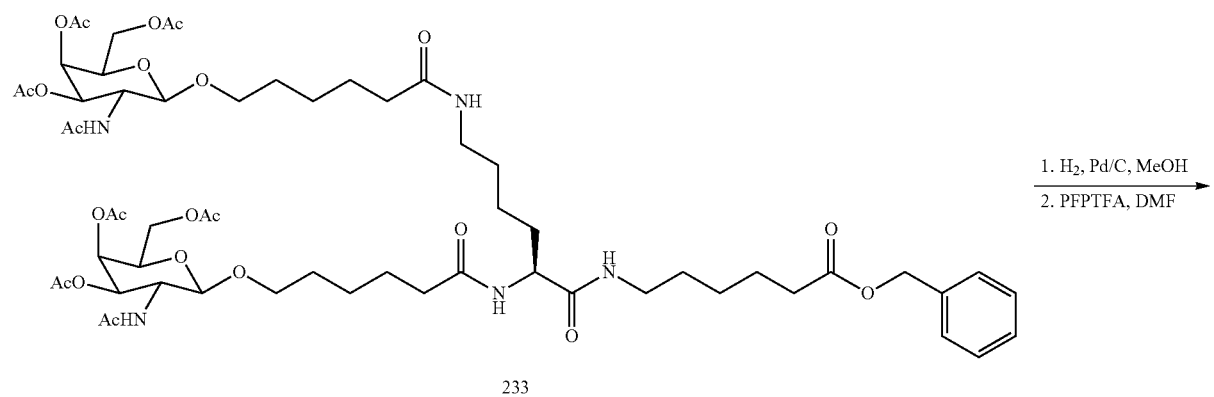
233
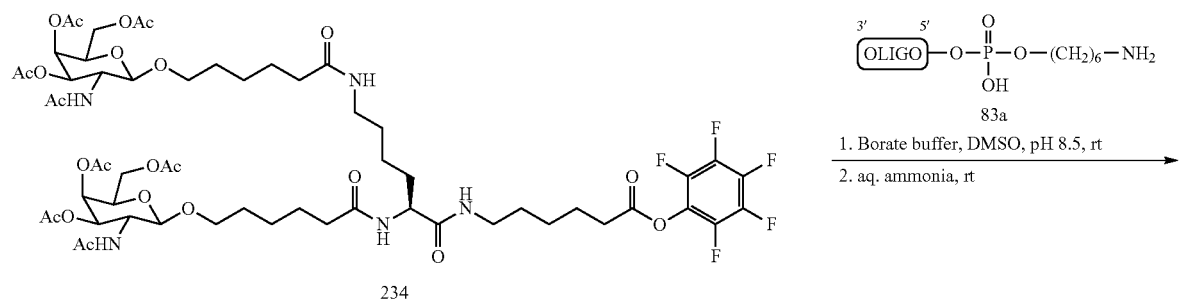
234

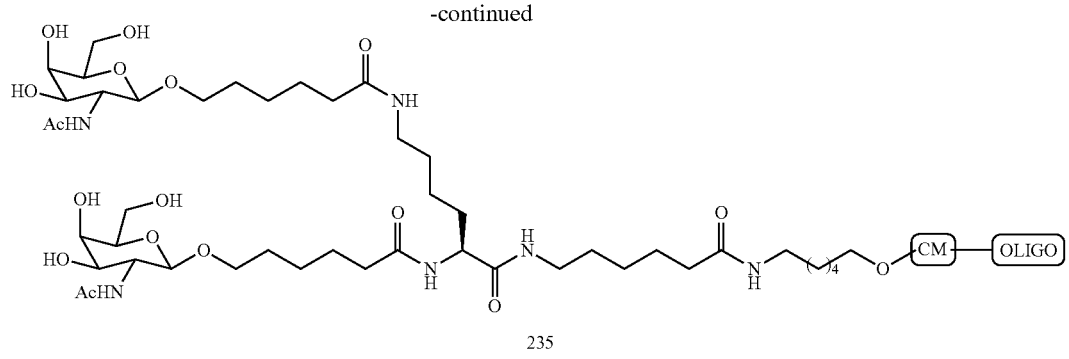

235

Compound 120 is commercially available, and the synthesis of compound 126 is described in Example 49. Compound 120 (1 g, 2.89 mmol), HBTU (0.39 g, 2.89 mmol), and HOBt (1.64 g, 4.33 mmol) were dissolved in DMF (10 mL, and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M NaHSO4 and extracted with 2×50 mL ethyl acetate. Organic layers were combined and washed with 3×40 mL sat NaHCO$_3$ and 2× brine, dried with Na$_2$SO$_4$, filtered and concentrated. The product was purified by silica gel column chromatography (DCM:EA:Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifluoracetate salt. The synthesis of compound 166 is described in Example 54. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×100 mL). The organic phase was separated and washed with sat, aqueous NaHCO$_3$ (3×80 mL), 1 M NaHSO$_4$ (3×80 mL) and brine (2×80 mL), then dried (Na$_2$SO$_4$), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylethylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Oligonucleotide 235 was prepared using the general procedure described in Example 46. The GalNAc$_2$ cluster portion (GalNAc$_2$-24$_a$) of the conjugate group GalNAc$_2$-24 can be combined with any cleavable moiety present on the oligonucleotide to provide a variety of conjugate groups. The structure of GalNAc$_2$-24 (GalNAc$_2$-24$_a$-CM) is shown below:

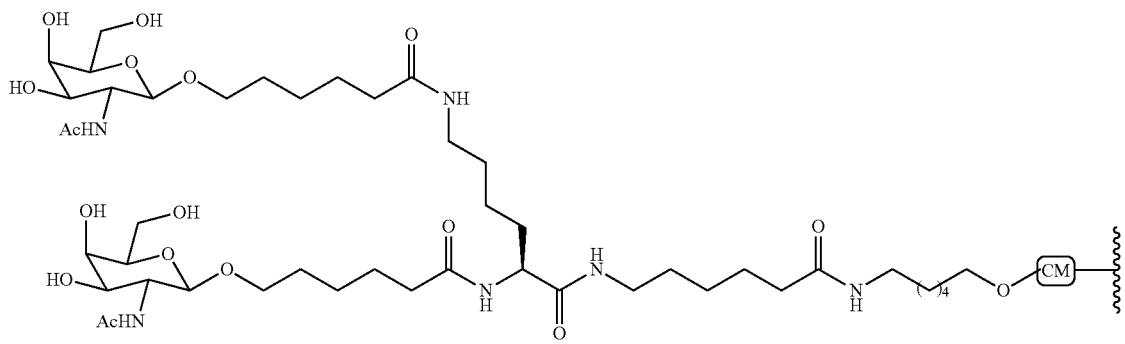

Example 105

Synthesis of Oligonucleotides Comprising a GalNAc$_1$-25 Conjugate

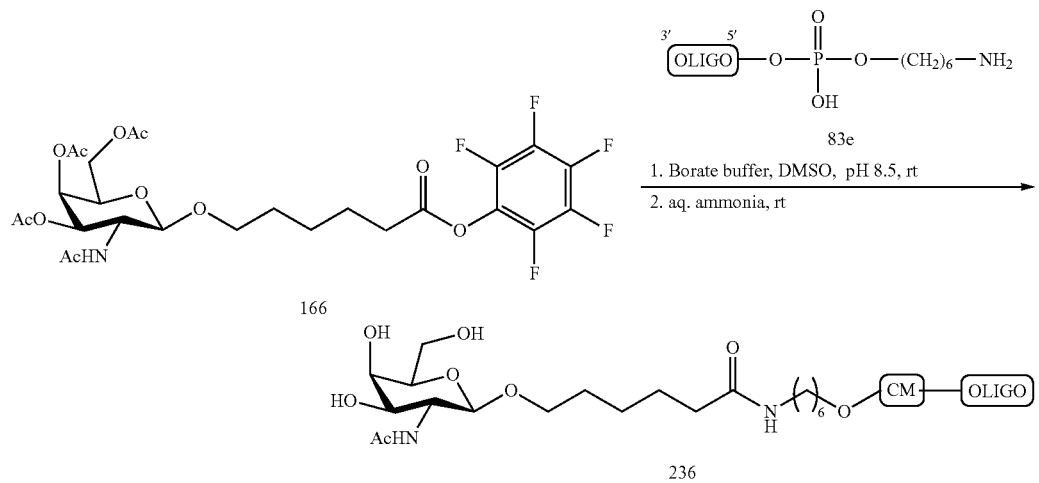

The synthesis of compound 166 is described in Example 54. Oligonucleotide 236 was prepared using the general procedure described in Example 46.

Alternatively, oligonucleotide 236 was synthesized using the scheme shown below, and compound 238 was used to form the oligonucleotide 236 using procedures described in Example 10.

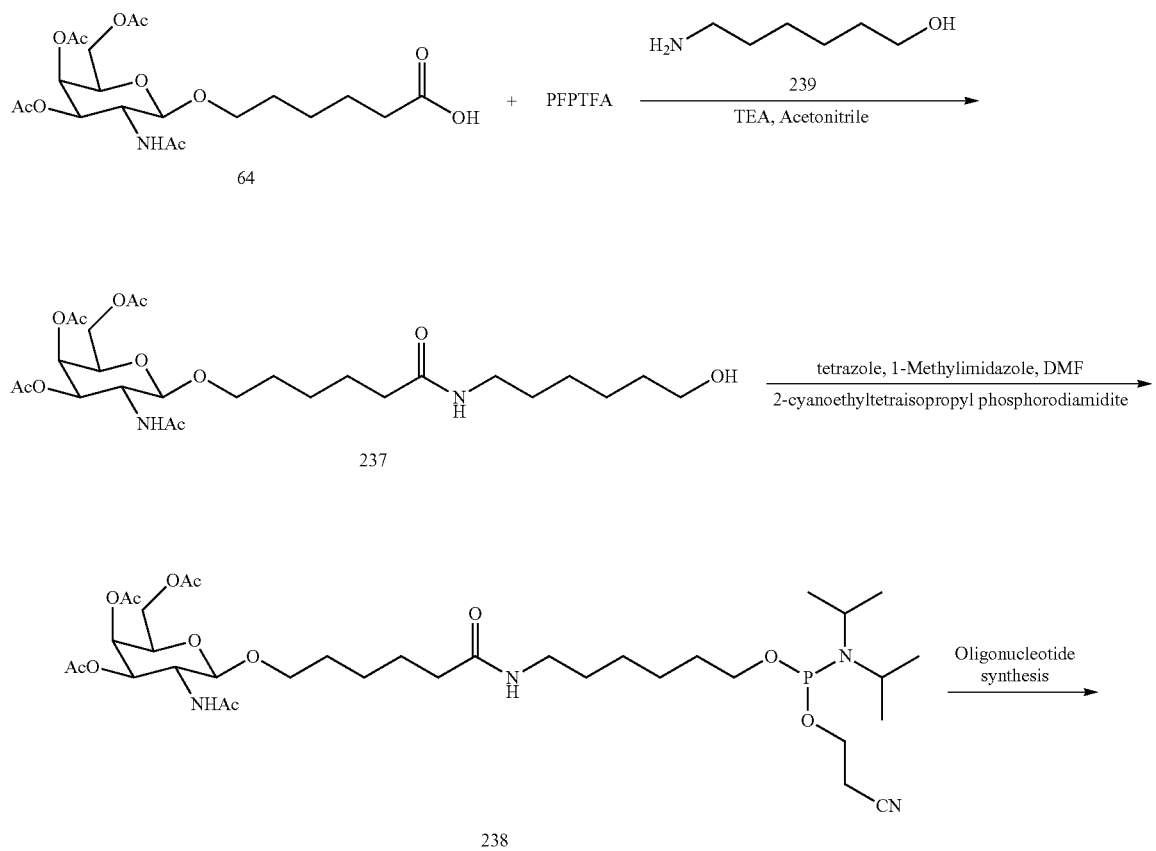

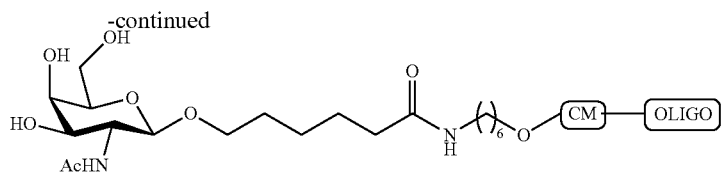

236

The GalNAc$_1$ cluster portion (GalNAc$_1$-25$_a$) of the conjugate group GalNAc$_1$-25 can be combined with any cleavable moiety present on the oligonucleotide to provide a variety of conjugate groups. The structure of GalNAc$_1$-25 (GalNAc$_1$-25$_a$-CM) is shown below:

Example 106

Antisense Inhibition In Vivo by Oligonucleotides Targeting SRB-1 Comprising a 5'-GalNAc$_2$ or a 5'-GalNAc$_3$ Conjugate Oligonucleotides listed in Tables 103 and 104 were tested in dose-dependent studies for antisense inhibition of SRB-1 in mice.

Treatment

Six to week old, male C57BL/6 mice (Jackson Laboratory, Bar Harbor, Me.) were injected subcutaneously once with 2, 7, or 20 mg/kg of ISIS No. 440762; or with 0.2, 0.6, 2, 6, or 20 mg/kg of ISIS No. 686221, 686222, or 708561; or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The antisense oligonucleotides lowered SRB-1 mRNA levels in a dose-dependent manner, and the ED$_{50}$ results are presented in Tables 103 and 104. Although previous studies showed that trivalent GalNAc-conjugated oligonucleotides were significantly more potent than divalent GalNAc-conjugated oligonucleotides, which were in turn significantly more potent than monovalent GalNAc conjugated oligonucleotides (see, e.g., Khorev et al., *Bioorg. & Med. Chem.*, Vol. 16, 5216-5231 (2008)), treatment with antisense oligonucleotides comprising monovalent, divalent, and trivalent GalNAc clusters lowered SRB-1 mRNA levels with similar potencies as shown in Tables 103 and 104.

TABLE 103

Modified oligonucleotides targeting SRB-1

| ISIS No. | Sequences (5' to 3') | GalNAc$_3$ Cluster | ED$_{50}$ (mg/kg) | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | 4.7 | 22 |
| 686221 | GalNAc$_2$-24$_a$-$_o$,A$_{do}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_2$-24$_a$ | 0.39 | 26 |
| 686222 | GalNAc$_3$-13$_a$-$_o$,A$_{do}$T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | GalNAc$_3$-13$_a$ | 0.41 | 26 |

See Example 93 for table legend. The structure of GalNAc$_3$-13a was shown in Example 62, and the structure of GalNAc$_2$-24a was shown in Example 104.

TABLE 104

Modified oligonucleotides targeting SRB-1

| ISIS No. | Sequences (5' to 3') | GalNAc$_3$ Cluster | ED$_{50}$ (mg/kg) | SEQ ID No |
|---|---|---|---|---|
| 440762 | T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{ks}$$^m$C$_k$ | n/a | 5 | 22 |
| 708561 | GalNAc$_1$-25$_a$-$_o$,T$_{ks}$$^m$C$_{ks}$A$_{ds}$G$_{ds}$T$_{ds}$$^m$C$_{ds}$A$_{ds}$T$_{ds}$G$_{ds}$A$_{ds}$$^m$C$_{ds}$T$_{ks}$$^m$C$_k$ | GalNAc$_1$-25$_a$ | 0.4 | 22 |

See Example 93 for table legend. The structure of GalNAc$_1$-25a was shown in Example 105.

The concentrations of the oligonucleotides in Tables 103 and 104 in liver were also assessed, using procedures described in Example 75. The results shown in Tables 104a and 104b below are the average total antisense oligonucleotide tissues levels for each treatment group, as measured by UV in units of μg oligonucleotide per gram of liver tissue. The results show that the oligonucleotides comprising a GalNAc conjugate group accumulated in the liver at significantly higher levels than the same dose of the oligonucleotide lacking a GalNAc conjugate group. Furthermore, the antisense oligonucleotides comprising one, two, or three GalNAc ligands in their respective conjugate groups all accumulated in the liver at similar levels. This result is surprising in view of the Khorev et al. literature reference cited above and is consistent with the activity data shown in Tables 103 and 104 above.

TABLE 104a

Liver concentrations of oligonucleotides comprising a GalNAc$_2$ or GalNAc$_3$ conjugate group

| ISIS No. | Dosage (mg/kg) | [Antisense oligonucleotide] (μg/g) | GalNAc cluster | CM |
|---|---|---|---|---|
| 440762 | 2 | 2.1 | n/a | n/a |
|  | 7 | 13.1 |  |  |
|  | 20 | 31.1 |  |  |
| 686221 | 0.2 | 0.9 | GalNAc$_2$-24$_a$ | A$_d$ |
|  | 0.6 | 2.7 |  |  |
|  | 2 | 12.0 |  |  |
|  | 6 | 26.5 |  |  |
| 686222 | 0.2 | 0.5 | GalNAc$_3$-13$_a$ | A$_d$ |
|  | 0.6 | 1.6 |  |  |
|  | 2 | 11.6 |  |  |
|  | 6 | 19.8 |  |  |

TABLE 104b

Liver concentrations of oligonucleotides comprising a GalNAc$_1$ conjugate group

| ISIS No. | Dosage (mg/kg) | [Antisense oligonucleotide] (μg/g) | GalNAc cluster | CM |
|---|---|---|---|---|
| 440762 | 2 | 2.3 | n/a | n/a |
|  | 7 | 8.9 |  |  |
|  | 20 | 23.7 |  |  |
| 708561 | 0.2 | 0.4 | GalNAc$_1$-25$_a$ | PO |
|  | 0.6 | 1.1 |  |  |
|  | 2 | 5.9 |  |  |
|  | 6 | 23.7 |  |  |
|  | 20 | 53.9 |  |  |

Example 107

Synthesis of Oligonucleotides Comprising a GalNAc$_1$-26 or GalNAc$_1$-27 Conjugate

239

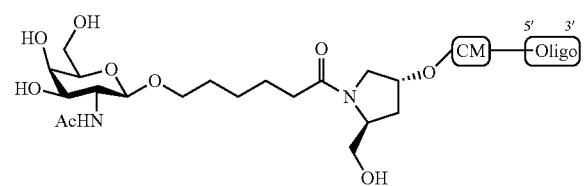

Oligonucleotide 239 is synthesized via coupling of compound 47 (see Example 15) to acid 64 (see Example 32) using HBTU and DIEA in DMF. The resulting amide containing compound is phosphitylated, then added to the 5'-end of an oligonucleotide using procedures described in Example 10. The GalNAc$_1$ cluster portion (GalNAc$_1$-26$_a$) of the conjugate group GalNAc$_1$-26 can be combined with any cleavable moiety present on the oligonucleotide to provide a variety of conjugate groups. The structure of GalNAc$_1$-26 (GalNAc$_1$-26$_a$-CM) is shown below:

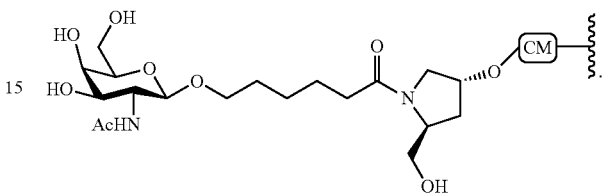

In order to add the GalNAc$_1$ conjugate group to the 3'-end of an oligonucleotide, the amide formed from the reaction of compounds 47 and 64 is added to a solid support using procedures described in Example 7. The oligonucleotide synthesis is then completed using procedures described in Example 9 in order to form oligonucleotide 240.

240

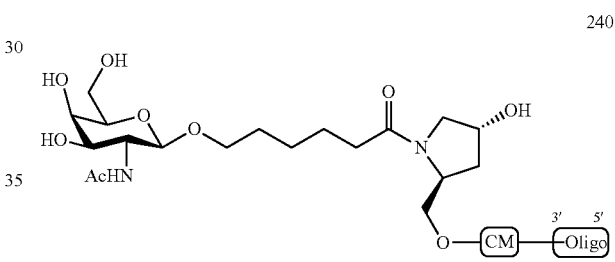

The GalNAc$_1$ cluster portion (GalNAc$_1$-27$_a$) of the conjugate group GalNAc$_1$-27 can be combined with any cleavable moiety present on the oligonucleotide to provide a variety of conjugate groups. The structure of GalNAc$_1$-27 (GalNAc$_1$-27$_a$-CM) is shown below:

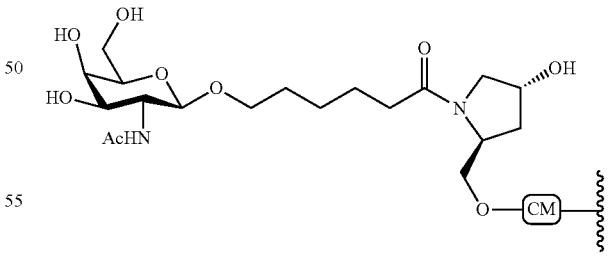

Example 108

Antisense Inhibition In Vivo by Oligonucleotides Comprising a GalNAc Conjugate Group Targeting Apo(a) In Vivo The oligonucleotides listed in Table 105 below were tested in a single dose study in mice.

TABLE 105

Modified ASOs targeting APO(a)

| ISIS No. | Sequences (5' to 3') | GalNAc₃ Cluster | CM | SEQ ID No. |
|---|---|---|---|---|
| 494372 | $T_{es}G_{es}{}^mC_{es}T_{es}{}^mC_{es}{}^mC_{ds}G_{ds}T_{ds}T_{ds}G_{ds}G_{ds}T_{ds}G_{ds}{}^mC_{ds}T_{ds}T_{es}G_{es}T_{es}T_{es}{}^mC_e$ | n/a | n/a | 53 |
| 681251 | GalNAc₃-7ₐ₋ₒ/$T_{es}G_{es}{}^mC_{es}T_{es}{}^mC_{es}{}^mC_{ds}G_{ds}T_{ds}T_{ds}G_{ds}G_{ds}T_{ds}G_{ds}{}^mC_{ds}$ $T_{ds}T_{es}G_{es}T_{es}T_{es}{}^mC_e$ | GalNAc₃-7a | PO | 53 |
| 681255 | GalNAc₃-3ₐ₋ₒ/$T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}$ $T_{ds}T_{eo}G_{eo}T_{es}T_{es}{}^mC_e$ | GalNAc₃-3a | PO | 53 |
| 681256 | GalNAc₃-10ₐ₋ₒ/$T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}$ $T_{ds}T_{eo}G_{eo}T_{es}T_{es}{}^mC_e$ | GalNAc₃-10a | PO | 53 |
| 681257 | GalNAc₃-7ₐ₋ₒ/$T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}$ $T_{ds}T_{eo}G_{eo}T_{es}T_{es}{}^mC_e$ | GalNAc₃-7a | PO | 53 |
| 681258 | GalNAc₃-13ₐ₋ₒ/$T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}$ $T_{ds}T_{eo}G_{eo}T_{es}T_{es}{}^mC_e$ | GalNAc₃-13a | PO | 53 |
| 681260 | $T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}T_{ds}T_{eo}G_{eo}T_{es}T_{es}{}^mC_{eo}A_{do}$/-GalNAc₃-19 | GalNAc₃-19a | $A_d$ | 52 |

The structure of GalNAc₃-7ₐ was shown in Example 48.

Treatment

Male transgenic mice that express human Apo(a) were each injected subcutaneously once with an oligonucleotide and dosage listed in Table 106 or with PBS. Each treatment group consisted of 4 animals. Blood was drawn the day before dosing to determine baseline levels of Apo(a) protein in plasma and at 1 week following the first dose. Additional blood draws will occur weekly for approximately 8 weeks. Plasma Apo(a) protein levels were measured using an ELISA. The results in Table 106 are presented as the average percent of plasma Apo(a) protein levels for each treatment group, normalized to baseline levels (% BL). The results show that the antisense oligonucleotides reduced Apo(a) protein expression. Furthermore, the oligonucleotides comprising a GalNAc conjugate group exhibited even more potent reduction in Apo(a) expression than the oligonucleotide that does not comprise a conjugate group.

TABLE 106

Apo(a) plasma protein levels

| ISIS No. | Dosage (mg/kg) | Apo(a) at 1 week (% BL) |
|---|---|---|
| PBS | n/a | 143 |
| 494372 | 50 | 58 |
| 681251 | 10 | 15 |
| 681255 | 10 | 14 |
| 681256 | 10 | 17 |
| 681257 | 10 | 24 |
| 681258 | 10 | 22 |
| 681260 | 10 | 26 |

Example 109

Synthesis of Oligonucleotides Comprising a GalNAc₁-28 or GalNAc₁-29 Conjugate

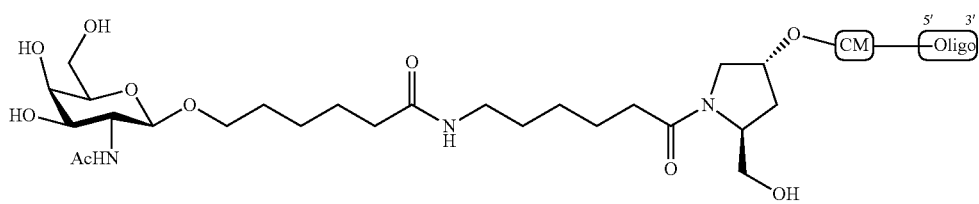

Oligonucleotide 241 is synthesized using procedures similar to those described in Example 71 to form the phosphoramidite intermediate, followed by procedures described in Example 10 to synthesize the oligonucleotide. The GalNAc$_1$ cluster portion (GalNAc$_1$-28$_a$) of the conjugate group GalNAc$_1$-28 can be combined with any cleavable moiety present on the oligonucleotide to provide a variety of conjugate groups. The structure of GalNAc$_1$-28 (GalNAc$_1$-28$_a$-CM) is shown below:

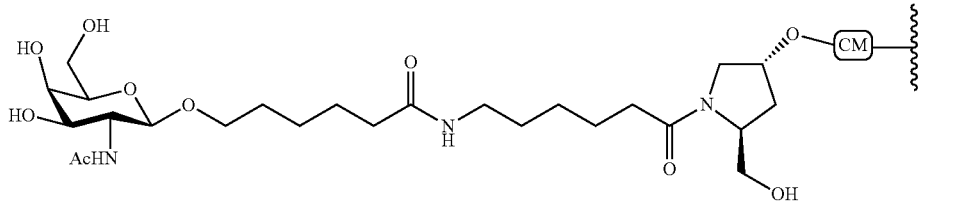

338

In order to add the GalNAc$_1$ conjugate group to the 3'-end of an oligonucleotide, procedures similar to those described in Example 71 are used to form the hydroxyl intermediate, which is then added to the solid support using procedures described in Example 7. The oligonucleotide synthesis is then completed using procedures described in Example 9 in order to form oligonucleotide 242.

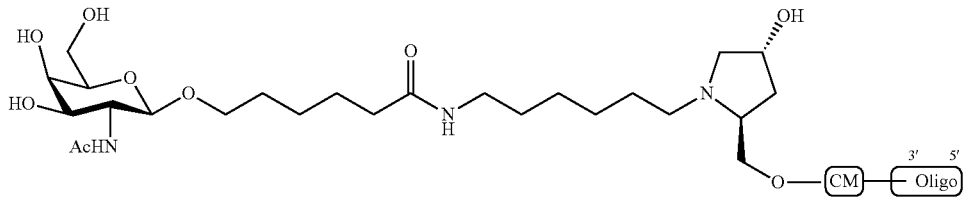

242

The GalNAc$_1$ cluster portion (GalNAc$_1$-29$_a$) of the conjugate group GalNAc$_1$-29 can be combined with any cleavable moiety present on the oligonucleotide to provide a variety of conjugate groups. The structure of GalNAc$_1$-29 (GalNAc$_1$-29$_a$-CM) is shown below:

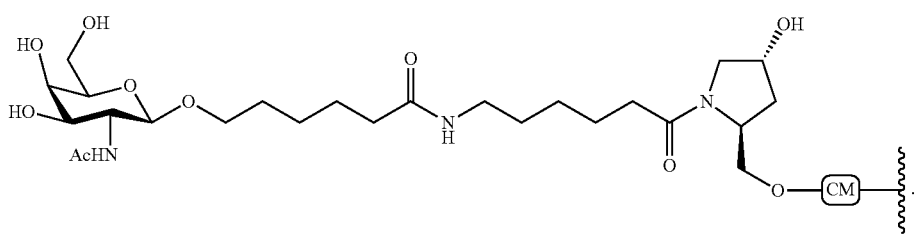

Example 110

Synthesis of Oligonucleotides Comprising a GalNAc₁-30 Conjugate

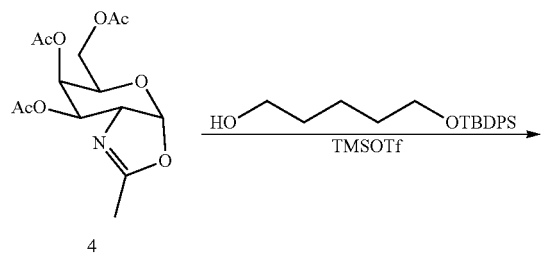

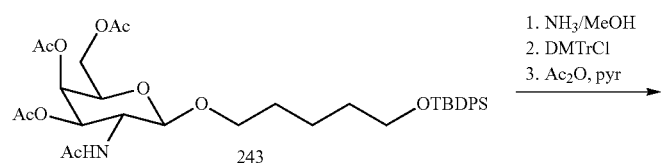

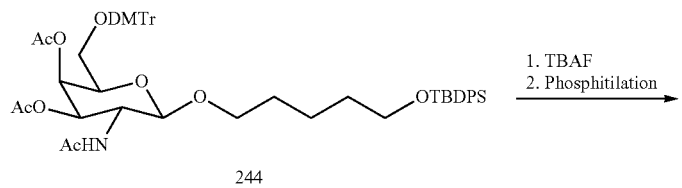

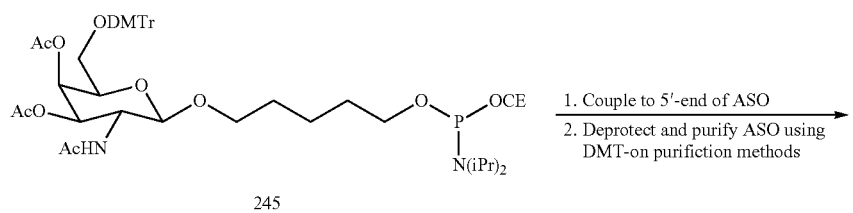

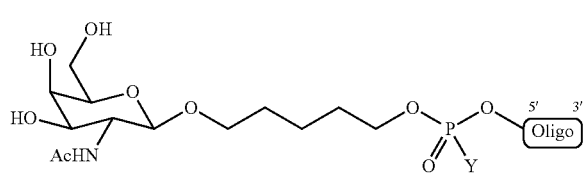

Oligonucleotide 246 comprising a GalNAc₁-30 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc₁ cluster portion (GalNAc₁-30$_a$) of the conjugate group GalNAc₁-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of GalNAc₁-30$_a$ is shown below:

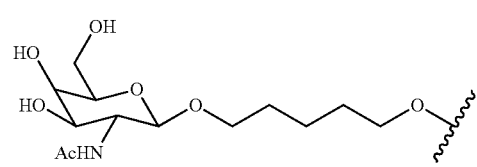 [SMILES: *OCCCCCOC1OC(CO)C(O)C(O)C1NC(C)=O]

Example 111

Synthesis of oligonucleotides comprising a GalNAc₂-31 or GalNAc₂-32 conjugate

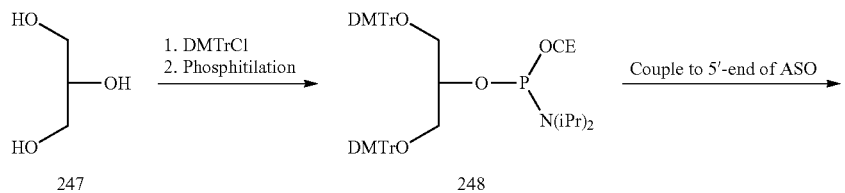

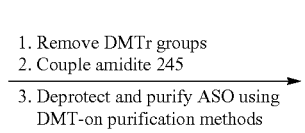

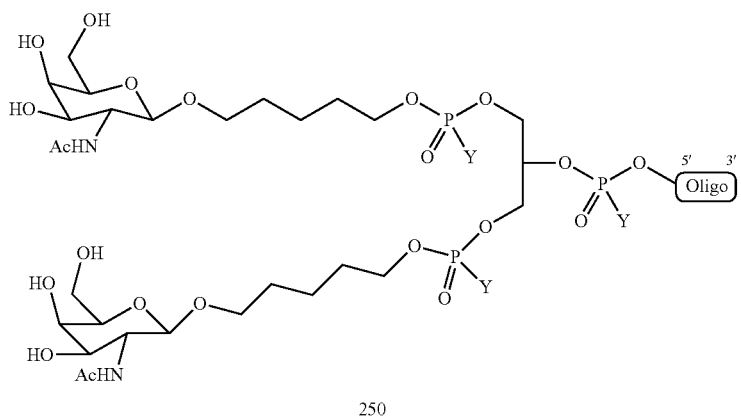

Oligonucleotide 250 comprising a GalNAc₂-31 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc₂ cluster portion (GalNAc₂-31$_a$) of the conjugate group GalNAc₂-31 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc₂-31$_a$ is shown below:

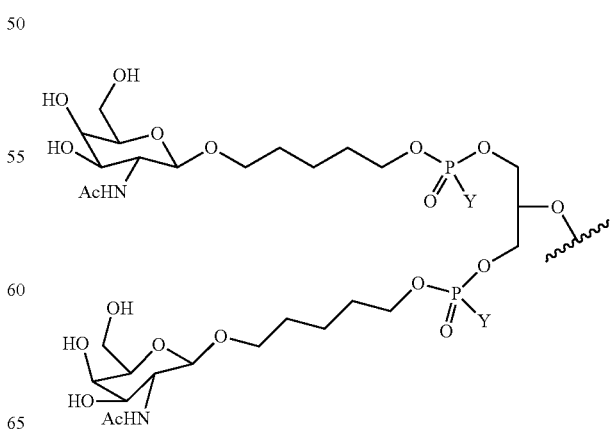

The synthesis of an oligonucleotide comprising a GalNAc₂-32 conjugate is shown below.

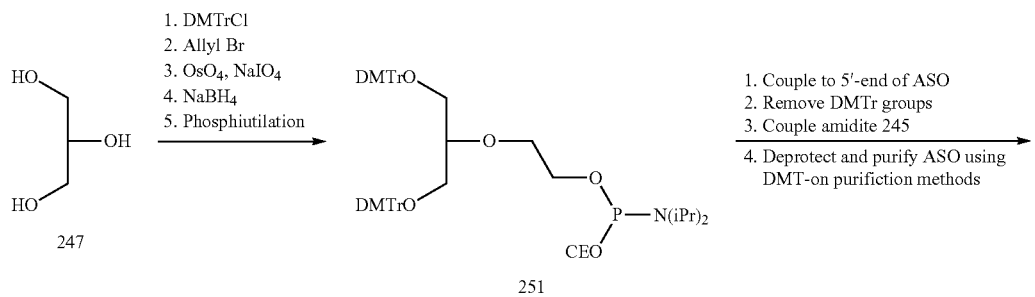

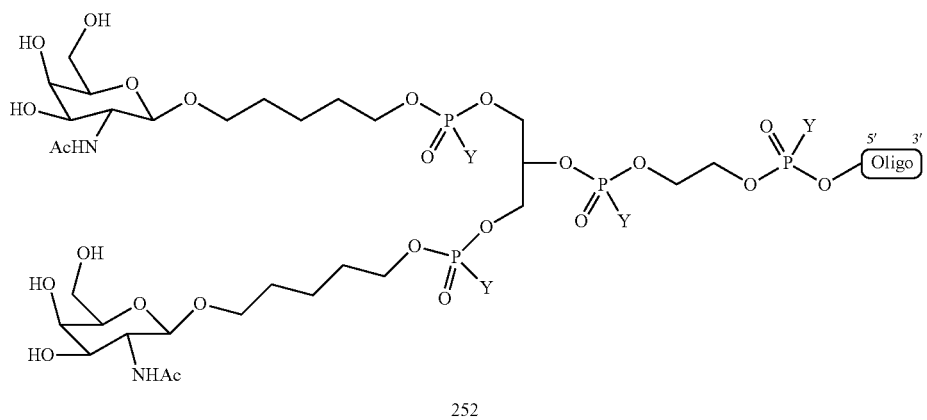

252

Oligonucleotide 252 comprising a GalNAc₂-32 conjugate group, wherein Y is selected from O, S, a substituted or unsubstituted $C_1$-$C_{10}$ alkyl, amino, substituted amino, azido, alkenyl or alkynyl, is synthesized as shown above. The GalNAc₂ cluster portion (GalNAc₂-32$_a$) of the conjugate group GalNAc₂-32 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of GalNAc₂-32$_a$ is shown below:

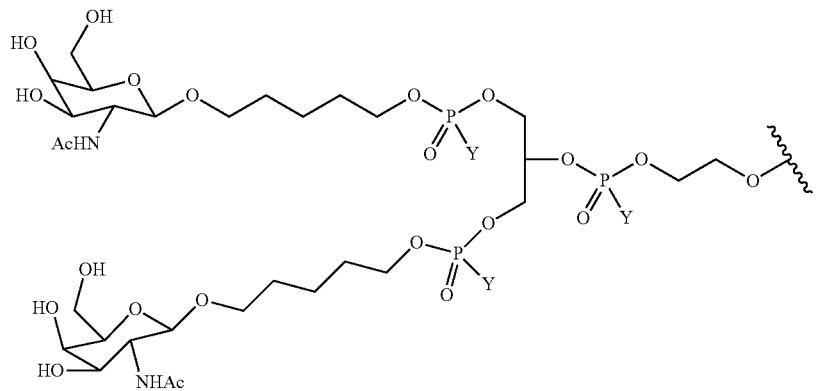

Example 112

Modified Oligonucleotides Comprising a GalNAc₁ Conjugate

The oligonucleotides in Table 107 targeting SRB-1 were synthesized with a GalNAc₁ conjugate group in order to further test the potency of oligonucleotides comprising conjugate groups that contain one GalNAc ligand.

TABLE 107

| ISIS No. | Sequences (5' to 3') | GalNAc cluster | CM | SEQ ID No |
|---|---|---|---|---|
| 711461 | GalNAc$_1$-25$_{a-o'}$A$_{ds}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-25$_a$ | A$_d$ | 30 |
| 711462 | GalNAc$_1$-25$_{a-o'}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-25$_a$ | PO | 28 |
| 711463 | GalNAc$_1$-25$_{a-o'}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{eo}$T$_{es}$T$_{e}$ | GalNAc$_1$-25$_a$ | PO | 28 |
| 711465 | GalNAc$_1$-26$_{a-o'}$A$_{ds}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-26$_a$ | A$_d$ | 30 |
| 711466 | GalNAc$_1$-26$_{a-o'}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-26$_a$ | PO | 28 |
| 711467 | GalNAc$_1$-26$_{a-o'}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{eo}$$^m$C$_{es}$T$_{es}$T$_{e}$ | GalNAc$_1$-26$_a$ | PO | 28 |
| 711468 | GalNAc$_1$-28$_{a-o'}$A$_{ds}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-28$_a$ | A$_d$ | 30 |
| 711469 | GalNAc$_1$-28$_{a-o'}$G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{e}$ | GalNAc$_1$-28$_a$ | PO | 28 |
| 711470 | GalNAc$_1$-28$_{a-o'}$G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_{e}$ | GalNAc$_1$-28$_a$ | PO | 28 |
| 713844 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo'}$GalNAc$_1$-27$_a$ | GalNAc$_1$-27$_a$ | PO | 28 |
| 713845 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_{eo'}$GalNAc$_1$-27$_a$ | GalNAc$_1$-27$_a$ | PO | 28 |
| 713846 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_{eo}$A$_{do'}$GalNAc$_1$-27$_a$ | GalNAc$_1$-27$_a$ | A$_d$ | 29 |
| 713847 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo'}$GalNAc$_1$-29$_a$ | GalNAc$_1$-29$_a$ | PO | 28 |
| 713848 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_{eo'}$GalNAc$_1$-29$_a$ | GalNAc$_1$-29$_a$ | PO | 28 |
| 713849 | G$_{es}$$^m$C$_{es}$T$_{es}$T$_{es}$$^m$C$_{es}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{es}$$^m$C$_{es}$$^m$C$_{es}$T$_{es}$T$_{eo}$A$_{do'}$GalNAc$_1$-29$_a$ | GalNAc$_1$-29$_a$ | A$_d$ | 29 |
| 713850 | G$_{es}$$^m$C$_{eo}$T$_{eo}$T$_{eo}$$^m$C$_{eo}$A$_{ds}$G$_{ds}$T$_{ds}$$^m$C$_{ds}$A$_{ds}$T$_{ds}$G$_{ds}$A$_{ds}$$^m$C$_{ds}$T$_{ds}$T$_{eo}$$^m$C$_{eo}$$^m$C$_{es}$T$_{es}$T$_{eo}$A$_{do'}$-GalNAc$_1$-29$_a$ | GalNAc$_1$-29$_a$ | A$_d$ | 29 |

The invention claimed is:

1. A compound comprising a modified oligonucleotide and a conjugate group, wherein the modified oligonucleotide is 10-30 linked nucleosides in length and consists of the nucleobase sequence of SEQ ID NO: 81, wherein the conjugate group comprises:

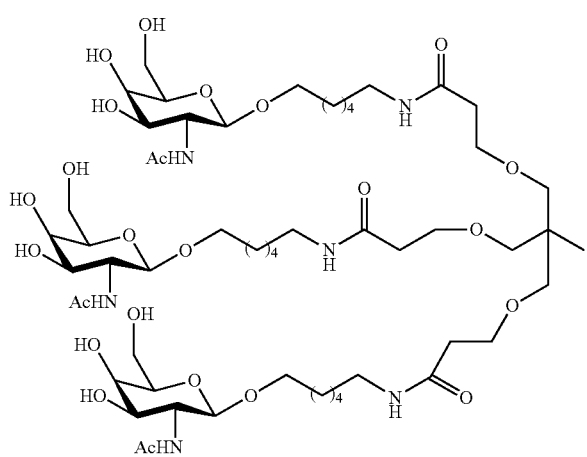

-continued

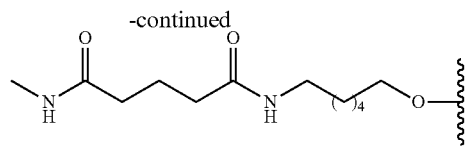

and wherein the conjugate group is linked to the modified oligonucleotide at the 5' end of the modified oligonucleotide.

2. The compound of claim 1, wherein the modified oligonucleotide comprises at least one modified sugar.

3. The compound of claim 2, wherein the modified sugar is a bicyclic sugar.

4. The compound of claim 3, wherein the bicyclic sugar is selected from the group consisting of: 4'-($CH_2$)—O-2' (LNA); 4'-($CH_2$)$_2$—O-2' (ENA); and 4'-CH($CH_3$)—O-2' (cEt).

5. The compound of claim 2, wherein the modified sugar is 2'-O-methoxyethyl.

6. The compound of claim 1, wherein the modified oligonucleotide comprises at least one modified nucleobase.

7. The compound of claim 6, wherein the modified nucleobase is a 5-methylcytosine.

8. The compound of claim 1, wherein the compound is single-stranded.

9. The compound of claim 1, wherein the compound is double-stranded.

10. The compound of claim 1, wherein the modified oligonucleotide comprises at least one modified internucleoside linkage.

11. The compound of claim 10, wherein the modified internucleoside linkage is a phosphorothioate internucleoside linkage.

12. The compound of claim 10, wherein the modified oligonucleotide comprises at least one phosphodiester internucleoside linkage.

13. A composition comprising the compound of claim 1 or salt thereof and at least one of a pharmaceutically acceptable carrier or diluent.

14. A prodrug comprising the compound of claim 1.

15. A method comprising administering to an animal the compound or composition of claim 1.

16. The method of claim 15, wherein the animal is a human.

17. The method of claim 15, comprising co-administering the compound or composition and a second agent.

* * * * *

UNITED STATES PATENT AND TRADEMARK OFFICE
CERTIFICATE OF CORRECTION

PATENT NO. : 9,714,421 B2
APPLICATION NO. : 14/888318
DATED : July 25, 2017
INVENTOR(S) : Thazha P. Prakash et al.

It is certified that error appears in the above-identified patent and that said Letters Patent is hereby corrected as shown below:

In the Claims

In Column 801 beginning at Line 47 and continuing in Column 802 at Line 40 please change "conjugate group comprises:

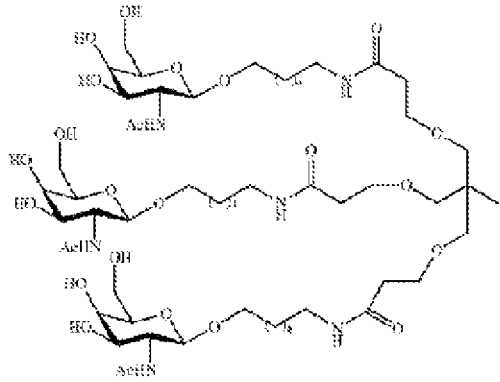
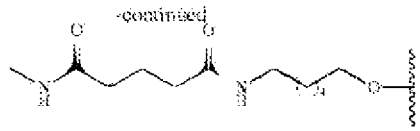

To -- conjugate group comprises:

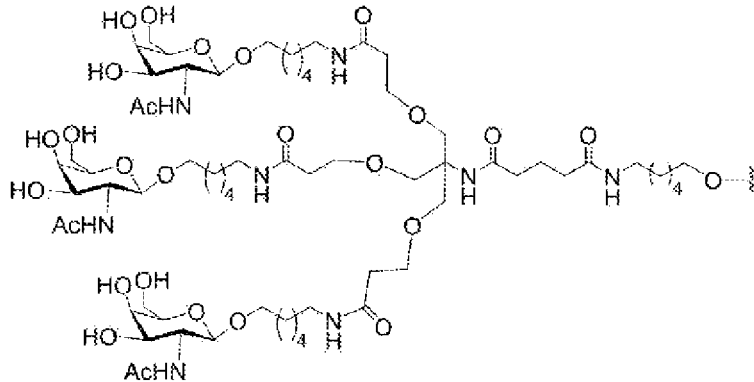

--

Signed and Sealed this
Twenty-ninth Day of August, 2017

Joseph Matal
*Performing the Functions and Duties of the
Under Secretary of Commerce for Intellectual Property and
Director of the United States Patent and Trademark Office*